US012624358B2

(12) United States Patent
Kubli et al.

(10) Patent No.: US 12,624,358 B2
(45) Date of Patent: May 12, 2026

(54) COMPOUNDS AND METHODS FOR REDUCING PLN EXPRESSION

(71) Applicant: Ionis Pharmaceuticals, Inc., Carlsbad, CA (US)

(72) Inventors: Dieter A. Kubli, Santee, CA (US); Brooke A. Anderson, San Diego, CA (US); Adam Mullick, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 19/268,623

(22) Filed: Jul. 14, 2025

(65) Prior Publication Data

US 2025/0340888 A1 Nov. 6, 2025

Related U.S. Application Data

(63) Continuation of application No. 18/626,889, filed on Apr. 4, 2024.

(60) Provisional application No. 63/561,700, filed on Mar. 5, 2024, provisional application No. 63/508,453, filed on Jun. 15, 2023, provisional application No. 63/494,415, filed on Apr. 5, 2023.

(51) Int. Cl.
*C12N 15/113* (2010.01)
*A61P 9/04* (2006.01)

(52) U.S. Cl.
CPC ............ *C12N 15/1138* (2013.01); *A61P 9/04* (2018.01); *C12N 2310/14* (2013.01); *C12N 2310/313* (2013.01); *C12N 2310/321* (2013.01); *C12N 2310/3341* (2013.01); *C12N 2310/3513* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan, Jr. et al. | |
| 4,415,732 A | 11/1983 | Caruthers et al. | |
| 4,469,863 A | 9/1984 | Ts'O et al. | |
| 4,476,301 A | 10/1984 | Imbach et al. | |
| 4,500,707 A | 2/1985 | Caruthers et al. | |
| 4,725,677 A | 2/1988 | Koster et al. | |
| 4,845,205 A | 7/1989 | Huynh Dinh et al. | |
| 4,973,679 A | 11/1990 | Caruthers et al. | |
| 4,981,957 A | 1/1991 | Lebleu et al. | |
| 5,013,830 A | 5/1991 | Ohtsuka et al. | |
| 5,023,243 A | 6/1991 | Tullis | |
| 5,034,506 A | 7/1991 | Summerton et al. | |
| 5,118,800 A | 6/1992 | Smith et al. | |

| | | | |
|---|---|---|---|
| 5,130,302 A | 7/1992 | Spielvogel et al. | |
| 5,132,418 A | 7/1992 | Caruthers et al. | |
| 5,134,066 A | 7/1992 | Rogers et al. | |
| 5,149,797 A | 9/1992 | Pederson et al. | |
| 5,166,315 A | 11/1992 | Summerton et al. | |
| 5,175,273 A | 12/1992 | Bischofberger et al. | |
| 5,177,196 A | 1/1993 | Meyer, Jr. et al. | |
| 5,177,198 A | 1/1993 | Spielvogel et al. | |
| 5,185,444 A | 2/1993 | Summerton et al. | |
| 5,188,897 A | 2/1993 | Suhadolnik et al. | |
| 5,194,599 A | 3/1993 | Froehler et al. | |
| 5,214,134 A | 5/1993 | Weis et al. | |
| 5,216,141 A | 6/1993 | Benner | |
| 5,220,007 A | 6/1993 | Pederson et al. | |
| 5,223,618 A | 6/1993 | Cook et al. | |
| 5,235,033 A | 8/1993 | Summerton et al. | |
| 5,256,775 A | 10/1993 | Froehler | |
| 5,264,423 A | 11/1993 | Cohen et al. | |
| 5,264,562 A | 11/1993 | Matteucci | |
| 5,264,564 A | 11/1993 | Matteucci | |
| 5,276,019 A | 1/1994 | Cohen et al. | |
| 5,286,717 A | 2/1994 | Cohen et al. | |
| 5,319,080 A | 6/1994 | Leumann | |
| 5,321,131 A | 6/1994 | Agrawal et al. | |
| 5,359,044 A | 10/1994 | Cook et al. | |
| 5,366,878 A | 11/1994 | Pederson et al. | |
| 5,367,066 A | 11/1994 | Urdea et al. | |
| 5,378,825 A | 1/1995 | Cook et al. | |
| 5,386,023 A | 1/1995 | Sanghvi et al. | |
| 5,393,878 A | 2/1995 | Leumann | |
| 5,399,676 A | 3/1995 | Froehler | |
| 5,403,711 A | 4/1995 | Walder et al. | |
| 5,405,938 A | 4/1995 | Summerton et al. | |
| 5,405,939 A | 4/1995 | Suhadolnik et al. | |
| 5,432,272 A | 7/1995 | Benner | |
| 5,434,257 A | 7/1995 | Matteucci et al. | |
| 5,446,137 A | 8/1995 | Maag et al. | |
| 5,453,496 A | 9/1995 | Caruthers et al. | |
| 5,455,233 A | 10/1995 | Spielvogel et al. | |
| 5,457,187 A | 10/1995 | Gmeiner et al. | |
| 5,457,191 A | 10/1995 | Cook et al. | |
| 5,459,255 A | 10/1995 | Cook et al. | |
| 5,466,677 A | 11/1995 | Baxter et al. | |

(Continued)

FOREIGN PATENT DOCUMENTS

| | | |
|---|---|---|
| EP | 1126866 B1 | 2/2007 |
| EP | 1939289 A1 | 7/2008 |

(Continued)

OTHER PUBLICATIONS

Nishina K., et al., "Efficient In Vivo Delivery of siRNA to the Liver by Conjugation of a-Tocopherol", Molecular Therapy, vol. 16, No. 4, Apr. 2008, pp. 734-740.

(Continued)

*Primary Examiner* — Nancy J Leith
*Assistant Examiner* — Ruth Sophia Arieti

(57) ABSTRACT

Provided are oligomeric compounds, methods, and pharmaceutical compositions for reducing the amount or activity of PLN RNA in a cell or animal, and in certain instances reducing the amount of phospholamban protein in a cell or animal. Such oligomeric compounds, methods, and pharmaceutical compositions are useful to treat cardiomyopathy, heart failure, or arrhythmia.

10 Claims, 4 Drawing Sheets

Specification includes a Sequence Listing.

(56) References Cited

U.S. PATENT DOCUMENTS

| | | | |
|---|---|---|---|
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,801,154 A | 9/1998 | Baracchini et al. |
| 5,808,027 A | 9/1998 | Cook et al. |
| 5,811,534 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,968,959 A | 10/1999 | Haikala et al. |
| 5,994,517 A | 11/1999 | Ts'O et al. |
| 6,005,087 A | 12/1999 | Cook et al. |
| 6,005,096 A | 12/1999 | Matteucci et al. |
| 6,166,199 A | 12/2000 | Cook et al. |
| 6,265,421 B1 | 7/2001 | Pystynen et al. |
| 6,268,490 B1 | 7/2001 | Imanishi et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,015,315 B1 | 3/2006 | Cook et al. |
| 7,034,133 B2 | 4/2006 | Wengel et al. |
| 7,053,207 B2 | 5/2006 | Wengel |
| 7,101,993 B1 | 9/2006 | Cook et al. |
| 7,208,174 B2 | 4/2007 | Huwyler et al. |
| 7,262,177 B2 | 8/2007 | Ts'O et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,534,775 B2 | 5/2009 | Zhang et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Seth et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Seth et al. |
| 8,030,467 B2 | 10/2011 | Seth et al. |
| 8,080,644 B2 | 12/2011 | Wengel et al. |
| 8,084,598 B1 | 12/2011 | Bentwich |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,178,503 B2 | 5/2012 | Rigoutsos et al. |
| 8,207,138 B2 | 6/2012 | Thakker et al. |
| 8,268,980 B2 | 9/2012 | Seth et al. |
| 8,273,866 B2 | 9/2012 | McSwiggen et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,314,227 B2 | 11/2012 | Wengel |
| 8,404,658 B2 | 3/2013 | Hajjar et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,796,437 B2 | 8/2014 | Swayze et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,034,329 B2 | 5/2015 | Chang et al. |
| 9,127,276 B2 | 9/2015 | Prakash et al. |
| 9,290,760 B2 | 3/2016 | Rajeev et al. |
| 9,745,586 B2 | 8/2017 | Bowser et al. |
| 10,138,483 B2 | 11/2018 | Chatterton et al. |
| 10,550,188 B2 | 2/2020 | Geall et al. |
| 10,759,864 B2 | 9/2020 | Sonoda et al. |
| 2001/0053519 A1 | 12/2001 | Fodor et al. |
| 2002/0040010 A1 | 4/2002 | Rosenzweig et al. |
| 2003/0050259 A1 | 3/2003 | Blatt et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0121942 A1 | 6/2004 | Chien et al. |
| 2004/0171570 A1 | 9/2004 | Allerson et al. |
| 2005/0095227 A1 | 5/2005 | Rosenzweig et al. |
| 2005/0130923 A1 | 6/2005 | Bhat et al. |
| 2005/0288244 A1 | 12/2005 | Manoharan et al. |

(56) References Cited

U.S. PATENT DOCUMENTS

| | | |
|---|---|---|
| 2006/0148740 A1 | 7/2006 | Platenburg |
| 2006/0198825 A1 | 9/2006 | Kaemmerer et al. |
| 2007/0031844 A1 | 2/2007 | Khvorova et al. |
| 2008/0039618 A1 | 2/2008 | Allerson et al. |
| 2008/0113351 A1 | 5/2008 | Naito et al. |
| 2010/0190837 A1 | 7/2010 | Migawa et al. |
| 2010/0197762 A1 | 8/2010 | Swayze |
| 2010/0298697 A1 | 11/2010 | Thakker et al. |
| 2010/0310521 A1 | 12/2010 | Fechner et al. |
| 2011/0078833 A1 | 3/2011 | Wu et al. |
| 2011/0098338 A1 | 4/2011 | Hajjar et al. |
| 2013/0096289 A1 | 4/2013 | Wengel |
| 2013/0130378 A1 | 5/2013 | Manoharan et al. |
| 2013/0190383 A1 | 7/2013 | Vaish et al. |
| 2013/0203836 A1 | 8/2013 | Rajeev et al. |
| 2014/0107330 A1 | 4/2014 | Freier et al. |
| 2015/0018540 A1 | 1/2015 | Prakash et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |
| 2017/0204407 A1 | 7/2017 | Gilbert et al. |
| 2019/0240346 A1 | 8/2019 | Sugo et al. |
| 2021/0038739 A1 | 2/2021 | Takahashi et al. |
| 2022/0033903 A1 | 2/2022 | Ho et al. |

FOREIGN PATENT DOCUMENTS

| | | | | |
|---|---|---|---|---|
| EP | 2126084 B1 | 3/2014 | | |
| WO | 9104753 A1 | 4/1991 | | |
| WO | 9900132 A1 | 1/1999 | | |
| WO | 9914226 A2 | 3/1999 | | |
| WO | 9915523 A1 | 4/1999 | | |
| WO | 0116312 A2 | 3/2001 | | |
| WO | 03070918 A2 | 8/2003 | | |
| WO | 2004045543 A2 | 6/2004 | | |
| WO | 2004106356 A1 | 12/2004 | | |
| WO | 2005100393 A1 | 10/2005 | | |
| WO | 2005116204 A1 | 12/2005 | | |
| WO | 2007134181 A2 | 11/2007 | | |
| WO | 2008080985 A1 | 7/2008 | | |
| WO | 2008101157 A1 | 8/2008 | | |
| WO | 2009088786 A1 | 7/2009 | | |
| WO | 2009120878 A2 | 10/2009 | | |
| WO | 2009142822 A9 | 1/2010 | | |
| WO | 2010135322 A1 | 11/2010 | | |
| WO | 2011133876 A2 | 10/2011 | | |
| WO | 2013036868 A1 | 3/2013 | | |
| WO | 2013103800 A1 | 7/2013 | | |
| WO | 2013163303 A2 | 10/2013 | | |
| WO | 2013173637 A1 | 11/2013 | | |
| WO | 2014144060 A1 | 9/2014 | | |
| WO | 2014179620 A1 | 11/2014 | | |
| WO | 2015106128 A2 | 7/2015 | | |
| WO | 2016081643 A1 | 5/2016 | | |
| WO | 2016179257 A2 | 11/2016 | | |
| WO | 2016207240 A1 | 12/2016 | | |
| WO | 2017015555 A1 | 1/2017 | | |
| WO | 2018098328 A1 | 5/2018 | | |
| WO | 2018129384 A1 | 7/2018 | | |
| WO | 2018154439 A1 | 8/2018 | | |
| WO | 2019033051 A1 | 2/2019 | | |
| WO | 2019140050 A1 | 7/2019 | | |
| WO | 2019157531 A1 | 8/2019 | | |
| WO | 2020028864 A1 | 2/2020 | | |
| WO | 2020037150 A2 | 2/2020 | | |
| WO | 2020124032 A1 | 6/2020 | | |
| WO | 2020132584 A1 | 6/2020 | | |
| WO | 2020191171 A1 | 9/2020 | | |
| WO | WO-2020236755 A2 * | 11/2020 | ......... | C12N 15/1138 |
| WO | 2020245198 A1 | 12/2020 | | |
| WO | 2021030778 A1 | 2/2021 | | |
| WO | WO-2022101633 A1 * | 5/2022 | ............ | A61K 47/55 |
| WO | 2022147249 A1 | 7/2022 | | |
| WO | 2022173976 A1 | 8/2022 | | |
| WO | 2023056388 A1 | 4/2023 | | |
| WO | 2023064530 A1 | 4/2023 | | |
| WO | 2025007063 A1 | 1/2025 | | |
| WO | 2025063238 A1 | 3/2025 | | |

OTHER PUBLICATIONS

Nishina T., et al., "Chimeric Antisense Oligonucleotide Conjugated to a-Tocopherol", Molecular Therapy Nucleic Acids, 2015, 4, e220, pp. 1-10.

Oberhauser B., et al., "Effective Incorporation of 2'-O-Methyl-Oligoribonucleotides into Liposomes and Enhanced Cell Association through Modification with Thiocholesterol," Nucleic Acids Research, 1992, vol. 20, No. 3, pp. 533-538.

Ostergaard M.E., "Harnessing the Transferrin Receptor (CD71) to Enhance Potency of RNA Therapeutics in Skeletal Muscle and Heart Tissues", Presentation for TIDES, Boston, MA, May 10, 2022, 28 Pages.

Reynolds A., et al., "Rational siRNA Design for RNA Interference", Nature Biotechnology, Mar. 2004, vol. 22, No. 3, pp. 326-330.

Saison-Behmoaras T., et al., "Short Modified Antisense Oligonucleotides Directed Against Ha-ras Point Mutation Induce Selective Cleavage of the mRNA and Inhibit T24 Cells Proliferation," The EMBO Journal, 1991, vol. 10, No. 5, pp. 1111-1118.

Sanghvi Y.S., "Heterocyclic Base Modifications in Nucleic Acids and Their Applications in Antisense Oligonucleotides," Antisense Research and Applications, Chapter 15, 1993, pp. 273-288.

Seth P.P., et al., "Short Antisense Oligonucleotides with Novel 2-4' Conformationaly Restricted Nucleoside Analogues Show Improved Potency Without Increased Toxicity in Animals," Journal of Medicinal Chemistry, 2009, vol. 52, No. 1, pp. 10-13.

Shea R G., et al., "Synthesis, Hybridization Properties and Antiviral Activity of Lipid-Oligodeoxynucleotide Conjugates", Nucleic Acids Research, vol. 18, No. 13, 1990, pp. 3777-3783.

Shen W., et al., "Acute Hepatotoxicity of 2' Fluoro-modified 5-10-5 Gapmer Phosphorothioate Oligonucleotides in Mice Correlates with Intracellular Protein Binding and the Loss of DBHS Proteins", Nucleic acids research, Jan. 30, 2018, vol. 46, No. 5, pp. 2204-2217.

Soller K.J., et al., "Reversal of Phospholamban Inhibition of the Sarco(endo)plasmic Reticulum Ca2+-ATPase (SERCA) Using Short, Protein-interacting RNAs and Oligonucleotide Analogs", Journal of Biological Chemistry, Oct. 7, 2016, vol. 291, vol. 41, pp. 21510-21518.

Soller K.J., etal., "Rheostatic Regulation of the SERCA/Phospholamban Membrane Protein Complex Using NonCoding RNA and Single-Stranded DNA oligonucleotides", Scientific Reports, Aug. 21, 2015, vol. 5, Article No. 13000, 14 Pages.

Spaeter D., et al., "Phospholamban Antisense Oligonucleotides Drive the Reversal of Cardiac Dysfunction and Multiple Heart Failure Parameters During Murine Dilated Cardiomyopathy", Abstract P6348 for ESC Congress, Aug. 31-Sep. 4, 2019, European Heart Journal, vol. 40, Supplement 1, pp. 3950, XP093218982, Retrieved from the Internet: URL: https://watermark.silverchair.com/ehz746. 0944.pdf?token=AQECAHi208BE49Ooan9kkhW_Ercy7Dm3ZL_9Cf3qfKAc485ysgAAA5owggOWBgkqhkiG9w0BBwagggOHMII.

Supplementary European Search Report in European Patent Application No. 22753363.5, dated Jun. 3, 2025, 17 Pages.

Supplementary Partial European Search Report in European Patent Application No. 22753363.5, dated Nov. 22, 2024, 14 Pages.

Svinarchuk F.P., et al., "Inhibition of HIV Proliferation in MT-4 Cells by Antisense Oligonucleotide Conjugated to Lipophilic Groups," Biochimie, 1993, vol. 75, No. 1-2, pp. 49-54.

University of Groningen: "Promising results new treatment option for heart failure", Aug. 30, 2021, Retrieved from https://umcgresearch. Org/w/promising-results-new-treatment-option-for-heart-failure, 2 Pages.

Watanabe A., et al., "Phospholamban Ablation by RNA Interference Increases Ca2+ Uptake into Rat Cardiac Myocyte Sarcoplasmic Reticulum", Journal of Molecular and Cellular Cardiology, Jul. 2004, vol. 37, pp. 691-698.

Woolf T.M., et al., "Specificity of Antisense Oligonucleotides in Vivo," Proceedings of the National Academy of Sciences of the United States of America (PNAS), Aug. 1992, vol. 89, No. 16, pp. 7305-7309.

(56) References Cited

OTHER PUBLICATIONS

Zhou C., et al., "Fine Tuning of Electrostatics around the Internucleotidic Phosphate through Incorporation of Modified 2',4'-Carbocyclic-LNAs and -ENAs Leads to Significant Modulation of Antisense Properties", J. Org. Chem, 2009, vol. 74, No. 1, pp. 118-134.

International Search Report and Written Opinion for International Application No. PCT/IB2024/053304, mailed Sep. 16, 2024, 14 Pages.

Wakamatsu A., et al., "Homo sapiens cDNA, FLJ92060, *Homo sapiens* phospholamban (PLN), mRNA", Genbank entry (online), National Institute of Biotechnology Information, May 24, 2008 (Retrieved on Aug. 7, 2024), Retrieved from the Internet: URL: https://www.ncbi.nlm.nih.gov/nucleotide/AK311799.1?report=genbank&amp;log$=nucltop&amp;blast_rank=5&amp;RID=87RD4F8S016, pp. 1-2.

Allerson C.R., et al., "Fully 2-Modified Oligonucleotide Duplexes with Improved in Vitro Potency and Stability Compared to Unmodified Small Interfering RNA", Journal of medicinal chemistry , Jan. 20, 2005, vol. 48, No. 4, pp. 901-904.

Anderson B.A., "Bicyclic Peptide Transferrin Receptor 1 Ligands Conjugated to Oligonucleotide Therapeutics Improve Potency in Skeletal and Cardiac Muscle", Presentation for Euro TIDES (Vienna, Austria), Nov. 17, 2022, 27 Pages.

Anderson B.A., et al., "Bicyclic Peptide Transferrin Receptor 1 Ligands Conjugated to Oligonucleotide Therapeutics Improve Potency in Skeletal and Cardiac Muscle", Presentation for 19th Annual Meeting of Oligonucleotide Therapeutics Society, Barcelona, Spain, Oct. 22-25, 2023, 1 page.

Andino L.M., et al., "AAV-mediated Knockdown of Phospholamban Leads to Improved Contractility and Calcium Handling in Cardiomyocytes", The Journal of Gene Medicine, Feb. 2008, vol. 10, No. 2, pp. 132-142.

Beverborg N.G., et al., "Phospholamban Antisense Oligonucleotides Improve Cardiac Function in Murine Cardiomyopathy", Nature Communication, Aug. 30, 2021, vol. 12, 15 Pages.

Bicycle Therapeutics: "Bicycles, Bi-cyclic Peptides, Novel Small Molecule Delivery Systems for RNA Therapeutics", Presentation for Euro TIDES, Nov. 19, 2021, 20 Pages.

Branch A.D., "A Good Antisense Molecule is Hard to Find," TIBS, Feb. 1998, vol. 23, No. 2, pp. 45-50.

Chin A., "On the Preparation and Utilization of Isolated and Purified Oligonucleotides," Document Purportedly Located on A CD-ROM and Contributed to the Public Collection of the Katherine R. Everett Law Library of the University of North Carolina, Mar. 9, 2002, p. C18.

Crooke S T., "Antisense Drug Technology", Second Edition, CRC Press, 2008, Chapters 1-28, 414 Pages.

Crooke S.T., "Basic Principles of Antisense Therapeutics," Antisense Research and Application, Chapter 1, 1998, pp. 1-50.

Crooke S.T., et al.. "Pharmacokinetic Properties of Several Novel Oligonucleotide Analogs in Mice," The Journal of Pharmacology and Experimental Therapeutics, 1996, vol. 277, No. 2, pp. 923-937.

Deiman F.E., et al., "Review: Precision Medicine Approaches for Genetic Cardiomyopathy: Targeting Phospholamban R14del", Current Heart Failure Reports, Jun. 14, 2022, vol. 19, No. 4, pp. 170-179.

Deiman F.E., etaL, "Phospholamban Antisense Treatment Attenuates Hallmarks of Disease in PLN R14del Human iPSC Derived Cardiomyocytes", Abstract 48, European Journal of Heart Failure, 2023, vol. 25, Supplement S1, pp. 27.

Del Monte F., et al., "Targeting Phospholamban by Gene Transfer in Human Heart Failure", Circulation, Feb. 2002, vol. 105, No. 8, pp. 904-907.

Egli M., et al., "Synthesis, Improved Antisense Activity and Structural Rationale for the Divergent RNA Affinities of 3'-Fluoro Hexitol Nucleic Acid (FHNAand Ara-FHNA) Modified Oligonucleotides," Journal of the American Chemical Society, Oct. 19, 2011, vol. 133, No. 41, pp. 16642-16649, 21 Pages.

Eijgenraam T.R., et al., "Antisense Therapy Attenuates Phospholamban p.(Arg14del) Cardiomyopathy in Mice and Reverses Protein Aggregation", International Journal of Molecular Sciences, Feb. 22, 2022, vol. 23, 16 Pages.

Eizema K., et al., "Adenovirus-based Phospholamban Antisense Expression as a Novel Approach to Improve Cardiac Contractile Dysfunction: Comparison of a Constitutive Viral Versus an Endothelin-1-responsive Cardiac Promoter", Circulation, May 9, 2000, vol. 101, No. 18, pp. 2193-2199.

Elmen J., et al., "Locked Nucleic Acid (LNA) Mediated Improvements in siRNA Stability and Functionality", Nucleic Acids Research, 2005, vol. 33, No. 1, pp. 439-447.

Frieden M., et al., "Expanding the Design Horizon of Antisense Oligonucleotides with Alpha-L-LNA," Nucleic Acids Research, 2003, vol. 31, No. 21, pp. 6365-6372.

Gautschi O., et al., "Activity of a Novel bcl-2/bcl-xL-Bispecific Antisense Oligonucleotide Against Tumors of Diverse Histologic Origins," Journal of the National Cancer Institute, Mar. 21, 2001, vol. 93, No. 6, pp. 463-471.

Grunweller A., et al., "Comparison of Different Antisense Strategies in Mammalian Cells Using Locked Nucleic Acids, 2'-O-methyl RNA, Phosphorothioates and Small Interfering RNA", Nucleic Acids Research, 2003, vol. 31, No. 12, pp. 3185-3193.

He H., et al., "Effects of Mutant and Antisense RNA of Phospholamban on SR Ca2+-ATPase Activity and Cardiac Myocyte Contractility", Circulation, Aug. 31, 1999, vol. 100, No. 9, pp. 974-980.

Hidalgo-Gonzalez A., et al., "Amelioration of Heart Failure in a Mouse Model of Dilated Cardiomyopathy Following Phospholamban (PLN) Anstisense Oligonucleotide Treatment", Poster for Heart Failure: Crossing the Translation Divide, Keystone, CO, Jan. 14-18, 2018, 1 Page.

International Search Report and Written Opinion for International Application No. PCT/US2022/016015, dated Jun. 29, 2022, 13 pages.

Janas M.M., et al., "Safety Evaluation of 2'-deoxy-2'-fluoro Nucleotides in GalNAc-siRNA Conjugates", Nucleic Acids Research, Mar. 1, 2019, vol. 47, No. 7, pp. 3306-3320.

Kabanov A.V., et al., "A New Class of Antivirals: Antisense Oligonucleotides Combined with a Hydrophobic Substituent Effectively Inhibit Influenza Virus Reproduction and Synthesis of Virus-Specific Proteins in MDCK Cells," FEBS Letters, Jan. 1990, vol. 259, No. 2, pp. 327-330.

Karakikes I., et al., "Correction of Human Phospholamban R14del Mutation Associated with Cardiomyopathy Using Targeted Nucleases and Combination Therapy", Nature Communication, Apr. 2015, 10 Pages.

Koss K.L, et al., "Phospholamban: A Prominent Regulator of Myocardial Contractility", Circulation Research, Dec. 1996, vol. 79, pp. 1059-1063.

Letsinger R L., et al., "Cholesteryl-Conjugated Oligonucleotides: Synthesis, Properties, and Activity as Inhibitors of Replication of Human Immunodeficiency Virus in Cell Culture", Proc. Natl. Acad. Sci. USA, Sep. 1989, vol. 86, pp. 6553-6556.

Leumann C J., "DNA Analogues: From Supramolecular Principles to Biological Properties", Bioorganic Medicinal Chemistry, 2002, vol. 10, pp. 841-854.

Lorenz J.N., et al., "Regulatory Effects of Phospholamban on Cardian Function in Intact Mice", The American journal of physiology, Dec. 1997, vol. 273, pp. H2826-H2831.

Maher III L.J., et al., "Comparative Hybrid Arrest by Tandem Antisense Oligodeoxyribonucleotides or Oligodeoxy-Ribonucleoside Methylpbosphonates in a Cell-Free System," Nucleic Acids Research, 1988, vol. 16, No. 8, pp. 3341-3358.

Manoharan M., et al., "Cholic Acid-Oligonucleotide Conjugates for Antisense Applications," Bioorganic and Medicinal Chemistry Letters, 1994, vol. 4, No. 8, pp. 1053-1060.

Manoharan M., et al., "Introduction of a Lipophilic Thioether Tether in the Minor Groove of Nucleic Acids for Antisense Applications," Bioorganic and Medicinal Chemistry Letters, 1993, vol. 3, No. 12, pp. 2765-2770.

Manoharan M., et al., "Lipidic Nucleic Acids," Tetrahedron Letters, 1995, vol. 36, No. 21, pp. 3651-3654.

(56) References Cited

OTHER PUBLICATIONS

Manoharan M., et al., "Oligonucleotide Conjugates: Alteration of the Pharmacokinetic Properties of Antisense Agents," Nucleosides Nucleotides, 1995, vol. 14, No. 3-5, pp. 969-973.

Manoharan M., etal., Chemical Modifications to Improve Uptake and Bioavailability of Antisense Oligonucleotides, Annals of the New York Academy of Sciences, 1992, vol. 660, pp. 306-309.

Minamisawa S., et al., "Chronic Phospholamban-Sarcoplasmic Reticulum Calcium ATPase Interaction Is the Critical Calcium Cycling Defect in Dilated Cardiomyopathy", Cell, Oct. 29, 1999, vol. 99, pp. 313-322.

Mishra R.K., et al., "Improved Leishmanicidal Effect of Phosphorotioate Antisense Oligonucleotides by LDL-Mediated Delivery," Biochimica et Biophysica Acta, 1995, vol. 1264, No. 2, pp. 229-237.

Mook O.R., et al., "Evaluation of Locked Nucleic Acid-modified Small Interfering RNA in Vitro and in Vivo", Molecular Cancer Therapeutics, Mar. 2007, vol. 6, No. 3, pp. 833-843.

Morihara H., et al., "Phospholamban Inhibition by a Single Dose of Locked Nucleic Acid Antisense Oligonucleotide Improves Cardiac Contractility in Pressure Overload-Induced Systolic Dysfunction in Mice", Journal of Cardiovascular Pharmacology and Therapeutics, May 2017, vol. 22, No. 3, pp. 273-282, Nov. 2, 2016, XP093218980, US ISSN: 1074-2484, DOI: 10.1177/1074248416676392, Retrieved from the Internet: URL: https://journals.sagepub.com/doi/full-xml/10.1177/1074248416676392, the whole document.

Mou Y., et al., "Partial Restoration of Left Ventricular Systolic Function by ASPLB Gene Transfer Using Ultrasound-mediated Microbubble Destruction", Ultrasound in Medicine Biology, Oct. 2009, vol. 35, No. 10, pp. 1638-1646.

Mullick A., "Antisense Oligonucleotide (ASO) Therapy Targeting Phospholamban Improves Cardiac Function", Presentation for TIDES, Boston, MA, May 11, 2022, 20 Pages.

Mullick A., "Antisense Oligonucleotides as Cardiovascular Therapeutics: Past, Present and Future", Presentation for AHA Scientific Sessions, Nov. 12, 2018, 16 Pages.

Mullick A., "Antisense Oligonucleotides as Cardiovascular Therapeutics: Past, Present and Future", Presentation for University of Kentucky College of Medicine, CVRC Cardiovascular Seminar Series, Feb. 14, 2020, 38 Pages.

Mullick A., et al., "Phospholamban Antisense Oligonucleotide Treatment Improved Cardiac Function and Reduced Transcriptional Markers of Heart Failure in a Mouse Model of Dilated Cardiomyopathy", Poster for Nature Conference: RNA athe Bench and Bedside, 2018, La Jolla, CA, Oct. 8-10, 1 Page.

Mullick A., etal., "Phospholamban Antisense Oligonucleotide Treatment Improved Cardiac Function and Reduced Transcriptional Markers of Heart Failure in a Mouse Model of Dilated Cardiomyopathy", Gordon Research Conference, New London, NH, Jun. 3-8, 2018, 1 Page.

Mullick A., "RNA Targeting Therapies for Heart Failure", Presentation for RNA at the Bench and Bedside Meeting, San Diego, CA, Nov. 12, 2020, 27 Pages.

Munker K., et al., "Effects of a Novel Phospholamban Inhibitor on Systolic, Diastolic and Mitochondrial Function in a Mouse Model of Dilated Cardiomyopathy", Clinical Research in Cardiology, Apr. 2019, vol. 108, Supplement 1, 1 Page.

New England Biolabs, Nucleic Acids, Linkersand Primers, 1998/1999, Catalog, 121 and 284.

* cited by examiner

Model of Improvements to Modified Oligomeric Compounds by Estimated $ED_{50}$ Legend:
- ASO1
- C16 - ASO1
- C16 - ASO2
- C16 - DUPchem1
- C16 - DUPchem2
- BCY - DUPchem1
- BCY - DUPchem2

SEQUENCE LISTING

```
Sequence total quantity: 1305
SEQ ID NO: 1           moltype = RNA  length = 3021
FEATURE                Location/Qualifiers
source                 1..3021
                       mol_type = mRNA
                       organism = Homo sapiens
SEQUENCE: 1
acttttctc ctccacctac tgcaactgtt cccataaact gggtgacaga gtcagaaaac   60
tccccagcta aacacccgta agacttcata caacacaata ctctatactg tgatgatcac   120
agctgccaag gctacctaaa agaagacagt tatctcatat ttggctgcca gcttttatc   180
tttctctcga ccacttaaaa cttcagactt cctgtcctgc tggtatcatg gagaaagtcc   240
aatacctcac tcgctcagct ataagaagag cctcaaccat tgaaatgcct caacaagcac   300
gtcaaaagct acagaatcta tttatcaatt tctgtctcat cttaatatgt ctcttgctga   360
tctgtatcat cgtgatgctt ctctgaagtt ctgctacaac ctctagatct gcagcttgcc   420
acatcagctt aaaatctgtc atcccatgca gacaggaaaa caatattgta taacagacca   480
cttcctgagt agaagagttt ctttgtgaaa aggtcaagat taagactaaa acttattgtt   540
accatatgta ttcatctgtt ggatcttgta aacatgaaaa gggctttatt ttcaaaaatt   600
aacttcaaaa taagtgtata aaatgcaact gttgatttcc tcaacatggc tcacaaattt   660
ctatcccaaa tcttttctga agatgaagag tttagtttta aaactgcact gccaacaagt   720
tcacttcata tataaagcat tattttract cttttgaggt gaatataatt tatattacaa   780
tgtaaaagct tctttaatac taagtatttt tcaggtcttc accaagtatc aaagtaataa   840
cacaaatgaa gtgtcattat tcaaaatagt ccactgactc ctcacatctg ttatcttatt   900
ataaagaact atttgtagta actatcagaa tctacattct aaaacagaaa ttgtattttt   960
tctatgccac attaacatct tttaaagttg atgagaatca agtatggaaa agtaaggcca   1020
tactcttaca taataaaatt cctttaagt aattttttca aagaatcaca gaattctagt   1080
acatgtaggt aaatcataaa tctgttctaa gacatatgat caacagatga gaactggtgg   1140
ttaatatgtg acagtgagat tagtcatatc actaatatac taacaacaga atctaatctt   1200
catttaaggc actgtagtga attatctgag ctagagttac ctagcttacc atactatatc   1260
tttggaatca tgaaacctta agacttcaga atgattttgc aggttgtctt ccattccagc   1320
ctaacatcca atgcaggcaa ggaaaataaa agatttccag tgacagaaaa atatattatc   1380
```

```
tcaagtattt tttaaaaata tatgaattct ctctccaaat attaactaat tattagatta 1440
tattttgaaa tgaacttgtt ggcccatcta ttacatctac agctgaccct tgaacatggg 1500
ggttagggga gctgacaatt cgtgggtccg caaaatctta actacctaat agcctactat 1560
tgaccataaa ccttactgat aacataaaca gtaaattaac acatattttg cgtgttatat 1620
gtattataca ctatattcct acaataaagt aagctagaga aaatgttatt tagaaaatca 1680
taagaaagag aaaatatatt tactattcat taaatggaag tgggtcaaca taaaagtctt 1740
cattctcatt gtcttcacat tgagtaggca gaggaggaga aagatgggga ggaagagaag 1800
gcgttggtct tgcagtcttg tcttaggggt gtggggagtg ggggaaagaa tattcatgta 1860
taagtggacc cttgcaattc aagcccttgt tgttcaaggg tcaactgtaa taggatatag 1920
ctatttttct tcctctatca accaaatggt aagcatctat tttgcagtcc actctactga 1980
gctaaattat agatccagct atgctattta taattatttt cttgatgaat aaattttcaa 2040
tttctcctct gaccatttca gaacatcttc caataactca taaaacaact gaagtaaaat 2100
tgagtgctgg aaaatatatt caccaaactt tggtaattta agttgactaa agtttaaaat 2160
taagtctaaa atagtttaca cctatactgc ataatccaac aattttaatt tcagttgaag 2220
acatgttact aatataacta ttattaaaag agtagaggat gtgtaattaa ccatatcttc 2280
taaaacatgg ttactaaaag aatatgtaac atcaatattg accttggttt cttacacaag 2340
tgttgctaac tcaatagtga aggagacact attaaatttt ctgaacccat gagagatact 2400
agagatgggg agtggaaagt gtttggttca gggatatctg aagaacagaa gggcagagat 2460
ttcttaagtg acgcctcatc tacaagctgg aaattcctaa aaacaagtag aaagcttata 2520
aacaacaggt gatacactca cctcactggt tttagtaaat taccaataca gaaagtatcc 2580
ctagtcttaa aaacaagtgg aaaatttgaa ctgattagtc atattccttt gattacactg 2640
tttgttacaa tattttttctc agtaaacaga aataactaat tttttttgttc ttcattcttt 2700
gatagaaatt aaaatcttat tctgtgagga ttacagaata ctataactca aattatataag 2760
tagaataaac tctttaaaata attattcttc atcataaagt gtaaagaata agatataaga 2820
aaacaattta tttttaaaat ttaatatact aaatgctcaa atatgttcta ctatagaata 2880
agttcttatc ttaatttaca gggcactaaa aacaatttta aaatgcttaa tgttgccttt 2940
tatattttaa ttggttaaga atatatattt gtttaatgca aatcagaatc actatattaa 3000
aatgaatgtt cttgaaaact c 3021
```

```
SEQ ID NO: 2          moltype = DNA  length = 20000
FEATURE               Location/Qualifiers
source                1..20000
                      mol_type = genomic DNA
                      organism = Homo sapiens
SEQUENCE: 2
gataggtaaa atcttcttcc tgggtgtcta ggagatctaa tctaaaaaaa gctccttatc 60
tttgatgtat tgtgaacatt acaaaaattg attcaaagct tgcattttac tgtatctctg 120
tctaaatatt aaaatgcttt aatttagtca tcacttatat taacttctgg tcaaaaattt 180
ccaaaaaccg attctatttt gaagcttctt cgccctccgg atacaccact acagactgga 240
gtttaaatgc tcaatgtaaa agattactac atacatcaca gtgcccttca caaaacgtta 300
gtaatatagc tgggcgcggt ggctcacgcc tgtaatccca gcactttggg aggccgaggt 360
gggcagatca cgaggtcagg agtttgagac cagcctgggc aatatggtga aacccccatct 420
ctactaaaaa tacaaaagtt agctgggcgt ggtggcacac gcctgtagtc tcagctactt 480
gggaggctga ggcaggagaa tcgcttgaac ccgagaggga gaggttgcag tgagctgaga 540
tcgcaccatt cactcggggc tgagtaacag agtgagactc cgcacccccct tccaaaaaaa 600
attagtaata cttttgagga acacatttaa aatgctacaa aactatataa aaacaaaagt 660
aaagacatga actcatgatt cagttgaaac tgaatactaa atttcattta gagcttagta 720
aaaataaatt tgtaattatt ttcccatcca agttcaaaga cacttacccc ttaagaatcc 780
accttctaaa ggaaaaaaga aaataagtgc taacactaaa tgaacactgt tgcaggatct 840
ctgataatca ctatgtacac ttcatgtcat taaaccatca caaatactat tccacagatt 900
aggctgctta ggaaagttat ttgtataaag ccatgtgacc aaaaatacat tcaaactata 960
gtgtaactcc aaaatgaagac tgtgacaaag cacctcaaaa aaattttcta gcctctagct 1020
gaggaatcat tgaggaacac tctactgata acactataac tcattaatac tcctattaaa 1080
caactttctg tttgggcaat taaaaacaat gttcagttaa aactaaaatc taatacttcc 1140
tagagttcca catgagatca tcaccatcat cgtcatcttc actagctaac ccaaaggaac 1200
aaggtaaaca caaaaactcc ccactcttgt accaatctaa aaagtaaatt tttgaatcca 1260
ttttccaact gtgtcacaca cagttgttag tatccttcta aggtgtgtat atgcctatgt 1320
atactttta agtaaactta taaacatgtg gtaactaggg catatttat tctgtctacg 1380
gcagcttctt ggtttatcca actaagtatt actaattcta tttcttaga atgagaagtt 1440
ctcagaacaa tgatctatca cctaaatttc aaatgaatgt gtaactggta gacaaactta 1500
aagcagactt tctaaaacta ttaacagtgc tcaagaatgc atctatttac atcttaaaaa 1560
tttctcagtt actatatgct actctaatga aagctatatt caaattataa ttttttccca 1620
cagcatgcca acagattagg aattataaac agacagatct ggatttgaat cctgtctatt 1680
ctttagcagc tggttatctc tgacaaatta ctgtaaacct cgttaggctt ctcggttttg 1740
tattatcaat catcattggt aactgatagt actgagagat cctcattatg taaggattga 1800
aagaaaaatg gttgtagcac tgagaaaagt atcaaacatt attctgcaat ttccttaact 1860
tgggttttac ttttaagttg taaattttcc cttggcaatg ttcacaggat atctttgcta 1920
aaatattatt tttcagttag ttttaagctg actctttaaa tatcaaatga tttgctctag 1980
agatggattt tctttctttg gaagaagcca agatcatttc catttaaggg catgtaagca 2040
gctgctgcta cacattttag ttacccataa gaaagtgaag tgggctaagt tcactctgtc 2100
ataagcattt aaaaaattaa aaattacaag tacctcctct aaaattaaag aagagattta 2160
agaattaata ttttcgagtg tggtgactta agtaaatcta acatctaaga caacaaatta 2220
gataaacaga gaagaggaga atgatgcccg gctttacaaa aaaattattt ccccagttct 2280
actgtaagat aaactgttct aggaagttca aaatatcatc tcacttacta gcatctcatt 2340
tttatagtaa ttttcaggaa agcaactgct agattaaatg aggcacatcc tttcaaaaac 2400
attacaaaac ttaaatttca acacatcaaa cctataaagc ctcattaact gagatgtaac 2460
tgatttggaa tctgtaatta tttctttttt gccataaagt tgcccttaat actgcatcag 2520
tttattaaaa atttggtaag attgtgtaat aatttaatgc aattgttttt aaaaaatctt 2580
aaatacttaa agtagcatat tgctattttg ggggtgttgt atgtatcagt ttaaatataa 2640
```

-continued

```
gtattactat tcacaaatat attgttaaac tgctaattga agaaaacaca aatgaattaa  2700
atacatttat tagttctta actgtaagat aaaaataatt ttttaaaaca aaaagcaatt  2760
agcctgattt tctcatactc cttctcccat acacacaaga acaagaacaa aataagaaaa  2820
caggtataaa attttattgt gtaaaaatat ttcactttca ctaaaagcta acattatgaa  2880
gacacgtatt aaagcaacag cagcaagaat tcaatgaaga ttgttttgct tatacctgtg  2940
tttatttttc tcataattaa aattcctgca gtaactattt tagctcttca acatcttcac  3000
cattaatatt caattatctc taagcctgaa gatgcatgaa tctttaacaa aagctttcca  3060
ccacctcaag tttacttatt tttttcattt atctaccata tactgtttta aattaaaaac  3120
aaaagatgaa gcacaaagtg ttaatgactt ttccatacct aaagtaagaa gttctaaagt  3180
ttggttgtga taagactgag actgtggcta accaatcgaa acttcagaat tcctatgtga  3240
catcataaga cctccctaga acacttttc tcctccacct actgcaactg ttcccataaa  3300
ctgggtgaca gagtcagaaa actccccagc taaacacccg taagacttca tacaacacaa  3360
tactctatac tgtgatgatc acagctgcca aggtaagaaa cagatttcgc tgactttggt  3420
aattcttact ttctataatt cttaattcct ataatttcta taatctgaac ttttaaaatg  3480
agttaatttt atgaatatca gttcaatctt aggcaataaa atgacatgac aaagtgctta  3540
aatttataaa tgcttatcca tttagtgaca ggaaaaatga gacaactttg aaatgaaaaa  3600
ggtcatattc atctttgatc ctggttactg gtttgtcatt taaatttatc tttcactttt  3660
attttgcttt tcaaatgtga atttctgcca attaaaaaat cttccaatta tgttaccata  3720
tttggtagta gtggttaatt tctccatgca aaaacaatga cttaattttg ttatttattg  3780
ctctgctgag aaacagtgca gaactgagct atttacatct gaactaatat gaatagtcat  3840
ttgactacaa catgcacatt atcagcatgc ctattccaat attatcataa tttcatacag  3900
tgaataatga aatggagttt cagaaatatat aatacaagct acttttaaag tgcccttgag  3960
gatgtttccc ctctaaagtc cagtcaactt ttaacaaaca tttctaaaaa aattccatgc  4020
tattaataaa ttgagttact gatattaaat tcaatattgt atcataaaga agtttagaaa  4080
ttttaaaaca atgttcacaa acacaaaaaa tctgacgtta gagaataatt tgatacttta  4140
aaaagttatt ttgacacacg aatattctta actatcttat tttcacacaa atttgattaa  4200
atggatttct gcctattaat gcctatagtt ttgtcaagtt attatcctcc agtggtactc  4260
catttcctct ctcggattta gaaagaaagg aaaaaataaa ataaatgcca ggaatggaga  4320
tgccacaatc aattttatga cttctgtttg aattctaccc tattctttat gttacaatcc  4380
tcaatttagt aaatgaaacg tttcctcatt cttagatctc tgtcagggca tacagaaaat  4440
tacatatatt ttatttattt tgattttcat atttcatata tatgttaaaa taaaatttat  4500
ctctaaaatt ctcaattcct atgacaaatg ttaattctat tgctcactac aaataagaac  4560
tttgtaactc tgtaagcagc tttccttaag acataaaaaa acataatttt tgtctaccac  4620
tgaggtatcc taattgtgtc tccatatctc tatactcata tttttccttt gatagtacat  4680
aaaagtcatt cagtgtaggt gtcttatgtt atttgtgcat ttttattcaa atatctatca  4740
aattacattc tcacacttca aattgggtgt tcacgagtta ttttattgta tcagaatttt  4800
gctatatcac atattactct aaaaagtaca catacttctg gatagagcag aaattatatt  4860
aaacttaccc ttagctcact agtatgtctc agttaacaga aattacagtt acagagactg  4920
ctaaaatttc aaatataatg tggtagtacc atacattgtg tcccaactag ttcatctata  4980
ccttaaggtg caagttaagt attatctttg tttatgaaga catgtggttt caaagtaagt  5040
gctaaaaaaa gtgttagatg aaatcaaatg gaaaaaatat gaaagatgtt taaattaaga  5100
agcattaagt tttaaaaacg catgaaagag ccagagtact tgctttacta aaaggcgtga  5160
cagcactatc atttcctaaa actcaaatat caaatccatt ttatttgtat tttagtaggc  5220
ataaaggaaa atgatcacat ttgggtatat aatcatatct ttaattagtg agattaagaa  5280
ataataaaat attgcataaa tacaatagtt tcagaaaatt ttaatgtatt ttaatgtttt  5340
aatgtactca ttacacatgt acactaaatt atgtaatata ttaaatttt aattaaaaaa  5400
cctaaagtct agttacctct ccaaattaga caatatatta ccaatcccag aaatgaggag  5460
ggccaatgaa cacttctttt ttattcttaa agagcaattt cctaatatac tcgtgtacac  5520
aaatatttca tttggtcctc ttaattatat atttgatact gcatccctat tctacaattt  5580
aggaaagatg caaaaaggtg aactgctcaa gatcacagaa ctaagaaaac agggaaacct  5640
tggcagaagt ttaggttttg tcactaagcc acatgcacat cctctatata ctgatcagca  5700
tggcttaaag taaaccatga cactgacaaa caaaatttga aagcccccaa atactgtaaa  5760
tgatattcta aaaggcaaaa ggcaaattca gagaatacaa acttctattt taattaaaag  5820
ccattccact ccatttaaat tcaatttatg catagcatta cattcttaat agtctaaatt  5880
atattctact gatcattttc aaaaccagaa atatacgaaa attacagatg cccttagtta  5940
ttaagcaata cctcctggaa ggcaaaattc aaactaactg cacagacttt aaaaaaaata  6000
acacacccca atcaatcaaa gtttcctttt atttgtttca ttgctaaaat actcatgcct  6060
tcaattcatc tgatacctaa aatccaagtt aacatctcct caaaactttc acaaaaatca  6120
catttcgata ctttattcta ggttccctag aatcaagtag tctctttgta caatttcaaa  6180
gttcttaccc agagtaattc tgaagcatgt gttaccaaat aaacacatga aaatgaagcc  6240
tggatgtaca gcatactcat agtcaactga ggacctctag tgcctttgaa aaggtactcc  6300
atctttagtt ttcaaccccc aaccccgca caaaaaaaa ggttgactaa ctcactcaca  6360
ttaatagggg gtatatttat taagtggcat tcattttaaa tccttaagac tttctcaata  6420
ctacctcccc atattctctt cccccagaaa agattctgaa ttccaactc ctacagggtt  6480
aagaagaata ttttacttgt aaatacactt gtaaagcatt gtttcaatat ttaaaaaaca  6540
ataatgaagg caaacctaca gacaatatag caacagcaat aagctaaatt gtcagtttta  6600
gagagaaaaa tatctctgtg ctgttgttta atgaattctc ctcaagacag agctttaaca  6660
tgagaagcac ttcattatgg gtcaatttag gaatgagaat atattgattt ttatgcatat  6720
acaattattt tcataaccag acagaagcag cttgaagatt cttcaaaca gccagtctgg  6780
accaacaaag ctctggaatg ttgctaccac aaagtaactt caaatagaat gtccaagttt  6840
agtattaggc aatctcaaaa ggaaaatgac tccactggag tgaactttg taagccaaca  6900
gattcatcgt aaatcaatg atgaactgtc ctaatttatt accacaagtc caaaaaaggg  6960
tatatgcaca ttcacttatg gcttatcagt ggaaatgtca gaaagtagta gaaaaataaa  7020
attccaaaca atccaaatat agacaagtcc tgtttatcaa atctataaga aattctaatc  7080
ttctaaacca attagatgga aaaaacatcc tagagtatat cagactgtag ccttagatat  7140
tacttgaatt caatttaata aagtatttct tcagtactcc catgtttact aaaagaataa  7200
acaaaattaa aaggagaaaa gcaaaattct aaattctaca aacataaaga atcccaggaa  7260
tttattattt cagcaaaagg aataccacca aaaaactga agtttgagaa gttctgcaag  7320
aagtgaacat acttaaagta tagatggaga ttaatgctca gcatatacaa catcattaaa  7380
```

-continued

```
gtatcaattg tctagcaagt cataaagcag gccaccaaaa gttttcagaa gactattgag  7440
gttccttccg cacaagaatg catctgtatat tacattgcta aaacaggact cactgcagac  7500
aaagtaagga ctcctgaagg agttgatata tagtagcttc caccaaacat gttgcctaac  7560
atggtatatg acattagtca aaagattaga gttgcctaat ggcttttcta tttccttctt  7620
ccacctcaaa aaaaaaacca gaataccatc ttgaacttga tttttttttt aatttccagc  7680
gttacttttc ttgaggaaag gacgacaacc aaaggattta taaatcccac aaagaatagt  7740
aaagaattct ttatttttat tcttctcatt cccctaaaaa gtagagtaat catggatcca  7800
cagacataag atactctgtg gatactttcc tgcctctgac atgtaactca agagacagga  7860
gtctggcatt tctacaccca aactcctaac aagcaccttt catgttttca atactcttga  7920
ttctagggcc tagaagacaa tttgatttta aaattcatct ataaatgaat accactcttg  7980
tgtcaaaaca accaatttat atatattgtc attcttttaa taaaagggtg gagagcagct  8040
tcagtttcca tggttgttta ggccatatac aagttcagaa aatcccaaaa ctatttatga  8100
ttagactaac agaatgctct aaaaagatca gataacatga aaataaaact aaactatttt  8160
tgtatgcttt ccatcgaaaa agtactctat taaacagctt agctgttaag aaattaaaaa  8220
aaaaaaaaaa aaggaaactc atacagtggt tgtcagtgca gagaagagaa tgataaacat  8280
ctgacaacca tgccataaat tataatgtag taaaggtcac agacaactcc aaaaatagga  8340
ttctgctgtt cccacaacaa aggttttcaa ttctcaatgt atgacaggaa gccccatctt  8400
ctatggataa aatctggcct aattatcatc atacaaatgt tggtattcag tagaactagg  8460
attccacaca tttcagatga taactgtaaa aaattgagcc caataaatta aatgtatatc  8520
attaacattt tagcgtgtaa agcagattta agtttaggca taaaatcata aagtagttac  8580
aaataacttt aggattatgg catatttcta aatctgacaa gaaacaggat actattttg  8640
gtcatctcct ttacacccaa tttgtttcca gaaacaaact cttctttttc aataacagtt  8700
agctgttgta ggattataag atcatctttta aagtatgtta actatgcttt aaacagtaaa  8760
gagctcatct ctttagggca tatctctgta tttcacaaat actaaaaacc catttataca  8820
aagcctagtt caggttaata ctgtgttaat caggtaacca ttaatttagg tgaatcctct  8880
aagcctcatt tttctcacct gtgatagaaa gagacttgag gaaaatatta gagcttacat  8940
gtccaactaa caaattgtta ttagaactag ttaatctgtc aatcacagca ttatttttaa  9000
aattgtttaa cttattatta aaaatgaggg ccaggcatgg tcattcacac ttgtaatccc  9060
aggaattacc tgagctcagg agtttgagac cagcctgtgc agcacagtga aaccctgtcc  9120
ctaccaaaaa tacaaaaatt agccaggcat ggtggcgcac acctgtggtc tcagctactc  9180
aggaggctga ggcagggaga tcgctagagc ctgggaagtt gaggtgcagt gagccacgat  9240
tgcacaactg cactccagcc tgggtgacag agcaagaccc tgtcagtcat tcattcatcc  9300
attcataaaa acaattaatt aattaaaaat gagatggggt ctcattatgt tgcccaagct  9360
ggtctcgaac tcctgggctc aaacattcgt cccgcctagg ccttccaaag tgttggaatt  9420
atagatgtga gccaccatgc cctgcccaca gcattatttt taattaacaa ttttctaata  9480
gttttagtca taaaaatccc ttatttaact ttagtgattt attgaagcat accaattatg  9540
cactaagtac taggatacta aataaacaca cagtttcttt acttcagaaa ctatcagtct  9600
agctggggat acaaacatgt aaattgaaat tgtgctataa tctgacagat atcctcatat  9660
agataacact aaagccctat taaaaaccag tagaggtgac aaccaattcc accttaataa  9720
ctaatgaaag gtttcactag gaagtgatat ttaaactgaa ccttaagaat caactgaagc  9780
ttgcatggca gacaatcaaa aggtggagaa cacattccag gcagagatag aacaacatgt  9840
gcaaagaaca aaatcacaaa agggaatgga gtatttatgg aaaggtgaca tgtttcatgt  9900
gactgaagta caacttacca gtgtcaacgt aggggatgac tcctgtatat gcttcatgat  9960
aaactcctgg ccaactccct cctttcccat gttttgtctc aaaataattt ttaaaatttc  10020
tgacctttta agaccactta agcccaaaaa cctcacaaaa ccatatgttc aaaataggaat  10080
taccaagtct aattattatt cctttcttaa ctgtattctg ctacacatct tcataaaagg  10140
tgactactcg gccaggtgca gtggctcacg cctgcaatcc cagcactttg ggaggccgag  10200
gcgggtggat cacgaggtcg ggagatcgag accatcctgg ctaacatggt gaaaccccgt  10260
ctctactaaa aacacaaaaa aattaggcat ggtggcgggc acctgtagtc ccagctactc  10320
gggaggctaa ggcaggagaa tggcgtgaac ccgggaggtg gagcttgcag tgagccgaga  10380
tcgtgccact gcactccagc ctgggcaaca cagcaagact gtctcaaaaa aaaaaaaaa  10440
aagtgactac tcaaatataa ataaaatctt cccataattt tccaatccac tagatctaca  10500
ataagcaaat atcaacataa gcaaatatca acataagcaa cttaaaggat gaatctcaat  10560
aaagaacaaa agaaaatcta tttatatttt acctgaagaa ttcaaacaaa agtcattaaa  10620
tatatgtcaa gtttaagctg ctatgtccct tatttttaac ttttgttttta agtttggggg  10680
tatgtgtgaa ggtttgttac acaggtaaac acatgtcatg gggagcttgt tgtatgtatt  10740
acttcatcat cccgttatta agcccagtac ccaacagttt tctgctcctc tgcctcctcc  10800
catcctcccc gctcaagtag accccagcgt ctgttgtttc cttctttgtg ttcataagtt  10860
cttatcatct tgctcccacc tgtaagtgag aacctgtggt atttggtttt cttttcctat  10920
gttagtttgc tagggataat gacctccagc tccatccatg ttcccgcaaa agacatgata  10980
tcattctttt ttatggctgc atagtattgc atggtgtata tgtaccacat tttctttatc  11040
cagtctgtca ctgatgagca cttaggccgg ttcatgtctt tgctattgtg aatagtgctg  11100
caatgaatat tcatgggtgt atgtctttac ggcagaaaga tttacactcc tctggatata  11160
tacccagtaa tgggattgtt gggtcgaatg gtagttctgc ttttataagc tgctattttc  11220
taagtagaag tgttatagac aacctaaata acagcctta gccacctgtt tagacaatga  11280
agaatatatg ctagaaaaat acaggtagtt aataactctt taaggaaaga aaatttgata  11340
gaagttgagt gtttggaact ccttgctaca gaccaatatt atgaaggggg acagagtctc  11400
aagccaaaaa tgcccagtct actatataat tcagaatata atagacccaa gttgaacact  11460
acagaatcta aacaccataa accatatggt ttctttgcca aagtaaatgc cgggttctaa  11520
ctagtcatgc ctgatactta ccttcccctt tgccattctt tcagcacttc cttctgctcc  11580
cttcagcact ttcctctctc aggaatgggc taacaggttg agatgggctt ttatgggatg  11640
tataaaagga cttaggagaa aataaaatct gacacctggg gtaaggtagt aatatgttga  11700
ttaacaataa tatatcaaca aatgttaaca gtcactatgt ctggcagtta attactgact  11760
ttttttctcc gttttctt tttcttattt caaaattgac acataagtat actgattgaa  11820
aacaaaatgt ccccaagtgt taataacgat tatctctgga cagttaatac agttaatttt  11880
cagtctatat ataatttttc tgtaatgaca tgtaaattct tattttatta atcatcaaag  11940
tataggcccc acaggcagca atagcttgtg ggatctctga aagaaggcat gatggaaact  12000
actactatta agtagaagtc tgtaaatagg atatgtctgt ggtagtgaga taataataat  12060
tactatgtgt tccaagcttg acagtcttca gtacttaaca tcaaatctta ttaaaatgtt  12120
```

-continued

```
acttaagata acattctata aaactataaa atcataaaaa ggaataacaa tttgaatcta  12180
tattttggt aaaacacttc ccatttaaca ctattttatt ttagattaaa attaagatcc  12240
agggaacaat ttgttgtatg catttccttt ttatgagatt ggctctggag ctattaatac  12300
agtgactgat caaaccaatt acatctacag agtaacagat ttaaagaaac tatatgttag  12360
aactttacc caaaagaata acccaaaaca agctgtacct taaaccaaat acagcaggtc  12420
ctcaaataac atcatttcta tgtcattttg ttataacatt taagtatgtg tggggcttgc  12480
atattctccc cacatctgtg ggactctggt ttcctcccat atcccaaaac agtgcacatt  12540
aggttcactg gcatgtttaa gttgtcctgg gttgagtgtg agtgtgtaca tgagtgtatc  12600
ctgtgatgga gtggcctcct atccaaggtg ggttcctccc tccttgagct gctgggattg  12660
gctccagcca ccagcacccc aaaccagaat aagagggttg aaaaatgaat gaatggatga  12720
atacaaatta ttatcgaata aaaattggta aagtctacgg tgatcataca aatgcatgac  12780
aataaacgct atggcacaaa agcactcaga gatcccaccg tatttgaatt gttttttgatc  12840
tgcatggagc tggatgtgct cctgacaatt ttcatttctc aaacatgatt ccatgttttt  12900
aatagaccac cacaaccact gttactcact gattccacaa atactgggta attatctttg  12960
ttggcttttt tttttttttc ctgggacaga gtttttgctct gtcacccagg ctggagtaca  13020
gtggcatgat ctgggctcaa tgcaacccct gcctcctggg ctccagcgat cctcccaagt  13080
agctaggatt acaggcacat gccaccagcc tagctaattt ttatattttt agtagagaca  13140
gggtttcacc atgttggcca ggctggtctc aaactcctga cctcagggga actgcccgcc  13200
ttggcctccc aaagtgctgg gattacaggc atgagccact gcacctggcc tatctggttt  13260
ttattaatct ttcttaaatg tatacatagt tcatatttct ctcaacgttt aatattagaa  13320
gtgtttgggg tctttattga gaagtttggt gatgtttttg tgaccagaaa tatgctatag  13380
gaacttaact cttgtttaca tcaatcagcc tagggtaaaa atggtttttgt tatatgttgt  13440
tttgcgtaaa gtcatggttt ccaggaactt atggaagaca ctgaggatta ctccaatact  13500
tgtagtaaat ttgggagaaa aaggcaagga ctaaagttac tactcctaac acaaatgaga  13560
cggtcatggt gtgccccatc aaaaaaggag agaaagagag acagacacat agaaacacgt  13620
gcacatacac acacacacac acacacacac agagagagag agagagagag agagagagag  13680
agagagaggg agagagacta tagaaacatg atgttataaa taacaatagt gctgaggaag  13740
atgaattagt gtaaaattgt attttttgtt ctgaggatag gttacataga tgattctaat  13800
ccatttatta tttttacatt ccaggctacc taaaagaaga cagttatctc atatttggct  13860
gccagctttt tatctttctc tcgaccactt aaaacttcag acttcctgtc ctgctggtat  13920
catggagaaa gtccaatacc tcactcgctc agctataaga agagcctcaa ccattgaaat  13980
gcctcaacaa gcacgtcaaa agctacgaaa tctatttatc aatttctgtc tcatcttaat  14040
atgtctcttg ctgatctgta tcatcgtgat gcttctctga agttctgcta caacctctag  14100
atctgcagct tgccacatca gcttaaaatc tgtcatccca tgcagacagg aaaacaatat  14160
tgtataacag accacttcct gagtagaaga gtttctttgt gaaaaggtca agattaagac  14220
taaaacttat tgttaccata tgtattcatc tgttggatct tgtaaacatg aaaagggctt  14280
tattttcaaa aattaacttc aaaataagtg tataaaatgc aactgttgat ttcctcaaca  14340
tggctcacaa atttctatcc caaatctttt ctgaagatga agagtttagt tttaaaactg  14400
cactgccaac aagttcactt catatataaa gcattatttt tactcttttg aggtgaatat  14460
aatttatatt acaatgtaaa agcttcttta atactaagta ttttttcaggt cttcaccaag  14520
tatcaaagta ataacacaaa tgaagtgtca ttattcaaaa tagtccactg actcctcaca  14580
tctgttatct tattataaag aactatttgt agtaactatc agaatctaca ttctaaaaca  14640
gaaattgtat tttttctatg ccacattaac atcttttaaa gttgatgaga atcaagtatg  14700
gaaaagtaag gccatactct tacataataa aattccttttt aagtaatttt ttcaaagaat  14760
cacagaattc tagtacatgt aggtaaatca taaatctgtt ctaagacata tgatcaacag  14820
atgagaactg gtggttaata tgtgacagtg agattagtca tatcactaat atactaacaa  14880
cagaatctaa tcttcattta aggcactgta gtgaattatc tgagctagag ttacctagct  14940
taccatacta tatctcttgga atcatgaaac cttaagactt cagaatgatt ttgcaggttg  15000
tcttccattc cagcctaaca tccaatgcag gcaaggaaaa taaaagattt ccagtgacag  15060
aaaaatatat tatctcaagt atttttttaaa aatatatgaa ttctctctcc aaatattaac  15120
taattattag attatatttt gaaatgaact tgttggccca tctattacat ctacagctga  15180
cccttgaaca tgggggttag gggagctgac aattcgtggg tccgcaaaat cttaactacc  15240
taatagccta ctattgacca taaaccttac tgataacata aacagtaaat taacacatat  15300
tttgcgtgtt atatgtatta tacactatat tcctacaata aagtaagcta gagaaaatgt  15360
tatttagaaa atcataagaa agagaaaata tatttactat tcattaaatg gaagtgggtc  15420
aacataaaag tcttcattct cattgtcttc acattgagta ggcagaggag gagaaagatg  15480
gggaggaaga gaaggcgttg gtcttgcagt cttgtcttag gggtgtgggg agtgggggaa  15540
agaatattca tgtataagtg gacccttgca attcaagccc ttgttgttca agggtcaact  15600
gtaataggat atagctattt ttcttcctct atcaaccaaa tggtaagcat ctattttgca  15660
gtccactcta ctgagctaaa ttatagatcc agctatgcta tttataatta ttttcttgat  15720
gaataaattt tcaatttctc ctctgaccat ttcagaacat cttccaataa ctcataaaac  15780
aactgaagta aaattgagtg ctggaaaata tattcaccaa actttggtaa tttaagttga  15840
ctaaagttta aaattaagtc taaaatagtt tacacctata ctgcataatc caacaatttt  15900
aatttcagtt gaagacatgt tactaatata actattatta aaagagtaga ggatgtgtaa  15960
ttaaccatat cttctaaaac atggttacta aaagaatatg taacatcaat attgaccttg  16020
gtttcttaca caagtgttgc taactcaata gtgaaggaga cactattaaa tttttctgaac  16080
ccatgagaga tactagagat ggggagtgga aagtgtttgg ttcagggata tctgaagaac  16140
agaagggcag agatttctta agtgacgcct catctacaag ctggaaattc ctaaaaacaa  16200
gtagaaagct tataaacaac aggtgataca ctcacctcac tggtttttagt aaattaccaa  16260
tacagaaagt atccctagtc ttaaaaacaa gtggaaaatt tgaactgatt agtcatattc  16320
ctttgattac actgtttgtt acaatatttt tctcagtaaa cagaaataac taatttttttt  16380
gttcttcatt ctttgataga aattaaaatc ttattctgtg aggattacag aatactataa  16440
ctcaaattat aaagtagaat aaactctta aataattatt cttcatcata aagtgtaaag  16500
aataagatat aagaaaacaa tttattttta aaatttaata tactaaatgc tcaaatatgt  16560
tctactatag aataagttct tatcttaatt tacagggcac taaaaacaat tttaaaatgc  16620
ttaatgttgc ctttttatatt ttaattggtt aagaatatat atttgtttaa tgcaaatcag  16680
aatcactata ttaaaatgaa tgttcttgaa aactcagtgg ggctgctcta taatacactt  16740
acaattgata ctaacgataa aacgctctaa ttatagtttt aattttatag gggttttttt  16800
ggtgactttc cccaaataaa acaaaatcaa gacgcccaag tccagacaca caagagggca  16860
```

```
gacgtatata agataacaaa ttgctactac atagcgatta tttatctttt gattattttt  16920
gagacttctg gcaaagtagg actataataa attttcagaa aagatctgct cttctgctaa  16980
gtaacagcac acttcaaaat gtccagaaat tttatgctaa tattacatag aaaacttgac  17040
agatgaaaaa agtgaaacac attactaatt ttattcatta aaacaggtat ataaaagtcc  17100
tctttaacta cctaatgaat gtgtcatatc ctaatatagg gagtgtcata gtgttcacat  17160
ctttgaatat ataaattatc tcaaacagtt aaaaaattaa agccagaaca gggtacaaaa  17220
ataagaataa aaataagaaa actttctgtt cacaggacgt aacagaatac tttaaacact  17280
ctcaagttat aaataaaact ttttcattat tatttcatgt tagacaaaaa acaagtcatt  17340
ttactttaac tcattttatc aatttttttt ttttaaatca agagacaggg tgttactctg  17400
tcatgcaggc tggaatgcag tcacatgatc attgcacact gcagccttga actcttgggg  17460
tgcaaaggat tctccaacct tggttcccaa gtagctggca ctacaggggc acatcaccat  17520
atatggctaa ttcttttttat tttttgtaga gatggggtct cattgcccag gctggtccca  17580
aactcctatc ctcaagctat ccacccccca tcagcctccc aaagtgttgg gattacaggg  17640
gtgagctacc atgcttggtc caattttttt gtttatacaa gggaaaatct ccagtaaaat  17700
atgtataggt gccaatacca taactgttca aacaccctta tgactaaata ggcacaaaat  17760
ttcatctttt taatgactgc cacctgaagt tcagaaacat cctagggaaa aaaggataaa  17820
caacttcatc aataaagagg ctactattat ttcactactg tctgggagat ccatcgtggg  17880
cttacaggaa tccaaatgga tactgccgtt acgtgtagaa gtgtttatcc tccatccctt  17940
ccaccctacc ttccccaaga aaaggaactc aaggggggcca tggaaaggga aggagtcttc  18000
ccaaaaagac cagactgttt ttcctcctct gtcatagtcc ctatagagtc aggcagctta  18060
ggggttgcag ggggtgggta gcataagtgt gatgtactac cgaggaaaga gtcaaagact  18120
agcagtaggc attacacatg gagccttctg tcataaacca tctgagggca taatggcttc  18180
ttttcattca caaaggaaaa tgattcagag tactacactc ctgcactctt gatgatttag  18240
cagaaaacca tggaaatcaa ggaacaacac acacataaga atgtgtgtct ggctcaataa  18300
ttattctgga ctaagtccta ggaagagcaa accttcaatg ttacaaatta acctggggag  18360
tggggagctg tgagaatcaa atgagataaa atactgtgaa agctacagaa ttctataaca  18420
tataaatcta aggtttttatt agattatgac tttcagccaa attccttttc ttagttgtaa  18480
aaatattgtt ttttcatggt gagtgtttag gagttgtgct tgcaaatcac aatttatcag  18540
acggcctggt ccttattaag gttcttctct ttatgtaaaa attagactaa aagaaaatca  18600
gtgtttctat gatttttatc tttttttcctt tttagagacg gggtctggcc atgttgccca  18660
ggctagtctc aaactcctgg actcaggcaa ttctcctgcc cttggcctccc aaattgctag  18720
gattacaggc gtgcgctaca gtgcctggcc agaagtcaat gtttcaaaga ggctttttaag  18780
aaacaactat gatgaaagct tttaaaataa agataatact acttggaggc tccaagaagg  18840
tatttaacaa cttttttctg tagttttcta aggaggaaat tgaaagggaa gcagtcattt  18900
aatgattaca acttagtttg tctagttttc tttacctgaa ttcatctttc tactccaaaa  18960
cttaaaagcg ctataaagag accatcccaa ataaagttaa tcaagaagta gggctttcca  19020
gggtatatgc aaattttgct ctttagttgc cttctctctc tactatgcac tagaaagaag  19080
atttaaaaac aaatttatct caacagtgtg tccccaacct ccctaccctc ctctgcattg  19140
ctttgaggct aagaaaaaca ccttgtttaa accagagatt tgtccaagca gaataaaaag  19200
catgaatcag tatttactcc ttgaaatttg cccaattatc tctatcacac ctactctagt  19260
ttggaatagc atactcagcc ccactggaca gctccaattc tgtgtaaaga caccagctgg  19320
agaaacaact gcctggatct ctgttttcct ataatgacaa acatttgaaa actaaaactt  19380
gacagtattt gaaaaattag gtttcctatt tttcatcact tgaatggata aatcacaaat  19440
ttctaattca atcataatga ttcttctgtt ttgattgtgt tgtttaaata cataatcaaa  19500
attataagaa ctgtatctaa aataagaata aaggtacatg cgacatgtta agggttctcc  19560
tatgaatgta gtatgttagg gttctatgtt ttgagatcat actcatattt gtgaggttcc  19620
tggacaagtg atttccttat cctttcatag cctatgttca tttattctat ttgtttttat  19680
tagtagtagt aatgaatacc aattttacat ttttactcta gggaaaattt gcaatttttt  19740
atagaattaa tttgtttcag aaaattctga tgataaaaaa cagatgacag gacttatatc  19800
agaaaattag tttccttgtt aaaacaagct acagaaaatt gtcttggaat agaaacattc  19860
ccagattaag aaatttacac atttacatgc tattccctag accaactggg ggctgtatac  19920
tatttttctt tatatatgat atcatcataa agcactttct ataagctgat taatgaatgc  19980
cttgacacat aatttttttt                                              20000
```

```
SEQ ID NO: 3            moltype = RNA  length = 23
FEATURE                 Location/Qualifiers
source                  1..23
                        mol_type = other RNA
                        organism = synthetic construct
SEQUENCE: 3
tcatcacagt atagagtatt gtg                                          23

SEQ ID NO: 4            moltype = RNA  length = 23
FEATURE                 Location/Qualifiers
source                  1..23
                        mol_type = other RNA
                        organism = synthetic construct
SEQUENCE: 4
ggtgtttagc tggggagttt tct                                          23

SEQ ID NO: 5            moltype = RNA  length = 23
FEATURE                 Location/Qualifiers
source                  1..23
                        mol_type = other RNA
                        organism = synthetic construct
SEQUENCE: 5
tctgactctg tcacccagtt tat                                          23

SEQ ID NO: 6            moltype = RNA  length = 23
```

-continued

```
FEATURE                 Location/Qualifiers
source                  1..23
                        mol_type = other RNA
                        organism = synthetic construct
SEQUENCE: 6
ggtagccttg gcagctgtga tca                                        23

SEQ ID NO: 7            moltype = RNA   length = 23
FEATURE                 Location/Qualifiers
source                  1..23
                        mol_type = other RNA
                        organism = synthetic construct
SEQUENCE: 7
gtgttgtatg aagtcttacg ggt                                        23

SEQ ID NO: 8            moltype = RNA   length = 23
FEATURE                 Location/Qualifiers
source                  1..23
                        mol_type = other RNA
                        organism = synthetic construct
SEQUENCE: 8
gagataactg tcttcttttta ggt                                       23

SEQ ID NO: 9            moltype = RNA   length = 23
FEATURE                 Location/Qualifiers
source                  1..23
                        mol_type = other RNA
                        organism = synthetic construct
SEQUENCE: 9
tttctccatg ataccagcag gac                                        23

SEQ ID NO: 10           moltype = RNA   length = 23
FEATURE                 Location/Qualifiers
source                  1..23
                        mol_type = other RNA
                        organism = synthetic construct
SEQUENCE: 10
aaaagctggc agccaaatat gag                                        23

SEQ ID NO: 11           moltype = RNA   length = 23
FEATURE                 Location/Qualifiers
source                  1..23
                        mol_type = other RNA
                        organism = synthetic construct
SEQUENCE: 11
aagtggtcga gagaaagata aaa                                        23

SEQ ID NO: 12           moltype = RNA   length = 23
FEATURE                 Location/Qualifiers
source                  1..23
                        mol_type = other RNA
                        organism = synthetic construct
SEQUENCE: 12
gacaggaagt ctgaagtttt aag                                        23

SEQ ID NO: 13           moltype = RNA   length = 23
FEATURE                 Location/Qualifiers
source                  1..23
                        mol_type = other RNA
                        organism = synthetic construct
SEQUENCE: 13
ttgaggctct tcttatagct gag                                        23

SEQ ID NO: 14           moltype = RNA   length = 23
FEATURE                 Location/Qualifiers
source                  1..23
                        mol_type = other RNA
                        organism = synthetic construct
SEQUENCE: 14
gagcgagtga ggtattggac ttt                                        23

SEQ ID NO: 15           moltype = RNA   length = 23
FEATURE                 Location/Qualifiers
source                  1..23
                        mol_type = other RNA
                        organism = synthetic construct
SEQUENCE: 15
ttgttgaggc atttcaatgg ttg                                        23
```

-continued

```
SEQ ID NO: 16          moltype = RNA   length = 23
FEATURE                Location/Qualifiers
source                 1..23
                       mol_type = other RNA
                       organism = synthetic construct
SEQUENCE: 16
ttctgtagct tttgacgtgc ttg                                              23

SEQ ID NO: 17          moltype = RNA   length = 23
FEATURE                Location/Qualifiers
source                 1..23
                       mol_type = other RNA
                       organism = synthetic construct
SEQUENCE: 17
tagcagaact tcagagaagc atc                                              23

SEQ ID NO: 18          moltype = RNA   length = 23
FEATURE                Location/Qualifiers
source                 1..23
                       mol_type = other RNA
                       organism = synthetic construct
SEQUENCE: 18
atcacgatga tacagatcag caa                                              23

SEQ ID NO: 19          moltype = RNA   length = 23
FEATURE                Location/Qualifiers
source                 1..23
                       mol_type = other RNA
                       organism = synthetic construct
SEQUENCE: 19
gacagaaatt gataaataga ttc                                              23

SEQ ID NO: 20          moltype = RNA   length = 23
FEATURE                Location/Qualifiers
source                 1..23
                       mol_type = other RNA
                       organism = synthetic construct
SEQUENCE: 20
caagagacat attaagatga gac                                              23

SEQ ID NO: 21          moltype = RNA   length = 23
FEATURE                Location/Qualifiers
source                 1..23
                       mol_type = other RNA
                       organism = synthetic construct
SEQUENCE: 21
agctgcagat ctagaggttg tag                                              23

SEQ ID NO: 22          moltype = RNA   length = 23
FEATURE                Location/Qualifiers
source                 1..23
                       mol_type = other RNA
                       organism = synthetic construct
SEQUENCE: 22
ctgttataca atattgtttt cct                                              23

SEQ ID NO: 23          moltype = RNA   length = 23
FEATURE                Location/Qualifiers
source                 1..23
                       mol_type = other RNA
                       organism = synthetic construct
SEQUENCE: 23
gattttaagc tgatgtggca agc                                              23

SEQ ID NO: 24          moltype = RNA   length = 23
FEATURE                Location/Qualifiers
source                 1..23
                       mol_type = other RNA
                       organism = synthetic construct
SEQUENCE: 24
cctgtctgca tgggatgaca gat                                              23

SEQ ID NO: 25          moltype = RNA   length = 23
FEATURE                Location/Qualifiers
source                 1..23
                       mol_type = other RNA
                       organism = synthetic construct
SEQUENCE: 25
tcttctactc aggaagtggt ctg                                              23
```

-continued

```
SEQ ID NO: 26            moltype = RNA   length = 23
FEATURE                  Location/Qualifiers
source                   1..23
                         mol_type = other RNA
                         organism = synthetic construct
SEQUENCE: 26
tgaccttttc acaaagaaac tct                                      23

SEQ ID NO: 27            moltype = RNA   length = 23
FEATURE                  Location/Qualifiers
source                   1..23
                         mol_type = other RNA
                         organism = synthetic construct
SEQUENCE: 27
atcaacagtt gcattttata cac                                      23

SEQ ID NO: 28            moltype = RNA   length = 23
FEATURE                  Location/Qualifiers
source                   1..23
                         mol_type = other RNA
                         organism = synthetic construct
SEQUENCE: 28
cacttatttt gaagttaatt ttt                                      23

SEQ ID NO: 29            moltype = RNA   length = 23
FEATURE                  Location/Qualifiers
source                   1..23
                         mol_type = other RNA
                         organism = synthetic construct
SEQUENCE: 29
ataagtttta gtcttaatct tga                                      23

SEQ ID NO: 30            moltype = RNA   length = 23
FEATURE                  Location/Qualifiers
source                   1..23
                         mol_type = other RNA
                         organism = synthetic construct
SEQUENCE: 30
catgtttaca agatccaaca gat                                      23

SEQ ID NO: 31            moltype = RNA   length = 23
FEATURE                  Location/Qualifiers
source                   1..23
                         mol_type = other RNA
                         organism = synthetic construct
SEQUENCE: 31
gatgaataca tatggtaaca ata                                      23

SEQ ID NO: 32            moltype = RNA   length = 23
FEATURE                  Location/Qualifiers
source                   1..23
                         mol_type = other RNA
                         organism = synthetic construct
SEQUENCE: 32
tttgaaaata aagccctttt cat                                      23

SEQ ID NO: 33            moltype = RNA   length = 23
FEATURE                  Location/Qualifiers
source                   1..23
                         mol_type = other RNA
                         organism = synthetic construct
SEQUENCE: 33
actaaactct tcatcttcag aaa                                      23

SEQ ID NO: 34            moltype = RNA   length = 23
FEATURE                  Location/Qualifiers
source                   1..23
                         mol_type = other RNA
                         organism = synthetic construct
SEQUENCE: 34
caaaagagta aaataatgc ttt                                       23

SEQ ID NO: 35            moltype = RNA   length = 23
FEATURE                  Location/Qualifiers
source                   1..23
                         mol_type = other RNA
                         organism = synthetic construct
SEQUENCE: 35
```

-continued

```
ttgtgagcca tgttgaggaa atc                                           23

SEQ ID NO: 36          moltype = RNA   length = 23
FEATURE                Location/Qualifiers
source                 1..23
                       mol_type = other RNA
                       organism = synthetic construct
SEQUENCE: 36
gttggcagtg cagttttaaa act                                           23

SEQ ID NO: 37          moltype = RNA   length = 23
FEATURE                Location/Qualifiers
source                 1..23
                       mol_type = other RNA
                       organism = synthetic construct
SEQUENCE: 37
tttatatatg aagtgaactt gtt                                           23

SEQ ID NO: 38          moltype = RNA   length = 23
FEATURE                Location/Qualifiers
source                 1..23
                       mol_type = other RNA
                       organism = synthetic construct
SEQUENCE: 38
aaaagatttg ggatagaaat ttg                                           23

SEQ ID NO: 39          moltype = RNA   length = 23
FEATURE                Location/Qualifiers
source                 1..23
                       mol_type = other RNA
                       organism = synthetic construct
SEQUENCE: 39
tactttgata cttggtgaag acc                                           23

SEQ ID NO: 40          moltype = RNA   length = 23
FEATURE                Location/Qualifiers
source                 1..23
                       mol_type = other RNA
                       organism = synthetic construct
SEQUENCE: 40
tgacacttca tttgtgttat tac                                           23

SEQ ID NO: 41          moltype = RNA   length = 23
FEATURE                Location/Qualifiers
source                 1..23
                       mol_type = other RNA
                       organism = synthetic construct
SEQUENCE: 41
aatataaatt atattcacct caa                                           23

SEQ ID NO: 42          moltype = RNA   length = 23
FEATURE                Location/Qualifiers
source                 1..23
                       mol_type = other RNA
                       organism = synthetic construct
SEQUENCE: 42
acctgaaaaa tacttagtat taa                                           23

SEQ ID NO: 43          moltype = RNA   length = 23
FEATURE                Location/Qualifiers
source                 1..23
                       mol_type = other RNA
                       organism = synthetic construct
SEQUENCE: 43
taaagaagct tttacattgt aat                                           23

SEQ ID NO: 44          moltype = RNA   length = 23
FEATURE                Location/Qualifiers
source                 1..23
                       mol_type = other RNA
                       organism = synthetic construct
SEQUENCE: 44
gttattactt tgatacttgg tga                                           23

SEQ ID NO: 45          moltype = RNA   length = 23
FEATURE                Location/Qualifiers
source                 1..23
                       mol_type = other RNA
                       organism = synthetic construct
```

-continued

```
SEQUENCE: 45
tgtagattct gatagttact aca                                               23

SEQ ID NO: 46             moltype = RNA   length = 23
FEATURE                   Location/Qualifiers
source                    1..23
                          mol_type = other RNA
                          organism = synthetic construct
SEQUENCE: 46
cagtggacta ttttgaataa tga                                               23

SEQ ID NO: 47             moltype = RNA   length = 23
FEATURE                   Location/Qualifiers
source                    1..23
                          mol_type = other RNA
                          organism = synthetic construct
SEQUENCE: 47
agataacaga tgtgaggagt cag                                               23

SEQ ID NO: 48             moltype = RNA   length = 23
FEATURE                   Location/Qualifiers
source                    1..23
                          mol_type = other RNA
                          organism = synthetic construct
SEQUENCE: 48
atacaatttc tgttttagaa tgt                                               23

SEQ ID NO: 49             moltype = RNA   length = 23
FEATURE                   Location/Qualifiers
source                    1..23
                          mol_type = other RNA
                          organism = synthetic construct
SEQUENCE: 49
acaaatagtt ctttataata aga                                               23

SEQ ID NO: 50             moltype = RNA   length = 23
FEATURE                   Location/Qualifiers
source                    1..23
                          mol_type = other RNA
                          organism = synthetic construct
SEQUENCE: 50
gttaatgtgg catagaaaaa ata                                               23

SEQ ID NO: 51             moltype = RNA   length = 23
FEATURE                   Location/Qualifiers
source                    1..23
                          mol_type = other RNA
                          organism = synthetic construct
SEQUENCE: 51
cttacttttc catacttgat tct                                               23

SEQ ID NO: 52             moltype = RNA   length = 23
FEATURE                   Location/Qualifiers
source                    1..23
                          mol_type = other RNA
                          organism = synthetic construct
SEQUENCE: 52
ttattatgta agagtatggc ctt                                               23

SEQ ID NO: 53             moltype = RNA   length = 23
FEATURE                   Location/Qualifiers
source                    1..23
                          mol_type = other RNA
                          organism = synthetic construct
SEQUENCE: 53
tctcatcaac tttaaaagat gtt                                               23

SEQ ID NO: 54             moltype = RNA   length = 23
FEATURE                   Location/Qualifiers
source                    1..23
                          mol_type = other RNA
                          organism = synthetic construct
SEQUENCE: 54
catacttgat tctcatcaac ttt                                               23

SEQ ID NO: 55             moltype = RNA   length = 23
FEATURE                   Location/Qualifiers
source                    1..23
                          mol_type = other RNA
```

-continued

```
                            organism = synthetic construct
SEQUENCE: 55
aaaattactt aaaaggaatt tta                                          23

SEQ ID NO: 56          moltype = RNA   length = 23
FEATURE                Location/Qualifiers
source                 1..23
                       mol_type = other RNA
                       organism = synthetic construct
SEQUENCE: 56
gaattctgtg attctttgaa aaa                                          23

SEQ ID NO: 57          moltype = RNA   length = 23
FEATURE                Location/Qualifiers
source                 1..23
                       mol_type = other RNA
                       organism = synthetic construct
SEQUENCE: 57
tatgtcttag aacagattta tga                                          23

SEQ ID NO: 58          moltype = RNA   length = 23
FEATURE                Location/Qualifiers
source                 1..23
                       mol_type = other RNA
                       organism = synthetic construct
SEQUENCE: 58
attagtgata tgactaatct cac                                          23

SEQ ID NO: 59          moltype = RNA   length = 23
FEATURE                Location/Qualifiers
source                 1..23
                       mol_type = other RNA
                       organism = synthetic construct
SEQUENCE: 59
cactgtcaca tattaaccac cag                                          23

SEQ ID NO: 60          moltype = RNA   length = 23
FEATURE                Location/Qualifiers
source                 1..23
                       mol_type = other RNA
                       organism = synthetic construct
SEQUENCE: 60
ttagattctg ttgttagtat att                                          23

SEQ ID NO: 61          moltype = RNA   length = 23
FEATURE                Location/Qualifiers
source                 1..23
                       mol_type = other RNA
                       organism = synthetic construct
SEQUENCE: 61
cagttctcat ctgttgatca tat                                          23

SEQ ID NO: 62          moltype = RNA   length = 23
FEATURE                Location/Qualifiers
source                 1..23
                       mol_type = other RNA
                       organism = synthetic construct
SEQUENCE: 62
tgatttacct acatgtacta gaa                                          23

SEQ ID NO: 63          moltype = RNA   length = 23
FEATURE                Location/Qualifiers
source                 1..23
                       mol_type = other RNA
                       organism = synthetic construct
SEQUENCE: 63
tagtatggta agctaggtaa ctc                                          23

SEQ ID NO: 64          moltype = RNA   length = 23
FEATURE                Location/Qualifiers
source                 1..23
                       mol_type = other RNA
                       organism = synthetic construct
SEQUENCE: 64
tacagtgcct taaatgaaga tta                                          23

SEQ ID NO: 65          moltype = RNA   length = 23
FEATURE                Location/Qualifiers
source                 1..23
```

-continued

```
                         mol_type = other RNA
                         organism = synthetic construct
SEQUENCE: 65
ctctagctca gataattcac tac                                                    23

SEQ ID NO: 66          moltype = RNA   length = 23
FEATURE                Location/Qualifiers
source                 1..23
                       mol_type = other RNA
                       organism = synthetic construct
SEQUENCE: 66
gatatagtat ggtaagctag gta                                                    23

SEQ ID NO: 67          moltype = RNA   length = 23
FEATURE                Location/Qualifiers
source                 1..23
                       mol_type = other RNA
                       organism = synthetic construct
SEQUENCE: 67
tgattccaaa gatatagtat ggt                                                    23

SEQ ID NO: 68          moltype = RNA   length = 23
FEATURE                Location/Qualifiers
source                 1..23
                       mol_type = other RNA
                       organism = synthetic construct
SEQUENCE: 68
ccaaagatat agtatggtaa gct                                                    23

SEQ ID NO: 69          moltype = RNA   length = 23
FEATURE                Location/Qualifiers
source                 1..23
                       mol_type = other RNA
                       organism = synthetic construct
SEQUENCE: 69
ctgcattgga tgttaggctg gaa                                                    23

SEQ ID NO: 70          moltype = RNA   length = 23
FEATURE                Location/Qualifiers
source                 1..23
                       mol_type = other RNA
                       organism = synthetic construct
SEQUENCE: 70
gtttcatgat tccaaagata tag                                                    23

SEQ ID NO: 71          moltype = RNA   length = 23
FEATURE                Location/Qualifiers
source                 1..23
                       mol_type = other RNA
                       organism = synthetic construct
SEQUENCE: 71
aaatctttta ttttccttgc ctg                                                    23

SEQ ID NO: 72          moltype = RNA   length = 23
FEATURE                Location/Qualifiers
source                 1..23
                       mol_type = other RNA
                       organism = synthetic construct
SEQUENCE: 72
gaatggaaga caacctgcaa aat                                                    23

SEQ ID NO: 73          moltype = RNA   length = 23
FEATURE                Location/Qualifiers
source                 1..23
                       mol_type = other RNA
                       organism = synthetic construct
SEQUENCE: 73
atatattttt ctgtcactgg aaa                                                    23

SEQ ID NO: 74          moltype = RNA   length = 23
FEATURE                Location/Qualifiers
source                 1..23
                       mol_type = other RNA
                       organism = synthetic construct
SEQUENCE: 74
aatcattctg aagtcttaag gtt                                                    23

SEQ ID NO: 75          moltype = RNA   length = 23
FEATURE                Location/Qualifiers
```

-continued

```
source                  1..23
                        mol_type = other RNA
                        organism = synthetic construct
SEQUENCE: 75
tttaaaaaat acttgagata ata                                           23

SEQ ID NO: 76           moltype = RNA   length = 23
FEATURE                 Location/Qualifiers
source                  1..23
                        mol_type = other RNA
                        organism = synthetic construct
SEQUENCE: 76
ctaataatta gttaatattt gga                                           23

SEQ ID NO: 77           moltype = RNA   length = 23
FEATURE                 Location/Qualifiers
source                  1..23
                        mol_type = other RNA
                        organism = synthetic construct
SEQUENCE: 77
ggagagagaa ttcatatatt ttt                                           23

SEQ ID NO: 78           moltype = RNA   length = 23
FEATURE                 Location/Qualifiers
source                  1..23
                        mol_type = other RNA
                        organism = synthetic construct
SEQUENCE: 78
atgtaataga tgggccaaca agt                                           23

SEQ ID NO: 79           moltype = RNA   length = 23
FEATURE                 Location/Qualifiers
source                  1..23
                        mol_type = other RNA
                        organism = synthetic construct
SEQUENCE: 79
tgttcaaggg tcagctgtag atg                                           23

SEQ ID NO: 80           moltype = RNA   length = 23
FEATURE                 Location/Qualifiers
source                  1..23
                        mol_type = other RNA
                        organism = synthetic construct
SEQUENCE: 80
agttcatttc aaaatataat cta                                           23

SEQ ID NO: 81           moltype = RNA   length = 23
FEATURE                 Location/Qualifiers
source                  1..23
                        mol_type = other RNA
                        organism = synthetic construct
SEQUENCE: 81
gtcagctccc ctaacccca tgt                                            23

SEQ ID NO: 82           moltype = RNA   length = 23
FEATURE                 Location/Qualifiers
source                  1..23
                        mol_type = other RNA
                        organism = synthetic construct
SEQUENCE: 82
tagttaagat tttgcggacc cac                                           23

SEQ ID NO: 83           moltype = RNA   length = 23
FEATURE                 Location/Qualifiers
source                  1..23
                        mol_type = other RNA
                        organism = synthetic construct
SEQUENCE: 83
atttactgtt tatgttatca gta                                           23

SEQ ID NO: 84           moltype = RNA   length = 23
FEATURE                 Location/Qualifiers
source                  1..23
                        mol_type = other RNA
                        organism = synthetic construct
SEQUENCE: 84
gtaaggttta tggtcaatag tag                                           23

SEQ ID NO: 85           moltype = RNA   length = 23
```

-continued

```
FEATURE             Location/Qualifiers
source              1..23
                    mol_type = other RNA
                    organism = synthetic construct
SEQUENCE: 85
taggctatta ggtagttaag att                                                    23

SEQ ID NO: 86       moltype = RNA   length = 23
FEATURE             Location/Qualifiers
source              1..23
                    mol_type = other RNA
                    organism = synthetic construct
SEQUENCE: 86
attttgcgga cccacgaatt gtc                                                     23

SEQ ID NO: 87       moltype = RNA   length = 23
FEATURE             Location/Qualifiers
source              1..23
                    mol_type = other RNA
                    organism = synthetic construct
SEQUENCE: 87
tattttctct ttcttatgat ttt                                                    23

SEQ ID NO: 88       moltype = RNA   length = 23
FEATURE             Location/Qualifiers
source              1..23
                    mol_type = other RNA
                    organism = synthetic construct
SEQUENCE: 88
tagcttactt tattgtagga ata                                                    23

SEQ ID NO: 89       moltype = RNA   length = 23
FEATURE             Location/Qualifiers
source              1..23
                    mol_type = other RNA
                    organism = synthetic construct
SEQUENCE: 89
catttaatga atagtaaata tat                                                    23

SEQ ID NO: 90       moltype = RNA   length = 23
FEATURE             Location/Qualifiers
source              1..23
                    mol_type = other RNA
                    organism = synthetic construct
SEQUENCE: 90
aacacgcaaa atatgtgtta att                                                    23

SEQ ID NO: 91       moltype = RNA   length = 23
FEATURE             Location/Qualifiers
source              1..23
                    mol_type = other RNA
                    organism = synthetic construct
SEQUENCE: 91
tttctaaata acattttctc tag                                                    23

SEQ ID NO: 92       moltype = RNA   length = 23
FEATURE             Location/Qualifiers
source              1..23
                    mol_type = other RNA
                    organism = synthetic construct
SEQUENCE: 92
atatagtgta taatacatat aac                                                    23

SEQ ID NO: 93       moltype = RNA   length = 23
FEATURE             Location/Qualifiers
source              1..23
                    mol_type = other RNA
                    organism = synthetic construct
SEQUENCE: 93
ctcctctgcc tactcaatgt gaa                                                    23

SEQ ID NO: 94       moltype = RNA   length = 23
FEATURE             Location/Qualifiers
source              1..23
                    mol_type = other RNA
                    organism = synthetic construct
SEQUENCE: 94
ccccacaccc ctaagacaag act                                                    23
```

-continued

```
SEQ ID NO: 95          moltype = RNA   length = 23
FEATURE                Location/Qualifiers
source                 1..23
                       mol_type = other RNA
                       organism = synthetic construct
SEQUENCE: 95
tcttcctccc catctttctc ctc                                                  23

SEQ ID NO: 96          moltype = RNA   length = 23
FEATURE                Location/Qualifiers
source                 1..23
                       mol_type = other RNA
                       organism = synthetic construct
SEQUENCE: 96
cttttatgtt gacccacttc cat                                                  23

SEQ ID NO: 97          moltype = RNA   length = 23
FEATURE                Location/Qualifiers
source                 1..23
                       mol_type = other RNA
                       organism = synthetic construct
SEQUENCE: 97
gaagacaatg agaatgaaga ctt                                                  23

SEQ ID NO: 98          moltype = RNA   length = 23
FEATURE                Location/Qualifiers
source                 1..23
                       mol_type = other RNA
                       organism = synthetic construct
SEQUENCE: 98
actgcaagac caacgccttc tct                                                  23

SEQ ID NO: 99          moltype = RNA   length = 23
FEATURE                Location/Qualifiers
source                 1..23
                       mol_type = other RNA
                       organism = synthetic construct
SEQUENCE: 99
tgaatattct ttcccccact ccc                                                  23

SEQ ID NO: 100         moltype = RNA   length = 23
FEATURE                Location/Qualifiers
source                 1..23
                       mol_type = other RNA
                       organism = synthetic construct
SEQUENCE: 100
tgcaagggtc cacttataca tga                                                  23

SEQ ID NO: 101         moltype = RNA   length = 23
FEATURE                Location/Qualifiers
source                 1..23
                       mol_type = other RNA
                       organism = synthetic construct
SEQUENCE: 101
atcctattac agttgaccct tga                                                  23

SEQ ID NO: 102         moltype = RNA   length = 23
FEATURE                Location/Qualifiers
source                 1..23
                       mol_type = other RNA
                       organism = synthetic construct
SEQUENCE: 102
agaggaagaa aaatagctat atc                                                  23

SEQ ID NO: 103         moltype = RNA   length = 23
FEATURE                Location/Qualifiers
source                 1..23
                       mol_type = other RNA
                       organism = synthetic construct
SEQUENCE: 103
atgcttacca tttggttgat aga                                                  23

SEQ ID NO: 104         moltype = RNA   length = 23
FEATURE                Location/Qualifiers
source                 1..23
                       mol_type = other RNA
                       organism = synthetic construct
SEQUENCE: 104
tgaacaacaa gggcttgaat tgc                                                  23
```

-continued

```
SEQ ID NO: 105           moltype = RNA   length = 23
FEATURE                  Location/Qualifiers
source                   1..23
                         mol_type = other RNA
                         organism = synthetic construct
SEQUENCE: 105
aaatttattc atcaagaaaa taa                                              23

SEQ ID NO: 106           moltype = RNA   length = 23
FEATURE                  Location/Qualifiers
source                   1..23
                         mol_type = other RNA
                         organism = synthetic construct
SEQUENCE: 106
ttattggaag atgttctgaa atg                                              23

SEQ ID NO: 107           moltype = RNA   length = 23
FEATURE                  Location/Qualifiers
source                   1..23
                         mol_type = other RNA
                         organism = synthetic construct
SEQUENCE: 107
ggatctataa tttagctcag tag                                              23

SEQ ID NO: 108           moltype = RNA   length = 23
FEATURE                  Location/Qualifiers
source                   1..23
                         mol_type = other RNA
                         organism = synthetic construct
SEQUENCE: 108
taattataaa tagcatagct gga                                              23

SEQ ID NO: 109           moltype = RNA   length = 23
FEATURE                  Location/Qualifiers
source                   1..23
                         mol_type = other RNA
                         organism = synthetic construct
SEQUENCE: 109
atggtcagag gagaaattga aaa                                              23

SEQ ID NO: 110           moltype = RNA   length = 23
FEATURE                  Location/Qualifiers
source                   1..23
                         mol_type = other RNA
                         organism = synthetic construct
SEQUENCE: 110
tagagtggac tgcaaaatag atg                                              23

SEQ ID NO: 111           moltype = RNA   length = 23
FEATURE                  Location/Qualifiers
source                   1..23
                         mol_type = other RNA
                         organism = synthetic construct
SEQUENCE: 111
ttaccaaagt ttggtgaata tat                                              23

SEQ ID NO: 112           moltype = RNA   length = 23
FEATURE                  Location/Qualifiers
source                   1..23
                         mol_type = other RNA
                         organism = synthetic construct
SEQUENCE: 112
gattatgcag tataggtgta aac                                              23

SEQ ID NO: 113           moltype = RNA   length = 23
FEATURE                  Location/Qualifiers
source                   1..23
                         mol_type = other RNA
                         organism = synthetic construct
SEQUENCE: 113
tattttccag cactcaattt tac                                              23

SEQ ID NO: 114           moltype = RNA   length = 23
FEATURE                  Location/Qualifiers
source                   1..23
                         mol_type = other RNA
                         organism = synthetic construct
SEQUENCE: 114
```

-continued

```
aactatttta gacttaattt taa                                        23

SEQ ID NO: 115             moltype = RNA   length = 23
FEATURE                    Location/Qualifiers
source                     1..23
                           mol_type = other RNA
                           organism = synthetic construct
SEQUENCE: 115
taaactttag tcaacttaaa tta                                        23

SEQ ID NO: 116             moltype = RNA   length = 23
FEATURE                    Location/Qualifiers
source                     1..23
                           mol_type = other RNA
                           organism = synthetic construct
SEQUENCE: 116
tacttcagtt gttttatgag tta                                        23

SEQ ID NO: 117             moltype = RNA   length = 23
FEATURE                    Location/Qualifiers
source                     1..23
                           mol_type = other RNA
                           organism = synthetic construct
SEQUENCE: 117
aactgaaatt aaaattgttg gat                                        23

SEQ ID NO: 118             moltype = RNA   length = 23
FEATURE                    Location/Qualifiers
source                     1..23
                           mol_type = other RNA
                           organism = synthetic construct
SEQUENCE: 118
tatattagta acatgtcttc aac                                        23

SEQ ID NO: 119             moltype = RNA   length = 23
FEATURE                    Location/Qualifiers
source                     1..23
                           mol_type = other RNA
                           organism = synthetic construct
SEQUENCE: 119
tagtaaccat gttttagaag ata                                        23

SEQ ID NO: 120             moltype = RNA   length = 23
FEATURE                    Location/Qualifiers
source                     1..23
                           mol_type = other RNA
                           organism = synthetic construct
SEQUENCE: 120
atatggttaa ttacacatcc tct                                        23

SEQ ID NO: 121             moltype = RNA   length = 23
FEATURE                    Location/Qualifiers
source                     1..23
                           mol_type = other RNA
                           organism = synthetic construct
SEQUENCE: 121
attgatgtta catattcttt tag                                        23

SEQ ID NO: 122             moltype = RNA   length = 23
FEATURE                    Location/Qualifiers
source                     1..23
                           mol_type = other RNA
                           organism = synthetic construct
SEQUENCE: 122
tctactcttt taataatagt tat                                        23

SEQ ID NO: 123             moltype = RNA   length = 23
FEATURE                    Location/Qualifiers
source                     1..23
                           mol_type = other RNA
                           organism = synthetic construct
SEQUENCE: 123
tatccctgaa ccaaacactt tcc                                        23

SEQ ID NO: 124             moltype = RNA   length = 23
FEATURE                    Location/Qualifiers
source                     1..23
                           mol_type = other RNA
                           organism = synthetic construct
```

```
SEQUENCE: 124
tctctcatgg gttcagaaaa ttt                                                          23

SEQ ID NO: 125          moltype = RNA   length = 23
FEATURE                 Location/Qualifiers
source                  1..23
                        mol_type = other RNA
                        organism = synthetic construct
SEQUENCE: 125
tattgagtta gcaacacttg tgt                                                          23

SEQ ID NO: 126          moltype = RNA   length = 23
FEATURE                 Location/Qualifiers
source                  1..23
                        mol_type = other RNA
                        organism = synthetic construct
SEQUENCE: 126
tgtaagaaac caaggtcaat att                                                          23

SEQ ID NO: 127          moltype = RNA   length = 23
FEATURE                 Location/Qualifiers
source                  1..23
                        mol_type = other RNA
                        organism = synthetic construct
SEQUENCE: 127
gaatttccag cttgtagatg agg                                                          23

SEQ ID NO: 128          moltype = RNA   length = 23
FEATURE                 Location/Qualifiers
source                  1..23
                        mol_type = other RNA
                        organism = synthetic construct
SEQUENCE: 128
tttaatagtg tctccttcac tat                                                          23

SEQ ID NO: 129          moltype = RNA   length = 23
FEATURE                 Location/Qualifiers
source                  1..23
                        mol_type = other RNA
                        organism = synthetic construct
SEQUENCE: 129
tccactcccc atctctagta tct                                                          23

SEQ ID NO: 130          moltype = RNA   length = 23
FEATURE                 Location/Qualifiers
source                  1..23
                        mol_type = other RNA
                        organism = synthetic construct
SEQUENCE: 130
actaaaacca gtgaggtgag tgt                                                          23

SEQ ID NO: 131          moltype = RNA   length = 23
FEATURE                 Location/Qualifiers
source                  1..23
                        mol_type = other RNA
                        organism = synthetic construct
SEQUENCE: 131
aggcgtcact taagaaatct ctg                                                          23

SEQ ID NO: 132          moltype = RNA   length = 23
FEATURE                 Location/Qualifiers
source                  1..23
                        mol_type = other RNA
                        organism = synthetic construct
SEQUENCE: 132
tgtatcacct gttgtttata agc                                                          23

SEQ ID NO: 133          moltype = RNA   length = 23
FEATURE                 Location/Qualifiers
source                  1..23
                        mol_type = other RNA
                        organism = synthetic construct
SEQUENCE: 133
ctgcccttct gttcttcaga tat                                                          23

SEQ ID NO: 134          moltype = RNA   length = 23
FEATURE                 Location/Qualifiers
source                  1..23
                        mol_type = other RNA
```

-continued

```
                        organism = synthetic construct
SEQUENCE: 134
agctttctac ttgtttttag gaa                                          23

SEQ ID NO: 135         moltype = RNA   length = 23
FEATURE                Location/Qualifiers
source                 1..23
                       mol_type = other RNA
                       organism = synthetic construct
SEQUENCE: 135
actttctgta ttggtaattt act                                          23

SEQ ID NO: 136         moltype = RNA   length = 23
FEATURE                Location/Qualifiers
source                 1..23
                       mol_type = other RNA
                       organism = synthetic construct
SEQUENCE: 136
aatcagttca aattttccac ttg                                          23

SEQ ID NO: 137         moltype = RNA   length = 23
FEATURE                Location/Qualifiers
source                 1..23
                       mol_type = other RNA
                       organism = synthetic construct
SEQUENCE: 137
aaaatattgt aacaaacagt gta                                          23

SEQ ID NO: 138         moltype = RNA   length = 23
FEATURE                Location/Qualifiers
source                 1..23
                       mol_type = other RNA
                       organism = synthetic construct
SEQUENCE: 138
gttatttctg tttactgaga aaa                                          23

SEQ ID NO: 139         moltype = RNA   length = 23
FEATURE                Location/Qualifiers
source                 1..23
                       mol_type = other RNA
                       organism = synthetic construct
SEQUENCE: 139
ttgtttttaa gactagggat act                                          23

SEQ ID NO: 140         moltype = RNA   length = 23
FEATURE                Location/Qualifiers
source                 1..23
                       mol_type = other RNA
                       organism = synthetic construct
SEQUENCE: 140
gtaatcaaag gaatatgact aat                                          23

SEQ ID NO: 141         moltype = RNA   length = 23
FEATURE                Location/Qualifiers
source                 1..23
                       mol_type = other RNA
                       organism = synthetic construct
SEQUENCE: 141
aatgaagaac aaaaaaatta gtt                                          23

SEQ ID NO: 142         moltype = RNA   length = 23
FEATURE                Location/Qualifiers
source                 1..23
                       mol_type = other RNA
                       organism = synthetic construct
SEQUENCE: 142
tatgatgaag aataattatt taa                                          23

SEQ ID NO: 143         moltype = RNA   length = 23
FEATURE                Location/Qualifiers
source                 1..23
                       mol_type = other RNA
                       organism = synthetic construct
SEQUENCE: 143
taaagagttt attctacttt ata                                          23

SEQ ID NO: 144         moltype = RNA   length = 23
FEATURE                Location/Qualifiers
source                 1..23
```

```
                          mol_type = other RNA
                          organism = synthetic construct
SEQUENCE: 144
gattttaatt tctatcaaag aat                                                23

SEQ ID NO: 145           moltype = RNA   length = 23
FEATURE                  Location/Qualifiers
source                   1..23
                         mol_type = other RNA
                         organism = synthetic construct
SEQUENCE: 145
ataatttgag ttatagtatt ctg                                                23

SEQ ID NO: 146           moltype = RNA   length = 23
FEATURE                  Location/Qualifiers
source                   1..23
                         mol_type = other RNA
                         organism = synthetic construct
SEQUENCE: 146
ctgtaatcct cacagaataa gat                                                23

SEQ ID NO: 147           moltype = RNA   length = 23
FEATURE                  Location/Qualifiers
source                   1..23
                         mol_type = other RNA
                         organism = synthetic construct
SEQUENCE: 147
attgttttta gtgccctgta aat                                                23

SEQ ID NO: 148           moltype = RNA   length = 23
FEATURE                  Location/Qualifiers
source                   1..23
                         mol_type = other RNA
                         organism = synthetic construct
SEQUENCE: 148
ctatagtaga acatatttga gca                                                23

SEQ ID NO: 149           moltype = RNA   length = 23
FEATURE                  Location/Qualifiers
source                   1..23
                         mol_type = other RNA
                         organism = synthetic construct
SEQUENCE: 149
aattaagata agaacttatt cta                                                23

SEQ ID NO: 150           moltype = RNA   length = 23
FEATURE                  Location/Qualifiers
source                   1..23
                         mol_type = other RNA
                         organism = synthetic construct
SEQUENCE: 150
atatcttatt ctttacactt tat                                                23

SEQ ID NO: 151           moltype = RNA   length = 23
FEATURE                  Location/Qualifiers
source                   1..23
                         mol_type = other RNA
                         organism = synthetic construct
SEQUENCE: 151
gcatttagta tattaaattt taa                                                23

SEQ ID NO: 152           moltype = RNA   length = 23
FEATURE                  Location/Qualifiers
source                   1..23
                         mol_type = other RNA
                         organism = synthetic construct
SEQUENCE: 152
taaaaataaa ttgttttctt ata                                                23

SEQ ID NO: 153           moltype = RNA   length = 23
FEATURE                  Location/Qualifiers
source                   1..23
                         mol_type = other RNA
                         organism = synthetic construct
SEQUENCE: 153
ttaaacaaat atatattctt aac                                                23

SEQ ID NO: 154           moltype = RNA   length = 23
FEATURE                  Location/Qualifiers
```

-continued

```
source                    1..23
                          mol_type = other RNA
                          organism = synthetic construct
SEQUENCE: 154
tgagttttca agaacattca ttt                                           23

SEQ ID NO: 155            moltype = RNA   length = 23
FEATURE                   Location/Qualifiers
source                    1..23
                          mol_type = other RNA
                          organism = synthetic construct
SEQUENCE: 155
aaccaattaa aatataaaag gca                                           23

SEQ ID NO: 156            moltype = RNA   length = 23
FEATURE                   Location/Qualifiers
source                    1..23
                          mol_type = other RNA
                          organism = synthetic construct
SEQUENCE: 156
gcaacattaa gcattttaaa att                                           23

SEQ ID NO: 157            moltype = RNA   length = 23
FEATURE                   Location/Qualifiers
source                    1..23
                          mol_type = other RNA
                          organism = synthetic construct
SEQUENCE: 157
acattcattt taatatagtg att                                           23

SEQ ID NO: 158            moltype = RNA   length = 23
FEATURE                   Location/Qualifiers
source                    1..23
                          mol_type = other RNA
                          organism = synthetic construct
SEQUENCE: 158
tatagtgatt ctgatttgca tta                                           23

SEQ ID NO: 159            moltype = RNA   length = 23
FEATURE                   Location/Qualifiers
source                    1..23
                          mol_type = other RNA
                          organism = synthetic construct
SEQUENCE: 159
atagagtatt gtgttgtatg aag                                           23

SEQ ID NO: 160            moltype = RNA   length = 23
FEATURE                   Location/Qualifiers
source                    1..23
                          mol_type = other RNA
                          organism = synthetic construct
SEQUENCE: 160
gcagctgtga tcatcacagt ata                                           23

SEQ ID NO: 161            moltype = RNA   length = 23
FEATURE                   Location/Qualifiers
source                    1..23
                          mol_type = other RNA
                          organism = synthetic construct
SEQUENCE: 161
aagtcttacg ggtgtttagc tgg                                           23

SEQ ID NO: 162            moltype = RNA   length = 23
FEATURE                   Location/Qualifiers
source                    1..23
                          mol_type = other RNA
                          organism = synthetic construct
SEQUENCE: 162
agccaaatat gagataactg tct                                           23

SEQ ID NO: 163            moltype = RNA   length = 23
FEATURE                   Location/Qualifiers
source                    1..23
                          mol_type = other RNA
                          organism = synthetic construct
SEQUENCE: 163
tcttctttta ggtagccttg gca                                           23

SEQ ID NO: 164            moltype = RNA   length = 23
```

-continued

```
FEATURE                 Location/Qualifiers
source                  1..23
                        mol_type = other RNA
                        organism = synthetic construct
SEQUENCE: 164
tggggagttt tctgactctg tca                                        23

SEQ ID NO: 165          moltype = RNA   length = 23
FEATURE                 Location/Qualifiers
source                  1..23
                        mol_type = other RNA
                        organism = synthetic construct
SEQUENCE: 165
atttcaatgg ttgaggctct tct                                        23

SEQ ID NO: 166          moltype = RNA   length = 23
FEATURE                 Location/Qualifiers
source                  1..23
                        mol_type = other RNA
                        organism = synthetic construct
SEQUENCE: 166
ctgaagtttt aagtggtcga gag                                        23

SEQ ID NO: 167          moltype = RNA   length = 23
FEATURE                 Location/Qualifiers
source                  1..23
                        mol_type = other RNA
                        organism = synthetic construct
SEQUENCE: 167
ataccagcag gacaggaagt ctg                                        23

SEQ ID NO: 168          moltype = RNA   length = 23
FEATURE                 Location/Qualifiers
source                  1..23
                        mol_type = other RNA
                        organism = synthetic construct
SEQUENCE: 168
gagaaagata aaaagctggc agc                                        23

SEQ ID NO: 169          moltype = RNA   length = 23
FEATURE                 Location/Qualifiers
source                  1..23
                        mol_type = other RNA
                        organism = synthetic construct
SEQUENCE: 169
ggtattggac tttctccatg ata                                        23

SEQ ID NO: 170          moltype = RNA   length = 23
FEATURE                 Location/Qualifiers
source                  1..23
                        mol_type = other RNA
                        organism = synthetic construct
SEQUENCE: 170
tcttatagct gagcgagtga ggt                                        23

SEQ ID NO: 171          moltype = RNA   length = 23
FEATURE                 Location/Qualifiers
source                  1..23
                        mol_type = other RNA
                        organism = synthetic construct
SEQUENCE: 171
attaagatga gacagaaatt gat                                        23

SEQ ID NO: 172          moltype = RNA   length = 23
FEATURE                 Location/Qualifiers
source                  1..23
                        mol_type = other RNA
                        organism = synthetic construct
SEQUENCE: 172
tacagatcag caagagacat att                                        23

SEQ ID NO: 173          moltype = RNA   length = 23
FEATURE                 Location/Qualifiers
source                  1..23
                        mol_type = other RNA
                        organism = synthetic construct
SEQUENCE: 173
tttgacgtgc ttgttgaggc att                                        23
```

-continued

```
SEQ ID NO: 174        moltype = RNA   length = 23
FEATURE               Location/Qualifiers
source                1..23
                      mol_type = other RNA
                      organism = synthetic construct
SEQUENCE: 174
ctagaggttg tagcagaact tca                                      23

SEQ ID NO: 175        moltype = RNA   length = 23
FEATURE               Location/Qualifiers
source                1..23
                      mol_type = other RNA
                      organism = synthetic construct
SEQUENCE: 175
tcagagaagc atcacgatga tac                                      23

SEQ ID NO: 176        moltype = RNA   length = 23
FEATURE               Location/Qualifiers
source                1..23
                      mol_type = other RNA
                      organism = synthetic construct
SEQUENCE: 176
gataaataga ttctgtagct ttt                                      23

SEQ ID NO: 177        moltype = RNA   length = 23
FEATURE               Location/Qualifiers
source                1..23
                      mol_type = other RNA
                      organism = synthetic construct
SEQUENCE: 177
acaaagaaac tcttctactc agg                                      23

SEQ ID NO: 178        moltype = RNA   length = 23
FEATURE               Location/Qualifiers
source                1..23
                      mol_type = other RNA
                      organism = synthetic construct
SEQUENCE: 178
tgatgtggca agctgcagat cta                                      23

SEQ ID NO: 179        moltype = RNA   length = 23
FEATURE               Location/Qualifiers
source                1..23
                      mol_type = other RNA
                      organism = synthetic construct
SEQUENCE: 179
gtcttaatct tgaccttttc aca                                      23

SEQ ID NO: 180        moltype = RNA   length = 23
FEATURE               Location/Qualifiers
source                1..23
                      mol_type = other RNA
                      organism = synthetic construct
SEQUENCE: 180
atattgtttt cctgtctgca tgg                                      23

SEQ ID NO: 181        moltype = RNA   length = 23
FEATURE               Location/Qualifiers
source                1..23
                      mol_type = other RNA
                      organism = synthetic construct
SEQUENCE: 181
aggaagtggt ctgttataca ata                                      23

SEQ ID NO: 182        moltype = RNA   length = 23
FEATURE               Location/Qualifiers
source                1..23
                      mol_type = other RNA
                      organism = synthetic construct
SEQUENCE: 182
tgggatgaca gattttaagc tga                                      23

SEQ ID NO: 183        moltype = RNA   length = 23
FEATURE               Location/Qualifiers
source                1..23
                      mol_type = other RNA
                      organism = synthetic construct
SEQUENCE: 183
tatggtaaca ataagtttta gtc                                      23
```

-continued

```
SEQ ID NO: 184            moltype = RNA   length = 23
FEATURE                   Location/Qualifiers
source                    1..23
                          mol_type = other RNA
                          organism = synthetic construct
SEQUENCE: 184
gcattttata cacttatttt gaa                                             23

SEQ ID NO: 185            moltype = RNA   length = 23
FEATURE                   Location/Qualifiers
source                    1..23
                          mol_type = other RNA
                          organism = synthetic construct
SEQUENCE: 185
agatccaaca gatgaataca tat                                             23

SEQ ID NO: 186            moltype = RNA   length = 23
FEATURE                   Location/Qualifiers
source                    1..23
                          mol_type = other RNA
                          organism = synthetic construct
SEQUENCE: 186
aagccctttt catgtttaca aga                                             23

SEQ ID NO: 187            moltype = RNA   length = 23
FEATURE                   Location/Qualifiers
source                    1..23
                          mol_type = other RNA
                          organism = synthetic construct
SEQUENCE: 187
gaagttaatt tttgaaaata aag                                             23

SEQ ID NO: 188            moltype = RNA   length = 23
FEATURE                   Location/Qualifiers
source                    1..23
                          mol_type = other RNA
                          organism = synthetic construct
SEQUENCE: 188
tgttgaggaa atcaacagtt gca                                             23

SEQ ID NO: 189            moltype = RNA   length = 23
FEATURE                   Location/Qualifiers
source                    1..23
                          mol_type = other RNA
                          organism = synthetic construct
SEQUENCE: 189
aagtgaactt gttggcagtg cag                                             23

SEQ ID NO: 190            moltype = RNA   length = 23
FEATURE                   Location/Qualifiers
source                    1..23
                          mol_type = other RNA
                          organism = synthetic construct
SEQUENCE: 190
cagtttaaa actaaactct tca                                              23

SEQ ID NO: 191            moltype = RNA   length = 23
FEATURE                   Location/Qualifiers
source                    1..23
                          mol_type = other RNA
                          organism = synthetic construct
SEQUENCE: 191
aaaataatgc tttatatatg aag                                             23

SEQ ID NO: 192            moltype = RNA   length = 23
FEATURE                   Location/Qualifiers
source                    1..23
                          mol_type = other RNA
                          organism = synthetic construct
SEQUENCE: 192
atattcacct caaaagagta aaa                                             23

SEQ ID NO: 193            moltype = RNA   length = 23
FEATURE                   Location/Qualifiers
source                    1..23
                          mol_type = other RNA
                          organism = synthetic construct
SEQUENCE: 193
```

-continued

```
ggatagaaat ttgtgagcca tgt                                           23

SEQ ID NO: 194          moltype = RNA   length = 23
FEATURE                 Location/Qualifiers
source                  1..23
                        mol_type = other RNA
                        organism = synthetic construct
SEQUENCE: 194
tcatcttcag aaaagatttg gga                                           23

SEQ ID NO: 195          moltype = RNA   length = 23
FEATURE                 Location/Qualifiers
source                  1..23
                        mol_type = other RNA
                        organism = synthetic construct
SEQUENCE: 195
tacttagtat taaagaagct ttt                                           23

SEQ ID NO: 196          moltype = RNA   length = 23
FEATURE                 Location/Qualifiers
source                  1..23
                        mol_type = other RNA
                        organism = synthetic construct
SEQUENCE: 196
ttttgaataa tgacacttca ttt                                           23

SEQ ID NO: 197          moltype = RNA   length = 23
FEATURE                 Location/Qualifiers
source                  1..23
                        mol_type = other RNA
                        organism = synthetic construct
SEQUENCE: 197
tgtgaggagt cagtggacta ttt                                           23

SEQ ID NO: 198          moltype = RNA   length = 23
FEATURE                 Location/Qualifiers
source                  1..23
                        mol_type = other RNA
                        organism = synthetic construct
SEQUENCE: 198
cttggtgaag acctgaaaaa tac                                           23

SEQ ID NO: 199          moltype = RNA   length = 23
FEATURE                 Location/Qualifiers
source                  1..23
                        mol_type = other RNA
                        organism = synthetic construct
SEQUENCE: 199
ctttataata agataacaga tgt                                           23

SEQ ID NO: 200          moltype = RNA   length = 23
FEATURE                 Location/Qualifiers
source                  1..23
                        mol_type = other RNA
                        organism = synthetic construct
SEQUENCE: 200
tttacattgt aatataaatt ata                                           23

SEQ ID NO: 201          moltype = RNA   length = 23
FEATURE                 Location/Qualifiers
source                  1..23
                        mol_type = other RNA
                        organism = synthetic construct
SEQUENCE: 201
catagaaaaa atacaatttc tgt                                           23

SEQ ID NO: 202          moltype = RNA   length = 23
FEATURE                 Location/Qualifiers
source                  1..23
                        mol_type = other RNA
                        organism = synthetic construct
SEQUENCE: 202
tgttttagaa tgtagattct gat                                           23

SEQ ID NO: 203          moltype = RNA   length = 23
FEATURE                 Location/Qualifiers
source                  1..23
                        mol_type = other RNA
                        organism = synthetic construct
```

-continued

```
SEQUENCE: 203
tttaaaagat gttaatgtgg cat                                          23

SEQ ID NO: 204         moltype = RNA   length = 23
FEATURE                Location/Qualifiers
source                 1..23
                       mol_type = other RNA
                       organism = synthetic construct
SEQUENCE: 204
agagtatggc cttactttc cat                                           23

SEQ ID NO: 205         moltype = RNA   length = 23
FEATURE                Location/Qualifiers
source                 1..23
                       mol_type = other RNA
                       organism = synthetic construct
SEQUENCE: 205
gatagttact acaaatagtt ctt                                          23

SEQ ID NO: 206         moltype = RNA   length = 23
FEATURE                Location/Qualifiers
source                 1..23
                       mol_type = other RNA
                       organism = synthetic construct
SEQUENCE: 206
aaaaggaatt ttattatgta aga                                          23

SEQ ID NO: 207         moltype = RNA   length = 23
FEATURE                Location/Qualifiers
source                 1..23
                       mol_type = other RNA
                       organism = synthetic construct
SEQUENCE: 207
aacagattta tgatttacct aca                                          23

SEQ ID NO: 208         moltype = RNA   length = 23
FEATURE                Location/Qualifiers
source                 1..23
                       mol_type = other RNA
                       organism = synthetic construct
SEQUENCE: 208
tattaaccac cagttctcat ctg                                          23

SEQ ID NO: 209         moltype = RNA   length = 23
FEATURE                Location/Qualifiers
source                 1..23
                       mol_type = other RNA
                       organism = synthetic construct
SEQUENCE: 209
attctttgaa aaaattactt aaa                                          23

SEQ ID NO: 210         moltype = RNA   length = 23
FEATURE                Location/Qualifiers
source                 1..23
                       mol_type = other RNA
                       organism = synthetic construct
SEQUENCE: 210
ctgttgatca tatgtcttag aac                                          23

SEQ ID NO: 211         moltype = RNA   length = 23
FEATURE                Location/Qualifiers
source                 1..23
                       mol_type = other RNA
                       organism = synthetic construct
SEQUENCE: 211
tgactaatct cactgtcaca tat                                          23

SEQ ID NO: 212         moltype = RNA   length = 23
FEATURE                Location/Qualifiers
source                 1..23
                       mol_type = other RNA
                       organism = synthetic construct
SEQUENCE: 212
acatgtacta gaattctgtg att                                          23

SEQ ID NO: 213         moltype = RNA   length = 23
FEATURE                Location/Qualifiers
source                 1..23
                       mol_type = other RNA
```

```
                            organism = synthetic construct
SEQUENCE: 213
aagtcttaag gtttcatgat tcc                                                   23

SEQ ID NO: 214           moltype = RNA  length = 23
FEATURE                  Location/Qualifiers
source                   1..23
                         mol_type = other RNA
                         organism = synthetic construct
SEQUENCE: 214
gataattcac tacagtgcct taa                                                   23

SEQ ID NO: 215           moltype = RNA  length = 23
FEATURE                  Location/Qualifiers
source                   1..23
                         mol_type = other RNA
                         organism = synthetic construct
SEQUENCE: 215
taaatgaaga ttagattctg ttg                                                   23

SEQ ID NO: 216           moltype = RNA  length = 23
FEATURE                  Location/Qualifiers
source                   1..23
                         mol_type = other RNA
                         organism = synthetic construct
SEQUENCE: 216
agctaggtaa ctctagctca gat                                                   23

SEQ ID NO: 217           moltype = RNA  length = 23
FEATURE                  Location/Qualifiers
source                   1..23
                         mol_type = other RNA
                         organism = synthetic construct
SEQUENCE: 217
tgcaaaatca ttctgaagtc tta                                                   23

SEQ ID NO: 218           moltype = RNA  length = 23
FEATURE                  Location/Qualifiers
source                   1..23
                         mol_type = other RNA
                         organism = synthetic construct
SEQUENCE: 218
ttgttagtat attagtgata tga                                                   23

SEQ ID NO: 219           moltype = RNA  length = 23
FEATURE                  Location/Qualifiers
source                   1..23
                         mol_type = other RNA
                         organism = synthetic construct
SEQUENCE: 219
ttttccttgc ctgcattgga tgt                                                   23

SEQ ID NO: 220           moltype = RNA  length = 23
FEATURE                  Location/Qualifiers
source                   1..23
                         mol_type = other RNA
                         organism = synthetic construct
SEQUENCE: 220
ttcatatatt tttaaaaaat act                                                   23

SEQ ID NO: 221           moltype = RNA  length = 23
FEATURE                  Location/Qualifiers
source                   1..23
                         mol_type = other RNA
                         organism = synthetic construct
SEQUENCE: 221
tgttaggctg gaatggaaga caa                                                   23

SEQ ID NO: 222           moltype = RNA  length = 23
FEATURE                  Location/Qualifiers
source                   1..23
                         mol_type = other RNA
                         organism = synthetic construct
SEQUENCE: 222
caacctgcaa aatcattctg aag                                                   23

SEQ ID NO: 223           moltype = RNA  length = 23
FEATURE                  Location/Qualifiers
source                   1..23
```

```
                         mol_type = other RNA
                         organism = synthetic construct
SEQUENCE: 223
acttgagata atatattttt ctg                                              23

SEQ ID NO: 224          moltype = RNA   length = 23
FEATURE                 Location/Qualifiers
source                  1..23
                        mol_type = other RNA
                        organism = synthetic construct
SEQUENCE: 224
ctgtcactgg aaatctttta ttt                                              23

SEQ ID NO: 225          moltype = RNA   length = 23
FEATURE                 Location/Qualifiers
source                  1..23
                        mol_type = other RNA
                        organism = synthetic construct
SEQUENCE: 225
tgggccaaca agttcatttc aaa                                              23

SEQ ID NO: 226          moltype = RNA   length = 23
FEATURE                 Location/Qualifiers
source                  1..23
                        mol_type = other RNA
                        organism = synthetic construct
SEQUENCE: 226
gttaatattt ggagagagaa ttc                                              23

SEQ ID NO: 227          moltype = RNA   length = 23
FEATURE                 Location/Qualifiers
source                  1..23
                        mol_type = other RNA
                        organism = synthetic construct
SEQUENCE: 227
ctaaccccca tgttcaaggg tca                                              23

SEQ ID NO: 228          moltype = RNA   length = 23
FEATURE                 Location/Qualifiers
source                  1..23
                        mol_type = other RNA
                        organism = synthetic construct
SEQUENCE: 228
aaaatataat ctaataatta gtt                                              23

SEQ ID NO: 229          moltype = RNA   length = 23
FEATURE                 Location/Qualifiers
source                  1..23
                        mol_type = other RNA
                        organism = synthetic construct
SEQUENCE: 229
gaattgtcag ctcccctaac ccc                                              23

SEQ ID NO: 230          moltype = RNA   length = 23
FEATURE                 Location/Qualifiers
source                  1..23
                        mol_type = other RNA
                        organism = synthetic construct
SEQUENCE: 230
tcagctgtag atgtaataga tgg                                              23

SEQ ID NO: 231          moltype = RNA   length = 23
FEATURE                 Location/Qualifiers
source                  1..23
                        mol_type = other RNA
                        organism = synthetic construct
SEQUENCE: 231
taatacatat aacacgcaaa ata                                              23

SEQ ID NO: 232          moltype = RNA   length = 23
FEATURE                 Location/Qualifiers
source                  1..23
                        mol_type = other RNA
                        organism = synthetic construct
SEQUENCE: 232
atatgtgtta atttactgtt tat                                              23

SEQ ID NO: 233          moltype = RNA   length = 23
FEATURE                 Location/Qualifiers
```

```
source                1..23
                      mol_type = other RNA
                      organism = synthetic construct
SEQUENCE: 233
tattgtagga atatagtgta taa                                       23

SEQ ID NO: 234        moltype = RNA   length = 23
FEATURE               Location/Qualifiers
source                1..23
                      mol_type = other RNA
                      organism = synthetic construct
SEQUENCE: 234
tatgttatca gtaaggttta tgg                                       23

SEQ ID NO: 235        moltype = RNA   length = 23
FEATURE               Location/Qualifiers
source                1..23
                      mol_type = other RNA
                      organism = synthetic construct
SEQUENCE: 235
cccacgaatt gtcagctccc cta                                       23

SEQ ID NO: 236        moltype = RNA   length = 23
FEATURE               Location/Qualifiers
source                1..23
                      mol_type = other RNA
                      organism = synthetic construct
SEQUENCE: 236
tggtcaatag taggctatta ggt                                       23

SEQ ID NO: 237        moltype = RNA   length = 23
FEATURE               Location/Qualifiers
source                1..23
                      mol_type = other RNA
                      organism = synthetic construct
SEQUENCE: 237
agaatgaaga cttttatgtt gac                                       23

SEQ ID NO: 238        moltype = RNA   length = 23
FEATURE               Location/Qualifiers
source                1..23
                      mol_type = other RNA
                      organism = synthetic construct
SEQUENCE: 238
atagtaaata tattttctct ttc                                       23

SEQ ID NO: 239        moltype = RNA   length = 23
FEATURE               Location/Qualifiers
source                1..23
                      mol_type = other RNA
                      organism = synthetic construct
SEQUENCE: 239
ttcttatgat tttctaaata aca                                       23

SEQ ID NO: 240        moltype = RNA   length = 23
FEATURE               Location/Qualifiers
source                1..23
                      mol_type = other RNA
                      organism = synthetic construct
SEQUENCE: 240
gacccacttc catttaatga ata                                       23

SEQ ID NO: 241        moltype = RNA   length = 23
FEATURE               Location/Qualifiers
source                1..23
                      mol_type = other RNA
                      organism = synthetic construct
SEQUENCE: 241
tactcaatgt gaagacaatg aga                                       23

SEQ ID NO: 242        moltype = RNA   length = 23
FEATURE               Location/Qualifiers
source                1..23
                      mol_type = other RNA
                      organism = synthetic construct
SEQUENCE: 242
acattttctc tagcttactt tat                                       23

SEQ ID NO: 243        moltype = RNA   length = 23
```

-continued

```
FEATURE              Location/Qualifiers
source               1..23
                     mol_type = other RNA
                     organism = synthetic construct
SEQUENCE: 243
gggcttgaat tgcaagggtc cac                                          23

SEQ ID NO: 244       moltype = RNA   length = 23
FEATURE              Location/Qualifiers
source               1..23
                     mol_type = other RNA
                     organism = synthetic construct
SEQUENCE: 244
catctttctc ctcctctgcc tac                                          23

SEQ ID NO: 245       moltype = RNA   length = 23
FEATURE              Location/Qualifiers
source               1..23
                     mol_type = other RNA
                     organism = synthetic construct
SEQUENCE: 245
ctaagacaag actgcaagac caa                                          23

SEQ ID NO: 246       moltype = RNA   length = 23
FEATURE              Location/Qualifiers
source               1..23
                     mol_type = other RNA
                     organism = synthetic construct
SEQUENCE: 246
ttcccccact ccccacaccc cta                                          23

SEQ ID NO: 247       moltype = RNA   length = 23
FEATURE              Location/Qualifiers
source               1..23
                     mol_type = other RNA
                     organism = synthetic construct
SEQUENCE: 247
cacttataca tgaatattct ttc                                          23

SEQ ID NO: 248       moltype = RNA   length = 23
FEATURE              Location/Qualifiers
source               1..23
                     mol_type = other RNA
                     organism = synthetic construct
SEQUENCE: 248
caacgccttc tcttcctccc cat                                          23

SEQ ID NO: 249       moltype = RNA   length = 23
FEATURE              Location/Qualifiers
source               1..23
                     mol_type = other RNA
                     organism = synthetic construct
SEQUENCE: 249
agttgaccct tgaacaacaa ggg                                          23

SEQ ID NO: 250       moltype = RNA   length = 23
FEATURE              Location/Qualifiers
source               1..23
                     mol_type = other RNA
                     organism = synthetic construct
SEQUENCE: 250
tttagctcag tagagtggac tgc                                          23

SEQ ID NO: 251       moltype = RNA   length = 23
FEATURE              Location/Qualifiers
source               1..23
                     mol_type = other RNA
                     organism = synthetic construct
SEQUENCE: 251
tagcatagct ggatctataa ttt                                          23

SEQ ID NO: 252       moltype = RNA   length = 23
FEATURE              Location/Qualifiers
source               1..23
                     mol_type = other RNA
                     organism = synthetic construct
SEQUENCE: 252
aaatagctat atcctattac agt                                          23
```

-continued

```
SEQ ID NO: 253          moltype = RNA   length = 23
FEATURE                 Location/Qualifiers
source                  1..23
                        mol_type = other RNA
                        organism = synthetic construct
SEQUENCE: 253
tttggttgat agaggaagaa aaa                                           23

SEQ ID NO: 254          moltype = RNA   length = 23
FEATURE                 Location/Qualifiers
source                  1..23
                        mol_type = other RNA
                        organism = synthetic construct
SEQUENCE: 254
tgcaaaatag atgcttacca ttt                                           23

SEQ ID NO: 255          moltype = RNA   length = 23
FEATURE                 Location/Qualifiers
source                  1..23
                        mol_type = other RNA
                        organism = synthetic construct
SEQUENCE: 255
cactcaattt tacttcagtt gtt                                           23

SEQ ID NO: 256          moltype = RNA   length = 23
FEATURE                 Location/Qualifiers
source                  1..23
                        mol_type = other RNA
                        organism = synthetic construct
SEQUENCE: 256
atgttctgaa atggtcagag gag                                           23

SEQ ID NO: 257          moltype = RNA   length = 23
FEATURE                 Location/Qualifiers
source                  1..23
                        mol_type = other RNA
                        organism = synthetic construct
SEQUENCE: 257
gttttatgag ttattggaag atg                                           23

SEQ ID NO: 258          moltype = RNA   length = 23
FEATURE                 Location/Qualifiers
source                  1..23
                        mol_type = other RNA
                        organism = synthetic construct
SEQUENCE: 258
atcaagaaaa taattataaa tag                                           23

SEQ ID NO: 259          moltype = RNA   length = 23
FEATURE                 Location/Qualifiers
source                  1..23
                        mol_type = other RNA
                        organism = synthetic construct
SEQUENCE: 259
attgaaaatt tattcatcaa gaa                                           23

SEQ ID NO: 260          moltype = RNA   length = 23
FEATURE                 Location/Qualifiers
source                  1..23
                        mol_type = other RNA
                        organism = synthetic construct
SEQUENCE: 260
gagaaattga aaatttattc atc                                           23

SEQ ID NO: 261          moltype = RNA   length = 23
FEATURE                 Location/Qualifiers
source                  1..23
                        mol_type = other RNA
                        organism = synthetic construct
SEQUENCE: 261
acatgtcttc aactgaaatt aaa                                           23

SEQ ID NO: 262          moltype = RNA   length = 23
FEATURE                 Location/Qualifiers
source                  1..23
                        mol_type = other RNA
                        organism = synthetic construct
SEQUENCE: 262
aaaattgttg gattatgcag tat                                           23
```

-continued

```
SEQ ID NO: 263           moltype = RNA  length = 23
FEATURE                  Location/Qualifiers
source                   1..23
                         mol_type = other RNA
                         organism = synthetic construct
SEQUENCE: 263
tcaacttaaa ttaccaaagt ttg                                          23

SEQ ID NO: 264           moltype = RNA  length = 23
FEATURE                  Location/Qualifiers
source                   1..23
                         mol_type = other RNA
                         organism = synthetic construct
SEQUENCE: 264
gacttaattt taaactttag tca                                          23

SEQ ID NO: 265           moltype = RNA  length = 23
FEATURE                  Location/Qualifiers
source                   1..23
                         mol_type = other RNA
                         organism = synthetic construct
SEQUENCE: 265
tataggtgta aactatttta gac                                          23

SEQ ID NO: 266           moltype = RNA  length = 23
FEATURE                  Location/Qualifiers
source                   1..23
                         mol_type = other RNA
                         organism = synthetic construct
SEQUENCE: 266
ttggtgaata tattttccag cac                                          23

SEQ ID NO: 267           moltype = RNA  length = 23
FEATURE                  Location/Qualifiers
source                   1..23
                         mol_type = other RNA
                         organism = synthetic construct
SEQUENCE: 267
caaggtcaat attgatgtta cat                                          23

SEQ ID NO: 268           moltype = RNA  length = 23
FEATURE                  Location/Qualifiers
source                   1..23
                         mol_type = other RNA
                         organism = synthetic construct
SEQUENCE: 268
catattcttt tagtaaccat gtt                                          23

SEQ ID NO: 269           moltype = RNA  length = 23
FEATURE                  Location/Qualifiers
source                   1..23
                         mol_type = other RNA
                         organism = synthetic construct
SEQUENCE: 269
gttttagaag atatggttaa tta                                          23

SEQ ID NO: 270           moltype = RNA  length = 23
FEATURE                  Location/Qualifiers
source                   1..23
                         mol_type = other RNA
                         organism = synthetic construct
SEQUENCE: 270
atagttatat tagtaacatg tct                                          23

SEQ ID NO: 271           moltype = RNA  length = 23
FEATURE                  Location/Qualifiers
source                   1..23
                         mol_type = other RNA
                         organism = synthetic construct
SEQUENCE: 271
ttacacatcc tctactcttt taa                                          23

SEQ ID NO: 272           moltype = RNA  length = 23
FEATURE                  Location/Qualifiers
source                   1..23
                         mol_type = other RNA
                         organism = synthetic construct
SEQUENCE: 272
```

-continued

```
taataatagt tatattagta aca                                              23

SEQ ID NO: 273           moltype = RNA   length = 23
FEATURE                  Location/Qualifiers
source                   1..23
                         mol_type = other RNA
                         organism = synthetic construct
SEQUENCE: 273
atctctagta tctctcatgg gtt                                              23

SEQ ID NO: 274           moltype = RNA   length = 23
FEATURE                  Location/Qualifiers
source                   1..23
                         mol_type = other RNA
                         organism = synthetic construct
SEQUENCE: 274
tagtatctct catgggttca gaa                                              23

SEQ ID NO: 275           moltype = RNA   length = 23
FEATURE                  Location/Qualifiers
source                   1..23
                         mol_type = other RNA
                         organism = synthetic construct
SEQUENCE: 275
tctccttcac tattgagtta gca                                              23

SEQ ID NO: 276           moltype = RNA   length = 23
FEATURE                  Location/Qualifiers
source                   1..23
                         mol_type = other RNA
                         organism = synthetic construct
SEQUENCE: 276
ccaaacactt tccactcccc atc                                              23

SEQ ID NO: 277           moltype = RNA   length = 23
FEATURE                  Location/Qualifiers
source                   1..23
                         mol_type = other RNA
                         organism = synthetic construct
SEQUENCE: 277
gttcagaaaa tttaatagtg tct                                              23

SEQ ID NO: 278           moltype = RNA   length = 23
FEATURE                  Location/Qualifiers
source                   1..23
                         mol_type = other RNA
                         organism = synthetic construct
SEQUENCE: 278
gcaacacttg tgtaagaaac caa                                              23

SEQ ID NO: 279           moltype = RNA   length = 23
FEATURE                  Location/Qualifiers
source                   1..23
                         mol_type = other RNA
                         organism = synthetic construct
SEQUENCE: 279
ttgtttttag gaatttccag ctt                                              23

SEQ ID NO: 280           moltype = RNA   length = 23
FEATURE                  Location/Qualifiers
source                   1..23
                         mol_type = other RNA
                         organism = synthetic construct
SEQUENCE: 280
cttgtagatg aggcgtcact taa                                              23

SEQ ID NO: 281           moltype = RNA   length = 23
FEATURE                  Location/Qualifiers
source                   1..23
                         mol_type = other RNA
                         organism = synthetic construct
SEQUENCE: 281
taagaaatct ctgcccttct gtt                                              23

SEQ ID NO: 282           moltype = RNA   length = 23
FEATURE                  Location/Qualifiers
source                   1..23
                         mol_type = other RNA
                         organism = synthetic construct
```

-continued

```
SEQUENCE: 282
tttaggaatt tccagcttgt aga                                              23

SEQ ID NO: 283          moltype = RNA   length = 23
FEATURE                 Location/Qualifiers
source                  1..23
                        mol_type = other RNA
                        organism = synthetic construct
SEQUENCE: 283
gttcttcaga tatccctgaa cca                                              23

SEQ ID NO: 284          moltype = RNA   length = 23
FEATURE                 Location/Qualifiers
source                  1..23
                        mol_type = other RNA
                        organism = synthetic construct
SEQUENCE: 284
gttgtttata agctttctac ttg                                              23

SEQ ID NO: 285          moltype = RNA   length = 23
FEATURE                 Location/Qualifiers
source                  1..23
                        mol_type = other RNA
                        organism = synthetic construct
SEQUENCE: 285
gaatatgact aatcagttca aat                                              23

SEQ ID NO: 286          moltype = RNA   length = 23
FEATURE                 Location/Qualifiers
source                  1..23
                        mol_type = other RNA
                        organism = synthetic construct
SEQUENCE: 286
gactagggat actttctgta ttg                                              23

SEQ ID NO: 287          moltype = RNA   length = 23
FEATURE                 Location/Qualifiers
source                  1..23
                        mol_type = other RNA
                        organism = synthetic construct
SEQUENCE: 287
acagtgtaat caaaggaata tga                                              23

SEQ ID NO: 288          moltype = RNA   length = 23
FEATURE                 Location/Qualifiers
source                  1..23
                        mol_type = other RNA
                        organism = synthetic construct
SEQUENCE: 288
ttggtaattt actaaaacca gtg                                              23

SEQ ID NO: 289          moltype = RNA   length = 23
FEATURE                 Location/Qualifiers
source                  1..23
                        mol_type = other RNA
                        organism = synthetic construct
SEQUENCE: 289
gtgaggtgag tgtatcacct gtt                                              23

SEQ ID NO: 290          moltype = RNA   length = 23
FEATURE                 Location/Qualifiers
source                  1..23
                        mol_type = other RNA
                        organism = synthetic construct
SEQUENCE: 290
aattttccac ttgtttttaa gac                                              23

SEQ ID NO: 291          moltype = RNA   length = 23
FEATURE                 Location/Qualifiers
source                  1..23
                        mol_type = other RNA
                        organism = synthetic construct
SEQUENCE: 291
tttactgaga aaaatattgt aac                                              23

SEQ ID NO: 292          moltype = RNA   length = 23
FEATURE                 Location/Qualifiers
source                  1..23
                        mol_type = other RNA
```

-continued

```
                              organism = synthetic construct
SEQUENCE: 292
aacaaacagt gtaatcaaag gaa                                            23

SEQ ID NO: 293          moltype = RNA  length = 23
FEATURE                 Location/Qualifiers
source                  1..23
                        mol_type = other RNA
                        organism = synthetic construct
SEQUENCE: 293
tctatcaaag aatgaagaac aaa                                            23

SEQ ID NO: 294          moltype = RNA  length = 23
FEATURE                 Location/Qualifiers
source                  1..23
                        mol_type = other RNA
                        organism = synthetic construct
SEQUENCE: 294
aataagattt taatttctat caa                                            23

SEQ ID NO: 295          moltype = RNA  length = 23
FEATURE                 Location/Qualifiers
source                  1..23
                        mol_type = other RNA
                        organism = synthetic construct
SEQUENCE: 295
aaaaaaatta gttatttctg ttt                                            23

SEQ ID NO: 296          moltype = RNA  length = 23
FEATURE                 Location/Qualifiers
source                  1..23
                        mol_type = other RNA
                        organism = synthetic construct
SEQUENCE: 296
cacagaataa gatttttaatt tct                                           23

SEQ ID NO: 297          moltype = RNA  length = 23
FEATURE                 Location/Qualifiers
source                  1..23
                        mol_type = other RNA
                        organism = synthetic construct
SEQUENCE: 297
ttatttaaag agtttattct act                                           23

SEQ ID NO: 298          moltype = RNA  length = 23
FEATURE                 Location/Qualifiers
source                  1..23
                        mol_type = other RNA
                        organism = synthetic construct
SEQUENCE: 298
ttatagtatt ctgtaatcct cac                                           23

SEQ ID NO: 299          moltype = RNA  length = 23
FEATURE                 Location/Qualifiers
source                  1..23
                        mol_type = other RNA
                        organism = synthetic construct
SEQUENCE: 299
ttgttttctt atatcttatt ctt                                           23

SEQ ID NO: 300          moltype = RNA  length = 23
FEATURE                 Location/Qualifiers
source                  1..23
                        mol_type = other RNA
                        organism = synthetic construct
SEQUENCE: 300
aataattatt taaagagttt att                                           23

SEQ ID NO: 301          moltype = RNA  length = 23
FEATURE                 Location/Qualifiers
source                  1..23
                        mol_type = other RNA
                        organism = synthetic construct
SEQUENCE: 301
attctacttt ataatttgag tta                                           23

SEQ ID NO: 302          moltype = RNA  length = 23
FEATURE                 Location/Qualifiers
source                  1..23
```

-continued

```
                        mol_type = other RNA
                        organism = synthetic construct
SEQUENCE: 302
ctttacactt tatgatgaag aat                                          23

SEQ ID NO: 303       moltype = RNA  length = 23
FEATURE              Location/Qualifiers
source               1..23
                     mol_type = other RNA
                     organism = synthetic construct
SEQUENCE: 303
gcattttaaa attgttttta gtg                                          23

SEQ ID NO: 304       moltype = RNA  length = 23
FEATURE              Location/Qualifiers
source               1..23
                     mol_type = other RNA
                     organism = synthetic construct
SEQUENCE: 304
agaacttatt ctatagtaga aca                                          23

SEQ ID NO: 305       moltype = RNA  length = 23
FEATURE              Location/Qualifiers
source               1..23
                     mol_type = other RNA
                     organism = synthetic construct
SEQUENCE: 305
ctgtaaatta agataagaac tta                                          23

SEQ ID NO: 306       moltype = RNA  length = 23
FEATURE              Location/Qualifiers
source               1..23
                     mol_type = other RNA
                     organism = synthetic construct
SEQUENCE: 306
gtgccctgta aattaagata aga                                          23

SEQ ID NO: 307       moltype = RNA  length = 23
FEATURE              Location/Qualifiers
source               1..23
                     mol_type = other RNA
                     organism = synthetic construct
SEQUENCE: 307
acatatttga gcatttagta tat                                          23

SEQ ID NO: 308       moltype = RNA  length = 23
FEATURE              Location/Qualifiers
source               1..23
                     mol_type = other RNA
                     organism = synthetic construct
SEQUENCE: 308
tattaaattt taaaaataaa ttg                                          23

SEQ ID NO: 309       moltype = RNA  length = 23
FEATURE              Location/Qualifiers
source               1..23
                     mol_type = other RNA
                     organism = synthetic construct
SEQUENCE: 309
aatataaaag gcaacattaa gca                                          23

SEQ ID NO: 310       moltype = RNA  length = 23
FEATURE              Location/Qualifiers
source               1..23
                     mol_type = other RNA
                     organism = synthetic construct
SEQUENCE: 310
ttcaagaaca ttcattttaa tat                                          23

SEQ ID NO: 311       moltype = RNA  length = 23
FEATURE              Location/Qualifiers
source               1..23
                     mol_type = other RNA
                     organism = synthetic construct
SEQUENCE: 311
atatattctt aaccaattaa aat                                          23

SEQ ID NO: 312       moltype = RNA  length = 23
FEATURE              Location/Qualifiers
```

-continued

```
source                  1..23
                        mol_type = other RNA
                        organism = synthetic construct
SEQUENCE: 312
ctgatttgca ttaaacaaat ata                                                 23

SEQ ID NO: 313          moltype = RNA   length = 23
FEATURE                 Location/Qualifiers
source                  1..23
                        mol_type = other RNA
                        organism = synthetic construct
SEQUENCE: 313
attttaatat agtgattctg att                                                 23

SEQ ID NO: 314          moltype = RNA   length = 23
FEATURE                 Location/Qualifiers
source                  1..23
                        mol_type = other RNA
                        organism = synthetic construct
SEQUENCE: 314
aaaaggcaac attaagcatt tta                                                 23

SEQ ID NO: 315          moltype = RNA   length = 21
FEATURE                 Location/Qualifiers
source                  1..21
                        mol_type = other RNA
                        organism = synthetic construct
SEQUENCE: 315
caatactcta tactgtgatg a                                                   21

SEQ ID NO: 316          moltype = RNA   length = 21
FEATURE                 Location/Qualifiers
source                  1..21
                        mol_type = other RNA
                        organism = synthetic construct
SEQUENCE: 316
aaaactcccc agctaaacac c                                                   21

SEQ ID NO: 317          moltype = RNA   length = 21
FEATURE                 Location/Qualifiers
source                  1..21
                        mol_type = other RNA
                        organism = synthetic construct
SEQUENCE: 317
aaactgggtg acagagtcag a                                                   21

SEQ ID NO: 318          moltype = RNA   length = 21
FEATURE                 Location/Qualifiers
source                  1..21
                        mol_type = other RNA
                        organism = synthetic construct
SEQUENCE: 318
atcacagctg ccaaggctac c                                                   21

SEQ ID NO: 319          moltype = RNA   length = 21
FEATURE                 Location/Qualifiers
source                  1..21
                        mol_type = other RNA
                        organism = synthetic construct
SEQUENCE: 319
ccgtaagact tcatacaaca c                                                   21

SEQ ID NO: 320          moltype = RNA   length = 21
FEATURE                 Location/Qualifiers
source                  1..21
                        mol_type = other RNA
                        organism = synthetic construct
SEQUENCE: 320
ctaaaagaag acagttatct c                                                   21

SEQ ID NO: 321          moltype = RNA   length = 21
FEATURE                 Location/Qualifiers
source                  1..21
                        mol_type = other RNA
                        organism = synthetic construct
SEQUENCE: 321
cctgctggta tcatggagaa a                                                   21

SEQ ID NO: 322          moltype = RNA   length = 21
```

-continued

```
FEATURE                 Location/Qualifiers
source                  1..21
                        mol_type = other RNA
                        organism = synthetic construct
SEQUENCE: 322
catatttggc tgccagcttt t                                        21

SEQ ID NO: 323          moltype = RNA  length = 21
FEATURE                 Location/Qualifiers
source                  1..21
                        mol_type = other RNA
                        organism = synthetic construct
SEQUENCE: 323
ttatctttct ctcgaccact t                                        21

SEQ ID NO: 324          moltype = RNA  length = 21
FEATURE                 Location/Qualifiers
source                  1..21
                        mol_type = other RNA
                        organism = synthetic construct
SEQUENCE: 324
taaaacttca gacttcctgt c                                        21

SEQ ID NO: 325          moltype = RNA  length = 21
FEATURE                 Location/Qualifiers
source                  1..21
                        mol_type = other RNA
                        organism = synthetic construct
SEQUENCE: 325
cagctataag aagagcctca a                                        21

SEQ ID NO: 326          moltype = RNA  length = 21
FEATURE                 Location/Qualifiers
source                  1..21
                        mol_type = other RNA
                        organism = synthetic construct
SEQUENCE: 326
agtccaatac ctcactcgct c                                        21

SEQ ID NO: 327          moltype = RNA  length = 21
FEATURE                 Location/Qualifiers
source                  1..21
                        mol_type = other RNA
                        organism = synthetic construct
SEQUENCE: 327
accattgaaa tgcctcaaca a                                        21

SEQ ID NO: 328          moltype = RNA  length = 21
FEATURE                 Location/Qualifiers
source                  1..21
                        mol_type = other RNA
                        organism = synthetic construct
SEQUENCE: 328
agcacgtcaa aagctacaga a                                        21

SEQ ID NO: 329          moltype = RNA  length = 21
FEATURE                 Location/Qualifiers
source                  1..21
                        mol_type = other RNA
                        organism = synthetic construct
SEQUENCE: 329
tgcttctctg aagttctgct a                                        21

SEQ ID NO: 330          moltype = RNA  length = 21
FEATURE                 Location/Qualifiers
source                  1..21
                        mol_type = other RNA
                        organism = synthetic construct
SEQUENCE: 330
gctgatctgt atcatcgtga t                                        21

SEQ ID NO: 331          moltype = RNA  length = 21
FEATURE                 Location/Qualifiers
source                  1..21
                        mol_type = other RNA
                        organism = synthetic construct
SEQUENCE: 331
atctatttat caatttctgt c                                        21
```

-continued

```
SEQ ID NO: 332           moltype = RNA   length = 21
FEATURE                  Location/Qualifiers
source                   1..21
                         mol_type = other RNA
                         organism = synthetic construct
SEQUENCE: 332
ctcatcttaa tatgtctctt g                                          21

SEQ ID NO: 333           moltype = RNA   length = 21
FEATURE                  Location/Qualifiers
source                   1..21
                         mol_type = other RNA
                         organism = synthetic construct
SEQUENCE: 333
acaacctcta gatctgcagc t                                          21

SEQ ID NO: 334           moltype = RNA   length = 21
FEATURE                  Location/Qualifiers
source                   1..21
                         mol_type = other RNA
                         organism = synthetic construct
SEQUENCE: 334
gaaaacaata ttgtataaca g                                          21

SEQ ID NO: 335           moltype = RNA   length = 21
FEATURE                  Location/Qualifiers
source                   1..21
                         mol_type = other RNA
                         organism = synthetic construct
SEQUENCE: 335
ttgccacatc agcttaaaat c                                          21

SEQ ID NO: 336           moltype = RNA   length = 21
FEATURE                  Location/Qualifiers
source                   1..21
                         mol_type = other RNA
                         organism = synthetic construct
SEQUENCE: 336
ctgtcatccc atgcagacag g                                          21

SEQ ID NO: 337           moltype = RNA   length = 21
FEATURE                  Location/Qualifiers
source                   1..21
                         mol_type = other RNA
                         organism = synthetic construct
SEQUENCE: 337
gaccacttcc tgagtagaag a                                          21

SEQ ID NO: 338           moltype = RNA   length = 21
FEATURE                  Location/Qualifiers
source                   1..21
                         mol_type = other RNA
                         organism = synthetic construct
SEQUENCE: 338
agtttctttg tgaaaaggtc a                                          21

SEQ ID NO: 339           moltype = RNA   length = 21
FEATURE                  Location/Qualifiers
source                   1..21
                         mol_type = other RNA
                         organism = synthetic construct
SEQUENCE: 339
gtataaaatg caactgttga t                                          21

SEQ ID NO: 340           moltype = RNA   length = 21
FEATURE                  Location/Qualifiers
source                   1..21
                         mol_type = other RNA
                         organism = synthetic construct
SEQUENCE: 340
aaattaactt caaaataagt g                                          21

SEQ ID NO: 341           moltype = RNA   length = 21
FEATURE                  Location/Qualifiers
source                   1..21
                         mol_type = other RNA
                         organism = synthetic construct
SEQUENCE: 341
aagattaaga ctaaaactta t                                          21
```

```
SEQ ID NO: 342          moltype = RNA   length = 21
FEATURE                 Location/Qualifiers
source                  1..21
                        mol_type = other RNA
                        organism = synthetic construct
SEQUENCE: 342
ctgttggatc ttgtaaacat g                                                 21

SEQ ID NO: 343          moltype = RNA   length = 21
FEATURE                 Location/Qualifiers
source                  1..21
                        mol_type = other RNA
                        organism = synthetic construct
SEQUENCE: 343
ttgttaccat atgtattcat c                                                 21

SEQ ID NO: 344          moltype = RNA   length = 21
FEATURE                 Location/Qualifiers
source                  1..21
                        mol_type = other RNA
                        organism = synthetic construct
SEQUENCE: 344
gaaaagggct ttattttcaa a                                                 21

SEQ ID NO: 345          moltype = RNA   length = 21
FEATURE                 Location/Qualifiers
source                  1..21
                        mol_type = other RNA
                        organism = synthetic construct
SEQUENCE: 345
tctgaagatg aagagtttag t                                                 21

SEQ ID NO: 346          moltype = RNA   length = 21
FEATURE                 Location/Qualifiers
source                  1..21
                        mol_type = other RNA
                        organism = synthetic construct
SEQUENCE: 346
agcattattt ttactctttt g                                                 21

SEQ ID NO: 347          moltype = RNA   length = 21
FEATURE                 Location/Qualifiers
source                  1..21
                        mol_type = other RNA
                        organism = synthetic construct
SEQUENCE: 347
tttcctcaac atggctcaca a                                                 21

SEQ ID NO: 348          moltype = RNA   length = 21
FEATURE                 Location/Qualifiers
source                  1..21
                        mol_type = other RNA
                        organism = synthetic construct
SEQUENCE: 348
ttttaaaact gcactgccaa c                                                 21

SEQ ID NO: 349          moltype = RNA   length = 21
FEATURE                 Location/Qualifiers
source                  1..21
                        mol_type = other RNA
                        organism = synthetic construct
SEQUENCE: 349
caagttcact tcatatataa a                                                 21

SEQ ID NO: 350          moltype = RNA   length = 21
FEATURE                 Location/Qualifiers
source                  1..21
                        mol_type = other RNA
                        organism = synthetic construct
SEQUENCE: 350
aatttctatc ccaaatcttt t                                                 21

SEQ ID NO: 351          moltype = RNA   length = 21
FEATURE                 Location/Qualifiers
source                  1..21
                        mol_type = other RNA
                        organism = synthetic construct
SEQUENCE: 351
```

-continued

```
tcttcaccaa gtatcaaagt a                                           21

SEQ ID NO: 352          moltype = RNA   length = 21
FEATURE                 Location/Qualifiers
source                  1..21
                        mol_type = other RNA
                        organism = synthetic construct
SEQUENCE: 352
aataacacaa atgaagtgtc a                                           21

SEQ ID NO: 353          moltype = RNA   length = 21
FEATURE                 Location/Qualifiers
source                  1..21
                        mol_type = other RNA
                        organism = synthetic construct
SEQUENCE: 353
gaggtgaata taatttatat t                                           21

SEQ ID NO: 354          moltype = RNA   length = 21
FEATURE                 Location/Qualifiers
source                  1..21
                        mol_type = other RNA
                        organism = synthetic construct
SEQUENCE: 354
aatactaagt atttttcagg t                                           21

SEQ ID NO: 355          moltype = RNA   length = 21
FEATURE                 Location/Qualifiers
source                  1..21
                        mol_type = other RNA
                        organism = synthetic construct
SEQUENCE: 355
tacaatgtaa aagcttcttt a                                           21

SEQ ID NO: 356          moltype = RNA   length = 21
FEATURE                 Location/Qualifiers
source                  1..21
                        mol_type = other RNA
                        organism = synthetic construct
SEQUENCE: 356
accaagtatc aaagtaataa c                                           21

SEQ ID NO: 357          moltype = RNA   length = 21
FEATURE                 Location/Qualifiers
source                  1..21
                        mol_type = other RNA
                        organism = synthetic construct
SEQUENCE: 357
tagtaactat cagaatctac a                                           21

SEQ ID NO: 358          moltype = RNA   length = 21
FEATURE                 Location/Qualifiers
source                  1..21
                        mol_type = other RNA
                        organism = synthetic construct
SEQUENCE: 358
attattcaaa atagtccact g                                           21

SEQ ID NO: 359          moltype = RNA   length = 21
FEATURE                 Location/Qualifiers
source                  1..21
                        mol_type = other RNA
                        organism = synthetic construct
SEQUENCE: 359
gactcctcac atctgttatc t                                           21

SEQ ID NO: 360          moltype = RNA   length = 21
FEATURE                 Location/Qualifiers
source                  1..21
                        mol_type = other RNA
                        organism = synthetic construct
SEQUENCE: 360
attctaaaac agaaattgta t                                           21

SEQ ID NO: 361          moltype = RNA   length = 21
FEATURE                 Location/Qualifiers
source                  1..21
                        mol_type = other RNA
                        organism = synthetic construct
```

-continued

```
SEQUENCE: 361
ttattataaa gaactatttg t                                          21

SEQ ID NO: 362          moltype = RNA  length = 21
FEATURE                 Location/Qualifiers
source                  1..21
                        mol_type = other RNA
                        organism = synthetic construct
SEQUENCE: 362
ttttttctat gccacattaa c                                          21

SEQ ID NO: 363          moltype = RNA  length = 21
FEATURE                 Location/Qualifiers
source                  1..21
                        mol_type = other RNA
                        organism = synthetic construct
SEQUENCE: 363
aatcaagtat ggaaaagtaa g                                          21

SEQ ID NO: 364          moltype = RNA  length = 21
FEATURE                 Location/Qualifiers
source                  1..21
                        mol_type = other RNA
                        organism = synthetic construct
SEQUENCE: 364
ggccatactc ttacataata a                                          21

SEQ ID NO: 365          moltype = RNA  length = 21
FEATURE                 Location/Qualifiers
source                  1..21
                        mol_type = other RNA
                        organism = synthetic construct
SEQUENCE: 365
catcttttaa agttgatgag a                                          21

SEQ ID NO: 366          moltype = RNA  length = 21
FEATURE                 Location/Qualifiers
source                  1..21
                        mol_type = other RNA
                        organism = synthetic construct
SEQUENCE: 366
agttgatgag aatcaagtat g                                          21

SEQ ID NO: 367          moltype = RNA  length = 21
FEATURE                 Location/Qualifiers
source                  1..21
                        mol_type = other RNA
                        organism = synthetic construct
SEQUENCE: 367
aaattccttt taagtaattt t                                          21

SEQ ID NO: 368          moltype = RNA  length = 21
FEATURE                 Location/Qualifiers
source                  1..21
                        mol_type = other RNA
                        organism = synthetic construct
SEQUENCE: 368
tttcaaagaa tcacagaatt c                                          21

SEQ ID NO: 369          moltype = RNA  length = 21
FEATURE                 Location/Qualifiers
source                  1..21
                        mol_type = other RNA
                        organism = synthetic construct
SEQUENCE: 369
ataaatctgt tctaagacat a                                          21

SEQ ID NO: 370          moltype = RNA  length = 21
FEATURE                 Location/Qualifiers
source                  1..21
                        mol_type = other RNA
                        organism = synthetic construct
SEQUENCE: 370
gagattagtc atatcactaa t                                          21

SEQ ID NO: 371          moltype = RNA  length = 21
FEATURE                 Location/Qualifiers
source                  1..21
                        mol_type = other RNA
```

```
                        organism = synthetic construct
SEQUENCE: 371
ggtggttaat atgtgacagt g                                            21

SEQ ID NO: 372          moltype = RNA   length = 21
FEATURE                 Location/Qualifiers
source                  1..21
                        mol_type = other RNA
                        organism = synthetic construct
SEQUENCE: 372
tatactaaca acagaatcta a                                            21

SEQ ID NO: 373          moltype = RNA   length = 21
FEATURE                 Location/Qualifiers
source                  1..21
                        mol_type = other RNA
                        organism = synthetic construct
SEQUENCE: 373
atgatcaaca gatgagaact g                                            21

SEQ ID NO: 374          moltype = RNA   length = 21
FEATURE                 Location/Qualifiers
source                  1..21
                        mol_type = other RNA
                        organism = synthetic construct
SEQUENCE: 374
ctagtacatg taggtaaatc a                                            21

SEQ ID NO: 375          moltype = RNA   length = 21
FEATURE                 Location/Qualifiers
source                  1..21
                        mol_type = other RNA
                        organism = synthetic construct
SEQUENCE: 375
gttacctagc ttaccatact a                                            21

SEQ ID NO: 376          moltype = RNA   length = 21
FEATURE                 Location/Qualifiers
source                  1..21
                        mol_type = other RNA
                        organism = synthetic construct
SEQUENCE: 376
atcttcattt aaggcactgt a                                            21

SEQ ID NO: 377          moltype = RNA   length = 21
FEATURE                 Location/Qualifiers
source                  1..21
                        mol_type = other RNA
                        organism = synthetic construct
SEQUENCE: 377
agtgaattat ctgagctaga g                                            21

SEQ ID NO: 378          moltype = RNA   length = 21
FEATURE                 Location/Qualifiers
source                  1..21
                        mol_type = other RNA
                        organism = synthetic construct
SEQUENCE: 378
cctagcttac catactatat c                                            21

SEQ ID NO: 379          moltype = RNA   length = 21
FEATURE                 Location/Qualifiers
source                  1..21
                        mol_type = other RNA
                        organism = synthetic construct
SEQUENCE: 379
catactatat ctttggaatc a                                            21

SEQ ID NO: 380          moltype = RNA   length = 21
FEATURE                 Location/Qualifiers
source                  1..21
                        mol_type = other RNA
                        organism = synthetic construct
SEQUENCE: 380
cttaccatac tatatctttg g                                            21

SEQ ID NO: 381          moltype = RNA   length = 21
FEATURE                 Location/Qualifiers
source                  1..21
```

-continued

```
                        mol_type = other RNA
                        organism = synthetic construct
SEQUENCE: 381
ccagcctaac atccaatgca g                                        21

SEQ ID NO: 382        moltype = RNA  length = 21
FEATURE               Location/Qualifiers
source                1..21
                      mol_type = other RNA
                      organism = synthetic construct
SEQUENCE: 382
atatctttgg aatcatgaaa c                                        21

SEQ ID NO: 383        moltype = RNA  length = 21
FEATURE               Location/Qualifiers
source                1..21
                      mol_type = other RNA
                      organism = synthetic construct
SEQUENCE: 383
ggcaaggaaa ataaaagatt t                                        21

SEQ ID NO: 384        moltype = RNA  length = 21
FEATURE               Location/Qualifiers
source                1..21
                      mol_type = other RNA
                      organism = synthetic construct
SEQUENCE: 384
tttgcaggtt gtcttccatt c                                        21

SEQ ID NO: 385        moltype = RNA  length = 21
FEATURE               Location/Qualifiers
source                1..21
                      mol_type = other RNA
                      organism = synthetic construct
SEQUENCE: 385
tccagtgaca gaaaaatata t                                        21

SEQ ID NO: 386        moltype = RNA  length = 21
FEATURE               Location/Qualifiers
source                1..21
                      mol_type = other RNA
                      organism = synthetic construct
SEQUENCE: 386
ccttaagact tcagaatgat t                                        21

SEQ ID NO: 387        moltype = RNA  length = 21
FEATURE               Location/Qualifiers
source                1..21
                      mol_type = other RNA
                      organism = synthetic construct
SEQUENCE: 387
ttatctcaag tattttttaa a                                        21

SEQ ID NO: 388        moltype = RNA  length = 21
FEATURE               Location/Qualifiers
source                1..21
                      mol_type = other RNA
                      organism = synthetic construct
SEQUENCE: 388
caaatattaa ctaattatta g                                        21

SEQ ID NO: 389        moltype = RNA  length = 21
FEATURE               Location/Qualifiers
source                1..21
                      mol_type = other RNA
                      organism = synthetic construct
SEQUENCE: 389
aaatatatga attctctctc c                                        21

SEQ ID NO: 390        moltype = RNA  length = 21
FEATURE               Location/Qualifiers
source                1..21
                      mol_type = other RNA
                      organism = synthetic construct
SEQUENCE: 390
ttgttggccc atctattaca t                                        21

SEQ ID NO: 391        moltype = RNA  length = 21
FEATURE               Location/Qualifiers
```

-continued

```
source                  1..21
                        mol_type = other RNA
                        organism = synthetic construct
SEQUENCE: 391
tctacagctg acccttgaac a                                          21

SEQ ID NO: 392          moltype = RNA   length = 21
FEATURE                 Location/Qualifiers
source                  1..21
                        mol_type = other RNA
                        organism = synthetic construct
SEQUENCE: 392
gattatattt tgaaatgaac t                                          21

SEQ ID NO: 393          moltype = RNA   length = 21
FEATURE                 Location/Qualifiers
source                  1..21
                        mol_type = other RNA
                        organism = synthetic construct
SEQUENCE: 393
atgggggtta ggggagctga c                                          21

SEQ ID NO: 394          moltype = RNA   length = 21
FEATURE                 Location/Qualifiers
source                  1..21
                        mol_type = other RNA
                        organism = synthetic construct
SEQUENCE: 394
gggtccgcaa aatcttaact a                                          21

SEQ ID NO: 395          moltype = RNA   length = 21
FEATURE                 Location/Qualifiers
source                  1..21
                        mol_type = other RNA
                        organism = synthetic construct
SEQUENCE: 395
ctgataacat aaacagtaaa t                                          21

SEQ ID NO: 396          moltype = RNA   length = 21
FEATURE                 Location/Qualifiers
source                  1..21
                        mol_type = other RNA
                        organism = synthetic construct
SEQUENCE: 396
actattgacc ataaacctta c                                          21

SEQ ID NO: 397          moltype = RNA   length = 21
FEATURE                 Location/Qualifiers
source                  1..21
                        mol_type = other RNA
                        organism = synthetic construct
SEQUENCE: 397
tcttaactac ctaatagcct a                                          21

SEQ ID NO: 398          moltype = RNA   length = 21
FEATURE                 Location/Qualifiers
source                  1..21
                        mol_type = other RNA
                        organism = synthetic construct
SEQUENCE: 398
caattcgtgg gtccgcaaaa t                                          21

SEQ ID NO: 399          moltype = RNA   length = 21
FEATURE                 Location/Qualifiers
source                  1..21
                        mol_type = other RNA
                        organism = synthetic construct
SEQUENCE: 399
aatcataaga aagagaaaat a                                          21

SEQ ID NO: 400          moltype = RNA   length = 21
FEATURE                 Location/Qualifiers
source                  1..21
                        mol_type = other RNA
                        organism = synthetic construct
SEQUENCE: 400
ttcctacaat aaagtaagct a                                          21

SEQ ID NO: 401          moltype = RNA   length = 21
```

-continued

```
FEATURE                 Location/Qualifiers
source                  1..21
                        mol_type = other RNA
                        organism = synthetic construct
SEQUENCE: 401
atatttacta ttcattaaat g                                     21

SEQ ID NO: 402          moltype = RNA   length = 21
FEATURE                 Location/Qualifiers
source                  1..21
                        mol_type = other RNA
                        organism = synthetic construct
SEQUENCE: 402
ttaacacata ttttgcgtgt t                                     21

SEQ ID NO: 403          moltype = RNA   length = 21
FEATURE                 Location/Qualifiers
source                  1..21
                        mol_type = other RNA
                        organism = synthetic construct
SEQUENCE: 403
agagaaaatg ttatttagaa a                                     21

SEQ ID NO: 404          moltype = RNA   length = 21
FEATURE                 Location/Qualifiers
source                  1..21
                        mol_type = other RNA
                        organism = synthetic construct
SEQUENCE: 404
tatatgtatt atacactata t                                     21

SEQ ID NO: 405          moltype = RNA   length = 21
FEATURE                 Location/Qualifiers
source                  1..21
                        mol_type = other RNA
                        organism = synthetic construct
SEQUENCE: 405
cacattgagt aggcagagga g                                     21

SEQ ID NO: 406          moltype = RNA   length = 21
FEATURE                 Location/Qualifiers
source                  1..21
                        mol_type = other RNA
                        organism = synthetic construct
SEQUENCE: 406
tcttgtctta ggggtgtggg g                                     21

SEQ ID NO: 407          moltype = RNA   length = 21
FEATURE                 Location/Qualifiers
source                  1..21
                        mol_type = other RNA
                        organism = synthetic construct
SEQUENCE: 407
ggagaaagat ggggaggaag a                                     21

SEQ ID NO: 408          moltype = RNA   length = 21
FEATURE                 Location/Qualifiers
source                  1..21
                        mol_type = other RNA
                        organism = synthetic construct
SEQUENCE: 408
ggaagtgggt caacataaaa g                                     21

SEQ ID NO: 409          moltype = RNA   length = 21
FEATURE                 Location/Qualifiers
source                  1..21
                        mol_type = other RNA
                        organism = synthetic construct
SEQUENCE: 409
gtcttcattc tcattgtctt c                                     21

SEQ ID NO: 410          moltype = RNA   length = 21
FEATURE                 Location/Qualifiers
source                  1..21
                        mol_type = other RNA
                        organism = synthetic construct
SEQUENCE: 410
agaaggcgtt ggtcttgcag t                                     21
```

-continued

```
SEQ ID NO: 411            moltype = RNA   length = 21
FEATURE                   Location/Qualifiers
source                    1..21
                          mol_type = other RNA
                          organism = synthetic construct
SEQUENCE: 411
gagtgggggga aagaatattc a                                     21

SEQ ID NO: 412            moltype = RNA   length = 21
FEATURE                   Location/Qualifiers
source                    1..21
                          mol_type = other RNA
                          organism = synthetic construct
SEQUENCE: 412
atgtataagt ggacccttgc a                                      21

SEQ ID NO: 413            moltype = RNA   length = 21
FEATURE                   Location/Qualifiers
source                    1..21
                          mol_type = other RNA
                          organism = synthetic construct
SEQUENCE: 413
aagggtcaac tgtaatagga t                                      21

SEQ ID NO: 414            moltype = RNA   length = 21
FEATURE                   Location/Qualifiers
source                    1..21
                          mol_type = other RNA
                          organism = synthetic construct
SEQUENCE: 414
tatagctatt tttcttcctc t                                      21

SEQ ID NO: 415            moltype = RNA   length = 21
FEATURE                   Location/Qualifiers
source                    1..21
                          mol_type = other RNA
                          organism = synthetic construct
SEQUENCE: 415
tatcaaccaa atggtaagca t                                      21

SEQ ID NO: 416            moltype = RNA   length = 21
FEATURE                   Location/Qualifiers
source                    1..21
                          mol_type = other RNA
                          organism = synthetic construct
SEQUENCE: 416
aattcaagcc cttgttgttc a                                      21

SEQ ID NO: 417            moltype = RNA   length = 21
FEATURE                   Location/Qualifiers
source                    1..21
                          mol_type = other RNA
                          organism = synthetic construct
SEQUENCE: 417
attttcttga tgaataaatt t                                      21

SEQ ID NO: 418            moltype = RNA   length = 21
FEATURE                   Location/Qualifiers
source                    1..21
                          mol_type = other RNA
                          organism = synthetic construct
SEQUENCE: 418
tttcagaaca tcttccaata a                                      21

SEQ ID NO: 419            moltype = RNA   length = 21
FEATURE                   Location/Qualifiers
source                    1..21
                          mol_type = other RNA
                          organism = synthetic construct
SEQUENCE: 419
actgagctaa attatagatc c                                      21

SEQ ID NO: 420            moltype = RNA   length = 21
FEATURE                   Location/Qualifiers
source                    1..21
                          mol_type = other RNA
                          organism = synthetic construct
SEQUENCE: 420
cagctatgct atttataatt a                                      21
```

-continued

```
SEQ ID NO: 421               moltype = RNA   length = 21
FEATURE                      Location/Qualifiers
source                       1..21
                             mol_type = other RNA
                             organism = synthetic construct
SEQUENCE: 421
ttcaatttct cctctgacca t                                            21

SEQ ID NO: 422               moltype = RNA   length = 21
FEATURE                      Location/Qualifiers
source                       1..21
                             mol_type = other RNA
                             organism = synthetic construct
SEQUENCE: 422
tctattttgc agtccactct a                                            21

SEQ ID NO: 423               moltype = RNA   length = 21
FEATURE                      Location/Qualifiers
source                       1..21
                             mol_type = other RNA
                             organism = synthetic construct
SEQUENCE: 423
atattcacca aactttggta a                                            21

SEQ ID NO: 424               moltype = RNA   length = 21
FEATURE                      Location/Qualifiers
source                       1..21
                             mol_type = other RNA
                             organism = synthetic construct
SEQUENCE: 424
ttcaccctat actgcataat c                                            21

SEQ ID NO: 425               moltype = RNA   length = 21
FEATURE                      Location/Qualifiers
source                       1..21
                             mol_type = other RNA
                             organism = synthetic construct
SEQUENCE: 425
aaaattgagt gctggaaaat a                                            21

SEQ ID NO: 426               moltype = RNA   length = 21
FEATURE                      Location/Qualifiers
source                       1..21
                             mol_type = other RNA
                             organism = synthetic construct
SEQUENCE: 426
aaaattaagt ctaaaatagt t                                            21

SEQ ID NO: 427               moltype = RNA   length = 21
FEATURE                      Location/Qualifiers
source                       1..21
                             mol_type = other RNA
                             organism = synthetic construct
SEQUENCE: 427
atttaagttg actaaagttt a                                            21

SEQ ID NO: 428               moltype = RNA   length = 21
FEATURE                      Location/Qualifiers
source                       1..21
                             mol_type = other RNA
                             organism = synthetic construct
SEQUENCE: 428
actcataaaa caactgaagt a                                            21

SEQ ID NO: 429               moltype = RNA   length = 21
FEATURE                      Location/Qualifiers
source                       1..21
                             mol_type = other RNA
                             organism = synthetic construct
SEQUENCE: 429
ccaacaattt taatttcagt t                                            21

SEQ ID NO: 430               moltype = RNA   length = 21
FEATURE                      Location/Qualifiers
source                       1..21
                             mol_type = other RNA
                             organism = synthetic construct
SEQUENCE: 430
```

-continued

```
tgaagacatg ttactaatat a                                          21

SEQ ID NO: 431         moltype = RNA   length = 21
FEATURE                Location/Qualifiers
source                 1..21
                       mol_type = other RNA
                       organism = synthetic construct
SEQUENCE: 431
tcttctaaaa catggttact a                                          21

SEQ ID NO: 432         moltype = RNA   length = 21
FEATURE                Location/Qualifiers
source                 1..21
                       mol_type = other RNA
                       organism = synthetic construct
SEQUENCE: 432
aggatgtgta attaaccata t                                          21

SEQ ID NO: 433         moltype = RNA   length = 21
FEATURE                Location/Qualifiers
source                 1..21
                       mol_type = other RNA
                       organism = synthetic construct
SEQUENCE: 433
aaaagaatat gtaacatcaa t                                          21

SEQ ID NO: 434         moltype = RNA   length = 21
FEATURE                Location/Qualifiers
source                 1..21
                       mol_type = other RNA
                       organism = synthetic construct
SEQUENCE: 434
aactattatt aaaagagtag a                                          21

SEQ ID NO: 435         moltype = RNA   length = 21
FEATURE                Location/Qualifiers
source                 1..21
                       mol_type = other RNA
                       organism = synthetic construct
SEQUENCE: 435
aaagtgtttg gttcagggat a                                          21

SEQ ID NO: 436         moltype = RNA   length = 21
FEATURE                Location/Qualifiers
source                 1..21
                       mol_type = other RNA
                       organism = synthetic construct
SEQUENCE: 436
attttctgaa cccatgagag a                                          21

SEQ ID NO: 437         moltype = RNA   length = 21
FEATURE                Location/Qualifiers
source                 1..21
                       mol_type = other RNA
                       organism = synthetic construct
SEQUENCE: 437
acaagtgttg ctaactcaat a                                          21

SEQ ID NO: 438         moltype = RNA   length = 21
FEATURE                Location/Qualifiers
source                 1..21
                       mol_type = other RNA
                       organism = synthetic construct
SEQUENCE: 438
tattgacctt ggtttcttac a                                          21

SEQ ID NO: 439         moltype = RNA   length = 21
FEATURE                Location/Qualifiers
source                 1..21
                       mol_type = other RNA
                       organism = synthetic construct
SEQUENCE: 439
tcatctacaa gctggaaatt c                                          21

SEQ ID NO: 440         moltype = RNA   length = 21
FEATURE                Location/Qualifiers
source                 1..21
                       mol_type = other RNA
                       organism = synthetic construct
```

-continued

```
SEQUENCE: 440
agtgaaggag acactattaa a                                                        21

SEQ ID NO: 441        moltype = RNA  length = 21
FEATURE               Location/Qualifiers
source                1..21
                      mol_type = other RNA
                      organism = synthetic construct
SEQUENCE: 441
atactagaga tggggagtgg a                                                        21

SEQ ID NO: 442        moltype = RNA  length = 21
FEATURE               Location/Qualifiers
source                1..21
                      mol_type = other RNA
                      organism = synthetic construct
SEQUENCE: 442
actcacctca ctggtttttag t                                                       21

SEQ ID NO: 443        moltype = RNA  length = 21
FEATURE               Location/Qualifiers
source                1..21
                      mol_type = other RNA
                      organism = synthetic construct
SEQUENCE: 443
gagatttctt aagtgacgcc t                                                        21

SEQ ID NO: 444        moltype = RNA  length = 21
FEATURE               Location/Qualifiers
source                1..21
                      mol_type = other RNA
                      organism = synthetic construct
SEQUENCE: 444
ttataaacaa caggtgatac a                                                        21

SEQ ID NO: 445        moltype = RNA  length = 21
FEATURE               Location/Qualifiers
source                1..21
                      mol_type = other RNA
                      organism = synthetic construct
SEQUENCE: 445
atctgaagaa cagaagggca g                                                        21

SEQ ID NO: 446        moltype = RNA  length = 21
FEATURE               Location/Qualifiers
source                1..21
                      mol_type = other RNA
                      organism = synthetic construct
SEQUENCE: 446
cctaaaaaca agtagaaagc t                                                        21

SEQ ID NO: 447        moltype = RNA  length = 21
FEATURE               Location/Qualifiers
source                1..21
                      mol_type = other RNA
                      organism = synthetic construct
SEQUENCE: 447
taaattacca atacagaaag t                                                        21

SEQ ID NO: 448        moltype = RNA  length = 21
FEATURE               Location/Qualifiers
source                1..21
                      mol_type = other RNA
                      organism = synthetic construct
SEQUENCE: 448
agtggaaaat ttgaactgat t                                                        21

SEQ ID NO: 449        moltype = RNA  length = 21
FEATURE               Location/Qualifiers
source                1..21
                      mol_type = other RNA
                      organism = synthetic construct
SEQUENCE: 449
cactgtttgt tacaatattt t                                                        21

SEQ ID NO: 450        moltype = RNA  length = 21
FEATURE               Location/Qualifiers
source                1..21
                      mol_type = other RNA
```

-continued

```
                            organism = synthetic construct
SEQUENCE: 450
ttctcagtaa acagaaataa c                                          21

SEQ ID NO: 451          moltype = RNA   length = 21
FEATURE                 Location/Qualifiers
source                  1..21
                        mol_type = other RNA
                        organism = synthetic construct
SEQUENCE: 451
tatccctagt cttaaaaaca a                                          21

SEQ ID NO: 452          moltype = RNA   length = 21
FEATURE                 Location/Qualifiers
source                  1..21
                        mol_type = other RNA
                        organism = synthetic construct
SEQUENCE: 452
tagtcatatt cctttgatta c                                          21

SEQ ID NO: 453          moltype = RNA   length = 21
FEATURE                 Location/Qualifiers
source                  1..21
                        mol_type = other RNA
                        organism = synthetic construct
SEQUENCE: 453
ctaatttttt tgttcttcat t                                          21

SEQ ID NO: 454          moltype = RNA   length = 21
FEATURE                 Location/Qualifiers
source                  1..21
                        mol_type = other RNA
                        organism = synthetic construct
SEQUENCE: 454
aaataattat tcttcatcat a                                          21

SEQ ID NO: 455          moltype = RNA   length = 21
FEATURE                 Location/Qualifiers
source                  1..21
                        mol_type = other RNA
                        organism = synthetic construct
SEQUENCE: 455
taaagtagaa taaactcttt a                                          21

SEQ ID NO: 456          moltype = RNA   length = 21
FEATURE                 Location/Qualifiers
source                  1..21
                        mol_type = other RNA
                        organism = synthetic construct
SEQUENCE: 456
tctttgatag aaattaaaat c                                          21

SEQ ID NO: 457          moltype = RNA   length = 21
FEATURE                 Location/Qualifiers
source                  1..21
                        mol_type = other RNA
                        organism = synthetic construct
SEQUENCE: 457
gaatactata actcaaatta t                                          21

SEQ ID NO: 458          moltype = RNA   length = 21
FEATURE                 Location/Qualifiers
source                  1..21
                        mol_type = other RNA
                        organism = synthetic construct
SEQUENCE: 458
cttattctgt gaggattaca g                                          21

SEQ ID NO: 459          moltype = RNA   length = 21
FEATURE                 Location/Qualifiers
source                  1..21
                        mol_type = other RNA
                        organism = synthetic construct
SEQUENCE: 459
ttacagggca ctaaaaacaa t                                          21

SEQ ID NO: 460          moltype = RNA   length = 21
FEATURE                 Location/Qualifiers
source                  1..21
```

-continued

```
                              mol_type = other RNA
                              organism = synthetic construct
SEQUENCE: 460
ctcaaatatg ttctactata g                                        21

SEQ ID NO: 461          moltype = RNA   length = 21
FEATURE                 Location/Qualifiers
source                  1..21
                        mol_type = other RNA
                        organism = synthetic construct
SEQUENCE: 461
gaataagttc ttatcttaat t                                        21

SEQ ID NO: 462          moltype = RNA   length = 21
FEATURE                 Location/Qualifiers
source                  1..21
                        mol_type = other RNA
                        organism = synthetic construct
SEQUENCE: 462
aaagtgtaaa gaataagata t                                        21

SEQ ID NO: 463          moltype = RNA   length = 21
FEATURE                 Location/Qualifiers
source                  1..21
                        mol_type = other RNA
                        organism = synthetic construct
SEQUENCE: 463
aaaatttaat atactaaatg c                                        21

SEQ ID NO: 464          moltype = RNA   length = 21
FEATURE                 Location/Qualifiers
source                  1..21
                        mol_type = other RNA
                        organism = synthetic construct
SEQUENCE: 464
taagaaaaca atttattttt a                                        21

SEQ ID NO: 465          moltype = RNA   length = 21
FEATURE                 Location/Qualifiers
source                  1..21
                        mol_type = other RNA
                        organism = synthetic construct
SEQUENCE: 465
taagaatata tatttgttta a                                        21

SEQ ID NO: 466          moltype = RNA   length = 21
FEATURE                 Location/Qualifiers
source                  1..21
                        mol_type = other RNA
                        organism = synthetic construct
SEQUENCE: 466
atgaatgttc ttgaaaactc a                                        21

SEQ ID NO: 467          moltype = RNA   length = 21
FEATURE                 Location/Qualifiers
source                  1..21
                        mol_type = other RNA
                        organism = synthetic construct
SEQUENCE: 467
ccttttatat tttaattggt t                                        21

SEQ ID NO: 468          moltype = RNA   length = 21
FEATURE                 Location/Qualifiers
source                  1..21
                        mol_type = other RNA
                        organism = synthetic construct
SEQUENCE: 468
ttttaaaatg cttaatgttg c                                        21

SEQ ID NO: 469          moltype = RNA   length = 21
FEATURE                 Location/Qualifiers
source                  1..21
                        mol_type = other RNA
                        organism = synthetic construct
SEQUENCE: 469
tcactatatt aaaatgaatg t                                        21

SEQ ID NO: 470          moltype = RNA   length = 21
FEATURE                 Location/Qualifiers
```

-continued

```
source                    1..21
                          mol_type = other RNA
                          organism = synthetic construct
SEQUENCE: 470
atgcaaatca gaatcactat a                                              21

SEQ ID NO: 471            moltype = RNA   length = 21
FEATURE                   Location/Qualifiers
source                    1..21
                          mol_type = other RNA
                          organism = synthetic construct
SEQUENCE: 471
tcatacaaca caatactcta t                                              21

SEQ ID NO: 472            moltype = RNA   length = 21
FEATURE                   Location/Qualifiers
source                    1..21
                          mol_type = other RNA
                          organism = synthetic construct
SEQUENCE: 472
tactgtgatg atcacagctg c                                              21

SEQ ID NO: 473            moltype = RNA   length = 21
FEATURE                   Location/Qualifiers
source                    1..21
                          mol_type = other RNA
                          organism = synthetic construct
SEQUENCE: 473
agctaaacac ccgtaagact t                                              21

SEQ ID NO: 474            moltype = RNA   length = 21
FEATURE                   Location/Qualifiers
source                    1..21
                          mol_type = other RNA
                          organism = synthetic construct
SEQUENCE: 474
acagttatct catatttggc t                                              21

SEQ ID NO: 475            moltype = RNA   length = 21
FEATURE                   Location/Qualifiers
source                    1..21
                          mol_type = other RNA
                          organism = synthetic construct
SEQUENCE: 475
ccaaggctac ctaaaagaag a                                              21

SEQ ID NO: 476            moltype = RNA   length = 21
FEATURE                   Location/Qualifiers
source                    1..21
                          mol_type = other RNA
                          organism = synthetic construct
SEQUENCE: 476
acagagtcag aaaactcccc a                                              21

SEQ ID NO: 477            moltype = RNA   length = 21
FEATURE                   Location/Qualifiers
source                    1..21
                          mol_type = other RNA
                          organism = synthetic construct
SEQUENCE: 477
aagagcctca accattgaaa t                                              21

SEQ ID NO: 478            moltype = RNA   length = 21
FEATURE                   Location/Qualifiers
source                    1..21
                          mol_type = other RNA
                          organism = synthetic construct
SEQUENCE: 478
ctcgaccact taaaacttca g                                              21

SEQ ID NO: 479            moltype = RNA   length = 21
FEATURE                   Location/Qualifiers
source                    1..21
                          mol_type = other RNA
                          organism = synthetic construct
SEQUENCE: 479
gacttcctgt cctgctggta t                                              21

SEQ ID NO: 480            moltype = RNA   length = 21
```

-continued

```
FEATURE            Location/Qualifiers
source             1..21
                   mol_type = other RNA
                   organism = synthetic construct
SEQUENCE: 480
tgccagcttt ttatctttct c                                    21

SEQ ID NO: 481     moltype = RNA   length = 21
FEATURE            Location/Qualifiers
source             1..21
                   mol_type = other RNA
                   organism = synthetic construct
SEQUENCE: 481
tcatggagaa agtccaatac c                                    21

SEQ ID NO: 482     moltype = RNA   length = 21
FEATURE            Location/Qualifiers
source             1..21
                   mol_type = other RNA
                   organism = synthetic construct
SEQUENCE: 482
ctcactcgct cagctataag a                                    21

SEQ ID NO: 483     moltype = RNA   length = 21
FEATURE            Location/Qualifiers
source             1..21
                   mol_type = other RNA
                   organism = synthetic construct
SEQUENCE: 483
caatttctgt ctcatcttaa t                                    21

SEQ ID NO: 484     moltype = RNA   length = 21
FEATURE            Location/Qualifiers
source             1..21
                   mol_type = other RNA
                   organism = synthetic construct
SEQUENCE: 484
tatgtctctt gctgatctgt a                                    21

SEQ ID NO: 485     moltype = RNA   length = 21
FEATURE            Location/Qualifiers
source             1..21
                   mol_type = other RNA
                   organism = synthetic construct
SEQUENCE: 485
tgcctcaaca agcacgtcaa a                                    21

SEQ ID NO: 486     moltype = RNA   length = 21
FEATURE            Location/Qualifiers
source             1..21
                   mol_type = other RNA
                   organism = synthetic construct
SEQUENCE: 486
aagttctgct acaacctcta g                                    21

SEQ ID NO: 487     moltype = RNA   length = 21
FEATURE            Location/Qualifiers
source             1..21
                   mol_type = other RNA
                   organism = synthetic construct
SEQUENCE: 487
atcatcgtga tgcttctctg a                                    21

SEQ ID NO: 488     moltype = RNA   length = 21
FEATURE            Location/Qualifiers
source             1..21
                   mol_type = other RNA
                   organism = synthetic construct
SEQUENCE: 488
aagctacaga atctatttat c                                    21

SEQ ID NO: 489     moltype = RNA   length = 21
FEATURE            Location/Qualifiers
source             1..21
                   mol_type = other RNA
                   organism = synthetic construct
SEQUENCE: 489
tgagtagaag agtttctttg t                                    21
```

-continued

```
SEQ ID NO: 490           moltype = RNA  length = 21
FEATURE                  Location/Qualifiers
source                   1..21
                         mol_type = other RNA
                         organism = synthetic construct
SEQUENCE: 490
gatctgcagc ttgccacatc a                                      21

SEQ ID NO: 491           moltype = RNA  length = 21
FEATURE                  Location/Qualifiers
source                   1..21
                         mol_type = other RNA
                         organism = synthetic construct
SEQUENCE: 491
tgaaaaggtc aagattaaga c                                      21

SEQ ID NO: 492           moltype = RNA  length = 21
FEATURE                  Location/Qualifiers
source                   1..21
                         mol_type = other RNA
                         organism = synthetic construct
SEQUENCE: 492
atgcagacag gaaaacaata t                                      21

SEQ ID NO: 493           moltype = RNA  length = 21
FEATURE                  Location/Qualifiers
source                   1..21
                         mol_type = other RNA
                         organism = synthetic construct
SEQUENCE: 493
ttgtataaca gaccacttcc t                                      21

SEQ ID NO: 494           moltype = RNA  length = 21
FEATURE                  Location/Qualifiers
source                   1..21
                         mol_type = other RNA
                         organism = synthetic construct
SEQUENCE: 494
agcttaaaat ctgtcatccc a                                      21

SEQ ID NO: 495           moltype = RNA  length = 21
FEATURE                  Location/Qualifiers
source                   1..21
                         mol_type = other RNA
                         organism = synthetic construct
SEQUENCE: 495
ctaaaactta ttgttaccat a                                      21

SEQ ID NO: 496           moltype = RNA  length = 21
FEATURE                  Location/Qualifiers
source                   1..21
                         mol_type = other RNA
                         organism = synthetic construct
SEQUENCE: 496
caaaataagt gtataaaatg c                                      21

SEQ ID NO: 497           moltype = RNA  length = 21
FEATURE                  Location/Qualifiers
source                   1..21
                         mol_type = other RNA
                         organism = synthetic construct
SEQUENCE: 497
atgtattcat ctgttggatc t                                      21

SEQ ID NO: 498           moltype = RNA  length = 21
FEATURE                  Location/Qualifiers
source                   1..21
                         mol_type = other RNA
                         organism = synthetic construct
SEQUENCE: 498
ttgtaaacat gaaaagggct t                                      21

SEQ ID NO: 499           moltype = RNA  length = 21
FEATURE                  Location/Qualifiers
source                   1..21
                         mol_type = other RNA
                         organism = synthetic construct
SEQUENCE: 499
ttattttcaa aaattaactt c                                      21
```

-continued

```
SEQ ID NO: 500          moltype = RNA  length = 21
FEATURE                 Location/Qualifiers
source                  1..21
                        mol_type = other RNA
                        organism = synthetic construct
SEQUENCE: 500
caactgttga tttcctcaac a                                         21

SEQ ID NO: 501          moltype = RNA  length = 21
FEATURE                 Location/Qualifiers
source                  1..21
                        mol_type = other RNA
                        organism = synthetic construct
SEQUENCE: 501
gcactgccaa caagttcact t                                         21

SEQ ID NO: 502          moltype = RNA  length = 21
FEATURE                 Location/Qualifiers
source                  1..21
                        mol_type = other RNA
                        organism = synthetic construct
SEQUENCE: 502
aagagtttag ttttaaaact g                                         21

SEQ ID NO: 503          moltype = RNA  length = 21
FEATURE                 Location/Qualifiers
source                  1..21
                        mol_type = other RNA
                        organism = synthetic construct
SEQUENCE: 503
tcatatataa agcattattt t                                         21

SEQ ID NO: 504          moltype = RNA  length = 21
FEATURE                 Location/Qualifiers
source                  1..21
                        mol_type = other RNA
                        organism = synthetic construct
SEQUENCE: 504
ttactctttt gaggtgaata t                                         21

SEQ ID NO: 505          moltype = RNA  length = 21
FEATURE                 Location/Qualifiers
source                  1..21
                        mol_type = other RNA
                        organism = synthetic construct
SEQUENCE: 505
atggctcaca aatttctatc c                                         21

SEQ ID NO: 506          moltype = RNA  length = 21
FEATURE                 Location/Qualifiers
source                  1..21
                        mol_type = other RNA
                        organism = synthetic construct
SEQUENCE: 506
ccaaatcttt tctgaagatg a                                         21

SEQ ID NO: 507          moltype = RNA  length = 21
FEATURE                 Location/Qualifiers
source                  1..21
                        mol_type = other RNA
                        organism = synthetic construct
SEQUENCE: 507
aagcttcttt aatactaagt a                                         21

SEQ ID NO: 508          moltype = RNA  length = 21
FEATURE                 Location/Qualifiers
source                  1..21
                        mol_type = other RNA
                        organism = synthetic construct
SEQUENCE: 508
atgaagtgtc attattcaaa a                                         21

SEQ ID NO: 509          moltype = RNA  length = 21
FEATURE                 Location/Qualifiers
source                  1..21
                        mol_type = other RNA
                        organism = synthetic construct
SEQUENCE: 509
```

-continued

```
atagtccact gactcctcac a                                                21

SEQ ID NO: 510            moltype = RNA   length = 21
FEATURE                   Location/Qualifiers
source                    1..21
                          mol_type = other RNA
                          organism = synthetic construct
SEQUENCE: 510
attttttcagg tcttcaccaa g                                               21

SEQ ID NO: 511            moltype = RNA   length = 21
FEATURE                   Location/Qualifiers
source                    1..21
                          mol_type = other RNA
                          organism = synthetic construct
SEQUENCE: 511
atctgttatc ttattataaa g                                               21

SEQ ID NO: 512            moltype = RNA   length = 21
FEATURE                   Location/Qualifiers
source                    1..21
                          mol_type = other RNA
                          organism = synthetic construct
SEQUENCE: 512
taatttatat tacaatgtaa a                                               21

SEQ ID NO: 513            moltype = RNA   length = 21
FEATURE                   Location/Qualifiers
source                    1..21
                          mol_type = other RNA
                          organism = synthetic construct
SEQUENCE: 513
agaaattgta tttttctat g                                                21

SEQ ID NO: 514            moltype = RNA   length = 21
FEATURE                   Location/Qualifiers
source                    1..21
                          mol_type = other RNA
                          organism = synthetic construct
SEQUENCE: 514
cagaatctac attctaaaac a                                               21

SEQ ID NO: 515            moltype = RNA   length = 21
FEATURE                   Location/Qualifiers
source                    1..21
                          mol_type = other RNA
                          organism = synthetic construct
SEQUENCE: 515
gccacattaa catcttttaa a                                               21

SEQ ID NO: 516            moltype = RNA   length = 21
FEATURE                   Location/Qualifiers
source                    1..21
                          mol_type = other RNA
                          organism = synthetic construct
SEQUENCE: 516
ggaaaagtaa ggccatactc t                                               21

SEQ ID NO: 517            moltype = RNA   length = 21
FEATURE                   Location/Qualifiers
source                    1..21
                          mol_type = other RNA
                          organism = synthetic construct
SEQUENCE: 517
gaactatttg tagtaactat c                                               21

SEQ ID NO: 518            moltype = RNA   length = 21
FEATURE                   Location/Qualifiers
source                    1..21
                          mol_type = other RNA
                          organism = synthetic construct
SEQUENCE: 518
ttacataata aaattccttt t                                               21

SEQ ID NO: 519            moltype = RNA   length = 21
FEATURE                   Location/Qualifiers
source                    1..21
                          mol_type = other RNA
                          organism = synthetic construct
```

-continued

```
SEQUENCE: 519
taggtaaatc ataaatctgt t                                                  21

SEQ ID NO: 520         moltype = RNA   length = 21
FEATURE                Location/Qualifiers
source                 1..21
                       mol_type = other RNA
                       organism = synthetic construct
SEQUENCE: 520
gatgagaact ggtggttaat a                                                  21

SEQ ID NO: 521         moltype = RNA   length = 21
FEATURE                Location/Qualifiers
source                 1..21
                       mol_type = other RNA
                       organism = synthetic construct
SEQUENCE: 521
taagtaattt tttcaaagaa t                                                  21

SEQ ID NO: 522         moltype = RNA   length = 21
FEATURE                Location/Qualifiers
source                 1..21
                       mol_type = other RNA
                       organism = synthetic construct
SEQUENCE: 522
tctaagacat atgatcaaca g                                                  21

SEQ ID NO: 523         moltype = RNA   length = 21
FEATURE                Location/Qualifiers
source                 1..21
                       mol_type = other RNA
                       organism = synthetic construct
SEQUENCE: 523
atgtgacagt gagattagtc a                                                  21

SEQ ID NO: 524         moltype = RNA   length = 21
FEATURE                Location/Qualifiers
source                 1..21
                       mol_type = other RNA
                       organism = synthetic construct
SEQUENCE: 524
tcacagaatt ctagtacatg t                                                  21

SEQ ID NO: 525         moltype = RNA   length = 21
FEATURE                Location/Qualifiers
source                 1..21
                       mol_type = other RNA
                       organism = synthetic construct
SEQUENCE: 525
aatcatgaaa ccttaagact t                                                  21

SEQ ID NO: 526         moltype = RNA   length = 21
FEATURE                Location/Qualifiers
source                 1..21
                       mol_type = other RNA
                       organism = synthetic construct
SEQUENCE: 526
aaggcactgt agtgaattat c                                                  21

SEQ ID NO: 527         moltype = RNA   length = 21
FEATURE                Location/Qualifiers
source                 1..21
                       mol_type = other RNA
                       organism = synthetic construct
SEQUENCE: 527
acagaatcta atcttcattt a                                                  21

SEQ ID NO: 528         moltype = RNA   length = 21
FEATURE                Location/Qualifiers
source                 1..21
                       mol_type = other RNA
                       organism = synthetic construct
SEQUENCE: 528
ctgagctaga gttacctagc t                                                  21

SEQ ID NO: 529         moltype = RNA   length = 21
FEATURE                Location/Qualifiers
source                 1..21
                       mol_type = other RNA
```

-continued

```
                                organism = synthetic construct
SEQUENCE: 529
agacttcaga atgattttgc a                                           21

SEQ ID NO: 530          moltype = RNA   length = 21
FEATURE                 Location/Qualifiers
source                  1..21
                        mol_type = other RNA
                        organism = synthetic construct
SEQUENCE: 530
atatcactaa tatactaaca a                                           21

SEQ ID NO: 531          moltype = RNA   length = 21
FEATURE                 Location/Qualifiers
source                  1..21
                        mol_type = other RNA
                        organism = synthetic construct
SEQUENCE: 531
atccaatgca ggcaaggaaa a                                           21

SEQ ID NO: 532          moltype = RNA   length = 21
FEATURE                 Location/Qualifiers
source                  1..21
                        mol_type = other RNA
                        organism = synthetic construct
SEQUENCE: 532
tattttttaa aaatatatga a                                           21

SEQ ID NO: 533          moltype = RNA   length = 21
FEATURE                 Location/Qualifiers
source                  1..21
                        mol_type = other RNA
                        organism = synthetic construct
SEQUENCE: 533
gtcttccatt ccagcctaac a                                           21

SEQ ID NO: 534          moltype = RNA   length = 21
FEATURE                 Location/Qualifiers
source                  1..21
                        mol_type = other RNA
                        organism = synthetic construct
SEQUENCE: 534
tcagaatgat tttgcaggtt g                                           21

SEQ ID NO: 535          moltype = RNA   length = 21
FEATURE                 Location/Qualifiers
source                  1..21
                        mol_type = other RNA
                        organism = synthetic construct
SEQUENCE: 535
gaaaaatata ttatctcaag t                                           21

SEQ ID NO: 536          moltype = RNA   length = 21
FEATURE                 Location/Qualifiers
source                  1..21
                        mol_type = other RNA
                        organism = synthetic construct
SEQUENCE: 536
ataaaagatt tccagtgaca g                                           21

SEQ ID NO: 537          moltype = RNA   length = 21
FEATURE                 Location/Qualifiers
source                  1..21
                        mol_type = other RNA
                        organism = synthetic construct
SEQUENCE: 537
tgaaatgaac ttgttggccc a                                           21

SEQ ID NO: 538          moltype = RNA   length = 21
FEATURE                 Location/Qualifiers
source                  1..21
                        mol_type = other RNA
                        organism = synthetic construct
SEQUENCE: 538
attctctctc caaatattaa c                                           21

SEQ ID NO: 539          moltype = RNA   length = 21
FEATURE                 Location/Qualifiers
source                  1..21
```

-continued

```
                              mol_type = other RNA
                              organism = synthetic construct
SEQUENCE: 539
acccttgaac atgggggtta g                                         21

SEQ ID NO: 540        moltype = RNA   length = 21
FEATURE               Location/Qualifiers
source                1..21
                      mol_type = other RNA
                      organism = synthetic construct
SEQUENCE: 540
ctaattatta gattatattt t                                         21

SEQ ID NO: 541        moltype = RNA   length = 21
FEATURE               Location/Qualifiers
source                1..21
                      mol_type = other RNA
                      organism = synthetic construct
SEQUENCE: 541
ggttagggga gctgacaatt c                                         21

SEQ ID NO: 542        moltype = RNA   length = 21
FEATURE               Location/Qualifiers
source                1..21
                      mol_type = other RNA
                      organism = synthetic construct
SEQUENCE: 542
atctattaca tctacagctg a                                         21

SEQ ID NO: 543        moltype = RNA   length = 21
FEATURE               Location/Qualifiers
source                1..21
                      mol_type = other RNA
                      organism = synthetic construct
SEQUENCE: 543
ttttgcgtgt tatatgtatt a                                         21

SEQ ID NO: 544        moltype = RNA   length = 21
FEATURE               Location/Qualifiers
source                1..21
                      mol_type = other RNA
                      organism = synthetic construct
SEQUENCE: 544
aaacagtaaa ttaacacata t                                         21

SEQ ID NO: 545        moltype = RNA   length = 21
FEATURE               Location/Qualifiers
source                1..21
                      mol_type = other RNA
                      organism = synthetic construct
SEQUENCE: 545
atacactata ttcctacaat a                                         21

SEQ ID NO: 546        moltype = RNA   length = 21
FEATURE               Location/Qualifiers
source                1..21
                      mol_type = other RNA
                      organism = synthetic construct
SEQUENCE: 546
ataaacctta ctgataacat a                                         21

SEQ ID NO: 547        moltype = RNA   length = 21
FEATURE               Location/Qualifiers
source                1..21
                      mol_type = other RNA
                      organism = synthetic construct
SEQUENCE: 547
ggggagctga caattcgtgg g                                         21

SEQ ID NO: 548        moltype = RNA   length = 21
FEATURE               Location/Qualifiers
source                1..21
                      mol_type = other RNA
                      organism = synthetic construct
SEQUENCE: 548
ctaatagcct actattgacc a                                         21

SEQ ID NO: 549        moltype = RNA   length = 21
FEATURE               Location/Qualifiers
```

-continued

```
source                    1..21
                          mol_type = other RNA
                          organism = synthetic construct
SEQUENCE: 549
caacataaaa gtcttcattc t                                              21

SEQ ID NO: 550            moltype = RNA  length = 21
FEATURE                   Location/Qualifiers
source                    1..21
                          mol_type = other RNA
                          organism = synthetic construct
SEQUENCE: 550
aagagaaaat atatttacta t                                              21

SEQ ID NO: 551            moltype = RNA  length = 21
FEATURE                   Location/Qualifiers
source                    1..21
                          mol_type = other RNA
                          organism = synthetic construct
SEQUENCE: 551
ttatttagaa aatcataaga a                                              21

SEQ ID NO: 552            moltype = RNA  length = 21
FEATURE                   Location/Qualifiers
source                    1..21
                          mol_type = other RNA
                          organism = synthetic construct
SEQUENCE: 552
ttcattaaat ggaagtgggt c                                              21

SEQ ID NO: 553            moltype = RNA  length = 21
FEATURE                   Location/Qualifiers
source                    1..21
                          mol_type = other RNA
                          organism = synthetic construct
SEQUENCE: 553
tcattgtctt cacattgagt a                                              21

SEQ ID NO: 554            moltype = RNA  length = 21
FEATURE                   Location/Qualifiers
source                    1..21
                          mol_type = other RNA
                          organism = synthetic construct
SEQUENCE: 554
aaagtaagct agagaaaatg t                                              21

SEQ ID NO: 555            moltype = RNA  length = 21
FEATURE                   Location/Qualifiers
source                    1..21
                          mol_type = other RNA
                          organism = synthetic construct
SEQUENCE: 555
ggacccttgc aattcaagcc c                                              21

SEQ ID NO: 556            moltype = RNA  length = 21
FEATURE                   Location/Qualifiers
source                    1..21
                          mol_type = other RNA
                          organism = synthetic construct
SEQUENCE: 556
aggcagagga ggagaaagat g                                              21

SEQ ID NO: 557            moltype = RNA  length = 21
FEATURE                   Location/Qualifiers
source                    1..21
                          mol_type = other RNA
                          organism = synthetic construct
SEQUENCE: 557
ggtcttgcag tcttgtctta g                                              21

SEQ ID NO: 558            moltype = RNA  length = 21
FEATURE                   Location/Qualifiers
source                    1..21
                          mol_type = other RNA
                          organism = synthetic construct
SEQUENCE: 558
ggggtgtggg gagtggggga a                                              21

SEQ ID NO: 559            moltype = RNA  length = 21
```

-continued

```
FEATURE             Location/Qualifiers
source              1..21
                    mol_type = other RNA
                    organism = synthetic construct
SEQUENCE: 559
aagaatattc atgtataagt g                                          21

SEQ ID NO: 560      moltype = RNA   length = 21
FEATURE             Location/Qualifiers
source              1..21
                    mol_type = other RNA
                    organism = synthetic construct
SEQUENCE: 560
ggggaggaag agaaggcgtt g                                          21

SEQ ID NO: 561      moltype = RNA   length = 21
FEATURE             Location/Qualifiers
source              1..21
                    mol_type = other RNA
                    organism = synthetic construct
SEQUENCE: 561
cttgttgttc aagggtcaac t                                          21

SEQ ID NO: 562      moltype = RNA   length = 21
FEATURE             Location/Qualifiers
source              1..21
                    mol_type = other RNA
                    organism = synthetic construct
SEQUENCE: 562
agtccactct actgagctaa a                                          21

SEQ ID NO: 563      moltype = RNA   length = 21
FEATURE             Location/Qualifiers
source              1..21
                    mol_type = other RNA
                    organism = synthetic construct
SEQUENCE: 563
attatagatc cagctatgct a                                          21

SEQ ID NO: 564      moltype = RNA   length = 21
FEATURE             Location/Qualifiers
source              1..21
                    mol_type = other RNA
                    organism = synthetic construct
SEQUENCE: 564
tgtaatagga tatagctatt t                                          21

SEQ ID NO: 565      moltype = RNA   length = 21
FEATURE             Location/Qualifiers
source              1..21
                    mol_type = other RNA
                    organism = synthetic construct
SEQUENCE: 565
tttcttcctc tatcaaccaa a                                          21

SEQ ID NO: 566      moltype = RNA   length = 21
FEATURE             Location/Qualifiers
source              1..21
                    mol_type = other RNA
                    organism = synthetic construct
SEQUENCE: 566
atggtaagca tctattttgc a                                          21

SEQ ID NO: 567      moltype = RNA   length = 21
FEATURE             Location/Qualifiers
source              1..21
                    mol_type = other RNA
                    organism = synthetic construct
SEQUENCE: 567
caactgaagt aaaattgagt g                                          21

SEQ ID NO: 568      moltype = RNA   length = 21
FEATURE             Location/Qualifiers
source              1..21
                    mol_type = other RNA
                    organism = synthetic construct
SEQUENCE: 568
cctctgacca tttcagaaca t                                          21
```

-continued

```
SEQ ID NO: 569          moltype = RNA   length = 21
FEATURE                 Location/Qualifiers
source                  1..21
                        mol_type = other RNA
                        organism = synthetic construct
SEQUENCE: 569
tcttccaata actcataaaa c                                       21

SEQ ID NO: 570          moltype = RNA   length = 21
FEATURE                 Location/Qualifiers
source                  1..21
                        mol_type = other RNA
                        organism = synthetic construct
SEQUENCE: 570
atttataatt attttcttga t                                       21

SEQ ID NO: 571          moltype = RNA   length = 21
FEATURE                 Location/Qualifiers
source                  1..21
                        mol_type = other RNA
                        organism = synthetic construct
SEQUENCE: 571
cttgatgaat aaattttcaa t                                       21

SEQ ID NO: 572          moltype = RNA   length = 21
FEATURE                 Location/Qualifiers
source                  1..21
                        mol_type = other RNA
                        organism = synthetic construct
SEQUENCE: 572
tgaataaatt ttcaatttct c                                       21

SEQ ID NO: 573          moltype = RNA   length = 21
FEATURE                 Location/Qualifiers
source                  1..21
                        mol_type = other RNA
                        organism = synthetic construct
SEQUENCE: 573
taatttcagt tgaagacatg t                                       21

SEQ ID NO: 574          moltype = RNA   length = 21
FEATURE                 Location/Qualifiers
source                  1..21
                        mol_type = other RNA
                        organism = synthetic construct
SEQUENCE: 574
actgcataat ccaacaattt t                                       21

SEQ ID NO: 575          moltype = RNA   length = 21
FEATURE                 Location/Qualifiers
source                  1..21
                        mol_type = other RNA
                        organism = synthetic construct
SEQUENCE: 575
aactttggta atttaagttg a                                       21

SEQ ID NO: 576          moltype = RNA   length = 21
FEATURE                 Location/Qualifiers
source                  1..21
                        mol_type = other RNA
                        organism = synthetic construct
SEQUENCE: 576
actaaagttt aaaattaagt c                                       21

SEQ ID NO: 577          moltype = RNA   length = 21
FEATURE                 Location/Qualifiers
source                  1..21
                        mol_type = other RNA
                        organism = synthetic construct
SEQUENCE: 577
ctaaaatagt ttcacctat a                                        21

SEQ ID NO: 578          moltype = RNA   length = 21
FEATURE                 Location/Qualifiers
source                  1..21
                        mol_type = other RNA
                        organism = synthetic construct
SEQUENCE: 578
gctggaaaat atattcacca a                                       21
```

-continued

```
SEQ ID NO: 579          moltype = RNA   length = 21
FEATURE                 Location/Qualifiers
source                  1..21
                        mol_type = other RNA
                        organism = synthetic construct
SEQUENCE: 579
gtaacatcaa tattgacctt g                                        21

SEQ ID NO: 580          moltype = RNA   length = 21
FEATURE                 Location/Qualifiers
source                  1..21
                        mol_type = other RNA
                        organism = synthetic construct
SEQUENCE: 580
catggttact aaaagaatat g                                        21

SEQ ID NO: 581          moltype = RNA   length = 21
FEATURE                 Location/Qualifiers
source                  1..21
                        mol_type = other RNA
                        organism = synthetic construct
SEQUENCE: 581
attaaccata tcttctaaaa c                                        21

SEQ ID NO: 582          moltype = RNA   length = 21
FEATURE                 Location/Qualifiers
source                  1..21
                        mol_type = other RNA
                        organism = synthetic construct
SEQUENCE: 582
acatgttact aatataacta t                                        21

SEQ ID NO: 583          moltype = RNA   length = 21
FEATURE                 Location/Qualifiers
source                  1..21
                        mol_type = other RNA
                        organism = synthetic construct
SEQUENCE: 583
aaaagagtag aggatgtgta a                                        21

SEQ ID NO: 584          moltype = RNA   length = 21
FEATURE                 Location/Qualifiers
source                  1..21
                        mol_type = other RNA
                        organism = synthetic construct
SEQUENCE: 584
ttactaatat aactattatt a                                        21

SEQ ID NO: 585          moltype = RNA   length = 21
FEATURE                 Location/Qualifiers
source                  1..21
                        mol_type = other RNA
                        organism = synthetic construct
SEQUENCE: 585
cccatgagag atactagaga t                                        21

SEQ ID NO: 586          moltype = RNA   length = 21
FEATURE                 Location/Qualifiers
source                  1..21
                        mol_type = other RNA
                        organism = synthetic construct
SEQUENCE: 586
ctgaacccat gagagatact a                                        21

SEQ ID NO: 587          moltype = RNA   length = 21
FEATURE                 Location/Qualifiers
source                  1..21
                        mol_type = other RNA
                        organism = synthetic construct
SEQUENCE: 587
ctaactcaat agtgaaggag a                                        21

SEQ ID NO: 588          moltype = RNA   length = 21
FEATURE                 Location/Qualifiers
source                  1..21
                        mol_type = other RNA
                        organism = synthetic construct
SEQUENCE: 588
```

-continued

```
tggggagtgg aaagtgtttg g                                           21

SEQ ID NO: 589          moltype = RNA   length = 21
FEATURE                 Location/Qualifiers
source                  1..21
                        mol_type = other RNA
                        organism = synthetic construct
SEQUENCE: 589
acactattaa attttctgaa c                                           21

SEQ ID NO: 590          moltype = RNA   length = 21
FEATURE                 Location/Qualifiers
source                  1..21
                        mol_type = other RNA
                        organism = synthetic construct
SEQUENCE: 590
ggtttcttac acaagtgttg c                                           21

SEQ ID NO: 591          moltype = RNA   length = 21
FEATURE                 Location/Qualifiers
source                  1..21
                        mol_type = other RNA
                        organism = synthetic construct
SEQUENCE: 591
gctggaaatt cctaaaaaca a                                           21

SEQ ID NO: 592          moltype = RNA   length = 21
FEATURE                 Location/Qualifiers
source                  1..21
                        mol_type = other RNA
                        organism = synthetic construct
SEQUENCE: 592
aagtgacgcc tcatctacaa g                                           21

SEQ ID NO: 593          moltype = RNA   length = 21
FEATURE                 Location/Qualifiers
source                  1..21
                        mol_type = other RNA
                        organism = synthetic construct
SEQUENCE: 593
cagaagggca gagatttctt a                                           21

SEQ ID NO: 594          moltype = RNA   length = 21
FEATURE                 Location/Qualifiers
source                  1..21
                        mol_type = other RNA
                        organism = synthetic construct
SEQUENCE: 594
tacaagctgg aaattcctaa a                                           21

SEQ ID NO: 595          moltype = RNA   length = 21
FEATURE                 Location/Qualifiers
source                  1..21
                        mol_type = other RNA
                        organism = synthetic construct
SEQUENCE: 595
gttcagggat atctgaagaa c                                           21

SEQ ID NO: 596          moltype = RNA   length = 21
FEATURE                 Location/Qualifiers
source                  1..21
                        mol_type = other RNA
                        organism = synthetic construct
SEQUENCE: 596
agtagaaagc ttataaacaa c                                           21

SEQ ID NO: 597          moltype = RNA   length = 21
FEATURE                 Location/Qualifiers
source                  1..21
                        mol_type = other RNA
                        organism = synthetic construct
SEQUENCE: 597
ttgaactgat tagtcatatt c                                           21

SEQ ID NO: 598          moltype = RNA   length = 21
FEATURE                 Location/Qualifiers
source                  1..21
                        mol_type = other RNA
                        organism = synthetic construct
```

-continued

```
SEQUENCE: 598
atacagaaag tatccctagt c                                            21

SEQ ID NO: 599            moltype = RNA   length = 21
FEATURE                   Location/Qualifiers
source                    1..21
                          mol_type = other RNA
                          organism = synthetic construct
SEQUENCE: 599
atattccttt gattacactg t                                            21

SEQ ID NO: 600            moltype = RNA   length = 21
FEATURE                   Location/Qualifiers
source                    1..21
                          mol_type = other RNA
                          organism = synthetic construct
SEQUENCE: 600
ctggttttag taaattacca a                                            21

SEQ ID NO: 601            moltype = RNA   length = 21
FEATURE                   Location/Qualifiers
source                    1..21
                          mol_type = other RNA
                          organism = synthetic construct
SEQUENCE: 601
caggtgatac actcacctca c                                            21

SEQ ID NO: 602            moltype = RNA   length = 21
FEATURE                   Location/Qualifiers
source                    1..21
                          mol_type = other RNA
                          organism = synthetic construct
SEQUENCE: 602
cttaaaaaca agtggaaaat t                                            21

SEQ ID NO: 603            moltype = RNA   length = 21
FEATURE                   Location/Qualifiers
source                    1..21
                          mol_type = other RNA
                          organism = synthetic construct
SEQUENCE: 603
tacaatattt ttctcagtaa a                                            21

SEQ ID NO: 604            moltype = RNA   length = 21
FEATURE                   Location/Qualifiers
source                    1..21
                          mol_type = other RNA
                          organism = synthetic construct
SEQUENCE: 604
cctttgatta cactgtttgt t                                            21

SEQ ID NO: 605            moltype = RNA   length = 21
FEATURE                   Location/Qualifiers
source                    1..21
                          mol_type = other RNA
                          organism = synthetic construct
SEQUENCE: 605
tgttcttcat tctttgatag a                                            21

SEQ ID NO: 606            moltype = RNA   length = 21
FEATURE                   Location/Qualifiers
source                    1..21
                          mol_type = other RNA
                          organism = synthetic construct
SEQUENCE: 606
gatagaaatt aaaatcttat t                                            21

SEQ ID NO: 607            moltype = RNA   length = 21
FEATURE                   Location/Qualifiers
source                    1..21
                          mol_type = other RNA
                          organism = synthetic construct
SEQUENCE: 607
acagaaataa ctaatttttt t                                            21

SEQ ID NO: 608            moltype = RNA   length = 21
FEATURE                   Location/Qualifiers
source                    1..21
                          mol_type = other RNA
```

```
                         organism = synthetic construct
SEQUENCE: 608
aaattaaaat cttattctgt g                                                21

SEQ ID NO: 609          moltype = RNA   length = 21
FEATURE                 Location/Qualifiers
source                  1..21
                        mol_type = other RNA
                        organism = synthetic construct
SEQUENCE: 609
tagaataaac tctttaaata a                                                21

SEQ ID NO: 610          moltype = RNA   length = 21
FEATURE                 Location/Qualifiers
source                  1..21
                        mol_type = other RNA
                        organism = synthetic construct
SEQUENCE: 610
gaggattaca gaatactata a                                                21

SEQ ID NO: 611          moltype = RNA   length = 21
FEATURE                 Location/Qualifiers
source                  1..21
                        mol_type = other RNA
                        organism = synthetic construct
SEQUENCE: 611
gaataagata taagaaaaca a                                                21

SEQ ID NO: 612          moltype = RNA   length = 21
FEATURE                 Location/Qualifiers
source                  1..21
                        mol_type = other RNA
                        organism = synthetic construct
SEQUENCE: 612
taaactcttt aaataattat t                                                21

SEQ ID NO: 613          moltype = RNA   length = 21
FEATURE                 Location/Qualifiers
source                  1..21
                        mol_type = other RNA
                        organism = synthetic construct
SEQUENCE: 613
actcaaatta taaagtagaa t                                                21

SEQ ID NO: 614          moltype = RNA   length = 21
FEATURE                 Location/Qualifiers
source                  1..21
                        mol_type = other RNA
                        organism = synthetic construct
SEQUENCE: 614
tcttcatcat aaagtgtaaa g                                                21

SEQ ID NO: 615          moltype = RNA   length = 21
FEATURE                 Location/Qualifiers
source                  1..21
                        mol_type = other RNA
                        organism = synthetic construct
SEQUENCE: 615
ctaaaaacaa ttttaaaatg c                                                21

SEQ ID NO: 616          moltype = RNA   length = 21
FEATURE                 Location/Qualifiers
source                  1..21
                        mol_type = other RNA
                        organism = synthetic construct
SEQUENCE: 616
ttctactata gaataagttc t                                                21

SEQ ID NO: 617          moltype = RNA   length = 21
FEATURE                 Location/Qualifiers
source                  1..21
                        mol_type = other RNA
                        organism = synthetic construct
SEQUENCE: 617
agttcttatc ttaatttaca g                                                21

SEQ ID NO: 618          moltype = RNA   length = 21
FEATURE                 Location/Qualifiers
source                  1..21
```

-continued

```
                            mol_type = other RNA
                            organism = synthetic construct
SEQUENCE: 618
ttatcttaat ttacagggca c                                          21

SEQ ID NO: 619          moltype = RNA   length = 21
FEATURE                 Location/Qualifiers
source                  1..21
                        mol_type = other RNA
                        organism = synthetic construct
SEQUENCE: 619
atactaaatg ctcaaatatg t                                          21

SEQ ID NO: 620          moltype = RNA   length = 21
FEATURE                 Location/Qualifiers
source                  1..21
                        mol_type = other RNA
                        organism = synthetic construct
SEQUENCE: 620
atttattttt aaaatttaat a                                          21

SEQ ID NO: 621          moltype = RNA   length = 21
FEATURE                 Location/Qualifiers
source                  1..21
                        mol_type = other RNA
                        organism = synthetic construct
SEQUENCE: 621
cttaatgttg cctttttatat t                                         21

SEQ ID NO: 622          moltype = RNA   length = 21
FEATURE                 Location/Qualifiers
source                  1..21
                        mol_type = other RNA
                        organism = synthetic construct
SEQUENCE: 622
attaaaatga atgttcttga a                                          21

SEQ ID NO: 623          moltype = RNA   length = 21
FEATURE                 Location/Qualifiers
source                  1..21
                        mol_type = other RNA
                        organism = synthetic construct
SEQUENCE: 623
tttaattggt taagaatata t                                          21

SEQ ID NO: 624          moltype = RNA   length = 21
FEATURE                 Location/Qualifiers
source                  1..21
                        mol_type = other RNA
                        organism = synthetic construct
SEQUENCE: 624
tatttgttta atgcaaatca g                                          21

SEQ ID NO: 625          moltype = RNA   length = 21
FEATURE                 Location/Qualifiers
source                  1..21
                        mol_type = other RNA
                        organism = synthetic construct
SEQUENCE: 625
tcagaatcac tatattaaaa t                                          21

SEQ ID NO: 626          moltype = RNA   length = 21
FEATURE                 Location/Qualifiers
source                  1..21
                        mol_type = other RNA
                        organism = synthetic construct
SEQUENCE: 626
aaatgcttaa tgttgccttt t                                          21

SEQ ID NO: 627          moltype = RNA   length = 23
FEATURE                 Location/Qualifiers
source                  1..23
                        mol_type = other RNA
                        organism = synthetic construct
SEQUENCE: 627
tagattctgt agcttttgac gtg                                        23

SEQ ID NO: 628          moltype = RNA   length = 23
FEATURE                 Location/Qualifiers
```

-continued

```
source                   1..23
                         mol_type = other RNA
                         organism = synthetic construct
SEQUENCE: 628
taaatagatt ctgtagcttt tga                                      23

SEQ ID NO: 629           moltype = RNA   length = 23
FEATURE                  Location/Qualifiers
source                   1..23
                         mol_type = other RNA
                         organism = synthetic construct
SEQUENCE: 629
tgataaatag attctgtagc ttt                                      23

SEQ ID NO: 630           moltype = RNA   length = 23
FEATURE                  Location/Qualifiers
source                   1..23
                         mol_type = other RNA
                         organism = synthetic construct
SEQUENCE: 630
ttgataaata gattctgtag ctt                                      23

SEQ ID NO: 631           moltype = RNA   length = 23
FEATURE                  Location/Qualifiers
source                   1..23
                         mol_type = other RNA
                         organism = synthetic construct
SEQUENCE: 631
tgagacagaa attgataaat aga                                      23

SEQ ID NO: 632           moltype = RNA   length = 23
FEATURE                  Location/Qualifiers
source                   1..23
                         mol_type = other RNA
                         organism = synthetic construct
SEQUENCE: 632
taagatgaga cagaaattga taa                                      23

SEQ ID NO: 633           moltype = RNA   length = 23
FEATURE                  Location/Qualifiers
source                   1..23
                         mol_type = other RNA
                         organism = synthetic construct
SEQUENCE: 633
ttaagatgag acagaaattg ata                                      23

SEQ ID NO: 634           moltype = RNA   length = 23
FEATURE                  Location/Qualifiers
source                   1..23
                         mol_type = other RNA
                         organism = synthetic construct
SEQUENCE: 634
tattaagatg agacagaaat tga                                      23

SEQ ID NO: 635           moltype = RNA   length = 23
FEATURE                  Location/Qualifiers
source                   1..23
                         mol_type = other RNA
                         organism = synthetic construct
SEQUENCE: 635
tagtcttaat cttgaccttt tca                                      23

SEQ ID NO: 636           moltype = RNA   length = 23
FEATURE                  Location/Qualifiers
source                   1..23
                         mol_type = other RNA
                         organism = synthetic construct
SEQUENCE: 636
ttagtcttaa tcttgacctt ttc                                      23

SEQ ID NO: 637           moltype = RNA   length = 23
FEATURE                  Location/Qualifiers
source                   1..23
                         mol_type = other RNA
                         organism = synthetic construct
SEQUENCE: 637
tttagtctta atcttgacct ttt                                      23

SEQ ID NO: 638           moltype = RNA   length = 23
```

-continued

```
FEATURE                Location/Qualifiers
source                 1..23
                       mol_type = other RNA
                       organism = synthetic construct
SEQUENCE: 638
ttttagtctt aatcttgacc ttt                                               23

SEQ ID NO: 639         moltype = RNA  length = 23
FEATURE                Location/Qualifiers
source                 1..23
                       mol_type = other RNA
                       organism = synthetic construct
SEQUENCE: 639
taagttttag tcttaatctt gac                                               23

SEQ ID NO: 640         moltype = RNA  length = 23
FEATURE                Location/Qualifiers
source                 1..23
                       mol_type = other RNA
                       organism = synthetic construct
SEQUENCE: 640
taacaataag ttttagtctt aat                                               23

SEQ ID NO: 641         moltype = RNA  length = 23
FEATURE                Location/Qualifiers
source                 1..23
                       mol_type = other RNA
                       organism = synthetic construct
SEQUENCE: 641
tggtaacaat aagttttagt ctt                                               23

SEQ ID NO: 642         moltype = RNA  length = 23
FEATURE                Location/Qualifiers
source                 1..23
                       mol_type = other RNA
                       organism = synthetic construct
SEQUENCE: 642
tatggtaaca ataagtttta gtc                                               23

SEQ ID NO: 643         moltype = RNA  length = 23
FEATURE                Location/Qualifiers
source                 1..23
                       mol_type = other RNA
                       organism = synthetic construct
SEQUENCE: 643
tccaacagat gaatacatat ggt                                               23

SEQ ID NO: 644         moltype = RNA  length = 23
FEATURE                Location/Qualifiers
source                 1..23
                       mol_type = other RNA
                       organism = synthetic construct
SEQUENCE: 644
tacaagatcc aacagatgaa tac                                               23

SEQ ID NO: 645         moltype = RNA  length = 23
FEATURE                Location/Qualifiers
source                 1..23
                       mol_type = other RNA
                       organism = synthetic construct
SEQUENCE: 645
ttacaagatc caacagatga ata                                               23

SEQ ID NO: 646         moltype = RNA  length = 23
FEATURE                Location/Qualifiers
source                 1..23
                       mol_type = other RNA
                       organism = synthetic construct
SEQUENCE: 646
tttacaagat ccaacagatg aat                                               23

SEQ ID NO: 647         moltype = RNA  length = 23
FEATURE                Location/Qualifiers
source                 1..23
                       mol_type = other RNA
                       organism = synthetic construct
SEQUENCE: 647
tgtttacaag atccaacaga tga                                               23
```

-continued

```
SEQ ID NO: 648          moltype = RNA   length = 23
FEATURE                 Location/Qualifiers
source                  1..23
                        mol_type = other RNA
                        organism = synthetic construct
SEQUENCE: 648
tcatgtttac aagatccaac aga                                        23

SEQ ID NO: 649          moltype = RNA   length = 23
FEATURE                 Location/Qualifiers
source                  1..23
                        mol_type = other RNA
                        organism = synthetic construct
SEQUENCE: 649
ttcatgttta caagatccaa cag                                        23

SEQ ID NO: 650          moltype = RNA   length = 23
FEATURE                 Location/Qualifiers
source                  1..23
                        mol_type = other RNA
                        organism = synthetic construct
SEQUENCE: 650
tttcatgttt acaagatcca aca                                        23

SEQ ID NO: 651          moltype = RNA   length = 23
FEATURE                 Location/Qualifiers
source                  1..23
                        mol_type = other RNA
                        organism = synthetic construct
SEQUENCE: 651
ttttcatgtt tacaagatcc aac                                        23

SEQ ID NO: 652          moltype = RNA   length = 23
FEATURE                 Location/Qualifiers
source                  1..23
                        mol_type = other RNA
                        organism = synthetic construct
SEQUENCE: 652
tacacttatt ttgaagttaa ttt                                        23

SEQ ID NO: 653          moltype = RNA   length = 23
FEATURE                 Location/Qualifiers
source                  1..23
                        mol_type = other RNA
                        organism = synthetic construct
SEQUENCE: 653
tatacactta ttttgaagtt aat                                        23

SEQ ID NO: 654          moltype = RNA   length = 23
FEATURE                 Location/Qualifiers
source                  1..23
                        mol_type = other RNA
                        organism = synthetic construct
SEQUENCE: 654
ttatacactt attttgaagt taa                                        23

SEQ ID NO: 655          moltype = RNA   length = 23
FEATURE                 Location/Qualifiers
source                  1..23
                        mol_type = other RNA
                        organism = synthetic construct
SEQUENCE: 655
tttatacact tattttgaag tta                                        23

SEQ ID NO: 656          moltype = RNA   length = 23
FEATURE                 Location/Qualifiers
source                  1..23
                        mol_type = other RNA
                        organism = synthetic construct
SEQUENCE: 656
ttttatacac ttattttgaa gtt                                        23

SEQ ID NO: 657          moltype = RNA   length = 23
FEATURE                 Location/Qualifiers
source                  1..23
                        mol_type = other RNA
                        organism = synthetic construct
SEQUENCE: 657
tgcattttat acacttattt tga                                        23
```

-continued

```
SEQ ID NO: 658              moltype = RNA   length = 23
FEATURE                     Location/Qualifiers
source                      1..23
                            mol_type = other RNA
                            organism = synthetic construct
SEQUENCE: 658
ttgcattta tacacttatt ttg                                            23

SEQ ID NO: 659              moltype = RNA   length = 23
FEATURE                     Location/Qualifiers
source                      1..23
                            mol_type = other RNA
                            organism = synthetic construct
SEQUENCE: 659
tcaacagttg cattttatac act                                           23

SEQ ID NO: 660              moltype = RNA   length = 23
FEATURE                     Location/Qualifiers
source                      1..23
                            mol_type = other RNA
                            organism = synthetic construct
SEQUENCE: 660
ttcatcttca gaaagattt ggg                                            23

SEQ ID NO: 661              moltype = RNA   length = 23
FEATURE                     Location/Qualifiers
source                      1..23
                            mol_type = other RNA
                            organism = synthetic construct
SEQUENCE: 661
tcttcatctt cagaaaagat ttg                                           23

SEQ ID NO: 662              moltype = RNA   length = 23
FEATURE                     Location/Qualifiers
source                      1..23
                            mol_type = other RNA
                            organism = synthetic construct
SEQUENCE: 662
taaactcttc atcttcagaa aag                                           23

SEQ ID NO: 663              moltype = RNA   length = 23
FEATURE                     Location/Qualifiers
source                      1..23
                            mol_type = other RNA
                            organism = synthetic construct
SEQUENCE: 663
taaaactaaa ctcttcatct tca                                           23

SEQ ID NO: 664              moltype = RNA   length = 23
FEATURE                     Location/Qualifiers
source                      1..23
                            mol_type = other RNA
                            organism = synthetic construct
SEQUENCE: 664
ttaaaactaa actcttcatc ttc                                           23

SEQ ID NO: 665              moltype = RNA   length = 23
FEATURE                     Location/Qualifiers
source                      1..23
                            mol_type = other RNA
                            organism = synthetic construct
SEQUENCE: 665
tttaaaacta aactcttcat ctt                                           23

SEQ ID NO: 666              moltype = RNA   length = 23
FEATURE                     Location/Qualifiers
source                      1..23
                            mol_type = other RNA
                            organism = synthetic construct
SEQUENCE: 666
ttttaaaact aaactcttca tct                                           23

SEQ ID NO: 667              moltype = RNA   length = 23
FEATURE                     Location/Qualifiers
source                      1..23
                            mol_type = other RNA
                            organism = synthetic construct
SEQUENCE: 667
```

-continued

```
tgcagtttta aaactaaact ctt                                           23

SEQ ID NO: 668         moltype = RNA   length = 23
FEATURE                Location/Qualifiers
source                 1..23
                       mol_type = other RNA
                       organism = synthetic construct
SEQUENCE: 668
tggcagtgca gttttaaaac taa                                           23

SEQ ID NO: 669         moltype = RNA   length = 23
FEATURE                Location/Qualifiers
source                 1..23
                       mol_type = other RNA
                       organism = synthetic construct
SEQUENCE: 669
ttggcagtgc agttttaaaa cta                                           23

SEQ ID NO: 670         moltype = RNA   length = 23
FEATURE                Location/Qualifiers
source                 1..23
                       mol_type = other RNA
                       organism = synthetic construct
SEQUENCE: 670
tatattttct ctttcttatg att                                           23

SEQ ID NO: 671         moltype = RNA   length = 23
FEATURE                Location/Qualifiers
source                 1..23
                       mol_type = other RNA
                       organism = synthetic construct
SEQUENCE: 671
taaatatatt ttctctttct tat                                           23

SEQ ID NO: 672         moltype = RNA   length = 23
FEATURE                Location/Qualifiers
source                 1..23
                       mol_type = other RNA
                       organism = synthetic construct
SEQUENCE: 672
tagtaaatat attttctctt tct                                           23

SEQ ID NO: 673         moltype = RNA   length = 23
FEATURE                Location/Qualifiers
source                 1..23
                       mol_type = other RNA
                       organism = synthetic construct
SEQUENCE: 673
tgaatagtaa atatattttc tct                                           23

SEQ ID NO: 674         moltype = RNA   length = 23
FEATURE                Location/Qualifiers
source                 1..23
                       mol_type = other RNA
                       organism = synthetic construct
SEQUENCE: 674
taatgaatag taaatatatt ttc                                           23

SEQ ID NO: 675         moltype = RNA   length = 23
FEATURE                Location/Qualifiers
source                 1..23
                       mol_type = other RNA
                       organism = synthetic construct
SEQUENCE: 675
ttaatgaata gtaaatatat ttt                                           23

SEQ ID NO: 676         moltype = RNA   length = 23
FEATURE                Location/Qualifiers
source                 1..23
                       mol_type = other RNA
                       organism = synthetic construct
SEQUENCE: 676
tttaatgaat agtaaatata ttt                                           23

SEQ ID NO: 677         moltype = RNA   length = 23
FEATURE                Location/Qualifiers
source                 1..23
                       mol_type = other RNA
                       organism = synthetic construct
```

-continued

```
SEQUENCE: 677
tttctgtagc ttttgacgtg ctt                                              23

SEQ ID NO: 678          moltype = RNA   length = 23
FEATURE                 Location/Qualifiers
source                  1..23
                        mol_type = other RNA
                        organism = synthetic construct
SEQUENCE: 678
tattctgtag cttttgacgt gct                                              23

SEQ ID NO: 679          moltype = RNA   length = 23
FEATURE                 Location/Qualifiers
source                  1..23
                        mol_type = other RNA
                        organism = synthetic construct
SEQUENCE: 679
tgattctgta gcttttgacg tgc                                              23

SEQ ID NO: 680          moltype = RNA   length = 23
FEATURE                 Location/Qualifiers
source                  1..23
                        mol_type = other RNA
                        organism = synthetic construct
SEQUENCE: 680
ttagattctg tagcttttga cgt                                              23

SEQ ID NO: 681          moltype = RNA   length = 23
FEATURE                 Location/Qualifiers
source                  1..23
                        mol_type = other RNA
                        organism = synthetic construct
SEQUENCE: 681
tatagattct gtagcttttg acg                                              23

SEQ ID NO: 682          moltype = RNA   length = 23
FEATURE                 Location/Qualifiers
source                  1..23
                        mol_type = other RNA
                        organism = synthetic construct
SEQUENCE: 682
taatagattc tgtagctttt gac                                              23

SEQ ID NO: 683          moltype = RNA   length = 23
FEATURE                 Location/Qualifiers
source                  1..23
                        mol_type = other RNA
                        organism = synthetic construct
SEQUENCE: 683
ttaaatagat tctgtagctt ttg                                              23

SEQ ID NO: 684          moltype = RNA   length = 23
FEATURE                 Location/Qualifiers
source                  1..23
                        mol_type = other RNA
                        organism = synthetic construct
SEQUENCE: 684
tataaataga ttctgtagct ttt                                              23

SEQ ID NO: 685          moltype = RNA   length = 23
FEATURE                 Location/Qualifiers
source                  1..23
                        mol_type = other RNA
                        organism = synthetic construct
SEQUENCE: 685
tttgataaat agattctgta gct                                              23

SEQ ID NO: 686          moltype = RNA   length = 23
FEATURE                 Location/Qualifiers
source                  1..23
                        mol_type = other RNA
                        organism = synthetic construct
SEQUENCE: 686
tattgataaa tagattctgt agc                                              23

SEQ ID NO: 687          moltype = RNA   length = 23
FEATURE                 Location/Qualifiers
source                  1..23
                        mol_type = other RNA
```

-continued

```
                              organism = synthetic construct
SEQUENCE: 687
taattgataa atagattctg tag                                              23

SEQ ID NO: 688          moltype = RNA   length = 23
FEATURE                 Location/Qualifiers
source                  1..23
                        mol_type = other RNA
                        organism = synthetic construct
SEQUENCE: 688
taaattgata aatagattct gta                                              23

SEQ ID NO: 689          moltype = RNA   length = 23
FEATURE                 Location/Qualifiers
source                  1..23
                        mol_type = other RNA
                        organism = synthetic construct
SEQUENCE: 689
tgaaattgat aaatagattc tgt                                              23

SEQ ID NO: 690          moltype = RNA   length = 23
FEATURE                 Location/Qualifiers
source                  1..23
                        mol_type = other RNA
                        organism = synthetic construct
SEQUENCE: 690
tagaaattga taaatagatt ctg                                              23

SEQ ID NO: 691          moltype = RNA   length = 23
FEATURE                 Location/Qualifiers
source                  1..23
                        mol_type = other RNA
                        organism = synthetic construct
SEQUENCE: 691
tcagaaattg ataaatagat tct                                              23

SEQ ID NO: 692          moltype = RNA   length = 23
FEATURE                 Location/Qualifiers
source                  1..23
                        mol_type = other RNA
                        organism = synthetic construct
SEQUENCE: 692
tacagaaatt gataaataga ttc                                              23

SEQ ID NO: 693          moltype = RNA   length = 23
FEATURE                 Location/Qualifiers
source                  1..23
                        mol_type = other RNA
                        organism = synthetic construct
SEQUENCE: 693
tgacagaaat tgataaatag att                                              23

SEQ ID NO: 694          moltype = RNA   length = 23
FEATURE                 Location/Qualifiers
source                  1..23
                        mol_type = other RNA
                        organism = synthetic construct
SEQUENCE: 694
tagacagaaa ttgataaata gat                                              23

SEQ ID NO: 695          moltype = RNA   length = 23
FEATURE                 Location/Qualifiers
source                  1..23
                        mol_type = other RNA
                        organism = synthetic construct
SEQUENCE: 695
ttgagacaga aattgataaa tag                                              23

SEQ ID NO: 696          moltype = RNA   length = 23
FEATURE                 Location/Qualifiers
source                  1..23
                        mol_type = other RNA
                        organism = synthetic construct
SEQUENCE: 696
tatgagacag aaattgataa ata                                              23

SEQ ID NO: 697          moltype = RNA   length = 23
FEATURE                 Location/Qualifiers
source                  1..23
```

-continued

```
                            mol_type = other RNA
                            organism = synthetic construct
SEQUENCE: 697
tgatgagaca gaaattgata aat                                              23

SEQ ID NO: 698          moltype = RNA   length = 23
FEATURE                 Location/Qualifiers
source                  1..23
                        mol_type = other RNA
                        organism = synthetic construct
SEQUENCE: 698
tagatgagac agaaattgat aaa                                              23

SEQ ID NO: 699          moltype = RNA   length = 23
FEATURE                 Location/Qualifiers
source                  1..23
                        mol_type = other RNA
                        organism = synthetic construct
SEQUENCE: 699
tttaagatga gacagaaatt gat                                              23

SEQ ID NO: 700          moltype = RNA   length = 23
FEATURE                 Location/Qualifiers
source                  1..23
                        mol_type = other RNA
                        organism = synthetic construct
SEQUENCE: 700
ttattaagat gagacagaaa ttg                                              23

SEQ ID NO: 701          moltype = RNA   length = 23
FEATURE                 Location/Qualifiers
source                  1..23
                        mol_type = other RNA
                        organism = synthetic construct
SEQUENCE: 701
tatattaaga tgagacagaa att                                              23

SEQ ID NO: 702          moltype = RNA   length = 23
FEATURE                 Location/Qualifiers
source                  1..23
                        mol_type = other RNA
                        organism = synthetic construct
SEQUENCE: 702
tcatattaag atgagacaga aat                                              23

SEQ ID NO: 703          moltype = RNA   length = 23
FEATURE                 Location/Qualifiers
source                  1..23
                        mol_type = other RNA
                        organism = synthetic construct
SEQUENCE: 703
tacatattaa gatgagacag aaa                                              23

SEQ ID NO: 704          moltype = RNA   length = 23
FEATURE                 Location/Qualifiers
source                  1..23
                        mol_type = other RNA
                        organism = synthetic construct
SEQUENCE: 704
tgacatatta agatgagaca gaa                                              23

SEQ ID NO: 705          moltype = RNA   length = 23
FEATURE                 Location/Qualifiers
source                  1..23
                        mol_type = other RNA
                        organism = synthetic construct
SEQUENCE: 705
tagacatatt aagatgagac aga                                              23

SEQ ID NO: 706          moltype = RNA   length = 23
FEATURE                 Location/Qualifiers
source                  1..23
                        mol_type = other RNA
                        organism = synthetic construct
SEQUENCE: 706
tgagacatat taagatgaga cag                                              23

SEQ ID NO: 707          moltype = RNA   length = 23
FEATURE                 Location/Qualifiers
```

-continued

```
source                  1..23
                        mol_type = other RNA
                        organism = synthetic construct
SEQUENCE: 707
tagagacata ttaagatgag aca                                                  23

SEQ ID NO: 708         moltype = RNA   length = 23
FEATURE                Location/Qualifiers
source                 1..23
                       mol_type = other RNA
                       organism = synthetic construct
SEQUENCE: 708
taagagacat attaagatga gac                                                  23

SEQ ID NO: 709         moltype = RNA   length = 23
FEATURE                Location/Qualifiers
source                 1..23
                       mol_type = other RNA
                       organism = synthetic construct
SEQUENCE: 709
tgtcttaatc ttgacctttt cac                                                  23

SEQ ID NO: 710         moltype = RNA   length = 23
FEATURE                Location/Qualifiers
source                 1..23
                       mol_type = other RNA
                       organism = synthetic construct
SEQUENCE: 710
tttttagtct taatcttgac ctt                                                  23

SEQ ID NO: 711         moltype = RNA   length = 23
FEATURE                Location/Qualifiers
source                 1..23
                       mol_type = other RNA
                       organism = synthetic construct
SEQUENCE: 711
tgttttagtc ttaatcttga cct                                                  23

SEQ ID NO: 712         moltype = RNA   length = 23
FEATURE                Location/Qualifiers
source                 1..23
                       mol_type = other RNA
                       organism = synthetic construct
SEQUENCE: 712
tagttttagt cttaatcttg acc                                                  23

SEQ ID NO: 713         moltype = RNA   length = 23
FEATURE                Location/Qualifiers
source                 1..23
                       mol_type = other RNA
                       organism = synthetic construct
SEQUENCE: 713
ttaagtttta gtcttaatct tga                                                  23

SEQ ID NO: 714         moltype = RNA   length = 23
FEATURE                Location/Qualifiers
source                 1..23
                       mol_type = other RNA
                       organism = synthetic construct
SEQUENCE: 714
tataagtttt agtcttaatc ttg                                                  23

SEQ ID NO: 715         moltype = RNA   length = 23
FEATURE                Location/Qualifiers
source                 1..23
                       mol_type = other RNA
                       organism = synthetic construct
SEQUENCE: 715
taataagttt tagtcttaat ctt                                                  23

SEQ ID NO: 716         moltype = RNA   length = 23
FEATURE                Location/Qualifiers
source                 1..23
                       mol_type = other RNA
                       organism = synthetic construct
SEQUENCE: 716
tcaataagtt ttagtcttaa tct                                                  23

SEQ ID NO: 717         moltype = RNA   length = 23
```

-continued

```
FEATURE             Location/Qualifiers
source              1..23
                    mol_type = other RNA
                    organism = synthetic construct
SEQUENCE: 717
tacaataagt tttagtctta atc                                        23

SEQ ID NO: 718      moltype = RNA   length = 23
FEATURE             Location/Qualifiers
source              1..23
                    mol_type = other RNA
                    organism = synthetic construct
SEQUENCE: 718
ttaacaataa gttttagtct taa                                        23

SEQ ID NO: 719      moltype = RNA   length = 23
FEATURE             Location/Qualifiers
source              1..23
                    mol_type = other RNA
                    organism = synthetic construct
SEQUENCE: 719
tgtaacaata agttttagtc tta                                        23

SEQ ID NO: 720      moltype = RNA   length = 23
FEATURE             Location/Qualifiers
source              1..23
                    mol_type = other RNA
                    organism = synthetic construct
SEQUENCE: 720
ttggtaacaa taagttttag tct                                        23

SEQ ID NO: 721      moltype = RNA   length = 23
FEATURE             Location/Qualifiers
source              1..23
                    mol_type = other RNA
                    organism = synthetic construct
SEQUENCE: 721
tgatgaatac atatggtaac aat                                        23

SEQ ID NO: 722      moltype = RNA   length = 23
FEATURE             Location/Qualifiers
source              1..23
                    mol_type = other RNA
                    organism = synthetic construct
SEQUENCE: 722
tagatgaata catatggtaa caa                                        23

SEQ ID NO: 723      moltype = RNA   length = 23
FEATURE             Location/Qualifiers
source              1..23
                    mol_type = other RNA
                    organism = synthetic construct
SEQUENCE: 723
tcagatgaat acatatggta aca                                        23

SEQ ID NO: 724      moltype = RNA   length = 23
FEATURE             Location/Qualifiers
source              1..23
                    mol_type = other RNA
                    organism = synthetic construct
SEQUENCE: 724
tacagatgaa tacatatggt aac                                        23

SEQ ID NO: 725      moltype = RNA   length = 23
FEATURE             Location/Qualifiers
source              1..23
                    mol_type = other RNA
                    organism = synthetic construct
SEQUENCE: 725
taacagatga atacatatgg taa                                        23

SEQ ID NO: 726      moltype = RNA   length = 23
FEATURE             Location/Qualifiers
source              1..23
                    mol_type = other RNA
                    organism = synthetic construct
SEQUENCE: 726
tcaacagatg aatacatatg gta                                        23
```

-continued

```
SEQ ID NO: 727          moltype = RNA   length = 23
FEATURE                 Location/Qualifiers
source                  1..23
                        mol_type = other RNA
                        organism = synthetic construct
SEQUENCE: 727
ttccaacaga tgaatacata tgg                                       23

SEQ ID NO: 728          moltype = RNA   length = 23
FEATURE                 Location/Qualifiers
source                  1..23
                        mol_type = other RNA
                        organism = synthetic construct
SEQUENCE: 728
tatccaacag atgaatacat atg                                       23

SEQ ID NO: 729          moltype = RNA   length = 23
FEATURE                 Location/Qualifiers
source                  1..23
                        mol_type = other RNA
                        organism = synthetic construct
SEQUENCE: 729
tgatccaaca gatgaataca tat                                       23

SEQ ID NO: 730          moltype = RNA   length = 23
FEATURE                 Location/Qualifiers
source                  1..23
                        mol_type = other RNA
                        organism = synthetic construct
SEQUENCE: 730
tagatccaac agatgaatac ata                                       23

SEQ ID NO: 731          moltype = RNA   length = 23
FEATURE                 Location/Qualifiers
source                  1..23
                        mol_type = other RNA
                        organism = synthetic construct
SEQUENCE: 731
taagatccaa cagatgaata cat                                       23

SEQ ID NO: 732          moltype = RNA   length = 23
FEATURE                 Location/Qualifiers
source                  1..23
                        mol_type = other RNA
                        organism = synthetic construct
SEQUENCE: 732
tcaagatcca acagatgaat aca                                       23

SEQ ID NO: 733          moltype = RNA   length = 23
FEATURE                 Location/Qualifiers
source                  1..23
                        mol_type = other RNA
                        organism = synthetic construct
SEQUENCE: 733
ttttacaaga tccaacagat gaa                                       23

SEQ ID NO: 734          moltype = RNA   length = 23
FEATURE                 Location/Qualifiers
source                  1..23
                        mol_type = other RNA
                        organism = synthetic construct
SEQUENCE: 734
ttgtttacaa gatccaacag atg                                       23

SEQ ID NO: 735          moltype = RNA   length = 23
FEATURE                 Location/Qualifiers
source                  1..23
                        mol_type = other RNA
                        organism = synthetic construct
SEQUENCE: 735
tatgtttaca agatccaaca gat                                       23

SEQ ID NO: 736          moltype = RNA   length = 23
FEATURE                 Location/Qualifiers
source                  1..23
                        mol_type = other RNA
                        organism = synthetic construct
SEQUENCE: 736
tttttcatgt ttacaagatc caa                                       23
```

-continued

```
SEQ ID NO: 737          moltype = RNA   length = 23
FEATURE                 Location/Qualifiers
source                  1..23
                        mol_type = other RNA
                        organism = synthetic construct
SEQUENCE: 737
tcttttcatg tttacaagat cca                                     23

SEQ ID NO: 738          moltype = RNA   length = 23
FEATURE                 Location/Qualifiers
source                  1..23
                        mol_type = other RNA
                        organism = synthetic construct
SEQUENCE: 738
tccttttcat gtttacaaga tcc                                     23

SEQ ID NO: 739          moltype = RNA   length = 23
FEATURE                 Location/Qualifiers
source                  1..23
                        mol_type = other RNA
                        organism = synthetic construct
SEQUENCE: 739
tcccttttca tgtttacaag atc                                     23

SEQ ID NO: 740          moltype = RNA   length = 23
FEATURE                 Location/Qualifiers
source                  1..23
                        mol_type = other RNA
                        organism = synthetic construct
SEQUENCE: 740
tgcccttttc atgtttacaa gat                                     23

SEQ ID NO: 741          moltype = RNA   length = 23
FEATURE                 Location/Qualifiers
source                  1..23
                        mol_type = other RNA
                        organism = synthetic construct
SEQUENCE: 741
tcacttattt tgaagttaat ttt                                     23

SEQ ID NO: 742          moltype = RNA   length = 23
FEATURE                 Location/Qualifiers
source                  1..23
                        mol_type = other RNA
                        organism = synthetic construct
SEQUENCE: 742
ttacacttat tttgaagtta att                                     23

SEQ ID NO: 743          moltype = RNA   length = 23
FEATURE                 Location/Qualifiers
source                  1..23
                        mol_type = other RNA
                        organism = synthetic construct
SEQUENCE: 743
tttttataca cttattttga agt                                     23

SEQ ID NO: 744          moltype = RNA   length = 23
FEATURE                 Location/Qualifiers
source                  1..23
                        mol_type = other RNA
                        organism = synthetic construct
SEQUENCE: 744
tattttatac acttattttg aag                                     23

SEQ ID NO: 745          moltype = RNA   length = 23
FEATURE                 Location/Qualifiers
source                  1..23
                        mol_type = other RNA
                        organism = synthetic construct
SEQUENCE: 745
tcattttata cacttatttt gaa                                     23

SEQ ID NO: 746          moltype = RNA   length = 23
FEATURE                 Location/Qualifiers
source                  1..23
                        mol_type = other RNA
                        organism = synthetic construct
SEQUENCE: 746
```

```
tttgcatttt atacacttat ttt                                             23

SEQ ID NO: 747         moltype = RNA   length = 23
FEATURE                Location/Qualifiers
source                 1..23
                       mol_type = other RNA
                       organism = synthetic construct
SEQUENCE: 747
tgttgcattt tatacactta ttt                                             23

SEQ ID NO: 748         moltype = RNA   length = 23
FEATURE                Location/Qualifiers
source                 1..23
                       mol_type = other RNA
                       organism = synthetic construct
SEQUENCE: 748
tagttgcatt ttatacactt att                                             23

SEQ ID NO: 749         moltype = RNA   length = 23
FEATURE                Location/Qualifiers
source                 1..23
                       mol_type = other RNA
                       organism = synthetic construct
SEQUENCE: 749
tcagttgcat tttatacact tat                                             23

SEQ ID NO: 750         moltype = RNA   length = 23
FEATURE                Location/Qualifiers
source                 1..23
                       mol_type = other RNA
                       organism = synthetic construct
SEQUENCE: 750
tacagttgca ttttatacac tta                                             23

SEQ ID NO: 751         moltype = RNA   length = 23
FEATURE                Location/Qualifiers
source                 1..23
                       mol_type = other RNA
                       organism = synthetic construct
SEQUENCE: 751
taacagttgc attttataca ctt                                             23

SEQ ID NO: 752         moltype = RNA   length = 23
FEATURE                Location/Qualifiers
source                 1..23
                       mol_type = other RNA
                       organism = synthetic construct
SEQUENCE: 752
tttcatcttc agaaaagatt tgg                                             23

SEQ ID NO: 753         moltype = RNA   length = 23
FEATURE                Location/Qualifiers
source                 1..23
                       mol_type = other RNA
                       organism = synthetic construct
SEQUENCE: 753
ttcttcatct tcagaaaaga ttt                                             23

SEQ ID NO: 754         moltype = RNA   length = 23
FEATURE                Location/Qualifiers
source                 1..23
                       mol_type = other RNA
                       organism = synthetic construct
SEQUENCE: 754
tctcttcatc ttcagaaaag att                                             23

SEQ ID NO: 755         moltype = RNA   length = 23
FEATURE                Location/Qualifiers
source                 1..23
                       mol_type = other RNA
                       organism = synthetic construct
SEQUENCE: 755
tactcttcat cttcagaaaa gat                                             23

SEQ ID NO: 756         moltype = RNA   length = 23
FEATURE                Location/Qualifiers
source                 1..23
                       mol_type = other RNA
                       organism = synthetic construct
```

-continued

```
SEQUENCE: 756
taactcttca tcttcagaaa aga                                            23

SEQ ID NO: 757        moltype = RNA   length = 23
FEATURE               Location/Qualifiers
source                1..23
                      mol_type = other RNA
                      organism = synthetic construct
SEQUENCE: 757
ttaaactctt catcttcaga aaa                                            23

SEQ ID NO: 758        moltype = RNA   length = 23
FEATURE               Location/Qualifiers
source                1..23
                      mol_type = other RNA
                      organism = synthetic construct
SEQUENCE: 758
tctaaactct tcatcttcag aaa                                            23

SEQ ID NO: 759        moltype = RNA   length = 23
FEATURE               Location/Qualifiers
source                1..23
                      mol_type = other RNA
                      organism = synthetic construct
SEQUENCE: 759
tactaaactc ttcatcttca gaa                                            23

SEQ ID NO: 760        moltype = RNA   length = 23
FEATURE               Location/Qualifiers
source                1..23
                      mol_type = other RNA
                      organism = synthetic construct
SEQUENCE: 760
taactaaact cttcatcttc aga                                            23

SEQ ID NO: 761        moltype = RNA   length = 23
FEATURE               Location/Qualifiers
source                1..23
                      mol_type = other RNA
                      organism = synthetic construct
SEQUENCE: 761
taaactaaac tcttcatctt cag                                            23

SEQ ID NO: 762        moltype = RNA   length = 23
FEATURE               Location/Qualifiers
source                1..23
                      mol_type = other RNA
                      organism = synthetic construct
SEQUENCE: 762
tttttaaaac taaactcttc atc                                            23

SEQ ID NO: 763        moltype = RNA   length = 23
FEATURE               Location/Qualifiers
source                1..23
                      mol_type = other RNA
                      organism = synthetic construct
SEQUENCE: 763
tgttttaaaa ctaaactctt cat                                            23

SEQ ID NO: 764        moltype = RNA   length = 23
FEATURE               Location/Qualifiers
source                1..23
                      mol_type = other RNA
                      organism = synthetic construct
SEQUENCE: 764
tagttttaaa actaaactct tca                                            23

SEQ ID NO: 765        moltype = RNA   length = 23
FEATURE               Location/Qualifiers
source                1..23
                      mol_type = other RNA
                      organism = synthetic construct
SEQUENCE: 765
tcagttttaa aactaaactc ttc                                            23

SEQ ID NO: 766        moltype = RNA   length = 23
FEATURE               Location/Qualifiers
source                1..23
                      mol_type = other RNA
```

-continued

```
                               organism = synthetic construct
SEQUENCE: 766
ttgcagtttt aaaactaaac tct                                              23

SEQ ID NO: 767            moltype = RNA   length = 23
FEATURE                   Location/Qualifiers
source                    1..23
                          mol_type = other RNA
                          organism = synthetic construct
SEQUENCE: 767
tgtgcagttt taaaactaaa ctc                                              23

SEQ ID NO: 768            moltype = RNA   length = 23
FEATURE                   Location/Qualifiers
source                    1..23
                          mol_type = other RNA
                          organism = synthetic construct
SEQUENCE: 768
tagtgcagtt ttaaaactaa act                                              23

SEQ ID NO: 769            moltype = RNA   length = 23
FEATURE                   Location/Qualifiers
source                    1..23
                          mol_type = other RNA
                          organism = synthetic construct
SEQUENCE: 769
tcagtgcagt tttaaaacta aac                                              23

SEQ ID NO: 770            moltype = RNA   length = 23
FEATURE                   Location/Qualifiers
source                    1..23
                          mol_type = other RNA
                          organism = synthetic construct
SEQUENCE: 770
tgcagtgcag ttttaaaact aaa                                              23

SEQ ID NO: 771            moltype = RNA   length = 23
FEATURE                   Location/Qualifiers
source                    1..23
                          mol_type = other RNA
                          organism = synthetic construct
SEQUENCE: 771
ttattttctc tttcttatga ttt                                              23

SEQ ID NO: 772            moltype = RNA   length = 23
FEATURE                   Location/Qualifiers
source                    1..23
                          mol_type = other RNA
                          organism = synthetic construct
SEQUENCE: 772
ttatattttc tctttcttat gat                                              23

SEQ ID NO: 773            moltype = RNA   length = 23
FEATURE                   Location/Qualifiers
source                    1..23
                          mol_type = other RNA
                          organism = synthetic construct
SEQUENCE: 773
tatatatttt ctctttctta tga                                              23

SEQ ID NO: 774            moltype = RNA   length = 23
FEATURE                   Location/Qualifiers
source                    1..23
                          mol_type = other RNA
                          organism = synthetic construct
SEQUENCE: 774
taatatattt tctctttctt atg                                              23

SEQ ID NO: 775            moltype = RNA   length = 23
FEATURE                   Location/Qualifiers
source                    1..23
                          mol_type = other RNA
                          organism = synthetic construct
SEQUENCE: 775
ttaaatatat tttctctttc tta                                              23

SEQ ID NO: 776            moltype = RNA   length = 23
FEATURE                   Location/Qualifiers
source                    1..23
```

-continued

```
                              mol_type = other RNA
                              organism = synthetic construct
SEQUENCE: 776
tgtaaatata ttttctcttt ctt                                           23

SEQ ID NO: 777         moltype = RNA   length = 23
FEATURE                Location/Qualifiers
source                 1..23
                       mol_type = other RNA
                       organism = synthetic construct
SEQUENCE: 777
ttagtaaata tattttctct ttc                                           23

SEQ ID NO: 778         moltype = RNA   length = 23
FEATURE                Location/Qualifiers
source                 1..23
                       mol_type = other RNA
                       organism = synthetic construct
SEQUENCE: 778
tatagtaaat atattttctc ttt                                           23

SEQ ID NO: 779         moltype = RNA   length = 23
FEATURE                Location/Qualifiers
source                 1..23
                       mol_type = other RNA
                       organism = synthetic construct
SEQUENCE: 779
taatagtaaa tatattttct ctt                                           23

SEQ ID NO: 780         moltype = RNA   length = 23
FEATURE                Location/Qualifiers
source                 1..23
                       mol_type = other RNA
                       organism = synthetic construct
SEQUENCE: 780
ttgaatagta aatatatttt ctc                                           23

SEQ ID NO: 781         moltype = RNA   length = 23
FEATURE                Location/Qualifiers
source                 1..23
                       mol_type = other RNA
                       organism = synthetic construct
SEQUENCE: 781
tatgaatagt aaatatattt tct                                           23

SEQ ID NO: 782         moltype = RNA   length = 23
FEATURE                Location/Qualifiers
source                 1..23
                       mol_type = other RNA
                       organism = synthetic construct
SEQUENCE: 782
ttttaatgaa tagtaaatat att                                           23

SEQ ID NO: 783         moltype = RNA   length = 21
FEATURE                Location/Qualifiers
source                 1..21
                       mol_type = other RNA
                       organism = synthetic construct
SEQUENCE: 783
cgtcaaaagc tacagaatct a                                             21

SEQ ID NO: 784         moltype = RNA   length = 21
FEATURE                Location/Qualifiers
source                 1..21
                       mol_type = other RNA
                       organism = synthetic construct
SEQUENCE: 784
aaaagctaca gaatctattt a                                             21

SEQ ID NO: 785         moltype = RNA   length = 21
FEATURE                Location/Qualifiers
source                 1..21
                       mol_type = other RNA
                       organism = synthetic construct
SEQUENCE: 785
agctacagaa tctatttatc a                                             21

SEQ ID NO: 786         moltype = RNA   length = 21
FEATURE                Location/Qualifiers
```

-continued

```
source                1..21
                      mol_type = other RNA
                      organism = synthetic construct
SEQUENCE: 786
gctacagaat ctatttatca a                                          21

SEQ ID NO: 787        moltype = RNA   length = 21
FEATURE               Location/Qualifiers
source                1..21
                      mol_type = other RNA
                      organism = synthetic construct
SEQUENCE: 787
tatttatcaa tttctgtctc a                                          21

SEQ ID NO: 788        moltype = RNA   length = 21
FEATURE               Location/Qualifiers
source                1..21
                      mol_type = other RNA
                      organism = synthetic construct
SEQUENCE: 788
atcaatttct gtctcatctt a                                          21

SEQ ID NO: 789        moltype = RNA   length = 21
FEATURE               Location/Qualifiers
source                1..21
                      mol_type = other RNA
                      organism = synthetic construct
SEQUENCE: 789
tcaatttctg tctcatctta a                                          21

SEQ ID NO: 790        moltype = RNA   length = 21
FEATURE               Location/Qualifiers
source                1..21
                      mol_type = other RNA
                      organism = synthetic construct
SEQUENCE: 790
aatttctgtc tcatcttaat a                                          21

SEQ ID NO: 791        moltype = RNA   length = 21
FEATURE               Location/Qualifiers
source                1..21
                      mol_type = other RNA
                      organism = synthetic construct
SEQUENCE: 791
aaaaggtcaa gattaagact a                                          21

SEQ ID NO: 792        moltype = RNA   length = 21
FEATURE               Location/Qualifiers
source                1..21
                      mol_type = other RNA
                      organism = synthetic construct
SEQUENCE: 792
aaaggtcaag attaagacta a                                          21

SEQ ID NO: 793        moltype = RNA   length = 21
FEATURE               Location/Qualifiers
source                1..21
                      mol_type = other RNA
                      organism = synthetic construct
SEQUENCE: 793
aaggtcaaga ttaagactaa a                                          21

SEQ ID NO: 794        moltype = RNA   length = 21
FEATURE               Location/Qualifiers
source                1..21
                      mol_type = other RNA
                      organism = synthetic construct
SEQUENCE: 794
aggtcaagat taagactaaa a                                          21

SEQ ID NO: 795        moltype = RNA   length = 21
FEATURE               Location/Qualifiers
source                1..21
                      mol_type = other RNA
                      organism = synthetic construct
SEQUENCE: 795
caagattaag actaaaactt a                                          21

SEQ ID NO: 796        moltype = RNA   length = 21
```

-continued

```
FEATURE          Location/Qualifiers
source           1..21
                 mol_type = other RNA
                 organism = synthetic construct
SEQUENCE: 796
taagactaaa acttattgtt a                                        21

SEQ ID NO: 797   moltype = RNA   length = 21
FEATURE          Location/Qualifiers
source           1..21
                 mol_type = other RNA
                 organism = synthetic construct
SEQUENCE: 797
gactaaaact tattgttacc a                                        21

SEQ ID NO: 798   moltype = RNA   length = 21
FEATURE          Location/Qualifiers
source           1..21
                 mol_type = other RNA
                 organism = synthetic construct
SEQUENCE: 798
ctaaaactta ttgttaccat a                                        21

SEQ ID NO: 799   moltype = RNA   length = 21
FEATURE          Location/Qualifiers
source           1..21
                 mol_type = other RNA
                 organism = synthetic construct
SEQUENCE: 799
catatgtatt catctgttgg a                                        21

SEQ ID NO: 800   moltype = RNA   length = 21
FEATURE          Location/Qualifiers
source           1..21
                 mol_type = other RNA
                 organism = synthetic construct
SEQUENCE: 800
attcatctgt tggatcttgt a                                        21

SEQ ID NO: 801   moltype = RNA   length = 21
FEATURE          Location/Qualifiers
source           1..21
                 mol_type = other RNA
                 organism = synthetic construct
SEQUENCE: 801
ttcatctgtt ggatcttgta a                                        21

SEQ ID NO: 802   moltype = RNA   length = 21
FEATURE          Location/Qualifiers
source           1..21
                 mol_type = other RNA
                 organism = synthetic construct
SEQUENCE: 802
tcatctgttg gatcttgtaa a                                        21

SEQ ID NO: 803   moltype = RNA   length = 21
FEATURE          Location/Qualifiers
source           1..21
                 mol_type = other RNA
                 organism = synthetic construct
SEQUENCE: 803
atctgttgga tcttgtaaac a                                        21

SEQ ID NO: 804   moltype = RNA   length = 21
FEATURE          Location/Qualifiers
source           1..21
                 mol_type = other RNA
                 organism = synthetic construct
SEQUENCE: 804
tgttggatct tgtaaacatg a                                        21

SEQ ID NO: 805   moltype = RNA   length = 21
FEATURE          Location/Qualifiers
source           1..21
                 mol_type = other RNA
                 organism = synthetic construct
SEQUENCE: 805
gttggatctt gtaaacatga a                                        21
```

-continued

```
SEQ ID NO: 806            moltype = RNA   length = 21
FEATURE                   Location/Qualifiers
source                    1..21
                          mol_type = other RNA
                          organism = synthetic construct
SEQUENCE: 806
ttggatcttg taaacatgaa a                                     21

SEQ ID NO: 807            moltype = RNA   length = 21
FEATURE                   Location/Qualifiers
source                    1..21
                          mol_type = other RNA
                          organism = synthetic construct
SEQUENCE: 807
tggatcttgt aaacatgaaa a                                     21

SEQ ID NO: 808            moltype = RNA   length = 21
FEATURE                   Location/Qualifiers
source                    1..21
                          mol_type = other RNA
                          organism = synthetic construct
SEQUENCE: 808
attaacttca aataagtgt a                                      21

SEQ ID NO: 809            moltype = RNA   length = 21
FEATURE                   Location/Qualifiers
source                    1..21
                          mol_type = other RNA
                          organism = synthetic construct
SEQUENCE: 809
taacttcaaa ataagtgtat a                                     21

SEQ ID NO: 810            moltype = RNA   length = 21
FEATURE                   Location/Qualifiers
source                    1..21
                          mol_type = other RNA
                          organism = synthetic construct
SEQUENCE: 810
aacttcaaaa taagtgtata a                                     21

SEQ ID NO: 811            moltype = RNA   length = 21
FEATURE                   Location/Qualifiers
source                    1..21
                          mol_type = other RNA
                          organism = synthetic construct
SEQUENCE: 811
acttcaaaat aagtgtataa a                                     21

SEQ ID NO: 812            moltype = RNA   length = 21
FEATURE                   Location/Qualifiers
source                    1..21
                          mol_type = other RNA
                          organism = synthetic construct
SEQUENCE: 812
cttcaaaata agtgtataaa a                                     21

SEQ ID NO: 813            moltype = RNA   length = 21
FEATURE                   Location/Qualifiers
source                    1..21
                          mol_type = other RNA
                          organism = synthetic construct
SEQUENCE: 813
aaaataagtg tataaaatgc a                                     21

SEQ ID NO: 814            moltype = RNA   length = 21
FEATURE                   Location/Qualifiers
source                    1..21
                          mol_type = other RNA
                          organism = synthetic construct
SEQUENCE: 814
aaataagtgt ataaaatgca a                                     21

SEQ ID NO: 815            moltype = RNA   length = 21
FEATURE                   Location/Qualifiers
source                    1..21
                          mol_type = other RNA
                          organism = synthetic construct
SEQUENCE: 815
tgtataaaat gcaactgttg a                                     21
```

-continued

```
SEQ ID NO: 816          moltype = RNA   length = 21
FEATURE                 Location/Qualifiers
source                  1..21
                        mol_type = other RNA
                        organism = synthetic construct
SEQUENCE: 816
caaatctttt ctgaagatga a                                         21

SEQ ID NO: 817          moltype = RNA   length = 21
FEATURE                 Location/Qualifiers
source                  1..21
                        mol_type = other RNA
                        organism = synthetic construct
SEQUENCE: 817
aatcttttct gaagatgaag a                                         21

SEQ ID NO: 818          moltype = RNA   length = 21
FEATURE                 Location/Qualifiers
source                  1..21
                        mol_type = other RNA
                        organism = synthetic construct
SEQUENCE: 818
tttctgaaga tgaagagttt a                                         21

SEQ ID NO: 819          moltype = RNA   length = 21
FEATURE                 Location/Qualifiers
source                  1..21
                        mol_type = other RNA
                        organism = synthetic construct
SEQUENCE: 819
aagatgaaga gtttagtttt a                                         21

SEQ ID NO: 820          moltype = RNA   length = 21
FEATURE                 Location/Qualifiers
source                  1..21
                        mol_type = other RNA
                        organism = synthetic construct
SEQUENCE: 820
agatgaagag tttagtttta a                                         21

SEQ ID NO: 821          moltype = RNA   length = 21
FEATURE                 Location/Qualifiers
source                  1..21
                        mol_type = other RNA
                        organism = synthetic construct
SEQUENCE: 821
gatgaagagt ttagttttaa a                                         21

SEQ ID NO: 822          moltype = RNA   length = 21
FEATURE                 Location/Qualifiers
source                  1..21
                        mol_type = other RNA
                        organism = synthetic construct
SEQUENCE: 822
atgaagagtt tagttttaaa a                                         21

SEQ ID NO: 823          moltype = RNA   length = 21
FEATURE                 Location/Qualifiers
source                  1..21
                        mol_type = other RNA
                        organism = synthetic construct
SEQUENCE: 823
gagtttagtt ttaaaactgc a                                         21

SEQ ID NO: 824          moltype = RNA   length = 21
FEATURE                 Location/Qualifiers
source                  1..21
                        mol_type = other RNA
                        organism = synthetic construct
SEQUENCE: 824
agttttaaaa ctgcactgcc a                                         21

SEQ ID NO: 825          moltype = RNA   length = 21
FEATURE                 Location/Qualifiers
source                  1..21
                        mol_type = other RNA
                        organism = synthetic construct
SEQUENCE: 825
```

-continued

```
gttttaaaac tgcactgcca a                                         21

SEQ ID NO: 826           moltype = RNA   length = 21
FEATURE                  Location/Qualifiers
source                   1..21
                         mol_type = other RNA
                         organism = synthetic construct
SEQUENCE: 826
tcataagaaa gagaaaatat a                                         21

SEQ ID NO: 827           moltype = RNA   length = 21
FEATURE                  Location/Qualifiers
source                   1..21
                         mol_type = other RNA
                         organism = synthetic construct
SEQUENCE: 827
aagaaagaga aaatatattt a                                         21

SEQ ID NO: 828           moltype = RNA   length = 21
FEATURE                  Location/Qualifiers
source                   1..21
                         mol_type = other RNA
                         organism = synthetic construct
SEQUENCE: 828
aaagagaaaa tatatttact a                                         21

SEQ ID NO: 829           moltype = RNA   length = 21
FEATURE                  Location/Qualifiers
source                   1..21
                         mol_type = other RNA
                         organism = synthetic construct
SEQUENCE: 829
agaaaatata tttactattc a                                         21

SEQ ID NO: 830           moltype = RNA   length = 21
FEATURE                  Location/Qualifiers
source                   1..21
                         mol_type = other RNA
                         organism = synthetic construct
SEQUENCE: 830
aaatatattt actattcatt a                                         21

SEQ ID NO: 831           moltype = RNA   length = 21
FEATURE                  Location/Qualifiers
source                   1..21
                         mol_type = other RNA
                         organism = synthetic construct
SEQUENCE: 831
aatatattta ctattcatta a                                         21

SEQ ID NO: 832           moltype = RNA   length = 21
FEATURE                  Location/Qualifiers
source                   1..21
                         mol_type = other RNA
                         organism = synthetic construct
SEQUENCE: 832
atatatttac tattcattaa a                                         21

SEQ ID NO: 833           moltype = RNA   length = 21
FEATURE                  Location/Qualifiers
source                   1..21
                         mol_type = other RNA
                         organism = synthetic construct
SEQUENCE: 833
gcacgtcaaa agctacagaa a                                         21

SEQ ID NO: 834           moltype = RNA   length = 21
FEATURE                  Location/Qualifiers
source                   1..21
                         mol_type = other RNA
                         organism = synthetic construct
SEQUENCE: 834
cacgtcaaaa gctacagaat a                                         21

SEQ ID NO: 835           moltype = RNA   length = 21
FEATURE                  Location/Qualifiers
source                   1..21
                         mol_type = other RNA
                         organism = synthetic construct
```

-continued

```
SEQUENCE: 835
acgtcaaaag ctacagaatc a                                                21

SEQ ID NO: 836         moltype = RNA   length = 21
FEATURE                Location/Qualifiers
source                 1..21
                       mol_type = other RNA
                       organism = synthetic construct
SEQUENCE: 836
gtcaaaagct acagaatcta a                                                21

SEQ ID NO: 837         moltype = RNA   length = 21
FEATURE                Location/Qualifiers
source                 1..21
                       mol_type = other RNA
                       organism = synthetic construct
SEQUENCE: 837
tcaaaagcta cagaatctat a                                                21

SEQ ID NO: 838         moltype = RNA   length = 21
FEATURE                Location/Qualifiers
source                 1..21
                       mol_type = other RNA
                       organism = synthetic construct
SEQUENCE: 838
caaaagctac agaatctatt a                                                21

SEQ ID NO: 839         moltype = RNA   length = 21
FEATURE                Location/Qualifiers
source                 1..21
                       mol_type = other RNA
                       organism = synthetic construct
SEQUENCE: 839
aaagctacag aatctattta a                                                21

SEQ ID NO: 840         moltype = RNA   length = 21
FEATURE                Location/Qualifiers
source                 1..21
                       mol_type = other RNA
                       organism = synthetic construct
SEQUENCE: 840
aagctacaga atctatttat a                                                21

SEQ ID NO: 841         moltype = RNA   length = 21
FEATURE                Location/Qualifiers
source                 1..21
                       mol_type = other RNA
                       organism = synthetic construct
SEQUENCE: 841
ctacagaatc tatttatcaa a                                                21

SEQ ID NO: 842         moltype = RNA   length = 21
FEATURE                Location/Qualifiers
source                 1..21
                       mol_type = other RNA
                       organism = synthetic construct
SEQUENCE: 842
tacagaatct atttatcaat a                                                21

SEQ ID NO: 843         moltype = RNA   length = 21
FEATURE                Location/Qualifiers
source                 1..21
                       mol_type = other RNA
                       organism = synthetic construct
SEQUENCE: 843
acagaatcta tttatcaatt a                                                21

SEQ ID NO: 844         moltype = RNA   length = 21
FEATURE                Location/Qualifiers
source                 1..21
                       mol_type = other RNA
                       organism = synthetic construct
SEQUENCE: 844
cagaatctat ttatcaattt a                                                21

SEQ ID NO: 845         moltype = RNA   length = 21
FEATURE                Location/Qualifiers
source                 1..21
                       mol_type = other RNA
```

-continued

```
                       organism = synthetic construct
SEQUENCE: 845
agaatctatt tatcaatttc a                                              21

SEQ ID NO: 846        moltype = RNA  length = 21
FEATURE               Location/Qualifiers
source                1..21
                      mol_type = other RNA
                      organism = synthetic construct
SEQUENCE: 846
gaatctattt atcaatttct a                                              21

SEQ ID NO: 847        moltype = RNA  length = 21
FEATURE               Location/Qualifiers
source                1..21
                      mol_type = other RNA
                      organism = synthetic construct
SEQUENCE: 847
aatctattta tcaatttctg a                                              21

SEQ ID NO: 848        moltype = RNA  length = 21
FEATURE               Location/Qualifiers
source                1..21
                      mol_type = other RNA
                      organism = synthetic construct
SEQUENCE: 848
atctatttat caatttctgt a                                              21

SEQ ID NO: 849        moltype = RNA  length = 21
FEATURE               Location/Qualifiers
source                1..21
                      mol_type = other RNA
                      organism = synthetic construct
SEQUENCE: 849
tctatttatc aatttctgtc a                                              21

SEQ ID NO: 850        moltype = RNA  length = 21
FEATURE               Location/Qualifiers
source                1..21
                      mol_type = other RNA
                      organism = synthetic construct
SEQUENCE: 850
ctatttatca atttctgtct a                                              21

SEQ ID NO: 851        moltype = RNA  length = 21
FEATURE               Location/Qualifiers
source                1..21
                      mol_type = other RNA
                      organism = synthetic construct
SEQUENCE: 851
atttatcaat tctgtctca a                                               21

SEQ ID NO: 852        moltype = RNA  length = 21
FEATURE               Location/Qualifiers
source                1..21
                      mol_type = other RNA
                      organism = synthetic construct
SEQUENCE: 852
tttatcaatt tctgtctcat a                                              21

SEQ ID NO: 853        moltype = RNA  length = 21
FEATURE               Location/Qualifiers
source                1..21
                      mol_type = other RNA
                      organism = synthetic construct
SEQUENCE: 853
ttatcaattt ctgtctcatc a                                              21

SEQ ID NO: 854        moltype = RNA  length = 21
FEATURE               Location/Qualifiers
source                1..21
                      mol_type = other RNA
                      organism = synthetic construct
SEQUENCE: 854
tatcaatttc tgtctcatct a                                              21

SEQ ID NO: 855        moltype = RNA  length = 21
FEATURE               Location/Qualifiers
source                1..21
```

-continued

```
                        mol_type = other RNA
                        organism = synthetic construct
SEQUENCE: 855
caatttctgt ctcatcttaa a                                         21

SEQ ID NO: 856          moltype = RNA   length = 21
FEATURE                 Location/Qualifiers
source                  1..21
                        mol_type = other RNA
                        organism = synthetic construct
SEQUENCE: 856
atttctgtct catcttaata a                                         21

SEQ ID NO: 857          moltype = RNA   length = 21
FEATURE                 Location/Qualifiers
source                  1..21
                        mol_type = other RNA
                        organism = synthetic construct
SEQUENCE: 857
tttctgtctc atcttaatat a                                         21

SEQ ID NO: 858          moltype = RNA   length = 21
FEATURE                 Location/Qualifiers
source                  1..21
                        mol_type = other RNA
                        organism = synthetic construct
SEQUENCE: 858
ttctgtctca tcttaatatg a                                         21

SEQ ID NO: 859          moltype = RNA   length = 21
FEATURE                 Location/Qualifiers
source                  1..21
                        mol_type = other RNA
                        organism = synthetic construct
SEQUENCE: 859
tctgtctcat cttaatatgt a                                         21

SEQ ID NO: 860          moltype = RNA   length = 21
FEATURE                 Location/Qualifiers
source                  1..21
                        mol_type = other RNA
                        organism = synthetic construct
SEQUENCE: 860
ctgtctcatc ttaatatgtc a                                         21

SEQ ID NO: 861          moltype = RNA   length = 21
FEATURE                 Location/Qualifiers
source                  1..21
                        mol_type = other RNA
                        organism = synthetic construct
SEQUENCE: 861
tgtctcatct taatatgtct a                                         21

SEQ ID NO: 862          moltype = RNA   length = 21
FEATURE                 Location/Qualifiers
source                  1..21
                        mol_type = other RNA
                        organism = synthetic construct
SEQUENCE: 862
gtctcatctt aatatgtctc a                                         21

SEQ ID NO: 863          moltype = RNA   length = 21
FEATURE                 Location/Qualifiers
source                  1..21
                        mol_type = other RNA
                        organism = synthetic construct
SEQUENCE: 863
tctcatctta atatgtctct a                                         21

SEQ ID NO: 864          moltype = RNA   length = 21
FEATURE                 Location/Qualifiers
source                  1..21
                        mol_type = other RNA
                        organism = synthetic construct
SEQUENCE: 864
ctcatcttaa tatgtctctt a                                         21

SEQ ID NO: 865          moltype = RNA   length = 21
FEATURE                 Location/Qualifiers
```

-continued

```
source                  1..21
                        mol_type = other RNA
                        organism = synthetic construct
SEQUENCE: 865
gaaaaggtca agattaagac a                                        21

SEQ ID NO: 866          moltype = RNA   length = 21
FEATURE                 Location/Qualifiers
source                  1..21
                        mol_type = other RNA
                        organism = synthetic construct
SEQUENCE: 866
ggtcaagatt aagactaaaa a                                        21

SEQ ID NO: 867          moltype = RNA   length = 21
FEATURE                 Location/Qualifiers
source                  1..21
                        mol_type = other RNA
                        organism = synthetic construct
SEQUENCE: 867
gtcaagatta agactaaaac a                                        21

SEQ ID NO: 868          moltype = RNA   length = 21
FEATURE                 Location/Qualifiers
source                  1..21
                        mol_type = other RNA
                        organism = synthetic construct
SEQUENCE: 868
tcaagattaa gactaaaact a                                        21

SEQ ID NO: 869          moltype = RNA   length = 21
FEATURE                 Location/Qualifiers
source                  1..21
                        mol_type = other RNA
                        organism = synthetic construct
SEQUENCE: 869
aagattaaga ctaaaactta a                                        21

SEQ ID NO: 870          moltype = RNA   length = 21
FEATURE                 Location/Qualifiers
source                  1..21
                        mol_type = other RNA
                        organism = synthetic construct
SEQUENCE: 870
agattaagac taaaacttat a                                        21

SEQ ID NO: 871          moltype = RNA   length = 21
FEATURE                 Location/Qualifiers
source                  1..21
                        mol_type = other RNA
                        organism = synthetic construct
SEQUENCE: 871
gattaagact aaaacttatt a                                        21

SEQ ID NO: 872          moltype = RNA   length = 21
FEATURE                 Location/Qualifiers
source                  1..21
                        mol_type = other RNA
                        organism = synthetic construct
SEQUENCE: 872
attaagacta aaacttattg a                                        21

SEQ ID NO: 873          moltype = RNA   length = 21
FEATURE                 Location/Qualifiers
source                  1..21
                        mol_type = other RNA
                        organism = synthetic construct
SEQUENCE: 873
ttaagactaa aacttattgt a                                        21

SEQ ID NO: 874          moltype = RNA   length = 21
FEATURE                 Location/Qualifiers
source                  1..21
                        mol_type = other RNA
                        organism = synthetic construct
SEQUENCE: 874
aagactaaaa cttattgtta a                                        21

SEQ ID NO: 875          moltype = RNA   length = 21
```

-continued

```
FEATURE              Location/Qualifiers
source               1..21
                     mol_type = other RNA
                     organism = synthetic construct
SEQUENCE: 875
agactaaaac ttattgttac a                                          21

SEQ ID NO: 876       moltype = RNA   length = 21
FEATURE              Location/Qualifiers
source               1..21
                     mol_type = other RNA
                     organism = synthetic construct
SEQUENCE: 876
actaaaactt attgttacca a                                          21

SEQ ID NO: 877       moltype = RNA   length = 21
FEATURE              Location/Qualifiers
source               1..21
                     mol_type = other RNA
                     organism = synthetic construct
SEQUENCE: 877
tgttaccata tgtattcatc a                                          21

SEQ ID NO: 878       moltype = RNA   length = 21
FEATURE              Location/Qualifiers
source               1..21
                     mol_type = other RNA
                     organism = synthetic construct
SEQUENCE: 878
gttaccatat gtattcatct a                                          21

SEQ ID NO: 879       moltype = RNA   length = 21
FEATURE              Location/Qualifiers
source               1..21
                     mol_type = other RNA
                     organism = synthetic construct
SEQUENCE: 879
ttaccatatg tattcatctg a                                          21

SEQ ID NO: 880       moltype = RNA   length = 21
FEATURE              Location/Qualifiers
source               1..21
                     mol_type = other RNA
                     organism = synthetic construct
SEQUENCE: 880
taccatatgt attcatctgt a                                          21

SEQ ID NO: 881       moltype = RNA   length = 21
FEATURE              Location/Qualifiers
source               1..21
                     mol_type = other RNA
                     organism = synthetic construct
SEQUENCE: 881
accatatgta ttcatctgtt a                                          21

SEQ ID NO: 882       moltype = RNA   length = 21
FEATURE              Location/Qualifiers
source               1..21
                     mol_type = other RNA
                     organism = synthetic construct
SEQUENCE: 882
ccatatgtat tcatctgttg a                                          21

SEQ ID NO: 883       moltype = RNA   length = 21
FEATURE              Location/Qualifiers
source               1..21
                     mol_type = other RNA
                     organism = synthetic construct
SEQUENCE: 883
atatgtattc atctgttgga a                                          21

SEQ ID NO: 884       moltype = RNA   length = 21
FEATURE              Location/Qualifiers
source               1..21
                     mol_type = other RNA
                     organism = synthetic construct
SEQUENCE: 884
tatgtattca tctgttggat a                                          21
```

-continued

```
SEQ ID NO: 885          moltype = RNA   length = 21
FEATURE                 Location/Qualifiers
source                  1..21
                        mol_type = other RNA
                        organism = synthetic construct
SEQUENCE: 885
atgtattcat ctgttggatc a                                           21

SEQ ID NO: 886          moltype = RNA   length = 21
FEATURE                 Location/Qualifiers
source                  1..21
                        mol_type = other RNA
                        organism = synthetic construct
SEQUENCE: 886
tgtattcatc tgttggatct a                                           21

SEQ ID NO: 887          moltype = RNA   length = 21
FEATURE                 Location/Qualifiers
source                  1..21
                        mol_type = other RNA
                        organism = synthetic construct
SEQUENCE: 887
gtattcatct gttggatctt a                                           21

SEQ ID NO: 888          moltype = RNA   length = 21
FEATURE                 Location/Qualifiers
source                  1..21
                        mol_type = other RNA
                        organism = synthetic construct
SEQUENCE: 888
tattcatctg ttggatcttg a                                           21

SEQ ID NO: 889          moltype = RNA   length = 21
FEATURE                 Location/Qualifiers
source                  1..21
                        mol_type = other RNA
                        organism = synthetic construct
SEQUENCE: 889
catctgttgg atcttgtaaa a                                           21

SEQ ID NO: 890          moltype = RNA   length = 21
FEATURE                 Location/Qualifiers
source                  1..21
                        mol_type = other RNA
                        organism = synthetic construct
SEQUENCE: 890
tctgttggat cttgtaaaca a                                           21

SEQ ID NO: 891          moltype = RNA   length = 21
FEATURE                 Location/Qualifiers
source                  1..21
                        mol_type = other RNA
                        organism = synthetic construct
SEQUENCE: 891
ctgttggatc ttgtaaacat a                                           21

SEQ ID NO: 892          moltype = RNA   length = 21
FEATURE                 Location/Qualifiers
source                  1..21
                        mol_type = other RNA
                        organism = synthetic construct
SEQUENCE: 892
ggatcttgta aacatgaaaa a                                           21

SEQ ID NO: 893          moltype = RNA   length = 21
FEATURE                 Location/Qualifiers
source                  1..21
                        mol_type = other RNA
                        organism = synthetic construct
SEQUENCE: 893
gatcttgtaa acatgaaaag a                                           21

SEQ ID NO: 894          moltype = RNA   length = 21
FEATURE                 Location/Qualifiers
source                  1..21
                        mol_type = other RNA
                        organism = synthetic construct
SEQUENCE: 894
atcttgtaaa catgaaaagg a                                           21
```

-continued

```
SEQ ID NO: 895          moltype = RNA   length = 21
FEATURE                 Location/Qualifiers
source                  1..21
                        mol_type = other RNA
                        organism = synthetic construct
SEQUENCE: 895
tcttgtaaac atgaaaaggg a                                          21

SEQ ID NO: 896          moltype = RNA   length = 21
FEATURE                 Location/Qualifiers
source                  1..21
                        mol_type = other RNA
                        organism = synthetic construct
SEQUENCE: 896
cttgtaaaca tgaaaagggc a                                          21

SEQ ID NO: 897          moltype = RNA   length = 21
FEATURE                 Location/Qualifiers
source                  1..21
                        mol_type = other RNA
                        organism = synthetic construct
SEQUENCE: 897
aattaacttc aaaataagtg a                                          21

SEQ ID NO: 898          moltype = RNA   length = 21
FEATURE                 Location/Qualifiers
source                  1..21
                        mol_type = other RNA
                        organism = synthetic construct
SEQUENCE: 898
ttaacttcaa aataagtgta a                                          21

SEQ ID NO: 899          moltype = RNA   length = 21
FEATURE                 Location/Qualifiers
source                  1..21
                        mol_type = other RNA
                        organism = synthetic construct
SEQUENCE: 899
ttcaaaataa gtgtataaaa a                                          21

SEQ ID NO: 900          moltype = RNA   length = 21
FEATURE                 Location/Qualifiers
source                  1..21
                        mol_type = other RNA
                        organism = synthetic construct
SEQUENCE: 900
tcaaaataag tgtataaaat a                                          21

SEQ ID NO: 901          moltype = RNA   length = 21
FEATURE                 Location/Qualifiers
source                  1..21
                        mol_type = other RNA
                        organism = synthetic construct
SEQUENCE: 901
caaaataagt gtataaaatg a                                          21

SEQ ID NO: 902          moltype = RNA   length = 21
FEATURE                 Location/Qualifiers
source                  1..21
                        mol_type = other RNA
                        organism = synthetic construct
SEQUENCE: 902
aataagtgta taaaatgcaa a                                          21

SEQ ID NO: 903          moltype = RNA   length = 21
FEATURE                 Location/Qualifiers
source                  1..21
                        mol_type = other RNA
                        organism = synthetic construct
SEQUENCE: 903
ataagtgtat aaaatgcaac a                                          21

SEQ ID NO: 904          moltype = RNA   length = 21
FEATURE                 Location/Qualifiers
source                  1..21
                        mol_type = other RNA
                        organism = synthetic construct
SEQUENCE: 904
```

-continued

```
taagtgtata aaatgcaact a                                           21

SEQ ID NO: 905          moltype = RNA   length = 21
FEATURE                 Location/Qualifiers
source                  1..21
                        mol_type = other RNA
                        organism = synthetic construct
SEQUENCE: 905
aagtgtataa aatgcaactg a                                           21

SEQ ID NO: 906          moltype = RNA   length = 21
FEATURE                 Location/Qualifiers
source                  1..21
                        mol_type = other RNA
                        organism = synthetic construct
SEQUENCE: 906
agtgtataaa atgcaactgt a                                           21

SEQ ID NO: 907          moltype = RNA   length = 21
FEATURE                 Location/Qualifiers
source                  1..21
                        mol_type = other RNA
                        organism = synthetic construct
SEQUENCE: 907
gtgtataaaa tgcaactgtt a                                           21

SEQ ID NO: 908          moltype = RNA   length = 21
FEATURE                 Location/Qualifiers
source                  1..21
                        mol_type = other RNA
                        organism = synthetic construct
SEQUENCE: 908
aaatcttttc tgaagatgaa a                                           21

SEQ ID NO: 909          moltype = RNA   length = 21
FEATURE                 Location/Qualifiers
source                  1..21
                        mol_type = other RNA
                        organism = synthetic construct
SEQUENCE: 909
atcttttctg aagatgaaga a                                           21

SEQ ID NO: 910          moltype = RNA   length = 21
FEATURE                 Location/Qualifiers
source                  1..21
                        mol_type = other RNA
                        organism = synthetic construct
SEQUENCE: 910
tcttttctga agatgaagag a                                           21

SEQ ID NO: 911          moltype = RNA   length = 21
FEATURE                 Location/Qualifiers
source                  1..21
                        mol_type = other RNA
                        organism = synthetic construct
SEQUENCE: 911
cttttctgaa gatgaagagt a                                           21

SEQ ID NO: 912          moltype = RNA   length = 21
FEATURE                 Location/Qualifiers
source                  1..21
                        mol_type = other RNA
                        organism = synthetic construct
SEQUENCE: 912
ttttctgaag atgaagagtt a                                           21

SEQ ID NO: 913          moltype = RNA   length = 21
FEATURE                 Location/Qualifiers
source                  1..21
                        mol_type = other RNA
                        organism = synthetic construct
SEQUENCE: 913
ttctgaagat gaagagttta a                                           21

SEQ ID NO: 914          moltype = RNA   length = 21
FEATURE                 Location/Qualifiers
source                  1..21
                        mol_type = other RNA
                        organism = synthetic construct
```

-continued

```
SEQUENCE: 914
tctgaagatg aagagtttag a                                              21

SEQ ID NO: 915          moltype = RNA  length = 21
FEATURE                 Location/Qualifiers
source                  1..21
                        mol_type = other RNA
                        organism = synthetic construct
SEQUENCE: 915
ctgaagatga agagtttagt a                                              21

SEQ ID NO: 916          moltype = RNA  length = 21
FEATURE                 Location/Qualifiers
source                  1..21
                        mol_type = other RNA
                        organism = synthetic construct
SEQUENCE: 916
tgaagatgaa gagtttagtt a                                              21

SEQ ID NO: 917          moltype = RNA  length = 21
FEATURE                 Location/Qualifiers
source                  1..21
                        mol_type = other RNA
                        organism = synthetic construct
SEQUENCE: 917
gaagatgaag agtttagttt a                                              21

SEQ ID NO: 918          moltype = RNA  length = 21
FEATURE                 Location/Qualifiers
source                  1..21
                        mol_type = other RNA
                        organism = synthetic construct
SEQUENCE: 918
tgaagagttt agttttaaaa a                                              21

SEQ ID NO: 919          moltype = RNA  length = 21
FEATURE                 Location/Qualifiers
source                  1..21
                        mol_type = other RNA
                        organism = synthetic construct
SEQUENCE: 919
gaagagttta gttttaaaac a                                              21

SEQ ID NO: 920          moltype = RNA  length = 21
FEATURE                 Location/Qualifiers
source                  1..21
                        mol_type = other RNA
                        organism = synthetic construct
SEQUENCE: 920
aagagtttag ttttaaaact a                                              21

SEQ ID NO: 921          moltype = RNA  length = 21
FEATURE                 Location/Qualifiers
source                  1..21
                        mol_type = other RNA
                        organism = synthetic construct
SEQUENCE: 921
agagtttagt tttaaaactg a                                              21

SEQ ID NO: 922          moltype = RNA  length = 21
FEATURE                 Location/Qualifiers
source                  1..21
                        mol_type = other RNA
                        organism = synthetic construct
SEQUENCE: 922
agtttagttt taaaactgca a                                              21

SEQ ID NO: 923          moltype = RNA  length = 21
FEATURE                 Location/Qualifiers
source                  1..21
                        mol_type = other RNA
                        organism = synthetic construct
SEQUENCE: 923
gtttagtttt aaaactgcac a                                              21

SEQ ID NO: 924          moltype = RNA  length = 21
FEATURE                 Location/Qualifiers
source                  1..21
                        mol_type = other RNA
```

```
                          organism = synthetic construct
SEQUENCE: 924
tttagtttta aaactgcact a                                            21

SEQ ID NO: 925           moltype = RNA   length = 21
FEATURE                  Location/Qualifiers
source                   1..21
                         mol_type = other RNA
                         organism = synthetic construct
SEQUENCE: 925
ttagttttaa aactgcactg a                                            21

SEQ ID NO: 926           moltype = RNA   length = 21
FEATURE                  Location/Qualifiers
source                   1..21
                         mol_type = other RNA
                         organism = synthetic construct
SEQUENCE: 926
tagttttaaa actgcactgc a                                            21

SEQ ID NO: 927           moltype = RNA   length = 21
FEATURE                  Location/Qualifiers
source                   1..21
                         mol_type = other RNA
                         organism = synthetic construct
SEQUENCE: 927
atcataagaa agagaaaata a                                            21

SEQ ID NO: 928           moltype = RNA   length = 21
FEATURE                  Location/Qualifiers
source                   1..21
                         mol_type = other RNA
                         organism = synthetic construct
SEQUENCE: 928
cataagaaag agaaaatata a                                            21

SEQ ID NO: 929           moltype = RNA   length = 21
FEATURE                  Location/Qualifiers
source                   1..21
                         mol_type = other RNA
                         organism = synthetic construct
SEQUENCE: 929
ataagaaaga gaaaatatat a                                            21

SEQ ID NO: 930           moltype = RNA   length = 21
FEATURE                  Location/Qualifiers
source                   1..21
                         mol_type = other RNA
                         organism = synthetic construct
SEQUENCE: 930
taagaaagag aaaatatatt a                                            21

SEQ ID NO: 931           moltype = RNA   length = 21
FEATURE                  Location/Qualifiers
source                   1..21
                         mol_type = other RNA
                         organism = synthetic construct
SEQUENCE: 931
agaaagagaa aatatattta a                                            21

SEQ ID NO: 932           moltype = RNA   length = 21
FEATURE                  Location/Qualifiers
source                   1..21
                         mol_type = other RNA
                         organism = synthetic construct
SEQUENCE: 932
gaaagagaaa atatatttac a                                            21

SEQ ID NO: 933           moltype = RNA   length = 21
FEATURE                  Location/Qualifiers
source                   1..21
                         mol_type = other RNA
                         organism = synthetic construct
SEQUENCE: 933
aagagaaaat atatttacta a                                            21

SEQ ID NO: 934           moltype = RNA   length = 21
FEATURE                  Location/Qualifiers
source                   1..21
```

-continued

```
                           mol_type = other RNA
                           organism = synthetic construct
SEQUENCE: 934
agagaaaata tatttactat a                                          21

SEQ ID NO: 935         moltype = RNA   length = 21
FEATURE                Location/Qualifiers
source                 1..21
                       mol_type = other RNA
                       organism = synthetic construct
SEQUENCE: 935
gagaaaatat atttactatt a                                          21

SEQ ID NO: 936         moltype = RNA   length = 21
FEATURE                Location/Qualifiers
source                 1..21
                       mol_type = other RNA
                       organism = synthetic construct
SEQUENCE: 936
gaaaatatat ttactattca a                                          21

SEQ ID NO: 937         moltype = RNA   length = 21
FEATURE                Location/Qualifiers
source                 1..21
                       mol_type = other RNA
                       organism = synthetic construct
SEQUENCE: 937
aaaatatatt tactattcat a                                          21

SEQ ID NO: 938         moltype = RNA   length = 21
FEATURE                Location/Qualifiers
source                 1..21
                       mol_type = other RNA
                       organism = synthetic construct
SEQUENCE: 938
tatatttact attcattaaa a                                          21

SEQ ID NO: 939         moltype = RNA   length = 23
FEATURE                Location/Qualifiers
source                 1..23
                       mol_type = other RNA
                       organism = synthetic construct
modified_base          1
                       mod_base = OTHER
                       note = thymine
SEQUENCE: 939
tttaagatga gacagaaatt gat                                        23

SEQ ID NO: 940         moltype = RNA   length = 23
FEATURE                Location/Qualifiers
source                 1..23
                       mol_type = other RNA
                       organism = synthetic construct
modified_base          1
                       mod_base = OTHER
                       note = thymine
SEQUENCE: 940
tataaataga ttctgtagct ttt                                        23

SEQ ID NO: 941         moltype = RNA   length = 23
FEATURE                Location/Qualifiers
source                 1..23
                       mol_type = other RNA
                       organism = synthetic construct
modified_base          1
                       mod_base = OTHER
                       note = thymine
SEQUENCE: 941
tttctttgaa aaaattactt aaa                                        23

SEQ ID NO: 942         moltype = RNA   length = 23
FEATURE                Location/Qualifiers
source                 1..23
                       mol_type = other RNA
                       organism = synthetic construct
modified_base          1
                       mod_base = OTHER
                       note = thymine
SEQUENCE: 942
```

-continued

```
ttaagtttta gtcttaatct tga                                               23

SEQ ID NO: 943          moltype = RNA   length = 23
FEATURE                 Location/Qualifiers
source                  1..23
                        mol_type = other RNA
                        organism = synthetic construct
modified_base           1
                        mod_base = OTHER
                        note = thymine
SEQUENCE: 943
tatgtttaca agatccaaca gat                                               23

SEQ ID NO: 944          moltype = RNA   length = 23
FEATURE                 Location/Qualifiers
source                  1..23
                        mol_type = other RNA
                        organism = synthetic construct
modified_base           1
                        mod_base = OTHER
                        note = thymine
SEQUENCE: 944
tcattttata cacttatttt gaa                                               23

SEQ ID NO: 945          moltype = RNA   length = 23
FEATURE                 Location/Qualifiers
source                  1..23
                        mol_type = other RNA
                        organism = synthetic construct
modified_base           1
                        mod_base = OTHER
                        note = thymine
SEQUENCE: 945
tagttttaaa actaaactct tca                                               23

SEQ ID NO: 946          moltype = RNA   length = 23
FEATURE                 Location/Qualifiers
source                  1..23
                        mol_type = other RNA
                        organism = synthetic construct
modified_base           1
                        mod_base = OTHER
                        note = thymine
SEQUENCE: 946
tctaaactct tcatcttcag aaa                                               23

SEQ ID NO: 947          moltype = RNA   length = 23
FEATURE                 Location/Qualifiers
source                  1..23
                        mol_type = other RNA
                        organism = synthetic construct
modified_base           1
                        mod_base = OTHER
                        note = thymine
SEQUENCE: 947
ttagtaaata tattttctct ttc                                               23

SEQ ID NO: 948          moltype = RNA   length = 23
FEATURE                 Location/Qualifiers
source                  1..23
                        mol_type = other RNA
                        organism = synthetic construct
modified_base           1
                        mod_base = OTHER
                        note = thymine
modified_base           23
                        mod_base = OTHER
                        note = thymine
SEQUENCE: 948
tttaagatga gacagaaatt gat                                               23

SEQ ID NO: 949          moltype = RNA   length = 23
FEATURE                 Location/Qualifiers
source                  1..23
                        mol_type = other RNA
                        organism = synthetic construct
modified_base           1
                        mod_base = OTHER
                        note = thymine
```

-continued

```
modified_base          23
                       mod_base = OTHER
                       note = thymine
SEQUENCE: 949
tttaagatga gacagaaatt gat                                        23

SEQ ID NO: 950        moltype = RNA   length = 23
FEATURE               Location/Qualifiers
source                1..23
                      mol_type = other RNA
                      organism = synthetic construct
modified_base         1
                      mod_base = OTHER
                      note = thymine
modified_base         23
                      mod_base = OTHER
                      note = thymine
SEQUENCE: 950
tttaagatga gacagaaatt gat                                        23

SEQ ID NO: 951        moltype = RNA   length = 23
FEATURE               Location/Qualifiers
source                1..23
                      mol_type = other RNA
                      organism = synthetic construct
modified_base         1
                      mod_base = OTHER
                      note = thymine
modified_base         23
                      mod_base = OTHER
                      note = thymine
SEQUENCE: 951
tttaagatga gacagaaatt gat                                        23

SEQ ID NO: 952        moltype = RNA   length = 23
FEATURE               Location/Qualifiers
source                1..23
                      mol_type = other RNA
                      organism = synthetic construct
modified_base         1
                      mod_base = OTHER
                      note = thymine
modified_base         23
                      mod_base = OTHER
                      note = thymine
SEQUENCE: 952
tttaagatga gacagaaatt gat                                        23

SEQ ID NO: 953        moltype = RNA   length = 23
FEATURE               Location/Qualifiers
source                1..23
                      mol_type = other RNA
                      organism = synthetic construct
modified_base         1
                      mod_base = OTHER
                      note = thymine
SEQUENCE: 953
tttaagatga gacagaaatt gat                                        23

SEQ ID NO: 954        moltype = RNA   length = 23
FEATURE               Location/Qualifiers
source                1..23
                      mol_type = other RNA
                      organism = synthetic construct
modified_base         1
                      mod_base = OTHER
                      note = thymine
SEQUENCE: 954
tttaagatga gacagaaatt gat                                        23

SEQ ID NO: 955        moltype = RNA   length = 23
FEATURE               Location/Qualifiers
source                1..23
                      mol_type = other RNA
                      organism = synthetic construct
modified_base         1
                      mod_base = OTHER
                      note = thymine
SEQUENCE: 955
```

-continued

```
tttaagatga gacagaaatt gat                                           23

SEQ ID NO: 956          moltype = RNA   length = 23
FEATURE                 Location/Qualifiers
source                  1..23
                        mol_type = other RNA
                        organism = synthetic construct
modified_base           1
                        mod_base = OTHER
                        note = thymine
SEQUENCE: 956
tttaagatga gacagaaatt gat                                           23

SEQ ID NO: 957          moltype = RNA   length = 23
FEATURE                 Location/Qualifiers
source                  1..23
                        mol_type = other RNA
                        organism = synthetic construct
modified_base           1
                        mod_base = OTHER
                        note = thymine
modified_base           23
                        mod_base = OTHER
                        note = thymine
SEQUENCE: 957
tttaagatga gacagaaatt gat                                           23

SEQ ID NO: 958          moltype = RNA   length = 23
FEATURE                 Location/Qualifiers
source                  1..23
                        mol_type = other RNA
                        organism = synthetic construct
modified_base           1
                        mod_base = OTHER
                        note = thymine
modified_base           23
                        mod_base = OTHER
                        note = thymine
SEQUENCE: 958
tttaagatga gacagaaatt gat                                           23

SEQ ID NO: 959          moltype = RNA   length = 23
FEATURE                 Location/Qualifiers
source                  1..23
                        mol_type = other RNA
                        organism = synthetic construct
modified_base           1
                        mod_base = OTHER
                        note = thymine
SEQUENCE: 959
tttaagatga gacagaaatt gat                                           23

SEQ ID NO: 960          moltype = RNA   length = 23
FEATURE                 Location/Qualifiers
source                  1..23
                        mol_type = other RNA
                        organism = synthetic construct
modified_base           1
                        mod_base = OTHER
                        note = thymine
SEQUENCE: 960
tttaagatga gacagaaatt gat                                           23

SEQ ID NO: 961          moltype = RNA   length = 23
FEATURE                 Location/Qualifiers
source                  1..23
                        mol_type = other RNA
                        organism = synthetic construct
modified_base           1
                        mod_base = OTHER
                        note = thymine
SEQUENCE: 961
tttaagatga gacagaaatt gat                                           23

SEQ ID NO: 962          moltype = RNA   length = 23
FEATURE                 Location/Qualifiers
source                  1..23
                        mol_type = other RNA
                        organism = synthetic construct
```

-continued

```
modified_base          1
                       mod_base = OTHER
                       note = thymine
SEQUENCE: 962
tttaagatga gacagaaatt gat                                              23

SEQ ID NO: 963        moltype = RNA   length = 23
FEATURE               Location/Qualifiers
source                1..23
                      mol_type = other RNA
                      organism = synthetic construct
modified_base         1
                      mod_base = OTHER
                      note = thymine
modified_base         23
                      mod_base = OTHER
                      note = thymine
SEQUENCE: 963
tttaagatga gacagaaatt gat                                              23

SEQ ID NO: 964        moltype = RNA   length = 23
FEATURE               Location/Qualifiers
source                1..23
                      mol_type = other RNA
                      organism = synthetic construct
modified_base         1
                      mod_base = OTHER
                      note = thymine
SEQUENCE: 964
tttaagatga gacagaaatt gat                                              23

SEQ ID NO: 965        moltype = RNA   length = 23
FEATURE               Location/Qualifiers
source                1..23
                      mol_type = other RNA
                      organism = synthetic construct
modified_base         1
                      mod_base = OTHER
                      note = thymine
modified_base         23
                      mod_base = OTHER
                      note = thymine
SEQUENCE: 965
tttaagatga gacagaaatt gat                                              23

SEQ ID NO: 966        moltype = RNA   length = 23
FEATURE               Location/Qualifiers
source                1..23
                      mol_type = other RNA
                      organism = synthetic construct
modified_base         1
                      mod_base = OTHER
                      note = thymine
SEQUENCE: 966
tttaagatga gacagaaatt gaa                                              23

SEQ ID NO: 967        moltype = RNA   length = 23
FEATURE               Location/Qualifiers
source                1..23
                      mol_type = other RNA
                      organism = synthetic construct
modified_base         1
                      mod_base = OTHER
                      note = thymine
SEQUENCE: 967
tttaagatga gacagaaatt gaa                                              23

SEQ ID NO: 968        moltype = RNA   length = 23
FEATURE               Location/Qualifiers
source                1..23
                      mol_type = other RNA
                      organism = synthetic construct
modified_base         1
                      mod_base = OTHER
                      note = thymine
SEQUENCE: 968
tttaagatga gacagaaatt gaa                                              23

SEQ ID NO: 969        moltype = RNA   length = 23
```

-continued

```
FEATURE            Location/Qualifiers
source             1..23
                   mol_type = other RNA
                   organism = synthetic construct
modified_base      1
                   mod_base = OTHER
                   note = thymine
SEQUENCE: 969
tttaagatga gacagaaatt gaa                                     23

SEQ ID NO: 970     moltype = RNA   length = 23
FEATURE            Location/Qualifiers
source             1..23
                   mol_type = other RNA
                   organism = synthetic construct
modified_base      1
                   mod_base = OTHER
                   note = thymine
SEQUENCE: 970
tttaagatga gacagaaatt gaa                                     23

SEQ ID NO: 971     moltype = RNA   length = 23
FEATURE            Location/Qualifiers
source             1..23
                   mol_type = other RNA
                   organism = synthetic construct
modified_base      1
                   mod_base = OTHER
                   note = thymine
modified_base      6
                   mod_base = OTHER
                   note = thymine
SEQUENCE: 971
ttaagtttta gtcttaatct taa                                     23

SEQ ID NO: 972     moltype = RNA   length = 23
FEATURE            Location/Qualifiers
source             1..23
                   mol_type = other RNA
                   organism = synthetic construct
modified_base      1
                   mod_base = OTHER
                   note = thymine
modified_base      7
                   mod_base = OTHER
                   note = thymine
SEQUENCE: 972
ttaagttta gtcttaatct taa                                      23

SEQ ID NO: 973     moltype = RNA   length = 23
FEATURE            Location/Qualifiers
source             1..23
                   mol_type = other RNA
                   organism = synthetic construct
modified_base      1
                   mod_base = OTHER
                   note = thymine
SEQUENCE: 973
tttaagatga gacagaaatt gaa                                     23

SEQ ID NO: 974     moltype = RNA   length = 23
FEATURE            Location/Qualifiers
source             1..23
                   mol_type = other RNA
                   organism = synthetic construct
modified_base      1
                   mod_base = OTHER
                   note = thymine
SEQUENCE: 974
tataaataga ttctgtagct taa                                     23

SEQ ID NO: 975     moltype = RNA   length = 23
FEATURE            Location/Qualifiers
source             1..23
                   mol_type = other RNA
                   organism = synthetic construct
modified_base      1
                   mod_base = OTHER
                   note = thymine
```

-continued

```
modified_base          7
                       mod_base = OTHER
                       note = thymine
SEQUENCE: 975
tataaataga ttctgtagct taa                                        23

SEQ ID NO: 976         moltype = RNA   length = 21
FEATURE                Location/Qualifiers
source                 1..21
                       mol_type = other RNA
                       organism = synthetic construct
modified_base          1
                       mod_base = OTHER
                       note = thymine
SEQUENCE: 976
tttaagatga gacagaaata a                                          21

SEQ ID NO: 977         moltype = RNA   length = 21
FEATURE                Location/Qualifiers
source                 1..21
                       mol_type = other RNA
                       organism = synthetic construct
SEQUENCE: 977
aagctacaga atctatttat a                                          21

SEQ ID NO: 978         moltype = RNA   length = 21
FEATURE                Location/Qualifiers
source                 1..21
                       mol_type = other RNA
                       organism = synthetic construct
SEQUENCE: 978
caatttctgt ctcatcttaa a                                          21

SEQ ID NO: 979         moltype = RNA   length = 21
FEATURE                Location/Qualifiers
source                 1..21
                       mol_type = other RNA
                       organism = synthetic construct
SEQUENCE: 979
taagtaattt tttcaaagaa a                                          21

SEQ ID NO: 980         moltype = RNA   length = 21
FEATURE                Location/Qualifiers
source                 1..21
                       mol_type = other RNA
                       organism = synthetic construct
SEQUENCE: 980
aagattaaga ctaaaactta a                                          21

SEQ ID NO: 981         moltype = RNA   length = 21
FEATURE                Location/Qualifiers
source                 1..21
                       mol_type = other RNA
                       organism = synthetic construct
SEQUENCE: 981
ctgttggatc ttgtaaacat a                                          21

SEQ ID NO: 982         moltype = RNA   length = 21
FEATURE                Location/Qualifiers
source                 1..21
                       mol_type = other RNA
                       organism = synthetic construct
SEQUENCE: 982
caaaataagt gtataaaatg a                                          21

SEQ ID NO: 983         moltype = RNA   length = 21
FEATURE                Location/Qualifiers
source                 1..21
                       mol_type = other RNA
                       organism = synthetic construct
SEQUENCE: 983
aagagtttag ttttaaaact a                                          21

SEQ ID NO: 984         moltype = RNA   length = 21
FEATURE                Location/Qualifiers
source                 1..21
                       mol_type = other RNA
                       organism = synthetic construct
SEQUENCE: 984
```

-continued

```
tctgaagatg aagagtttag a                                            21

SEQ ID NO: 985          moltype = RNA   length = 21
FEATURE                 Location/Qualifiers
source                  1..21
                        mol_type = other RNA
                        organism = synthetic construct
SEQUENCE: 985
aagagaaaat atatttacta a                                            21

SEQ ID NO: 986          moltype = RNA   length = 21
FEATURE                 Location/Qualifiers
source                  1..21
                        mol_type = other RNA
                        organism = synthetic construct
SEQUENCE: 986
caatttctgt ctcatcttaa a                                            21

SEQ ID NO: 987          moltype = RNA   length = 21
FEATURE                 Location/Qualifiers
source                  1..21
                        mol_type = other RNA
                        organism = synthetic construct
SEQUENCE: 987
caatttctgt ctcatcttaa a                                            21

SEQ ID NO: 988          moltype = RNA   length = 21
FEATURE                 Location/Qualifiers
source                  1..21
                        mol_type = other RNA
                        organism = synthetic construct
SEQUENCE: 988
caatttctgt ctcatcttaa a                                            21

SEQ ID NO: 989          moltype = RNA   length = 21
FEATURE                 Location/Qualifiers
source                  1..21
                        mol_type = other RNA
                        organism = synthetic construct
SEQUENCE: 989
caatttctgt ctcatcttaa a                                            21

SEQ ID NO: 990          moltype = RNA   length = 21
FEATURE                 Location/Qualifiers
source                  1..21
                        mol_type = other RNA
                        organism = synthetic construct
SEQUENCE: 990
caatttctgt ctcatcttaa a                                            21

SEQ ID NO: 991          moltype = RNA   length = 21
FEATURE                 Location/Qualifiers
source                  1..21
                        mol_type = other RNA
                        organism = synthetic construct
SEQUENCE: 991
caatttctgt ctcatcttaa a                                            21

SEQ ID NO: 992          moltype = RNA   length = 21
FEATURE                 Location/Qualifiers
source                  1..21
                        mol_type = other RNA
                        organism = synthetic construct
SEQUENCE: 992
caatttctgt ctcatcttaa a                                            21

SEQ ID NO: 993          moltype = RNA   length = 21
FEATURE                 Location/Qualifiers
source                  1..21
                        mol_type = other RNA
                        organism = synthetic construct
SEQUENCE: 993
caatttctgt ctcatcttaa a                                            21

SEQ ID NO: 994          moltype = RNA   length = 21
FEATURE                 Location/Qualifiers
source                  1..21
                        mol_type = other RNA
                        organism = synthetic construct
```

-continued

```
SEQUENCE: 994
caatttctgt ctcatcttaa a                                                21

SEQ ID NO: 995          moltype = RNA  length = 21
FEATURE                 Location/Qualifiers
source                  1..21
                        mol_type = other RNA
                        organism = synthetic construct
SEQUENCE: 995
caatttctgt ctcatcttaa a                                                21

SEQ ID NO: 996          moltype = RNA  length = 21
FEATURE                 Location/Qualifiers
source                  1..21
                        mol_type = other RNA
                        organism = synthetic construct
SEQUENCE: 996
caatttctgt ctcatcttaa a                                                21

SEQ ID NO: 997          moltype = RNA  length = 21
FEATURE                 Location/Qualifiers
source                  1..21
                        mol_type = other RNA
                        organism = synthetic construct
SEQUENCE: 997
caatttctgt ctcatcttaa a                                                21

SEQ ID NO: 998          moltype = RNA  length = 19
FEATURE                 Location/Qualifiers
source                  1..19
                        mol_type = other RNA
                        organism = synthetic construct
SEQUENCE: 998
atttctgtct catcttaaa                                                   19

SEQ ID NO: 999          moltype = RNA  length = 19
FEATURE                 Location/Qualifiers
source                  1..19
                        mol_type = other RNA
                        organism = synthetic construct
SEQUENCE: 999
atttctgtct catcttaaa                                                   19

SEQ ID NO: 1000         moltype = RNA  length = 19
FEATURE                 Location/Qualifiers
source                  1..19
                        mol_type = other RNA
                        organism = synthetic construct
SEQUENCE: 1000
atttctgtct catcttaaa                                                   19

SEQ ID NO: 1001         moltype = RNA  length = 21
FEATURE                 Location/Qualifiers
source                  1..21
                        mol_type = other RNA
                        organism = synthetic construct
SEQUENCE: 1001
caatttctgt ctcatcttaa a                                                21

SEQ ID NO: 1002         moltype = RNA  length = 21
FEATURE                 Location/Qualifiers
source                  1..21
                        mol_type = other RNA
                        organism = synthetic construct
SEQUENCE: 1002
aagctacaga atctatttat a                                                21

SEQ ID NO: 1003         moltype = RNA  length = 21
FEATURE                 Location/Qualifiers
source                  1..21
                        mol_type = other RNA
                        organism = synthetic construct
SEQUENCE: 1003
taagtaattt tttcaaagaa a                                                21

SEQ ID NO: 1004         moltype = RNA  length = 21
FEATURE                 Location/Qualifiers
source                  1..21
                        mol_type = other RNA
```

-continued

```
                            organism = synthetic construct
SEQUENCE: 1004
aagattaaga ctaaaactta a                                          21

SEQ ID NO: 1005          moltype = RNA   length = 21
FEATURE                  Location/Qualifiers
source                   1..21
                         mol_type = other RNA
                         organism = synthetic construct
SEQUENCE: 1005
ctgttggatc ttgtaaacat a                                          21

SEQ ID NO: 1006          moltype = RNA   length = 21
FEATURE                  Location/Qualifiers
source                   1..21
                         mol_type = other RNA
                         organism = synthetic construct
SEQUENCE: 1006
caaaataagt gtataaaatg a                                          21

SEQ ID NO: 1007          moltype = RNA   length = 21
FEATURE                  Location/Qualifiers
source                   1..21
                         mol_type = other RNA
                         organism = synthetic construct
SEQUENCE: 1007
aagagtttag ttttaaaact a                                          21

SEQ ID NO: 1008          moltype = RNA   length = 21
FEATURE                  Location/Qualifiers
source                   1..21
                         mol_type = other RNA
                         organism = synthetic construct
SEQUENCE: 1008
tctgaagatg aagagtttag a                                          21

SEQ ID NO: 1009          moltype = RNA   length = 21
FEATURE                  Location/Qualifiers
source                   1..21
                         mol_type = other RNA
                         organism = synthetic construct
SEQUENCE: 1009
aagagaaaat atatttacta a                                          21

SEQ ID NO: 1010          moltype = RNA   length = 21
FEATURE                  Location/Qualifiers
source                   1..21
                         mol_type = other RNA
                         organism = synthetic construct
SEQUENCE: 1010
caatttctgt ctcatcttaa a                                          21

SEQ ID NO: 1011          moltype = RNA   length = 21
FEATURE                  Location/Qualifiers
source                   1..21
                         mol_type = other RNA
                         organism = synthetic construct
SEQUENCE: 1011
caatttctgt ctcatcttaa a                                          21

SEQ ID NO: 1012          moltype = RNA   length = 21
FEATURE                  Location/Qualifiers
source                   1..21
                         mol_type = other RNA
                         organism = synthetic construct
SEQUENCE: 1012
caatttctgt ctcatcttaa a                                          21

SEQ ID NO: 1013          moltype = RNA   length = 21
FEATURE                  Location/Qualifiers
source                   1..21
                         mol_type = other RNA
                         organism = synthetic construct
modified_base            20
                         mod_base = OTHER
                         note = thymine
SEQUENCE: 1013
aagctacaga atctatttat a                                          21
```

-continued

```
SEQ ID NO: 1014        moltype = RNA   length = 21
FEATURE                Location/Qualifiers
source                 1..21
                       mol_type = other RNA
                       organism = synthetic construct
SEQUENCE: 1014
aagctacaga atctatttat a                                      21

SEQ ID NO: 1015        moltype = RNA   length = 21
FEATURE                Location/Qualifiers
source                 1..21
                       mol_type = other RNA
                       organism = synthetic construct
SEQUENCE: 1015
aagattaaga ctaaaactta a                                      21

SEQ ID NO: 1016        moltype = RNA   length = 21
FEATURE                Location/Qualifiers
source                 1..21
                       mol_type = other RNA
                       organism = synthetic construct
SEQUENCE: 1016
aagattaaga ctaaaactta a                                      21

SEQ ID NO: 1017        moltype = DNA   length = 16
FEATURE                Location/Qualifiers
source                 1..16
                       mol_type = other DNA
                       organism = synthetic construct
SEQUENCE: 1017
acgagtatat taggaa                                            16

SEQ ID NO: 1018        moltype = DNA   length = 16
FEATURE                Location/Qualifiers
source                 1..16
                       mol_type = other DNA
                       organism = synthetic construct
SEQUENCE: 1018
acgagtatat taggaa                                            16

SEQ ID NO: 1019        moltype = DNA   length = 16
FEATURE                Location/Qualifiers
source                 1..16
                       mol_type = other DNA
                       organism = synthetic construct
SEQUENCE: 1019
tgagaattgt agaggt                                            16

SEQ ID NO: 1020        moltype = DNA   length = 16
FEATURE                Location/Qualifiers
source                 1..16
                       mol_type = other DNA
                       organism = synthetic construct
SEQUENCE: 1020
tgagaattgt agaggt                                            16

SEQ ID NO: 1021        moltype = DNA   length = 16
FEATURE                Location/Qualifiers
source                 1..16
                       mol_type = other DNA
                       organism = synthetic construct
SEQUENCE: 1021
tgagaattgt agaggt                                            16

SEQ ID NO: 1022        moltype = DNA   length = 16
FEATURE                Location/Qualifiers
source                 1..16
                       mol_type = other DNA
                       organism = synthetic construct
SEQUENCE: 1022
tgagaattgt agaggt                                            16

SEQ ID NO: 1023        moltype = DNA   length = 16
FEATURE                Location/Qualifiers
source                 1..16
                       mol_type = other DNA
                       organism = synthetic construct
SEQUENCE: 1023
tgagaattgt agaggt                                            16
```

-continued

```
SEQ ID NO: 1024          moltype = DNA   length = 16
FEATURE                  Location/Qualifiers
source                   1..16
                         mol_type = other DNA
                         organism = synthetic construct
SEQUENCE: 1024
acacgagtat attagg                                              16

SEQ ID NO: 1025          moltype = DNA   length = 16
FEATURE                  Location/Qualifiers
source                   1..16
                         mol_type = other DNA
                         organism = synthetic construct
SEQUENCE: 1025
acacgagtat attagg                                              16

SEQ ID NO: 1026          moltype = AA   length = 13
FEATURE                  Location/Qualifiers
source                   1..13
                         mol_type = protein
                         organism = synthetic construct
SEQUENCE: 1026
CXXDXXXGCI SYC                                                 13

SEQ ID NO: 1027          moltype = RNA   length = 21
FEATURE                  Location/Qualifiers
source                   1..21
                         mol_type = other RNA
                         organism = synthetic construct
modified_base            1
                         mod_base = OTHER
                         note = 2'-O-methoxyethyl 5-methylcytidine
                          3'-phosphorothioate
modified_base            2
                         mod_base = OTHER
                         note = 2'-O-methoxyethyl adenosine 3'-phosphorothioate
modified_base            3
                         mod_base = OTHER
                         note = 2'-O-methyl adenosine 3'-phosphodiester
modified_base            4..6
                         mod_base = OTHER
                         note = 2'-O-methyl uridine 3'-phosphodiester
modified_base            7
                         mod_base = OTHER
                         note = 2'-O-methyl cytidine 3'-phosphodiester
modified_base            8
                         mod_base = OTHER
                         note = 2'-O-methyl uridine 3'-phosphodiester
modified_base            9
                         mod_base = OTHER
                         note = 2'-O-methyl guanosine 3'-phosphodiester
modified_base            10
                         mod_base = OTHER
                         note = 2'-fluoro uridine 3'-phosphodiester
modified_base            11
                         mod_base = OTHER
                         note = 2'-fluoro cytidine 3'-phosphodiester
modified_base            12
                         mod_base = OTHER
                         note = 2'-O-methyl uridine 3'-phosphodiester
modified_base            13
                         mod_base = OTHER
                         note = 2'-O-methyl cytidine 3'-phosphodiester
modified_base            14
                         mod_base = OTHER
                         note = 2'-O-methyl adenosine 3'-phosphodiester
modified_base            15
                         mod_base = OTHER
                         note = 2'-O-methyl uridine 3'-phosphodiester
modified_base            16
                         mod_base = OTHER
                         note = 2'-O-methyl cytidine 3'-phosphodiester
modified_base            17..18
                         mod_base = OTHER
                         note = 2'-O-methyl uridine 3'-phosphodiester
modified_base            19
                         mod_base = OTHER
                         note = 2'-O-methyl adenosine 3'-phosphorothioate
```

-continued

```
modified_base          20
                       mod_base = OTHER
                       note = 2'-O-methoxyethyl adenosine 3'-phosphorothioate
modified_base          21
                       mod_base = OTHER
                       note = 2'-O-methoxyethyl adenosine
SEQUENCE: 1027
caatttctgt ctcatcttaa a                                                21

SEQ ID NO: 1028        moltype = RNA  length = 21
FEATURE                Location/Qualifiers
source                 1..21
                       mol_type = other RNA
                       organism = synthetic construct
modified_base          1
                       mod_base = OTHER
                       note = 2'-O-methoxyethyl cytidine 3'-phosphorothioate
modified_base          2
                       mod_base = OTHER
                       note = 2'-O-methoxyethyl adenosine 3'-phosphorothioate
modified_base          3
                       mod_base = OTHER
                       note = 2'-O-methyl adenosine 3'-phosphodiester
modified_base          4..6
                       mod_base = OTHER
                       note = 2'-O-methyl uridine 3'-phosphodiester
modified_base          7
                       mod_base = OTHER
                       note = 2'-fluoro cytidine 3'-phosphodiester
modified_base          8
                       mod_base = OTHER
                       note = 2'-O-methyl uridine 3'-phosphodiester
modified_base          9
                       mod_base = OTHER
                       note = 2'-fluoro guanosine 3'-phosphodiester
modified_base          10
                       mod_base = OTHER
                       note = 2'-O-methyl uridine 3'-phosphodiester
modified_base          11
                       mod_base = OTHER
                       note = 2'-fluoro cytidine 3'-phosphodiester
modified_base          12
                       mod_base = OTHER
                       note = 2'-O-methyl uridine 3'-phosphodiester
modified_base          13
                       mod_base = OTHER
                       note = 2'-O-methyl cytidine 3'-phosphodiester
modified_base          14
                       mod_base = OTHER
                       note = 2'-O-methyl adenosine 3'-phosphodiester
modified_base          15
                       mod_base = OTHER
                       note = 2'-O-methyl uridine 3'-phosphodiester
modified_base          16
                       mod_base = OTHER
                       note = 2'-O-methyl cytidine 3'-phosphodiester
modified_base          17..18
                       mod_base = OTHER
                       note = 2'-O-methyl uridine 3'-phosphodiester
modified_base          19
                       mod_base = OTHER
                       note = 2'-O-methyl adenosine 3'-phosphorothioate
modified_base          20
                       mod_base = OTHER
                       note = 2'-O-methoxyethyl adenosine 3'-phosphorothioate
modified_base          21
                       mod_base = OTHER
                       note = 2'-O-methoxyethyl adenosine
SEQUENCE: 1028
caatttctgt ctcatcttaa a                                                21

SEQ ID NO: 1029        moltype = RNA  length = 21
FEATURE                Location/Qualifiers
source                 1..21
                       mol_type = other RNA
                       organism = synthetic construct
modified_base          20
                       mod_base = OTHER
                       note = thymine
```

-continued

```
modified_base          1..2
                       mod_base = OTHER
                       note = 2'-O-methoxyethyl adenosine 3'-phosphorothioate
modified_base          3
                       mod_base = OTHER
                       note = 2'-O-methyl guanosine 3'-phosphodiester
modified_base          4
                       mod_base = OTHER
                       note = 2'-O-methyl cytidine 3'-phosphodiester
modified_base          5
                       mod_base = OTHER
                       note = 2'-O-methyl uridine 3'-phosphodiester
modified_base          6
                       mod_base = OTHER
                       note = 2'-O-methyl adenosine 3'-phosphodiester
modified_base          7
                       mod_base = OTHER
                       note = 2'-O-methyl cytidine 3'-phosphodiester
modified_base          8
                       mod_base = OTHER
                       note = 2'-O-methyl adenosine 3'-phosphodiester
modified_base          9
                       mod_base = OTHER
                       note = 2'-O-methyl guanosine 3'-phosphodiester
modified_base          10..11
                       mod_base = OTHER
                       note = 2'-fluoro adenosine 3'-phosphodiester
modified_base          12
                       mod_base = OTHER
                       note = 2'-O-methyl uridine 3'-phosphodiester
modified_base          13
                       mod_base = OTHER
                       note = 2'-O-methyl cytidine 3'-phosphodiester
modified_base          14
                       mod_base = OTHER
                       note = 2'-O-methyl uridine 3'-phosphodiester
modified_base          15
                       mod_base = OTHER
                       note = 2'-O-methyl adenosine 3'-phosphodiester
modified_base          16..18
                       mod_base = OTHER
                       note = 2'-O-methyl uridine 3'-phosphodiester
modified_base          19
                       mod_base = OTHER
                       note = 2'-O-methyl adenosine 3'-phosphorothioate
modified_base          20
                       mod_base = OTHER
                       note = 2'-O-methoxyethyl thymidine 3'-phosphorothioate
modified_base          21
                       mod_base = OTHER
                       note = 2'-O-methoxyethyl adenosine
SEQUENCE: 1029
aagctacaga atctatttat a                                                  21

SEQ ID NO: 1030        moltype = RNA   length = 21
FEATURE                Location/Qualifiers
source                 1..21
                       mol_type = other RNA
                       organism = synthetic construct
modified_base          1..2
                       mod_base = OTHER
                       note = 2'-O-methoxyethyl adenosine 3'-phosphorothioate
modified_base          3
                       mod_base = OTHER
                       note = 2'-O-methyl guanosine 3'-phosphodiester
modified_base          4
                       mod_base = OTHER
                       note = 2'-O-methyl cytidine 3'-phosphodiester
modified_base          5
                       mod_base = OTHER
                       note = 2'-O-methyl uridine 3'-phosphodiester
modified_base          6
                       mod_base = OTHER
                       note = 2'-O-methyl adenosine 3'-phosphodiester
modified_base          7
                       mod_base = OTHER
                       note = 2'-fluoro cytidine 3'-phosphodiester
modified_base          8
                       mod_base = OTHER
```

-continued

```
                        note = 2'-O-methyl adenosine 3'-phosphodiester
modified_base          9
                        mod_base = OTHER
                        note = 2'-fluoro guanosine 3'-phosphodiester
modified_base          10
                        mod_base = OTHER
                        note = 2'-O-methyl adenosine 3'-phosphodiester
modified_base          11
                        mod_base = OTHER
                        note = 2'-fluoro adenosine 3'-phosphodiester
modified_base          12
                        mod_base = OTHER
                        note = 2'-O-methyl uridine 3'-phosphodiester
modified_base          13
                        mod_base = OTHER
                        note = 2'-O-methyl cytidine 3'-phosphodiester
modified_base          14
                        mod_base = OTHER
                        note = 2'-O-methyl uridine 3'-phosphodiester
modified_base          15
                        mod_base = OTHER
                        note = 2'-O-methyl adenosine 3'-phosphodiester
modified_base          16..18
                        mod_base = OTHER
                        note = 2'-O-methyl uridine 3'-phosphodiester
modified_base          19
                        mod_base = OTHER
                        note = 2'-O-methyl adenosine 3'-phosphorothioate
modified_base          20
                        mod_base = OTHER
                        note = 2'-O-methoxyethyl uridine 3'-phosphorothioate
modified_base          21
                        mod_base = OTHER
                        note = 2'-O-methoxyethyl adenosine
SEQUENCE: 1030
aagctacaga atctatttat a                                               21

SEQ ID NO: 1031        moltype = RNA  length = 21
FEATURE                Location/Qualifiers
source                 1..21
                        mol_type = other RNA
                        organism = synthetic construct
modified_base          1..2
                        mod_base = OTHER
                        note = 2'-O-methoxyethyl adenosine 3'-phosphorothioate
modified_base          3
                        mod_base = OTHER
                        note = 2'-O-methyl guanosine 3'-phosphodiester
modified_base          4
                        mod_base = OTHER
                        note = 2'-O-methyl adenosine 3'-phosphodiester
modified_base          5..6
                        mod_base = OTHER
                        note = 2'-O-methyl uridine 3'-phosphodiester
modified_base          7..8
                        mod_base = OTHER
                        note = 2'-O-methyl adenosine 3'-phosphodiester
modified_base          9
                        mod_base = OTHER
                        note = 2'-O-methyl guanosine 3'-phosphodiester
modified_base          10
                        mod_base = OTHER
                        note = 2'-fluoro adenosine 3'-phosphodiester
modified_base          11
                        mod_base = OTHER
                        note = 2'-fluoro cytidine 3'-phosphodiester
modified_base          12
                        mod_base = OTHER
                        note = 2'-O-methyl uridine 3'-phosphodiester
modified_base          13..16
                        mod_base = OTHER
                        note = 2'-O-methyl adenosine 3'-phosphodiester
modified_base          17
                        mod_base = OTHER
                        note = 2'-O-methyl cytidine 3'-phosphodiester
modified_base          18
                        mod_base = OTHER
                        note = 2'-O-methyl uridine 3'-phosphodiester
modified_base          19
```

```
                               mod_base = OTHER
                               note = 2'-O-methyl uridine 3'-phosphorothioate
modified_base                  20
                               mod_base = OTHER
                               note = 2'-O-methoxyethyl adenosine 3'-phosphorothioate
modified_base                  21
                               mod_base = OTHER
                               note = 2'-O-methoxyethyl adenosine
SEQUENCE: 1031
aagattaaga ctaaaactta a                                                   21

SEQ ID NO: 1032               moltype = RNA  length = 21
FEATURE                       Location/Qualifiers
source                        1..21
                               mol_type = other RNA
                               organism = synthetic construct
modified_base                  1..2
                               mod_base = OTHER
                               note = 2'-O-methoxyethyl adenosine 3'-phosphorothioate
modified_base                  3
                               mod_base = OTHER
                               note = 2'-O-methyl guanosine 3'-phosphodiester
modified_base                  4
                               mod_base = OTHER
                               note = 2'-O-methyl adenosine 3'-phosphodiester
modified_base                  5..6
                               mod_base = OTHER
                               note = 2'-O-methyl uridine 3'-phosphodiester
modified_base                  7
                               mod_base = OTHER
                               note = 2'-fluoro adenosine 3'-phosphodiester
modified_base                  8
                               mod_base = OTHER
                               note = 2'-O-methyl adenosine 3'-phosphodiester
modified_base                  9
                               mod_base = OTHER
                               note = 2'-fluoro guanosine 3'-phosphodiester
modified_base                  10
                               mod_base = OTHER
                               note = 2'-O-methyl adenosine 3'-phosphodiester
modified_base                  11
                               mod_base = OTHER
                               note = 2'-fluoro cytidine 3'-phosphodiester
modified_base                  12
                               mod_base = OTHER
                               note = 2'-O-methyl uridine 3'-phosphodiester
modified_base                  13..16
                               mod_base = OTHER
                               note = 2'-O-methyl adenosine 3'-phosphodiester
modified_base                  17
                               mod_base = OTHER
                               note = 2'-O-methyl cytidine 3'-phosphodiester
modified_base                  18
                               mod_base = OTHER
                               note = 2'-O-methyl uridine 3'-phosphodiester
modified_base                  19
                               mod_base = OTHER
                               note = 2'-O-methyl uridine 3'-phosphorothioate
modified_base                  20
                               mod_base = OTHER
                               note = 2'-O-methoxyethyl adenosine 3'-phosphorothioate
modified_base                  21
                               mod_base = OTHER
                               note = 2'-O-methoxyethyl adenosine
SEQUENCE: 1032
aagattaaga ctaaaactta a                                                   21

SEQ ID NO: 1033               moltype = RNA  length = 23
FEATURE                       Location/Qualifiers
source                        1..23
                               mol_type = other RNA
                               organism = synthetic construct
modified_base                  1
                               mod_base = OTHER
                               note = thymine
modified_base
                               mod_base = OTHER
                               note = vinyl phosphonate
modified_base                  1
```

-continued

```
                         mod_base = OTHER
                         note = 2'-O-methoxyethyl thymidine 3'-phosphorothioate
modified_base            2
                         mod_base = OTHER
                         note = 2'-fluoro uridine 3'-phosphorothioate
modified_base            3
                         mod_base = OTHER
                         note = 2'-O-methyl uridine 3'-phosphodiester
modified_base            4..5
                         mod_base = OTHER
                         note = 2'-O-methyl adenosine 3'-phosphodiester
modified_base            6
                         mod_base = OTHER
                         note = 2'-deoxyguanosine 3'-phosphodiester
modified_base            7
                         mod_base = OTHER
                         note = 2'-O-methyl adenosine 3'-phosphodiester
modified_base            8
                         mod_base = OTHER
                         note = 2'-O-methyl uridine 3'-phosphodiester
modified_base            9
                         mod_base = OTHER
                         note = 2'-O-methyl guanosine 3'-phosphodiester
modified_base            10
                         mod_base = OTHER
                         note = 2'-O-methyl adenosine 3'-phosphodiester
modified_base            11
                         mod_base = OTHER
                         note = 2'-O-methyl guanosine 3'-phosphodiester
modified_base            12
                         mod_base = OTHER
                         note = 2'-O-methyl adenosine 3'-phosphodiester
modified_base            13
                         mod_base = OTHER
                         note = 2'-O-methyl cytidine 3'-phosphodiester
modified_base            14
                         mod_base = OTHER
                         note = 2'-fluoro adenosine 3'-phosphodiester
modified_base            15
                         mod_base = OTHER
                         note = 2'-O-methyl guanosine 3'-phosphodiester
modified_base            16
                         mod_base = OTHER
                         note = 2'-fluoro adenosine 3'-phosphodiester
modified_base            17..18
                         mod_base = OTHER
                         note = 2'-O-methyl adenosine 3'-phosphodiester
modified_base            19..20
                         mod_base = OTHER
                         note = 2'-O-methyl uridine 3'-phosphodiester
modified_base            21
                         mod_base = OTHER
                         note = 2'-O-methyl guanosine 3'-phosphorothioate
modified_base            22
                         mod_base = OTHER
                         note = 2'-O-methoxyethyl adenosine 3'-phosphorothioate
modified_base            23
                         mod_base = OTHER
                         note = 2'-O-methoxyethyl adenosine
SEQUENCE: 1033
tttaagatga gacagaaatt gaa                                        23

SEQ ID NO: 1034          moltype = RNA  length = 23
FEATURE                  Location/Qualifiers
source                   1..23
                         mol_type = other RNA
                         organism = synthetic construct
modified_base            1
                         mod_base = OTHER
                         note = thymine
modified_base
                         mod_base = OTHER
                         note = vinyl phosphonate
modified_base            1
                         mod_base = OTHER
                         note = 2'-O-methoxyethyl thymidine 3'-phosphorothioate
modified_base            2
                         mod_base = OTHER
                         note = 2'-fluoro uridine 3'-phosphorothioate
```

-continued

```
modified_base       3
                    mod_base = OTHER
                    note = 2'-O-methyl uridine 3'-phosphodiester
modified_base       4
                    mod_base = OTHER
                    note = 2'-O-methyl adenosine 3'-phosphodiester
modified_base       5
                    mod_base = OTHER
                    note = 2'-deoxyadenosine 3'-phosphodiester
modified_base       6
                    mod_base = OTHER
                    note = 2'-O-methyl guanosine 3'-phosphodiester
modified_base       7
                    mod_base = OTHER
                    note = 2'-deoxyadenosine 3'-phosphodiester
modified_base       8
                    mod_base = OTHER
                    note = 2'-O-methyl uridine 3'-phosphodiester
modified_base       9
                    mod_base = OTHER
                    note = 2'-O-methyl guanosine 3'-phosphodiester
modified_base       10
                    mod_base = OTHER
                    note = 2'-O-methyl adenosine 3'-phosphodiester
modified_base       11
                    mod_base = OTHER
                    note = 2'-O-methyl guanosine 3'-phosphodiester
modified_base       12
                    mod_base = OTHER
                    note = 2'-O-methyl adenosine 3'-phosphodiester
modified_base       13
                    mod_base = OTHER
                    note = 2'-O-methyl cytidine 3'-phosphodiester
modified_base       14
                    mod_base = OTHER
                    note = 2'-fluoro adenosine 3'-phosphodiester
modified_base       15
                    mod_base = OTHER
                    note = 2'-O-methyl guanosine 3'-phosphodiester
modified_base       16
                    mod_base = OTHER
                    note = 2'-fluoro adenosine 3'-phosphodiester
modified_base       17..18
                    mod_base = OTHER
                    note = 2'-O-methyl adenosine 3'-phosphodiester
modified_base       19..20
                    mod_base = OTHER
                    note = 2'-O-methyl uridine 3'-phosphodiester
modified_base       21
                    mod_base = OTHER
                    note = 2'-O-methyl guanosine 3'-phosphorothioate
modified_base       22
                    mod_base = OTHER
                    note = 2'-O-methoxyethyl adenosine 3'-phosphorothioate
modified_base       23
                    mod_base = OTHER
                    note = 2'-O-methoxyethyl adenosine
SEQUENCE: 1034
tttaagatga gacagaaatt gaa                                    23

SEQ ID NO: 1035     moltype = RNA  length = 23
FEATURE             Location/Qualifiers
source              1..23
                    mol_type = other RNA
                    organism = synthetic construct
modified_base       1
                    mod_base = OTHER
                    note = thymine
modified_base
                    mod_base = OTHER
                    note = vinyl phosphonate
modified_base       1
                    mod_base = OTHER
                    note = 2'-O-methoxyethyl thymidine 3'-phosphorothioate
modified_base       2
                    mod_base = OTHER
                    note = 2'-fluoro adenosine 3'-phosphorothioate
modified_base       3
                    mod_base = OTHER
```

-continued

```
                        note = 2'-O-methyl uridine 3'-phosphodiester
modified_base           4..5
                        mod_base = OTHER
                        note = 2'-O-methyl adenosine 3'-phosphodiester
modified_base           6
                        mod_base = OTHER
                        note = 2'-deoxyadenosine 3'-phosphodiester
modified_base           7
                        mod_base = OTHER
                        note = 2'-O-methyl uridine 3'-phosphodiester
modified_base           8
                        mod_base = OTHER
                        note = 2'-O-methyl adenosine 3'-phosphodiester
modified_base           9
                        mod_base = OTHER
                        note = 2'-O-methyl guanosine 3'-phosphodiester
modified_base           10
                        mod_base = OTHER
                        note = 2'-O-methyl adenosine 3'-phosphodiester
modified_base           11..12
                        mod_base = OTHER
                        note = 2'-O-methyl uridine 3'-phosphodiester
modified_base           13
                        mod_base = OTHER
                        note = 2'-O-methyl cytidine 3'-phosphodiester
modified_base           14
                        mod_base = OTHER
                        note = 2'-fluoro uridine 3'-phosphodiester
modified_base           15
                        mod_base = OTHER
                        note = 2'-O-methyl guanosine 3'-phosphodiester
modified_base           16
                        mod_base = OTHER
                        note = 2'-fluoro uridine 3'-phosphodiester
modified_base           17
                        mod_base = OTHER
                        note = 2'-O-methyl adenosine 3'-phosphodiester
modified_base           18
                        mod_base = OTHER
                        note = 2'-O-methyl guanosine 3'-phosphodiester
modified_base           19
                        mod_base = OTHER
                        note = 2'-O-methyl cytidine 3'-phosphodiester
modified_base           20
                        mod_base = OTHER
                        note = 2'-O-methyl uridine 3'-phosphodiester
modified_base           21
                        mod_base = OTHER
                        note = 2'-O-methyl uridine 3'-phosphorothioate
modified_base           22
                        mod_base = OTHER
                        note = 2'-O-methoxyethyl adenosine 3'-phosphorothioate
modified_base           23
                        mod_base = OTHER
                        note = 2'-O-methoxyethyl adenosine
SEQUENCE: 1035
tataaataga ttctgtagct taa                                          23

SEQ ID NO: 1036         moltype = RNA  length = 23
FEATURE                 Location/Qualifiers
source                  1..23
                        mol_type = other RNA
                        organism = synthetic construct
modified_base           1
                        mod_base = OTHER
                        note = thymine
modified_base           7
                        mod_base = OTHER
                        note = thymine
modified_base
                        mod_base = OTHER
                        note = vinyl phosphonate
modified_base           1
                        mod_base = OTHER
                        note = 2'-O-methoxyethyl thymidine 3'-phosphorothioate
modified_base           2
                        mod_base = OTHER
                        note = 2'-fluoro adenosine 3'-phosphorothioate
modified_base           3
```

-continued

```
                        mod_base = OTHER
                        note = 2'-O-methyl uridine 3'-phosphodiester
modified_base           4
                        mod_base = OTHER
                        note = 2'-O-methyl adenosine 3'-phosphodiester
modified_base           5
                        mod_base = OTHER
                        note = 2'-deoxyadenosine 3'-phosphodiester
modified_base           6
                        mod_base = OTHER
                        note = 2'-O-methyl adenosine 3'-phosphodiester
modified_base           7
                        mod_base = OTHER
                        note = 2'-deoxythymidine 3'-phosphodiester
modified_base           8
                        mod_base = OTHER
                        note = 2'-O-methyl adenosine 3'-phosphodiester
modified_base           9
                        mod_base = OTHER
                        note = 2'-O-methyl guanosine 3'-phosphodiester
modified_base           10
                        mod_base = OTHER
                        note = 2'-O-methyl adenosine 3'-phosphodiester
modified_base           11..12
                        mod_base = OTHER
                        note = 2'-O-methyl uridine 3'-phosphodiester
modified_base           13
                        mod_base = OTHER
                        note = 2'-O-methyl cytidine 3'-phosphodiester
modified_base           14
                        mod_base = OTHER
                        note = 2'-fluoro uridine 3'-phosphodiester
modified_base           15
                        mod_base = OTHER
                        note = 2'-O-methyl guanosine 3'-phosphodiester
modified_base           16
                        mod_base = OTHER
                        note = 2'-fluoro uridine 3'-phosphodiester
modified_base           17
                        mod_base = OTHER
                        note = 2'-O-methyl adenosine 3'-phosphodiester
modified_base           18
                        mod_base = OTHER
                        note = 2'-O-methyl guanosine 3'-phosphodiester
modified_base           19
                        mod_base = OTHER
                        note = 2'-O-methyl cytidine 3'-phosphodiester
modified_base           20
                        mod_base = OTHER
                        note = 2'-O-methyl uridine 3'-phosphodiester
modified_base           21
                        mod_base = OTHER
                        note = 2'-O-methyl uridine 3'-phosphorothioate
modified_base           22
                        mod_base = OTHER
                        note = 2'-O-methoxyethyl adenosine 3'-phosphorothioate
modified_base           23
                        mod_base = OTHER
                        note = 2'-O-methoxyethyl adenosine
SEQUENCE: 1036
tataaataga ttctgtagct taa                                              23

SEQ ID NO: 1037         moltype = RNA   length = 23
FEATURE                 Location/Qualifiers
source                  1..23
                        mol_type = other RNA
                        organism = synthetic construct
modified_base           1
                        mod_base = OTHER
                        note = thymine
modified_base           6
                        mod_base = OTHER
                        note = thymine
modified_base
                        mod_base = OTHER
                        note = vinyl phosphonate
modified_base           1
                        mod_base = OTHER
                        note = 2'-O-methoxyethyl thymidine 3'-phosphorothioate
```

-continued

```
modified_base        2
                     mod_base = OTHER
                     note = 2'-fluoro uridine 3'-phosphorothioate
modified_base        3..4
                     mod_base = OTHER
                     note = 2'-O-methyl adenosine 3'-phosphodiester
modified_base        5
                     mod_base = OTHER
                     note = 2'-O-methyl guanosine 3'-phosphodiester
modified_base        6
                     mod_base = OTHER
                     note = 2'-deoxythymidine 3'-phosphodiester
modified_base        7..9
                     mod_base = OTHER
                     note = 2'-O-methyl uridine 3'-phosphodiester
modified_base        10
                     mod_base = OTHER
                     note = 2'-O-methyl adenosine 3'-phosphodiester
modified_base        11
                     mod_base = OTHER
                     note = 2'-O-methyl guanosine 3'-phosphodiester
modified_base        12
                     mod_base = OTHER
                     note = 2'-O-methyl uridine 3'-phosphodiester
modified_base        13
                     mod_base = OTHER
                     note = 2'-O-methyl cytidine 3'-phosphodiester
modified_base        14
                     mod_base = OTHER
                     note = 2'-fluoro uridine 3'-phosphodiester
modified_base        15
                     mod_base = OTHER
                     note = 2'-O-methyl uridine 3'-phosphodiester
modified_base        16
                     mod_base = OTHER
                     note = 2'-fluoro adenosine 3'-phosphodiester
modified_base        17
                     mod_base = OTHER
                     note = 2'-O-methyl adenosine 3'-phosphodiester
modified_base        18
                     mod_base = OTHER
                     note = 2'-O-methyl uridine 3'-phosphodiester
modified_base        19
                     mod_base = OTHER
                     note = 2'-O-methyl cytidine 3'-phosphodiester
modified_base        20
                     mod_base = OTHER
                     note = 2'-O-methyl uridine 3'-phosphodiester
modified_base        21
                     mod_base = OTHER
                     note = 2'-O-methyl uridine 3'-phosphorothioate
modified_base        22
                     mod_base = OTHER
                     note = 2'-O-methoxyethyl adenosine 3'-phosphorothioate
modified_base        23
                     mod_base = OTHER
                     note = 2'-O-methoxyethyl adenosine SEQUENCE: 1037
ttaagttttta gtcttaatct taa                                    23

SEQ ID NO: 1038      moltype = RNA  length = 23
FEATURE              Location/Qualifiers
source               1..23
                     mol_type = other RNA
                     organism = synthetic construct
modified_base        1
                     mod_base = OTHER
                     note = thymine
modified_base        7
                     mod_base = OTHER
                     note = thymine
modified_base
                     mod_base = OTHER
                     note = vinyl phosphonate
modified_base        1
                     mod_base = OTHER
                     note = 2'-O-methoxyethyl thymidine 3'-phosphorothioate
modified_base        2
                     mod_base = OTHER
```

-continued

```
                          note = 2'-fluoro uridine 3'-phosphorothioate
modified_base             3..4
                          mod_base = OTHER
                          note = 2'-O-methyl adenosine 3'-phosphodiester
modified_base             5
                          mod_base = OTHER
                          note = 2'-deoxyguanosine 3'-phosphodiester
modified_base             6
                          mod_base = OTHER
                          note = 2'-O-methyl uridine 3'-phosphodiester
modified_base             7
                          mod_base = OTHER
                          note = 2'-deoxythymidine 3'-phosphodiester
modified_base             8..9
                          mod_base = OTHER
                          note = 2'-O-methyl uridine 3'-phosphodiester
modified_base             10
                          mod_base = OTHER
                          note = 2'-O-methyl adenosine 3'-phosphodiester
modified_base             11
                          mod_base = OTHER
                          note = 2'-O-methyl guanosine 3'-phosphodiester
modified_base             12
                          mod_base = OTHER
                          note = 2'-O-methyl uridine 3'-phosphodiester
modified_base             13
                          mod_base = OTHER
                          note = 2'-O-methyl cytidine 3'-phosphodiester
modified_base             14
                          mod_base = OTHER
                          note = 2'-fluoro uridine 3'-phosphodiester
modified_base             15
                          mod_base = OTHER
                          note = 2'-O-methyl uridine 3'-phosphodiester
modified_base             16
                          mod_base = OTHER
                          note = 2'-fluoro adenosine 3'-phosphodiester
modified_base             17
                          mod_base = OTHER
                          note = 2'-O-methyl adenosine 3'-phosphodiester
modified_base             18
                          mod_base = OTHER
                          note = 2'-O-methyl uridine 3'-phosphodiester
modified_base             19
                          mod_base = OTHER
                          note = 2'-O-methyl cytidine 3'-phosphodiester
modified_base             20
                          mod_base = OTHER
                          note = 2'-O-methyl uridine 3'-phosphodiester
modified_base             21
                          mod_base = OTHER
                          note = 2'-O-methyl uridine 3'-phosphorothioate
modified_base             22
                          mod_base = OTHER
                          note = 2'-O-methoxyethyl adenosine 3'-phosphorothioate
modified_base             23
                          mod_base = OTHER
                          note = 2'-O-methoxyethyl adenosine
SEQUENCE: 1038
ttaagtttta gtcttaatct taa                                             23

SEQ ID NO: 1039          moltype = RNA  length = 21
FEATURE                  Location/Qualifiers
source                   1..21
                          mol_type = other RNA
                          organism = synthetic construct
modified_base
                          mod_base = OTHER
                          note = [X]n , wherein [X] = a conjugate group comprising a
                           bicycle ligand, and n and k (at 21) are 0 or 1, wherein
                           if n=1 then k=0, and if n=0 then k=1
modified_base             1
                          mod_base = OTHER
                          note = 2'-O-methoxyethyl 5-methylcytidine
                           3'-phosphorothioate
modified_base             2
                          mod_base = OTHER
                          note = 2'-O-methoxyethyl adenosine 3'-phosphorothioate
modified_base             3
```

-continued

```
                        mod_base = OTHER
                        note = 2'-O-methyl adenosine 3'-phosphodiester
modified_base           4..6
                        mod_base = OTHER
                        note = 2'-O-methyl uridine 3'-phosphodiester
modified_base           7
                        mod_base = OTHER
                        note = 2'-O-methyl cytidine 3'-phosphodiester
modified_base           8
                        mod_base = OTHER
                        note = 2'-O-methyl uridine 3'-phosphodiester
modified_base           9
                        mod_base = OTHER
                        note = 2'-O-methyl guanosine 3'-phosphodiester
modified_base           10
                        mod_base = OTHER
                        note = 2'-fluoro uridine 3'-phosphodiester
modified_base           11
                        mod_base = OTHER
                        note = 2'-fluoro cytidine 3'-phosphodiester
modified_base           12
                        mod_base = OTHER
                        note = 2'-O-methyl uridine 3'-phosphodiester
modified_base           13
                        mod_base = OTHER
                        note = 2'-O-methyl cytidine 3'-phosphodiester
modified_base           14
                        mod_base = OTHER
                        note = 2'-O-methyl adenosine 3'-phosphodiester
modified_base           15
                        mod_base = OTHER
                        note = 2'-O-methyl uridine 3'-phosphodiester
modified_base           16
                        mod_base = OTHER
                        note = 2'-O-methyl cytidine 3'-phosphodiester
modified_base           17..18
                        mod_base = OTHER
                        note = 2'-O-methyl uridine 3'-phosphodiester
modified_base           19
                        mod_base = OTHER
                        note = 2'-O-methyl adenosine 3'-phosphorothioate
modified_base           20
                        mod_base = OTHER
                        note = 2'-O-methoxyethyl adenosine 3'-phosphorothioate
modified_base           21
                        mod_base = OTHER
                        note = 2'-O-methoxyethyl adenosine
modified_base           21
                        mod_base = OTHER
                        note = [X]k , wherein [X] = a conjugate group comprising a
                         bicycle ligand, and n (at
                         n=1 then k=0, and if n=0 then k=1
SEQUENCE: 1039
caatttctgt ctcatcttaa a                                                     21

SEQ ID NO: 1040         moltype = RNA  length = 21
FEATURE                 Location/Qualifiers
source                  1..21
                        mol_type = other RNA
                        organism = synthetic construct
modified_base
                        mod_base = OTHER
                        note = [X]n , wherein [X] = a conjugate group comprising a
                         bicycle ligand, and n and k (at 21) are 0 or 1, wherein
                         if n=1 then k=0, and if n=0 then k=1
modified_base           1
                        mod_base = OTHER
                        note = 2'-O-methoxyethyl cytidine 3'-phosphorothioate
modified_base           2
                        mod_base = OTHER
                        note = 2'-O-methoxyethyl adenosine 3'-phosphorothioate
modified_base           3
                        mod_base = OTHER
                        note = 2'-O-methyl adenosine 3'-phosphodiester
modified_base           4..6
                        mod_base = OTHER
                        note = 2'-O-methyl uridine 3'-phosphodiester
modified_base           7
                        mod_base = OTHER
```

-continued

```
                        note = 2'-fluoro cytidine 3'-phosphodiester
modified_base           8
                        mod_base = OTHER
                        note = 2'-O-methyl uridine 3'-phosphodiester
modified_base           9
                        mod_base = OTHER
                        note = 2'-fluoro guanosine 3'-phosphodiester
modified_base           10
                        mod_base = OTHER
                        note = 2'-O-methyl uridine 3'-phosphodiester
modified_base           11
                        mod_base = OTHER
                        note = 2'-fluoro cytidine 3'-phosphodiester
modified_base           12
                        mod_base = OTHER
                        note = 2'-O-methyl uridine 3'-phosphodiester
modified_base           13
                        mod_base = OTHER
                        note = 2'-O-methyl cytidine 3'-phosphodiester
modified_base           14
                        mod_base = OTHER
                        note = 2'-O-methyl adenosine 3'-phosphodiester
modified_base           15
                        mod_base = OTHER
                        note = 2'-O-methyl uridine 3'-phosphodiester
modified_base           16
                        mod_base = OTHER
                        note = 2'-O-methyl cytidine 3'-phosphodiester
modified_base           17..18
                        mod_base = OTHER
                        note = 2'-O-methyl uridine 3'-phosphodiester
modified_base           19
                        mod_base = OTHER
                        note = 2'-O-methyl adenosine 3'-phosphorothioate
modified_base           20
                        mod_base = OTHER
                        note = 2'-O-methoxyethyl adenosine 3'-phosphorothioate
modified_base           21
                        mod_base = OTHER
                        note = 2'-O-methoxyethyl adenosine
modified_base           21
                        mod_base = OTHER
                        note = [X]k , wherein [X] = a conjugate group comprising a
                         bicycle ligand, and n (at
                         n=1 then k=0, and if n=0 then k=1
SEQUENCE: 1040
caatttctgt ctcatcttaa a                                                 21

SEQ ID NO: 1041         moltype = RNA  length = 21
FEATURE                 Location/Qualifiers
source                  1..21
                        mol_type = other RNA
                        organism = synthetic construct
modified_base           20
                        mod_base = OTHER
                        note = thymine
modified_base
                        mod_base = OTHER
                        note = [X]n , wherein [X] = a conjugate group comprising a
                         bicycle ligand, and n and k (at 21) are 0 or 1, wherein
                         if n=1 then k=0, and if n=0 then k=1
modified_base           1..2
                        mod_base = OTHER
                        note = 2'-O-methoxyethyl adenosine 3'-phosphorothioate
modified_base           3
                        mod_base = OTHER
                        note = 2'-O-methyl guanosine 3'-phosphodiester
modified_base           4
                        mod_base = OTHER
                        note = 2'-O-methyl cytidine 3'-phosphodiester
modified_base           5
                        mod_base = OTHER
                        note = 2'-O-methyl uridine 3'-phosphodiester
modified_base           6
                        mod_base = OTHER
                        note = 2'-O-methyl adenosine 3'-phosphodiester
modified_base           7
                        mod_base = OTHER
                        note = 2'-O-methyl cytidine 3'-phosphodiester
```

-continued

```
modified_base          8
                       mod_base = OTHER
                       note = 2'-O-methyl adenosine 3'-phosphodiester
modified_base          9
                       mod_base = OTHER
                       note = 2'-O-methyl guanosine 3'-phosphodiester
modified_base          10..11
                       mod_base = OTHER
                       note = 2'-fluoro adenosine 3'-phosphodiester
modified_base          12
                       mod_base = OTHER
                       note = 2'-O-methyl uridine 3'-phosphodiester
modified_base          13
                       mod_base = OTHER
                       note = 2'-O-methyl cytidine 3'-phosphodiester
modified_base          14
                       mod_base = OTHER
                       note = 2'-O-methyl uridine 3'-phosphodiester
modified_base          15
                       mod_base = OTHER
                       note = 2'-O-methyl adenosine 3'-phosphodiester
modified_base          16..18
                       mod_base = OTHER
                       note = 2'-O-methyl uridine 3'-phosphodiester
modified_base          19
                       mod_base = OTHER
                       note = 2'-O-methyl adenosine 3'-phosphorothioate
modified_base          20
                       mod_base = OTHER
                       note = 2'-O-methoxyethyl thymidine 3'-phosphorothioate
modified_base          21
                       mod_base = OTHER
                       note = 2'-O-methoxyethyl adenosine
modified_base          21
                       mod_base = OTHER
                       note = [X]k , wherein [X] = a conjugate group comprising a
                        bicycle ligand, and n (at
                        n=1 then k=0, and if n=0 then k=1

SEQUENCE: 1041
aagctacaga atctatttat a                                                   21

SEQ ID NO: 1042        moltype = RNA  length = 21
FEATURE                Location/Qualifiers
source                 1..21
                       mol_type = other RNA
                       organism = synthetic construct
modified_base
                       mod_base = OTHER
                       note = [X]n , wherein [X] = a conjugate group comprising a
                        bicycle ligand, and n and k (at 21) are 0 or 1, wherein
                        if n=1 then k=0, and if n=0 then k=1
modified_base          1..2
                       mod_base = OTHER
                       note = 2'-O-methoxyethyl adenosine 3'-phosphorothioate
modified_base          3
                       mod_base = OTHER
                       note = 2'-O-methyl guanosine 3'-phosphodiester
modified_base          4
                       mod_base = OTHER
                       note = 2'-O-methyl cytidine 3'-phosphodiester
modified_base          5
                       mod_base = OTHER
                       note = 2'-O-methyl uridine 3'-phosphodiester
modified_base          6
                       mod_base = OTHER
                       note = 2'-O-methyl adenosine 3'-phosphodiester
modified_base          7
                       mod_base = OTHER
                       note = 2'-fluoro cytidine 3'-phosphodiester
modified_base          8
                       mod_base = OTHER
                       note = 2'-O-methyl adenosine 3'-phosphodiester
modified_base          9
                       mod_base = OTHER
                       note = 2'-fluoro guanosine 3'-phosphodiester
modified_base          10
                       mod_base = OTHER
                       note = 2'-O-methyl adenosine 3'-phosphodiester
modified_base          11
```

```
                        mod_base = OTHER
                        note = 2'-fluoro adenosine 3'-phosphodiester
modified_base           12
                        mod_base = OTHER
                        note = 2'-O-methyl uridine 3'-phosphodiester
modified_base           13
                        mod_base = OTHER
                        note = 2'-O-methyl cytidine 3'-phosphodiester
modified_base           14
                        mod_base = OTHER
                        note = 2'-O-methyl uridine 3'-phosphodiester
modified_base           15
                        mod_base = OTHER
                        note = 2'-O-methyl adenosine 3'-phosphodiester
modified_base           16..18
                        mod_base = OTHER
                        note = 2'-O-methyl uridine 3'-phosphodiester
modified_base           19
                        mod_base = OTHER
                        note = 2'-O-methyl adenosine 3'-phosphorothioate
modified_base           20
                        mod_base = OTHER
                        note = 2'-O-methoxyethyl uridine 3'-phosphorothioate
modified_base           21
                        mod_base = OTHER
                        note = 2'-O-methoxyethyl adenosine
modified_base           21
                        mod_base = OTHER
                        note = [X]k , wherein [X] = a conjugate group comprising a
                         bicycle ligand, and n (at
                         n=1 then k=0, and if n=0 then k=1
SEQUENCE: 1042
aagctacaga atctatttat a                                              21

SEQ ID NO: 1043         moltype = RNA  length = 21
FEATURE                 Location/Qualifiers
source                  1..21
                        mol_type = other RNA
                        organism = synthetic construct
modified_base
                        mod_base = OTHER
                        note = [X]n , wherein [X] = a conjugate group comprising a
                         bicycle ligand, and n and k (at 21) are 0 or 1, wherein
                         if n=1 then k=0, and if n=0 then k=1
modified_base           1..2
                        mod_base = OTHER
                        note = 2'-O-methoxyethyl adenosine 3'-phosphorothioate
modified_base           3
                        mod_base = OTHER
                        note = 2'-O-methyl guanosine 3'-phosphodiester
modified_base           4
                        mod_base = OTHER
                        note = 2'-O-methyl adenosine 3'-phosphodiester
modified_base           5..6
                        mod_base = OTHER
                        note = 2'-O-methyl uridine 3'-phosphodiester
modified_base           7..8
                        mod_base = OTHER
                        note = 2'-O-methyl adenosine 3'-phosphodiester
modified_base           9
                        mod_base = OTHER
                        note = 2'-O-methyl guanosine 3'-phosphodiester
modified_base           10
                        mod_base = OTHER
                        note = 2'-fluoro adenosine 3'-phosphodiester
modified_base           11
                        mod_base = OTHER
                        note = 2'-fluoro cytidine 3'-phosphodiester
modified_base           12
                        mod_base = OTHER
                        note = 2'-O-methyl uridine 3'-phosphodiester
modified_base           13..16
                        mod_base = OTHER
                        note = 2'-O-methyl adenosine 3'-phosphodiester
modified_base           17
                        mod_base = OTHER
                        note = 2'-O-methyl cytidine 3'-phosphodiester
modified_base           18
                        mod_base = OTHER
```

```
                        note = 2'-O-methyl uridine 3'-phosphodiester
modified_base           19
                        mod_base = OTHER
                        note = 2'-O-methyl uridine 3'-phosphorothioate
modified_base           20
                        mod_base = OTHER
                        note = 2'-O-methoxyethyl adenosine 3'-phosphorothioate
modified_base           21
                        mod_base = OTHER
                        note = 2'-O-methoxyethyl adenosine
modified_base           21
                        mod_base = OTHER
                        note = [X]k , wherein [X] = a conjugate group comprising a
                         bicycle ligand, and n (at
                         n=1 then k=0, and if n=0 then k=1
SEQUENCE: 1043
aagattaaga ctaaaactta a                                                    21

SEQ ID NO: 1044         moltype = RNA  length = 21
FEATURE                 Location/Qualifiers
source                  1..21
                        mol_type = other RNA
                        organism = synthetic construct
modified_base
                        mod_base = OTHER
                        note = [X]n , wherein [X] = a conjugate group comprising a
                         bicycle ligand, and n and k (at 21) are 0 or 1, wherein
                         if n=1 then k=0, and if n=0 then k=1
modified_base           1..2
                        mod_base = OTHER
                        note = 2'-O-methoxyethyl adenosine 3'-phosphorothioate
modified_base           3
                        mod_base = OTHER
                        note = 2'-O-methyl guanosine 3'-phosphodiester
modified_base           4
                        mod_base = OTHER
                        note = 2'-O-methyl adenosine 3'-phosphodiester
modified_base           5..6
                        mod_base = OTHER
                        note = 2'-O-methyl uridine 3'-phosphodiester
modified_base           7
                        mod_base = OTHER
                        note = 2'-fluoro adenosine 3'-phosphodiester
modified_base           8
                        mod_base = OTHER
                        note = 2'-O-methyl adenosine 3'-phosphodiester
modified_base           9
                        mod_base = OTHER
                        note = 2'-fluoro guanosine 3'-phosphodiester
modified_base           10
                        mod_base = OTHER
                        note = 2'-O-methyl adenosine 3'-phosphodiester
modified_base           11
                        mod_base = OTHER
                        note = 2'-fluoro cytidine 3'-phosphodiester
modified_base           12
                        mod_base = OTHER
                        note = 2'-O-methyl uridine 3'-phosphodiester
modified_base           13..16
                        mod_base = OTHER
                        note = 2'-O-methyl adenosine 3'-phosphodiester
modified_base           17
                        mod_base = OTHER
                        note = 2'-O-methyl cytidine 3'-phosphodiester
modified_base           18
                        mod_base = OTHER
                        note = 2'-O-methyl uridine 3'-phosphodiester
modified_base           19
                        mod_base = OTHER
                        note = 2'-O-methyl uridine 3'-phosphorothioate
modified_base           20
                        mod_base = OTHER
                        note = 2'-O-methoxyethyl adenosine 3'-phosphorothioate
modified_base           21
                        mod_base = OTHER
                        note = 2'-O-methoxyethyl adenosine
modified_base           21
                        mod_base = OTHER
                        note = [X]k , wherein [X] = a conjugate group comprising a
```

```
                              bicycle ligand, and n (at
                              n=1 then k=0, and if n=0 then k=1
SEQUENCE: 1044
aagattaaga ctaaaactta a                                    21

SEQ ID NO: 1045          moltype = AA  length = 17
FEATURE                  Location/Qualifiers
source                   1..17
                         mol_type = protein
                         organism = synthetic construct
SITE                     1
                         note = Acetylation at N-terminus. Cysteines 1, 9 and 13 are
                          linked by thioether bonds with the molecular scaffold
                          1,1',1''-(1,3,5-triazinane-1,3,5-triyl)tris(2-bromoethanone
                          ) (TATB)
SITE                     3
                         note = 4Hyp
SITE                     9
                         note = Cysteines 1, 9 and 13 are linked by thioether bonds
                          with the molecular scaffold
                          1,1',1''-(1,3,5-triazinane-1,3,5-triyl)tris(2-bromoethanone
                          ) (TATB)
SITE                     13
                         note = Cysteines 1, 9 and 13 are linked by thioether bonds
                          with the molecular scaffold
                          1,1',1''-(1,3,5-triazinane-1,3,5-triyl)tris(2-bromoethanone
                          ) (TATB)
SITE                     17
                         note = 6-azido lysine. Amidation at C-terminus
SITE                     10
                         note = t-butyl glycine
SEQUENCE: 1045
CPXDAYLGCX SYCEPWX                                         17

SEQ ID NO: 1046          moltype = DNA  length = 22
FEATURE                  Location/Qualifiers
source                   1..22
                         mol_type = other DNA
                         organism = synthetic construct
SEQUENCE: 1046
gaagaacaga agggcagaga tt                                   22

SEQ ID NO: 1047          moltype = DNA  length = 22
FEATURE                  Location/Qualifiers
source                   1..22
                         mol_type = other DNA
                         organism = synthetic construct
SEQUENCE: 1047
aaaccagtga ggtgagtgta tc                                   22

SEQ ID NO: 1048          moltype = DNA  length = 26
FEATURE                  Location/Qualifiers
source                   1..26
                         mol_type = other DNA
                         organism = synthetic construct
SEQUENCE: 1048
tttccagctt gtagatgagg cgtcac                               26

SEQ ID NO: 1049          moltype = DNA  length = 19
FEATURE                  Location/Qualifiers
source                   1..19
                         mol_type = other DNA
                         organism = synthetic construct
SEQUENCE: 1049
gctgccaagg ctacctaaa                                       19

SEQ ID NO: 1050          moltype = DNA  length = 23
FEATURE                  Location/Qualifiers
source                   1..23
                         mol_type = other DNA
                         organism = synthetic construct
SEQUENCE: 1050
gagtgaggta ttggactttc tcc                                  23

SEQ ID NO: 1051          moltype = DNA  length = 26
FEATURE                  Location/Qualifiers
source                   1..26
                         mol_type = other DNA
                         organism = synthetic construct
```

-continued

```
SEQUENCE: 1051
tcagacttcc tgtcctgctg gtatca                                          26

SEQ ID NO: 1052        moltype = DNA  length = 14000
FEATURE                Location/Qualifiers
source                 1..14000
                       mol_type = genomic DNA
                       organism = Mus musculus
SEQUENCE: 1052
ctctttccct ttgctgttgg atggacccac ggatggagaa tccacagatt gacactaaac    60
cctataacat tatctgccaa attattatta gcaagagcca aatgcactgc tagcatttta   120
gtagcttata gtctacagta aaaaaatgaa tgaacagtgc tttcctcact tcagctcctc   180
ccactgttgg gagtttttct cactttccct taataaatct gcctgctctg cagaaaacaa   240
aactgaataa acaaacattt cactgagagc ttagtgaaaa tcacaagtaa ctgtttccac   300
agcatgttca agggcctgag ctatggctac ccacggccat gtcaccagtt cactttctga   360
aggcaaagga cactgagcac taacatgaaa cagataactt gccacagtct gggaccatca   420
ctggatacac ttcttgctgc taaccctcag ctgcaatacc attccacaca tctctttgtg   480
tcatgtgccc aatgtggact ccagtgataa gggattccaa atgaagactg acaagtagtt   540
gtacaagttt tccaagactc aagtggagca ggttgttagc aacactcaat aactgaccag   600
tgtttctact aaacaatctg tgtttacgga atcttggtaa aaacaaacct acctcctaaa   660
actccatcag agtcatcatg accagcacag caaaagtaaa ggatagtatt tctcatacac   720
atctacagaa tgtgacttag attccagttt tcaactgtca ggactctata gtcccttcct   780
tgggtgtgtg tttgtgaaat atgtatttt aaaatcacct tgcaaacatg taaaataagt   840
atgatatgtt ggtctgcagc aattccttat cttctccaac caagaattat cagttctatt   900
gttcctaagc tttattctca aataaataca tatatttgac agacaaagca gactttggaa   960
aaatagttac agccctgaat aattaccttc agaactgatg tgttaacata tgcagttgta  1020
tcagagcaaa atccaactgt tggctttgcc ctccaatatg ccaatcattc tggaagttat  1080
aatgtaaact tggctccatc ccagacctcc tctgcccttc ccacctgcca cctttgataa  1140
gctactataa gccactgcac tttctaaggt ttcatattac tagcagttat ttgcagctga  1200
taatgtgacc tttttttttt ttaatcatat aaagacagaa agaaaactgt cttaaggtac  1260
agcggaaagt accaaacaat gacgcttttg cctctacaca cagtgacagg gaattcttgc  1320
aataagatag tctgcacttt actttacgt ggtaaatatg tccttaaata atatttatag  1380
actttctttg ataaaatatt ttccagttag ttttagctaa cattttaagc aacaggagat  1440
ttgctctaga gaagtgtttc atcttgcttt gcaagaaggc aagatcatat ccatttaagg  1500
acttcagtga gcagctgcag gcacacagtt ttcatactca caggaaagag ggaggctgat  1560
tttactctac tatacactaa gaattacgca taggttctct aaagctaaac agtgaaactg  1620
aaaaatcagg gtccacacat gtgctgattt acatacatgt aatataaaaa cagtgaagca  1680
cggtaggaga cagcaggacg tgctcggctc tgcagcatgg ctcagttcta ctcaaagtca  1740
gtccagacct actgtggtgg cattctaaaa tttttctcac atttcagaca aaaaaaaatg  1800
ctacattagg tgaaaaactt tcagaaataa atactggaca cttatttcat ctcttggaga  1860
cctggtcagc accgccacac tgccatacag ctgacagaaa cctgcagctc atcttttcta  1920
gaaaagctac tcctgacact aggtcagctt actaaaaacc tatttggttt ctgtggtaat  1980
acaatgtagc tatagaaaac tcttaaggcc ttaaacgtat aaagtgcatc tttctgggga  2040
ataatacata gctattgaaa tacagattca tttctcagag cacgggtgaa aaccttaact  2100
gaagaaaatg taagttgaat gtatttgctc ctctaactat aaatttcttt ttcaaaacac  2160
aaagtattga cctagttttc ttttatgcat tcattctctt acctagacag caatacctag  2220
acagatgtga aacacaaaca taaataagac aaggaaaggc atcaaatatc acctgagaat  2280
gtttgctgct ctgacaagca aggctctgcg agggcagctc cattaaccct gcctctgttg  2340
agcctacatt atccctccca agctacctgc attccttcac aactatgtta gctcttccac  2400
tccaacagca gtgtgtaact atctccaagt ctgacgactt ataactcttt aaggaaagct  2460
acctactata aagcagtatc ttcaaactta ctttattctc agttatctgt tatacacatt  2520
tttaagttaa aaactaaaag caaagcacaa agtgttaatg gcatttccaa acctaacata  2580
aaataagttc taaggtttgg ttgtgataag aacatggcta accaatcaca tgttagaatt  2640
cctacgtgat gtcataagac ctccctagaa tccttttct cctccaccta ctgcagctgc  2700
tcccataaac ctgggaacag aaaactgccc agctaagctc ccataagact tcatacagct  2760
tcatgctctg cactgtgacg atcaccgaag ccaaggtaag acgtgagatc attgactttg  2820
gacattctta ctttctgata ttcaatctta ttaaactctt aaaagaattc taactcccaa  2880
attccaattc aaagctacat aataaaagaa cctgctatga caaaatgctt aatttctaaa  2940
taaattctta cccatttact gacagtgaaa attagacaac tttaaaagag attctattca  3000
tctttaaatt ttgattacta ggttttttg ggttttcaca tatgaactcc caatttaacc  3060
ccccattata ttagcatata tggtaggaga ggtatattaa ttttcataca aaagcaatgg  3120
tttcatgtgc tatgtgttgc ttgttaaaac acagtgcagg acgaggccac ttatttacag  3180
ctggggcaca gcttattttc agcttattta taactgaagg gtatgcacac tgtgagtaca  3240
cttatttgac gacattactg tagttcttaa ggtgatacaa taaaagagat ttttaagaac  3300
agatagtagg aactacttt caaatgctct tgaagactgt tactctctaa aattccagtc  3360
aacctttaaa cacttctaga acttttattt taatgaaaat agcttgtttt agtttgaagc  3420
tataaagaac aagttagata gttttaaaac aagcacatgt ctttattaag tgacagaaaa  3480
taattcaaca tttttaaaag taaaaaggac attttagcat acaaacattt ctcaagaaat  3540
ttaataagtg tatattcctc taacaacaga gtacatttat caagttttta ttctccagtg  3600
ttcttaagtt tcctgctgtg aatttagaag taaaacaaaa tattcaggaa attgatatgc  3660
aacaaaaact ttattattgc tatttgttaa aatctcaatc tactaagtaa aatattttct  3720
cactattaaa tccaatagat cacatagaaa ataaacagat ttttatttta ctatttatat  3780
tcctatcata tttaaatgct aaataaaact tacctctaca attctcaatt cctataattc  3840
taactctgct gcttatgaca aacacagctg tctcctacac aacattcttg tcatgtaaaa  3900
acatttttag tatgtgcttt aactccaagg aacactggtc tctcaataat tttgtaaccc  3960
taaaaatatt ttttctttga tattatacaa attcacttg gtgccaagtt tatttgtcat  4020
atttctgcta tttttatta tctatccact gtgttgctgg gggactaggg aagagagtga  4080
gagagagaga gagagagaga gaaagagaga gagagagaga gagtgtca ttgcatgtct  4140
gtgaaggtca gaagagtttg taggagtcag ttctttcttc ccaccatgta ggtctcagga  4200
```

-continued

```
gtcaagcttg ggtcgtcagg cttggcagca agtgccttac ctactgagcc cttttccccgg  4260
tccctgaagg tttaccttaa tgcctatcca atagcattct caaacttgaa cagtgtgtgc  4320
aaaagttttt ttcagtggag taaggggtag gtaatgagtt tctttccacc agaatttcct  4380
tatatcacaa ttagttacaa aaaaaaggaa gcaacttcta gaaaaaaata taaattctgc  4440
tatagaaagc atctttagca gattaagcag atgctgcctg tagttaaaat tttcaatata  4500
aagcacagtt tctacatagc tttatggtga cattgaagta ttttgtttat aaaggtacat  4560
gctttaaaag taagcacaaa aaaggataaa atcaatgaag aaatgtaaca gatacactaa  4620
aaaagaatga gatgatttgc tttgccaaaa ggagttgccg cagtgtcatt tcctaaagca  4680
aatcaaaatt gttttagaa tattttagta gacatagagg aaaattgctg catttgggtc  4740
attattaaca aatattgttt cttaatctca ccaatttatc aagacataat atttgcattg  4800
gctatagaat tcaaagtata tattaaaaca tcaagtgagg atgattaaag tatagatcac  4860
tgctataaat tacacagcat aagcacattt tttctgaaga acattttcct aagtgcactt  4920
acacacagac actccctctt aattctttgt atgcatctct acatcatcat ttggagaaca  4980
gattttaaaa caagtgagct ctgtgaagtt cacagagcta caagcaaata ggagaccttg  5040
tgggagaggc catttgcacc tctgatcccg ttcagtgatg agcatggtta agatacatca  5100
tcatcctgac aaggtacaga aaaagaaaag caaatgcaaa atgctgtgaa tggtcatttt  5160
ctgagaaaat gaggatgcaa actactgcta actaaaaagc attcctctgt ttcatttaaa  5220
tccatcaagt gttggatctg tactattctg tatgatattc taaacattat cttcaaagtc  5280
aggcataaag ttactgatgt ccttagtttt taagcagtaa attctagtca gcaaagttca  5340
aaataatcac atagacatga acataccaga atcaaattaa aatatacaat cattaagttt  5400
gctctattga taaaaaatat acctccaatc catttaagct tgttatctaa aaatcagact  5460
gattttcca taactctgaa caaaggcttc aacactctat tgcatcccta cagtgcatca  5520
atttcatttc ttacctgctc actctaccca aggtcactgt tttcaaggtt cctggataaa  5580
agaatcttgc attgttattt acacaatgaa tataattttc atctaatata ggaattcaca  5640
cattgatcag accaacaaaa acaaaaattt agagttggga atgaaaaata tagtctttct  5700
aaattatagc agcatggctg ataagcagca gtctctttg acattccaag agtgtgtagt  5760
acttcagttt ccttacccaa cacaattctg aagcatgcat taccaaataa acacatgaaa  5820
ataaagcctt cttgggtatt ctaataccca tggagggatt tacagagaca aagtttggag  5880
ctgagacaga aggaaggacc atccagagac tgtcccaccc ggggatccat cccataaaca  5940
gccaccaaac ccagacacta ttgcatatgc cagcaagatt ttgctgaagg gacactgata  6000
tagctgtctc ttgtgaagct atgccagtac ctggcaaata caaaagtgga tgttcacagt  6060
catctattgg atagaacata gggcccccaa tggaggagct agagaaagta cccaaggagc  6120
taaaggggtc tgcaaccctg taggaggaac aacaatatga actaaccaat accccccagag  6180
ctcgtgtctc tagctgcata tgtagcagaa gatggcctag tcagccatca ttgggaaaag  6240
aggcccttgg tcttatgaag attatatgcc ccagtatagg ggaatgccag agccaggagc  6300
aggagtgggt gggttggaga gcagagcggc gggagggtaa agggactttc gggatagcat  6360
ttgaaatgta aatgaagaaa atatctaata aaaaaaatct tttttaaagaa atgaggaaaa  6420
aaagaaagga aggaaagcct tcatgtgtat gctctgcccc atcagtagag cttacaggca  6480
actgaggacc tctagtgctt cagagcacgt actacatctt cagggcttc catgaattgg  6540
gtgcatcact cactcctcta catgaacagg ggtttatttg ctaagtgccc ctcaattttc  6600
cttagaactt cccaaatact gtctccctac agcctgttta aaaaaaaaaa aaacagactc  6660
tgaagcttca gtataaggct aaaaatcact ttcatggagg cacaggagcc ttgtaatccc  6720
aggcaaaagc aggactgcag agttcaagac taaccagtgt gacacacagt aagtttaaga  6780
ccagcctaga ctacacagtc caaaatcggg gctgtgttaa ttcaaataaa tatgttcaat  6840
ttcacataag tatacatcaa taaaaataaa cctacggacg aaaatatcaa ttgccatgag  6900
ctaatttcag agggaaattt ttaacagaat tttttaattg gtccaatttc attctgttta  6960
cacaatttt atcacaacta gacagaagca ggtgaagaga ctctgacgct tcagtctgca  7020
caacaaagct gggaccaaag gaacttgcca gcttacaatt ctgcagtctt aaaggggctt  7080
catcccagtg agctttcctg cgtaacaggt tgatctaact tttttgtttt tgttttttgtt  7140
ttttttgtttt ttttgttttg gtttggtttg gtttggtttt ggtttggttt ggtttggttt  7200
ttggtttttc gagacagggt ttctctgtgt agccctggct gtcctggaac tcactttgta  7260
gaccaggctg gtcttgaact cagaaattcg cctgcctctg cctcccgact gttgggatta  7320
aaggaatgca ccaccacgcc cggctccttc agggtttttat acagataact tctaccccta  7380
cccaacaggt tcctaacaaa ggatatgact tttttttttt tttttttttt tttttttttt  7440
ggctaggacc tcactgtcta gccctggttg ccctggaact tgctatgtag agcagactgg  7500
ctgaaactca gagctcagcc taactctgct ctccgtctgg agtgataaga cctaaggcaa  7560
gagccgccac acctgacagt atggtactgt aggattactg ccgtctgtag ctttcctctt  7620
cctcctccta ctaaaacaaa aatgatactt ctgaacttaa tttcctaaat tccgatttat  7680
tctctttaaa cagagagaga gaagataata caaggtccca ctaggaaaag taaagaattg  7740
ctggtagcga tcaatccttc caaaagtgag aacagatccc acacacatag aacacaaaac  7800
ttgggttctc ttctgcttct tacataacta aaatacggga tctcatattt cccacaacca  7860
aatatacatt gtatttccag cactctggta caaaaatcag aaagattaaa cttcaaatta  7920
gtctgtaagt aaagaggctc tgtgtctcca gtaaacaccc aatgaacata tacagtcatc  7980
tttttaaacc tgtagctaat tttctgttaa cacgctttat tttgttgtat ttactatcaa  8040
agctttgaac cttacatatt cagccatagt ttagaagttc tgaaagaagg ccagacacaa  8100
acccacccct ggtagccaag attagctgaa aactggcact gtgatagttt aaaacgatag  8160
tccttactgt gccttctgag tttggaagtc tttagtactt aacatcttct taaagtgttt  8220
aaaataacat tcaccaagag gctggatctg ggaggagtcc ggaggatgta tatatgatca  8280
aatacactga atgattctac aaatctataa atcataaaag agaatggcaa gtggctagaa  8340
tctgcttttt atttcatatt tttcacttaa ctattttatt ttggactaaa actaggatcc  8400
aagatatgtt actatatgca tttctttttta caagattatt tctgaaacat taatagtaaa  8460
tgttaaaatc aattgtgttt acagagaaac agagctttaa aaaagtaac caagaaaata  8520
gccccaaaga agcacctcat aaatcaagta ctagccgcca aagccgtggc tctccccgct  8580
cacccaggac agtgagagc tcacacatga gagacagaag agaggccttg gggactggag  8640
aaggggatgg gatttaaaat acagctgagg aacgagctgc tgcaaagctg tgcatatcta  8700
cccagagaac gggtttaggt atgaacctaa tctgttgact attttttaca tcccaggtct  8760
cctaaaagaa gacagctcac atttggctgc ctgttgtcaa ctttttatct ttctcttgac  8820
cacttagaaa aacttgtctc cctacttttg ccttcctggc ataatggaaa aagtgcaata  8880
cctcactcgc tcggctatca ggagagcctc cactattgaa atgcctcagc aagcacgtca  8940
```

```
gaatctccag aacctattta tcaatttctg cctcatcttg atatgtctgc tgctgatctg   9000
catcattgtg atgcttctgt gaagagctgc cgccactcca gacctgcaac atgccaactc   9060
agcttaaagc cgagcactcc gtcatggggg aagcaacgca ccgctgcctt ccggctgaga   9120
acagctttgt gagggtcacg attaagagtg aaactaattg ttagccagtg tattcatctg   9180
ctggatcttg taaacaaact ttacagtggc taagtgtgca taatgtagct gccaatttcc   9240
tcaacatggc tcataaattt cttcctaaa tatttctgac aatgaagtat gagtttaat   9300
tttgaaacac cactaccaaa aaagttcact ttctatatcc aactctagca aggtcacttt   9360
atagctccag tctgggggaat aaatggaata tatactgcat tgccactacc tttttatag   9420
gaactaagtg ttcttcagtt ctccacaaag tagaaaatga tcatttaaat gaagtgttct   9480
tattgaaaat agctcactgg gtcctcacat agatgacaca atgatgacga tgatgatgat   9540
gacgacgatg atgatgatga cgacgattca aatctcttgg tcactactgt cagaacaaat   9600
accttgaaaa aatgttgtgc ccttttttcta cacactagta tttttaagct tatgagagtt   9660
aaaggggaa atgtaagaac atattctcat ataaaattat tcactaattt tgctcaaggg   9720
ctgtgtacat gtacatgtac attaaccaca aatctgctct ctctagggtt tgatcaacaa   9780
gcaggaacat cttgctgtgt tggctgtgat aatcactaaa gatccagagt ctccacctgaa  9840
gcttgtcgct ctcatgtatc tccttggtttt aatagcgttt ctcaaataat gaagataaca   9900
gtaataacca agctgtagta agacacagct cttttcttttc ctgatctccc agagaggaag   9960
tggttgtccc ctaactttag aagtagaact agagagctag tgtataattc ttactgacca  10020
tggtttcaat ttccctttct aagtttctac tatctctcaa taactactaa aatagaagca  10080
aaaaatagat tggaaaatat attcaccaaa atttagtgac ttaaactgga tcaagtacaa  10140
aacagtttat gcctaacttt gcaaacccac aatttttaag tccagttcaa aacatgctac  10200
taacatagca attattaagg aagagaattg taattagata tattttccat aaccattact  10260
acaaagacat aaaacatcag tattcacttt ggtcttagc agagcagctg aaggctgctg  10320
atttaaactg tttgaacccc tggtagaaag gaagctgttc gggttcagaa attatctaaa  10380
gagtagcccc taaaggagtc caatggtaac agggggtctc ttcataaagg ctggagggggc  10440
ccatcacaga aactataaaa catggatgac atcatctcta actcagtggt atttaacgtt  10500
cccttctga cgctgtggcc cttttatata gttcctcatg ttgtggtgat acccaacaat  10560
aaaatcattt ttgttgctat ttcataactg taatttcgcc tccttacctc cactatgaat  10620
tgtaaatatt ttggaaacag gtttgcatga ggggttgcaa cccacaggtt gagaaccact  10680
ggtaagagagt ctgtaaaaaa tacataagtt gtgtagttgg ccatgctgag agaaacgtga  10740
cgctgaagct gaaaagcacc aggcatttgt tatattgctc actaccacat caacttcaag  10800
gtataaactg tcagctcata aggctcttct cattaaacat ttaatgctgc cttttacatt  10860
tttagtagtt tatttgtagt ttatctgtaa ctgtttatct gtaaaatgaa attggaatga  10920
cctatattca aatggagttt tgattttggt gaaattacta tacaattata ttctattgac  10980
tataaaatgt tgtcttgtta caaagagttt tgtgttataa agggcagagt gggggaactt  11040
ttaccaaaca aagtaaaaat caagatttcc agagaaaaac acaaaagagg ataggcctac  11100
acataataat attttttagc ctccaattat tttgagtctt ctggcaaagt aggagtgcaa  11160
tcagtaacat aagaaggctt ggttacacac taataccaga tttttaatgt cttgaaagga  11220
catgataaat tatatagaca tggaaataga gatagcaaaa tcaatccgta aagcatgtat  11280
ccactagcag atgctttaag ctacccacta tgtcacaaac tgtgactgca tgtgtcatag  11340
tcacctcctc agtatacaga ttgtctcagc taaagagtta aagataaaac agcatgaaaa  11400
ataatgaaac taagaaaatt ttcttttttaa aaaaacataa gaaaatccga gttacaagcc  11460
agactttttc attcacaatt catttcgaag aagtcttttta tgttatttaa tcaaaatctt  11520
catttaaata acagaaagtc tctgctaaca tgagttagca atcccttaac tgatcaaacc  11580
acttatgat ttatatacat acaaaatttc atctccattt ttaacaacta cagtccaggg  11640
aacatgagac aatgcaaagt tagcaataga gttccctact taaccaccag ggggcagacc  11700
cactgtgggc ttacgagaag ctaatggtta tttttatgtgt tgaggaggtc tacattctca  11760
cacccctcct tgaaaacaag gagtacagaa gagcacattt caatgaaaca gtccctcctg  11820
aacaaggccg agactatcac aaccctacag agacaatttg gggtactatg ggtgaggtat  11880
caaaacgcaa agaaaagagc caagactgtg gtgaactata acgtgaacca aacaaaggca  11940
aatcgttttt cttcaaccac aaaggaaaaa tggttcagaa tattacacag gatggtgcac  12000
agtggttctc aacctccctg atgctgtgac cctgtaatag tctcttgtgt tgtggtgacc  12060
cccaaccata taattttgct cctttttatga atcataatgt gtctgtttttc caatagtctt  12120
aggtgactcc atcagccgtt ccaccgctca gagtggttgg gcccctcggg ctgagaatca  12180
ctgctctaag tcataggggga gcttcccatt agctgtcttc tccctccctc tactgtgttc  12240
tacaaagatt cacacctgag tggttgctcc ttagtgcata tcttacaaag aaatttccct  12300
attagcatgt tattccacag accttatagg gattaataca ccatgtttct ctgtatgtgg  12360
ttattatcat aaagtagttc ctttaaacta attcaataaa tcttggtgtt ccattcattt  12420
cttgaaaact gcagctgatt tatatgctca tatacaaaga aagcattatc aaaatagtac  12480
aaggaactgg gttccacctt ctcattttat agaaggccca aagaaattaa gtgccaggtc  12540
aaaagacacc tgagttctca ccagactaaa ttcccaaaga gtctactaaa agtcatagaa  12600
atgagtacag tcccatgttt actaacattc atagcaacta gaaataaaac cagcctagag  12660
atccatccac ctgtaagcat gtaagaaaat gtggtacata tacacgatgc aactttattt  12720
ggccataaag gaaaattaaa ttgtgacttc tgcagaaaac aatggggac ttgaaatcac  12780
tacattaatc aaagcatgcc agacccggga aggcaaatgc gtcatgtttt ctctcatatt  12840
gttaatctag atttgaaatc ttgttcatgt gaattcttgt tctacttgtg aaactagaaa  12900
gagctaagct agagaagaat aaagagggag gcagagtata gagagggtgt gtaaggaggg  12960
ggacagagca aagggctctt gtgggaaagg gaggggcagt agggtggaac caggctgagg  13020
gcaagcagag gaccaagaag acgactgtat gaaaatccta taatgaaata aacactttga  13080
atgcagatta aaaaataaat gaaaaactaa cttatgaaga aaaagaaaaa aaatatccaa  13140
gctcaaatg tgacatgatc agaacaaagt ccacggcctg tttgttccaa tcagtttcct  13200
tcctatgata ccgtgacagc ttctgtctgt tttccgtttc tttcaactga atgtgtttaa  13260
tttctatgcc tacttaacaa gagagaaagt aaaggccaag ttaagtacaa tgtttaaggc  13320
tatcaaatta attaatctca aaacagtttg aagttttct tgtcaattt  13380
atagcactta acggtttttt taacttgtgt acttgctgca atacataaaa catccactgg  13440
agggaagcaa acactaggtt ttcagcctta cctgcattgg cgtctcactt ccttgctgaa  13500
actcttcagt ttgtggctgt tgccaaggag ctaaactgta agaatcgtct gtggttctgc  13560
cttccaatgg gtttgtccgt aactgctctg tcagccacat ctgagtcctc acagaaggtt  13620
gaatgggaac tccacctact gcctgctggc ccagcattaa atactttgga gactcaaaag  13680
```

-continued

```
tctctgagcc tgtcacaatg ggcttgctct caggtaaggc actgtatgtc atgtctaaag     13740
tctgtctcct gagagcagag gaagagactc tgacatcttc tttgttgcag ctctcaaatt     13800
tatatttgca gtccagagtt gatgaccgct ttttatttat ttccttgtct tccagcttaa     13860
gcagctccat actgtcatgt aagcaacttg gcccaaaggt ccgtaagtgg gacataaaag     13920
gcttgccctt ccctgtcatc tccaagctat tcctcagctc ttgcgggtat gcaatgccac     13980
tgtggttgcg ggtatctggg                                                 14000

SEQ ID NO: 1053          moltype = DNA   length = 21
FEATURE                  Location/Qualifiers
source                   1..21
                         mol_type = other DNA
                         organism = synthetic construct
SEQUENCE: 1053
tctgctctct ctagggtttg a                                                21

SEQ ID NO: 1054          moltype = DNA   length = 22
FEATURE                  Location/Qualifiers
source                   1..22
                         mol_type = other DNA
                         organism = synthetic construct
SEQUENCE: 1054
ggagatacat gagagcgaca ag                                               22

SEQ ID NO: 1055          moltype = DNA   length = 24
FEATURE                  Location/Qualifiers
source                   1..24
                         mol_type = other DNA
                         organism = synthetic construct
SEQUENCE: 1055
acagccaaca cagcaagatg ttcc                                             24

SEQ ID NO: 1056          moltype = DNA   length = 25
FEATURE                  Location/Qualifiers
source                   1..25
                         mol_type = other DNA
                         organism = synthetic construct
SEQUENCE: 1056
cacccgtaag acttcataca acaca                                            25

SEQ ID NO: 1057          moltype = DNA   length = 25
FEATURE                  Location/Qualifiers
source                   1..25
                         mol_type = other DNA
                         organism = synthetic construct
SEQUENCE: 1057
tggcagccaa atatgagata actgt                                            25

SEQ ID NO: 1058          moltype = DNA   length = 16
FEATURE                  Location/Qualifiers
source                   1..16
                         mol_type = other DNA
                         organism = synthetic construct
SEQUENCE: 1058
tgccaaggct acctaa                                                      16

SEQ ID NO: 1059          moltype = DNA   length = 20
FEATURE                  Location/Qualifiers
source                   1..20
                         mol_type = other DNA
                         organism = synthetic construct
SEQUENCE: 1059
ggcaaattca acggcacagt                                                  20

SEQ ID NO: 1060          moltype = DNA   length = 20
FEATURE                  Location/Qualifiers
source                   1..20
                         mol_type = other DNA
                         organism = synthetic construct
SEQUENCE: 1060
gggtctcgct cctggaagat                                                  20

SEQ ID NO: 1061          moltype = DNA   length = 27
FEATURE                  Location/Qualifiers
source                   1..27
                         mol_type = other DNA
                         organism = synthetic construct
SEQUENCE: 1061
aaggccgaga atgggaagct tgtcatc                                          27
```

-continued

```
SEQ ID NO: 1062        moltype = AA  length = 13
FEATURE                Location/Qualifiers
source                 1..13
                       mol_type = protein
                       organism = synthetic construct
SEQUENCE: 1062
CSPDAHLGCI SYC                                                     13

SEQ ID NO: 1063        moltype = AA  length = 13
FEATURE                Location/Qualifiers
source                 1..13
                       mol_type = protein
                       organism = synthetic construct
SEQUENCE: 1063
CSPDAYLGCI SYC                                                     13

SEQ ID NO: 1064        moltype = AA  length = 13
FEATURE                Location/Qualifiers
source                 1..13
                       mol_type = protein
                       organism = synthetic construct
SITE                   3
                       note = 4Hyp
SEQUENCE: 1064
CPXDAYLGCI SYC                                                     13

SEQ ID NO: 1065        moltype = AA  length = 13
FEATURE                Location/Qualifiers
source                 1..13
                       mol_type = protein
                       organism = synthetic construct
SITE                   3
                       note = 4Hyp
SEQUENCE: 1065
CSXDAHLGCI SYC                                                     13

SEQ ID NO: 1066        moltype = AA  length = 13
FEATURE                Location/Qualifiers
source                 1..13
                       mol_type = protein
                       organism = synthetic construct
SITE                   3
                       note = azetidine
SEQUENCE: 1066
CSXDAHLGCI SYC                                                     13

SEQ ID NO: 1067        moltype = AA  length = 13
FEATURE                Location/Qualifiers
source                 1..13
                       mol_type = protein
                       organism = synthetic construct
SITE                   3
                       note = 4Hyp
SITE                   10
                       note = t-butyl glycine
SEQUENCE: 1067
CPXDAYLGCX SYC                                                     13

SEQ ID NO: 1068        moltype = AA  length = 13
FEATURE                Location/Qualifiers
source                 1..13
                       mol_type = protein
                       organism = synthetic construct
SITE                   2
                       note = 6-azido lysine
SEQUENCE: 1068
CXPDAHLGCI SYC                                                     13

SEQ ID NO: 1069        moltype = AA  length = 13
FEATURE                Location/Qualifiers
source                 1..13
                       mol_type = protein
                       organism = synthetic construct
SITE                   3
                       note = 6-azido lysine
SEQUENCE: 1069
CSXDAHLGCI SYC                                                     13

SEQ ID NO: 1070        moltype = AA  length = 13
```

-continued

```
FEATURE                Location/Qualifiers
source                 1..13
                       mol_type = protein
                       organism = synthetic construct
SITE                   5
                       note = 6-azido lysine
SEQUENCE: 1070
CSPDXHLGCI SYC                                                  13

SEQ ID NO: 1071        moltype = AA  length = 15
FEATURE                Location/Qualifiers
source                 1..15
                       mol_type = protein
                       organism = synthetic construct
SEQUENCE: 1071
ACSADDWLGC ISWCA                                                15

SEQ ID NO: 1072        moltype = AA  length = 22
FEATURE                Location/Qualifiers
source                 1..22
                       mol_type = protein
                       organism = synthetic construct
SITE                   16..21
                       note = MeGly
SITE                   22
                       note = 6-fluorescein lysine
SEQUENCE: 1072
ACSADDWLGC ISWCAXXXXX XX                                        22

SEQ ID NO: 1073        moltype = AA  length = 15
FEATURE                Location/Qualifiers
source                 1..15
                       mol_type = protein
                       organism = synthetic construct
SEQUENCE: 1073
ACSSDAYLGC ISWCA                                                15

SEQ ID NO: 1074        moltype = AA  length = 22
FEATURE                Location/Qualifiers
source                 1..22
                       mol_type = protein
                       organism = synthetic construct
SITE                   16..21
                       note = MeGly
SITE                   22
                       note = 6-fluorescein lysine
SEQUENCE: 1074
ACSSDAYLGC ISWCAXXXXX XX                                        22

SEQ ID NO: 1075        moltype = AA  length = 15
FEATURE                Location/Qualifiers
source                 1..15
                       mol_type = protein
                       organism = synthetic construct
SEQUENCE: 1075
ACPPDAHLGC ISWCA                                                15

SEQ ID NO: 1076        moltype = AA  length = 13
FEATURE                Location/Qualifiers
source                 1..13
                       mol_type = protein
                       organism = synthetic construct
SEQUENCE: 1076
CPPDAHLGCI SWC                                                  13

SEQ ID NO: 1077        moltype = AA  length = 15
FEATURE                Location/Qualifiers
source                 1..15
                       mol_type = protein
                       organism = synthetic construct
SEQUENCE: 1077
ACPQDAYLGC ISWCA                                                15

SEQ ID NO: 1078        moltype = AA  length = 13
FEATURE                Location/Qualifiers
source                 1..13
                       mol_type = protein
                       organism = synthetic construct
SEQUENCE: 1078
```

-continued

```
CPQDAYLGCI SWC                                                    13

SEQ ID NO: 1079          moltype = AA   length = 15
FEATURE                  Location/Qualifiers
source                   1..15
                         mol_type = protein
                         organism = synthetic construct
SEQUENCE: 1079
ACPPDSWQGC ISYCA                                                  15

SEQ ID NO: 1080          moltype = AA   length = 22
FEATURE                  Location/Qualifiers
source                   1..22
                         mol_type = protein
                         organism = synthetic construct
SITE                     16..21
                         note = MeGly
SITE                     22
                         note = 6-fluorescein lysine
SEQUENCE: 1080
ACPPDSWQGC ISYCAXXXXX XX                                          22

SEQ ID NO: 1081          moltype = AA   length = 15
FEATURE                  Location/Qualifiers
source                   1..15
                         mol_type = protein
                         organism = synthetic construct
SEQUENCE: 1081
ACSPDAHLGC ISYCA                                                  15

SEQ ID NO: 1082          moltype = AA   length = 22
FEATURE                  Location/Qualifiers
source                   1..22
                         mol_type = protein
                         organism = synthetic construct
SITE                     16..21
                         note = MeGly
SITE                     22
                         note = 6-fluorescein lysine
SEQUENCE: 1082
ACSPDAHLGC ISYCAXXXXX XX                                          22

SEQ ID NO: 1083          moltype = AA   length = 20
FEATURE                  Location/Qualifiers
source                   1..20
                         mol_type = protein
                         organism = synthetic construct
SITE                     14..19
                         note = MeGly
SITE                     20
                         note = 6-fluorescein lysine
SEQUENCE: 1083
CSPDAHLGCI SYCXXXXXXX                                             20

SEQ ID NO: 1084          moltype = AA   length = 21
FEATURE                  Location/Qualifiers
source                   1..21
                         mol_type = protein
                         organism = synthetic construct
SITE                     15..20
                         note = MeGly
SITE                     21
                         note = 6-fluorescein lysine
SEQUENCE: 1084
CSPDAHLGCI SYCAXXXXXX X                                           21

SEQ ID NO: 1085          moltype = AA   length = 20
FEATURE                  Location/Qualifiers
source                   1..20
                         mol_type = protein
                         organism = synthetic construct
SITE                     14..19
                         note = MeGly
SITE                     20
                         note = 6-fluorescein lysine
SEQUENCE: 1085
CSPDAHLGCI SYCXXXXXXX                                             20

SEQ ID NO: 1086          moltype = AA   length = 21
```

```
FEATURE              Location/Qualifiers
source               1..21
                     mol_type = protein
                     organism = synthetic construct
SITE                 1
                     note = N-Fluorescein glycine
SITE                 2..6
                     note = MeGly
SEQUENCE: 1086
GXXXXXACSP DAHLGCISYC A                                               21

SEQ ID NO: 1087      moltype = AA  length = 16
FEATURE              Location/Qualifiers
source               1..16
                     mol_type = protein
                     organism = synthetic construct
SITE                 2
                     note = 1-Naphthylalanine
SEQUENCE: 1087
NXNCSPDAHL GCISYC                                                     16

SEQ ID NO: 1088      moltype = AA  length = 16
FEATURE              Location/Qualifiers
source               1..16
                     mol_type = protein
                     organism = synthetic construct
SITE                 15
                     note = Pipecolic Acid
SEQUENCE: 1088
CSPDAHLGCI SYCEXW                                                     16

SEQ ID NO: 1089      moltype = AA  length = 16
FEATURE              Location/Qualifiers
source               1..16
                     mol_type = protein
                     organism = synthetic construct
SEQUENCE: 1089
CSPDAHLGCI SYCEPW                                                     16

SEQ ID NO: 1090      moltype = AA  length = 16
FEATURE              Location/Qualifiers
source               1..16
                     mol_type = protein
                     organism = synthetic construct
SEQUENCE: 1090
NWNCSPDAHL GCISYC                                                     16

SEQ ID NO: 1091      moltype = AA  length = 17
FEATURE              Location/Qualifiers
source               1..17
                     mol_type = protein
                     organism = synthetic construct
SEQUENCE: 1091
NWNCSPDAHL GCISYCA                                                    17

SEQ ID NO: 1092      moltype = AA  length = 16
FEATURE              Location/Qualifiers
source               1..16
                     mol_type = protein
                     organism = synthetic construct
SITE                 15
                     note = azetidine
SEQUENCE: 1092
CSPDAHLGCI SYCEXW                                                     16

SEQ ID NO: 1093      moltype = AA  length = 16
FEATURE              Location/Qualifiers
source               1..16
                     mol_type = protein
                     organism = synthetic construct
SEQUENCE: 1093
NWNCSPDAHL GCISYC                                                     16

SEQ ID NO: 1094      moltype = AA  length = 16
FEATURE              Location/Qualifiers
source               1..16
                     mol_type = protein
                     organism = synthetic construct
SITE                 15
```

-continued

```
                              note = D-Proline
SEQUENCE: 1094
CSPDAHLGCI SYCEXW                                                16

SEQ ID NO: 1095           moltype = AA  length = 16
FEATURE                   Location/Qualifiers
source                    1..16
                          mol_type = protein
                          organism = synthetic construct
SITE                      2
                          note = 1-Naphthylalanine
SEQUENCE: 1095
NXNCSPDAHL GCISYC                                                16

SEQ ID NO: 1096           moltype = AA  length = 16
FEATURE                   Location/Qualifiers
source                    1..16
                          mol_type = protein
                          organism = synthetic construct
SITE                      2
                          note = D-tryptophan
SEQUENCE: 1096
NXNCSPDAHL GCISYC                                                16

SEQ ID NO: 1097           moltype = AA  length = 16
FEATURE                   Location/Qualifiers
source                    1..16
                          mol_type = protein
                          organism = synthetic construct
SITE                      2
                          note = D-tryptophan
SEQUENCE: 1097
NXNCSPDAHL GCISYC                                                16

SEQ ID NO: 1098           moltype = AA  length = 17
FEATURE                   Location/Qualifiers
source                    1..17
                          mol_type = protein
                          organism = synthetic construct
SEQUENCE: 1098
HWMCSPDAHL GCISYCA                                               17

SEQ ID NO: 1099           moltype = AA  length = 17
FEATURE                   Location/Qualifiers
source                    1..17
                          mol_type = protein
                          organism = synthetic construct
SEQUENCE: 1099
ACSPDAHLGC ISYCPHP                                               17

SEQ ID NO: 1100           moltype = AA  length = 17
FEATURE                   Location/Qualifiers
source                    1..17
                          mol_type = protein
                          organism = synthetic construct
SEQUENCE: 1100
ACSPDAHLGC ISYCEPW                                               17

SEQ ID NO: 1101           moltype = AA  length = 17
FEATURE                   Location/Qualifiers
source                    1..17
                          mol_type = protein
                          organism = synthetic construct
SEQUENCE: 1101
NEVCSPDAHL GCISYCA                                               17

SEQ ID NO: 1102           moltype = AA  length = 18
FEATURE                   Location/Qualifiers
source                    1..18
                          mol_type = protein
                          organism = synthetic construct
SEQUENCE: 1102
ACSPDAHLGC ISYCPIVH                                              18

SEQ ID NO: 1103           moltype = AA  length = 13
FEATURE                   Location/Qualifiers
source                    1..13
                          mol_type = protein
                          organism = synthetic construct
```

```
SEQUENCE: 1103
CSPDAHLGCI SYC                                                  13

SEQ ID NO: 1104         moltype = AA  length = 17
FEATURE                 Location/Qualifiers
source                  1..17
                        mol_type = protein
                        organism = synthetic construct
SEQUENCE: 1104
HTSCSPDAHL GCISYCA                                              17

SEQ ID NO: 1105         moltype = AA  length = 16
FEATURE                 Location/Qualifiers
source                  1..16
                        mol_type = protein
                        organism = synthetic construct
SITE                    2
                        note = N-methyl tryptophan
SEQUENCE: 1105
NXNCSPDAHL GCISYC                                               16

SEQ ID NO: 1106         moltype = AA  length = 16
FEATURE                 Location/Qualifiers
source                  1..16
                        mol_type = protein
                        organism = synthetic construct
SITE                    2
                        note = N-methyl tryptophan
SEQUENCE: 1106
NXNCSPDAHL GCISYC                                               16

SEQ ID NO: 1107         moltype = AA  length = 15
FEATURE                 Location/Qualifiers
source                  1..15
                        mol_type = protein
                        organism = synthetic construct
SEQUENCE: 1107
ACSPDAHLGC ISYCA                                                15

SEQ ID NO: 1108         moltype = AA  length = 18
FEATURE                 Location/Qualifiers
source                  1..18
                        mol_type = protein
                        organism = synthetic construct
SEQUENCE: 1108
ACSPDAHLGC ISYCEHQE                                             18

SEQ ID NO: 1109         moltype = AA  length = 17
FEATURE                 Location/Qualifiers
source                  1..17
                        mol_type = protein
                        organism = synthetic construct
SEQUENCE: 1109
ESFCSPDAHL GCISYCA                                              17

SEQ ID NO: 1110         moltype = AA  length = 17
FEATURE                 Location/Qualifiers
source                  1..17
                        mol_type = protein
                        organism = synthetic construct
SITE                    17
                        note = 6-azido lysine
SEQUENCE: 1110
NWNCSPDAHL GCISYCX                                              17

SEQ ID NO: 1111         moltype = AA  length = 17
FEATURE                 Location/Qualifiers
source                  1..17
                        mol_type = protein
                        organism = synthetic construct
SITE                    17
                        note = 6-azido lysine
SEQUENCE: 1111
NWNCSPDAHL GCISYCX                                              17

SEQ ID NO: 1112         moltype = AA  length = 16
FEATURE                 Location/Qualifiers
source                  1..16
                        mol_type = protein
```

-continued

```
                                 organism = synthetic construct
SEQUENCE: 1112
NWNCSPDAHL GCISYC                                              16

SEQ ID NO: 1113      moltype = AA   length = 17
FEATURE              Location/Qualifiers
source               1..17
                     mol_type = protein
                     organism = synthetic construct
SITE                 17
                     note = 6-azido lysine
SEQUENCE: 1113
CSPDAHLGCI SYCEPWX                                             17

SEQ ID NO: 1114      moltype = AA   length = 16
FEATURE              Location/Qualifiers
source               1..16
                     mol_type = protein
                     organism = synthetic construct
SEQUENCE: 1114
CSPDAHLGCI SYCEPW                                              16

SEQ ID NO: 1115      moltype = AA   length = 14
FEATURE              Location/Qualifiers
source               1..14
                     mol_type = protein
                     organism = synthetic construct
SITE                 14
                     note = 6-azido lysine
SEQUENCE: 1115
CSPDAHLGCI SYCX                                                14

SEQ ID NO: 1116      moltype = AA   length = 13
FEATURE              Location/Qualifiers
source               1..13
                     mol_type = protein
                     organism = synthetic construct
SEQUENCE: 1116
CSPDAHLGCI SYC                                                 13

SEQ ID NO: 1117      moltype = AA   length = 17
FEATURE              Location/Qualifiers
source               1..17
                     mol_type = protein
                     organism = synthetic construct
SITE                 2
                     note = D-tyrosine
SITE                 17
                     note = 6-azido lysine
SEQUENCE: 1117
NXNCSPDAHL GCISYCX                                             17

SEQ ID NO: 1118      moltype = AA   length = 17
FEATURE              Location/Qualifiers
source               1..17
                     mol_type = protein
                     organism = synthetic construct
SITE                 15
                     note = D-Proline
SITE                 17
                     note = 6-azido lysine
SEQUENCE: 1118
CSPDAHLGCI SYCEXWX                                             17

SEQ ID NO: 1119      moltype = AA   length = 17
FEATURE              Location/Qualifiers
source               1..17
                     mol_type = protein
                     organism = synthetic construct
SITE                 15
                     note = azetidine
SITE                 17
                     note = 6-azido lysine
SEQUENCE: 1119
CSPDAHLGCI SYCEXWX                                             17

SEQ ID NO: 1120      moltype = AA   length = 17
FEATURE              Location/Qualifiers
source               1..17
```

-continued

```
                        mol_type = protein
                        organism = synthetic construct
SITE                    15
                        note = Pipecolic Acid
SITE                    17
                        note = 6-azido lysine
SEQUENCE: 1120
CSPDAHLGCI SYCEXWX                                              17

SEQ ID NO: 1121         moltype = AA   length = 14
FEATURE                 Location/Qualifiers
source                  1..14
                        mol_type = protein
                        organism = synthetic construct
SITE                    14
                        note = K(N3)(PYA-Maleimide)
SEQUENCE: 1121
CSPDAHLGCI SYCX                                                 14

SEQ ID NO: 1122         moltype = AA   length = 16
FEATURE                 Location/Qualifiers
source                  1..16
                        mol_type = protein
                        organism = synthetic construct
SEQUENCE: 1122
CSPDAHLGCI SYCEPW                                               16

SEQ ID NO: 1123         moltype = AA   length = 16
FEATURE                 Location/Qualifiers
source                  1..16
                        mol_type = protein
                        organism = synthetic construct
SEQUENCE: 1123
CSPDAHLGCI SYCEPW                                               16

SEQ ID NO: 1124         moltype = AA   length = 23
FEATURE                 Location/Qualifiers
source                  1..23
                        mol_type = protein
                        organism = synthetic construct
SITE                    23
                        note = 6-azido lysine
SEQUENCE: 1124
CSPDAHLGCI SYCEPWGGSG GSX                                       23

SEQ ID NO: 1125         moltype = AA   length = 15
FEATURE                 Location/Qualifiers
source                  1..15
                        mol_type = protein
                        organism = synthetic construct
SEQUENCE: 1125
ACPGDAHLGC ISYCA                                                15

SEQ ID NO: 1126         moltype = AA   length = 13
FEATURE                 Location/Qualifiers
source                  1..13
                        mol_type = protein
                        organism = synthetic construct
SEQUENCE: 1126
CPGDAHLGCI SYC                                                  13

SEQ ID NO: 1127         moltype = AA   length = 15
FEATURE                 Location/Qualifiers
source                  1..15
                        mol_type = protein
                        organism = synthetic construct
SEQUENCE: 1127
ACPPDSHLGC ISYCA                                                15

SEQ ID NO: 1128         moltype = AA   length = 13
FEATURE                 Location/Qualifiers
source                  1..13
                        mol_type = protein
                        organism = synthetic construct
SEQUENCE: 1128
CPPDSHLGCI SYC                                                  13

SEQ ID NO: 1129         moltype = AA   length = 15
FEATURE                 Location/Qualifiers
```

-continued

```
source                   1..15
                         mol_type = protein
                         organism = synthetic construct
SEQUENCE: 1129
ACSADDWLGC ISYCA                                                    15

SEQ ID NO: 1130          moltype = AA   length = 13
FEATURE                  Location/Qualifiers
source                   1..13
                         mol_type = protein
                         organism = synthetic construct
SEQUENCE: 1130
CSADDWLGCI SYC                                                      13

SEQ ID NO: 1131          moltype = AA   length = 13
FEATURE                  Location/Qualifiers
source                   1..13
                         mol_type = protein
                         organism = synthetic construct
SITE                     3
                         note = 4Hyp
SITE                     10
                         note = t-butyl glycine
SEQUENCE: 1131
CPXDAYLGCX SYC                                                      13

SEQ ID NO: 1132          moltype = AA   length = 16
FEATURE                  Location/Qualifiers
source                   1..16
                         mol_type = protein
                         organism = synthetic construct
SITE                     3
                         note = 4Hyp
SITE                     10
                         note = t-butyl glycine
SEQUENCE: 1132
CPXDAYLGCX SYCEPW                                                   16

SEQ ID NO: 1133          moltype = AA   length = 16
FEATURE                  Location/Qualifiers
source                   1..16
                         mol_type = protein
                         organism = synthetic construct
SITE                     6
                         note = 4Hyp
SITE                     13
                         note = t-butyl glycine
SEQUENCE: 1133
NWNCPXDAYL GCXSYC                                                   16

SEQ ID NO: 1134          moltype = AA   length = 15
FEATURE                  Location/Qualifiers
source                   1..15
                         mol_type = protein
                         organism = synthetic construct
SITE                     4
                         note = 4Hyp
SITE                     11
                         note = t-butyl glycine
SEQUENCE: 1134
ACPXDAYLGC XSYCA                                                    15

SEQ ID NO: 1135          moltype = AA   length = 16
FEATURE                  Location/Qualifiers
source                   1..16
                         mol_type = protein
                         organism = synthetic construct
SITE                     6
                         note = 4Hyp
SITE                     13
                         note = t-butyl glycine
SEQUENCE: 1135
NWNCPXDAYL GCXSYC                                                   16

SEQ ID NO: 1136          moltype = AA   length = 14
FEATURE                  Location/Qualifiers
source                   1..14
                         mol_type = protein
                         organism = synthetic construct
```

-continued

```
SITE                      3
                          note = 4Hyp
SITE                      10
                          note = t-butyl glycine
SITE                      14
                          note = 6-azido lysine
SEQUENCE: 1136
CPXDAYLGCX SYCX                                                           14

SEQ ID NO: 1137           moltype = AA   length = 17
FEATURE                   Location/Qualifiers
source                    1..17
                          mol_type = protein
                          organism = synthetic construct
SITE                      6
                          note = 4Hyp
SITE                      13
                          note = t-butyl glycine
SITE                      17
                          note = 6-azido lysine
SEQUENCE: 1137
NWNCPXDAYL GCXSYCX                                                        17

SEQ ID NO: 1138           moltype = AA   length = 13
FEATURE                   Location/Qualifiers
source                    1..13
                          mol_type = protein
                          organism = synthetic construct
SITE                      3
                          note = 4Hyp
SEQUENCE: 1138
CPXDAYLGCI SYC                                                            13

SEQ ID NO: 1139           moltype = AA   length = 14
FEATURE                   Location/Qualifiers
source                    1..14
                          mol_type = protein
                          organism = synthetic construct
SITE                      3
                          note = 4Hyp
SITE                      14
                          note = 6-azido lysine
SEQUENCE: 1139
CPXDAYLGCI SYCX                                                           14

SEQ ID NO: 1140           moltype = AA   length = 13
FEATURE                   Location/Qualifiers
source                    1..13
                          mol_type = protein
                          organism = synthetic construct
SITE                      3
                          note = 4Hyp
SEQUENCE: 1140
CPXDAYLGCI SYC                                                           13

SEQ ID NO: 1141           moltype = AA   length = 13
FEATURE                   Location/Qualifiers
source                    1..13
                          mol_type = protein
                          organism = synthetic construct
SITE                      3
                          note = 4Hyp
SEQUENCE: 1141
CSXDAHLGCI SYC                                                           13

SEQ ID NO: 1142           moltype = AA   length = 15
FEATURE                   Location/Qualifiers
source                    1..15
                          mol_type = protein
                          organism = synthetic construct
SITE                      4
                          note = 4Hyp
SEQUENCE: 1142
ACSXDAHLGC ISYCA                                                         15

SEQ ID NO: 1143           moltype = AA   length = 14
FEATURE                   Location/Qualifiers
source                    1..14
                          mol_type = protein
```

-continued

```
                          organism = synthetic construct
SITE                      3
                          note = 4Hyp
SITE                      14
                          note = 6-azido lysine
SEQUENCE: 1143
CSXDAHLGCI SYCX                                                            14

SEQ ID NO: 1144           moltype = AA   length = 13
FEATURE                   Location/Qualifiers
source                    1..13
                          mol_type = protein
                          organism = synthetic construct
SITE                      3
                          note = 4Hyp
SEQUENCE: 1144
CSXDAHLGCI SYC                                                             13

SEQ ID NO: 1145           moltype = AA   length = 15
FEATURE                   Location/Qualifiers
source                    1..15
                          mol_type = protein
                          organism = synthetic construct
SITE                      4
                          note = Aib
SITE                      11
                          note = t-butyl glycine
SEQUENCE: 1145
ACPXDAHLGC XSYCA                                                           15

SEQ ID NO: 1146           moltype = AA   length = 18
FEATURE                   Location/Qualifiers
source                    1..18
                          mol_type = protein
                          organism = synthetic construct
SEQUENCE: 1146
TYMNCPPDAH LGCISYCA                                                        18

SEQ ID NO: 1147           moltype = AA   length = 15
FEATURE                   Location/Qualifiers
source                    1..15
                          mol_type = protein
                          organism = synthetic construct
SEQUENCE: 1147
ACPPDAHLGC ISYCA                                                           15

SEQ ID NO: 1148           moltype = AA   length = 15
FEATURE                   Location/Qualifiers
source                    1..15
                          mol_type = protein
                          organism = synthetic construct
SITE                      4
                          note = Aib
SITE                      11
                          note = t-butyl glycine
SEQUENCE: 1148
ACPXDAYLGC XSYCA                                                           15

SEQ ID NO: 1149           moltype = AA   length = 13
FEATURE                   Location/Qualifiers
source                    1..13
                          mol_type = protein
                          organism = synthetic construct
SEQUENCE: 1149
CSADAHLGCI SYC                                                             13

SEQ ID NO: 1150           moltype = AA   length = 15
FEATURE                   Location/Qualifiers
source                    1..15
                          mol_type = protein
                          organism = synthetic construct
SITE                      4
                          note = Aib
SITE                      11
                          note = t-butyl glycine
SEQUENCE: 1150
ACSXDAHLGC XSYCA                                                           15

SEQ ID NO: 1151           moltype = AA   length = 15
```

-continued

```
FEATURE              Location/Qualifiers
source               1..15
                     mol_type = protein
                     organism = synthetic construct
SITE                 11
                     note = 2-amino-3-ethyl-pentanoic acid
SEQUENCE: 1151
ACSPDAHLGC XSYCA                                             15

SEQ ID NO: 1152      moltype = AA  length = 15
FEATURE              Location/Qualifiers
source               1..15
                     mol_type = protein
                     organism = synthetic construct
SITE                 11
                     note = t-butyl glycine
SEQUENCE: 1152
ACPPDAYLGC XSYCA                                             15

SEQ ID NO: 1153      moltype = AA  length = 15
FEATURE              Location/Qualifiers
source               1..15
                     mol_type = protein
                     organism = synthetic construct
SITE                 4
                     note = Aib
SITE                 11
                     note = t-butyl glycine
SEQUENCE: 1153
ACSXDAYLGC XSYCA                                             15

SEQ ID NO: 1154      moltype = AA  length = 13
FEATURE              Location/Qualifiers
source               1..13
                     mol_type = protein
                     organism = synthetic construct
SEQUENCE: 1154
CAPDAHLGCI SYC                                               13

SEQ ID NO: 1155      moltype = AA  length = 15
FEATURE              Location/Qualifiers
source               1..15
                     mol_type = protein
                     organism = synthetic construct
SITE                 4
                     note = Aib
SEQUENCE: 1155
ACPXDAHLGC ISYCA                                             15

SEQ ID NO: 1156      moltype = AA  length = 15
FEATURE              Location/Qualifiers
source               1..15
                     mol_type = protein
                     organism = synthetic construct
SITE                 11
                     note = t-butyl glycine
SEQUENCE: 1156
ACSPDAYLGC XSYCA                                             15

SEQ ID NO: 1157      moltype = AA  length = 15
FEATURE              Location/Qualifiers
source               1..15
                     mol_type = protein
                     organism = synthetic construct
SITE                 11
                     note = t-butyl glycine
SEQUENCE: 1157
ACSPDAHLGC XSYCA                                             15

SEQ ID NO: 1158      moltype = AA  length = 18
FEATURE              Location/Qualifiers
source               1..18
                     mol_type = protein
                     organism = synthetic construct
SEQUENCE: 1158
IDSNCPNDAH LGCISYCA                                          18

SEQ ID NO: 1159      moltype = AA  length = 18
FEATURE              Location/Qualifiers
```

-continued

```
source                  1..18
                        mol_type = protein
                        organism = synthetic construct
SEQUENCE: 1159
WGKSCPIDAH LGCISYCA                                              18

SEQ ID NO: 1160         moltype = AA  length = 15
FEATURE                 Location/Qualifiers
source                  1..15
                        mol_type = protein
                        organism = synthetic construct
SEQUENCE: 1160
ACSPDAYLGC ISYCA                                                 15

SEQ ID NO: 1161         moltype = AA  length = 15
FEATURE                 Location/Qualifiers
source                  1..15
                        mol_type = protein
                        organism = synthetic construct
SEQUENCE: 1161
ACPPDAYLGC ISYCA                                                 15

SEQ ID NO: 1162         moltype = AA  length = 15
FEATURE                 Location/Qualifiers
source                  1..15
                        mol_type = protein
                        organism = synthetic construct
SITE                    4
                        note = Aib
SEQUENCE: 1162
ACSXDAHLGC ISYCA                                                 15

SEQ ID NO: 1163         moltype = AA  length = 15
FEATURE                 Location/Qualifiers
source                  1..15
                        mol_type = protein
                        organism = synthetic construct
SITE                    11
                        note = cyclohexyl glycine
SEQUENCE: 1163
ACSPDAHLGC XSYCA                                                 15

SEQ ID NO: 1164         moltype = AA  length = 22
FEATURE                 Location/Qualifiers
source                  1..22
                        mol_type = protein
                        organism = synthetic construct
SITE                    16..21
                        note = MeGly
SITE                    22
                        note = 6-fluorescein lysine
SEQUENCE: 1164
ACAPDAHLGC ISYCAXXXXX XX                                         22

SEQ ID NO: 1165         moltype = AA  length = 15
FEATURE                 Location/Qualifiers
source                  1..15
                        mol_type = protein
                        organism = synthetic construct
SITE                    8
                        note = t-butyl alanine
SEQUENCE: 1165
ACYLPDWXCG DEYCA                                                 15

SEQ ID NO: 1166         moltype = AA  length = 15
FEATURE                 Location/Qualifiers
source                  1..15
                        mol_type = protein
                        organism = synthetic construct
SITE                    13
                        note = 2-Naphthylalanine
SEQUENCE: 1166
ACSPDAHLGC ISXCA                                                 15

SEQ ID NO: 1167         moltype = AA  length = 15
FEATURE                 Location/Qualifiers
source                  1..15
                        mol_type = protein
                        organism = synthetic construct
```

-continued

```
SITE                      13
                          note = 3-t-Butyl-Tyrosine
SEQUENCE: 1167
ACSPDAHLGC ISXCA                                                  15

SEQ ID NO: 1168           moltype = AA  length = 15
FEATURE                   Location/Qualifiers
source                    1..15
                          mol_type = protein
                          organism = synthetic construct
SITE                      6
                          note = Aib
SEQUENCE: 1168
ACSPDXHLGC ISYCA                                                  15

SEQ ID NO: 1169           moltype = AA  length = 15
FEATURE                   Location/Qualifiers
source                    1..15
                          mol_type = protein
                          organism = synthetic construct
SITE                      13
                          note = 1-Naphthylalanine
SEQUENCE: 1169
ACSPDAHLGC ISXCA                                                  15

SEQ ID NO: 1170           moltype = AA  length = 15
FEATURE                   Location/Qualifiers
source                    1..15
                          mol_type = protein
                          organism = synthetic construct
SITE                      8
                          note = t-butyl alanine
SEQUENCE: 1170
ACSPDAHXGC ISYCA                                                  15

SEQ ID NO: 1171           moltype = AA  length = 15
FEATURE                   Location/Qualifiers
source                    1..15
                          mol_type = protein
                          organism = synthetic construct
SITE                      8
                          note = beta-cyclobutylalanine
SEQUENCE: 1171
ACSPDAHXGC ISYCA                                                  15

SEQ ID NO: 1172           moltype = AA  length = 15
FEATURE                   Location/Qualifiers
source                    1..15
                          mol_type = protein
                          organism = synthetic construct
SEQUENCE: 1172
ACSPDAHLGC ISWCA                                                  15

SEQ ID NO: 1173           moltype = AA  length = 15
FEATURE                   Location/Qualifiers
source                    1..15
                          mol_type = protein
                          organism = synthetic construct
SITE                      6
                          note = Abu
SEQUENCE: 1173
ACSPDXHLGC ISYCA                                                  15

SEQ ID NO: 1174           moltype = AA  length = 15
FEATURE                   Location/Qualifiers
source                    1..15
                          mol_type = protein
                          organism = synthetic construct
SITE                      4
                          note = azetidine
SEQUENCE: 1174
ACSXDAHLGC ISYCA                                                  15

SEQ ID NO: 1175           moltype = AA  length = 13
FEATURE                   Location/Qualifiers
source                    1..13
                          mol_type = protein
                          organism = synthetic construct
SITE                      3
```

-continued

```
                             note = azetidine
SEQUENCE: 1175
CSXDAHLGCI SYC                                                      13

SEQ ID NO: 1176             moltype = AA  length = 14
FEATURE                     Location/Qualifiers
source                      1..14
                            mol_type = protein
                            organism = synthetic construct
SITE                        3
                            note = azetidine
SITE                        14
                            note = 6-azido lysine
SEQUENCE: 1176
CSXDAHLGCI SYCX                                                     14

SEQ ID NO: 1177             moltype = AA  length = 13
FEATURE                     Location/Qualifiers
source                      1..13
                            mol_type = protein
                            organism = synthetic construct
SITE                        3
                            note = azetidine
SEQUENCE: 1177
CSXDAHLGCI SYC                                                      13

SEQ ID NO: 1178             moltype = AA  length = 15
FEATURE                     Location/Qualifiers
source                      1..15
                            mol_type = protein
                            organism = synthetic construct
SEQUENCE: 1178
ACSPDDHLGC ISYCA                                                    15

SEQ ID NO: 1179             moltype = AA  length = 15
FEATURE                     Location/Qualifiers
source                      1..15
                            mol_type = protein
                            organism = synthetic construct
SEQUENCE: 1179
ACSPDSHLGC ISYCA                                                    15

SEQ ID NO: 1180             moltype = AA  length = 15
FEATURE                     Location/Qualifiers
source                      1..15
                            mol_type = protein
                            organism = synthetic construct
SITE                        8
                            note = Abu
SEQUENCE: 1180
ACSPDAHXGC ISYCA                                                    15

SEQ ID NO: 1181             moltype = AA  length = 15
FEATURE                     Location/Qualifiers
source                      1..15
                            mol_type = protein
                            organism = synthetic construct
SITE                        13
                            note = 4-pyridylalanine
SEQUENCE: 1181
ACSPDAHLGC ISXCA                                                    15

SEQ ID NO: 1182             moltype = AA  length = 15
FEATURE                     Location/Qualifiers
source                      1..15
                            mol_type = protein
                            organism = synthetic construct
SITE                        4
                            note = D-Alanine
SEQUENCE: 1182
ACPXDAHLGC ISYCA                                                    15

SEQ ID NO: 1183             moltype = AA  length = 15
FEATURE                     Location/Qualifiers
source                      1..15
                            mol_type = protein
                            organism = synthetic construct
SITE                        11
                            note = t-butyl alanine
```

-continued

```
SEQUENCE: 1183
ACSPDAYLGC XSYCA                                                          15

SEQ ID NO: 1184        moltype = AA  length = 15
FEATURE                Location/Qualifiers
source                 1..15
                       mol_type = protein
                       organism = synthetic construct
SITE                   11
                       note = cyclopentyl glycine
SEQUENCE: 1184
ACSPDAHLGC XSYCA                                                          15

SEQ ID NO: 1185        moltype = AA  length = 15
FEATURE                Location/Qualifiers
source                 1..15
                       mol_type = protein
                       organism = synthetic construct
SITE                   11
                       note = cyclobutyl glycine
SEQUENCE: 1185
ACSPDAHLGC XSYCA                                                          15

SEQ ID NO: 1186        moltype = AA  length = 15
FEATURE                Location/Qualifiers
source                 1..15
                       mol_type = protein
                       organism = synthetic construct
SITE                   9
                       note = D-alanine
SEQUENCE: 1186
ACSPDAHLXC ISYCA                                                          15

SEQ ID NO: 1187        moltype = AA  length = 15
FEATURE                Location/Qualifiers
source                 1..15
                       mol_type = protein
                       organism = synthetic construct
SITE                   8
                       note = Aib
SEQUENCE: 1187
ACSPDAHXGC ISYCA                                                          15

SEQ ID NO: 1188        moltype = AA  length = 15
FEATURE                Location/Qualifiers
source                 1..15
                       mol_type = protein
                       organism = synthetic construct
SITE                   11
                       note = cyclopropyl glycine
SEQUENCE: 1188
ACSPDAHLGC XSYCA                                                          15

SEQ ID NO: 1189        moltype = AA  length = 15
FEATURE                Location/Qualifiers
source                 1..15
                       mol_type = protein
                       organism = synthetic construct
SITE                   11
                       note = beta-methyl isoleucine
SEQUENCE: 1189
ACSPDAHLGC XSYCA                                                          15

SEQ ID NO: 1190        moltype = AA  length = 22
FEATURE                Location/Qualifiers
source                 1..22
                       mol_type = protein
                       organism = synthetic construct
SITE                   16..21
                       note = MeGly
SITE                   22
                       note = 6-fluorescein lysine
SEQUENCE: 1190
ACSADAHLGC ISYCAXXXXX XX                                                  22

SEQ ID NO: 1191        moltype = AA  length = 22
FEATURE                Location/Qualifiers
source                 1..22
                       mol_type = protein
```

```
                          organism = synthetic construct
SITE                      16..21
                          note = MeGly
SITE                      22
                          note = 6-fluorescein lysine
SEQUENCE: 1191
ACSPAAHLGC ISYCAXXXXX XX                                        22

SEQ ID NO: 1192           moltype = AA  length = 22
FEATURE                   Location/Qualifiers
source                    1..22
                          mol_type = protein
                          organism = synthetic construct
SITE                      16..21
                          note = MeGly
SITE                      22
                          note = 6-fluorescein lysine
SEQUENCE: 1192
ACSPDAALGC ISYCAXXXXX XX                                        22

SEQ ID NO: 1193           moltype = AA  length = 22
FEATURE                   Location/Qualifiers
source                    1..22
                          mol_type = protein
                          organism = synthetic construct
SITE                      16..21
                          note = MeGly
SITE                      22
                          note = 6-fluorescein lysine
SEQUENCE: 1193
ACSPDAHAGC ISYCAXXXXX XX                                        22

SEQ ID NO: 1194           moltype = AA  length = 22
FEATURE                   Location/Qualifiers
source                    1..22
                          mol_type = protein
                          organism = synthetic construct
SITE                      16..21
                          note = MeGly
SITE                      22
                          note = 6-fluorescein lysine
SEQUENCE: 1194
ACSPDAHLAC ISYCAXXXXX XX                                        22

SEQ ID NO: 1195           moltype = AA  length = 22
FEATURE                   Location/Qualifiers
source                    1..22
                          mol_type = protein
                          organism = synthetic construct
SITE                      16..21
                          note = MeGly
SITE                      22
                          note = 6-fluorescein lysine
SEQUENCE: 1195
ACSPDAHLGC ASYCAXXXXX XX                                        22

SEQ ID NO: 1196           moltype = AA  length = 22
FEATURE                   Location/Qualifiers
source                    1..22
                          mol_type = protein
                          organism = synthetic construct
SITE                      16..21
                          note = MeGly
SITE                      22
                          note = 6-fluorescein lysine
SEQUENCE: 1196
ACSPDAHLGC IAYCAXXXXX XX                                        22

SEQ ID NO: 1197           moltype = AA  length = 22
FEATURE                   Location/Qualifiers
source                    1..22
                          mol_type = protein
                          organism = synthetic construct
SITE                      16..21
                          note = MeGly
SITE                      22
                          note = 6-fluorescein lysine
SEQUENCE: 1197
ACSPDAHLGC ISACAXXXXX XX                                        22
```

-continued

```
SEQ ID NO: 1198          moltype = AA  length = 13
FEATURE                  Location/Qualifiers
source                   1..13
                         mol_type = protein
                         organism = synthetic construct
SITE                     2
                         note = 6-azido lysine
SEQUENCE: 1198
CXPDAHLGCI SYC                                                      13

SEQ ID NO: 1199          moltype = AA  length = 13
FEATURE                  Location/Qualifiers
source                   1..13
                         mol_type = protein
                         organism = synthetic construct
SITE                     3
                         note = 6-azido lysine
SEQUENCE: 1199
CSXDAHLGCI SYC                                                      13

SEQ ID NO: 1200          moltype = AA  length = 13
FEATURE                  Location/Qualifiers
source                   1..13
                         mol_type = protein
                         organism = synthetic construct
SITE                     5
                         note = 6-azido lysine
SEQUENCE: 1200
CSPDXHLGCI SYC                                                      13

SEQ ID NO: 1201          moltype = AA  length = 16
FEATURE                  Location/Qualifiers
source                   1..16
                         mol_type = protein
                         organism = synthetic construct
SITE                     2..3
                         note = 4Hyp
SITE                     10
                         note = t-butyl glycine
SEQUENCE: 1201
CXXDAYLGCX SYCEPW                                                   16

SEQ ID NO: 1202          moltype = AA  length = 17
FEATURE                  Location/Qualifiers
source                   1..17
                         mol_type = protein
                         organism = synthetic construct
SITE                     3
                         note = 4Hyp
SITE                     10
                         note = t-butyl glycine
SEQUENCE: 1202
CPXDAYLGCX SYCEPWK                                                  17

SEQ ID NO: 1203          moltype = AA  length = 17
FEATURE                  Location/Qualifiers
source                   1..17
                         mol_type = protein
                         organism = synthetic construct
SITE                     3
                         note = 4Hyp
SITE                     10
                         note = t-butyl glycine
SEQUENCE: 1203
CPXDAYLGCX SYCEPWC                                                  17

SEQ ID NO: 1204          moltype = AA  length = 16
FEATURE                  Location/Qualifiers
source                   1..16
                         mol_type = protein
                         organism = synthetic construct
SITE                     2
                         note = oxazolidine-4-carboxylic acid
SITE                     3
                         note = 4Hyp
SITE                     10
                         note = t-butyl glycine
SEQUENCE: 1204
```

-continued

```
CXXDAYLGCX SYCEPW                                              16

SEQ ID NO: 1205          moltype = AA  length = 16
FEATURE                  Location/Qualifiers
source                   1..16
                         mol_type = protein
                         organism = synthetic construct
SITE                     2
                         note = cis-L-4-hydroxyproline
SITE                     3
                         note = 4Hyp
SITE                     10
                         note = t-butyl glycine
SEQUENCE: 1205
CXXDAYLGCX SYCEPW                                              16

SEQ ID NO: 1206          moltype = AA  length = 16
FEATURE                  Location/Qualifiers
source                   1..16
                         mol_type = protein
                         organism = synthetic construct
SITE                     3
                         note = oxazolidine-4-carboxylic acid
SITE                     10
                         note = t-butyl glycine
SEQUENCE: 1206
CPXDAYLGCX SYCEPW                                              16

SEQ ID NO: 1207          moltype = AA  length = 16
FEATURE                  Location/Qualifiers
source                   1..16
                         mol_type = protein
                         organism = synthetic construct
SITE                     3
                         note = cis-L-4-hydroxyproline
SITE                     10
                         note = t-butyl glycine
SEQUENCE: 1207
CPXDAYLGCX SYCEPW                                              16

SEQ ID NO: 1208          moltype = AA  length = 16
FEATURE                  Location/Qualifiers
source                   1..16
                         mol_type = protein
                         organism = synthetic construct
SITE                     3
                         note = 4Hyp
SITE                     6
                         note = 3,4-dihydroxy-phenylalanine
SITE                     10
                         note = t-butyl glycine
SEQUENCE: 1208
CPXDAXLGCX SYCEPW                                              16

SEQ ID NO: 1209          moltype = AA  length = 16
FEATURE                  Location/Qualifiers
source                   1..16
                         mol_type = protein
                         organism = synthetic construct
SITE                     3
                         note = 4Hyp
SITE                     6
                         note = L-4-carbamoylphenylalanine
SITE                     10
                         note = t-butyl glycine
SEQUENCE: 1209
CPXDAXLGCX SYCEPW                                              16

SEQ ID NO: 1210          moltype = AA  length = 16
FEATURE                  Location/Qualifiers
source                   1..16
                         mol_type = protein
                         organism = synthetic construct
SITE                     3
                         note = 4Hyp
SITE                     6
                         note = 4-carboxy-L-phenylalanine
SITE                     10
                         note = t-butyl glycine
```

-continued

```
SEQUENCE: 1210
CPXDAXLGCX SYCEPW                                                              16

SEQ ID NO: 1211      moltype = AA  length = 16
FEATURE              Location/Qualifiers
source               1..16
                     mol_type = protein
                     organism = synthetic construct
SITE                 3
                     note = 4Hyp
SITE                 6
                     note = homo-tyrosine
SITE                 10
                     note = t-butyl glycine
SEQUENCE: 1211
CPXDAXLGCX SYCEPW                                                              16

SEQ ID NO: 1212      moltype = AA  length = 16
FEATURE              Location/Qualifiers
source               1..16
                     mol_type = protein
                     organism = synthetic construct
SITE                 3
                     note = 4Hyp
SITE                 8
                     note = D-Serine
SITE                 10
                     note = t-butyl glycine
SEQUENCE: 1212
CPXDAYLXCX SYCEPW                                                              16

SEQ ID NO: 1213      moltype = AA  length = 16
FEATURE              Location/Qualifiers
source               1..16
                     mol_type = protein
                     organism = synthetic construct
SITE                 3
                     note = 4Hyp
SITE                 8
                     note = D-Threonine
SITE                 10
                     note = t-butyl glycine
SEQUENCE: 1213
CPXDAYLXCX SYCEPW                                                              16

SEQ ID NO: 1214      moltype = AA  length = 16
FEATURE              Location/Qualifiers
source               1..16
                     mol_type = protein
                     organism = synthetic construct
SITE                 3
                     note = 4Hyp
SITE                 8
                     note = D-Aspartic Acid
SITE                 10
                     note = t-butyl glycine
SEQUENCE: 1214
CPXDAYLXCX SYCEPW                                                              16

SEQ ID NO: 1215      moltype = AA  length = 16
FEATURE              Location/Qualifiers
source               1..16
                     mol_type = protein
                     organism = synthetic construct
SITE                 3
                     note = 4Hyp
SITE                 8
                     note = D-glutamic acid
SITE                 10
                     note = t-butyl glycine
SEQUENCE: 1215
CPXDAYLXCX SYCEPW                                                              16

SEQ ID NO: 1216      moltype = AA  length = 16
FEATURE              Location/Qualifiers
source               1..16
                     mol_type = protein
                     organism = synthetic construct
SITE                 3
```

-continued

```
                                    note = 4Hyp
SITE                                8
                                    note = D-asparagine
SITE                                10
                                    note = t-butyl glycine
SEQUENCE: 1216
CPXDAYLXCX SYCEPW                                                                           16

SEQ ID NO: 1217                     moltype = AA  length = 16
FEATURE                             Location/Qualifiers
source                              1..16
                                    mol_type = protein
                                    organism = synthetic construct
SITE                                3
                                    note = 4Hyp
SITE                                8
                                    note = D-Glutamine
SITE                                10
                                    note = t-butyl glycine
SEQUENCE: 1217
CPXDAYLXCX SYCEPW                                                                           16

SEQ ID NO: 1218                     moltype = AA  length = 16
FEATURE                             Location/Qualifiers
source                              1..16
                                    mol_type = protein
                                    organism = synthetic construct
SITE                                3
                                    note = 4Hyp
SITE                                8
                                    note = D-Tyrosine
SITE                                10
                                    note = t-butyl glycine
SEQUENCE: 1218
CPXDAYLXCX SYCEPW                                                                           16

SEQ ID NO: 1219                     moltype = AA  length = 16
FEATURE                             Location/Qualifiers
source                              1..16
                                    mol_type = protein
                                    organism = synthetic construct
SITE                                3
                                    note = 4Hyp
SITE                                10
                                    note = t-butyl glycine
SEQUENCE: 1219
CPXDAYLSCX SYCEPW                                                                           16

SEQ ID NO: 1220                     moltype = AA  length = 16
FEATURE                             Location/Qualifiers
source                              1..16
                                    mol_type = protein
                                    organism = synthetic construct
SITE                                3
                                    note = 4Hyp
SITE                                10
                                    note = t-butyl glycine
SEQUENCE: 1220
CPXDAYLDCX SYCEPW                                                                           16

SEQ ID NO: 1221                     moltype = AA  length = 16
FEATURE                             Location/Qualifiers
source                              1..16
                                    mol_type = protein
                                    organism = synthetic construct
SITE                                3
                                    note = 4Hyp
SITE                                10
                                    note = t-butyl glycine
SEQUENCE: 1221
CPXDAYLYCX SYCEPW                                                                           16

SEQ ID NO: 1222                     moltype = AA  length = 16
FEATURE                             Location/Qualifiers
source                              1..16
                                    mol_type = protein
                                    organism = synthetic construct
SITE                                3
                                    note = 4Hyp
```

-continued

```
SITE                  10
                      note = t-butyl glycine
SEQUENCE: 1222
CPXDAYLNCX SYCEPW                                                16

SEQ ID NO: 1223       moltype = AA  length = 16
FEATURE               Location/Qualifiers
source                1..16
                      mol_type = protein
                      organism = synthetic construct
SITE                  3
                      note = 4Hyp
SITE                  10
                      note = t-butyl glycine
SITE                  12
                      note = 3,4-dihydroxy-phenylalanine
SEQUENCE: 1223
CPXDAYLGCX SXCEPW                                                16

SEQ ID NO: 1224       moltype = AA  length = 16
FEATURE               Location/Qualifiers
source                1..16
                      mol_type = protein
                      organism = synthetic construct
SITE                  3
                      note = 4Hyp
SITE                  10
                      note = t-butyl glycine
SITE                  12
                      note = L-4-carbamoylphenylalanine
SEQUENCE: 1224
CPXDAYLGCX SXCEPW                                                16

SEQ ID NO: 1225       moltype = AA  length = 16
FEATURE               Location/Qualifiers
source                1..16
                      mol_type = protein
                      organism = synthetic construct
SITE                  3
                      note = 4Hyp
SITE                  10
                      note = t-butyl glycine
SITE                  12
                      note = 4-carboxy-L-phenylalanine
SEQUENCE: 1225
CPXDAYLGCX SXCEPW                                                16

SEQ ID NO: 1226       moltype = AA  length = 16
FEATURE               Location/Qualifiers
source                1..16
                      mol_type = protein
                      organism = synthetic construct
SITE                  3
                      note = 4Hyp
SITE                  10
                      note = t-butyl glycine
SITE                  12
                      note = homo-tyrosine
SEQUENCE: 1226
CPXDAYLGCX SXCEPW                                                16

SEQ ID NO: 1227       moltype = AA  length = 16
FEATURE               Location/Qualifiers
source                1..16
                      mol_type = protein
                      organism = synthetic construct
SITE                  3
                      note = 4Hyp
SITE                  15
                      note = 4Hyp
SITE                  10
                      note = t-butyl glycine
SEQUENCE: 1227
CPXDAYLGCX SYCEXW                                                16

SEQ ID NO: 1228       moltype = AA  length = 16
FEATURE               Location/Qualifiers
source                1..16
                      mol_type = protein
```

```
                         organism = synthetic construct
SITE                     3
                         note = 4Hyp
SITE                     10
                         note = t-butyl glycine
SITE                     15
                         note = oxazolidine-4-carboxylic acid
SEQUENCE: 1228
CPXDAYLGCX SYCEXW                                               16

SEQ ID NO: 1229          moltype = AA  length = 16
FEATURE                  Location/Qualifiers
source                   1..16
                         mol_type = protein
                         organism = synthetic construct
SITE                     3
                         note = 4Hyp
SITE                     10
                         note = t-butyl glycine
SITE                     15
                         note = cis-L-4-hydroxyproline
SEQUENCE: 1229
CPXDAYLGCX SYCEXW                                               16

SEQ ID NO: 1230          moltype = AA  length = 16
FEATURE                  Location/Qualifiers
source                   1..16
                         mol_type = protein
                         organism = synthetic construct
SITE                     3
                         note = 4Hyp
SITE                     10
                         note = t-butyl glycine
SEQUENCE: 1230
CPXDAYLGCX SYCEPY                                               16

SEQ ID NO: 1231          moltype = AA  length = 16
FEATURE                  Location/Qualifiers
source                   1..16
                         mol_type = protein
                         organism = synthetic construct
SITE                     3
                         note = 4Hyp
SITE                     10
                         note = t-butyl glycine
SITE                     16
                         note = 3,4-dihydroxy-phenylalanine
SEQUENCE: 1231
CPXDAYLGCX SYCEPX                                               16

SEQ ID NO: 1232          moltype = AA  length = 16
FEATURE                  Location/Qualifiers
source                   1..16
                         mol_type = protein
                         organism = synthetic construct
SITE                     3
                         note = 4Hyp
SITE                     10
                         note = t-butyl glycine
SITE                     16
                         note = L-4-carbamoylphenylalanine
SEQUENCE: 1232
CPXDAYLGCX SYCEPX                                               16

SEQ ID NO: 1233          moltype = AA  length = 16
FEATURE                  Location/Qualifiers
source                   1..16
                         mol_type = protein
                         organism = synthetic construct
SITE                     3
                         note = 4Hyp
SITE                     10
                         note = t-butyl glycine
SITE                     16
                         note = 4-carboxy-L-phenylalanine
SEQUENCE: 1233
CPXDAYLGCX SYCEPX                                               16

SEQ ID NO: 1234          moltype = AA  length = 16
```

-continued

```
FEATURE            Location/Qualifiers
source             1..16
                   mol_type = protein
                   organism = synthetic construct
SITE               3
                   note = 4Hyp
SITE               10
                   note = t-butyl glycine
SITE               16
                   note = homo-tyrosine
SEQUENCE: 1234
CPXDAYLGCX SYCEPX                                                16

SEQ ID NO: 1235    moltype = AA  length = 16
FEATURE            Location/Qualifiers
source             1..16
                   mol_type = protein
                   organism = synthetic construct
SITE               3
                   note = 4Hyp
SITE               10
                   note = t-butyl glycine
SEQUENCE: 1235
CPXEAYLGCX SYCEPW                                                16

SEQ ID NO: 1236    moltype = AA  length = 16
FEATURE            Location/Qualifiers
source             1..16
                   mol_type = protein
                   organism = synthetic construct
SITE               3
                   note = 4Hyp
SITE               4
                   note = L-gamma-carboxyglutamic acid
SITE               10
                   note = t-butyl glycine
SEQUENCE: 1236
CPXXAYLGCX SYCEPW                                                16

SEQ ID NO: 1237    moltype = AA  length = 16
FEATURE            Location/Qualifiers
source             1..16
                   mol_type = protein
                   organism = synthetic construct
SITE               3
                   note = 4Hyp
SITE               10
                   note = t-butyl glycine
SEQUENCE: 1237
CPXDAYSGCX SYCEPW                                                16

SEQ ID NO: 1238    moltype = AA  length = 16
FEATURE            Location/Qualifiers
source             1..16
                   mol_type = protein
                   organism = synthetic construct
SITE               3
                   note = 4Hyp
SITE               10
                   note = t-butyl glycine
SEQUENCE: 1238
CPXDAYTGCX SYCEPW                                                16

SEQ ID NO: 1239    moltype = AA  length = 16
FEATURE            Location/Qualifiers
source             1..16
                   mol_type = protein
                   organism = synthetic construct
SITE               3
                   note = 4Hyp
SITE               10
                   note = t-butyl glycine
SEQUENCE: 1239
CPXDAYDGCX SYCEPW                                                16

SEQ ID NO: 1240    moltype = AA  length = 16
FEATURE            Location/Qualifiers
source             1..16
                   mol_type = protein
```

-continued

```
                          organism = synthetic construct
SITE                      3
                          note = 4Hyp
SITE                      10
                          note = t-butyl glycine
SEQUENCE: 1240
CPXDAYEGCX SYCEPW                                                                16

SEQ ID NO: 1241           moltype = AA  length = 16
FEATURE                   Location/Qualifiers
source                    1..16
                          mol_type = protein
                          organism = synthetic construct
SITE                      3
                          note = 4Hyp
SITE                      10
                          note = t-butyl glycine
SEQUENCE: 1241
CPXDAYNGCX SYCEPW                                                                16

SEQ ID NO: 1242           moltype = AA  length = 16
FEATURE                   Location/Qualifiers
source                    1..16
                          mol_type = protein
                          organism = synthetic construct
SITE                      3
                          note = 4Hyp
SITE                      10
                          note = t-butyl glycine
SEQUENCE: 1242
CPXDAYQGCX SYCEPW                                                                16

SEQ ID NO: 1243           moltype = AA  length = 16
FEATURE                   Location/Qualifiers
source                    1..16
                          mol_type = protein
                          organism = synthetic construct
SITE                      3
                          note = 4Hyp
SITE                      10
                          note = t-butyl glycine
SITE                      11
                          note = homoserine
SEQUENCE: 1243
CPXDAYLGCX XYCEPW                                                                16

SEQ ID NO: 1244           moltype = AA  length = 16
FEATURE                   Location/Qualifiers
source                    1..16
                          mol_type = protein
                          organism = synthetic construct
SITE                      3
                          note = 4Hyp
SITE                      10
                          note = t-butyl glycine
SEQUENCE: 1244
CPXDAYLGCX TYCEPW                                                                16

SEQ ID NO: 1245           moltype = AA  length = 16
FEATURE                   Location/Qualifiers
source                    1..16
                          mol_type = protein
                          organism = synthetic construct
SITE                      3
                          note = 4Hyp
SITE                      10
                          note = t-butyl glycine
SEQUENCE: 1245
CPXDAYLGCX DYCEPW                                                                16

SEQ ID NO: 1246           moltype = AA  length = 16
FEATURE                   Location/Qualifiers
source                    1..16
                          mol_type = protein
                          organism = synthetic construct
SITE                      3
                          note = 4Hyp
SITE                      10
                          note = t-butyl glycine
```

-continued

```
SEQUENCE: 1246
CPXDAYLGCX EYCEPW                                                        16

SEQ ID NO: 1247      moltype = AA  length = 16
FEATURE              Location/Qualifiers
source               1..16
                     mol_type = protein
                     organism = synthetic construct
SITE                 3
                     note = 4Hyp
SITE                 10
                     note = t-butyl glycine
SEQUENCE: 1247
CPXDAYLGCX NYCEPW                                                        16

SEQ ID NO: 1248      moltype = AA  length = 16
FEATURE              Location/Qualifiers
source               1..16
                     mol_type = protein
                     organism = synthetic construct
SITE                 3
                     note = 4Hyp
SITE                 10
                     note = t-butyl glycine
SEQUENCE: 1248
CPXDAYLGCX QYCEPW                                                        16

SEQ ID NO: 1249      moltype = AA  length = 16
FEATURE              Location/Qualifiers
source               1..16
                     mol_type = protein
                     organism = synthetic construct
SITE                 3
                     note = 4Hyp
SITE                 10
                     note = t-butyl glycine
SEQUENCE: 1249
CPXDAYLGCX SYCDPW                                                        16

SEQ ID NO: 1250      moltype = AA  length = 16
FEATURE              Location/Qualifiers
source               1..16
                     mol_type = protein
                     organism = synthetic construct
SITE                 3
                     note = 4Hyp
SITE                 10
                     note = t-butyl glycine
SITE                 14
                     note = L-gamma-carboxyglutamic acid
SEQUENCE: 1250
CPXDAYLGCX SYCXPW                                                        16

SEQ ID NO: 1251      moltype = AA  length = 16
FEATURE              Location/Qualifiers
source               1..16
                     mol_type = protein
                     organism = synthetic construct
SITE                 3
                     note = 4Hyp
SEQUENCE: 1251
CPXDAYLGCY SYCEPW                                                        16

SEQ ID NO: 1252      moltype = AA  length = 16
FEATURE              Location/Qualifiers
source               1..16
                     mol_type = protein
                     organism = synthetic construct
SITE                 3
                     note = 4Hyp
SITE                 10
                     note = 3-hydroxy-L-valine
SEQUENCE: 1252
CPXDAYLGCX SYCEPW                                                        16

SEQ ID NO: 1253      moltype = AA  length = 17
FEATURE              Location/Qualifiers
source               1..17
                     mol_type = protein
```

-continued

```
                      organism = synthetic construct
SITE                  3
                      note = 4Hyp
SITE                  10
                      note = t-butyl glycine
SITE                  17
                      note = 6-azido lysine
SEQUENCE: 1253
CPXDAYLGCX SYCEPWX                                                   17

SEQ ID NO: 1254       moltype = RNA  length = 23
FEATURE               Location/Qualifiers
source                1..23
                      mol_type = other RNA
                      organism = synthetic construct
modified_base         1
                      mod_base = OTHER
                      note = thymidine
SEQUENCE: 1254
tataaataga ttctgtagct taa                                           23

SEQ ID NO: 1255       moltype = RNA  length = 23
FEATURE               Location/Qualifiers
source                1..23
                      mol_type = other RNA
                      organism = synthetic construct
modified_base         1
                      mod_base = OTHER
                      note = thymidine
modified_base
                      mod_base = OTHER
                      note = vinyl phosphonate
modified_base         1
                      mod_base = OTHER
                      note = 2'-O-methoxyethyl thymidine 3'-phosphorothioate
modified_base         2
                      mod_base = OTHER
                      note = 2'-fluoro adenosine 3'-phosphorothioate
modified_base         3
                      mod_base = OTHER
                      note = 2'-O-methyl uridine 3'-phosphodiester
modified_base         4..6
                      mod_base = OTHER
                      note = 2'-O-methyl adenosine 3'-phosphodiester
modified_base         7
                      mod_base = OTHER
                      note = 2'-O-methyl uridine 3'-phosphodiester
modified_base         8
                      mod_base = OTHER
                      note = 2'-O-methyl adenosine 3'-phosphodiester
modified_base         9
                      mod_base = OTHER
                      note = 2'-O-methyl guanosine 3'-phosphodiester
modified_base         10
                      mod_base = OTHER
                      note = 2'-O-methyl adenosine 3'-phosphodiester
modified_base         11..12
                      mod_base = OTHER
                      note = 2'-O-methyl uridine 3'-phosphodiester
modified_base         13
                      mod_base = OTHER
                      note = 2'-O-methyl cytidine 3'-phosphodiester
modified_base         14
                      mod_base = OTHER
                      note = 2'-fluoro uridine 3'-phosphodiester
modified_base         15
                      mod_base = OTHER
                      note = 2'-O-methyl guanosine 3'-phosphodiester
modified_base         16
                      mod_base = OTHER
                      note = 2'-fluoro uridine 3'-phosphodiester
modified_base         17
                      mod_base = OTHER
                      note = 2'-O-methyl adenosine 3'-phosphodiester
modified_base         18
                      mod_base = OTHER
                      note = 2'-O-methyl guanosine 3'-phosphodiester
modified_base         19
                      mod_base = OTHER
```

```
                              note = 2'-O-methyl cytidine 3'-phosphodiester
modified_base                 20
                              mod_base = OTHER
                              note = 2'-O-methyl uridine 3'-phosphodiester
modified_base                 21
                              mod_base = OTHER
                              note = 2'-O-methyl uridine 3'-phosphorothioate
modified_base                 22
                              mod_base = OTHER
                              note = 2'-O-methoxyethyl adenosine 3'-phosphorothioate
modified_base                 23
                              mod_base = OTHER
                              note = 2'-O-methoxyethyl adenosine
SEQUENCE: 1255
tataaataga ttctgtagct taa                                              23

SEQ ID NO: 1256           moltype = RNA   length = 21
FEATURE                   Location/Qualifiers
source                    1..21
                          mol_type = other RNA
                          organism = synthetic construct
SEQUENCE: 1256
caatttctgt ctcatcttaa a                                                21

SEQ ID NO: 1257           moltype = RNA   length = 21
FEATURE                   Location/Qualifiers
source                    1..21
                          mol_type = other RNA
                          organism = synthetic construct
SEQUENCE: 1257
aagctacaga atctatttat a                                                21

SEQ ID NO: 1258           moltype = RNA   length = 23
FEATURE                   Location/Qualifiers
source                    1..23
                          mol_type = other RNA
                          organism = synthetic construct
modified_base             23
                          mod_base = i
modified_base             1
                          mod_base = OTHER
                          note = thymine
SEQUENCE: 1258
tttaagatga gacagaaatt gan                                              23

SEQ ID NO: 1259           moltype = RNA   length = 23
FEATURE                   Location/Qualifiers
source                    1..23
                          mol_type = other RNA
                          organism = synthetic construct
modified_base             22..23
                          mod_base = i
modified_base             1
                          mod_base = OTHER
                          note = thymine
SEQUENCE: 1259
tttaagatga gacagaaatt gnn                                              23

SEQ ID NO: 1260           moltype = RNA   length = 23
FEATURE                   Location/Qualifiers
source                    1..23
                          mol_type = other RNA
                          organism = synthetic construct
modified_base             22
                          mod_base = i
modified_base             1
                          mod_base = OTHER
                          note = thymine
SEQUENCE: 1260
tttaagatga gacagaaatt gna                                              23

SEQ ID NO: 1261           moltype = RNA   length = 23
FEATURE                   Location/Qualifiers
source                    1..23
                          mol_type = other RNA
                          organism = synthetic construct
modified_base             23
                          mod_base = i
modified_base             1
```

-continued

```
                               mod_base = OTHER
                               note = thymine
SEQUENCE: 1261
tataaataga ttctgtagct tan                                         23

SEQ ID NO: 1262        moltype = RNA  length = 23
FEATURE                Location/Qualifiers
source                 1..23
                       mol_type = other RNA
                       organism = synthetic construct
modified_base          22..23
                       mod_base = i
modified_base          1
                       mod_base = OTHER
                       note = thymine
SEQUENCE: 1262
tataaataga ttctgtagct tnn                                         23

SEQ ID NO: 1263        moltype = RNA  length = 23
FEATURE                Location/Qualifiers
source                 1..23
                       mol_type = other RNA
                       organism = synthetic construct
modified_base          22
                       mod_base = i
modified_base          1
                       mod_base = OTHER
                       note = thymine
SEQUENCE: 1263
tataaataga ttctgtagct tna                                         23

SEQ ID NO: 1264        moltype = RNA  length = 23
FEATURE                Location/Qualifiers
source                 1..23
                       mol_type = other RNA
                       organism = synthetic construct
modified_base          23
                       mod_base = i
modified_base          1
                       mod_base = OTHER
                       note = thymine
modified_base          7
                       mod_base = OTHER
                       note = thymine
SEQUENCE: 1264
tataaataga ttctgtagct tan                                         23

SEQ ID NO: 1265        moltype = RNA  length = 23
FEATURE                Location/Qualifiers
source                 1..23
                       mol_type = other RNA
                       organism = synthetic construct
modified_base          22..23
                       mod_base = i
modified_base          7
                       mod_base = OTHER
                       note = thymine
modified_base          1
                       mod_base = OTHER
                       note = thymine
SEQUENCE: 1265
tataaataga ttctgtagct tnn                                         23

SEQ ID NO: 1266        moltype = RNA  length = 23
FEATURE                Location/Qualifiers
source                 1..23
                       mol_type = other RNA
                       organism = synthetic construct
modified_base          22
                       mod_base = i
modified_base          7
                       mod_base = OTHER
                       note = thymine
modified_base          1
                       mod_base = OTHER
                       note = thymine
SEQUENCE: 1266
tataaataga ttctgtagct tna                                         23
```

-continued

```
SEQ ID NO: 1267        moltype = RNA   length = 23
FEATURE                Location/Qualifiers
source                 1..23
                       mol_type = other RNA
                       organism = synthetic construct
modified_base          23
                       mod_base = i
modified_base          6
                       mod_base = OTHER
                       note = thymine
modified_base          1
                       mod_base = OTHER
                       note = thymine
SEQUENCE: 1267
ttaagtttta gtcttaatct tan                                            23

SEQ ID NO: 1268        moltype = RNA   length = 23
FEATURE                Location/Qualifiers
source                 1..23
                       mol_type = other RNA
                       organism = synthetic construct
modified_base          22..23
                       mod_base = i
modified_base          1
                       mod_base = OTHER
                       note = thymine
modified_base          6
                       mod_base = OTHER
                       note = thymine
SEQUENCE: 1268
ttaagtttta gtcttaatct tnn                                            23

SEQ ID NO: 1269        moltype = RNA   length = 23
FEATURE                Location/Qualifiers
source                 1..23
                       mol_type = other RNA
                       organism = synthetic construct
modified_base          22
                       mod_base = i
modified_base          1
                       mod_base = OTHER
                       note = thymine
modified_base          6
                       mod_base = OTHER
                       note = thymine
SEQUENCE: 1269
ttaagtttta gtcttaatct tna                                            23

SEQ ID NO: 1270        moltype = RNA   length = 23
FEATURE                Location/Qualifiers
source                 1..23
                       mol_type = other RNA
                       organism = synthetic construct
modified_base          23
                       mod_base = i
modified_base          1
                       mod_base = OTHER
                       note = thymine
modified_base          7
                       mod_base = OTHER
                       note = thymine
SEQUENCE: 1270
ttaagtttta gtcttaatct tan                                            23

SEQ ID NO: 1271        moltype = RNA   length = 23
FEATURE                Location/Qualifiers
source                 1..23
                       mol_type = other RNA
                       organism = synthetic construct
modified_base          22..23
                       mod_base = i
modified_base          1
                       mod_base = OTHER
                       note = thymine
modified_base          7
                       mod_base = OTHER
                       note = thymine
SEQUENCE: 1271
ttaagtttta gtcttaatct tnn                                            23
```

-continued

```
SEQ ID NO: 1272        moltype = RNA  length = 23
FEATURE                Location/Qualifiers
source                 1..23
                       mol_type = other RNA
                       organism = synthetic construct
modified_base          22
                       mod_base = i
modified_base          1
                       mod_base = OTHER
                       note = thymine
modified_base          7
                       mod_base = OTHER
                       note = thymine
SEQUENCE: 1272
ttaagtttta gtcttaatct tna                                           23

SEQ ID NO: 1273        moltype = RNA  length = 22
FEATURE                Location/Qualifiers
source                 1..22
                       mol_type = other RNA
                       organism = synthetic construct
modified_base          1
                       mod_base = OTHER
                       note = thymine
SEQUENCE: 1273
tttaagatga gacagaaatt ga                                            22

SEQ ID NO: 1274        moltype = RNA  length = 22
FEATURE                Location/Qualifiers
source                 1..22
                       mol_type = other RNA
                       organism = synthetic construct
modified_base          22
                       mod_base = i
modified_base          1
                       mod_base = OTHER
                       note = thymine
SEQUENCE: 1274
tttaagatga gacagaaatt gn                                            22

SEQ ID NO: 1275        moltype = RNA  length = 21
FEATURE                Location/Qualifiers
source                 1..21
                       mol_type = other RNA
                       organism = synthetic construct
modified_base          1
                       mod_base = OTHER
                       note = thymine
SEQUENCE: 1275
tttaagatga gacagaaatt g                                             21

SEQ ID NO: 1276        moltype = RNA  length = 22
FEATURE                Location/Qualifiers
source                 1..22
                       mol_type = other RNA
                       organism = synthetic construct
modified_base          1
                       mod_base = OTHER
                       note = thymine
SEQUENCE: 1276
tataaataga ttctgtagct ta                                            22

SEQ ID NO: 1277        moltype = RNA  length = 22
FEATURE                Location/Qualifiers
source                 1..22
                       mol_type = other RNA
                       organism = synthetic construct
modified_base          22
                       mod_base = i
modified_base          1
                       mod_base = OTHER
                       note = thymine
SEQUENCE: 1277
tataaataga ttctgtagct tn                                            22

SEQ ID NO: 1278        moltype = RNA  length = 21
FEATURE                Location/Qualifiers
source                 1..21
```

-continued

```
                        mol_type = other RNA
                        organism = synthetic construct
modified_base           1
                        mod_base = OTHER
                        note = thymine
SEQUENCE: 1278
tataaataga ttctgtagct t                                          21

SEQ ID NO: 1279         moltype = RNA   length = 22
FEATURE                 Location/Qualifiers
source                  1..22
                        mol_type = other RNA
                        organism = synthetic construct
modified_base           1
                        mod_base = OTHER
                        note = thymine
modified_base           7
                        mod_base = OTHER
                        note = thymine
SEQUENCE: 1279
tataaataga ttctgtagct ta                                         22

SEQ ID NO: 1280         moltype = RNA   length = 22
FEATURE                 Location/Qualifiers
source                  1..22
                        mol_type = other RNA
                        organism = synthetic construct
modified_base           22
                        mod_base = i
modified_base           1
                        mod_base = OTHER
                        note = thymine
modified_base           7
                        mod_base = OTHER
                        note = thymine
SEQUENCE: 1280
tataaataga ttctgtagct tn                                         22

SEQ ID NO: 1281         moltype = RNA   length = 21
FEATURE                 Location/Qualifiers
source                  1..21
                        mol_type = other RNA
                        organism = synthetic construct
modified_base           1
                        mod_base = OTHER
                        note = thymine
modified_base           7
                        mod_base = OTHER
                        note = thymine
SEQUENCE: 1281
tataaataga ttctgtagct t                                          21

SEQ ID NO: 1282         moltype = RNA   length = 22
FEATURE                 Location/Qualifiers
source                  1..22
                        mol_type = other RNA
                        organism = synthetic construct
modified_base           1
                        mod_base = OTHER
                        note = thymine
modified_base           6
                        mod_base = OTHER
                        note = thymine
SEQUENCE: 1282
ttaagtttta gtcttaatct ta                                         22

SEQ ID NO: 1283         moltype = RNA   length = 22
FEATURE                 Location/Qualifiers
source                  1..22
                        mol_type = other RNA
                        organism = synthetic construct
modified_base           22
                        mod_base = i
modified_base           1
                        mod_base = OTHER
                        note = thymine
modified_base           6
                        mod_base = OTHER
                        note = thymine
```

-continued

```
SEQUENCE: 1283
ttaagtttta gtcttaatct tn                                                22

SEQ ID NO: 1284      moltype = RNA   length = 21
FEATURE              Location/Qualifiers
source               1..21
                     mol_type = other RNA
                     organism = synthetic construct
modified_base        1
                     mod_base = OTHER
                     note = thymine
modified_base        6
                     mod_base = OTHER
                     note = thymine
SEQUENCE: 1284
ttaagtttta gtcttaatct t                                                 21

SEQ ID NO: 1285      moltype = RNA   length = 22
FEATURE              Location/Qualifiers
source               1..22
                     mol_type = other RNA
                     organism = synthetic construct
modified_base        1
                     mod_base = OTHER
                     note = thymine
modified_base        7
                     mod_base = OTHER
                     note = thymine
SEQUENCE: 1285
ttaagtttta gtcttaatct ta                                                22

SEQ ID NO: 1286      moltype = RNA   length = 22
FEATURE              Location/Qualifiers
source               1..22
                     mol_type = other RNA
                     organism = synthetic construct
modified_base        22
                     mod_base = i
modified_base        1
                     mod_base = OTHER
                     note = thymine
modified_base        7
                     mod_base = OTHER
                     note = thymine
SEQUENCE: 1286
ttaagtttta gtcttaatct tn                                                22

SEQ ID NO: 1287      moltype = RNA   length = 21
FEATURE              Location/Qualifiers
source               1..21
                     mol_type = other RNA
                     organism = synthetic construct
modified_base        1
                     mod_base = OTHER
                     note = thymine
modified_base        7
                     mod_base = OTHER
                     note = thymine
SEQUENCE: 1287
ttaagtttta gtcttaatct t                                                 21

SEQ ID NO: 1288      moltype = RNA   length = 21
FEATURE              Location/Qualifiers
source               1..21
                     mol_type = other RNA
                     organism = synthetic construct
SEQUENCE: 1288
aagctacaga atctatttat a                                                 21

SEQ ID NO: 1289      moltype = RNA   length = 21
FEATURE              Location/Qualifiers
source               1..21
                     mol_type = other RNA
                     organism = synthetic construct
SEQUENCE: 1289
caatttctgt ctcatcttaa a                                                 21

SEQ ID NO: 1290      moltype = RNA   length = 21
FEATURE              Location/Qualifiers
```

-continued

```
source                1..21
                      mol_type = other RNA
                      organism = synthetic construct
modified_base         20
                      mod_base = OTHER
                      note = thymine
SEQUENCE: 1290
aagctacaga atctatttat a                                               21

SEQ ID NO: 1291       moltype = AA  length = 17
FEATURE               Location/Qualifiers
source                1..17
                      mol_type = protein
                      organism = synthetic construct
SITE                  3
                      note = Trans-4-hydroxy-L-proline
SITE                  10
                      note = T-butyl-glycine
SITE                  17
                      note = Amidated 6-azido
                       lysine-6-((bicyclo[6.1.0]nonyne)-formyl-carbamate)hexyl
SITE                  1..9
                      note = Residues linked via thioether bond
SITE                  9..13
                      note = Residues linked via thioether bond
SEQUENCE: 1291
CPXDAYLGCX SYCEPWK                                                    17

SEQ ID NO: 1292       moltype = AA  length = 17
FEATURE               Location/Qualifiers
source                1..17
                      mol_type = protein
                      organism = synthetic construct
SITE                  3
                      note = Trans-4-hydroxy-L-proline
SITE                  10
                      note = T-butyl-glycine
SITE                  17
                      note = Amidated 6-azido
                       lysine-6-((bicyclo[6.1.0]nonyne)-formyl-carbamate)-2-(hydro
                       xymethyl)hexyl
SITE                  1..9
                      note = Residues linked via thioether bond
SITE                  9..13
                      note = Residues linked via thioether bond
SEQUENCE: 1292
CPXDAYLGCX SYCEPWK                                                    17

SEQ ID NO: 1293       moltype = AA  length = 17
FEATURE               Location/Qualifiers
source                1..17
                      mol_type = protein
                      organism = synthetic construct
SITE                  3
                      note = Trans-4-hydroxy-L-proline
SITE                  10
                      note = T-butyl-glycine
SITE                  17
                      note = Amidated 6-azido lysine attached to another sequence
                       via 6-((bicyclo[6.1.0]nonyne)-formyl-carbamate)hexyl
SITE                  1..9
                      note = Residues linked via thioether bond
SITE                  9..13
                      note = Residues linked via thioether bond
SEQUENCE: 1293
CPXDAYLGCX SYCEPWK                                                    17

SEQ ID NO: 1294       moltype = AA  length = 17
FEATURE               Location/Qualifiers
source                1..17
                      mol_type = protein
                      organism = synthetic construct
SITE                  3
                      note = Trans-4-hydroxy-L-proline
SITE                  10
                      note = T-butyl-glycine
SITE                  17
                      note = Amidated 6-azido lysine attached to another sequence
                       via 6-((bicyclo[6.1.0]nonyne)-formyl-carbamate)hexyl
```

-continued

```
SITE                     1..9
                         note = Residues linked via thioether bond
SITE                     9..13
                         note = Residues linked via thioether bond
SEQUENCE: 1294
CPXDAYLGCX SYCEPWK                                                        17

SEQ ID NO: 1295          moltype = AA  length = 17
FEATURE                  Location/Qualifiers
source                   1..17
                         mol_type = protein
                         organism = synthetic construct
SITE                     3
                         note = Trans-4-hydroxy-L-proline
SITE                     10
                         note = T-butyl-glycine
SITE                     17
                         note = Amidated 6-azido lysine attached to another sequence
                          via 6-((bicyclo[6.1.0]nonyne)-formyl-carbamate)hexyl
SITE                     1..9
                         note = Residues linked via thioether bond
SITE                     9..13
                         note = Residues linked via thioether bond
SEQUENCE: 1295
CPXDAYLGCX SYCEPWK                                                        17

SEQ ID NO: 1296          moltype = AA  length = 17
FEATURE                  Location/Qualifiers
source                   1..17
                         mol_type = protein
                         organism = synthetic construct
SITE                     3
                         note = Trans-4-hydroxy-L-proline
SITE                     10
                         note = T-butyl-glycine
SITE                     17
                         note = Amidated 6-azido lysine attached to another sequence
                          via 6-((bicyclo[6.1.0]nonyne)-formyl-carbamate)hexyl
SITE                     1..9
                         note = Residues linked via thioether bond
SITE                     9..13
                         note = Residues linked via thioether bond
SEQUENCE: 1296
CPXDAYLGCX SYCEPWK                                                        17

SEQ ID NO: 1297          moltype = AA  length = 17
FEATURE                  Location/Qualifiers
source                   1..17
                         mol_type = protein
                         organism = synthetic construct
SITE                     3
                         note = Trans-4-hydroxy-L-proline
SITE                     10
                         note = T-butyl-glycine
SITE                     17
                         note = Amidated 6-azido lysine attached to another sequence
                          via 6-((bicyclo[6.1.0]nonyne)-formyl-carbamate)hexyl
SITE                     1..9
                         note = Residues linked via thioether bond
SITE                     9..13
                         note = Residues linked via thioether bond
SEQUENCE: 1297
CPXDAYLGCX SYCEPWK                                                        17

SEQ ID NO: 1298          moltype = AA  length = 17
FEATURE                  Location/Qualifiers
source                   1..17
                         mol_type = protein
                         organism = synthetic construct
SITE                     3
                         note = Trans-4-hydroxy-L-proline
SITE                     10
                         note = T-butyl-glycine
SITE                     17
                         note = Amidated 6-azido lysine attached to another sequence
                          via 6-((bicyclo[6.1.0]nonyne)-formyl-carbamate)hexyl
SITE                     1..9
                         note = Residues linked via thioether bond
SITE                     9..13
```

```
                                    note = Residues linked via thioether bond
SEQUENCE: 1298
CPXDAYLGCX SYCEPWK                                                                  17

SEQ ID NO: 1299          moltype = AA  length = 17
FEATURE                  Location/Qualifiers
source                   1..17
                         mol_type = protein
                         organism = synthetic construct
SITE                     3
                         note = Trans-4-hydroxy-L-proline
SITE                     10
                         note = T-butyl-glycine
SITE                     17
                         note = Amidated 6-azido
                           lysine-6-((bicyclo[6.1.0]nonyne)-formyl-carbamate)hexyl
SITE                     1..9
                         note = Residues linked via thioether bond
SITE                     9..13
                         note = Residues linked via thioether bond
SEQUENCE: 1299
CPXDAYLGCX SYCEPWK                                                                  17

SEQ ID NO: 1300          moltype = AA  length = 17
FEATURE                  Location/Qualifiers
source                   1..17
                         mol_type = protein
                         organism = synthetic construct
SITE                     3
                         note = Trans-4-hydroxy-L-proline
SITE                     10
                         note = T-butyl-glycine
SITE                     17
                         note = Amidated 6-azido
                           lysine-6-((bicyclo[6.1.0]nonyne)-formyl-carbamate)hexyl
SITE                     1..9
                         note = Residues linked via thioether bond
SITE                     9..13
                         note = Residues linked via thioether bond
SEQUENCE: 1300
CPXDAYLGCX SYCEPWK                                                                  17

SEQ ID NO: 1301          moltype = AA  length = 17
FEATURE                  Location/Qualifiers
source                   1..17
                         mol_type = protein
                         organism = synthetic construct
SITE                     3
                         note = Trans-4-hydroxy-L-proline
SITE                     10
                         note = T-butyl-glycine
SITE                     17
                         note = Amidated 6-azido
                           lysine-6-((bicyclo[6.1.0]nonyne)-formyl-carbamate)hexyl
SITE                     1..9
                         note = Residues linked via thioether bond
SITE                     9..13
                         note = Residues linked via thioether bond
SEQUENCE: 1301
CPXDAYLGCX SYCEPWK                                                                  17

SEQ ID NO: 1302          moltype = AA  length = 17
FEATURE                  Location/Qualifiers
source                   1..17
                         mol_type = protein
                         organism = synthetic construct
SITE                     3
                         note = Trans-4-hydroxy-L-proline
```

-continued

```
SITE                    10
                        note = T-butyl-glycine
SITE                    17
                        note = Amidated 6-azido
                         lysine-6-((bicyclo[6.1.0]nonyne)-formyl-carbamate)hexyl
SITE                    1..9
                        note = Residues linked via thioether bond
SITE                    9..13
                        note = Residues linked via thioether bond
SEQUENCE: 1302
CPXDAYLGCX SYCEPWK                                                               17

SEQ ID NO: 1303         moltype = AA  length = 17
FEATURE                 Location/Qualifiers
source                  1..17
                        mol_type = protein
                        organism = synthetic construct
SITE                    3
                        note = Trans-4-hydroxy-L-proline
SITE                    10
                        note = T-butyl-glycine
SITE                    17
                        note = Amidated 6-azido
                         lysine-6-((bicyclo[6.1.0]nonyne)-formyl-carbamate)hexyl
SITE                    1..9
                        note = Residues linked via thioether bond
SITE                    9..13
                        note = Residues linked via thioether bond
SEQUENCE: 1303
CPXDAYLGCX SYCEPWK                                                               17

SEQ ID NO: 1304         moltype = AA  length = 17
FEATURE                 Location/Qualifiers
source                  1..17
                        mol_type = protein
                        organism = synthetic construct
SITE                    3
                        note = Trans-4-hydroxy-L-proline
SITE                    10
                        note = T-butyl-glycine
SITE                    17
                        note = Amidated 6-azido
                         lysine-6-((bicyclo[6.1.0]nonyne)-formyl-carbamate)hexyl
SITE                    1..9
                        note = Residues linked via thioether bond
SITE                    9..13
                        note = Residues linked via thioether bond
SEQUENCE: 1304
CPXDAYLGCX SYCEPWK                                                               17

SEQ ID NO: 1305         moltype = AA  length = 17
FEATURE                 Location/Qualifiers
source                  1..17
                        mol_type = protein
                        organism = synthetic construct
SITE                    3
                        note = Trans-4-hydroxy-L-proline
SITE                    10
```

-continued

```
                    note = T-butyl-glycine
SITE                17
                    note = Amidated 6-azido
                     lysine-6-((bicyclo[6.1.0]nonyne)-formyl-carbamate)hexyl
SITE                1..9
                    note = Residues linked via thioether bond
SITE                9..13
                    note = Residues linked via thioether bond
SEQUENCE: 1305
CPXDAYLGCX SYCEPWK                                                  17
```

COMPOUNDS AND METHODS FOR REDUCING PLN EXPRESSION

CROSS-REFERENCE TO RELATED PATENT APPLICATIONS

This specification claims the benefit of priority to U.S. patent application Ser. No. 18/626,889 (filed 4 Apr. 2024), U.S. Provisional Patent Application No. 63/494,415 (filed 5 Apr. 2023), U.S. Provisional Patent Application No. 63/508, 453 (filed 15 Jun. 2023) and U.S. Provisional Patent Application No. 63/561,700 (filed 5 Mar. 2024). The entire text of the above-referenced patent applications is incorporated by reference into this specification.

SEQUENCE LISTING

The present application is being filed concurrently with a Sequence Listing in electronic format. The Sequence Listing is provided as a file entitled 201366-US01-NP-CON-_SL.xml, created on Nov. 24, 2025, which is 1,598,369 bytes in size. The contents of the electronic format of the sequence listing are incorporated herein by reference in their entirety.

FIELD

The present invention relates to compounds, compositions, and uses therefor, including methods for decreasing the levels of PLN expression, PLN RNA, and/or the levels (and/or activity) of phospholamban protein, as well as to methods for preventing, treating, and/or ameliorating at least one symptom of, a cardiac disease, disorder or condition, such as, for example, cardiomyopathy, heart failure, or arrhythmia.

BACKGROUND

Heart pumping action, which forces blood throughout the body, is generated by the repetitive contraction of cardiac muscle (i.e., myocardium). The rhythmic contraction process of cardiac muscle is regulated by changes in cytosolic calcium ion concentration in cardiac muscle cells (referred to as cardiomyocytes). Increases in cytosolic calcium ion concentration are associated with myocardial contraction (during systole), whereas decreases in cytosolic calcium ion concentration are associated with heart muscle relaxation (during diastole). The sarcoplasmic reticulum, a membranous intracellular tubular structure within cardiac and skeletal muscle cells, is responsible for contractile calcium handling (i.e., uptake and storage of calcium ions from the cytosol during relaxation and release of sequestered calcium ions into the cytosol for muscle contraction); and is associated with multiple proteins that facilitate and regulate its uptake and release of calcium ions. One such protein is sarco(endo) plasmic reticulum calcium ATPase (SERCA), which functions to pump cytosolic calcium into the sarcoplasmic reticulum during relaxation of cardiac muscle. SERCA is regulated by phospholamban (encoded by PLN), a phosphoprotein which inhibits SERCA activity in its dephosphorylated state by decreasing affinity of SERCA for calcium ions. This in turn attenuates filling the sarcoplasmic reticulum calcium store and diminishes contractile force development. Phospholamban phosphorylation reverses its inhibition of SERCA.

Heart failure, a condition wherein the heart is not able to provide sufficient blood flow to the body, is a leading cause of death worldwide. Heart failure can be chronic, developing gradually over time, or acute, which is a more sudden, rapid decline in heart functioning. Heart failure may be caused by conditions that damage, weaken and/or overwork the heart, including cardiomyopathy. Cardiomyopathy refers to heart muscle diseases, disorders and conditions that weaken the heart, eventually resulting in inability to pump effectively. As the heart weakens, normal heart muscle can thicken, stiffen, or thin out, impairing its ability to pump blood which can lead to heart failure.

Arrhythmia is an irregular or abnormal heartbeat and the leading cause of sudden cardiac deaths. Arrhythmia originating in the ventricles (lower chambers of the heart) is particularly dangerous and cause the heart to beat too fast, which impairs blood circulation and can result in cardiac arrest. Ventricular fibrillation (vfib) is a rapid uncoordinated heart rhythm in which the heart's electrical signals often lack a normal and repetitive pattern. Ventricular tachycardia (vtac) is a rapid heart rhythm, which if too fast, can prevent the heart from effectively beating or pumping blood to the entire body and cause loss of consciousness.

Effective management of intracellular calcium is a significant factor in regulation of contractile force in cardiac muscle. Symptoms of heart failure include reduced contractile function, which can appear as blunted, slowed, dysynchronous contraction, and impaired relaxation of the heart. Aberrant calcium cycling and defective intracellular calcium ion homeostasis within cardiac muscle cells are associated with contractile dysfunction and arrhythmias in failing myocardium. There remains a need for therapies targeting cardiac dysfunction in heart failure and conditions associated with heart failure. Therapeutics targeting cardiac calcium regulation may provide a new class of compounds for effective management of contractile function and therapy for subjects at risk of cardiomyopathy and heart failure.

SUMMARY

Provided herein are compounds, pharmaceutical compositions, and methods of use for reducing the amount or activity of PLN RNA, and in certain embodiments reducing the expression of phospholamban in a cell or subject. In certain embodiments, the subject has a disease or disorder associated with cardiac calcium regulation, regulation of contractile force of cardiac muscle or a mutation in PLN. In certain embodiments, the subject has a cardiomyopathy. In certain embodiments, the subject has cardiac arrythmia. In certain embodiments, the subject has heart failure. In certain embodiments, compounds useful for reducing the amount or activity of PLN RNA are oligomeric compounds, oligomeric duplexes, antisense compounds. RNAi agents. In certain embodiments, compounds useful for decreasing expression of phospholamban are oligomeric compounds, oligomeric duplexes, antisense compounds, and RNAi agents.

Also provided are methods useful for ameliorating at least one symptom of a cardiac disorder or cardiac injury. In certain embodiments the disorder is cardiomyopathy. In certain embodiments, the disorder is arrythmia. In certain embodiments the injury is heart failure. In certain embodiments, the symptom is selected from pain, hypokalemia, heart palpitations (e.g., irregular tempo, fast heartbeat, forceful heartbeat, or fluttering), chest pain, fatigue, shortness of breath, weakness, lightheadedness, dizziness, fainting episode(s), nausea, confusion, intolerance to exertion, blood clots, or a combination thereof.

Provided are modified oligonucleotides and compounds and compositions comprising them, including, but not limited to, antisense compounds, oligomeric compounds, oligomeric duplexes and pharmaceutical compositions comprising modified oligonucleotides. In certain embodiments, a modified oligonucleotide provided herein comprises a nucleobase sequence at least 80% complementary to an equal length portion of a PLN nucleic acid. In certain embodiments, the modified oligonucleotide consists of 12 to 35, 14 to 30, 15 to 28, 16 to 25, or 18 to 23 linked nucleosides targeting PLN nucleic acid. In certain embodiments, a modified oligonucleotide provided herein comprises a sequence of nucleobases complementary to an equal length portion of the nucleobase sequence of SEQ ID NO: 1 and/or SEQ ID NO:2.

In certain embodiments, a modified oligonucleotide provided herein comprises at least one modified sugar moiety and/or at least one modified internucleoside linkage. Modified oligonucleotides and compositions comprising them, including, but not limited to, oligomeric compounds, oligomeric duplexes, antisense compounds and pharmaceutical compositions, described herein are useful for reducing or inhibiting PLN expression in a cell, organ, tissue, system, organism or animal.

Additionally provided herein are methods for reducing or inhibiting PLN expression. PLN RNA levels and/or phospholamban protein levels and/or activity in a cell or organism, including, for example, an animal. In certain embodiments, the methods include contacting a cell or subject with a composition provided herein, comprising a modified oligonucleotide, oligomeric compound, and/or oligomeric duplex. In certain embodiments, the subject is a human who has or is at risk of having a disease, disorder, condition or injury associated with cardiac calcium regulation, regulation of contractile force of cardiac muscle or a mutation in PLN. In particular embodiments, the subject is a human who has or is at risk of having heart failure. In certain particular embodiments, the subject is a human who has or is at risk of having arrythmia and/or cardiomyopathy, including, for example, dilated, hypertrophic, arrhythmogenic or restrictive cardiomyopathy.

Also provided herein are methods of preventing, treating, slowing the development or progression of, or ameliorating a disease, disorder, condition or injury associated with cardiac calcium regulation, regulation of contractile force of cardiac muscle or a mutation in PLN. In certain embodiments, methods provided herein include methods of preventing, treating, slowing the development or progression of, or ameliorating cardiomyopathy, heart failure, and/or arrhythmia. In some embodiments, methods provided herein for preventing, treating, slowing the development or progression of, or ameliorating a disease, disorder, condition or injury associated with cardiac calcium regulation, regulation of contractile force of cardiac muscle or a mutation in PLN, e.g., cardiomyopathy, heart failure, and/or arrhythmia, comprise administering to a subject, e.g., a human subject, having or at risk of having a disease, disorder, condition or injury associated with cardiac calcium regulation, regulation of contractile force of cardiac muscle or a mutation in PLN, e.g., cardiomyopathy, heart failure, and/or arrhythmia, a composition provided herein, e.g., a modified oligonucleotide, oligomeric compound, oligomeric duplex or pharmaceutical composition provided herein. Also provided herein are methods of preventing, treating, ameliorating, delaying the onset of, or reducing frequency of at least one symptom of cardiomyopathy, arrhythmia, and/or heart failure. Symptoms of cardiomyopathy, arrhythmia and/or heart failure include, but are not limited to, shortness of breath, trouble breathing, fatigue, swelling in the ankles, legs or feet, cough, irregular heart beat, heart palpitations, dizziness, lightheadedness, syncope, weakness, reduced ability to exercise and abdominal bloating. In some embodiments, methods provided herein for preventing, treating, ameliorating, delaying the onset of, or reducing frequency of at least one symptom of cardiomyopathy, arrhythmia and/or heart failure include administering to a subject, e.g., a human subject, having or at risk of having the at least one symptom, a composition provided herein, e.g., a modified oligonucleotide, oligomeric compound, oligomeric duplex or pharmaceutical composition provided herein.

DETAILED DESCRIPTION

Figure 1A:
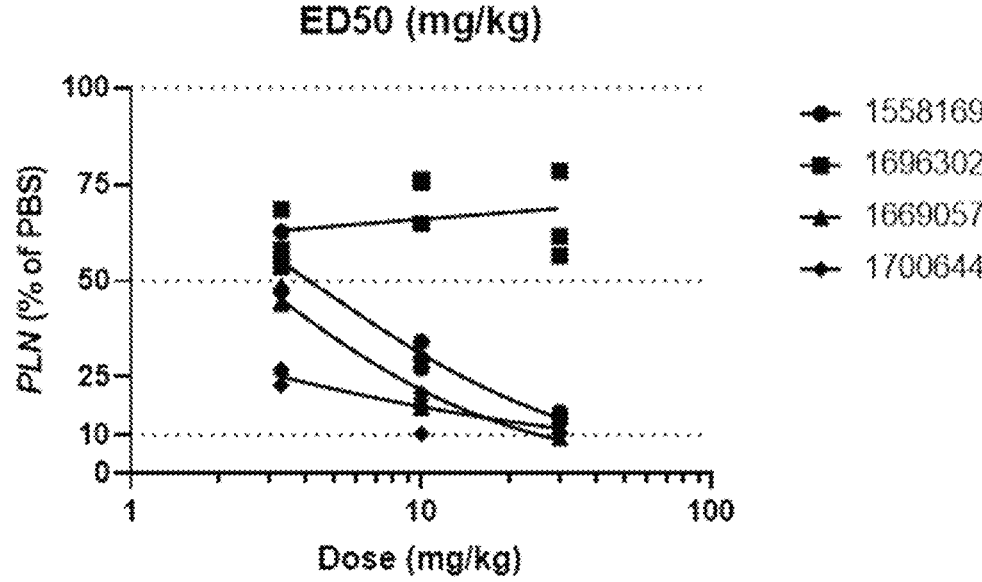
FIGS. 1A-1B depict experimental results from studies described in Example 6 showing potency of 5'-C16, 3-C16, 5'-BCY17901, or 3-BCY17901 conjugated modified oligonucleotides and oligomeric duplexes targeting human PLN.

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

Section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

The following definitions are provided, along with additional definitions throughout the specification, for a complete understanding of the instant invention. Unless specific definitions are provided herein, nomenclature used in connection with, and procedures and techniques of, analytical chemistry, synthetic organic chemistry, and medicinal and pharmaceutical chemistry described herein are those well-known and commonly used in the art. Unless otherwise indicated, certain terms have the following meanings:

As used herein, "2'-deoxynucleoside" means a nucleoside comprising a 2'-deoxy sugar moiety. Unless otherwise indicated, a 2'-deoxynucleoside is a 2'-β-D-deoxynucleoside which comprises a 2'-β-D-deoxyribosyl sugar moiety, which has the β-D ribosyl configuration as found in naturally occurring deoxyribonucleic acid (DNA).

As used herein, "2'-deoxy sugar moiety" means a 2-H(H) deoxyribosyl sugar moiety. Unless otherwise indicated, a 2'-deoxy sugar moiety is a 2-β-D-deoxyribosyl sugar moiety, which has the β-D ribosyl configuration as found in naturally occurring deoxyribonucleic acids (DNA). Herein, in the context of an oligomeric compound comprising a ribonucleic acid oligonucleotide (e.g., an siRNA), a 2'-deoxy sugar moiety is considered e.g., a modified sugar moiety.

As used herein, "2'-MOE" means a 2'-OCH$_2$CH$_2$OCH$_3$ group in place of the 2'-OH group of a ribosyl sugar moiety. A "2'-MOE sugar moiety" means a sugar moiety with a 2'-OCH$_2$CH$_2$OCH$_3$ group in place of the 2'-OH group of a ribosyl sugar moiety. Unless otherwise indicated, a 2'-MOE sugar moiety is in the β-D-ribosyl configuration. "MOE" means O-methoxyethyl.

As used herein, "2'-MOE nucleoside" or "2'-O(CH$_2$)$_2$OCH$_3$ nucleoside" means a nucleoside comprising a 2'-MOE sugar moiety (or 2'-OCH$_2$CH$_2$OCH$_3$ ribosyl sugar moiety).

As used herein, "2'-OMe" means a 2'-OCH$_3$ group in place of the 2'-OH group of a ribosyl sugar moiety. A "2'-OMe sugar moiety" or "2'-O-methyl sugar moiety" means a sugar moiety with a 2'-OCH$_3$ group in place of the 2'-OH group of a ribosyl sugar moiety. Unless otherwise indicated, a 2'-OMe has the β-D-ribosyl stereochemical configuration.

As used herein, "2'-OMe nucleoside" means a nucleoside comprising a 2'-OMe sugar moiety. As used herein, "2'-F" means a 2'-fluoro group in place of the 2'-OH group of a furanosyl sugar moiety. A "2'-F sugar moiety" (i.e., a "2'-fluoro sugar moiety") means a sugar moiety with a 2'-F (i.e., a 2'-fluoro) group in place of the 2'-OH group of a furanosyl sugar moiety. Unless otherwise indicated, a 2'-F sugar moiety is in the β-D-ribosyl configuration.

As used herein, "2'-F nucleoside" means a nucleoside comprising a 2-F sugar moiety.

As used herein, "2'-substituted nucleoside" means a nucleoside comprising a 2-substituted furanosyl sugar moiety. As used herein, "2'-substituted" in reference to a sugar moiety means a sugar moiety wherein at least one 2'-substituent group is other than H. Examples of 2'-substituted modified sugar moieties include sugar moieties comprising a 2'-substituent group independently selected from 2'-F, 2'-MOE, 2'-OMe, and cEt.

As used herein, "5-methylcytosine" means a cytosine modified with a methyl group attached at the 5 position. A 5-methylcytosine is a modified nucleobase.

As used herein, "abasic sugar moiety" means a sugar moiety of a nucleoside that is not attached to a nucleobase. Such abasic sugar moieties are sometimes referred to in the art as "abasic nucleosides."

As used herein, "ameliorate" means improvement in or lessening of at least one symptom of an associated disease, disorder or condition. In certain embodiments, amelioration is reduction in severity or frequency of a symptom or the delayed onset or slowing of progression in the severity or frequency of a symptom. Progression, frequency, or severity indicators may be determined by subjective or objective measures known in the art and/or described herein.

As used herein, "antisense activity" means any detectable and/or measurable change attributable (whether directly and/or indirectly) to hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound. In certain embodiments, compounds have antisense activity when they reduce or inhibit the amount or activity of a target nucleic acid by 25% or more in an in vitro assay. In certain embodiments, compounds have antisense activity when they reduce or inhibit the amount or activity of a target nucleic acid by 25% or more in an in vivo assay. In certain embodiments antisense activity is assessed in a standard assay.

As used herein, "antisense compound" means an antisense oligonucleotide and optionally one or more additional features, e.g., a paired oligonucleotide, a conjugate group and/or a terminal group. As used herein, "antisense oligonucleotide" means an oligonucleotide that is capable of hybridizing to a target nucleic acid and is capable of at least one antisense activity. In certain embodiments, antisense compounds selectively affect one or more target nucleic acid. In certain embodiments, an antisense compound is a modified oligonucleotide provided herein that is capable of hybridizing to a target nucleic acid and is capable of at least one antisense activity. An antisense oligonucleotide may be paired with a second oligonucleotide (herein, a "sense oligonucleotide") that is complementary to the antisense oligonucleotide (that is capable of hybridizing to an anti-sense oligonucleotide to form a double-stranded antisense oligonucleotide, a duplex antisense oligonucleotide), may be an unpaired antisense oligonucleotide (a singled-stranded antisense oligonucleotide) or may be a "hairpin" oligonucleotide that has at least one region that is self-complementary. As used herein, "sense compound" means a sense oligonucleotide and optionally one or more additional features, e.g., a conjugate group.

As used herein, "bicyclic nucleoside" means a nucleoside comprising a bicyclic sugar moiety.

As used herein, "bicyclic sugar" or "bicyclic sugar moiety" means a modified sugar moiety comprising two rings, wherein the second ring is formed via a bridge connecting two of the atoms in the first ring thereby forming a bicyclic structure, wherein the first ring of the bicyclic sugar moiety is a furanosyl ring. Examples of bicyclic sugar moieties include LNA (locked nucleic acid) sugar moiety and cEt sugar moiety as defined herein.

As used herein. "blunt" or "blunt ended" in reference to an oligomeric duplex means that there are no terminal unpaired nucleotides (i.e., no overhanging nucleotides). One or both ends of an oligomeric duplex can be blunt.

As used herein. "cell-targeting moiety" means a conjugate group or portion of a conjugate group that is capable of binding to a particular cell type or particular cell types. In certain embodiments, a cell-targeting moiety binds to a surface moiety, such as a surface receptor on a particular cell type.

As used herein. "cleavable moiety" means a bond or group of atoms that is cleaved under physiological conditions, e.g., in a cell and/or upon administration to a subject.

As used herein. "complementary" in reference to an oligonucleotide or portion thereof means that at least 70% of the nucleobases of such oligonucleotide or portion thereof and the nucleobases of another nucleic acid or portion thereof are capable of hydrogen bonding with one another when the nucleobase sequence of the oligonucleotide and the other nucleic acid are aligned in opposing directions. As used herein. "complementary nucleobases" means nucleobases that are capable of forming hydrogen bonds with one another. Complementary nucleobase pairs include adenine (A) and thymine (T); adenine (A) and uracil (U); cytosine (C) and guanine (G); and 5-methylcytosine ($^mC$) and guanine (G). Certain modified nucleobases that pair with unmodified nucleobases or with other modified nucleobases are known in the art. For example, hypoxanthine (I), the nucleobase of the nucleoside inosine, can pair with adenine, cytosine, thymine, or uracil. Herein, hypoxanthine (I) is considered a complementary nucleobase to thymine (T), adenine (A), uracil (U), and cytosine (C). Complementary oligonucleotides and/or nucleic acids need not have nucleobase complementarity at each nucleoside. Rather, some mismatches are tolerated. As used herein. "fully complementary" or "100% complementary" in reference to an oligonucleotide, or a portion thereof, means that the oligonucleotide, or portion thereof, is complementary to another oligonucleotide or nucleic acid at each nucleobase of the shorter of the two oligonucleotides, or at each nucleoside if the oligonucleotides are the same length.

As used herein. "complementary region" in reference to an oligonucleotide or portion thereof is a range of nucleobases of the oligonucleotide that is complementary to a nucleobase sequence of an equal-length region of a second oligonucleotide or region thereof (e.g., an oligonucleotide and a target nucleic acid, or an antisense oligonucleotide and a sense oligonucleotide), or to a nucleobase sequence of an equal-length region within a second region of the oligonucleotide (e.g., in a "hairpin oligonucleotide"). A complementary region of an oligonucleotide may be a portion of an oligonucleotide or may include the entire oligonucleotide or may include substantially all of the oligonucleotide.

As used herein. "constrained ethyl" or "cEt" or "cEt sugar moiety" means a β-D ribosyl bicyclic sugar moiety wherein the second ring of the bicyclic sugar is formed via a bridge connecting the 4"-carbon and the 2'-carbon of the β-D ribosyl sugar moiety, wherein the bridge has the formula 4'-CH(CH$_3$)—O-2', and wherein the methyl group of the bridge is in the S' configuration.

As used herein. "cEt nucleoside" means a nucleoside comprising a cEt sugar moiety.

As used herein. "hybridization" means the process of two complementary nucleic acid sequences (e.g., oligonucleotides, nucleic acids) annealing or bonding together to form a duplex or double stranded region or molecule. While not limited to a particular mechanism, the most common mechanism of hybridization involves hydrogen bonding, which may be Watson-Crick. Hoogsteen or reversed Hoogsteen hydrogen bonding, between complementary nucleobases. In certain embodiments, complementary nucleic acid sequences in separate molecules include, but are not limited to, an antisense compound and a nucleic acid target. In certain embodiments, complementary nucleic acid sequences in separate molecules include, but are not limited to, an oligonucleotide of the invention and a nucleic acid target. In certain embodiments, complementary nucleic acid sequences in separate molecules include, but are not limited to, an antisense compound and a sense compound. In certain embodiments, complementary nucleic acid sequences in a same molecule includes, but is not limited to, an oligomeric compound comprising oligonucleotides of the invention (e.g., a hairpin oligo).

As used herein. "internucleoside linkage" is the covalent linkage between adjacent nucleosides in an oligonucleotide. As used herein "modified internucleoside linkage" means any internucleoside linkage other than a phosphodiester internucleoside linkage. A "phosphorothioate internucleoside linkage" is a modified internucleoside linkage in which one of the non-bridging oxygen atoms of a phosphodiester internucleoside linkage is replaced with a sulfur atom.

As used herein. "inverted nucleoside" means a nucleoside having a 3' to 3' and/or 5' to 5' internucleoside linkage, as shown herein. As used herein. "inverted sugar moiety" means the sugar moiety of an inverted nucleoside or an abasic sugar moiety having a 3' to 3' and/or 5' to 5' internucleoside linkage.

As used herein. "linked nucleosides" are nucleosides that are connected in a contiguous sequence (i.e., nucleosides immediately adjacent to one another, no additional nucleosides are presented between those that are linked).

As used herein. "linker-nucleoside" means a nucleoside that links, either directly or indirectly, an oligonucleotide to a conjugate moiety. When present in a compound, linker-nucleosides are located within the conjugate linker of a compound of the invention. Linker-nucleosides are not considered part of the oligonucleotide portion of a compound even if they are contiguous with the oligonucleotide.

As used herein. "mismatch" or "non-complementary" means a nucleobase of a first nucleic acid sequence that is not complementary with the corresponding nucleobase of a second nucleic acid sequence when the first and second nucleic acid sequences are aligned in opposing directions.

As used herein, "modified nucleoside" means a nucleoside comprising a modified nucleobase and/or a modified sugar moiety. Modified nucleosides include abasic nucleosides.

As used herein. "modified sugar moiety" means a furanosyl sugar moiety of a nucleoside other than β-D-ribosyl sugar moiety (the sugar moiety of unmodified RNA).

As used herein. "motif" means the pattern of unmodified and/or modified sugar moieties, nucleobases, and/or internucleoside linkages, in an oligonucleotide.

As used herein. "non-bicyclic modified sugar moiety" means a modified sugar moiety that comprises a modification, such as a substituent, that does not form a bridge between two atoms of the sugar to form a second ring.

As used herein. "nucleobase" means an unmodified nucleobase or a modified nucleobase. As used herein an "unmodified nucleobase" is unmodified adenine (A), unmodified thymine (T), unmodified cytosine (C), unmodified uracil (U), or unmodified guanine (G). As used herein, a "modified nucleobase" is a group of atoms other than unmodified A, T, C, U, or G capable of pairing with at least one unmodified nucleobase. A 5-methylcytosine and hypoxanthine are modified nucleobases.

As used herein. "the nucleobase sequence of" a reference SEQ ID NO, refers only to the nucleobase sequence provided in such SEQ ID NO and therefore, unless otherwise indicated, includes compounds wherein each sugar moiety and each internucleoside linkage, independently, is modified or unmodified, irrespective of the presence or absence of modifications, indicated in the referenced SEQ ID NO.

As used herein. "nucleobase sequence" means the order of contiguous nucleobases in a nucleic acid or oligonucleotide independent of any sugar or internucleoside linkage modification.

As used herein. "nucleoside overhang" or "overhang" refers to unpaired nucleosides at either or both ends of an oligomeric duplex formed by hybridization of two nucleotide sequences.

As used herein. "nucleoside" means a compound or fragment of a compound comprising a nucleobase and a sugar moiety. The nucleobase and the sugar moiety of each nucleoside are each, independently, unmodified or modified. Notwithstanding the foregoing and as described herein, a modified nucleoside includes abasic nucleosides.

As used herein. "oligomeric compound" means an oligonucleotide and optionally one or more additional features, e.g., a conjugate group or terminal group. A "singled-stranded oligomeric compound" is an unpaired oligomeric compound. A "double-stranded oligomeric compound" is a paired oligomeric compound which may be formed by a single oligonucleotide of an oligomeric compound forming a hairpin structure resulting in at least a region of double strand oligonucleotide sequence; or by two oligonucleotides, each of a separate oligomeric compound, either or both of which optionally include additional features, and wherein the oligonucleotide sequences, or portions thereof, pair to form a double strand, an oligomeric duplex. The term "oligomeric duplex" means a duplex formed by two oligomeric compounds, at least a portion of which are complementary to and hybridize to each other. Each oligomeric compound of an oligomeric duplex may be referred to as a "duplexed oligomeric compound."

As used herein. "oligonucleotide" means a strand of linked nucleosides connected via internucleoside linkages, wherein each nucleoside and/or each internucleoside linkage may be independently modified or unmodified. Unless otherwise indicated, oligonucleotides consist of 12-50 linked nucleosides. As used herein. "modified oligonucleotide" means an oligonucleotide comprising one or more modified nucleosides and/or having one or more modified internucleoside linkages. As used herein. "unmodified oligonucleotide" means an oligonucleotide that does not comprise any nucleoside modifications or internucleoside linkage modifications. An oligonucleotide may be paired with a second oligonucleotide that is complementary to the oligonucleotide or it may be unpaired. As used herein. "single-stranded" means a nucleic acid (including but not limited to an oligonucleotide) that is unpaired and is not part of a duplex. Single-stranded nucleic acids (e.g., oligonucleotides) are capable of hybridizing with complementary nucleic acids to form duplexes, at which point they are no longer single-stranded. As used herein. "duplex" means a structure formed by two separate nucleic acid molecules or portions thereof (e.g., two separate oligonucleotides), at least a portion of which are complementary and that are hybridized to one another, but are not covalently bonded to one another. As used herein. "double-stranded" refers to a region of hybridized oligonucleotide(s). A double-stranded oligonucleotide means either two separate oligonucleotides that are hybridized to one another (a duplex) or a single molecule (e.g., oligonucleotide) that has folded onto itself (e.g., a hairpin structure). In certain embodiments, such double-strand results from hybridization of an oligonucleotide (or portion thereof) to a target region of a transcript. In certain embodiments, a double-strand results from hybridization of two oligonucleotides (or portions thereof) to one another. In certain embodiments, the hybridized regions are portions (including the entirety) of two separate molecules (e.g., no covalent bond connects the two complementary strands together). In certain embodiments, the hybridized regions are portions of the same molecule that have hybridized (e.g., a hairpin structure).

As used herein "pharmaceutical composition" means a mixture of substances suitable for administering to a subject. For example, a pharmaceutical composition may comprise a compound of the invention (e.g., an oligomeric compound, modified oligonucleotide, oligomeric duplex, or antisense compound) and a sterile aqueous solution. In certain embodiments, a pharmaceutical composition shows activity in certain cell lines. As used herein. "pharmaceutically acceptable carrier or diluent" means an ingredient in a pharmaceutical composition suitable for use in administering to a subject. Typically, a "carrier" or "diluent" lacks pharmacological activity, but is necessary or desirable in preparing a pharmaceutical composition. For example, a diluent in an injected composition can be a liquid, e.g., PBS, or saline solution. Certain carriers or diluents enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water, sterile saline, sterile buffer solution or sterile artificial cerebrospinal fluid.

As used herein. "reduced fluorine content" with respect to a contiguous sequence of linked nucleosides, for example, an oligonucleotide (including, for example an antisense oligonucleotide and a sense oligonucleotide) refers to a contiguous linked sequence of nucleosides in which fewer than 51% of the nucleosides contain a sugar moiety or sugar surrogate that includes a fluorine atom, e.g., a 2'-fluoro sugar moiety or a fluoro hexitol (3'-FHNA) sugar moiety. In certain embodiments, no more than 42%, no more than 40%, no more than 35%, no more than 30%, no more than 25%, no more than 20%, no more than 16%, no more than 15%, no more than 14%, no more than 13%, no more than 12%, no more than 10%, no more than 9%, or no more than 5% of the nucleosides in the contiguous linked sequence of nucleosides contain a sugar moiety containing a fluorine atom. In certain embodiments, none of the nucleosides in the contiguous linked sequence of nucleosides contain a sugar moiety containing a fluorine atom. In some embodiments, fewer than 48%, fewer than 45%, fewer than 42%, fewer than 40%, fewer than 35%, fewer than 30%, fewer than 25%, fewer than 20%, fewer than 15%, fewer than 14%, fewer than 13%, fewer than 12%, fewer than 10%, or fewer than 5%, of the nucleosides in the contiguous linked sequence of nucleosides contain a sugar moiety containing a fluorine atom. "Reduced fluorine content" when referring to the total fluorine content of a double-stranded or duplex nucleic acid refers to a double-stranded or duplex nucleic acid in which fewer than 50% of the total nucleosides (i.e., all the nucleosides contained in both strands) of the nucleic acid contain a sugar moiety containing a fluorine atom. In certain embodiments, no more than 45%, no more than 42%, no more than 40%, no more than 35%, no more than 30%, no more than 27%, no more than 26%, no more than 25%, no more than 22%, no more than 15%, no more than 10%, or no more than 5% of the total nucleosides in the double-stranded or duplex nucleic acid contain a sugar moiety containing a fluorine atom. In certain embodiments, none of the nucleosides in the double-stranded or duplex nucleic acid contain a sugar moiety containing a fluorine atom. In some embodiments, fewer than 42%, fewer than 40%, fewer than 35%, fewer than 30%, fewer than 27%, fewer than 26%, fewer than 22%, fewer than 20%, fewer than 15%, fewer than 10%, or fewer than 5% of the total nucleosides in the double-stranded or duplex nucleic acid contain a sugar moiety containing a fluorine atom.

As used herein. "RNAi agent" means an antisense compound that acts, at least in part, through RISC or Ago2 to modulate a target nucleic acid and/or protein encoded by a target nucleic acid. RNAi agents include, but are not limited to double-stranded siRNA, single-stranded RNAi (ssRNAi), and microRNA, including microRNA mimics. RNAi agents may comprise conjugate groups and/or terminal groups. In certain embodiments, an RNAi agent modulates the amount and/or activity, of a target nucleic acid. The term RNAi agent excludes antisense compounds that act through RNase H.

As used herein. "stabilized phosphate group" means a 5'-phosphate analog that is metabolically more stable than a 5'-phosphate as naturally occurs on DNA or RNA.

As used herein. "standard cell assay" means the assays described in the Examples and reasonable variations thereof.

As used herein. "stereorandom" or "stereorandom chiral center" in the context of a population of molecules of identical molecular formula means a chiral center that is not controlled during synthesis, or enriched following synthesis, for a particular absolute stereochemical configuration. It is understood that a stereorandom chiral center may not be racemic because one absolute configuration predominates following synthesis, e.g., due to steric and electronic interactions of reagents with the reactant molecule. In certain embodiments, the stereorandom chiral center is at the phosphorous atom of a stereorandom phosphorothioate or mesyl phosphoramidate internucleoside linkage.

As used herein. "subject" means a human or non-human animal. In certain embodiments, the subject is a human.

As used herein. "sugar moiety" means an unmodified sugar moiety or a modified sugar moiety. As used herein. "unmodified sugar moiety" means a 2'-OH(H)-D-ribosyl sugar moiety, as found in RNA (an "unmodified RNA sugar moiety"). Unmodified sugar moieties have one hydrogen at each of the 1', 3', and 4' positions, an oxygen at the 3' position, a hydrogen and an OH at the 2' position, and two hydrogens at the 5' position. Modified sugar moieties differ from unmodified RNA by having different substituent(s) (e.g., 2'-F, 2'-MOE, cEt, etc.), having a 2'-deoxy sugar moiety and/or having different stereochemistry (e.g., a 2'-α-L-deoxyribosyl sugar moiety). In certain embodiments, a modified sugar moiety is a modified ribosyl sugar moiety. In certain embodiments, modified sugar moieties differ from unmodified RNA by having both different chemistry (e.g., different substituent(s), 2"-deoxy sugar moiety) and different stereochemistry.

As used herein. "sugar surrogate" means a moiety that can link a nucleobase to another group, such as an internucleoside linkage, conjugate group, or terminal group in an oligonucleotide, but which is not a furanosyl sugar moiety or a bicyclic sugar moiety or a non-bicyclic sugar moiety. Sugar surrogates may comprise one or more substitutions corresponding to those of other types of modified sugar moietics. Modified nucleosides comprising sugar surrogates can be incorporated into one or more positions within an oligonucleotide and such oligonucleotides are capable of hybridizing to complementary oligonucleotide compounds or target nucleic acids. Examples of sugar surrogates include GNA (glycol nucleic acid), FHNA (fluoro hexitol nucleic acid), morpholino, and other structures described herein and known in the art for use in oligonucleotides.

As used herein. "symptom" means any manifestation, indication, sign, evidence, or physical feature or test result that indicates the existence or extent of a disease or disorder. Symptoms include subjective and objective indicia of a disease and may be perceived, experienced, detected, observed, measured, and/or quantified. In certain embodiments, a symptom is apparent to a subject or to a medical professional examining or testing said subject. In certain embodiments, a symptom is apparent upon invasive diagnostic testing, including, but not limited to, post-mortem tests. A symptom may be an absence of a feature, such as failing to reach expected developmental milestones.

As used herein. "target nucleic acid" means a PLN nucleic acid that an antisense compound is designed to affect. As used herein. "target RNA" means a PLN RNA transcript and includes pre-mRNA and/or mRNA unless otherwise specified or specifically relevant (e.g., intron sequence in pre-mRNA). As used herein. "target region" means a portion of a PLN target nucleic acid to which a compound of the invention (e.g., a modified oligonucleotide, an antisense compound) is designed to hybridize. As used herein. "therapeutic index" refers to a quantitative relationship, e.g., ratio, between the concentration (or dose) at which a compound becomes toxic or induces unacceptable adverse effects (or the highest concentration or dose at which a compound is not toxic, or is tolerated, before it becomes toxic or induces unacceptable adverse effects) to a subject and the concentration (or dose) at which the compound is pharmacologically effective, or produces the desired efficacy. These concentrations or doses can be determined using various parameters depending in part on the indication for which the compound is being used as a therapeutic agent. The higher the therapeutic index, the more favorable the safety profile is for the compound. The therapeutic index provides a range of effective concentrations (or doses) for a compound to achieve effective results without unacceptable adverse events. A therapeutic index can be increased by raising the concentration (or dose) at which a compound becomes toxic or induces adverse effects and/or lowering the concentration (or dose) at which a compound is effective.

As used herein, "treating" means improving, or preventing, or delaying development or progression of a subject's disease, disorder or condition or injury by administering a compound or therapeutic agent (e.g., a modified oligonucleotide, oligomeric duplex, an antisense compound described herein) to a subject, e.g., a subject having or at risk of developing a disease, disorder or condition or injury. In certain embodiments, treating a subject improves a symptom relative to the same symptom in the absence of the treatment. In certain embodiments, treatment reduces the severity or frequency of a symptom, or delays the onset of a symptom, slows the progression of a symptom, or slows the increase of the severity or slows the frequency (or increase in frequency) of a symptom. In some embodiments, treatment reduces, improves, and/or prevents one or more symptom(s) such that a symptom of the disorder or disease is diminished or no longer apparent.

EMBODIMENTS

Embodiment 1

An oligomeric duplex comprising a first oligomeric compound and a second oligomeric compound, wherein:
  (1) the first oligomeric compound comprises a modified oligonucleotide consisting of 8 to 50 linked nucleosides, wherein the nucleobase sequence of the first modified oligonucleotide comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of the nucleobase sequence of any one of SEQ ID NOs: 3-314, 627-782, 939-976, 1033-1038, 1254-1255, or 1258-1287, wherein each of the nucleosides of the first modified oligonucleotide independently comprises a modified sugar moiety or sugar surrogate and wherein at least one modified nucleoside and less than 40% of the nucleosides of the first modified oligonucleotide comprises a fluorine; and
  (2) the second oligomeric compound comprises a second modified oligonucleotide consisting of 8 to 50 contiguous linked nucleosides comprising a region having a nucleobase sequence complementary to a region of the first modified oligonucleotide, wherein the nucleobase sequence of the second modified oligonucleotide comprises at least 8, at least 9, at least 10, at least 11, at least 12, at least 13, at least 14, at least 15, at least 16, at least 17, at least 18, at least 19, at least 20, or at least 21 contiguous nucleobases of the nucleobase sequence of any one of SEQ ID NOs: 315-626, 783-938, 977-1016, 1027-1032, 1256-1257, or 1288-1290, wherein each of the nucleosides of the second modified oligonucleotide independently comprises a modified sugar moiety or sugar surrogate and wherein less than 40% of the nucleosides of the second modified oligonucleotide comprises a fluorine.

Embodiment 2

The oligomeric duplex of embodiment 1, wherein the first modified oligonucleotide is at least 80%, at least 85%, at least 90%, at least 95%, or at least 99% or 100% complementary to an equal length portion of a PLN nucleic acid, wherein the PLN nucleic acid has the nucleobase sequence of SEQ ID NO: 1 or SEQ ID NO: 2.

Embodiment 3

The oligomeric duplex of embodiment 1 or embodiment 2, wherein each of the nucleosides of the first modified oligonucleotide independently comprises and each of the nucleosides of the second modified oligonucleotide independently comprises (i) a modified sugar moiety or sugar surrogate, or (ii) a sugar moiety independently selected from a 2'-F sugar moiety, a 2'-MOE sugar moiety, a 2'-OMe sugar moiety, a 2'-deoxy sugar moiety, and a 3-fluoro-hexitol sugar moiety, or (iii) a modified sugar moiety.

Embodiment 4

The oligomeric duplex of any one of embodiments 1-3, wherein fewer than 35%, fewer than 30%, fewer than 25%, fewer than 20%, fewer than 15%, fewer than 14%, fewer than 13%, fewer than 12%, fewer than 10%, fewer than 5%, or fewer than 1% of the nucleosides in the first modified oligonucleotide comprises a fluorine.

Embodiment 5

The oligomeric duplex of any one of embodiments 1-4, wherein no more than 1 nucleoside, no more than 2 nucleosides, no more than 3 nucleosides, or no more than 4 nucleosides in the first modified oligonucleotide comprise a modified sugar moiety comprising a fluorine or a sugar surrogate comprising a fluorine.

Embodiment 6

The oligomeric duplex of any one of embodiments 1-5, wherein no more than 1 nucleoside, no more than 2 nucleosides, or no more than 3 nucleosides within the sequence of the first modified oligonucleotide between and including the third and twenty-first nucleosides counting from the 5' end of the modified oligonucleotide comprise a modified sugar moiety comprising a fluorine or a sugar surrogate comprising a fluorine.

Embodiment 7

The oligomeric duplex of any one of embodiments 1-6, wherein one or more nucleoside(s) of the first modified oligonucleotide comprising i) a modified sugar moiety comprising a fluorine or ii) a sugar surrogate comprising a fluorine is/are independently selected from:

i. the second nucleoside counting from the 5' end, ii. the fourteenth and sixteenth nucleosides counting from the 5' end, or iii. the second, fourteenth and sixteenth nucleosides counting from the 5' end:

wherein each i) modified sugar moiety comprising a fluorine or ii) sugar surrogate comprising a fluorine is independently a 2'-fluoro sugar moiety or a 3'-fluoro-hexitol sugar moiety.

Embodiment 8

The oligomeric duplex of any one of embodiments 1-7, wherein no more than one of the sugar moieties comprising a fluorine in the first modified oligonucleotide is a 3'-fluoro-hexitol sugar moiety.

Embodiment 9

The oligomeric duplex of any one of embodiments 1-8, wherein one or more nucleosides of the first modified oligonucleotide is a 2'-deoxynucleoside.

Embodiment 10

The oligomeric duplex of embodiment 9, wherein the one or more 2'-deoxynucleosides is one or more nucleosides in a region of the sequence of the first modified oligonucleotide between and including the fifth nucleoside to the sixteenth nucleoside counting from the 5' end of the first modified oligonucleotide.

Embodiment 11

The oligomeric duplex of embodiment 10, wherein the one or more 2'-deoxynucleosides is in a region of the sequence of the first modified oligonucleotide that is any of the fifth, and/or sixth, and/or seventh nucleosides or that is any of the fourteenth, and/or fifteenth, and/or sixteenth nucleosides counting from the 5' end of the first modified oligonucleotide.

Embodiment 12

The oligomeric duplex of any one of embodiments 9-11, wherein fewer than 20%, or fewer than 15%, of the nucleosides of the first modified oligonucleotide comprises a fluorine.

Embodiment 13

The oligomeric duplex of any one of embodiments 9-12, wherein the one or more 2'-deoxynucleosides is the fifth, and/or sixth, and/or seventh nucleoside(s) counting from the 5' end of the first modified oligonucleotide.

Embodiment 14

The oligomeric duplex of any one of embodiments 9-13, wherein only one or only two nucleosides of the first modified oligonucleotide are 2'-deoxynucleosides.

Embodiment 15

The oligomeric duplex of embodiment 14, wherein the two 2'-deoxynucleosides are the fifth and seventh nucleosides, or the fourteenth and sixteenth nucleosides, counting from the 5' end of the first modified oligonucleotide.

Embodiment 16

The oligomeric duplex of embodiment 14, wherein the only 2'-deoxynucleoside is the sixth or sixteenth nucleoside counting from the 5' end of the first modified oligonucleotide.

Embodiment 17

The oligomeric duplex of any one of embodiments 1-8, wherein none of the nucleosides of the first modified oligonucleotide is a 2-deoxynucleoside.

Embodiment 18

The oligomeric duplex of any one of embodiments 1-17, wherein the first oligomeric compound comprises a two-nucleoside overhang comprising the 3'-terminal nucleoside and the nucleoside immediately 5' of the 3'-terminal nucleoside of the first modified oligonucleotide.

Embodiment 19

The oligomeric duplex of embodiment 18, wherein the overhang nucleosides are two modified adenosine (AA) nucleosides, two modified uridine (UU) nucleosides, two modified inosine (II) nucleosides, or two modified nucleosides wherein one is inosine and one is adenosine (AI or IA).

Embodiment 20

The oligomeric duplex of any one of embodiments 1-19, wherein one or more of the nucleosides of the first modified oligonucleotide independently comprises a sugar surrogate or a bicyclic sugar moiety.

Embodiment 21

The oligomeric duplex of embodiment 20, wherein the bicyclic sugar moiety comprises a 2'-4' bridge selected from —O—$CH_2$—; and —O—$CH(CH_3)$—.

Embodiment 22

The oligomeric duplex of any one of embodiments 1-21, wherein one or more of the nucleosides of the first modified oligonucleotide comprises a 2'-OMe sugar moiety.

Embodiment 23

The oligomeric duplex of embodiment 22, wherein at least 10%, at least 20%, at least 30%, at least 40%, at least 50% or at least 60% of the nucleosides of the first modified oligonucleotide comprise a 2'-OMe sugar moiety.

Embodiment 24

The oligomeric duplex of embodiment 22 or embodiment 23, wherein the one or more nucleosides comprising a 2-OMe sugar moiety are in a region of the sequence of the first modified oligonucleotide between and including the third and twenty-first nucleosides counting from the 5' end of the first modified oligonucleotide, and/or wherein the first two nucleosides counting from the 5' end of the first modified oligonucleotide and/or the first two nucleosides counting from the 3' end of the first modified oligonucleotide are modified nucleosides independently comprising a sugar surrogate or a modified sugar moiety other than a 2'-OMe sugar moiety.

Embodiment 25

The oligomeric duplex of embodiment 22 or embodiment 23, wherein the 3'-terminal nucleoside of the first modified oligonucleotide comprises a 2'-OMe sugar moiety and/or the nucleoside immediately 5' of the 3'-terminal nucleoside of the first modified oligonucleotide comprises a 2'-OMe sugar moiety.

Embodiment 26

The oligomeric duplex of any one of embodiments 1-25, wherein one or more of the nucleosides of the first modified oligonucleotide comprise a 2'-MOE sugar moiety.

Embodiment 27

The oligomeric duplex of embodiment 26, wherein the 5'- and/or 3'-terminal nucleosides of the first modified oligonucleotide comprise a 2-MOE sugar moiety.

Embodiment 28

The oligomeric duplex of any one of embodiments 1-27, wherein the nucleoside immediately 5' of the 3'-terminal nucleoside of the first modified oligonucleotide comprises a 2'-MOE sugar moiety.

Embodiment 29

The oligomeric duplex of any one of embodiments 1-24 and 26-28, wherein the 5'- and 3'-terminal nucleosides of the first modified oligonucleotide comprise a 2'-MOE sugar moiety and the nucleoside immediately 5' of the 3'-terminal nucleoside of the first modified oligonucleotide comprises a 2'-MOE sugar moiety.

Embodiment 30

The oligomeric duplex of any one of embodiments 1-29, wherein the first oligomeric compound comprises a stabilized phosphate group attached to the 5'-terminal nucleoside of the first modified oligonucleotide.

Embodiment 31

The oligomeric duplex of embodiment 30, wherein the stabilized phosphate group comprises a cyclopropyl phosphonate or a vinyl phosphonate.

Embodiment 32

The oligomeric duplex of any one of embodiments 1-31, wherein the duplex comprises a conjugate group comprising a conjugate moiety and a conjugate linker.

Embodiment 33

The oligomeric duplex of embodiment 32, wherein the conjugate group comprises a cell-targeting moiety.

Embodiment 34

The oligomeric duplex of embodiment 32, wherein the conjugate moiety comprises an active drug substance, an aliphatic chain, a lipid, a peptide, a protein, a hydrocarbon, a polyamine, a polyamide, a polyether, a thioether, an aptamer, an antibody, an antibody fragment, a vitamin, a fatty acid, a carbohydrate, an intercalator, or a reporter molecule.

Embodiment 35

The oligomeric duplex of embodiment 32, wherein the conjugate group comprises a C22 alkyl, C20 alkyl, C17 alkyl, C16 alkyl, C10 alkyl, C21 alkyl, C19 alkyl, C18 alkyl, C15 alkyl, C14 alkyl, C13 alkyl, C12 alkyl, C11 alkyl, C9 alkyl, C8 alkyl, C7 alkyl, C6 alkyl, or C5 alkyl, wherein the alkyl chain optionally has one or more unsaturated bonds.

Embodiment 36

The oligomeric duplex of embodiment 32, wherein the conjugate group comprises a 6-palmitamidohexyl moiety or a 2-(hydroxymethyl)-6-palmitamidohexyl moiety.

Embodiment 37

The oligomeric duplex of embodiment 32, wherein the conjugate group comprises a conjugate moiety that binds type 1 transferrin receptor (TfR1).

Embodiment 38

The oligomeric duplex of embodiment 37, wherein the conjugate moiety is selected from an antibody or fragment thereof, a protein or peptide, and an aptamer capable of binding TfR1.

18

Embodiment 39

The oligomeric duplex of embodiment 38, wherein the conjugate moiety is a cyclic protein or cyclic peptide.

Embodiment 40

The oligomeric duplex of embodiment 37, wherein the conjugate group comprises a bicycle ligand and a conjugate linker.

Embodiment 41

The oligomeric duplex of embodiment 40, wherein the bicycle ligand comprises a peptide consisting of 13-22 linked amino acids or amino acid mimetics and a molecular scaffold, wherein each of a first, a second, and a third amino acid of the peptide comprises a reactive group, each of which separately forms a bond with the molecular scaffold, thereby forming two peptide loops attached to the molecular scaffold.

Embodiment 42

The oligomeric duplex of embodiment 41, wherein the peptide has an amino acid sequence selected from any one of SEQ ID NOs: 1062-1253 and wherein each cysteine forms a covalent bond with the molecular scaffold 1,1',1"-(1,3,5-triazinane-1,3,5-triyl)tris(2-bromoethanone) (TATB) or the molecular scaffold 1,1',1"-(1,3,5-triazinane-1,3,5-triyl)triprop-2-en-1-one (TATA).

Embodiment 43

The oligomeric duplex of embodiment 41, wherein the bicycle ligand or conjugate group has the structure:

or a salt thereof, wherein Q is $N_3$ (BCY17901, SEQ ID NO: 1045), $NH_2$ (BCY21757, SEQ ID NO: 1202), SH (BCY21758, SEQ ID NO: 1203), a conjugate linker, or a conjugate linker covalently connected to an oligonucleotide.

Embodiment 44

The oligomeric duplex of any one of embodiments 32-43, wherein the conjugate group is conjugated to the second modified oligonucleotide.

Embodiment 45

The oligomeric duplex of any one of embodiments 32-43, wherein the conjugate group is attached to the 5' end or 3' end of the second modified oligonucleotide.

Embodiment 46

The oligomeric duplex of any one of embodiments 32-43, wherein the conjugate group is attached to the 5'-terminal nucleoside or the 3'-terminal nucleoside of the second modified oligonucleotide.

Embodiment 47

The oligomeric duplex of any one of embodiments 32-43, wherein the conjugate group is attached to the 5'-terminal nucleoside of the second modified oligonucleotide.

Embodiment 48

The oligomeric duplex of any one of embodiments 32-43, wherein the conjugate group is attached to the 3'-terminal nucleoside of the second modified oligonucleotide.

Embodiment 49

The oligomeric duplex of any one of embodiments 32-48, wherein the conjugate linker of the conjugate group consists of a single bond.

Embodiment 50

The oligomeric duplex of any one of embodiments 32-48, wherein the conjugate linker of the conjugate group is cleavable.

Embodiment 51

The oligomeric duplex of any one of embodiments 32-50, wherein the conjugate linker comprises 1 to 3 linker-nucleosides.

Embodiment 52

The oligomeric duplex of any one of embodiments 32-48, wherein the conjugate linker comprises a (bicyclo[6.1.0] nonyne)-formyl (BCN) moiety.

Embodiment 53

The oligomeric duplex of any one of embodiments 32-48, wherein the conjugate linker comprises a 6-(BCN-carbamate)-2-(hydroxymethyl)hexyl phosphoryl moiety or a 6-(BCN-carbamate)hexyl phosphoryl moiety.

Embodiment 54

The oligomeric duplex of embodiment 41, wherein the conjugate group has the structure (SEQ ID NO: 1291):

Embodiment 55

The oligomeric duplex of embodiment 41, wherein the conjugate group has the structure (SEQ ID NO: 1292):

Embodiment 56

The oligomeric duplex of any one of embodiments 1-55, wherein, the nucleobase sequence of the first modified oligonucleotide is at least 80%, at least 85%, at least 90%, at least 95%, or at least 99% or 100% complementary to an equal length portion within nucleobases selected from any one of 295-316, 296-317, 297-318, 298-320, 299-320, 300-321, 301-322, 302-324, 303-324, 304-325, 304-326, 305-327, 306-325, 306-328, 307-328, 308-329, 309-330, 310-331, 311-332, 312-333, 313-334, 314-335, 315-336, 316-337, 317-339, 318-339, 319-340, 320-341, 321-342, 322-344, 323-345, 324-345, 324-346, 325-345, 325-347, 326-347, 327-348, 328-349, 329-350, 330-351, 331-352, 332-353, 333-354, 334-355, 505-526, 506-528, 507-529, 508-530, 509-531, 510-531, 511-532, 512-533, 513-535, 514-535, 514-536, 515-536, 516-535, 516-537, 517-538, 518-539, 519-541, 520-541, 521-542, 522-544, 523-544, 524-546, 535-556, 536-557, 537-558, 538-559, 539-560, 540-561, 541-563, 542-563, 543-564, 544-565, 545-566, 546-567, 547-568, 548-570, 549-571, 550-572, 551-572, 552-574, 553-574, 554-575, 555-577, 556-578, 557-579, 558-580, 559-580, 560-581, 561-582, 562-583, 563-584, 595-616, 596-618, 597-618, 598-620, 599-621, 600-622, 601-623, 602-623, 603-624, 604-625, 605-627, 606-628, 607-628, 608-629, 609-630, 610-631, 611-632, 612-633, 613-635, 665-687, 666-687, 667-689, 668-689, 669-690, 670-691, 671-692, 672-694, 673-694, 674-695, 675-696, 676-697, 677-698, 678-700, 679-701, 680-702, 681-703, 682-703, 683-704, 684-705, 685-706, 686-708, 687-708, 688-709, 689-710, 690-711, 691-712, 692-714, 693-715, 1675-1696, 1676-1698, 1677-1698, 1678-1699, 1679-1700, 1680-

1702, 1681-1702, 1682-1703, 1683-1705, 1684-1705, 1685-1706, 1686-1707, 1687-1709, 1688-1709, 1689-1710, 1690-1712, 1691-1713, 1692-1714, or 1693-1714 of SEQ ID NO: 1.

Embodiment 57

The oligomeric duplex of any one of embodiments 1-55, wherein the nucleobase sequence of the first modified oligonucleotide is at least 80%, at least 85%, at least 90%, at least 95%, or 100% complementary to an equal length portion within the sequence of nucleobases 304-326, 306-325, 324-346, 325-345, 514-536, or 516-535 of SEQ ID NO: 1.

Embodiment 58

The oligomeric duplex of any one of embodiments 1-55, wherein the nucleobase sequence of the first modified oligonucleotide comprises at least 16, at least 17, at least 18, at least 19, at least 20, at least 21, at least 22, or at least 23 contiguous nucleobases of any one of the nucleobase sequences of SEQ ID NOs: 3-314, 627-782, 939-976, 1033-1038, 1254-1255, or 1258-1287.

Embodiment 59

The oligomeric duplex of any one of embodiments 1-55, wherein the nucleobase sequence of the first modified oligonucleotide comprises the nucleobase sequence of any one of SEQ ID NOs: 3-314, 627-782, 939-976, 1033-1038, 1254-1255 or 1258-1287.

Embodiment 60

The oligomeric duplex of any one of embodiments 1-55, wherein the nucleobase sequence of the first modified oligonucleotide consists of the nucleobase sequence of any one of SEQ ID NOs: 3-314, 627-782, 939-976, 1033-1038, 1254-1255 or 1258-1287.

Embodiment 61

The oligomeric duplex of any one of embodiments 1-55, wherein the nucleobase sequence of the first modified oligonucleotide comprises at least 18, at least 19, at least 20, at least 21, at least 22, or at least 23 contiguous nucleobases of any one of the nucleobase sequences of SEQ ID NOs: 29, 171, 176, 967, 968, 971, 972, 974, 975, 1254, 1255, 1033-1038, 1254-1255, or 1258-1287.

Embodiment 62

The oligomeric duplex of any one of embodiments 1-55, wherein the nucleobase sequence of the first modified oligonucleotide comprises the nucleobase sequence of any one of SEQ ID NOs: 29, 171, 176, 967, 968, 971, 972, 974, 975, 1254, 1255, or 1033-1038, 1254-1255, or 1258-1287.

Embodiment 63

The oligomeric duplex of any one of embodiments 1-55, wherein the nucleobase sequence of the first modified oligonucleotide consists of the nucleobase sequence of any one of SEQ ID NOs: 29, 171, 176, 967, 968, 971, 972, 974, 975, 1254, 1255, 1033-1038, 1254-1255, or 1258-1287.

Embodiment 64

The oligomeric duplex of any one of embodiments 1-63, wherein the first modified oligonucleotide and the second modified oligonucleotide each independently consist of 18 to 30, 18 to 25, 18 to 24, 18 to 23, 18 to 22, 18 to 21, 18 to 19, 19 to 30, 19 to 25, 19 to 24, 19 to 23, 19 to 21, 19 to 20, 20 to 30, to 25, 20 to 24, 20 to 23, 20 to 22, 20 to 21, 21 and 19, 21 and 20, 23 and 21, 23 and 22, or 22 and 21 linked nucleosides.

Embodiment 65

The oligomeric duplex of any one of embodiments 1-64, wherein the first modified oligonucleotide consists of 23, 22, or 21 nucleosides.

Embodiment 66

The oligomeric duplex of any one of embodiments 1-65, wherein the second modified oligonucleotide consists of 21 nucleosides.

Embodiment 67

The oligomeric duplex of any one of embodiments 1-65, wherein the first modified oligonucleotide consists of 23 nucleosides and the second modified oligonucleotide consists of 21 nucleosides.

Embodiment 68

The oligomeric duplex of any one of embodiments 1-65, wherein the first modified oligonucleotide consists of 22 nucleosides and the second modified oligonucleotide consists of 21 nucleosides.

Embodiment 69

The oligomeric duplex of any one of embodiments 1-65, wherein the first modified oligonucleotide consists of 21 nucleosides and the second modified oligonucleotide consists of 21 nucleosides.

Embodiment 70

The oligomeric duplex of any one of embodiments 1-69, wherein the first modified oligonucleotide has a sugar motif (5' to 3') selected from among: efyyydyyyyyyyfyfyyyyyee, efyyydyyyyyyfyfyyyyyyy, e[FHNA] yyydyyyyyyfyfyyyyyee, e[FHNA] yyydyyyyyyfyfyyyyyyy, efyydydyyyyyfyfyyyyyee, efyydydyyyyyfyfyyyyyyy, e[FHNA] yydydyyyyyfyfyyyyyee, e[FHNA] yydydyyyyyfyfyyyyyyy, efyyyfyyyyyyyfyfyyyyyyy, efyyyfyyyyyyyfyfyyyyyey, efyyyyyyyyyyyyfyfyyyyyee, efyyyfyyyyyyyfyfyyyyyee, efyyyyyyyyyyyyfyyyyyyyee, efyyyyyyyyyyyyfyyyyyyyyy, e[FHNA] yyyfyyyyyyyfyfyyyyyee, e[FHNA] yyyfyyyyyyyfyfyyyyyyy, efyyydyyyyyyydydyyyyyee, efyyydyyyyyyydydyyyyyyy, efyyydydyyyyyfyfyyyyyyy, efyyyfyyyyyyyfyyyyyyyee, efyyyfyyyyyyyfyyyyyyyyy, efyyyyyyyyyyyyfyfyyyyyee, efyyyyyyyyyyyyyfyfyyyyyyy, e[FHNA]yydydyyyyfyfyfyyyyyyyy, efyyyfyyyyyyyfydyyyyyyy, efyyyfyyyyyyyfydyyyyyee, efyydydyyyyyfyfyyyyyee, efyydydyyyyyfyfyyyyyyy, efyyydyyyyyyyfyfyyyyyee, efyyydyyyyyyyfyfyyyyyyy, efyyyyyyyyyyyyfyfyyyyyee, efyyyyyyyyyyyyfyfyyyyyyy, efyydydyyyyyfyfyyyyyy, efyyydyyyyyyyfyfyyyyyy, efyyyyyyyyyyyyfyfyyyyyy, efyyyfyyyyyyyfyfyyyee, and efyyyfyyyyyyyfyfyyyyyy, wherein each "d" represents a 2'-deoxy sugar moiety, each "y" represents a 2'-OMe sugar moiety, each "e" represents a 2'-MOE sugar moiety, each "f" represents a 2'-fluoro sugar moiety, and each "[FHNA]" represents a 3-fluoro-hexitol sugar moiety.

Embodiment 71

The oligomeric duplex of any one of embodiments 1-69, wherein the first modified oligonucleotide has a sugar motif (5' to 3') selected from among: efyydydyyyyyyfyfyyyyyee.

Embodiment 72

The oligomeric duplex of any one of embodiments 1-71, wherein the first modified oligonucleotide comprises at least one modified internucleoside linkage.

Embodiment 73

The oligomeric duplex of embodiment 72, wherein at least one modified internucleoside linkage is a phosphorothioate or mesyl phosphoramidate internucleoside linkage.

Embodiment 74

The oligomeric duplex of embodiment 72, wherein fewer than 50%, fewer than 40%, fewer than 30%, fewer than 20%, or fewer than 10% of the internucleoside linkages of the first modified oligonucleotide are modified internucleoside linkages.

Embodiment 75

The oligomeric duplex of any one of embodiments 1-74, wherein each internucleoside linkage of the first modified oligonucleotide is independently selected from a phosphodiester internucleoside linkage and a phosphorothioate internucleoside linkage.

Embodiment 76

The oligomeric duplex of embodiment 75, wherein the internucleoside linkages between the first and second nucleosides and the second and third nucleosides counting from the 5' end of the first modified oligonucleotide are modified internucleoside linkages.

Embodiment 77

The oligomeric duplex of embodiment 75, wherein the internucleoside linkages between the first and second nucleosides and the second and third nucleosides counting from the 3' end of the first modified oligonucleotide are modified internucleoside linkages.

Embodiment 78

The oligomeric duplex of embodiment 75, wherein the internucleoside linkages between the first and second nucleosides and the second and third nucleosides counting from the 5' end of the first modified oligonucleotide, and the internucleoside linkages between the first and second nucleosides and the second and third nucleosides counting from the 3' end of the first modified oligonucleotide are modified internucleoside linkages.

Embodiment 79

The oligomeric duplex of any one of embodiments 72-78, wherein the modified internucleoside linkages are phosphorothioate internucleoside linkages.

Embodiment 80

The oligomeric duplex of embodiment 78 or embodiment 79, wherein all other internucleoside linkages in the first modified oligonucleotide are phosphodiester internucleoside linkages.

Embodiment 81

The oligomeric duplex of embodiment 80, wherein the first modified oligonucleotide has an internucleoside linkage motif of ssooooooooooooooooooss and a sugar motif (5' to 3') selected from among: efyydydyyyyyyfyfyyyyyee, efyyydyyyyyyfyfyyyyyee, efyydydyyyyyyfyfyyyyyyy, e[FHNA]yydydyyyyfyfyfyyyyyyy, efyyyyyyyyyyyyfyfyyyyyee and efyyydyyyyyyfyfyyyyyyy; wherein each "d" represents a 2'-deoxy sugar moiety, each "y" represents a 2'-OMe sugar moiety, each "e" represents a 2'-MOE sugar moiety, each "f" represents a 2'-fluoro sugar moiety, each "[FHNA]" represents a 3-fluoro-hexitol sugar moiety, each "o" represents a phosphodiester internucleoside linkage and each "s" represents a phosphorothioate internucleoside linkage.

Embodiment 82

The oligomeric duplex of embodiment 72, wherein: 1) the first modified oligonucleotide has an internucleoside linkage motif of ssooooooooooooooooooos and a sugar motif (5' to 3') selected from among: efyydydyyyyyyfyfyyyyye, efyydydyyyyyyfyfyyyyyy, efyyydyyyyyyfyfyyyyye, efyyydyyyyyyfyfyyyyyy, efyyyyyyyyyyyyfyfyyyyye, and efyyyyyyyyyyyyfyfyyyyyy; or 2) the first modified oligonucleotide has an internucleoside linkage motif of ssooooooooooooooooooo and a sugar motif (5' to 3') selected from among: efyydydyyyyyyfyfyyyyy, efyyydyyyyyyfyfyyyyy, and efyyyyyyyyyyyyfyfyyyyy; wherein each "d" represents a 2'-deoxy sugar moiety, each "y" represents a 2'-OMe sugar moiety, each "e" represents a 2'-MOE sugar moiety, each "f" represents a 2'-fluoro sugar moiety, each "o" represents a phosphodiester internucleoside linkage and each "s" represents a phosphorothioate internucleoside linkage.

Embodiment 83

The oligomeric duplex of any one of embodiments 1-82, wherein fewer than 30%, fewer than 25%, fewer than 20%, fewer than 15%, fewer than 14%, fewer than 13%, fewer than 12%, fewer than 10%, or fewer than 5% of the nucleosides in the second modified oligonucleotide comprise a fluorine.

Embodiment 84

The oligomeric duplex of any one of embodiments 1-82, wherein no more than 4 nucleosides, no more than 3 nucleosides, no more than 2 nucleosides, or no more than 1 nucleoside in the second modified oligonucleotide comprise a modified sugar moiety comprising a fluorine or a sugar surrogate comprising a fluorine; and wherein optionally none of the nucleosides before the seventh or after the eleventh nucleoside counting from the 5' end of the second modified oligonucleotide comprise a modified sugar moiety comprising a fluorine or a sugar surrogate comprising a fluorine.

Embodiment 85

The oligomeric duplex of any one of embodiments 1-84, wherein one or more of the seventh, ninth and eleventh nucleosides counting from the 5' end of the second modified oligonucleotide comprises a modified sugar moiety comprising a fluorine.

Embodiment 86

The oligomeric duplex of embodiment 85, wherein two or more of the seventh, ninth and eleventh nucleosides counting from the 5' end of the second modified oligonucleotide comprise a modified sugar moiety comprising a fluorine.

Embodiment 87

The oligomeric duplex of embodiment 85, wherein the seventh, ninth and eleventh nucleosides counting from the 5' end of the second modified oligonucleotide comprise a modified sugar moiety comprising a fluorine.

Embodiment 88

The oligomeric duplex of any one of embodiments 1-84, wherein one or both of the tenth and eleventh nucleosides counting from the 5' end of the second modified oligonucleotide comprises a modified sugar moiety comprising a fluorine.

Embodiment 89

The oligomeric duplex of any one of embodiments 84-88, wherein the modified sugar moiety comprising a fluorine is a 2-fluoro sugar moiety.

Embodiment 90

The oligomeric duplex of any one of embodiments 1-89, wherein fewer than 30%, fewer than 25%, fewer than 20%, fewer than 15%, fewer than 14%, fewer than 13%, fewer than 12%, fewer than 10%, fewer than 5%, or fewer than 1% of the total nucleosides in the oligomeric duplex comprise a fluorine.

Embodiment 91

The oligomeric duplex of any one of embodiments 1-90, wherein one or more of the nucleosides of the second modified oligonucleotide independently comprises a sugar surrogate or a bicyclic sugar moiety.

Embodiment 92

The oligomeric duplex of embodiment 91, wherein the bicyclic sugar moiety comprises a 2'-4' bridge selected from —O—CH$_2$—; and —O—CH(CH$_3$)—.

Embodiment 93

The oligomeric duplex of any one of embodiments 1-92, wherein one or more of the nucleosides of the second modified oligonucleotide comprises a 2-OMe sugar moiety.

Embodiment 94

The oligomeric duplex of embodiment 93, wherein at least 10%, at least 20%, at least 30%, at least 40%, at least 50%, at least 60%, at least 65%, at least 70%, at least 80%, at least 85%, or at least 90% of the nucleosides of the second modified oligonucleotide comprise a 2'-OMe sugar moiety.

Embodiment 95

The oligomeric duplex of embodiment 93 or embodiment 94, wherein the one or more nucleosides comprising a 2-OMe sugar moiety are in a region of the sequence of the second modified oligonucleotide between and including the third and nineteenth nucleosides counting from the 5' end of the second modified oligonucleotide.

Embodiment 96

The oligomeric duplex of embodiment 93 or embodiment 94, wherein the 3'-terminal nucleoside of the second modified oligonucleotide comprises a 2-OMe sugar moiety and/or the nucleoside immediately 5' of the 3'-terminal nucleoside of the second modified oligonucleotide comprises a 2'-OMe sugar moiety.

Embodiment 97

The oligomeric duplex of any one of embodiments 93, 94, and 96, wherein the 5'-terminal nucleoside of the second modified oligonucleotide comprises a 2-OMe sugar moiety and/or the nucleoside immediately 3' of the 5'-terminal nucleoside of the second modified oligonucleotide comprises a 2'-OMe sugar moiety.

Embodiment 98

The oligomeric duplex of embodiment 93 or embodiment 94, wherein the 5'-terminal nucleoside, the nucleoside immediately 3' of the 5'-terminal nucleoside, the 3'-terminal nucleoside, and the nucleoside immediately 5' of the 3'-terminal nucleoside of the second modified oligonucleotide comprises a 2-OMe sugar moiety.

Embodiment 99

The oligomeric duplex of any one of embodiments 1-98, wherein one or more of the nucleosides of the second modified oligonucleotide comprise a 2'-MOE sugar moiety.

Embodiment 100

The oligomeric duplex of any one of embodiments 1-95, wherein the 3'-terminal nucleoside of the second modified oligonucleotide comprises a 2"-MOE sugar moiety and/or the nucleoside immediately 5' of the 3'-terminal nucleoside of the second modified oligonucleotide comprises a 2'-MOE sugar moiety.

Embodiment 101

The oligomeric duplex of any one of embodiments 1-96, 99 and 100, wherein the 5'-terminal nucleoside of the second modified oligonucleotide comprises a 2'-MOE sugar moiety and/or the nucleoside immediately 3' of the 5'-terminal nucleoside of the second modified oligonucleotide comprises a 2'-MOE sugar moiety.

Embodiment 102

The oligomeric duplex of any one of embodiments 1-95, wherein the 5'-terminal nucleoside, the nucleoside immediately 3' of the 5'-terminal nucleoside, the 3'-terminal nucleoside, and the nucleoside immediately 5' of the 3'-terminal nucleoside of the second modified oligonucleotide comprises a 2'-MOE sugar moiety.

Embodiment 103

The oligomeric duplex of any one of embodiments 1-102, wherein the second modified oligonucleotide has a sugar motif (5' to 3') selected from among: eeyyyyfyfyfyyyyyyyyee, eeyyyyfyfyfyyyyyyyyyy, yyyyyyfyfyfyyyyyyyyee, yyyyyyfyfyfyyyyyyyyyy, eeyyyyfyfffyyyyyyyyee, eeyyyyfyfffyyyyyyyyyy, yyyyyyfyfffyyyyyyyyee, yyyyyyfyfffyyyyyyyyyy, eeyyyyyyyffyyyyyyyyee, eeyyyyyyyffyyyyyyyyyy, yyyyyyyyyffyyyyyyyyee, yyyyyyyyyffyyyyyyyyyy, eeyyyyyffyyyyyyyyee, eeyyyyyffyyyyyyyyyy, yyyyyyyffyyyyyyyyee, yyyyyyyffyyyyyyyyyy, yyyyyyfyfffyyyyyyyy, eeyyyyfyfffyyyyyyee, eeyyyyfyfffyyyyyyyy, yyyyyyfyfffyyyyyyee, eeyyfyfffyyyyyyyyee, eeyyfyfffyyyyyyyyyy, yyyyfyfffyyyyyyyyee, yyyyfyfffyyyyyyyyyy, eeyyyyyyyydyyyyyyyyee, eeyyyyyyyydyyyyyyyyyy, yyyyyyyyyydyyyyyyyyee, yyyyyyyyyydyyyyyyyyyy, eeyyyyyyyyyyyyyyyyyyee, eeyyyyyyyyyyyyyyyyyyyy, yyyyyyyyyyyyyyyyyyyyee, and yyyyyyyyyyyyyyyyyyyyyy wherein each "y" represents a 2'-OMe sugar moiety, each "e" represents a 2'-MOE sugar moiety, each "f" represents a 2'-fluoro sugar moiety, and each "d" represents a 2'-deoxy sugar moiety.

Embodiment 104

The oligomeric duplex of any one of embodiments 1-102, wherein the second modified oligonucleotide has a sugar motif (5' to 3') selected from among: eeyyyyyyyyffyyyyyyyyee, eeyyyyyfyfyfyyyyyyyyee, yyyyyyyyyffyyyyyyyyyy, and yyyyyyyyyfyfyyyyyyyyyy, wherein each "y" represents a 2'-OMe sugar moiety, each "e" represents a 2'-MOE sugar moiety, and each "f" represents a 2'-fluoro sugar moiety.

Embodiment 105

The oligomeric duplex of any one of embodiments 1-104, wherein (1) the nucleobase of the 3'-terminal nucleoside and/or of the nucleoside immediately 5' of the 3'-terminal nucleoside of the first modified oligonucleotide and/or of the second modified oligonucleotide is an adenine or thymine; and/or (2) the nucleobase of the 5'-terminal nucleoside of the first modified oligonucleotide is a thymine.

Embodiment 106

The oligomeric duplex of any one of embodiments 1-104, wherein the nucleobase of the 3'-terminal nucleoside and the nucleoside immediately 5' of the 3'-terminal nucleoside of the first modified oligonucleotide is an adenine, and the nucleobase of the 5'-terminal nucleoside of the first modified oligonucleotide is a thymine; and wherein the nucleobase of the 3'-terminal nucleoside of the second modified oligonucleotide is an adenine and the nucleobase of the nucleoside immediately 5' of the 3'-terminal nucleoside of the second modified oligonucleotide is a thymine or uracil.

Embodiment 107

The oligomeric duplex of any one of embodiments 1-106, wherein the second modified oligonucleotide comprises at least one modified internucleoside linkage.

Embodiment 108

The oligomeric duplex of embodiment 107, wherein at least one modified internucleoside linkage is a phosphorothioate or mesyl phosphoramidate internucleoside linkage.

Embodiment 109

The oligomeric duplex of embodiment 107, wherein fewer than 50%, fewer than 40%, fewer than 30%, fewer than 20%, or fewer than 10% of the internucleoside linkages of the second modified oligonucleotide are modified internucleoside linkages.

Embodiment 110

The oligomeric duplex of any one of embodiments 107-109, wherein each internucleoside linkage of the second modified oligonucleotide is independently selected from a phosphodiester internucleoside linkage and a phosphorothioate internucleoside linkage.

Embodiment 111

The oligomeric duplex of any one of embodiments 107-109, wherein the internucleoside linkages between the first and second nucleosides and the second and third nucleosides counting from the 5' end of the second modified oligonucleotide are modified internucleoside linkages.

Embodiment 112

The oligomeric duplex of any one of embodiments 107-109 and 111, wherein the internucleoside linkages between the first and second nucleosides and the second and third nucleosides counting from the 3' end of the second modified oligonucleotide are modified internucleoside linkages.

Embodiment 113

The oligomeric duplex of any one of embodiments 107-109, wherein the internucleoside linkages between the first and second nucleosides and the second and third nucleosides counting from the 5' end of the second modified oligonucleotide, and the internucleoside linkages between the first and second nucleosides and the second and third nucleosides counting from the 3' end of the second modified oligonucleotide are modified internucleoside linkages.

Embodiment 114

The oligomeric duplex of any one of embodiments 107-113, wherein the modified internucleoside linkages are phosphorothioate internucleoside linkages.

Embodiment 115

The oligomeric duplex of embodiment 114, wherein all other internucleoside linkages in the second modified oligonucleotide are phosphodiester internucleoside linkages.

Embodiment 116

The oligomeric duplex of embodiment 115, wherein the second modified oligonucleotide has an internucleoside linkage motif of ssooooooooooooooooss and a sugar motif (5' to 3') selected from among: eeyyyyyyyyffyyyyyyyyee, eeyyyyyfyfyfyyyyyyyyee, yyyyyyyyyffyyyyyyyyyy, and yyyyyyyfyfyfyyyyyyyyyy; wherein each "y" represents a 2'-OMe sugar moiety, each "e" represents a 2'-MOE sugar moiety, each "f" represents a 2'-fluoro sugar moiety, each "o" represents a phosphodiester internucleoside linkage and each "s" represents a phosphorothioate internucleoside linkage.

Embodiment 117

The oligomeric duplex of any one of embodiments 1-116, wherein the nucleobase sequence of the second modified oligonucleotide comprises at least 14, at least 15, at least 16, at least 17, at least 18, at least 19, at least 20, or at least 21 contiguous nucleobases of any one of the nucleobase sequences of SEQ ID NOs: 315-626, 783-938, 977-1016, 1027-1032, 1256-1257, or 1288-1290.

Embodiment 118

The oligomeric duplex of any one of embodiments 1-116, wherein the nucleobase sequence of the second modified oligonucleotide comprises the nucleobase sequence of any one of SEQ ID NOs: 315-626, 783-938, 977-1016, 1027-1032, 1256-1257, or 1288-1290.

Embodiment 119

The oligomeric duplex of any one of embodiments 1-116, wherein the nucleobase sequence of the second modified oligonucleotide consists of the nucleobase sequence of any one of SEQ ID NOs: 315-626, 783-938, 977-1016, 1027-1032, 1256-1257, or 1288-1290.

Embodiment 120

The oligomeric duplex of any one of embodiments 1-116, wherein the nucleobase sequence of the second modified oligonucleotide comprises at least 16 contiguous nucleobases of any one of the nucleobase sequences of SEQ ID NOs: 341, 483, 488, 1011-1016, 1027-1032, 1256-1257, or 1288-1290.

Embodiment 121

The oligomeric duplex of any one of embodiments 1-116, wherein the nucleobase sequence of the second modified oligonucleotide comprises the nucleobase sequence of any one of SEQ ID NOs: 341, 483, 488, 1011-1016, 1027-1032, 1256-1257, or 1288-1290.

Embodiment 122

The oligomeric duplex of any one of embodiments 1-116, wherein the nucleobase sequence of the second modified oligonucleotide consists of the nucleobase sequence of any one of SEQ ID NOs: 341, 483, 488, 1011-1016, 1027-1032, 1256-1257, or 1288-1290.

Embodiment 123

An oligomeric duplex comprising:
(1) a first oligomeric compound comprising a first modified oligonucleotide consisting of 18 to 30 contiguous linked nucleosides that is at least 80%, at least 85%, at least 90%, at least 95%, or at least 99% complementary, or 100% complementary to an equal length portion within nucleobases selected from any one of 295-316, 296-317, 297-318, 298-320, 299-320, 300-321, 301-322, 302-324, 303-324, 304-325, 304-326, 305-327, 306-325, 306-328, 307-328, 308-329, 309-330, 310-331, 311-332, 312-333, 313-334, 314-335, 315-336, 316-337, 317-339, 318-339, 319-340, 320-341, 321-342, 322-344, 323-345, 324-345, 324-346, 325-345, 325-347, 326-347, 327-348, 328-345, 328-349, 329-350, 330-351, 331-352, 332-353, 333-354, 334-355, 505-526, 506-528, 507-529, 508-530, 509-531, 510-531, 511-532, 512-533, 513-535, 514-535, 514-536, 515-536, 516-535, 516-537, 517-538, 518-539, 519-541, 520-541, 521-542, 522-544, 523-544, 524-546, 535-556, 536-557, 537-558, 538-559, 539-560, 540-561, 541-563, 542-563, 543-564, 544-565, 545-566, 546-567, 547-568, 548-570, 549-571, 550-572, 551-572, 552-574, 553-574, 554-575, 555-577, 556-578, 557-579, 558-580, 559-580, 560-581, 561-582, 562-583, 563-584, 595-616, 596-618, 597-618, 598-620, 599-621, 600-622, 601-623, 602-623, 603-624, 604-625, 605-627, 606-628, 607-628, 608-629, 609-630, 610-631, 611-632, 612-633, 613-635, 665-687, 666-687, 667-689, 668-689, 669-690, 670-691, 671-692, 672-694, 673-694, 674-695, 675-696, 676-697, 677-698, 678-700, 679-701, 680-702, 681-703, 682-703, 683-704, 684-705, 685-706, 686-708, 687-708, 688-

709, 689-710, 690-711, 691-712, 692-714, 693-715, 1675-1696, 1676-1698, 1677-1698, 1678-1699, 1679-1700, 1680-1702, 1681-1702, 1682-1703, 1683-1705, 1684-1705, 1685-1706, 1686-1707, 1687-1709, 1688-1709, 1689-1710, 1690-1712, 1691-1713, 1692-1714, or 1693-1714 of SEQ ID NO: 1, and
(2) a second oligomeric compound comprising a second modified oligonucleotide consisting of 16 to 28 contiguous linked nucleosides that is at least 90% complementary to an equal length portion of the first modified oligonucleotide:
wherein:
(a) each of the nucleosides of the first modified oligonucleotide and each of the nucleosides of the second modified oligonucleotide comprise a modified sugar moiety or a sugar surrogate,
(b) at least one of the modified sugar moiety or sugar surrogate of the first modified oligonucleotide comprises a fluorine, and
(c) fewer than 40% of the nucleosides of the first modified oligonucleotide comprise a fluorine.

Embodiment 124

An oligomeric duplex comprising. (1) a first oligomeric compound comprising a first modified oligonucleotide consisting of 18 to 30 contiguous linked nucleosides, wherein the nucleobase sequence of the first modified oligonucleotide comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of any one of the nucleobase sequences of SEQ ID NOs: 3-314, 627-782, 939-976, 1033-1038, 1254-1255, or 1258-1287; and (2) a second oligomeric compound comprising a second modified oligonucleotide consisting of 16 to 28 contiguous linked nucleosides that is at least 90% complementary to an equal length portion of the first modified oligonucleotide; wherein: (a) each of the nucleosides of the first modified oligonucleotide and each of the nucleosides of the second modified oligonucleotide comprise a modified sugar moiety or a sugar surrogate, (b) at least one of the modified sugar moiety or sugar surrogate of the first modified oligonucleotide comprises a fluorine, and (c) fewer than 40% of the nucleosides of the first modified oligonucleotide comprise a fluorine.

Embodiment 125

The oligomeric duplex of embodiment 124, wherein each nucleoside of the oligomeric duplex comprises (i) a modified sugar moiety or (ii) a sugar moiety independently selected from a 2'-F sugar moiety, a 2'-MOE sugar moiety, a 2'-OMe sugar moiety, a 2'-deoxy sugar moiety, and a 3'-fluorohexitol sugar moiety.

Embodiment 126

The oligomeric duplex of embodiment 124, wherein the nucleobase sequence of the first modified oligonucleotide comprises or consists of the nucleobase sequence of any one of SEQ ID NOs: 3-314, 627-782, 939-976, 1033-1038, 1254-1255, or 1258-1287.

Embodiment 127

The oligomeric duplex of embodiment 124, wherein the nucleobase sequence of the first modified oligonucleotide comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of any one of the nucleobase sequences of SEQ ID NOs: 29, 171, 176, 967, 968, 971, 972, 974, 975, 1033-1038, 1254-1255, or 1258-1287.

Embodiment 128

The oligomeric duplex of embodiment 124, wherein the nucleobase sequence of the first modified oligonucleotide comprises the nucleobase sequence of any one of SEQ ID NOs: 29, 171, 176, 967, 968, 971, 972, 974, 975, 1033-1038, 1254-1255, or 1258-1287.

Embodiment 129

The oligomeric duplex of embodiment 124, wherein the nucleobase sequence of the first modified oligonucleotide consists of the nucleobase sequence of any one of SEQ ID NOs: 29, 171, 176, 967, 968, 971, 972, 974, 975, 1033-1038, 1254-1255, or 1258-1287.

Embodiment 130

The oligomeric duplex of embodiment 124, wherein the nucleobase sequence of the second modified oligonucleotide comprises least 8, at least 9, at least 10, at least 11, at least 12, at least 13, at least 14, at least 15, at least 16, at least 17, at least 18, at least 19, at least 20, or at least 21 contiguous nucleobases of any one of the nucleobase sequences of SEQ ID NOs: 315-626, 783-938, 977-1016, 1027-1032, 1256-1257, or 1288-1290.

Embodiment 131

The oligomeric duplex of embodiment 126, wherein the nucleobase sequence of the second modified oligonucleotide comprises the nucleobase sequence of any one of SEQ ID NOs: 315-626, 783-938, 977-1016, 1027-1032, 1256-1257, or 1288-1290.

Embodiment 132

The oligomeric duplex of embodiment 126, wherein the nucleobase sequence of the second modified oligonucleotide consists of the nucleobase sequence of any one of SEQ ID NOs: 315-626, 783-938, 977-1016, 1027-1032, 1256-1257, or 1288-1290.

Embodiment 133

The oligomeric duplex of embodiment 127, wherein the nucleobase sequence of the second modified oligonucleotide comprises at least 8, at least 9, at least 10, at least 11, at least 12, at least 13, at least 14, at least 15, at least 16, at least 17, at least 18, at least 19, at least 20, or at least 21 contiguous nucleobases of any one of the nucleobase sequences of SEQ ID NOs: 341, 483, 488, 1011-1016, 1027-1032, 1256-1257, or 1288-1290.

Embodiment 134

The oligomeric duplex of embodiment 128, wherein the nucleobase sequence of the second modified oligonucleotide comprises the nucleobase sequence of any one of SEQ ID NOs: 341, 483, 488, 1011-1016, 1027-1032, 1256-1257, or 1288-1290.

Embodiment 135

The oligomeric duplex of embodiment 129, wherein the nucleobase sequence of the second modified oligonucleotide consists of the nucleobase sequence of any one of SEQ ID NOs: 341, 483, 488, 1011-1016, 1027-1032, 1256-1257, or 1288-1290.

Embodiment 136

The oligomeric duplex of any one of embodiments 123-135, wherein (1) the nucleobase of the 3'-terminal nucleoside and/or of the nucleoside immediately 5' of the 3'-terminal nucleoside of the first modified oligonucleotide and/or of the second modified oligonucleotide is an adenine or thymine; and/or (2) the nucleobase of the 5'-terminal nucleoside of the first modified oligonucleotide is a thymine.

Embodiment 137

The oligomeric duplex of any one of embodiments 123-135, wherein the nucleobase of the 3'-terminal nucleoside and the nucleoside immediately 5' of the 3'-terminal nucleoside of the first modified oligonucleotide is an adenine, and the nucleobase of the 5'-terminal nucleoside of the first modified oligonucleotide is a thymine; and wherein the nucleobase of the 3'-terminal nucleoside of the second modified oligonucleotide is an adenine and the nucleobase of the nucleoside immediately 5' of the 3'-terminal nucleoside of the second modified oligonucleotide is a thymine or uracil.

Embodiment 138

The oligomeric duplex of any one of embodiments 123-135, wherein the first oligomeric compound comprises a two-nucleoside overhang comprising the 3'-terminal nucleoside and the nucleoside immediately 5' of the 3'-terminal nucleoside of the first modified oligonucleotide.

Embodiment 139

The oligomeric duplex of embodiment 138, wherein the overhang nucleosides are two modified adenosine (AA) nucleosides, two modified uridine (UU) nucleosides, two modified inosine (II) nucleosides, or two modified nucleosides wherein one is inosine and one is adenosine (AI or IA).

Embodiment 140

The oligomeric duplex of any one of embodiments 123-139, wherein none of the modified sugar moieties or sugar surrogates of the nucleosides of the second modified oligonucleotide comprises a fluorine.

Embodiment 141

The oligomeric duplex of any one of embodiments 123-139, wherein at least one of the modified sugar moieties or sugar surrogates of the second modified oligonucleotide comprises a fluorine and wherein fewer than 40%, fewer than 30%, fewer than 25%, fewer than 20%, fewer than 15%, fewer than 14%, fewer than 13%, fewer than 12%, fewer than 10%, or fewer than 5% of the nucleosides of the second modified oligonucleotide comprises a fluorine; and/or wherein fewer than 30%, fewer than 25%, fewer than 20%, fewer than 15%, fewer than 14%, fewer than 13%, fewer than 12%, fewer than 10%, or fewer than 5% of the total nucleosides in the oligomeric duplex comprise a fluorine.

Embodiment 142

The oligomeric duplex of any one of embodiments 123-139, wherein two, three or four of the nucleosides of the second modified oligonucleotide independently comprise a modified sugar moiety comprising a fluorine or a sugar surrogate comprising a fluorine or no more than 4 nucleosides, no more than 3 nucleosides, no more than 2 nucleosides, or no more than 1 nucleoside of the second modified oligonucleotide comprise a modified sugar moiety comprising a fluorine or a sugar surrogate comprising a fluorine.

Embodiment 143

The oligomeric duplex of any one of embodiments 123-142, wherein two, three or four of the nucleosides of the first modified oligonucleotide independently comprise a modified sugar moiety comprising a fluorine or a sugar surrogate comprising a fluorine or no more than 4 nucleosides, no more than 3 nucleosides, no more than 2 nucleosides, or no more than 1 nucleoside of the first modified oligonucleotide comprise a modified sugar moiety comprising a fluorine or a sugar surrogate comprising a fluorine.

Embodiment 144

The oligomeric duplex of any one of embodiments 123-143, wherein no more than 1 nucleoside, no more than 2 nucleosides, or no more than 3 nucleosides within the sequence of the first modified oligonucleotide between and including the third and twenty-first nucleosides counting from the 5' end of the modified oligonucleotide comprise a modified sugar moiety comprising a fluorine or a sugar surrogate comprising a fluorine.

Embodiment 145

The oligomeric duplex of any one of embodiments 123-144, wherein one or more nucleoside comprising a modified sugar moiety comprising a fluorine or a sugar surrogate comprising a fluorine of the first modified oligonucleotide is/are independently selected from:
  i. the second nucleoside counting from the 5' end,
  ii. the fourteenth and sixteenth nucleosides counting from the 5' end, or
  iii. the second, fourteenth and sixteenth nucleosides counting from the 5' end:
  wherein each modified sugar moiety comprising a fluorine or sugar surrogate comprising a fluorine is independently a 2'-fluoro sugar moiety or a 3'-fluoro-hexitol sugar moiety.

Embodiment 146

The oligomeric duplex of any one of embodiments 123-145, wherein none of the nucleosides of the second modified oligonucleotide is a 2'-deoxynucleoside and/or none of the nucleosides of the first modified oligonucleotide is a 2-deoxynucleoside.

Embodiment 147

The oligomeric duplex of any one of embodiments 123-146, wherein all of the nucleosides of the second modified oligonucleotide comprise a modified ribosyl sugar moiety.

Embodiment 148

The oligomeric duplex of any one of embodiments 123-145 and 147, wherein one, two, or three of the nucleosides of the first modified oligonucleotide is/are a 2'-deoxynucleoside or wherein no more than 3, nor more than 2, or no more than one nucleoside(s) of the first modified oligonucleotide is/are a 2'-deoxynucleoside(s), or wherein only 3, only 2, or only one nucleoside(s) of the first modified oligonucleotide is/are a 2'-deoxynucleoside(s).

Embodiment 149

The oligomeric duplex of embodiment 148, wherein the fifth and seventh nucleosides counting from the 5' end of the first modified oligonucleotide are 2"-deoxynucleosides, or wherein the sixth nucleoside counting from the 5' end of the first modified oligonucleotide is a 2'-deoxynucleoside.

Embodiment 150

The oligomeric duplex of any one of embodiments 123-149, wherein:
  (a) the 5'- and 3'-terminal nucleosides, the nucleoside immediately 3' of the 5'-terminal nucleoside, and the nucleoside immediately 5' of the 3'-terminal nucleoside of the second modified oligonucleotide comprise a 2-MOE sugar moiety, and/or
  (b) the 5'- and 3'-terminal nucleosides and the nucleoside immediately 5' of the 3'-terminal nucleoside of the first modified oligonucleotide comprise a 2'-MOE sugar moiety, and/or
  (c) any nucleoside in the first and second modified oligonucleotides that does not comprise a fluorine or a 2'-MOE sugar moiety comprises a 2'-OMe sugar moiety.

Embodiment 151

The oligomeric duplex of any one of embodiments 123-149, wherein the 3'-terminal nucleoside of the first modified oligonucleotide comprises a 2'-OMe sugar moiety and/or the nucleoside immediately 5' of the 3'-terminal nucleoside of the first modified oligonucleotide comprises a 2'-OMe sugar moiety and optionally the 5'-terminal nucleoside of the first modified oligonucleotide comprises a 2'-MOE sugar moiety.

Embodiment 152

The oligomeric duplex of any one of embodiments 123-151, wherein the first oligomeric compound comprises a stabilized phosphate group attached to the 5'-terminal nucleoside of the first modified oligonucleotide.

Embodiment 153

The oligomeric duplex of embodiment 152, wherein the stabilized phosphate group comprises a cyclopropyl phosphonate or a vinyl phosphonate.

Embodiment 154

The oligomeric duplex of any one of embodiments 123-153, wherein no more than four of the nucleosides of the first modified oligonucleotide comprise a modified sugar moiety comprising a fluorine or a sugar surrogate comprising a fluorine.

Embodiment 155

The oligomeric duplex of embodiment 154, wherein the first modified oligonucleotide has a sugar motif (5' to 3') selected from among: efyyyfyyyyyyyfyfyyyyyee, efyyyfyyyyyyyfyfyyyyyyy, e[FHNA] yyyfyyyyyyyfyfyyyyyee, e[FHNA] yyyfyyyyyyyfyfyyyyyyy, efyyyfyyyyyyyfyfyyyyyey, e[FHNA]yydydyyyyfyfyfyyyyyyy and efyyyfyyyyyyyfyfyyyee; wherein each "d" represents a 2'-deoxy sugar moiety, each "y" represents a 2'-OMe sugar moiety, each "e" represents a 2'-MOE sugar moiety, each "f" represents a 2'-fluoro sugar moiety, and each "[FHNA]" represents a 3-fluoro-hexitol sugar moiety.

Embodiment 156

The oligomeric duplex of any one of embodiments 123-153, wherein no more than three of the nucleosides of the first modified oligonucleotide comprise a modified sugar moiety comprising a fluorine or a sugar surrogate comprising a fluorine.

Embodiment 157

The oligomeric duplex of embodiment 156, wherein the first modified moiety, each "y" represents a 2'-OMe sugar moiety, each "e" represents a 2'-MOE sugar moiety, each "f" represents a 2'-fluoro sugar moiety, and each "[FHNA]" represents a 3'-fluoro-hexitol sugar moiety.

Embodiment 158

The oligomeric duplex of any one of embodiments 123-153, wherein no more than two of the nucleosides of the first modified oligonucleotide comprise a modified sugar moiety comprising a fluorine or a sugar surrogate comprising a fluorine.

Embodiment 159

The oligomeric duplex of embodiment 158, wherein the first modified oligonucleotide has a sugar motif (5' to 3') selected from among: efyyydyyyyyyyfyfyyyyyee, efyyydyyyyyyyfyfyyyyyyy, e[FHNA] yyyydyyyyyyyfyfyyyyyee, e[FHNA] yyyydyyyyyyyfyfyyyyyyy, efyydydyyyyyfyfyyyyyee, efyydydyyyyyfyfyyyyyyy, e[FHNA] yydydyyyyyfyfyyyyyee, e[FHNA] yydydyyyyyfyfyyyyyyy, efyyyyyyyyyyyfyfyyyyyee, efyyyfyyyyyyyfyyyyyyyyy, efyyyfyyyyyyyfydyyyyyee, efyyyfyyyyyyyfydyyyyyy, efyyyfyyyyyyyfydyyyyyee, efyyyfyyyyyyyfydyyyyyy, efyydydyyyyyfyfyyyyye, efyydydyyyyyfyfyyyyyy, efyyydyyyyyyyfyfyyyyye, efyyydyyyyyyyfyfyyyyyy, efyyyyyyyyyyyfyfyyyyye, efyyyyyyyyyyyfyfyyyyyy, efyydydyyyyyfyfyyyyy, efyyydyyyyyyyfyfyyyyy, and efyyyyyyyyyyyfyfyyyyy; wherein each "d" represents a 2'-deoxy sugar oligonucleotide has a sugar motif (5' to 3") selected from among: efyyyyyyyyyyyfyyyyyyyee, efyyyyyyyyyyyfyyyyyyyyy, e[FHNA]yyyyyyyyyyy[FHNA]yyyyyyyee, and e[FHNA] yyyyyyyyyy[FHNA]yyyyyyyyy; wherein each "y" represents a 2'-OMe sugar moiety, each "e" represents a 2'-MOE sugar moiety, each "f" represents a 2'-fluoro sugar moiety, and each "[FHNA]" represents a 3-fluoro-hexitol sugar moiety.

Embodiment 160

The oligomeric duplex of any one of embodiments 123-153, wherein only one of the nucleosides of the first modified oligonucleotide comprises a modified sugar moiety comprising a fluorine or a sugar surrogate comprising a fluorine.

Embodiment 161

The oligomeric duplex of embodiment 160, wherein the first modified oligonucleotide has a sugar motif (5' to 3') selected from among: efyyydyyyyyyydydyyyyyyy, efyyydyyyyyyydydyyyyyee, e[FHNA] yyyydyyyyyyydydyyyyyyy, and e[FHNA] yyyydyyyyyyydydyyyyyee; wherein each "d" represents a 2'-deoxy sugar moiety, each "y" represents a 2'-OMe sugar moiety, each "e" represents a 2'-MOE sugar moiety, each "f" represents a 2'-fluoro sugar moiety, and each "[FHNA]" represents a 3-fluoro-hexitol sugar moiety.

Embodiment 162

The oligomeric duplex of any one of embodiments 123-158 and 160, wherein no more than two of the nucleosides of the first modified oligonucleotide are 2"-deoxynucleosides. Embodiment 163. The oligomeric duplex of embodiment 162 wherein the first modified oligonucleotide has a sugar motif (5' to 3') selected from among: efyydydyyyyyfyfyyyyyee, efyydydyyyyyfyfyyyyyyy, e[FHNA]yydydyyyyyfyfyyyyyee, e[FHNA] yydydyyyyyfyfyyyyyyy, efyydydyyyyyfyfyyyyye, efyydydyyyyyfyfyyyyyy, and efyydydyyyyyfyfyyyyy; wherein each "d" represents a 2'-deoxy sugar moiety, each "y" represents a 2'-OMe sugar moiety, each "e" represents a 2'-MOE sugar moiety, each "f" represents a 2'-fluoro sugar moiety, and each "[FHNA]" represents a 3-fluoro-hexitol sugar moiety.

Embodiment 164

The oligomeric duplex of any one of embodiments 123-154, 156, 158 and 160, wherein only one of the nucleosides of the first modified oligonucleotide is a 2'-deoxynucleoside.

Embodiment 165

The oligomeric duplex of embodiment 164, wherein the first modified oligonucleotide has a sugar motif (5' to 3") selected from among: efyyydyyyyyyyfyfyyyyyee, efyyydyyyyyyyfyfyyyyyyy, e[FHNA] yyyydyyyyyyyfyfyyyyyee, e[FHNA] yyyydyyyyyyyfyfyyyyyyy, eyyyfyyyyyyyfydyyyyyyy, efyyyfyyyyyyyfydyyyyyee, eyyy[FHNA] yyyyyyyfydyyyyyyy, e[FHNA]yyyfyyyyyyyfydyyyyyee, efyyydyyyyyyyfyfyyyye, efyyydyyyyyyyfyfyyyyyy, and efyyydyyyyyyyfyfyyyyy; wherein each "d" represents a 2'-deoxy sugar moiety, each "y" represents a 2'-OMe sugar moiety, each "e" represents a 2'-MOE sugar moiety, each "f" represents a 2'-fluoro sugar moiety, and each "[FHNA]" represents a 3'-fluoro-hexitol sugar moiety.

Embodiment 165a

The oligomeric duplex of embodiment 164, wherein the first modified oligonucleotide has a sugar motif (5' to 3')

selected from among: efyyydyyyyyyyfyfyyyyyee, efyyydyyyyyyyfyfyyyyyyy, e[FHNA] yyydyyyyyyyfyfyyyyyee, e[FHNA] yyydyyyyyyyfyfyyyyyyy, eyyyfyyyyyyyyfydyyyyyyy, efyyyfyyyyyyyyfydyyyyyee, efyyy[FHNA] yyyyyyyfydyyyyyyy, e[FHNA]yyyfyyyyyyyyfydyyyyyee, efyyydyyyyyyyfyfyyyyye, efyyydyyyyyyyfyfyyyyyyy, and efyyydyyyyyyyfyfyyyyyy; wherein each "d" represents a 2'-deoxy sugar moiety, each "y" represents a 2'-OMe sugar moiety, each "e" represents a 2'-MOE sugar moiety, each "f" represents a 2'-fluoro sugar moiety, and each "[FHNA]" represents a 3'-fluoro-hexitol sugar moiety.

Embodiment 166

The oligomeric duplex of any one of embodiments 123-154, wherein none of the nucleosides of the first modified oligonucleotide comprises a 2'-deoxy sugar moiety.

Embodiment 167

The oligomeric duplex of embodiment 166, wherein the first modified oligonucleotide has a sugar motif (5' to 3") selected from among: efyyyyyyyyyyyyfyfyyyyyee, efyyyfyyyyyyyfyyyyyyyyy, efyyyyyyyyyyyyfyfyyyyye, efyyyyyyyyyyyyfyfyyyyyy, and efyyyyyyyyyyyyfyfyyyyyy, wherein each "y" represents a 2'-OMe sugar moiety, each "e" represents a 2'-MOE sugar moiety, and each "f" represents a 2'-fluoro sugar moiety.

Embodiment 168

The oligomeric duplex of any one of embodiments 123-139 and 141-167, wherein no more than four of the nucleosides of the second modified oligonucleotide comprise a modified sugar moiety comprising a fluorine or a sugar surrogate comprising a fluorine.

Embodiment 169

The oligomeric duplex of embodiment 168, wherein the second modified oligonucleotide has a sugar motif (5' to 3') selected from among: yyyyyyfyfffyyyyyyyyyy, eeyyyyfyfffyyyyyyyyee, yyyyyyfyfffyyyyyyyyy, eeyyyyfyfffyyyyyyyee, yyyyfyfffyyyyyyyyyy, and eeyyfyfffyyyyyyyyee; wherein each "y" represents a 2'-OMe sugar moiety, each "e" represents a 2'-MOE sugar moiety, and each "f" represents a 2'-fluoro sugar moiety.

Embodiment 170

The oligomeric duplex of any one of embodiments 123-139 and 141-167, wherein no more than three of the nucleosides of the second modified oligonucleotide comprise a modified sugar moiety comprising a fluorine or a sugar surrogate comprising a fluorine.

Embodiment 171

The oligomeric duplex of embodiment 170, wherein the second modified oligonucleotide has a sugar motif (5' to 3') selected from among: eeyyyfyfyfyyyyyyyyee and yyyyyyfyfyfyyyyyyyyy; wherein each "y" represents a 2'-OMe sugar moiety, each "e" represents a 2'-MOE sugar moiety, and each "f" represents a 2'-fluoro sugar moiety.

Embodiment 172

The oligomeric duplex of any one of embodiments 123-139 and 141-167, wherein no more than two of the nucleosides of the second modified oligonucleotide comprise a modified sugar moiety comprising a fluorine or a sugar surrogate comprising a fluorine.

Embodiment 173

The oligomeric duplex of embodiment 172, wherein the second modified oligonucleotide has a sugar motif (5' to 3") selected from among: eeyyyyyyyffyyyyyyyyee, yyyyyyyyyffyyyyyyyyy, eeyyyyyffyyyyyyyyee, and yyyyyyffyyyyyyyyy; wherein each "y" represents a 2'-OMe sugar moiety, each "e" represents a 2'-MOE sugar moiety, and each "f" represents a 2'-fluoro sugar moiety.

Embodiment 174

The oligomeric duplex of any one of embodiments 123-167, wherein none of the nucleosides of the second modified oligonucleotide comprises a modified sugar moiety comprising a fluorine or a sugar surrogate comprising a fluorine and wherein the second modified oligonucleotide has a sugar motif (5' to 3') selected from among: yyyyyyyyyyyyyyyyyyyy, eeyyyyyyyyyyyyyyyyyee, yyyyyyyyydyyyyyyyyy, and eeyyyyyyyydyyyyyyyee; wherein each "y" represent a 2'-OMe sugar moiety, each "e" represents a 2'-MOE sugar moiety, and each "d" represents a 2'-deoxy sugar moiety.

Embodiment 175

The oligomeric duplex of any one of embodiments 123-174, wherein one or more of the internucleoside linkages of the first modified oligonucleotide is/are a modified internucleoside linkage and/or wherein fewer than 50%, fewer than 40%, fewer than 30%, fewer than 20%, or fewer than 10% of the internucleoside linkages of the first modified oligonucleotide are modified internucleoside linkages.

Embodiment 176

The oligomeric duplex of any one of embodiments 123-175, wherein the internucleoside linkages between the first and second nucleosides and the second and third nucleosides counting from the 5' end of the first modified oligonucleotide, and the internucleoside linkages between the first and second nucleosides and the second and third nucleosides counting from the 3' end of the first modified oligonucleotide are phosphorothioate internucleoside linkages.

Embodiment 177

The oligomeric duplex of any one of embodiments 123-175, wherein the first modified oligonucleotide has an internucleoside linkage motif (5' to 3') selected from among: ssooooooooooooooooooss, ssoooosooooooooooooooss, ssoosoooooooooooooooss, ssooooooooooooooooooos, ssoooooooooooooooooo, and ssooooooooooooooooooss; wherein each "o" represents a phosphodiester internucleoside linkage and each "s" represents a phosphorothioate internucleoside linkage.

Embodiment 178

The oligomeric duplex of any one of embodiments 123-177, wherein one or more of the internucleoside linkages of the second modified oligonucleotide is/are a modified internucleoside linkage(s).

Embodiment 179

The oligomeric duplex of any one of embodiments 123-178, wherein fewer than 50%, fewer than 40%, fewer than 30%, fewer than 20%, or fewer than 10% of the internucleoside linkages of the second modified oligonucleotide are modified internucleoside linkages.

Embodiment 180

The oligomeric duplex of any one of embodiments 123-179, wherein the internucleoside linkages between the first and second nucleosides and the second and third nucleosides counting from the 5' end of the second modified oligonucleotide, and the internucleoside linkages between the first and second nucleosides and the second and third nucleosides counting from the 3' end of the second modified oligonucleotide are phosphorothioate internucleoside linkages.

Embodiment 181

The oligomeric duplex of any one of embodiments 123-180, wherein the second modified oligonucleotide has an internucleoside linkage motif (5' to 3') selected from among: ssoooooooooooooooooss, ssoooooooosooooooooss, ssooooooozozoooooooss, and ssooooooooooooooooss; wherein each "o" represents a phosphodiester internucleoside linkage, each "s" represents a phosphorothioate internucleoside linkage, and each 'z' represents a mesyl phosphoramidate internucleoside linkage.

Embodiment 182

The oligomeric duplex of any one of embodiments 1-4, 12, 18, 19, 30-69, 72, 80, 105-115, 117-139, 152, 153, and 175-181, wherein the first modified oligonucleotide has a first sugar motif ($1^{st}$) and the second modified oligonucleotide has a second sugar motif ($2^{nd}$) and the first and second sugar motifs are selected from among the following combinations (5' to 3'): $1^{st}$: efyydydyyyyyfyfyyyyyee and $2^{nd}$: eeyyyyyfyfyfyyyyyyyyee; $1^{st}$: efyydydyyyyyfyfyyyyyy and $2^{nd}$: yyyyyyfyfyfyyyyyyyyyy; $1^{st}$: efyydydyyyyyfyfyyyyyee and $2^{nd}$: yyyyyyfyfyfyyyyyyyyyy; $1^{st}$: efyydydyyyyyfyfyyyyyy and $2^{nd}$: eeyyyyyfyfyfyyyyyyyyee; $1^{st}$: efyyyyyyyyyyyfyfyyyyee and $2^{nd}$: eeyyyyyyffyyyyyyyyee; $1^{st}$: efyyyyyyyyyyyfyfyyyyyy and $2^{nd}$: YYYYYYYYYffYYyYYYYYYY; $1^{st}$: efyyyyyyyyyyyfyfyyyyee and $2^{nd}$: yyyyyyyyyffyyyyyyyyyY; $1^{st}$: efyyyyyyyyyyyfyfyyyyyy and $2^{nd}$: eeyyyyyyffyyyyyyyyee; $1^{st}$: efyydyyyyyyfyfyyyyyee and $2^{nd}$: eeyyyyyyffyyyyyyyyee; $1^{st}$: efyydyyyyyyfyfyyyyyyy and $2^{nd}$: yyyyyyyyyffyyyyyyyyyy; $1^{st}$: efyydyyyyyyfyfyyyyyee and $2^{nd}$: yyyyyyyyyffyyyyyyyyyy; $1^{st}$: efyydydyyyyyfyfyyyyee and $2^{nd}$: eeyyyyyyffyyyyyyyyee; $1^{st}$: efyydydyyyyyfyfyyyyyy and $2^{nd}$: yyyyyyyyyffyyyyyyyyyy; $1^{st}$: efyydydyyyyyfyfyyyyee and $2^{nd}$: eeyyyyyyffyyyyyyyyee; $1^{st}$: efyyyyyyyyyyyfyfyyyyyy and $2^{nd}$: yyyyyyffffyyyyyyyyyy; $1^{st}$: efyyydyyyyyyfyfyyyyyee and $2^{nd}$:

yyyyyyfyfyfyyyyyyyyyy; $1^{st}$: efyyydyyyyyyyfyfyyyyyy and $2^{nd}$: eeyyyyfyfyfyyyyyyyyee; $1^{st}$: efyyyyyyyyyyyfyfyyyyee and $2^{nd}$: eeyyyyfyfyfyyyyyyyyee; $1^{st}$: efyyyyyyyyyyyfyfyyyyyy and $2^{nd}$: yyyyyyfyfyfyyyyyyyyyy; $1^{st}$: efyyyyyyyyyyyfyfyyyyee and $2^{nd}$: yyyyyyfyfyfyyyyyyyyyy; $1^{st}$: efyyyyyyyyyyyfyfyyyyyy and $2^{nd}$: eeyyyyfyfyfyyyyyyyyee; $1^{st}$: efyyyyyyyyyyyfyfyyyyye and $2^{nd}$: eeyyyyyyffyyyyyyyyee; $1^{st}$: efyyyyyyyyyyyyfyfyyyyyy and $2^{nd}$: yyyyyyyyyffyyyyyyyyyy; $1^{st}$: efyyyyyyyyyyyfyfyyyyye and $2^{nd}$: yyyyyyyyyffyyyyyyyyyy; $1^{st}$: efyyyyyyyyyyyfyfyyyyyy and $2^{nd}$: eeyyyyyyffyyyyyyyyee; $1^{st}$: efyyyyyyyyyyyfyfyyyyye and $2^{nd}$: yyYYYYfYfrfYYYyYYYYY; $1^{st}$: efyyyyyyyyyyyfyfyyyyye and $2^{nd}$: yyyyyyfyfyfyyyyyyyyyY; $1^{st}$: efyyyyyyyyyyyfyfyyyyyy and $2^{nd}$: eeyyyyfyfyfyyyyyyyyee; $1^{st}$: efyydydyyyyyyfyfyyyyye and $2^{nd}$: eeyyyyfyfyfyyyyyyyyee; $1^{st}$: efyydydyyyyyyfyfyyyyyy and $2^{nd}$: yyyyyyfyfyfyyyyyyyyyy; $1^{st}$: efyydydyyyyyyfyfyyyyye and $2^{nd}$: yyyyyyfyfyfyyyyyyyyyy; $1^{st}$: efyydydyyyyyyfyfyyyyyy and $2^{nd}$: eeyyyyyyffyyyyyyyyee; $1^{st}$: efyydydyyyyyyfyfyyyyye and $2^{nd}$: eeyyyyyyffyyyyyyyyyee; $1^{st}$: efyydydyyyyyyfyfyyyyyy and $2^{nd}$: yyyyyyyyyffyyyyyyyyyy; $1^{st}$: efyydydyyyyyyfyfyyyyye and $2^{nd}$: yyyyyyyyyffyyyyyyyyyy; $1^{st}$: efyydydyyyyyyfyfyyyyyy and $2^{nd}$: eeyyyyyyffyyyyyyyyee; $1^{st}$: efyyydyyyyyyyfyfyyyyye and $2^{nd}$: eeyyyyyyffyyyyyyyyyee; $1^{st}$: efyyydyyyyyyyfyfyyyyyy and $2^{nd}$: yyYYYYYYffyYYYYYYYYY; $1^{st}$: efyyydyyyyyyyfyfyyyyye and $2^{nd}$: yyyyyyyyyffyyyyyyyyyy; $1^{st}$: efyyydyyyyyyyfyfyyyyyy and $2^{nd}$: eeyyyyyyffyyyyyyyyee; $1^{st}$: efyyydyyyyyyyfyfyyyyye and $2^{nd}$: eeyyyyyfyfyfyyyyyyyyyy and $2^{nd}$: yyyyyyfyfyfyyyyyyyyyy; $1^{st}$: efyyydyyyyyyyfyfyyyyye and $2^{nd}$: yyyYYyfyfYfYYYYYYYYYY; $1^{st}$: efyyydyyyyyyyfyfyyyyyy and $2^{nd}$: eeyyyyfyfyfyyyyyyyyyee; $1^{st}$: efyyyyyyyyyyyfyfyyyyy and $2^{nd}$: eeyyyyyyffyyyyyyyyee; $1^{st}$: efyyyyyyyyyyyfyfyyyyy and $2^{nd}$: yyyyyyyyyffyyyyyyyyyy; $1^{st}$: efyyyyyyyyyyyfyfyyyyyy and $2^{nd}$: eeyyyyfyfyfyyyyyyyyyee; $1^{st}$: efyyyyyyyyyyyfyfyyyyyy and $2^{nd}$: yyyyyyfyfyfyyyyyyyyyy; $1^{st}$: efyydydyyyyyyfyfyyyyy and $2^{nd}$: eeyyyyfyfyfyyyyyyyyyee; $1^{st}$: efyydydyyyyyyfyfyyyyy and $2^{nd}$: yyyyyyfyjrYryYYyyyyyy; $1^{st}$: efyydydyyyyyyfyfyyyyy and $2^{nd}$: eeyyyyyyffyyyyyyyyyee; $1^{st}$: efyydydyyyyyyfyfyyyyy and $2^{nd}$: yyyyyyyyyffyyyyyyyyyy; $1^{st}$: efyydydyyyyyyfyfyyyyy and $2^{nd}$: eeyyyyyyffyyyyyyyyyee; $1^{st}$: efyydydyyyyyyfyfyyyyy and $2^{nd}$: yyyyyyyyyffyyyyyyyyyy; $1^{st}$: efyydydyyyyyyfyfyyyyy and $2^{nd}$: eeyyyyyfyfyfyyyyyyyyyee; $1^{st}$: efyydyyyyyyfyfyyyyy and $2^{nd}$: yyyyyyfyfyfyyyyyyyyyy; wherein each "y" represents a 2'-OMe sugar moiety, each "e" represents a 2'-MOE sugar moiety, each "f" represents a 2'-fluoro sugar moiety, and each "d" represents a 2'-deoxy sugar moiety.

Embodiment 183

The oligomeric duplex of any one of embodiments 1-4, 12, 18, 19, 30-69, 72, 80, 105-115, 117-139, 152, 153, and 175-181, wherein the first modified oligonucleotide has a first sugar motif ($1^{st}$) and the second modified oligonucleotide has a second sugar motif ($2^{nd}$) and the first and second sugar motifs are selected from among the following combinations (5' to 3'): $1^{st}$: efyydydyyyyyyfyfyyyyyee and $2^{nd}$: eeyyyyyfyfffyyyyyyyyyee; $1^{st}$: efyydydyyyyyyfyfyyyyyyy and $2^{nd}$: yyyyyyfyfffyyyyyyyyyy; $1^{st}$: efyydydyyyyyyfyfyyyyyee and $2^{nd}$: yyyyyyfyfffyyyyyyyyyy; $1^{st}$: efyydydyyyyyyfyfyyyyyyy and $2^{nd}$: eeyyyyyfyfffyyyyyyyyyee; $1^{st}$: efyyyyyyyyyyyyfyfyyyyyee and $2^{nd}$: eeyyyyyfyfffyyyyyyyyyee; $1^{st}$: efyyyyyyyyyyyyfyfyyyyyyy and $2^{nd}$: yyyyyyfyfffyyyyyyyyyy; $1^{st}$: efyyyyyyyyyyyyfyfyyyyyee and $2^{nd}$: yyyyyyfyfffyyyyyyyyyy; $1^{st}$: efyyyyyyyyyyyyfyfyyyyyyy and $2^{nd}$: eeyyyyyfyfffyyyyyyyyyee; $1^{st}$: efyyyyyyyyyyyyfyfyyyyyee and $2^{nd}$: eeyyyyyyyffyyyyyyyyee; $1^{st}$: efyyyyyyyyyyyyfyfyyyyyyy and $2^{nd}$: yyyyyyyyyffyyyyyyyyyy; $1^{st}$: efyyyyyyyyyyyyfyfyyyyyee and $2^{nd}$: yyyyyyyyyffyyyyyyyyyy; $1^{st}$: efyyyyyyyyyyyyfyfyyyyyee and $2^{nd}$: eeyyyyyfyfyfyyyyyyyyee; $1^{st}$: efyyyyyyyyyyyyfyfyyyyyyy and $2^{nd}$: yyyyyyfyfyfyyyyyyyyyy; $1^{st}$: efyyyyyyyyyyyyfyfyyyyyee and $2^{nd}$: yyyyyyfyfyfyyyyyyyyyy; $1^{st}$: efyyyfyyyyyyyfyfyyyyyyy and $2^{nd}$: yyyyyyyyyffyyyyyyyyyy; $1^{st}$: efyyyfyyyyyyyfyfyyyyyee and $2^{nd}$: eeyyyyyyyffyyyyyyyyee; $1^{st}$: efyyyfyyyyyyyfyfyyyyyyy and $2^{nd}$: eeyyyyyyyffyyyyyyyyee; $1^{st}$: efyyyfyyyyyyyfyfyyyyyee and $2^{nd}$: yyyyyyyyyffyyyyyyyyyyY; $1^{st}$: efyyyfyyyyyyyfyfyyyyyyy and $2^{nd}$: yy yyf yYYyyyyyy; $1^{st}$: efyyyfyyyyyyyfyfyyyyyee and $2^{nd}$: eeyyyyyfyfyfyyyyyyyyee; $1^{st}$: efyyyfyyyyyyyfyfyyyyyyy and $2^{nd}$: eeyyyyyfyfyfyyyyyyyyee; $1^{st}$: efyyyfyyyyyyyfyfyyyyyee and $2^{nd}$: yyyyyyfyjfYy yyyyyyy; $1^{st}$: efyyyfyyyyyyyfyfyyyee and $2^{nd}$: eeyyyyyfyfffyyyyyyyee; $1^{st}$: efyyyfyyyyyyyfyfyyyyy and $2^{nd}$: yyyyyyfyfffyyyyyyyyy; $1^{st}$: efyyyfyyyyyyyfyfyyyee and $2^{nd}$: yyyyyyfyfffyyyyyyyyy; $1^{st}$: efyyyfyyyyyyyfyfyyyyy and $2^{nd}$: eeyyyyyfyfffyyyyyyyee; $1^{st}$: efyyyfyyyyyyyfyfyyyee and $2^{nd}$: eeyyyyfyyyyyyyyee; $1^{st}$: efyyyfyyyyyyyfyfyyyyy and $2^{nd}$: yyyyyyffyyyyyyyyyy; $1^{st}$: efyyyfyyyyyyyfyfyyyee and $2^{nd}$: yyyyyyffyyyyyyyyyy; $1^{st}$: efyyyfyyyyyyyfyfyyyyy and $2^{nd}$: eeyyyyfyyyyyyyyee; $1^{st}$: e[FHNA]yydydyyyyfyfyfyyyyyee and $2^{nd}$: eeyyyyfyfffyyyyyyyee; $1^{st}$: efyyyfyyyyyyyfyfyyyyyey and $2^{nd}$: eeyyyyfyfffyyyyyyyee; $1^{st}$: efyyyfyyyyyyyfyfyyyyyey and $2^{nd}$: yyyyyyfyfffyyyyyyyyyy; $1^{st}$: e[FHNA] yydydyyyyfyfyfyyyyyy and $2^{nd}$: yyyyyyfyfffyyyyyyyyyy; $1^{st}$: e[FHNA]yydydyyyyfyfyfyyyyyee and $2^{nd}$: yyyyyyfyfffyyyyyyyyyy; $1^{st}$: e[FHNA] yydydyyyyfyfyfyyyyyy and $2^{nd}$: eeyyyyfyfffyyyyyyyyyee; $1^{st}$: e[FHNA]yydydyyyyfyfyfyyyyyee and $2^{nd}$: eeyyyyfyfyfyyyyyyyyyee; $1^{st}$: e[FHNA] yydydyyyyfyfyfyyyyyy and $2^{nd}$: yyyyyyfyfyfyyyyyyyyyy; $1^{st}$: e[FHNA]yydydyyyyfyfyfyyyyyee and $2^{nd}$: yyyyyyfyfyyyyyyyyyy; and $1^{st}$: e[FHNA] yydydyyyyfyfyfyyyyyy and $2^{nd}$: eeyyyyfyfyfyyyyyyyyee, wherein each "y" represents a 2'-OMe sugar moiety, each "e" represents a 2'-MOE sugar moiety, each "f" represents a 2'-fluoro sugar moiety, each "[FHNA]" represents a 3'-fluoro-hexitol sugar moiety, and each "d" represents a 2'-deoxy sugar moiety.

Embodiment 184

The oligomeric duplex of any one of embodiments 1-4, 12, 18, 19, 30-69, 72, 80, 105-115, 117-139, 152, 153, and 175-181, wherein the first modified oligonucleotide has a first sugar motif ($1^{st}$) and the second modified oligonucleotide has a second sugar motif ($2^{nd}$) and the first and second sugar motifs are selected from among the following combinations (5' to 3'); $1^{st}$: efyyyfyyyyyyyfyfyyyyyyy and $2^{nd}$: yyyyyyfyfffyyyyyyyyyy; $1^{st}$: efyyyfyyyyyyyfyfyyyyyee and $2^{nd}$: eeyyyyyfyfffyyyyyyyyyee; $1^{st}$: efyyyfyyyyyyyfyfyyyyyee and $2^{nd}$: yyyyyyfyfffyyyyyyyyyy; and $1^{st}$: efyyyfyyyyyyyfyfyyyyyyy and $2^{nd}$: eeyyyyyfyfffyyyyyyyyyee, wherein each "y" represents a 2'-OMe sugar moiety, each "e" represents a 2'-MOE sugar moiety, and each "f" represents a 2'-fluoro sugar moiety.

Embodiment 185

The oligomeric duplex of any one of embodiments 1-4, 12, 18, 19, 30-69, 72, 80, 105-115, 117-139, 152, 153, and 175-181, wherein the first modified oligonucleotide has a first sugar motif ($1^{st}$) and the second modified oligonucleotide has a second sugar motif ($2^{nd}$) and the first and second sugar motifs are selected from among the following combinations (5' to 3'); $1^{st}$: efyyyfyyyyyyyfyfyyyyyyy and $2^{nd}$: yyyyyyyyyyyyyyyyyyyy; $1^{st}$: efyyyfyyyyyyyfyfyyyyyee and $2^{nd}$: eeyyyyyyyyyyyyyyyyyyee; $1^{st}$: efyyyfyyyyyyyfyfyyyyyee and $2^{nd}$: yyyyyyyyyyyyyyyyyyyy; $1^{st}$: efyyyfyyyyyyyfyfyyyyyyy and $2^{nd}$: eeyyyyyyyyyyyyyyyyyyee; $1^{st}$: efyyyfyyyyyyyfyfyyyyyyy and $2^{nd}$: yyyyyyyyyydyyyyyyyyyy; $1^{st}$: efyyyfyyyyyyyfyfyyyyyee and $2^{nd}$: eeyyyyyyyydyyyyyyyyee; $1^{st}$: efyyyfyyyyyyyfyfyyyyyyy and $2^{nd}$: eeyyyyyyyydyyyyyyyyee; $1^{st}$: efyyyfyyyyyyyfyfyyyyyee and $2^{nd}$: yyyyyyyyyydyyyyyyyyyy; $1^{st}$: efyyyyfyfffyyyyyyyyee; $1^{st}$: efYyyyyyyyyyyyfyyyyyyyyy and $2^{nd}$: yyyyyyfyfffyyyyyyyyyy; $1^{st}$: efyyyyyyyyyyyfyyyyyyyee and $2^{nd}$: yyyyyyfyfffyyyyyyyyyy; $1^{st}$: efyyyyyyyyyyyyfyyyyyyyyy and $2^{nd}$: eeyyyyyfyfffyyyyyyyyee; $1^{st}$: efyyyyyyyyyyyfyyyyyyyee and $2^{nd}$: eeyyyyyfyfyyyyyyyyyyy; $1^{st}$: efyyyyyyyyyyyyfyyyyyyyyy and $2^{nd}$: yyyyyyfyfyyyyyyyyyyy; $1^{st}$: efyyyyyyyyyyyfyyyyyyyee and $2^{nd}$: eeyyyyfyfyyyyyyyyyee; $1^{st}$: efyyydyyyyyyfyfyyyyyee and $2^{nd}$: eeyyyyfyfffyyyyyyyee; $1^{st}$: efyyydyyyyyyfyfyyyyyyy and $2^{nd}$: yyyyyyfyfffyyyyyyyyyy; $1^{st}$: efyyydyyyyyyfyfyyyyyee and $2^{nd}$: yyyyyyfyfffyyyyyyyyyy; $1^{st}$: efyyydyyyyyyfyfyyyyyyy and $2^{nd}$: eeyyyyfyfffyyyyyyyee; $1^{st}$: efyyyfyyyyyyyfyfyyyee and $2^{nd}$: eeyyfyfffyyyyyyyyee; $1^{st}$: efyyyfyyyyyyyfyfyyyyy and $2^{nd}$: yyyyfyfffyyyyyyyyyy; $1^{st}$: efyyyfyyyyyyyfyfyyyee and $2^{nd}$: yyyyfyfffyyyyyyyyyy; $1^{st}$: efyyyfyyyyyyyfyfyyyyy and $2^{nd}$: eeyyfyfffyyyyyyyee; $1^{st}$: efyyyfyyyyyyyfydyyyyee and $2^{nd}$: eeyyyyfyfffyyyyyyyee; $1^{st}$: efyyyfyyyyyyyfydyyyyyy and $2^{nd}$: yyyyyyfyfffyyyyyyyyyy; $1^{st}$: efyyyfyyyyyyyfydyyyyee and $2^{nd}$: yyyyyyfyfffyyyyyyyyyy; $1^{st}$: efyyyfyyyyyyyfydyyyyyy and $2^{nd}$: eeyyyyyfyfffyyyyyyyyee; $1^{st}$: e[FHNA] yyyfyyyyyyyfyfyyyyyee and $2^{nd}$: eeyyyyfyfffyyyyyyyyee; $1^{st}$e[FHNA]yyyfyyyyyyyfyfyyyyyyy and $2^{nd}$:

yyyyyyfyfffyyyyyyyyyy; 1$^{st}$: e[FHNA]
yyyfyyyyyyyfyfyyyyyee and 2$^{nd}$: yyyyyyfyfffyyyyyyyyyy;
and 1$^{st}$: e[FHNA]yyyfyyyyyyyfyfyyyyyyy and 2$^{nd}$:
eeyyyyfyfffyyyyyyyyee, wherein each "y" represents a
2'-OMe sugar moiety, each "e" represents a 2'-MOE sugar
moiety, each "f" represents a 2'-fluoro sugar moiety, each
"[FHNA]" represents a 3'-fluoro-hexitol sugar moiety, and
each "d" represents a 2'-deoxy sugar moiety.

Embodiment 186

The oligomeric duplex of any one of embodiments 1-4,
12, 18, 19, 30-69, 72, 80, 105-115, 117-139, 152, 153, and
175-181, wherein the first modified oligonucleotide has a
first sugar motif (1$^{st}$) and the second modified oligonucle-
otide has a second sugar motif (2$^{nd}$) and the first and second
sugar motifs are selected from among the following com-
binations (5' to 3'); 1$^{st}$: efyyyyyyyyyyyyfyyyyyyyee and 2$^{nd}$:
eeyyyyyyyffyyyyyyyyee; 1$^{st}$: efyyyyyyyyyyyyfyyyyyyyyy
and 2$^{nd}$: yyyyyyyyyffyyyyyyyyyY; 1$^{st}$:
efyyyyyyyyyyyyfyyyyyyyee and 2$^{nd}$:
yyyyyyyyyffyyyyyyyyyy; 1$^{st}$: efyyyyyyyyyyyyfYyyyyyyyy
and 2$^{nd}$: eeyyyyyyyffyyyyyyyyee; 1$^{st}$:
efyyyfyyyyyyyfyyyyyyyee and 2$^{nd}$:
eeyyyyfyfffyyyyyyyyee; 1$^{st}$: efyyyfyyyyyyyfyyyyyyyyy
and 2$^{nd}$: yyyyyyfyfffyyyyyyyyyy; 1$^{st}$:
efyyyfyyyyyyyfyyyyyyyee and 2$^{nd}$:
yyyyyyfyfffyyyyyyyyyy; 1$^{st}$: efyyyfyyyyyyyfyyyyyyyyy
and 2$^{nd}$: eeyyyyfyfffyyyyyyyyee; 1$^{st}$:
efyyyfyyyyyyyfyyyyyyyee and 2$^{nd}$:
eeyyyyyyyffyyyyyyyyee; 1$^{st}$: efyyyfyyyyyyyfyyyyyyyyy
and 2$^{nd}$: yyyyyyyyyffyyyyyyyyyy; 1$^{st}$:
efyyyfyyyyyyyfyyyyyyyee and 2$^{nd}$:
yyyyyyfyfffyyyyyyyyyy; and 1$^{st}$:
efyyyfyyyyyyyfyyyyyyyy and 2$^{nd}$:
eeyyyyfyfffyyyyyyyyee, wherein each "y" represents a
2'-OMe sugar moiety, each "c" represents a 2'-MOE sugar
moiety, and each "f" represents a 2'-fluoro sugar moiety.

Embodiment 187

The oligomeric duplex of any one of embodiments 123-
186, wherein the internucleoside linkages between the first
and second nucleosides and the second and third nucleosides
counting from the 5' end of the first modified oligonucle-
otide, and the internucleoside linkages between the first and
second nucleosides and the second and third nucleosides
counting from the 3' end of the first modified oligonucleotide
are phosphorothioate internucleoside linkages and wherein
all other internucleoside linkages of the first modified oli-
gonucleotide are phosphodiester internucleoside linkages.

Embodiment 188

The oligomeric duplex of any one of embodiments 123-
187, wherein the internucleoside linkages between the first
and second nucleosides and the second and third nucleosides
counting from the 5' end of the second modified oligonucle-
otide, and the internucleoside linkages between the first and
second nucleosides and the second and third nucleosides
counting from the 3' end of the second modified oligonucle-
otide are phosphorothioate internucleoside linkages and
wherein all other internucleoside linkages of the second
modified oligonucleotide are phosphodiester internucleoside
linkages.

Embodiment 189

The oligomeric duplex of any one of embodiments 123-
188, wherein the nucleobase sequence of the first modified oligonucleotide comprises or consists of the nucleobase
sequence of any one of SEQ ID NOs: 967, 968, 971, 972,
974, 975, 1033-1038, 1254-1255, or 1258-1287.

Embodiment 190

The oligomeric duplex of any one of embodiments 1-189,
wherein a cytosine nucleobase in the first and/or second
modified oligonucleotide is optionally 5-methylcytosine.

Embodiment 191

The oligomeric duplex of any one of embodiments 123-
190, wherein the oligomeric duplex comprises a conjugate
group comprising a conjugate moiety and a conjugate linker.

Embodiment 192

The oligomeric duplex of embodiment 191, wherein the
conjugate moiety comprises an active drug substance, an
aliphatic chain, a lipid, a peptide, a protein, a hydrocarbon,
a polyamine, a polyamide, a polyether, a thioether, an
aptamer, an antibody, an antibody fragment, a vitamin, a
fatty acid, a carbohydrate, an intercalator or a reporter
molecule.

Embodiment 193

The oligomeric duplex of embodiment 191, wherein the
conjugate group comprises a C22 alkyl, C20 alkyl, C17
alkyl, C16 alkyl, C10 alkyl, C21 alkyl, C19 alkyl, C18 alkyl,
C15 alkyl, C14 alkyl, C13 alkyl, C12 alkyl, C11 alkyl, C9
alkyl, C8 alkyl, C7 alkyl, C6 alkyl, or C5 alkyl, wherein the
alkyl chain optionally has one or more unsaturated bonds.

Embodiment 194

The oligomeric duplex of embodiment 191, wherein the
conjugate group comprises a 6-palmitamidohexyl moiety or
a 2-(hydroxymethyl)-6-palmitamidohexyl moiety.

Embodiment 195

The oligomeric duplex of embodiment 191, wherein the
oligomeric duplex comprises a conjugate moiety that binds
type 1 transferrin receptor (TfR1).

Embodiment 196

The oligomeric duplex of embodiment 195, wherein the
conjugate moiety is selected from an antibody or fragment
thereof, a protein or peptide, and an aptamer capable of
binding TfR1.

Embodiment 197

The oligomeric duplex of embodiment 196, wherein the
conjugate moiety is a cyclic protein or cyclic peptide.

Embodiment 198

The oligomeric duplex of embodiment 195, wherein the
conjugate group comprises a bicycle ligand and a conjugate
linker.

Embodiment 199

The oligomeric duplex of embodiment 198, wherein the
bicycle ligand comprises a peptide consisting of 13-22 linked amino acids or amino acid mimetics and a molecular scaffold, wherein each of a first, a second, and a third amino acid of the peptide comprises a reactive group, each of which separately forms a bond with the molecular scaffold, thereby forming two peptide loops attached to the molecular scaffold.

Embodiment 200

The oligomeric duplex of embodiment 199 wherein the bicycle ligand comprises an amino acid sequence selected from any one of SEQ ID NO: 1062-1253.

Embodiment 201

The oligomeric duplex of any one of embodiments 198-200, wherein the conjugate linker comprises a (bicyclo[6.1.0]nonyne)-formyl (BCN) moiety.

Embodiment 202

The oligomeric duplex of any one of embodiments 198-200, wherein the conjugate linker comprises a 6-(BCN-carbamate)-2-(hydroxymethyl)hexyl phosphoryl moiety or a 6-(BCN-carbamate)hexyl phosphoryl moiety.

Embodiment 203

The oligomeric duplex of any one of embodiments 123-190, comprising a conjugate group consisting of a conjugate moiety and a conjugate linker wherein the conjugate linker comprises a 6-(BCN-carbamate)-2-(hydroxymethyl)hexyl phosphoryl moiety or a 6-(BCN-carbamate) hexyl phosphoryl moiety.

Embodiment 204

The oligomeric duplex of any one of embodiments 123-190, comprising a bicycle ligand comprising a peptide having an amino acid sequence selected from any one of SEQ ID NOs: 1062-1253 and wherein each cysteine forms a covalent bond with the molecular scaffold 1,1',1"-(1,3,5-triazinane-1,3,5-triyl)tris(2-bromoethanone) (TATB) or the molecular scaffold is 1,1',1"-(1,3,5-triazinane-1,3,5-triyl) triprop-2-en-1-one (TATA).

Embodiment 205

An oligomeric compound comprising a modified oligonucleotide according to the following chemical notation:

(SEQ ID NO: 1033)

$vPT_{es}U_{fs}U_{yo}A_{yo}A_{yo}G_{do}A_{yo}U_{yo}G_{yo}A_{yo}G_{yo}A_{yo}C_{yo}A_{yo}G_{yo}A_{yo}A_{yo}A_{yo}$ $U_{yo}U_{yo}G_{ys}A_{es}A^e$, wherein:
    A=an adenine nucleobase,
    C=a cytosine nucleobase,
    G=a guanine nucleobase,
    T=a thymine nucleobase,
    U=a uracil nucleobase,
    d=a 2'-deoxy sugar moiety,
    e=a 2'-MOE sugar moiety,
    f=a 2'-fluoro sugar moiety,
    y=a 2'-OMe sugar moiety,
    o=a phosphodiester internucleoside linkage,

48 s=a phosphorothioate internucleoside linkage, and
    vP=a 5' vinyl phosphonate group.

Embodiment 206

An oligomeric compound comprising a modified oligonucleotide according to the (SEQ ID NO: 1027)

$^mC_{es}A_{es}A_{yo}U_{yo}U_{yo}U_{yo}C_{yo}U_{yo}G_{yo}U_{fo}C_{fo}U_{yo}C_{yo}A_{yo}U_{yo}C_{yo}$ $U_{yo}U_{yo}A_{ys}A_{es}A_e$, wherein:
    A=an adenine nucleobase,
    $^mC$=a 5-methyl cytosine nucleobase,
    C=a cytosine nucleobase,
    G=a guanine nucleobase,
    U=a uracil nucleobase,
    e=a 2'-MOE sugar moiety,
    f=a 2'-fluoro sugar moiety,
    y=a 2'-OMe sugar moiety,
    o=a phosphodiester internucleoside linkage, and
    s=a phosphorothioate internucleoside linkage.

Embodiment 207

An oligomeric compound comprising a conjugated modified oligonucleotide according to the following chemical notation:

(SEQ ID NO: 1039)

$[X]_1\text{-}^mC_{es}A_{es}A_{yo}U_{yo}U_{yo}U_{yo}C_{yo}U_{yo}G_{yo}U_{fo}C_{fo}U_{yo}C_{yo}A_{yo}$ $U_{yo}C_{yo}U_{yo}U_{yo}A_{ys}A_{es}A_e$, wherein:
    $^mC$=a 5-methyl cytosine nucleobase,
    C=a cytosine nucleobase,
    A=an adenine nucleobase,
    G=a guanine nucleobase,
    U=a uracil nucleobase,
    e=a 2'-MOE sugar moiety,
    f=a 2'-fluoro sugar moiety,
    y=a 2'-OMe sugar moiety,
    o=a phosphodiester internucleoside linkage,
    s=a phosphorothioate internucleoside linkage,
    [X]=a conjugate group comprising a bicycle ligand, and
    n and k are 0 or 1, wherein if n=1 then k=0, and if n=0 then k=1.

Embodiment 208

An oligomeric duplex comprising the oligomeric compound according to embodiment 205 and the oligomeric compound according to embodiment 206.

Embodiment 209

An oligomeric duplex comprising the oligomeric compound according to embodiment 205 and the oligomeric compound according to embodiment 207.

Embodiment 210

An oligomeric compound comprising a modified oligonucleotide according to the following chemical notation:

(SEQ ID NO: 1034)

$vPT_{es}U_{fs}U_{yo}A_{yo}A_{do}G_{yo}A_{do}U_{yo}G_{yo}A_{yo}G_{yo}A_{yo}C_{yo}A_{ro}G_{yo}$ $A_{ro}A_{yo}A_{yo}U_{yo}U_{yo}G_{ys}A_{es}A_{e}$, wherein:

A=an adenine nucleobase,

C=a cytosine nucleobase,

G=a guanine nucleobase,

T=a thymine nucleobase,

U=a uracil nucleobase, d=a 2'-deoxy sugar moiety, e=a 2'-MOE sugar moiety, f=a 2'-fluoro sugar moiety, y=a 2'-OMe sugar moiety, o=a phosphodiester internucleoside linkage, s=a phosphorothioate internucleoside linkage, and vP=a 5' vinyl phosphonate group.

Embodiment 211

An oligomeric compound comprising a modified oligonucleotide according to the following chemical notation:

(SEQ ID NO: 1028)

$C_{es}A_{es}A_{yo}U_{yo}U_{yo}U_{yo}C_{fo}U_{yo}G_{ro}U_{yo}C_{fo}U_{yo}C_{yo}A_{yo}U_{yo}C_{yo}$ $U_{yo}U_{yo}A_{ys}A_{es}A_{e}$, wherein:

A=an adenine nucleobase,

C=a cytosine nucleobase,

G=a guanine nucleobase,

U=a uracil nucleobase, e=a 2'-MOE sugar moiety, f=a 2'-fluoro sugar moiety, y=a 2'-Ome sugar moiety, o=a phosphodiester internucleoside linkage, and s=a phosphorothioate internucleoside linkage.

Embodiment 212

An oligomeric compound comprising a conjugated modified oligonucleotide according to the following chemical notation:

(SEQ ID NO: 1040)

$[X]_1-C_{es}A_{es}A_{yo}U_{yo}U_{yo}U_{yo}C_{fo}U_{yo}G_{ro}U_{yo}C_{fo}U_{yo}C_{yo}A_{yo}$ $U_{yo}C_{yo}U_{yo}U_{yo}A_{ys}A_{es}A_{e}$, wherein:

C=a cytosine nucleobase,

A=an adenine nucleobase,

G=a guanine nucleobase,

U=a uracil nucleobase, e=a 2'-MOE sugar moiety, f=a 2'-fluoro sugar moiety, y=a 2'-Ome sugar moiety, o=a phosphodiester internucleoside linkage, s=a phosphorothioate internucleoside linkage,

[X]=a conjugate group comprising a bicycle ligand, and n and k are 0 or 1, wherein if n=1 then k=0, and if n=0 then k=1.

Embodiment 213

An oligomeric duplex comprising an oligomeric compound of embodiment 210 and an oligomeric compound of embodiment 211.

Embodiment 214

An oligomeric duplex comprising an oligomeric compound of embodiment 210 and an oligomeric compound of embodiment 212.

Embodiment 215

An oligomeric compound comprising a modified oligonucleotide according to the following chemical notation:

(SEQ ID NO: 1035)

$vPT_{es}A_{fs}U_{yo}A_{yo}A_{yo}A_{do}U_{yo}A_{yo}G_{yo}A_{yo}U_{yo}U_{yo}C_{yo}U_{fo}G_{yo}U_{fo}$ $A_{yo}G_{yo}C_{yo}U_{yo}U_{ys}A_{es}A_{e}$, wherein:

A=an adenine nucleobase,

C=a cytosine nucleobase,

G=a guanine nucleobase,

T=a thymine nucleobase,

U=a uracil nucleobase, d=a 2'-deoxy sugar moiety, e=a 2'-MOE sugar moiety, f=a 2'-fluoro sugar moiety, y=a 2'-OMe sugar moiety, o=a phosphodiester internucleoside linkage, s=a phosphorothioate internucleoside linkage, and vP=a 5' vinyl phosphonate group.

Embodiment 216

An oligomeric compound comprising a modified oligonucleotide according to the following chemical notation:

{319

(SEQ ID NO: 1029)

$A_{es}A_{es}G_{yo}C_{yo}U_{yo}A_{yo}C_{yo}A_{yo}G_{yo}A_{yo}A_{yo}U_{yo}C_{yo}U_{yo}A_{yo}U_{yo}$ $U_{yo}U_{yo}A_{ys}T_{es}A_{e}$, wherein:

A=an adenine nucleobase,

C=a cytosine nucleobase,

G=a guanine nucleobase,

T=a thymine nucleobase,

U=a uracil nucleobase, e=a 2'-MOE sugar moiety, f=a 2'-fluoro sugar moiety, y=a 2'-OMe sugar moiety, o=a phosphodiester internucleoside linkage, and s=a phosphorothioate internucleoside linkage.

Embodiment 217

An oligomeric compound comprising a conjugated modified oligonucleotide according to the following chemical notation:

(SEQ ID NO: 1041)

$[X]_1-A_{es}A_{es}G_{yo}C_{yo}U_{yo}A_{yo}C_{yo}A_{yo}G_{yo}A_{fo}A_{fo}U_{yo}C_{yo}U_{yo}$ $A_{yo}U_{yo}U_{yo}U_{yo}A_{ys}T_{es}A_e$, wherein:
C=a cytosine nucleobase,
A=an adenine nucleobase,
G=a guanine nucleobase,
T=a thymine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage,
[X]=a conjugate group comprising a bicycle ligand, and
n and k are 0 or 1, wherein if n=1 then k=0, and if n=0 then k=1.

Embodiment 218

An oligomeric duplex comprising an oligomeric compound of embodiment 215 and an oligomeric compound of embodiment 216.

Embodiment 219

An oligomeric compound comprising an oligomeric compound of embodiment 215 and an oligomeric compound of embodiment 217.

Embodiment 220

An oligomeric compound comprising a modified oligonucleotide according to the following chemical notation:

(SEQ ID NO: 1036)

$vPT_{es}A_{fs}U_{yo}A_{yo}A_{do}A_{yo}T_{do}A_{yo}G_{yo}A_{yo}U_{yo}U_{yo}C_{yo}U_{fo}G_{yo}U_{fo}$ $A_{yo}G_{yo}C_{yo}U_{yo}U_{ys}A_{es}A_e$, wherein:
A=an adenine nucleobase,
C=a cytosine nucleobase,
G=a guanine nucleobase,
T=a thymine nucleobase,
U=a uracil nucleobase,
d=a 2'-deoxy sugar moiety,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage, and
vP=a 5' vinyl phosphonate group.

Embodiment 221

An oligomeric compound comprising a modified oligonucleotide according to the (SEQ ID NO: 1030)

$A_{es}A_{es}G_{yo}C_{yo}U_{yo}A_{yo}C_{fo}A_{yo}G_{fo}A_{yo}A_{fo}U_{yo}C_{yo}U_{yo}A_{yo}U_{yo}$ $U_{yo}U_{yo}A_{ys}U_{es}A_e$, wherein:
A=an adenine nucleobase,
C=a cytosine nucleobase,
G=a guanine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage, and
s=a phosphorothioate internucleoside linkage.

Embodiment 222

An oligomeric compound comprising a conjugated modified oligonucleotide according to the following chemical notation:

(SEQ ID NO: 1042)

$[X]_n-A_{es}A_{es}G_{yo}C_{yo}U_{yo}A_{yo}C_{fo}A_{yo}G_{fo}A_{yo}A_{fo}U_{yo}C_{yo}U_{yo}$ $A_{yo}U_{yo}U_{yo}U_{yo}A_{ys}U_{es}A_e-[X]_k$, wherein:
C=a cytosine nucleobase,
A=an adenine nucleobase,
G=a guanine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage,
[X]=a conjugate group comprising a bicycle ligand, and
n and k are 0 or 1, wherein if n=1 then k=0, and if n=0 then k=1.

Embodiment 223

An oligomeric duplex comprising an oligomeric compound of embodiment 220 and an oligomeric compound of embodiment 221.

Embodiment 224

An oligomeric duplex comprising an oligomeric compound of embodiment 220 and an oligomeric compound of embodiment 222.

Embodiment 225

An oligomeric compound comprising a modified oligonucleotide according to the following chemical notation:

(SEQ ID NO: 1037)

$vPT_{es}U_{fs}A_{yo}A_{yo}G_{yo}T_{do}U_{yo}U_{yo}U_{yo}A_{yo}G_{yo}U_{yo}C_{yo}U_{fo}U_{yo}A_{fo}$ $A_{yo}U_{yo}C_{yo}U_{yo}U_{ys}A_{es}A_e$, wherein:
A=an adenine nucleobase,
C=a cytosine nucleobase,
G=a guanine nucleobase,
T=a thymine nucleobase,
U=a uracil nucleobase,
d=a 2'-deoxy sugar moiety,
e=a 2'-MOE sugar moiety,
f=a 2'-fluoro sugar moiety,
y=a 2'-OMe sugar moiety,

53 o=a phosphodiester internucleoside linkage,
s=a phosphorothioate internucleoside linkage, and
vP=a 5' vinyl phosphonate group.

Embodiment 226

An oligomeric compound comprising a modified oligo-nucleotide according to the following chemical notation:

(SEQ ID NO: 1031)

$A_{es}A_{es}G_{yo}A_{yo}U_{yo}U_{yo}A_{yo}A_{yo}G_{yo}A_{fo}C_{fo}U_{yo}A_{yo}A_{yo}A_{yo}A_{yo}$ $C_{yo}U_{yo}U_{ys}A_{es}A_{e}$, wherein:
A=an adenine nucleobase,
C=a cytosine nucleobase,
G=a guanine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage, and
s=a phosphorothioate internucleoside linkage.

Embodiment 227

An oligomeric compound comprising a conjugated modi-fied oligonucleotide according to the following chemical notation:

(SEQ ID NO: 1043)

$[X]_1-A_{es}A_{es}G_{yo}A_{yo}U_{yo}U_{yo}A_{yo}A_{yo}G_{yo}A_{fo}C_{fo}U_{yo}A_{yo}A_{yo}$ $A_{yo}A_{yo}C_{yo}U_{yo}U_{ys}A_{es}A_{e}$, wherein:
C=a cytosine nucleobase,
A=an adenine nucleobase,
G=a guanine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage,
[X]=a conjugate group comprising a bicycle ligand, and
n and k are 0 or 1, wherein if n=1 then k=0, and if n=0 then k=1.

Embodiment 228

An oligomeric duplex comprising the modified oligo-nucleotide according to embodiment 225 and the modified oligonucleotide according to embodiment 226.

Embodiment 229

An oligomeric duplex comprising the modified oligo-nucleotide according to embodiment 225 and the conjugate according to embodiment 227.

54

Embodiment 230

An oligomeric compound comprising a modified oligo-nucleotide according to the following chemical notation:

(SEQ ID NO: 1038)

$vPT_{es}U_{fs}A_{yo}A_{yo}G_{do}U_{yo}T_{do}U_{yo}U_{yo}A_{yo}G_{yo}U_{yo}C_{yo}U_{fo}U_{yo}A_{fo}$ $A_{yo}U_{yo}C_{yo}U_{yo}U_{ys}A_{es}A_{e}$, wherein:
A=an adenine nucleobase,
C=a cytosine nucleobase,
G=a guanine nucleobase,
T=a thymine nucleobase,
U=a uracil nucleobase,
d=a 2'-deoxy sugar moiety,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage, and
vP=a 5' vinyl phosphonate group.

Embodiment 231

An oligomeric compound comprising a modified oligo-nucleotide according to the (SEQ ID NO: 1032)

$A_{es}A_{es}G_{yo}A_{yo}U_{yo}U_{yo}A_{fo}A_{yo}G_{fo}A_{yo}C_{fo}U_{yo}A_{yo}A_{yo}A_{yo}A_{yo}$ $C_{yo}U_{yo}U_{ys}A_{es}A_{e}$, wherein:
A=an adenine nucleobase,
C=a cytosine nucleobase,
G=a guanine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage, and
s=a phosphorothioate internucleoside linkage.

Embodiment 232

An oligomeric compound comprising a conjugated modi-fied oligonucleotide according to the following chemical notation:

(SEQ ID NO: 1044)

$[X]_1-A_{es}A_{es}G_{yo}A_{yo}U_{yo}U_{yo}A_{fo}A_{yo}G_{fo}A_{yo}C_{fo}U_{yo}A_{yo}A_{yo}$ $A_{yo}A_{yo}C_{yo}U_{yo}U_{ys}A_{es}A_{e}$, wherein:

C=a cytosine nucleobase,

A=an adenine nucleobase,

G=a guanine nucleobase,

U=a uracil nucleobase, e=a 2'-MOE sugar moiety, f=a 2'-fluoro sugar moiety, y=a 2'-OMe sugar moiety, o=a phosphodiester internucleoside linkage, s=a phosphorothioate internucleoside linkage,

[X]=a conjugate group comprising a bicycle ligand, and n and k are 0 or 1, wherein if n=1 then k=0, and if n=0 then k=1.

Embodiment 233

An oligomeric duplex comprising an oligomeric compound of embodiment 230 and an oligomeric compound of embodiment 231.

Embodiment 234

An oligomeric duplex comprising an oligomeric compound of embodiment 230 and an oligomeric compound of embodiment 232.

Embodiment 235

An oligomeric compound comprising a modified oligonucleotide according to the following chemical notation:

(SEQ ID NO: 1255)

$vPT_{es}A_{fs}U_{yo}A_{yo}A_{yo}A_{yo}U_{yo}A_{yo}G_{yo}A_{yo}U_{yo}U_{yo}C_{yo}U_{fo}G_{yo}U_{fo}$ $A_{yo}G_{yo}C_{yo}U_{yo}U_{ys}A_{es}A_{e}$, wherein:

A=an adenine nucleobase,

C=a cytosine nucleobase,

G=a guanine nucleobase,

T=a thymine nucleobase,

U=a uracil nucleobase, e=a 2'-MOE sugar moiety, f=a 2'-fluoro sugar moiety, y=a 2'-OMe sugar moiety, o=a phosphodiester internucleoside linkage, s=a phosphorothioate internucleoside linkage, and vP=a 5' vinyl phosphonate group.

Embodiment 236

An oligomeric compound comprising a modified oligonucleotide according to the (SEQ ID NO: 1029)

$A_{es}A_{es}G_{yo}C_{yo}U_{yo}A_{yo}C_{yo}A_{yo}G_{yo}A_{fo}A_{fo}U_{yo}C_{yo}U_{yo}A_{yo}U_{yo}$ $U_{yo}U_{yo}A_{ys}T_{es}A_{e}$, wherein:

A=an adenine nucleobase,

C=a cytosine nucleobase,

G=a guanine nucleobase,

U=a uracil nucleobase,

T=a thymine nucleobase, e=a 2'-MOE sugar moiety, f=a 2'-fluoro sugar moiety, y=a 2'-OMe sugar moiety, o=a phosphodiester internucleoside linkage, and s=a phosphorothioate internucleoside linkage.

Embodiment 237

An oligomeric compound comprising a conjugated modified oligonucleotide according to the following chemical notation:

(SEQ ID NO: 1041)

$[X]_1-A_{es}A_{es}G_{yo}C_{yo}U_{yo}A_{yo}C_{yo}A_{yo}G_{yo}A_{fo}A_{fo}U_{yo}C_{yo}U_{yo}$ $A_{yo}U_{yo}U_{yo}U_{yo}A_{ys}T_{es}A_{e}$, wherein:

C=a cytosine nucleobase,

A=an adenine nucleobase,

G=a guanine nucleobase,

U=a uracil nucleobase,

T=a thymine nucleobase, e=a 2'-MOE sugar moiety, f=a 2'-fluoro sugar moiety, y=a 2'-OMe sugar moiety, o=a phosphodiester internucleoside linkage, s=a phosphorothioate internucleoside linkage,

[X]=a conjugate group comprising a bicycle ligand, and n and k are 0 or 1, wherein if n=1 then k=0, and if n=0 then k=1.

Embodiment 238

An oligomeric duplex comprising the oligomeric compound according to embodiment 235 and the oligomeric compound according to embodiment 236.

Embodiment 239

An oligomeric duplex comprising the oligomeric compound according to embodiment 235 and the oligomeric compound according to embodiment 237.

Embodiment 240

The oligomeric duplex of any one of embodiments 123-190, 209, 214, 219, 224, 229, 234, 239, or the oligomeric compound of any one of embodiments 207, 212, 217, 222, 227, 232, or 237, comprising a bicycle ligand or conjugate group having the following structure:

or a salt thereof, wherein Q is $N_3$ (BCY17901, SEQ ID NO: 1045), $NH_2$ (BCY21757, SEQ ID NO: 1202), SH (BCY21758, SEQ ID NO:1203), or a conjugate linker, or a conjugate linker covalently connected to an oligonucleotide.

Embodiment 241

The oligomeric duplex or oligomeric compound of embodiment 240, wherein Q is $N_3$ or a conjugate linker.

Embodiment 242

The oligomeric duplex of any one of embodiments 123-190, 209, 214, 219, 224, 229, 234, 239, or the oligomeric compound of any one of embodiments 207, 212, 217, 222, 227, 232, or 237, comprising a conjugate group having the following structure (SEQ ID NO: 1291):

Embodiment 243

The oligomeric duplex of any one of embodiments 123-190, 209, 214, 219, 224, 229, 234, 239, or the oligomeric compound of any one of embodiments 207, 212, 217, 222, 227, 232, or 237, comprising a conjugate group having the following structure (SEQ ID NO: 1292):

61
62

Embodiment 244

The oligomeric duplex or oligomeric compound of any one of embodiments 191-243, wherein the conjugate group is attached to the second modified oligonucleotide.

Embodiment 245

The oligomeric duplex or compound of any one of embodiments 191-243, wherein the conjugate group is attached to the 5'- or 3'-end of the second modified oligonucleotide.

Embodiment 246

The oligomeric duplex or oligomeric compound of any one of embodiments 191-243, wherein the conjugate group is attached to the 5'-terminal nucleoside of the second modified oligonucleotide.

Embodiment 247

An oligomeric duplex according to the following chemical structure:

(SEQ ID NO: 1033 and SEQ ID NO: 1027)

-continued or a salt thereof.

Embodiment 248

The oligomeric duplex of embodiment 247, which is the sodium salt or potassium

Embodiment 249

An oligomeric duplex according to the following chemical structure:

(SEQ ID NO: 1033 and SEQ ID NO: 1027)

-continued

Embodiment 250

An oligomeric duplex according to the following chemical structure:

(SEQ ID NO: 1033 and SEQ ID NO: 1039; peptide sequence disclosed as SEQ ID NO: 1293)

or a salt thereof.

Embodiment 251

The oligomeric duplex of embodiment 250, which is the sodium salt or potassium salt.

Embodiment 252

An oligomeric duplex according to the following chemical structure:

(SEQ ID NO: 1033 and SEQ ID NO: 1039; peptide sequence disclosed as SEQ ID NO: 1293)

-continued

Embodiment 253

An oligomeric duplex according to the following chemical structure:

(SEQ ID NO: 1034 and SEQ ID NO: 1028)

-continued

-continued

Embodiment 254

The oligomeric duplex of embodiment 253, which is the sodium salt or potassium

Embodiment 255

An oligomeric duplex according to the following chemical structure:

(SEQ ID NO: 1034 and SEQ ID NO: 1028)

Embodiment 256

An oligomeric duplex according to the following chemical structure:

(SEQ ID NO: 1034 and SEQ ID NO: 1040; peptide sequence disclosed as SEQ ID NO: 1294)

-continued or a salt thereof.

Embodiment 257

The oligomeric duplex of embodiment 256, which is the sodium salt or potassium salt.

Embodiment 258

An oligomeric duplex according to the following chemical structure:

(SEQ ID NO: 1034 and SEQ ID NO: 1040; perptide sequence disclosed as SEQ ID NO: 1294)

-continued

Embodiment 259

An oligomeric duplex according to the following chemical structure:

(SEQ ID NO: 1035 and SEQ ID NO: 1029)

111
112

-continued or a salt thereof.

Embodiment 260

The oligomeric duplex of embodiment 259, which is the sodium salt or potassium

Embodiment 261

An oligomeric duplex according to the following chemical structure:

115                                                              116

(SEQ ID NO: 1035 and SEQ ID NO: 1029)

-continued

-continued

Embodiment 262

An oligomeric duplex according to the following chemical structure:

(SEQ ID NO: 1035 and SEQ ID NO: 1041; peptide sequence disclosed as SEQ ID NO: 1295)

-continued

-continued or a salt thereof.

Embodiment 263

The oligomeric duplex of embodiment 262, which is the sodium salt or potassium salt.

Embodiment 264

An oligomeric duplex according to the following chemical structure:

(SEQ ID NO: 1035 and SEQ ID NO: 1041; peptide sequence disclosed as SEQ ID NO: 1295)

-continued

Embodiment 265

An oligomeric duplex according to the following chemical structure:

133                                                                 134

(SEQ ID NO: 1036 and SEQ ID NO: 1030)

-continued

-continued or a salt thereof.

Embodiment 266

The oligomeric duplex of embodiment 265, which is the sodium salt or potassium

Embodiment 267

An oligomeric duplex according to the following chemical structure:

(SEQ ID NO: 1036 and SEQ ID NO: 1030)

-continued

Embodiment 268

An oligomeric duplex according to the following chemical structure:

(SEQ ID NO: 1036 and SEQ ID NO: 1042; peptide sequence disclosed as SEQ ID NO: 1296)

-continued

-continued or a salt thereof.

Embodiment 269

The oligomeric duplex of embodiment 268, which is the sodium salt or potassium salt.

Embodiment 270

An oligomeric duplex according to the following chemical structure:

(SEQ ID NO: 1036 and SEQ ID NO: 1042; peptide sequence disclosed as SEQ ID NO: 1296)

-continued

Embodiment 271

An oligomeric duplex according to the following chemical structure:

157 158

(SEQ ID NO: 1037 and SEQ ID NO: 1031)

-continued

-continued or a salt thereof.

Embodiment 272

The oligomeric duplex of embodiment 271, which is the sodium salt or potassium

Embodiment 273

An oligomeric duplex according to the following chemical structure:

(SEQ ID NO: 1037 and SEQ ID NO: 1031)

-continued

Embodiment 274

An oligomeric duplex according to the following chemical structure:

(SEQ ID NO: 1037 and SEQ ID NO: 1043; peptide sequence disclosed as SEQ ID NO: 1297)

-continued or a salt thereof.

Embodiment 275

The oligomeric duplex of embodiment 274, which is the sodium salt or potassium salt.

Embodiment 276

An oligomeric duplex according to the following chemical structure:

(SEQ ID NO: 1037 and SEQ ID NO: 1043; peptide sequence disclosed as SEQ ID NO: 1297)

-continued

-continued

Embodiment 277

An oligomeric duplex according to the following chemical structure:

181

182

(SEQ ID NO: 1038 and SEQ ID NO: 1032)

-continued

-continued or a salt thereof.

Embodiment 278

The oligomeric duplex of embodiment 277, which is the sodium salt or potassium salt.

Embodiment 279

An oligomeric duplex according to the following chemical structure:

(SEQ ID NO: 1038 and SEQ ID NO: 1032)

-continued

-continued

Embodiment 280

An oligomeric duplex according to the following chemical structure:

(SEQ ID NO: 1038 and SEQ ID NO: 1044, peptide sequence disclosed as SEQ ID NO: 1298)

-continued or a salt thereof.

Embodiment 281

The oligomeric duplex of embodiment 280, which is the sodium salt or potassium salt.

Embodiment 282

An oligomeric duplex according to the following chemical structure:

(SEQ ID NO: 1038 and SEQ ID NO: 1044, peptide sequence disclosed as SEQ ID NO: 1298)

201

202

-continued

Embodiment 283

An oligomeric duplex according to the following chemical structure:

205

206

(SEQ ID NO: 1255 and SEQ ID NO: 1029)

-continued

-continued or a salt thereof.

Embodiment 284

The oligomeric duplex of embodiment 283, which is the sodium salt or potassium

Embodiment 285

An oligomeric duplex according to the following chemical structure:

211

212

(SEQ ID NO: 1255 and SEQ ID NO: 1029)

213                                                                                        214

-continued

Embodiment 286

An oligomeric duplex according to the following chemical structure:

(SEQ ID NO: 1255 and SEQ ID NO: 1041; peptide sequence disclosed as SEQ ID NO: 1295)

-continued

-continued or a salt thereof.

Embodiment 287

The oligomeric duplex of embodiment 286, which is the sodium salt or potassium

Embodiment 288

An oligomeric duplex according to the following chemical structure:

(SEQ ID NO: 1255 and SEQ ID NO: 1041; peptide sequence disclosed as SEQ ID NO: 1295)

225                                                                                                                              226

-continued

-continued

Embodiment 289

A population of oligomeric duplexes or oligomeric compounds of any one of embodiments 1-288, wherein the population is enriched for first and/or second modified oligonucleotides comprising at least one particular phosphorothioate internucleoside linkage having a particular stereochemical configuration.

Embodiment 290

The population of embodiment 289, wherein the population is enriched for first and/or second modified oligonucleotides comprising at least one particular phosphorothioate internucleoside linkage having the (Sp) or (Rp) configuration.

Embodiment 291

The oligomeric duplex or oligomeric compound of any one of embodiments 1-288, wherein the first modified oligonucleotide consists of 23 linked nucleosides and the second modified oligonucleotide consists of 21 linked nucleosides.

Embodiment 292

An antisense compound comprising or consisting of an oligomeric duplex or oligomeric compound of any one of embodiments 1-288.

Embodiment 293

The antisense compound of embodiment 292, wherein the antisense compound is an RNAi agent capable of reducing the amount of PLN nucleic acid through the activation of RISC/Ago2.

Embodiment 294

A pharmaceutical composition comprising the oligomeric duplex or oligomeric compound of any one of embodiments 1-288 or 291, the population of any one of embodiments 289-290, or the antisense compound of embodiment 292 or embodiment 293, and a pharmaceutically acceptable diluent or carrier.

Embodiment 295

The pharmaceutical composition of embodiment 294, wherein the pharmaceutically acceptable diluent is water or phosphate-buffered saline.

Embodiment 296

The pharmaceutical composition of embodiment 295, wherein the pharmaceutical composition consists essentially of the oligomeric duplex, oligomeric compound or the antisense compound, and water or phosphate-buffered saline.

Embodiment 297

A method of decreasing the amount of PLN RNA and/or PLN protein in a cell, tissue, organ or subject, comprising contacting the cell, tissue, organ or subject with the oligomeric duplex or oligomeric compound of any one of embodiments 1-288 or 291, the population of any one of embodiments 289-290, or the antisense compound of embodiment 292 or embodiment 293, or the pharmaceutical composition of any one of embodiments 294-296.

Embodiment 298

The method of embodiment 297, wherein the cell is a muscle cell and/or a cardiac cell.

Embodiment 299

A method comprising administering to a subject the oligomeric duplex or oligomeric compound of any one of embodiments 1-288 or 291, the population of any one of embodiments 289-290, or the antisense compound of embodiment 292 or embodiment 293, or the pharmaceutical composition of any one of embodiments 294-296; wherein the subject has or is at risk for developing a cardiovascular or cardiac injury, disease, condition or disorder, cardiomyopathy, cardiac arrythmia, and/or heart failure.

Embodiment 300

A method of preventing or treating a disease, disorder, condition or injury associated with cardiac calcium misregulation, or postponing a symptom of a disease, disorder or condition associated with a damaged, weakened and/or overworked heart, comprising administering to a subject having, or at risk of having, a disease, disorder or condition associated with cardiac calcium misregulation a therapeutically effective amount of the oligomeric duplex or oligomeric compound of any one of embodiments 1-288 or 291, the population of any one of embodiments 289-290, or the antisense compound of embodiment 292 or embodiment 293, or the pharmaceutical composition of any one of embodiments 294-296; wherein the disease, disorder, condition or injury is selected from a cardiac or cardiovascular disease, disorder, condition or injury, a cardiomyopathy, cardiac arrythmia, and/or heart failure.

Embodiment 301

A method of preventing or treating a cardiac or cardiovascular disease, disorder, condition or injury associated with heart failure, or postponing a symptom of heart failure, comprising administering to a subject having, or at risk of having, a cardiac or cardiovascular disease, disorder, condition or injury a therapeutically effective amount of the oligomeric duplex or oligomeric compound of any one of embodiments 1-288 or 291, the population of any one of embodiments 289-290, or the antisense compound of embodiment 292 or embodiment 293, or the pharmaceutical composition of any one of embodiments 294-296; wherein the disease, disorder, condition or injury is a cardiomyopathy, cardiac arrythmia, and/or heart failure.

Embodiment 302

A method of decreasing the amount of PLN RNA and/or PLN protein in the heart of a subject having or at risk of developing a disease, disorder or condition associated with a damaged, weakened and/or overworked heart, comprising administering to a subject having, or at risk of having, a disease, disorder or condition associated with a damaged, weakened and/or overworked heart a therapeutically effective amount of the oligomeric duplex or oligomeric compound of any one of embodiments 1-288 or 291, the population of any one of embodiments 289-290, or the antisense compound of embodiment 292 or embodiment 293, or the pharmaceutical composition of any one of embodiments 294-296; wherein the disease, disorder, condition or injury is a cardiomyopathy, cardiac arrythmia, and/or heart failure.

Embodiment 303

The method of any one of embodiments 297-302, wherein the amount of PLN RNA and/or PLN protein in cardiac muscle of the subject is decreased.

Embodiment 304

The method of any one of embodiments 297-302, wherein the disease, disorder or condition is cardiomyopathy or arrhythmia.

Embodiment 305

The method of embodiment 304, wherein the cardiomyopathy is genetic cardiomyopathy.

Embodiment 306

The method of embodiment 305, wherein the genetic cardiomyopathy is associated with PLN p.Arg14del, Arg9Cys (R9C), or Arg25Cys (R25C) genetic mutations.

Embodiment 307

The method of embodiment 304, wherein the cardiomyopathy is dilated cardiomyopathy (DCM).

Embodiment 308

The method of embodiment 307 wherein the DCM is genetic DCM.

Embodiment 309

The method of embodiment 308, wherein the genetic DCM is associated with TTN, LMNA, RBM20, SCN5A, MYH7, TNNT2, or TPM1 mutations.

Embodiment 310

The method of embodiment 307, wherein the DCM is arrhythmogenic DCM.

Embodiment 311

The method of any one of embodiments 299-303, wherein the heart failure is heart failure with preserved ejection fraction (HFpEF), heart failure with reduced ejection fraction (HFrEF), acute heart failure, or worsening of chronic heart failure.

Embodiment 312

The method of embodiment 304, wherein the arrhythmia is ventricular tachycardia (vtac) or ventricular fibrillation (vfib).

Embodiment 313

The method of embodiment 300 or embodiment 301, wherein the symptom of a disease, disorder or condition associated with a damaged, weakened and/or overworked heart, or heart failure is reduced myocardial contractile function and/or impaired relaxation of the heart.

Embodiment 314

The method of any one of embodiments 299-313, wherein the method prevents or slows progression of damaged, weakened and/or overworked heart effects and/or heart failure.

Embodiment 315

The method of any one of embodiments 299-313, wherein administering of the oligomeric duplex or oligomeric compound of any one of embodiments 1-288 or 291, the population of any one of embodiments 289-290, or the antisense compound of embodiment 292 or embodiment 293, or the pharmaceutical composition of any one of embodiments 294-296 improves cardiac function, cardiovascular death, cardiac dilation, cardiac fibrosis, low voltage ECG, diastolic calcium uptake, ejection fraction (EF), left ventricular ejection fraction (LVEF), left ventricular end systolic volume (LVESV), left ventricular end diastolic volume (LVEDV), mitral valve flow profile, left ventricle (LV) strain, left ventricle (LV) strain rate, infarct size, heart failure hospitalization, 6 minute walk test (6MWT), the Kansas City Cardiomyopathy Questionnaire Score (KCCQS), heart rate, or heart rhythm in the subject.

Embodiment 316

The method of any one of embodiments 297-315, wherein the oligomeric duplex or oligomeric compound of any one of embodiments 1-288 or 291, the population of any one of embodiments 289-290, or the antisense compound of embodiment 292 or embodiment 293, or the pharmaceutical composition of any one of embodiments 294-296 comprises a conjugate moiety having affinity for a transferrin receptor.

Embodiment 317

The method any one of embodiments 297-315, wherein the oligomeric duplex or oligomeric compound of any one of embodiments 1-288 or 291, the population of any one of embodiments 289-290, or the antisense compound of embodiment 292 or embodiment 293, or the pharmaceutical composition of any one of embodiments 294-296 comprises a bicycle ligand having affinity for a transferrin receptor.

Embodiment 318

The oligomeric duplex or oligomeric compound of any one of embodiments 1-288 or 291, the population of any one of embodiments 289-290, or the antisense compound of embodiment 292 or embodiment 293, or the pharmaceutical composition of any one of embodiments 294-296 for use in for treating or preventing a disease, disorder or condition associated with a damaged, weakened and/or overworked heart or heart failure.

Embodiment 319

Use of the oligomeric duplex or oligomeric compound of any one of embodiments 1-288 or 291, the population of any one of embodiments 289-290, or the antisense compound of embodiment 292 or embodiment 293, or the pharmaceutical composition of any one of embodiments 294-296 for treating or preventing a disease, disorder or condition associated with a damaged, weakened and/or overworked heart or heart failure.

Embodiment 320

Use of the oligomeric duplex or oligomeric compound of any one of embodiments 1-288 or 291, the population of any one of embodiments 289-290, or the antisense compound of embodiment 292 or embodiment 293, or the pharmaceutical composition of any one of embodiments 294-296 in the manufacture of a medicament for treating or preventing a disease, disorder or condition associated with a damaged, weakened and/or overworked heart or heart failure.

Embodiment 321

The use of any one of embodiments 318-320, wherein the disease, disorder or condition associated with a damaged, weakened and/or overworked heart or associated with heart failure is cardiomyopathy, cardiac arrythmia, and/or heart failure.

Embodiment 322

The use of embodiment 321, wherein the cardiomyopathy is genetic cardiomyopathy.

Embodiment 323

The use of embodiment 322, wherein the genetic cardio-myopathy is associated with PLN p.Arg14del, Arg9Cys (R9C), or Arg25Cys (R25C) genetic mutations.

Embodiment 324

The use of embodiment 321, wherein the cardiomyopathy is dilated cardiomyopathy (DCM).

Embodiment 325

The use of embodiment 324, wherein the DCM is genetic DCM.

Embodiment 326

The use of embodiment 325, wherein the genetic DCM is associated with TTN, LMNA, RBM20, SCN5A, MYH7, TNNT2, or TPM1 mutations.

Embodiment 327

The use of embodiment 324, wherein the DCM is arrhythmogenic DCM.

Embodiment 328

The use of embodiment 321, wherein the heart failure is heart failure with preserved ejection fraction (HFpEF), heart failure with reduced ejection fraction (HFrEF), acute heart failure, or worsening of chronic heart failure.

Embodiment 329

The use of embodiment 321, wherein the arrhythmia is ventricular tachycardia (vtac) or ventricular fibrillation (vfib).

Embodiment A1

An oligomeric duplex comprising a first oligomeric com-pound and a second oligomeric compound, wherein:
(1) a first oligomeric compound comprises a modified oligonucleotide consisting of 8 to 50 linked nucleo-sides, wherein the nucleobase sequence of the first modified oligonucleotide comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of the nucleobase sequence of any of SEQ ID NOs: 3-314, 627-782, 939-976, 1033-1038, and 1254-1255 wherein each of the nucleosides of the first modified oligonucleotide comprises a modi-fied sugar moiety or sugar surrogate and wherein at least one modified nucleoside and less than 40% of the nucleosides of the first modified oligonucleotide com-prises a fluorine; and
(2) a second oligomeric compound comprises a modified oligonucleotide consisting of 8 to 50 contiguous linked nucleosides wherein the nucleobase sequence of the second modified oligonucleotide comprises at least 8, at least 9, at least 10, at least 11, at least 12, at least 13, at least 14, at least 15, at least 16, at least 17, at least 18, at least 19, at least 20, or at least 21 contiguous nucleobases of the nucleobase sequence of any of SEQ ID NOs: 315-626, 783-938, 977-1016 and 1027-1032, wherein each of the nucleosides of the second modified oligonucleotide comprises a modified sugar moiety or sugar surrogate and wherein less than 40% of the nucleosides of the second modified oligonucleotide comprises a fluorine.

Embodiment A2

The oligomeric duplex of embodiment A1, wherein the first modified oligonucleotide is at least 80%, at least 85%, at least 90%, at least 95%, or at least 99% complementary to an equal length portion of a PLN nucleic acid, wherein the PLN nucleic acid has the nucleobase sequence of SEQ ID NO: 1 or SEQ ID NO: 2.

Embodiment A3

The oligomeric duplex of embodiment A1 or embodiment A2, wherein each of the nucleosides of the first modified oligonucleotide independently and the second modified oli-gonucleotide independently comprises a modified sugar moiety or sugar surrogate independently selected from 2'-F, 2'-MOE, 2'-OMe, 2'-deoxyribosyl, and FHNA.

Embodiment A4

The oligomeric duplex of any one of embodiments A1-A3, wherein fewer than 35%, fewer than 30%, fewer than 25%, fewer than 20%, fewer than 15%, fewer than 14%, fewer than 13%, fewer than 12%, fewer than 10%, fewer than 5%, or fewer than 1% of the nucleosides in the first modified oligonucleotide comprises a fluorine.

Embodiment A5

The oligomeric duplex of any one of embodiments A1-A4, wherein no more than 1 nucleoside, no more than 2 nucleosides, no more than 3 nucleosides, or no more than 4 nucleosides in the first modified oligonucleotide comprise a modified sugar moiety or sugar surrogate comprising a fluorine.

Embodiment A6

The oligomeric duplex of any one of embodiments A1-A5, wherein no more than 1 nucleoside, no more than 2 nucleosides, or no more than 3 nucleosides within the sequence of the first modified oligonucleotide between and including the third and twenty-first nucleosides counting from the 5' end of the modified oligonucleotide comprise a modified sugar moiety or sugar surrogate comprising a fluorine.

Embodiment A7

The oligomeric duplex of any one of embodiments A1-A6, wherein a nucleoside comprising a modified sugar moiety or sugar surrogate comprising a fluorine of the first modified oligonucleotide is independently selected from one of:

i. the second nucleoside counting from the 5' end, ii. the fourteenth and sixteenth nucleosides counting from the 5' end, or iii. the second, fourteenth and sixteenth nucleosides counting from the 5' end:

wherein each modified sugar moiety or sugar surrogate comprising a fluorine is independently a 2'-fluoro sugar moiety or a 3'-fluoro-hexitol sugar moiety.

Embodiment A8

The oligomeric duplex of any one of embodiments A1-A7, wherein no more than one of the modified sugar moiety and/or sugar surrogate comprising a fluorine in the first modified oligonucleotide is a 3'-fluoro-hexitol sugar moiety.

Embodiment A9

The oligomeric duplex of any one of embodiments A1-A8, wherein one or more nucleosides of the first modified oligonucleotide is a 2'-deoxynucleoside.

Embodiment A10

The oligomeric duplex of embodiment A9, wherein the one or more 2'-deoxynucleosides is one or more nucleosides in a region of the sequence of the first modified oligonucleotide between and including the fifth nucleoside to the sixteenth nucleoside counting from the 5' end of the first modified oligonucleotide.

Embodiment A11

The oligomeric duplex of embodiment A10, wherein the one or more 2'-deoxynucleosides is in a region of the sequence of the first modified oligonucleotide that is any of the fifth, sixth, and/or seventh nucleosides or that is any of the fourteenth, fifteenth, and/or sixteenth nucleosides counting from the 5' end of the first modified oligonucleotide.

Embodiment A12

The oligomeric duplex of any one of embodiments A9-A11, wherein fewer than 20%, or fewer than 15%, of the nucleosides of the first modified oligonucleotide comprises a fluorine.

Embodiment A13

The oligomeric duplex of any one of embodiments A9-A12, wherein the one or more 2'-deoxynucleosides is the fifth, sixth and/or seventh nucleoside(s) counting from the 5' end of the first modified oligonucleotide.

Embodiment A14

The oligomeric duplex of any one of embodiments A9-A13, wherein only two nucleosides of the first modified oligonucleotide are 2'-deoxynucleosides.

Embodiment A15

The oligomeric duplex of embodiment A14, wherein the two 2'-deoxynucleosides are the fifth and seventh nucleosides, or the fourteenth and sixteenth nucleosides, counting from the 5' end of the first modified oligonucleotide.

Embodiment A16

The oligomeric duplex of embodiment A14, wherein the two 2'-deoxynucleosides are the fifth and seventh nucleosides counting from the 5' end of the first modified oligonucleotide.

Embodiment A17

The oligomeric duplex of any one of embodiments A9-A13, wherein only one of the nucleosides of the first modified oligonucleotide is a 2'-deoxynucleoside.

Embodiment A18

The oligomeric duplex of embodiment A17, wherein the 2'-deoxynucleoside is the sixth or sixteenth nucleoside counting from the 5' end of the first modified oligonucleotide.

Embodiment A19

The oligomeric duplex of embodiment A17, wherein the 2"-deoxynucleoside is the sixth nucleoside counting from the 5' end of the first modified oligonucleotide.

Embodiment A20

The oligomeric duplex of any one of embodiments A1-A19, wherein one or more of the nucleosides of the first modified oligonucleotide independently comprises a sugar surrogate or a bicyclic sugar moiety.

Embodiment A21

The oligomeric duplex of embodiment A20, wherein the bicyclic sugar moiety comprises a 2'-4' bridge selected from —O—CH$_2$—; and —O—CH(CH$_3$)—.

Embodiment A22

The oligomeric duplex of any one of embodiments A1-A21, wherein one or more of the nucleosides of the first modified oligonucleotide comprises a 2'-OMe sugar moiety.

Embodiment A23

The oligomeric duplex of embodiment A22, wherein at least 10%, at least 20%, at least 30%, at least 40%, at least 50% or at least 60% of the nucleosides of the first modified oligonucleotide comprise a 2'-OMe sugar moiety.

Embodiment A24

The oligomeric duplex of embodiment A22 or embodiment A23, wherein the one or more nucleosides comprising a 2'-OMe sugar moiety are in a region of the sequence of the first modified oligonucleotide between and including the third and twenty-first nucleosides counting from the 5' end of the first modified oligonucleotide.

Embodiment A25

The oligomeric duplex of embodiment A22 or embodiment A23, wherein the 3'-terminal nucleoside of the first modified oligonucleotide comprises a 2'-OMe sugar moiety and/or the nucleoside immediately 5' of the 3'-terminal nucleoside of the first modified oligonucleotide comprises a 2'-OMe sugar moiety.

Embodiment A26

The oligomeric duplex of any one of embodiments A1-A25, wherein one or more of the nucleosides of the first modified oligonucleotide comprise a 2-MOE sugar moiety.

Embodiment A27

The oligomeric duplex of embodiment A26, wherein the 5'- and/or 3'-terminal nucleosides of the first modified oligonucleotide comprise a 2-MOE sugar moiety.

Embodiment A28

The oligomeric duplex of any one of embodiments A1-A27, wherein the nucleoside immediately 5' of the 3'-terminal nucleoside of the first modified oligonucleotide comprises a 2'-MOE sugar moiety.

Embodiment A29

The oligomeric duplex of any one of embodiments A1-A24 and A26-A28, wherein the 5'- and 3'-terminal nucleosides of the first modified oligonucleotide comprise a 2'-MOE sugar moiety and the nucleoside immediately 5' of the 3'-terminal nucleoside of the first modified oligonucleotide comprises a 2'-MOE sugar moiety.

Embodiment A30

The oligomeric duplex of any one of embodiments A1-A29, wherein the first modified oligonucleotide comprises a stabilized phosphate group attached to the 5'-terminal nucleoside.

Embodiment A31

The oligomeric duplex of embodiment A30, wherein the stabilized phosphate group comprises a cyclopropyl phosphonate or a vinyl phosphonate.

Embodiment A32

The oligomeric duplex of any one of embodiments A1-A31, wherein the duplex comprises a conjugate group comprising a conjugate moiety and a conjugate linker.

Embodiment A33

The oligomeric duplex of embodiment A32, wherein the conjugate group comprises a cell-targeting moiety.

Embodiment A34

The oligomeric duplex of embodiment A32, wherein the conjugate moiety comprises an active drug substance, an aliphatic chain, a lipid, a peptide, a protein, a hydrocarbon, a polyamine, a polyamide, a polyether, a thioether, an aptamer, an antibody or antibody fragment, a vitamin, a fatty acid, a carbohydrate, an intercalator or a reporter molecule.

Embodiment A35

The oligomeric duplex of embodiment A32, wherein the conjugate group comprises a C22 alkyl, C20 alkyl, C17 alkyl, C16 alkyl, C10 alkyl, C21 alkyl, C19 alkyl, C18 alkyl, C15 alkyl, C14 alkyl, C13 alkyl, C12 alkyl, C11 alkyl, C9 alkyl, C8 alkyl, C7 alkyl, C6 alkyl, or C5 alkyl, wherein the alkyl chain optionally has one or more unsaturated bonds.

Embodiment A36

The oligomeric duplex of embodiment A32, wherein the conjugate group comprises a 6-palmitamidohexyl moiety or a 2-(hydroxymethyl)-6-palmitamidohexyl moiety.

Embodiment A37

The oligomeric duplex of embodiment A32, wherein the duplex comprises a conjugate moiety that binds type 1 transferrin receptor (TfR1).

Embodiment A38

The oligomeric duplex of embodiment A37, wherein the conjugate moiety is selected from antibody or fragment thereof, a protein or peptide or an aptamer capable of binding TfR1.

Embodiment A39

The oligomeric duplex of embodiment A38, wherein the conjugate moiety is a cyclic protein or cyclic peptide.

Embodiment A40

The oligomeric duplex of embodiment A37, wherein the conjugate group consists of the bicycle ligand and a conjugate linker.

Embodiment A41

The oligomeric duplex of embodiment A40, wherein the bicycle compound comprises a polypeptide consisting of 13-22 linked amino acids or amino acid mimetics and a molecular scaffold, wherein each of a first, a second, and a third amino acid of the polypeptide comprises a reactive group, each of which separately forms a bond with the molecular scaffold, thereby forming two polypeptide loops attached to the molecular scaffold.

Embodiment A42

The oligomeric duplex of embodiment A41, wherein the peptide of the bicycle compound has the following chemical notation:

```
                              (SEQ ID NO: 1045)
    Ac-CP[HyP]DAYLGC[tBuGly]SYCEPW[K(N₃)]-NH₂,
```

Ac=acetyl,
C=cysteine,
P=proline,
D=aspartate,
A=alanine,
Y=tyrosine,
L=leucine,
G=glycine,
S=serine,
E=glutamate,
W=tryptophan,
[HyP]=trans-4-hydroxy-L-proline,
[tBuGly]=t-butyl-glycine, and
[K(N₃)]=6-azido lysine;
and wherein each cysteine forms a covalent bond with the molecular scaffold 1,1',1"-(1,3,5-triazinane-1,3,5-triyl) tris(2-bromoethanone) (TATB).

Embodiment A43

The oligomeric duplex of embodiment A41, wherein the bicycle compound has the structure:

or a salt thereof, wherein Q is N₃ (BCY17901, SEQ ID NO: 1045), NH₂ (BCY21757, SEQ ID NO: 1202), SH (BCY21758, SEQ ID NO: 1203), a conjugate linker, or a conjugate linker covalently connected to an oligonucleotide.

Embodiment A44

The oligomeric duplex of any one of embodiments A32-A43, wherein the second oligomeric compound comprises the conjugate group conjugated to the second modified oligonucleotide.

Embodiment A45

The oligomeric duplex of any one of embodiments A32-A43, wherein the conjugate group is conjugated to the 5' end or 3' end of the second modified oligonucleotide.

Embodiment A46

The oligomeric duplex of any one of embodiments A32-A43, wherein the conjugate group is attached to the 5'-terminal nucleoside or the 3'-terminal nucleoside of the second modified oligonucleotide.

Embodiment A47

The oligomeric duplex of any one of embodiments A32-A43, wherein the conjugate group is attached to the 5'-terminal nucleoside of the second modified oligonucleotide.

Embodiment A48

The oligomeric duplex of any one of embodiments A32-A43, wherein the conjugate group is attached to the 3'-terminal nucleoside of the second modified oligonucleotide.

Embodiment A49

The oligomeric duplex of any one of embodiments A32-A48, wherein the conjugate linker of the conjugate group consists of a single bond.

Embodiment A50

The oligomeric duplex of any one of embodiments A32-A48, wherein the conjugate linker of the conjugate group is cleavable.

Embodiment A51

The oligomeric duplex of any one of embodiments A32-A50, wherein the conjugate linker comprises 1 to 3 linker-nucleosides.

Embodiment A52

The oligomeric duplex of any one of embodiments A32-A48, wherein the conjugate linker comprises a (bicyclo [6.1.0]nonyne)-formyl (BCN) moiety.

Embodiment A53

The oligomeric duplex of embodiment A52, wherein the conjugate linker comprises a 6-(BCN-carbamate)-2-(hydroxymethyl)hexyl phosphoryl moiety or a 6-(BCN-carbamate) hexyl phosphoryl moiety.

Embodiment A54

The oligomeric duplex of embodiment A53, wherein the conjugate group has the structure (SEQ ID NO: 1291):

Embodiment A55

The oligomeric duplex of embodiment A53, wherein the conjugate group has the structure (SEQ ID NO: 1292):

Embodiment A56

The oligomeric duplex of any one of embodiments A1-A55, wherein, the nucleobase sequence of the first modified oligonucleotide is at least 80%, at least 85%, at least 90%, at least 95%, or 100% complementary to an equal length portion within nucleobases 295-316, 296-317, 297-318, 298-320, 299-320, 300-321, 301-322, 302-324, 303-324, 304-325, 304-326, 305-327, 306-325, 306-328, 307-328, 308-329, 309-330, 310-331, 311-332, 312-333, 313-334, 314-335, 315-336, 316-337, 317-339, 318-339, 319-340, 320-341, 321-342, 322-344, 323-345, 324-345, 324-346, 325-345, 325-347, 326-347, 327-348, 328-349, 329-350, 330-351, 331-352, 332-353, 333-354, 334-355, 505-526, 506-528, 507-529, 508-530, 509-531, 510-531, 511-532, 512-533, 513-535, 514-535, 514-536, 515-536, 516-535, 516-537, 517-538, 518-539, 519-541, 520-541, 521-542, 522-544, 523-544, 524-546, 535-556, 536-557, 537-558, 538-559, 539-560, 540-561, 541-563, 542-563, 543-564, 544-565, 545-566, 546-567, 547-568, 548-570, 549-571, 550-572, 551-572, 552-574, 553-574, 554-575, 555-577, 556-578, 557-579, 558-580, 559-580, 560-581, 561-582, 562-583, 563-584, 595-616, 596-618, 597-618, 598-620, 599-621, 600-622, 601-623, 602-623, 603-624, 604-625, 605-627, 606-628, 607-628, 608-629, 609-630, 610-631, 611-632, 612-633, 613-635, 665-687, 666-687, 667-689, 668-689, 669-690, 670-691, 671-692, 672-694, 673-694, 674-695, 675-696, 676-697, 677-698, 678-700, 679-701, 680-702, 681-703, 682-703, 683-704, 684-705, 685-706, 686-708, 687-708, 688-709, 689-710, 690-711, 691-712, 692-714, 693-715, 1675-1696, 1676-1698, 1677-1698, 1678-1699, 1679-1700, 1680-1702, 1681-1702, 1682-1703, 1683-1705, 1684-1705, 1685-1706, 1686-1707, 1687-1709, 1688-1709, 1689-1710, 1690-1712, 1691-1713, 1692-1714, and 1693-1714 of SEQ ID NO: 1.

Embodiment A57

The oligomeric duplex of any one of embodiments A1-A55, wherein the nucleobase sequence of the first modified oligonucleotide is at least 80%, at least 85%, at least 90%, at least 95%, or 100% complementary to an equal length portion within nucleobases 304-326, 306-325, 324-346, 325-345, 514-536, and 516-535 of SEQ ID NO: 1.

Embodiment A58

The oligomeric duplex of any one of embodiments A1-A55, wherein the nucleobase sequence of the first modified oligonucleotide comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of any of the nucleobase sequences of any of SEQ ID NOs: 3-314, 627-782, 939-976, 1033-1038, and 1254-1255.

Embodiment A59

The oligomeric duplex of any one of embodiments A1-A55, wherein the nucleobase sequence of the first modified oligonucleotide comprises the nucleobase sequence of any of SEQ ID NOs: 3-314, 627-782, 939-976, 1033-1038, and 1254-1255.

Embodiment A60

The oligomeric duplex of any one of embodiments A1-A55, wherein the nucleobase sequence of the first modified oligonucleotide consists of the nucleobase sequence of any of SEQ ID NOs: 3-314, 627-782, 939-976, 1033-1038, and 1254-1255.

Embodiment A61

The oligomeric duplex of any one of embodiments A1-A55, wherein the nucleobase sequence of the first modified oligonucleotide comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of any of the nucleobase sequences of SEQ ID NOs: 29, 171, 176, 967, 968, 971, 972, 974, 975, 1254, 1255, and 1033-1038.

Embodiment A62

The oligomeric duplex of any one of embodiments A1-A55, wherein the nucleobase sequence of the first modified oligonucleotide comprises the nucleobase sequence of any of SEQ ID NOs: 29, 171, 176, 967, 968, 971, 972, 974, 975, 1254, 1255, and 1033-1038.

Embodiment A63

The oligomeric duplex of any one of embodiments A1-A55, wherein the nucleobase sequence of the first modified oligonucleotide consists of the nucleobase sequence of any one of SEQ ID NOs: 29, 171, 176, 967, 968, 971, 972, 974, 975, 1254, 1255, and 1033-1038.

Embodiment A64

The oligomeric duplex of any one of embodiments A1-A55, wherein the first modified oligonucleotide and the second modified oligonucleotide each independently consist of 18 to 30, 18 to 25, 18 to 24, 18 to 23, 18-22, 18-21, 18-19, 19 to 30, 19 to 25, 19 to 24, 19 to 23, 19-21, 19-20, 20 to 30, to 25, 20 to 24, 20 to 23, 20 to 22, 20 to 21 linked nucleosides.

Embodiment A65

The oligomeric duplex of any one of embodiments A1-A55, wherein the first modified oligonucleotide consists of 23 nucleosides.

Embodiment A66

The oligomeric duplex of any one of embodiments A1-A65, wherein the first modified oligonucleotide has a sugar motif (5' to 3') selected from: efyyydyyyyyyyfyfyyyyyee, efyyydyyyyyyyfyfyyyyyyy, e[FHNA]yyydyyyyyyyfyfyyyyyee, e[FHNA] yyydyyyyyyyfyfyyyyyyy, efyydydyyyyyyfyfyyyyyee, efyydydyyyyyyfyfyyyyyyy, e[FHNA] yydydyyyyyyfyfyyyyyee, e[FHNA] yydydyyyyyyfyfyyyyyyy, efyyyfyyyyyyyfyfyyyyyyy, efyyyfyyyyyyyfyfyyyyyey, efyyyyyyyyyyyfyfyyyyyee, efyyyfyyyyyyyfyfyyyyyee, efyyyyyyyyyyyfyyyyyyyee, efyyyyyyyyyyyfyyyyyyyyy, e[FHNA] yyyfyyyyyyyfyfyyyyyee, e[FHNA] yyyfyyyyyyyfyfyyyyyyy, efyyydyyyyyyydydyyyyyee, efyyydyyyyyyydydyyyyyyy, efyydydyyyyyyfyfyyyyyyy, efyyyfyyyyyyyfyyyyyyyyy, efyyyfyyyyyyyfyyyyyyyyy, efyyyyyyyyyyyfyfyyyyyyy, efyyyyyyyyyyyfyfyyyyyyy, e[FHNA]yydydyyyyfyfyfyyyyyyyy, efyyyfyyyyyyyfydyyyyyy, efyyyfyyyyyyyfydyyyyee, efyyyfyyyyyyyfyfyyyee, and efyyyfyyyyyyyfyfyyyyy, wherein each "d" represents a 2-β-D-deoxyribosyl sugar moiety, each "y" represents a 2'-OMe sugar moiety, each "e" represents a 2'-MOE sugar moiety, each "f" represents a 2'-fluoro sugar moiety, and each "[FHNA]" represents a 3-fluoro-hexitol sugar moiety.

Embodiment A67

The oligomeric duplex of any one of embodiments A1-A65, wherein the first modified oligonucleotide has a sugar motif (5' to 3) selected from: efyydydyyyyyyfyfyyyyyee, efyyydyyyyyyyfyfyyyyyee, efyydydyyyyyyfyfyyyyyyy, e[FHNA] yydydyyyyfyfyfyyyyyyy, and efyyydyyyyyyyfyfyyyyyyy.

Embodiment A68

The oligomeric duplex of any one of embodiments A1-A67, wherein the first modified oligonucleotide comprises at least one modified internucleoside linkage.

Embodiment A69

The oligomeric duplex of embodiment A68, wherein at least one modified internucleoside linkage is a phosphorothioate or mesyl phosphoramidate internucleoside linkage.

Embodiment A70

The oligomeric duplex of embodiment A68, wherein fewer than 50%, fewer than 40%, fewer than 30%, fewer than 20%, or fewer than 10% of the internucleoside linkages of the first modified oligonucleotide are modified internucleoside linkages.

Embodiment A71

The oligomeric duplex of any of embodiments A1-A70, wherein each internucleoside linkage of the first modified oligonucleotide is independently selected from a phosphodiester internucleoside linkage and a phosphorothioate internucleoside linkage.

Embodiment A72

The oligomeric duplex of embodiment A71, wherein the internucleoside linkages between the first and second nucleosides and the second and third nucleosides counting from the 5' end of the first modified oligonucleotide are modified internucleoside linkages.

Embodiment A73

The oligomeric duplex of embodiment A71, wherein the internucleoside linkages between the first and second nucleosides and the second and third nucleosides counting from the 3' end of the first modified oligonucleotide are modified internucleoside linkages.

Embodiment A74

The oligomeric duplex of embodiment A72, wherein the internucleoside linkages between the first and second nucleosides and the second and third nucleosides counting from the 5' end of the first modified oligonucleotide, and the internucleoside linkages between the first and second nucleosides and the second and third nucleosides counting from the 3' end of the first modified oligonucleotide are modified internucleoside linkages.

Embodiment A75

The oligomeric duplex of any one of embodiments A71-A74, wherein the modified internucleoside linkages are phosphorothioate internucleoside linkages.

Embodiment A76

The oligomeric duplex of embodiment A74 or embodiment A75, wherein all other internucleoside linkages in the first modified oligonucleotide are phosphodiester internucleoside linkages.

Embodiment A77

The oligomeric duplex of embodiment A76, wherein the first modified oligonucleotide has an internucleoside linkage motif of ssooooooooooooooooooss and a sugar motif (5' to 3') selected from: efyydydyyyyyyfyfyyyyyee, efyyydyyyyyyyfyfyyyyyee, efyydydyyyyyyfyfyyyyyyy, e[FHNA]yydydyyyyfyfyfyyyyyyy, and efyyydyyyyyyyfyfyyyyyyy; wherein each "d" represents a 2'-β-D-deoxyribosyl sugar moiety, each "y" represents a 2'-OMe sugar moiety, each "e" represents a 2'-MOE sugar moiety, each "f" represents a 2'-fluoro sugar moiety, each "[FHNA]" represents a 3-fluoro-hexitol sugar moiety, each "o" represents a phosphodiester internucleoside linkage and each "s" represents a phosphorothioate internucleoside linkage.

Embodiment A78

The oligomeric duplex of any one of embodiments A1-A77, wherein fewer than 30%, fewer than 25%, fewer than 20%, fewer than 15%, fewer than 14%, fewer than 13%, fewer than 12%, fewer than 10%, or fewer than 5% of the nucleosides in the second modified oligonucleotide comprise a fluorine.

Embodiment A79

The oligomeric duplex of any one of embodiments A1-A77, wherein no more than 4 nucleosides, no more than 3 nucleosides, no more than 2 nucleosides, or no more than 1 nucleoside in the second modified oligonucleotide comprise a modified sugar moiety comprising a fluorine.

Embodiment A80

The oligomeric duplex of any one of embodiments A1-A77, wherein none of the nucleosides before the seventh or after the eleventh nucleoside counting from the 5' end of the second modified oligonucleotide comprise a modified sugar moiety comprising a fluorine.

Embodiment A81

The oligomeric duplex of any one of embodiments A1-A77, wherein one or more of the seventh, ninth and eleventh nucleosides counting from the 5' end of the second modified oligonucleotide comprises a modified sugar moiety comprising a fluorine.

Embodiment A82

The oligomeric duplex embodiment A81, wherein two or more of the seventh, ninth and eleventh nucleosides counting from the 5' end of the second modified oligonucleotide comprise a modified sugar moiety comprising a fluorine.

Embodiment A83

The oligomeric duplex embodiment A81, wherein the seventh, ninth and eleventh nucleosides counting from the 5' end of the second modified oligonucleotide comprise a modified sugar moiety comprising a fluorine.

Embodiment A84

The oligomeric duplex of any one of embodiments A1-A80, wherein one or both of the tenth and eleventh nucleosides counting from the 5' end of the second modified oligonucleotide comprises a modified sugar moiety comprising a fluorine.

Embodiment A85

The oligomeric duplex of any one of embodiments A77-A84, wherein the modified sugar moiety comprising a fluorine is a 2'-fluoro sugar moiety.

Embodiment A86

The oligomeric duplex of any one of embodiments A1-A85, wherein fewer than 30%, fewer than 25%, fewer than 20%, fewer than 15%, fewer than 14%, fewer than 13%, fewer than 12%, fewer than 10%, fewer than 5%, or fewer than 1% of the total nucleosides in the compound comprise a fluorine.

Embodiment A87

The oligomeric duplex of any one of embodiments A1-86, wherein one or more of the nucleosides of the second modified oligonucleotide independently comprises a sugar surrogate or a bicyclic sugar moiety.

Embodiment A88

The oligomeric duplex of embodiment A87, wherein the bicyclic sugar moiety comprises a 2'-4' bridge selected from —O—CH$_2$—; and —O—CH(CH$_3$)—.

Embodiment A89

The oligomeric duplex of any one of embodiments A1-88, wherein one or more of the nucleosides of the second modified oligonucleotide comprises a 2'-OMe sugar moiety.

Embodiment A90

The oligomeric duplex of embodiment A89, wherein at least 10%, at least 20%, at least 30%, at least 40%, at least 50%, or at least 60%, or at least 65%, or at least 70%, or at least 80%, or at least 85%, or at least 90% of the nucleosides of the second modified oligonucleotide comprise a 2'-OMe sugar moiety.

Embodiment A91

The oligomeric duplex of embodiment A89 or embodiment A90, wherein the one or more nucleosides comprising a 2'-OMe sugar moiety are in a region of the sequence of the second modified oligonucleotide between and including the third and nineteenth nucleosides counting from the 5' end of the second modified oligonucleotide.

Embodiment A92

The oligomeric duplex of embodiment A89 or embodiment A90, wherein the 3'-terminal nucleoside of the second modified oligonucleotide comprises a 2'-OMe sugar moiety and/or the nucleoside immediately 5' of the 3'-terminal nucleoside of the second modified oligonucleotide comprises a 2'-OMe sugar moiety.

Embodiment A93

The oligomeric duplex of any one of embodiments A89, A90 and A92, wherein the 5'-terminal nucleoside of the second modified oligonucleotide comprises a 2'-OMe sugar moiety and/or the nucleoside immediately 3' of the 5'-terminal nucleoside of the second modified oligonucleotide comprises a 2'-OMe sugar moiety.

Embodiment A94

The oligomeric duplex of embodiment A89 or embodiment A90, wherein the 5'-terminal nucleoside, the nucleoside immediately 3' of the 5'-terminal nucleoside, the 3'-terminal nucleoside, and the nucleoside immediately 5' of the 3'-terminal nucleoside of the second modified oligonucleotide comprises a 2'-OMe sugar moiety.

Embodiment A95

The oligomeric duplex of any one of embodiments A1-A94, wherein one or more of the nucleosides of the second modified oligonucleotide comprise a 2'-MOE sugar moiety.

Embodiment A96

The oligomeric duplex of any one of embodiments A1-A93, wherein the 3'-terminal nucleoside of the second modified oligonucleotide comprises a 2'-MOE sugar moiety and/or the nucleoside immediately 5' of the 3'-terminal nucleoside of the second modified oligonucleotide comprises a 2'-MOE sugar moiety.

Embodiment A97

The oligomeric duplex of any one of embodiments A1-A93, A95 and A96, wherein the 5'-terminal nucleoside of the second modified oligonucleotide comprises a 2'-MOE sugar moiety and/or the nucleoside immediately 3' of the 5'-terminal nucleoside of the second modified oligonucleotide comprises a 2'-MOE sugar moiety.

Embodiment A98

The oligomeric duplex of any one of embodiments A1-A91, wherein the 5'-terminal nucleoside, the nucleoside immediately 3' of the 5'-terminal nucleoside, the 3'-terminal nucleoside, and the nucleoside immediately 5' of the 3'-terminal nucleoside of the second modified oligonucleotide comprises a 2'-MOE sugar moiety.

Embodiment A99

The oligomeric duplex of any one of embodiments A1-A98, wherein the second modified oligonucleotide has a sugar motif (5' to 3') selected from: eeyyyyfyfyfyyyyyyyyee, eeyyyyfyfyfyyyyyyyyyy, yyyyyyfyfyfyyyyyyyyee, yyyyyyfyfyfyyyyyyyyyy, eeyyyyfyfffyyyyyyyyee, eeyyyyfyfffyyyyyyyyyy, yyyyyyfyfffyyyyyyyyee, yyyyyyfyfffyyyyyyyyyy, eeyyyyyyyffyyyyyyyyee, eeyyyyyyyffyyyyyyyyyy, yyyyyyyyyffyyyyyyyyee, yyyyyyyyyffyyyyyyyyyy, eeyyyyyffyyyyyyyyee, eeyyyyyffyyyyyyyyyy, yyyyyyyffyyyyyyyyee, yyyyyyyyffyyyyyyyyyy, yyyyyyfyfffyyyyyyyy, eeyyyyfyfffyyyyyyee, eeyyyyfyfffyyyyyyyy, yyyyyyfyfffyyyyyyee, eeyyfyfffyyyyyyyyyy, eeyyfyfffyyyyyyyyee, yyyyyfyfffyyyyyyyyyy, yyyyyfyfffyyyyyyyyee, eeyyyyyyyydyyyyyyyyee, eeyyyyyyyydyyyyyyyyyy, yyyyyyyyyydyyyyyyyyee, yyyyyyyyyydyyyyyyyyyy, eeyyyyyyyyyyyyyyyyyyee, eeyyyyyyyyyyyyyyyyyyyy, yyyyyyyyyyyyyyyyyyyee, and yyyyyyyyyyyyyyyyyyyy wherein each "y" represents a 2'-OMe sugar moiety, each "e" represents a 2'-MOE sugar moiety, each "f" represents a 2'-fluoro sugar moiety, and each "d" represents a 2-β-D-deoxyribosyl sugar moiety.

Embodiment A100

The oligomeric duplex of any one of embodiments A1-A98, wherein the second modified oligonucleotide has a sugar motif (5' to 3') selected from: eeyyyyyyyffyyyyyyyyee, eeyyyyfyfyfyyyyyyyyee, yyyyyyyyyffyyyyyyyyyy, and yyyyyyfyfyfyyyyyyyyyy, wherein each "y" represents a 2'-OMe sugar moiety, each "e" represents a 2'-MOE sugar moiety, and each "f" represents a 2'-fluoro sugar moiety.

Embodiment A101

The oligomeric duplex of any one of embodiments A1-A100, wherein the nucleobase of the 3'-terminal nucleoside and/or of the nucleoside immediately 5' of the 3'-terminal nucleoside of the second modified oligonucleotide is an adenine.

Embodiment A102

The oligomeric duplex of any one of embodiments A1-A100, wherein the nucleobase of the 3'-terminal nucleoside is an adenine and the nucleobase of the nucleoside immediately 5' of the 3'-terminal nucleoside of the second modified oligonucleotide is a thymine or uracil.

Embodiment A103

The oligomeric duplex of any one of embodiments A1-A100, wherein the second modified oligonucleotide comprises at least one modified internucleoside linkage.

Embodiment A104

The oligomeric duplex of embodiment A103, wherein at least one modified internucleoside linkage is a phosphorothioate or mesyl phosphoramidate internucleoside linkage.

Embodiment A105

The oligomeric duplex of embodiment A103, wherein fewer than 50%, fewer than 40%, fewer than 30%, fewer than 20%, or fewer than 10% of the internucleoside linkages of the first modified oligonucleotide are modified internucleoside linkages.

Embodiment A106

The oligomeric duplex of any one of embodiments A103-A105, wherein each internucleoside linkage of the second modified oligonucleotide is independently selected from a phosphodiester internucleoside linkage and a phosphorothioate internucleoside linkage.

Embodiment A107

The oligomeric duplex of any one of embodiments A103-A105, wherein the internucleoside linkages between the first and second nucleosides and the second and third nucleosides counting from the 5' end of the second modified oligonucleotide are modified internucleoside linkages.

Embodiment A108

The oligomeric duplex of any one of embodiments A103-A105 and A107, wherein the internucleoside linkages between the first and second nucleosides and the second and third nucleosides counting from the 3' end of the first modified oligonucleotide are modified internucleoside linkages.

Embodiment A109

The oligomeric duplex of any one of embodiments A103-A105, wherein the internucleoside linkages between the first and second nucleosides and the second and third nucleosides counting from the 5' end of the second modified oligonucleotide, and the internucleoside linkages between the first and second nucleosides and the second and third nucleosides counting from the 3' end of the second modified oligonucleotide are modified internucleoside linkages.

Embodiment A110

The oligomeric duplex of any one of embodiments A103-A109, wherein the modified internucleoside linkages are phosphorothioate internucleoside linkages.

Embodiment A111

The oligomeric duplex of embodiment A110, wherein all other internucleoside linkages in the second modified oligonucleotide are phosphodiester internucleoside linkages.

Embodiment A112

The oligomeric duplex of embodiment A111, wherein the second modified oligonucleotide has an internucleoside linkage motif of ssooooooooooooooooss and a sugar motif (5' to 3') selected from: eeyyyyyyyffyyyyyyyyee, eeyyyyfyfyfyyyyyyyyee, yyyyyyyyyffyyyyyyyyyy, and yyyyyyfyfyfyyyyyyyyyy; wherein each "y" represents a 2'-OMe sugar moiety, each "e" represents a 2'-MOE sugar moiety, each "f" represents a 2'-fluoro sugar moiety, each "o" represents a phosphodiester internucleoside linkage and each "s" represents a phosphorothioate internucleoside linkage.

Embodiment A113

The oligomeric duplex of any of embodiments A1-A112, wherein the nucleobase sequence of the second modified oligonucleotide comprises least 8, at least 9, at least 10, at least 11, at least 12, at least 13, at least 14, at least 15, at least 16, at least 17, at least 18, at least 19, at least 20, or at least 21 contiguous nucleobases of any of the nucleobase sequences of any of SEQ ID NOs: 315-626, 783-938, 977-1016, and 1027-1032.

Embodiment A114

The oligomeric duplex of any of embodiments A1-A112, wherein the nucleobase sequence of the second modified oligonucleotide comprises the nucleobase sequence of any of SEQ ID NOs: 315-626, 783-938, 977-1016, and 1027-1032.

Embodiment A115

The oligomeric duplex of any of embodiments A1-A112, wherein the nucleobase sequence of the second modified oligonucleotide consists of the nucleobase sequence of any of SEQ ID NOs: 315-626, 783-938, 977-1016, and 1027-1032.

Embodiment A116

The oligomeric duplex of any one of embodiments A1-A112, wherein the nucleobase sequence of the second modified oligonucleotide comprises at least 8, at least 9, at least 10, at least 11, at least 12, at least 13, at least 14, at least 15, or at least 16 contiguous nucleobases of any of the nucleobase sequences of SEQ ID NOs: 341, 483, 488, 1011-1016, and 1027-1032.

Embodiment A117

The oligomeric duplex of any of embodiments A1-A112, wherein the nucleobase sequence of the second modified oligonucleotide comprises the nucleobase sequence of any of SEQ ID NOs: 341, 483, 488, 1011-1016, and 1027-1032.

Embodiment A118

The oligomeric duplex of any of embodiments A1-A112, wherein the nucleobase sequence of the second modified oligonucleotide consists of the nucleobase sequence of any of SEQ ID NOs: 341, 483, 488, 1011-1016, and 1027-1032.

Embodiment A119

An oligomeric duplex comprising:
(1) a first oligomeric compound comprising a first modified oligonucleotide consisting of 18 to 30 contiguous linked nucleosides that is at least 85%, at least 90%, at least 95% or at least 95% complementary or 100% complementary to an equal length portion within nucleobases 295-316, 296-317, 297-318, 298-320, 299-320, 300-321, 301-322, 302-324, 303-324, 304-325, 304-326, 305-327, 306-325, 306-328, 307-328, 308-329, 309-330, 310-331, 311-332, 312-333, 313-334, 314-335, 315-336, 316-337, 317-339, 318-339, 319-340, 320-341, 321-342, 322-344, 323-345, 324-345, 324-346, 325-345, 325-347, 326-347, 327-348, 328-349, 329-350, 330-351, 331-352, 332-353, 333-354, 334-355, 505-526, 506-528, 507-529, 508-530, 509-531, 510-531, 511-532, 512-533, 513-535, 514-535, 514-536, 515-536, 516-535, 516-537, 517-538, 518-539, 519-541, 520-541, 521-542, 522-544, 523-544, 524-546, 535-556, 536-557, 537-558, 538-559, 539-560, 540-561, 541-563, 542-563, 543-564, 544-565, 545-566, 546-567, 547-568, 548-570, 549-571, 550-572, 551-572, 552-574, 553-574, 554-575, 555-577, 556-578, 557-579, 558-580, 559-580, 560-581, 561-582, 562-583, 563-584, 595-616, 596-618, 597-618, 598-620, 599-621, 600-622, 601-623, 602-623, 603-624, 604-625, 605-627, 606-628, 607-628, 608-629, 609-630, 610-631, 611-632, 612-633, 613-635, 665-687, 666-687, 667-689, 668-689, 669-690, 670-691, 671-692, 672-694, 673-694, 674-695, 675-696, 676-697, 677-698, 678-700, 679-701, 680-702, 681-703, 682-703, 683-704, 684-705, 685-706, 686-708, 687-708, 688-709, 689-710, 690-711, 691-712, 692-714, 693-715, 1675-1696, 1676-1698, 1677-1698, 1678-1699, 1679-1700, 1680-1702, 1681-1702, 1682-1703, 1683-1705, 1684-1705, 1685-1706, 1686-1707, 1687-1709, 1688-1709, 1689-1710, 1690-1712, 1691-1713, 1692-1714, and 1693-1714 of SEQ ID NO: 1, and
(2) a second oligomeric compound comprising a second modified oligonucleotide consisting of 16 to 28 contiguous linked nucleosides that is at least 90% complementary to an equal length portion of the first modified oligonucleotide:
wherein:
(a) each of the nucleosides of the first modified oligonucleotide and each of the nucleosides of the second modified oligonucleotide comprise a modified sugar moiety or a sugar surrogate,
(b) at least one of the modified sugar moiety or sugar surrogate of the first modified oligonucleotide comprises a fluorine, and
(c) fewer than 40% of the nucleosides of the first modified oligonucleotide comprise a fluorine.

Embodiment A120

The oligomeric duplex of embodiment A119, wherein the nucleobase sequence of the first modified oligonucleotide comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of any of the nucleobase sequences of any of SEQ ID NOs: 3-314, 627-782, 939-976, 1033-1038 and 1254-1255.

Embodiment A121

The oligomeric duplex of embodiment A119, wherein the nucleobase sequence of the first modified oligonucleotide comprises the nucleobase sequence of any of SEQ ID NOs: 3-314, 627-782, 939-976, 1033-1038, and 1254-1255.

Embodiment A122

The oligomeric duplex of embodiment A119, wherein the nucleobase sequence of the first modified oligonucleotide consists of the nucleobase sequence of any of SEQ ID NOs: 3-314, 627-782, 939-976, 1033-1038, and 1254-1255.

Embodiment A123

The oligomeric duplex of embodiment A119, wherein the nucleobase sequence of the first modified oligonucleotide comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of any of the nucleobase sequences of SEQ ID NOs: 29, 171, 176, 967, 968, 971, 972, 974, 975, 1254, 1255, and 1033-1038.

Embodiment A124

The oligomeric duplex of embodiment A119, wherein the nucleobase sequence of the first modified oligonucleotide comprises the nucleobase sequence of any of SEQ ID NOs: 29, 171, 176, 967, 968, 971, 972, 974, 975, 1254, 1255, and 1033-1038.

Embodiment A125

The oligomeric duplex of embodiment A119, wherein the nucleobase sequence of the first modified oligonucleotide consists of the nucleobase sequence of any of SEQ ID NOs: 29, 171, 176, 967, 968, 971, 972, 974, 975, 1254, 1255, and 1033-1038.

Embodiment A126

The oligomeric duplex of embodiment A120, wherein the nucleobase sequence of the second modified oligonucleotide comprises least 8, at least 9, at least 10, at least 11, at least 12, at least 13, at least 14, at least 15, at least 16, at least 17, at least 18, at least 19, at least 20, or at least 21 contiguous nucleobases of any of the nucleobase sequences of any of SEQ ID NOs: 315-626, 783-938, 977-1016, and 1027-1032.

Embodiment A127

The oligomeric duplex of embodiment A121, wherein the nucleobase sequence of the second modified oligonucleotide comprises the nucleobase sequence of any of SEQ ID NOs: 315-626, 783-938, 977-1016, and 1027-1032.

Embodiment A128

The oligomeric duplex of embodiment A122, wherein the nucleobase sequence of the second modified oligonucleotide consists of the nucleobase sequence of any of SEQ ID NOS: 315-626, 783-938, 977-1016, and 1027-1032.

Embodiment A129

The oligomeric duplex of embodiment A123, wherein the nucleobase sequence of the second modified oligonucleotide comprises at least 8, at least 9, at least 10, at least 11, at least 12, at least 13, at least 14, at least 15, at least 16, at least 17, at least 18, at least 19, at least 20, or at least 21 contiguous nucleobases of any of the nucleobase sequences of SEQ ID NOs: 341, 483, 488, 1011-1016, and 1027-1032.

Embodiment A130

The oligomeric duplex of embodiment A124, wherein the nucleobase sequence of the second modified oligonucleotide comprises the nucleobase sequence of any of SEQ ID NOs: 341, 483, 488, 1011-1016, and 1027-1032.

Embodiment A131

The oligomeric duplex of embodiment A125, wherein the nucleobase sequence of the second modified oligonucleotide consists of the nucleobase sequence of any of SEQ ID NOS: 341, 483, 488, 1011-1016, and 1027-1032.

Embodiment A132

The oligomeric duplex of any one of embodiments A119-A131, wherein none of the modified sugar moieties of the nucleosides of the second modified oligonucleotide comprises a fluorine.

Embodiment A133

The oligomeric duplex of any one of embodiments A119-A131, wherein at least one of the modified sugar moieties of the second modified oligonucleotide comprises a fluorine and wherein fewer than 40% of the nucleosides of the second modified oligonucleotide comprises a fluorine.

Embodiment A134

The oligomeric duplex of any one of embodiments A119-A131, wherein two, three or four of the nucleosides of the second modified oligonucleotide comprise a modified sugar moiety comprising a fluorine.

Embodiment A135

The oligomeric duplex of any one of embodiments A119-A134, wherein two, three or four of the nucleosides of the first modified oligonucleotide comprise a modified sugar moiety comprising a fluorine.

Embodiment A136

The oligomeric duplex of any one of embodiments A119-A135 wherein none of the nucleosides of the second modified oligonucleotide is a 2'-deoxynucleoside.

Embodiment A137

The oligomeric duplex of any one of embodiments A119-A135 wherein all of the nucleosides of the second modified oligonucleotide comprise a modified ribosyl sugar moiety.

Embodiment A138

The oligomeric duplex of any one of embodiments A119-A137, wherein one, two or three of the nucleosides of the first modified oligonucleotide is/are a 2'-deoxynucleoside.

Embodiment A139

The oligomeric duplex of any one of embodiments A119-A138, wherein:
(a) the 5'- and 3'-terminal nucleosides, the nucleoside immediately adjacent to the 5'-terminal nucleoside, and the nucleoside immediately adjacent to the 3'-terminal nucleoside of the second modified oligonucleotide comprise a 2-MOE sugar moiety,
(b) the 5'- and 3'-terminal nucleosides and the nucleoside immediately 5' of the 3'-terminal nucleoside of the first modified oligonucleotide comprise a 2'-MOE sugar moiety, and/or
(b) any nucleoside in the first and second modified oligonucleotides that does not comprise a fluorine or a 2'-MOE sugar moiety comprises a 2'-OMe sugar moiety.

Embodiment A140

The oligomeric duplex of any one of embodiments A119-A139, wherein no more than four of the nucleosides of the first modified oligonucleotide comprise a modified sugar moiety comprising a fluorine.

Embodiment A141

The oligomeric duplex of embodiment A140, wherein the first modified oligonucleotide has a sugar motif (5' to 3') selected from: efyyyfyyyyyyyfyfyyyyyee, efyyyfyyyyyyyfyfyyyyyyy, e[FHNA] yyyfyyyyyyyfyfyyyyyee, e[FHNA] yyyfyyyyyyyfyfyyyyyyy, efyyyfyyyyyyyfyfyyyyyey, e[FHNA]yydydyyyyfyfyfyyyyyyy and efyyyfyyyyyyyfyfyyyee; wherein each "d" represents a 2'-β-D-deoxyribosyl sugar moiety, each "y" represents a 2'-OMe sugar moiety, each "c" represents a 2'-MOE sugar moiety, each "f" represents a 2'-fluoro sugar moiety, and each "[FHNA]" represents a 3-fluoro-hexitol sugar moiety.

Embodiment A142

The oligomeric duplex of any one of embodiments A119-A139, wherein no more than three of the nucleosides of the first modified oligonucleotide comprise a modified sugar moiety comprising a fluorine.

Embodiment A143

The oligomeric duplex of embodiment A142 wherein the first modified oligonucleotide has a sugar motif (5' to 3') selected from: efyyydyyyyyyyfyfyyyyyee, efyyydyyyyyyyfyfyyyyyyy, e[FHNA] yyydyyyyyyyfyfyyyyyee, e[FHNA] yyydyyyyyyyfyfyyyyyyy, efyydydyyyyyyfyfyyyyyee, efyydydyyyyyyfyfyyyyyyy, e[FHNA] yydydyyyyyyfyfyyyyyee, e[FHNA] yydydyyyyyyfyfyyyyyyy, efyyyyyyyyyyyyfyfyyyyyee, efyyyfyyyyyyyfyyyyyyyyy, efyyyfyyyyyyyfydyyyyyee, efyyyfyyyyyyyfydyyyyyyy, efyyyfyyyyyyyfydyyyyyee, efyyyfyyyyyyyfydyyyyyyy; wherein each "d" represents a 2'-β-D-deoxyribosyl sugar moiety, each "y" represents a 2'-OMe sugar moiety, each "e" represents a 2'-MOE sugar moiety, each "f" represents a 2'-fluoro sugar moiety, and each "[FHNA]" represents a 3'-fluoro-hexitol sugar moiety.

Embodiment A144

The oligomeric duplex of any one of embodiments A119-A139, wherein no more than two of the nucleosides of the first modified oligonucleotide comprise a modified sugar moiety comprising a fluorine.

Embodiment A145

The oligomeric duplex of embodiment A144 wherein the first modified oligonucleotide has a sugar motif (5' to 3') selected from: efyyyyyyyyyyyyfyyyyyyee, efyyyyyyyyyyyyfyyyyyyyy, e[FHNA]yyyyyyyyyy [FHNA]yyyyyyyee, and e[FHNA]yyyyyyyyyyy[FHNA]yyyyyyyyy; wherein each "y" represents a 2'-OMe sugar moiety, each "e" represents a 2'-MOE sugar moiety, each "f" represents a 2'-fluoro sugar moiety, and each "[FHNA]" represents a 3-fluoro-hexitol sugar moiety.

Embodiment A146

The oligomeric duplex of any one of embodiments A119-A139, wherein only one of the nucleosides of the first modified oligonucleotide comprise a modified sugar moiety comprising a fluorine.

Embodiment A147

The oligomeric duplex of embodiment A146 wherein the first modified oligonucleotide has a sugar motif (5' to 3") selected from: efyyydyyyyyyydydyyyyyyy, efyyydyyyyyyydydyyyyyee, e[FHNA] yyydyyyyyyydydyyyyyyy, and e[FHNA] yyydyyyyyyydydyyyyyee; wherein each "d" represents a 2'-β-D-deoxyribosyl sugar moiety, each "y" represents a 2'-OMe sugar moiety, each "e" represents a 2'-MOE sugar moiety, and each "f" represents a 2'-fluoro sugar moiety.

Embodiment A148

The oligomeric duplex of any one of embodiments A119-A146, wherein no more than two of the nucleosides of the first modified oligonucleotide are 2'-deoxynucleosides.

Embodiment A149

The oligomeric duplex of embodiment A148 wherein the first modified oligonucleotide has a sugar motif (5' to 3') selected from: efyydydyyyyyyfyfyyyyyee, efyydydyyyyyyfyfyyyyyyy, e[FHNA] yydydyyyyyyfyfyyyyyee, and e[FHNA] yydydyyyyyyfyfyyyyyyy; wherein each "d" represents a 2'-β-D-deoxyribosyl sugar moiety, each "y" represents a 2'-OMe sugar moiety, each "e" represents a 2'-MOE sugar moiety, each "f" represents a 2'-fluoro sugar moiety, and each "[FHNA]" represents a 3'-fluoro-hexitol sugar moiety.

Embodiment A150

The oligomeric duplex of any one of embodiments A119-A147, wherein only one of the nucleosides of the first modified oligonucleotide is a 2'-deoxynucleoside.

Embodiment A151

The oligomeric duplex of embodiment A150, wherein the first modified oligonucleotide has a sugar motif (5' to 3') selected from: efyyydyyyyyyyfyfyyyyyee, efyyydyyyyyyyfyfyyyyyyy, e[FHNA] yyydyyyyyyyfyfyyyyyee, e[FHNA] yyydyyyyyyyfyfyyyyyyy, eyyyfyyyyyyyfydyyyyyyy, efyyyfyyyyyyyfydyyyyyee, eyyy[FHNA] yyyyyyyfydyyyyyyy, and e[FHNA] yyyfyyyyyyyfydyyyyyee; wherein each "d" represents a 2'-β-D-deoxyribosyl sugar moiety, each "y" represents a 2'-OMe sugar moiety, each "e" represents a 2'-MOE sugar moiety, each "f" represents a 2'-fluoro sugar moiety, and each "[FHNA]" represents a 3'-fluoro-hexitol sugar moiety.

Embodiment A152

The oligomeric duplex of any one of embodiments A119-A151, wherein no more than four of the nucleosides of the second modified oligonucleotide comprise a modified sugar moiety comprising a fluorine.

Embodiment A153

The oligomeric duplex of embodiment A152, wherein the second modified oligonucleotide has a sugar motif (5' to 3') selected from: yyyyyyfyfffyyyyyyyyyyy, eeyyyyfyfffyyyyyyyyee, yyyyyyyfyfffyyyyyyyyy, eeyyyyfyfffyyyyyyyee, yyyyfyfffyyyyyyyyyyy, and eeyyfyfffyyyyyyyyee; wherein each "y" represents a 2'-OMe sugar moiety, each "e" represents a 2'-MOE sugar moiety, and each "f" represents a 2'-fluoro sugar moiety.

Embodiment A154

The oligomeric duplex of any one of embodiments A119-A151, wherein no more than three of the nucleosides of the second modified oligonucleotide comprise a modified sugar moiety comprising a fluorine.

Embodiment A155

The oligomeric duplex of embodiment A154, wherein the second modified oligonucleotide has a sugar motif (5' to 3') selected from: eeyyyyfyfyfyyyyyyyee and yyyyyyfyfyfyyyyyyyyyy; wherein each "y" represents a 2'-OMe sugar moiety, each "e" represents a 2'-MOE sugar moiety, and each "f" represents a 2'-fluoro sugar moiety.

Embodiment A156

The oligomeric duplex of any one of embodiments A119-A152, wherein no more than two of the nucleosides of the second modified oligonucleotide comprise a modified sugar moiety comprising a fluorine.

Embodiment A157

The oligomeric duplex of embodiment A156, wherein the second modified oligonucleotide has a sugar motif (5' to 3') selected from: eeyyyyyyyyffyyyyyyyyee, yyyyyyyyyyffyyyyyyyyyy, eeyyyyyyffyyyyyyyyee, and yyyyyyyyffyyyyyyyyyy; wherein each "y" represents a 2'-OMe sugar moiety, each "e" represents a 2'-MOE sugar moiety, and each "f" represents a 2'-fluoro sugar moiety.

Embodiment A158

The oligomeric duplex of any one of embodiments A119-A151, wherein none of the nucleosides of the second modified oligonucleotide comprises a modified sugar moiety comprising a fluorine.

Embodiment A159

The oligomeric duplex of embodiment A158, wherein the second modified oligonucleotide has a sugar motif (5' to 3') selected from: yyyyyyyyyyyyyyyyyyyy, eeyyyyyyyyyyyyyyyyyyee, yyyyyyyyyydyyyyyyyyyy, and eeyyyyyyyyydyyyyyyyee.

Embodiment A160

The oligomeric duplex of any one of embodiments A119-A159, wherein fewer than 50%, fewer than 40%, fewer than 30%, fewer than 20%, or fewer than 10% of the internucleoside linkages of the first modified oligonucleotide are modified internucleoside linkages.

Embodiment A161

The oligomeric duplex of any one of embodiments A119-A160, wherein the internucleoside linkages between the first and second nucleosides and the second and third nucleosides counting from the 5' end of the first modified oligonucleotide, and the internucleoside linkages between the first and second nucleosides and the second and third nucleosides counting from the 3' end of the first modified oligonucleotide are phosphorothioate internucleoside linkages.

Embodiment A162

The oligomeric duplex of any one of embodiments A119-A161, wherein the first modified oligonucleotide has an internucleoside linkage motif (5' to 3') selected from: ssooooooooooooooooooss, ssooosooooooooooooooss, ssoosososoooooooooooss, and ssoooooooooooooooooss; wherein each "o" represents a phosphodiester internucleoside linkage and each "s" represents a phosphorothioate internucleoside linkage.

Embodiment A163

The oligomeric duplex of any one of embodiments A119-A162, wherein fewer than 50%, fewer than 40%, fewer than 30%, fewer than 20%, or fewer than 10% of the internucleoside linkages of the second modified oligonucleotide are modified internucleoside linkages.

Embodiment A164

The oligomeric duplex of any one of embodiments A119-A163, wherein the internucleoside linkages between the first and second nucleosides and the second and third nucleosides counting from the 5' end of the second modified oligonucleotide, and the internucleoside linkages between the first and second nucleosides and the second and third nucleosides counting from the 3' end of the second modified oligonucleotide are phosphorothioate internucleoside linkages.

Embodiment A165

The oligomeric duplex of any one of embodiments A119-A164, wherein the second modified oligonucleotide has an internucleoside linkage motif (5' to 3') selected from: wherein each "o" represents a phosphodiester internucleoside linkage, each "s" represents a phosphorothioate internucleoside linkage, and each 'z' represents a mesyl phosphoramidate internucleoside linkage.

Embodiment A166

The oligomeric duplex of any one of embodiments A1-A165, wherein the first modified oligonucleotide has a first sugar motif ($1^{st}$) and the second modified oligonucleotide has a second sugar motif ($2^{nd}$) and the first and second sugar motifs are selected from among the following combinations (5' to 3'); $1^{st}$: efyydydyyyyyyfyfyyyyyee and $2^{nd}$: eeyyyyfyfyfyyyyyyyyee; $1^{st}$: efyydydyyyyyyfyfyyyyyyy and $2^{nd}$: yyyyyyffyyyyyyyyyyy; $1^{st}$: efyydydyyyyyyfyfyyyyyee and $2^{nd}$: yyyyyyfyfyfyyyyyyyyyy; $1^{st}$: efyydydyyyyyyfyfyyyyyyy and $2^{nd}$: eeyyyyfyfyfyyyyyyyyee; $1^{st}$: efyydydyyyyyyfyfyyyyyee and $2^{nd}$: eeyyyyyyyffyyyyyyyyee; $1^{st}$: efyydydyyyyyyfyfyyyyyyy and $2^{nd}$: yyyyyyyyyffyyyyyyyyyy; $1^{st}$: efyydydyyyyyyfyfyyyyyee and $2^{nd}$: yyyyyyyyyffyyyyyyyyyy; $1^{st}$: efyydydyyyyyyfyfyyyyyyy and $2^{nd}$: eeyyyyyyyffyyyyyyyyee; $1^{st}$: efyydydyyyyyyfyfyyyyyee and $2^{nd}$: eeyyyyyyyffyyyyyyyyee; $1^{st}$: efyydydyyyyyyfyfyyyyyyy and $2^{nd}$: yyyyyyyyffyyyyyyyyyy; $1^{st}$: efyydydyyyyyyfyfyyyyyee and $2^{nd}$: yyyyyyyyffyyyyyyyyyy; $1^{st}$: efyydydyyyyyyfyfyyyyyyy and $2^{nd}$: eeyyyyyyyffyyyyyyyyee; $1^{st}$: efyydydyyyyyyfyfyyyyyee and $2^{nd}$: eeyyyyfyfyfyyyyyyyyee; $1^{st}$: efyydydyyyyyyfyfyyyyyyy and $2^{nd}$: yyyyyyfyfyfyyyyyyyyyy; $1^{st}$:

efyyydyyyyyyyfyfyyyyyee and 2$^{nd}$: yyyyyyfyfyfyyyyyyyyyy; and 1$^{st}$: efyyydyyyyyyyfyfyyyyyyy and 2$^{nd}$: eeyyyyfyfyfyyyyyyyyee, wherein each "y" represents a 2'-OMe sugar moiety, each "e" represents a 2'-MOE sugar moiety, each "f" represents a 2'-fluoro sugar moiety, and each "d" represents a 2'-β-D-deoxyribosyl sugar moiety.

Embodiment A167

The oligomeric duplex of any one of embodiments A1-A165, wherein the first modified oligonucleotide has a first sugar motif (1$^{st}$) and the second modified oligonucleotide has a second sugar motif (2$^{nd}$) and the first and second sugar motifs are selected from among the following combinations (5' to 3'); 1$^{st}$: efyydydyyyyyyfyfyyyyyee and 2$^{nd}$: eeyyyyfyfffyyyyyyyyyee; 1$^{st}$: efyydydyyyyyyfyfyyyyyyy and 2$^{nd}$: yyyyyyfyfffyyyyyyyyyyy; 1$^{st}$: efyydydyyyyyyfyfyyyyyee and 2$^{nd}$: yyyyyyfyfffyyyyyyyyyyy; 1$^{st}$: efyydydyyyyyyfyfyyyyyyy and 2$^{nd}$: eeyyyyfyfffyyyyyyyyyee; 1$^{st}$: efyyyyyyyyyyyyfyfyyyyyee and 2$^{nd}$: eeyyyyyyyyfffyyyyyyyyyee; 1$^{st}$: efyyyyyyyyyyyyfyfyyyyyyy and 2$^{nd}$: yyyyyyfyfffyyyyyyyyyyy; 1$^{st}$: efyyyyyyyyyyyyfyfyyyyyee and 2$^{nd}$: yyyyyyfyfffyyyyyyyyyyy; 1$^{st}$: efyyyyyyyyyyyyfyfyyyyyyy and 2$^{nd}$: eeyyyyfyfffyyyyyyyyyee; 1$^{st}$: efyyyyyyyyyyyyfyfyyyyyee and 2$^{nd}$: eeyyyyyyyffyyyyyyyyee; 1$^{st}$: efyyyyyyyyyyyyfyfyyyyyyy and 2$^{nd}$: yyyyyyyyyffyyyyyyyyyy; 1$^{st}$: efyyyyyyyyyyyyfyfyyyyyee and 2$^{nd}$: yyyyyyyyyffyyyyyyyyyy; 1$^{st}$: efyyyyyyyyyyyyfyfyyyyyyy and 2$^{nd}$: eeyyyyyyyffyyyyyyyyee; 1$^{st}$: efyyyyyyyyyyyyfyfyyyyyee and 2$^{nd}$: eeyyyyfyfyfyyyyyyyyee; 1$^{st}$: efyyyyyyyyyyyyfyfyyyyyyy and 2$^{nd}$: yyyyyyfyfyfyyyyyyyyyy; 1$^{st}$: efyyyyyyyyyyyyfyfyyyyyee and 2$^{nd}$: yyyyyyfyfyfyyyyyyyyyy; 1$^{st}$: efyyyyyyyyyyyyfyfyyyyyyy and 2$^{nd}$: eeyyyyfyfyfyyyyyyyyee; 1$^{st}$: efyyyfyyyyyyyfyfyyyyyyy and 2$^{nd}$: yyyyyyyyyffyyyyyyyyyy; 1$^{st}$: efyyyfyyyyyyyfyfyyyyyee and 2$^{nd}$: eeyyyyyyyffyyyyyyyyee; 1$^{st}$: efyyyfyyyyyyyfyfyyyyyyy and 2$^{nd}$: eeyyyyyyyffyyyyyyyyee; 1$^{st}$: efyyyfyyyyyyyfyfyyyyyee and 2$^{nd}$: yyyyyyyyyffyyyyyyyyyy; 1$^{st}$: efyyyfyyyyyyyfyfyyyyyee and 2$^{nd}$: yyyyyyfyfyfyyyyyyyyyy; 1$^{st}$: efyyyfyyyyyyyfyfyyyyyyy and 2$^{nd}$: eeyyyyfyfyfyyyyyyyyee; 1$^{st}$: efyyyfyyyyyyyfyfyyyyyee and 2$^{nd}$: yyyyyyfyfyfyyyyyyyyyy; 1$^{st}$: efyyyfyyyyyyyfyfyyyyyyy and 2$^{nd}$: eeyyyyfyfyfyyyyyyyyee; 1$^{st}$: efyyyfyyyyyyyfyfyyyyee and 2$^{nd}$: eeyyyyfyfffyyyyyyyyee; 1$^{st}$: efyyyfyyyyyyyfyfyyyyyy and 2$^{nd}$: yyyyyyfyfffyyyyyyyyyy; 1$^{st}$: efyyyfyyyyyyyfyfyyyyee and 2$^{nd}$: yyyyyyfyfffyyyyyyyyyy; 1$^{st}$: efyyyfyyyyyyyfyfyyyyyy and 2$^{nd}$: eeyyyyfyfffyyyyyyyyee; 1$^{st}$: efyyyfyyyyyyyfyfyyyee and 2$^{nd}$: eeyyyyffyyyyyyyyee; 1$^{st}$: efyyyfyyyyyyyfyfyyyyyy and 2$^{nd}$: yyyyyyffyyyyyyyyyy; 1$^{st}$: efyyyfyyyyyyyfyfyyyee and 2$^{nd}$: yyyyyyffyyyyyyyyyy; 1$^{st}$: efyyyfyyyyyyyfyfyyyyyy and 2$^{nd}$: eeyyyyffyyyyyyyyee; 1$^{st}$: e[FHNA]yydydyyyyfyfyfyyyyyee and 2$^{nd}$: eeyyyyfyfffyyyyyyyyee; 1$^{st}$: efyyyfyyyyyyyfyfyyyyyyy and 2$^{nd}$: eeyyyyfyfffyyyyyyyyyyyey and 2$^{nd}$: yyyyyyfyfffyyyyyyyyyyy; 1$^{st}$: e[FHNA] yydydyyyyfyfyfyyyyyy and 2$^{nd}$: yyyyyyfyfffyyyyyyyyyyy; 1$^{st}$: e[FHNA]yydydyyyyfyfyfYyyyyee and 2$^{nd}$: yyyyyyfyfffyyyyyyyyyyy; 1$^{st}$: e[FHNA] yydydyyyyfyfyfyyyyyy and 2$^{nd}$: eeyyyyfyfffyyyyyyyyyee; 1$^{st}$: e[FHNA]yydydyyyyfyfyfyyyyyee and 2$^{nd}$: eeyyyyfyfyfyyyyyyyyee; 1$^{st}$: e[FHNA] yydydyyyyfyfyfyyyyyy and 2$^{nd}$: yyyyyyfyfyfyyyyyyyyyy; 1$^{st}$: e[FHNA]yydydyyyyfyfyfyyyyyee and 2$^{nd}$:

yyyyyyfyfyfyyyyyyyyyy; and 1$^{st}$: e[FHNA] yydydyyyyfyfyfyyyyyyy and 2$^{nd}$: eeyyyyfyfyfyyyyyyyyee, wherein each "y" represents a 2'-OMe sugar moiety, each "e" represents a 2'-MOE sugar moiety, each "f" represents a 2'-fluoro sugar moiety, each "[FHNA]" represents a 3'-fluoro-hexitol sugar moiety, and each "d" represents a 2'-β-D-deoxyribosyl sugar moiety.

Embodiment A168

The oligomeric duplex of any one of embodiments A1-A165, wherein the first modified oligonucleotide has a first sugar motif (1$^{st}$) and the second modified oligonucleotide has a second sugar motif (2$^{nd}$) and the first and second sugar motifs are selected from among the following combinations (5' to 3'); 1$^{st}$: efyyyfyyyyyyyfyfyyyyyyy and 2$^{nd}$: yyyyyyfyfffyyyyyyyyyy; 1$^{st}$: efyyyfyyyyyyyfyfyyyyyee and 2$^{nd}$: eeyyyyfyfffyyyyyyyyyee; 1$^{st}$: efyyyfyyyyyyyfyfyyyyyee and 2$^{nd}$: yyyyyyfyfffyyyyyyyyyy; 1$^{st}$: efyyyfyyyyyyyfyfyyyyyyy and 2$^{nd}$: eeyyyyfyfffyyyyyyyyyee, wherein each "y" represents a 2'-OMe sugar moiety, each "e" represents a 2'-MOE sugar moiety, and each "f" represents a 2'-fluoro sugar moiety.

Embodiment A169

The oligomeric duplex of any one of embodiments A1-A165, wherein the first modified oligonucleotide has a first sugar motif (1$^{st}$) and the second modified oligonucleotide has a second sugar motif (2$^{nd}$) and the first and second sugar motifs are selected from among the following combinations (5' to 3'); 1$^{st}$: efyyyfyyyyyyyfyfyyyyyyy and 2$^{nd}$: yyyyyyyyyyyyyyyyyyyyyy; 1$^{st}$: efyyyfyyyyyyyfyfyyyyyee and 2$^{nd}$: eeyyyyyyyyyyyyyyyyyyee; 1$^{st}$: efyyyfyyyyyyyfyfyyyyyyy and 2$^{nd}$: eeyyyyyyyyyyyyyyyyyyee; 1$^{st}$: efyyyfyyyyyyyfyfyyyyyee and 2$^{nd}$: yyyyyyyyyyyyyyyyyyyyyy; 1$^{st}$: efyyyfyyyyyyyfyfyyyyyyy and 2$^{nd}$: yyyyyyyyydyyyyyyyyyy; 1$^{st}$: efyyyfyyyyyyyfyfyyyyyee and 2$^{nd}$: eeyyyyyyyydyyyyyyyyee; 1$^{st}$: efyyyfyyyyyyyfyfyyyyyyy and 2$^{nd}$: eeyyyyyyyydyyyyyyyyee; 1$^{st}$: efyyyfyyyyyyyfyfyyyyyee and 2$^{nd}$: yyyyyyyyydyyyyyyyyyy; 1$^{st}$: efyyyyyyyyyyyyfyyyyyyee and 2$^{nd}$: yyyyyyfyfffyyyyyyyyyy; 1$^{st}$: efyyyyyyyyyyyyfyyyyyyee and 2$^{nd}$: eeyyyyfyfffyyyyyyyyyee; 1$^{st}$: efyyyyyyyyyyyyfyyyyyyyy and 2$^{nd}$: yyyyyyfyfffyyyyyyyyyy; 1$^{st}$: efyyyyyyyyyyyyfyyyyyyee and 2$^{nd}$: eeyyyyfyfffyyyyyyyyyee; 1$^{st}$: efyyyyyyyyyyyyfyyyyyyyy and 2$^{nd}$: yyyyyyfyfyyyyyyyyyyy; 1$^{st}$: efyyyyyyyyyyyyfyyyyyyee and 2$^{nd}$: yyyyyyfyfyyyyyyyyyyy; 1$^{st}$: efyyyyyyyyyyyyfyyyyyyyy and 2$^{nd}$: eeyyyyfyfyyyyyyyyyee; 1$^{st}$: efyyydyyyyyyfyfyyyyyee and 2$^{nd}$: eeyyyyfyfffyyyyyyyyyee; 1$^{st}$: efyyydyyyyyyfyfyyyyyyy and 2$^{nd}$: yyyyyyfyfffyyyyyyyyyyy; 1$^{st}$: efyyydyyyyyyfyfyyyyyee and 2$^{nd}$: yyyyyyfyfffyyyyyyyyyyy; 1$^{st}$: efyyydyyyyyyfyfyyyyyyy and 2$^{nd}$: eeyyyyfyfffyyyyyyyyyee; 1$^{st}$: efyyyfyyyyyyyfyfyyyee and 2$^{nd}$: eeyyfyfffyyyyyyyyee; 1$^{st}$: efyyyfyyyyyyyfyfyyyyyy and 2$^{nd}$: yyyyfyfffyyyyyyyyyy; 1$^{st}$: efyyyfyyyyyyyfyfyyyee and 2$^{nd}$: yyyyfyfffyyyyyyyyyy; 1$^{st}$: efyyyfyyyyyyyfyfyyyyyy and 2$^{nd}$: eeyyfyfffyyyyyyyyee; 1$^{st}$: efyyyfyyyyyyyfydyyyyee and 2$^{nd}$: eeyyyyfyfffyyyyyyyyyee; 1$^{st}$: efyyyfyyyyyyyfydyyyyyy and 2$^{nd}$: yyyyyyfyfffyyyyyyyyyyy; 1$^{st}$: efyyyfyyyyyyyfydyyyyyee and 2$^{nd}$: yyyyyyfyfffyyyyyyyyyyy; 1$^{st}$: efyyyfyyyyyyyyfydyyyyyy and 2$^{nd}$: eeyyyyfyfffyyyyyyyyee; 1$^{st}$: e[FHNA] yyyfyyyyyyyyfyfyyyyyee and 2$^{nd}$: eeyyyyfyfffyyyyyyyyee; 1$^{st}$: e[FHNA]yyyfyyyyyyyfyfyyyyyyy and 2$^{nd}$: yyyyyyfyfffyyyyyyyyyy; 1$^{st}$: e[FHNA] yyyfyyyyyyyfyfyyyyyee and 2$^{nd}$: yyyyyyfyfffyyyyyyyyyy; and 1$^{st}$: e[FHNA]yyyfyyyyyyyfyfyyyyyyy and 2$^{nd}$: eeyyyyfyfffyyyyyyyyee, wherein each "y" represents a 2'-OMe sugar moiety, each "e" represents a 2'-MOE sugar moiety, each "f" represents a 2'-fluoro sugar moiety, each "[FHNA]" represents a 3-fluoro-hexitol sugar moiety, and each "d" represents a 2-β-D-deoxyribosyl sugar moiety.

Embodiment A170

The oligomeric duplex of any one of embodiments A1-A165, wherein the first modified oligonucleotide has a first sugar motif (1$^{st}$) and the second modified oligonucleotide has a second sugar motif (2$^{nd}$) and the first and second sugar motifs are selected from among the following combinations (5 to 3'); 1$^{st}$: efyyyyyyyyyyyyfyyyyyyyee and 2$^{nd}$: eeyyyyyyyffyyyyyyyyee; 1$^{st}$: efyyyyyyyyyyyyfyyyyyyyyy and 2$^{nd}$: yyyyyyyyffyyyyyyyyyy; 1$^{st}$: efyyyyyyyyyyyyfyyyyyyyee and 2$^{nd}$: yyyyyyyyffyyyyyyyyyy; 1$^{st}$: efYyyyyyyyyyyyfyyyyyyyyy and 2$^{nd}$: eeyyyyyyyffyyyyyyyyee; 1$^{st}$: efyyyfyyyyyyyfyyyyyyyee and 2$^{nd}$: eeyyyyfyfffyyyyyyyyee; 1$^{st}$: efyyyfyyyyyyyfyyyyyyyyy and 2$^{nd}$: yyyyyyfyfffyyyyyyyyyy; 1$^{st}$: efyyyfyyyyyyyfyyyyyyyee and 2$^{nd}$: yyyyyyfyfffyyyyyyyyyy; 1$^{st}$: efyyyfyyyyyyyfyyyyyyyyy and 2$^{nd}$: eeyyyyfyfffyyyyyyyyee; 1$^{st}$: efyyyfyyyyyyyfyyyyyyyee and 2$^{nd}$: eeyyyyyyyffyyyyyyyyee; 1$^{st}$: efyyyfyyyyyyyfyyyyyyyyy and 2$^{nd}$: yyyyyyyyffyyyyyyyyyy; 1$^{st}$: efyyyfyyyyyyyfyyyyyyyee and 2$^{nd}$: yyyyyyfyfffyyyyyyyyyy; and 1$^{st}$: efyyyfyyyyyyyfyyyyyyyyy and 2$^{nd}$: eeyyyyfyfffyyyyyyyyee, wherein each "y" represents a 2'-OMe sugar moiety, each "e" represents a 2'-MOE sugar moiety, and each "f" represents a 2'-fluoro sugar moiety.

Embodiment A171

The oligomeric duplex of any one of embodiments A119-A170, wherein the internucleoside linkages between the first and second nucleosides and the second and third nucleosides counting from the 5' end of the first modified oligonucleotide, and the internucleoside linkages between the first and second nucleosides and the second and third nucleosides counting from the 3' end of the first modified oligonucleotide are phosphorothioate internucleoside linkages and wherein all other internucleoside linkages of the first modified oligonucleotide are phosphodiester internucleoside linkages.

Embodiment A172

The oligomeric duplex of any one of embodiments A119-A171, wherein the internucleoside linkages between the first and second nucleosides and the second and third nucleosides counting from the 5' end of the second modified oligonucleotide, and the internucleoside linkages between the first and second nucleosides and the second and third nucleosides counting from the 3' end of the second modified oligonucleotide are phosphorothioate internucleoside linkages and wherein all other internucleoside linkages of the second modified oligonucleotide are phosphodiester internucleoside linkages.

Embodiment A173

The oligomeric duplex of any one of embodiments A119-A172, wherein the nucleobase sequence of the first modified oligonucleotide comprises or consists of the nucleobase sequence of any one of SEQ ID NOs: 967, 968, 971, 972, 974, 975, 1254, 1255, and 1033-1038.

Embodiment A174

The oligomeric duplex of any one of embodiments A1-171, wherein a cytosine nucleobase in the first and/or second modified oligonucleotide is optionally 5-methylcytosine.

Embodiment A175

The oligomeric duplex of any one of embodiments A119-A174, wherein the duplex comprises a conjugate group comprising a conjugate moiety and a conjugate linker.

Embodiment A176

The oligomeric duplex of embodiment A175, wherein the conjugate moiety comprises an active drug substance, an aliphatic chain, a lipid, a peptide, a protein, a hydrocarbon, a polyamine, a polyamide, a polyether, a thioether, an aptamer, an antibody or antibody fragment, a vitamin, a fatty acid, a carbohydrate, an intercalator or a reporter molecule.

Embodiment A177

The oligomeric duplex of embodiment A175, wherein the conjugate group comprises a C22 alkyl, C20 alkyl, C17 alkyl, C16 alkyl, C10 alkyl, C21 alkyl, C19 alkyl, C18 alkyl, C15 alkyl, C14 alkyl, C13 alkyl, C12 alkyl, C11 alkyl, C9 alkyl, C8 alkyl, C7 alkyl, C6 alkyl, or C5 alkyl, wherein the alkyl chain optionally has one or more unsaturated bonds.

Embodiment A178

The oligomeric duplex of embodiment A175, wherein the conjugate group comprises a 6-palmitamidohexyl moiety or a 2-(hydroxymethyl)-6-palmitamidohexyl moiety.

Embodiment A179

The oligomeric duplex of embodiment A175, wherein the duplex comprises a conjugate moiety that binds type 1 transferrin receptor (TfR1).

Embodiment A180

The oligomeric duplex of embodiment A179, wherein the conjugate moiety is selected from antibody or fragment thereof, a protein or peptide or an aptamer capable of binding TfR1.

Embodiment A181

The oligomeric duplex of embodiment A180, wherein the conjugate moiety is a cyclic protein or cyclic peptide.

Embodiment A182

The oligomeric duplex of embodiment A181, wherein the conjugate group consists of the bicycle ligand and a conjugate linker.

Embodiment A183

The oligomeric duplex of embodiment A182, wherein the bicycle ligand comprises a polypeptide consisting of 13-22 linked amino acids or amino acid mimetics and a molecular scaffold, wherein each of a first, a second, and a third amino acid of the polypeptide comprises a reactive group, each of which separately forms a bond with the molecular scaffold, thereby forming two polypeptide loops attached to the molecular scaffold.

Embodiment A184

The oligomeric duplex of embodiment A183 wherein the bicycle ligand comprises a sequence selected from any one of SEQ ID NO: 1071-1252.

Embodiment A185

The oligomeric duplex of any one of embodiments A182-A184, wherein the conjugate linker comprises a (bicyclo[6.1.0]nonyne)-formyl (BCN) moiety.

Embodiment A186

The oligomeric duplex of embodiment A185, wherein the conjugate linker comprises a 6-(BCN-carbamate)-2-(hydroxymethyl)hexyl phosphoryl moiety or a 6-(BCN-carbamate)hexyl phosphoryl moiety.

Embodiment A187

The oligomeric duplex of any one of embodiments A119-A174, comprising a conjugate group consisting of a conjugate moiety and a conjugate linker wherein the linker comprises a 6-(BCN-carbamate)-2-(hydroxymethyl)hexyl phosphoryl moiety or a 6-(BCN-carbamate) hexyl phosphoryl moiety.

Embodiment A188

The oligomeric duplex of any one of embodiments A119-A174, comprising a bicycle compound comprising a peptide having the following chemical notation:

```
                                    (SEQ ID NO: 1045)
        Ac-CP[HyP]DAYLGC[tBuGly]SYCEPW[K(N₃)]-NH₂,
``` wherein:
    Ac=acetyl,
    C=cysteine,
    P=proline,
    D=aspartate,
    A=alanine,
    Y=tyrosine,
    L=leucine,
    G=glycine,
    S=serine,
    E=glutamate,
    W=tryptophan,
    [HyP]=trans-4-hydroxy-L-proline,
    [tBuGly]=t-butyl-glycine, and
    [K(N₃)]=6-azido lysine; and
wherein each cysteine forms a covalent bond with the molecular scaffold 1,1',1"-(1,3,5-triazinane-1,3,5-triyl) tris(2-bromoethanone) (TATB).

Embodiment A189

The oligomeric duplex of any one of embodiments A119-A174, comprising a bicycle compound having the following structure:

or a salt thereof, wherein Q is N₃ (BCY17901, SEQ ID NO: 1045), NH₂ (BCY21757, SEQ ID NO: 1202), SH (BCY21758, SEQ ID NO:1203), a conjugate linker, or a conjugate linker covalently connected to an oligonucleotide.

Embodiment A190

The oligomeric duplex of embodiment A188, wherein Q is N₃.

Embodiment A191

The oligomeric duplex of any one of embodiments A119-A174, comprising a conjugate group having the following structure (SEQ ID NO: 1291):

Embodiment A192

The oligomeric duplex of any one of embodiments A119-A174, comprising a conjugate group having the following structure (SEQ ID NO: 1292):

Embodiment A193

The oligomeric duplex of any one of embodiments A175-A191, wherein the bicycle compound or conjugate group is attached to the second modified oligonucleotide.

Embodiment A194

The oligomeric duplex of any one of embodiments A175-A191, wherein the bicycle compound or conjugate group is attached to the 5'- or 3'-end of the second modified oligonucleotide.

Embodiment A195

The oligomeric duplex of any one of embodiments A175-191, wherein the bicycle compound or conjugate group is attached to the 5'-terminal nucleoside of the second modified oligonucleotide.

Embodiment A196

An oligomeric compound comprising a modified oligonucleotide according to the following chemical notation:

(SEQ ID NO: 1033)

$vPT_{es}U_{fs}U_{yo}A_{yo}A_{yo}G_{do}A_{yo}U_{yo}G_{yo}A_{yo}G_{yo}A_{yo}C_{yo}A_{yo}G_{yo}A_{yo}$ $A_{yo}A_{yo}U_{yo}U_{yo}G_{ys}A_{es}A_{e}$, wherein:
A=an adenine nucleobase,
C=a cytosine nucleobase,
G=a guanine nucleobase,
T=a thymine nucleobase, U=a uracil nucleobase,
d=a 2'-β-D-deoxyribosyl sugar moiety,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage, and
vP=a 5' vinyl phosphonate moiety.

Embodiment A197

An oligomeric compound comprising a modified oligonucleotide according to the following chemical notation:

(SEQ ID NO: 1027)

$^{m}C_{es}A_{es}A_{yo}U_{yo}U_{yo}U_{yo}C_{yo}U_{yo}G_{yo}U_{fo}C_{fo}U_{yo}C_{yo}A_{yo}U_{yo}C_{yo}$ $U_{yo}U_{yo}A_{ys}A_{es}A_{e}$, wherein:
A=an adenine nucleobase,
$^{m}C$=a 5-methyl cytosine nucleobase,
C=a cytosine nucleobase,
G=a guanine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage, and
s=a phosphorothioate internucleoside linkage.

Embodiment A198

An oligomeric compound comprising a conjugated modified oligonucleotide according to the following chemical notation:

(SEQ ID NOS 1293 and 1039)

[Ac-C̲ P [HyP] D A Y L G C [tBuGly] S Y C E P W

[K̲(N₃)]-NH₂]-[6-(BCN-carbamate)hexyl]ₒ⁻ᵐC$_{es}$A$_{es}$A$_{yo}$

U$_{yo}$U$_{yo}$U$_{yo}$C$_{yo}$U$_{yo}$G$_{yo}$U$_{fo}$C$_{fo}$U$_{yo}$C$_{yo}$A$_{yo}$U$_{yo}$C$_{yo}$U$_{yo}$U$_{yo}$A$_{ys}$

A$_{es}$A$_{e}$, wherein:
 Ac=acetyl, C=cysteine, [HyP]=trans-4-hydroxy-L-pro-
  line, D=aspartate, A=alanine, Y=tyrosine, L-leucine,
  G=glycine, [tBuGly]=t-butyl-glycine, S=serine,
  E=glutamate, P=proline, W=tryptophan, [K(N₃)]=6-
  azido lysine, NH₂=amino, BCN=(bicyclo[6.1.0]non-
  yne)-formyl, ᵐC=a 5-methyl cytosine nucleobase, C=a
  cytosine nucleobase, A=an adenine nucleobase, G=a
  guanine nucleobase, U=a uracil nucleobase, e=a
  2'-MOE sugar moiety, f=a 2'-fluoro sugar moiety, y=a
  2'-OMe sugar moiety, o=a phosphodiester internucleo-
  side linkage, and s=a phosphorothioate internucleoside
  linkage;
 and wherein each cysteine forms a covalent bond with the
molecular scaffold 1,1',1"-(1,3,5-triazinane-1,3,5-triyl)tris
(2-bromoethanone) (TATB).

Embodiment A199

An oligomeric duplex comprising the oligomeric com-
pound according to embodiment A195 and the oligomeric
compound according to embodiment A196.

Embodiment A200

An oligomeric duplex comprising the oligomeric com-
pound according to embodiment A 195 and the oligomeric
compound according to embodiment A197.

Embodiment A201

An oligomeric compound comprising a modified oligo-
nucleotide according to the following chemical notation:

(SEQ ID NO: 1034)

vPT$_{es}$U$_{fs}$U$_{yo}$A$_{yo}$A$_{do}$G$_{yo}$A$_{do}$U$_{yo}$G$_{yo}$A$_{yo}$G$_{yo}$A$_{yo}$C$_{yo}$A$_{ro}$G$_{yo}$

A$_{ro}$A$_{yo}$A$_{yo}$U$_{yo}$U$_{yo}$G$_{ys}$A$_{es}$A$_{e}$, wherein:
 A=an adenine nucleobase,
 C=a cytosine nucleobase,
 G=a guanine nucleobase,
 T=a thymine nucleobase,
 U=a uracil nucleobase,
 d=a 2'-β-D-deoxyribosyl sugar moiety,
 e=a 2'-MOE sugar moiety,
 f=a 2'-fluoro sugar moiety,
 y=a 2'-OMe sugar moiety,
 o=a phosphodiester internucleoside linkage,
 s=a phosphorothioate internucleoside linkage, and
 vP=a 5' vinyl phosphonate moiety.

Embodiment A202

An oligomeric compound comprising a modified oligo-
nucleotide according to the following chemical notation:

(SEQ ID NO: 1028)

C$_{es}$A$_{es}$A$_{yo}$U$_{yo}$U$_{yo}$U$_{yo}$C$_{yo}$U$_{yo}$G$_{yo}$U$_{yo}$C$_{fo}$U$_{yo}$C$_{yo}$A$_{yo}$U$_{yo}$C$_{yo}$

U$_{yo}$U$_{yo}$A$_{ys}$A$_{es}$A$_{e}$, wherein:
 A=an adenine nucleobase,
 C=a cytosine nucleobase,
 G=a guanine nucleobase,
 U=a uracil nucleobase,
 e=a 2'-MOE sugar moiety,
 f=a 2'-fluoro sugar moiety,
 y=a 2'-OMe sugar moiety,
 o=a phosphodiester internucleoside linkage, and
 s=a phosphorothioate internucleoside linkage.

Embodiment A203

An oligomeric compound comprising a conjugated modi-
fied oligonucleotide according to the following chemical
notation:

(SEQ ID NOS 1294 and 1040)

[Ac-C̲ P [HyP] D A Y L G C [tBuGly] S Y C E P W

[K̲(N₃)]-NH₂]-[6-(BCN-carbamate)hexyl]ₒC$_{es}$A$_{es}$A$_{yo}$

U$_{yo}$U$_{yo}$U$_{yo}$C$_{fo}$U$_{yo}$G$_{yo}$U$_{yo}$C$_{fo}$U$_{yo}$C$_{yo}$A$_{yo}$U$_{yo}$C$_{yo}$U$_{yo}$U$_{yo}$A$_{ys}$

A$_{es}$A$_{e}$, wherein:
 Ac=acetyl, C=cysteine, [HyP]=trans-4-hydroxy-L-pro-
  line, D=aspartate, A=alanine, Y=tyrosine, L-leucine,
  G-glycine, [tBuGly]=t-butyl-glycine, S=serine,
  E=glutamate, P=proline, W=tryptophan, [K(N₃)]=6-
  azido lysine, NH₂=amino, BCN=(bicyclo[6.1.0]non-
  yne)-formyl, C=a cytosine nucleobase, A=an adenine
  nucleobase, G=a guanine nucleobase, U=a uracil nucle-
  obase, e=a 2'-MOE sugar moiety, f=a 2'-fluoro sugar
  moiety, y=a 2'-OMe sugar moiety, o=a phosphodiester
  internucleoside linkage, and s=a phosphorothioate
  internucleoside linkage;
 and wherein each cysteine of the peptide forms a covalent
 bond with a molecular scaffold of 1,1',1"-(1,3,5-triazinane-
1,3,5-triyl)tris(2-bromoethanone) (TATB).

Embodiment A204

An oligomeric duplex comprising an oligomeric com-
pound of embodiment A200 and an oligomeric compound of
embodiment A201.

Embodiment A205

An oligomeric duplex comprising an oligomeric com-
pound of embodiment A200 and an oligomeric compound of
embodiment A202.

Embodiment A206

An oligomeric compound comprising a modified oligonucleotide according to the following chemical notation:

(SEQ ID NO: 1035)

$vPT_{es}A_{fs}U_{yo}A_{yo}A_{yo}A_{do}U_{yo}A_{yo}G_{yo}A_{yo}U_{yo}U_{yo}C_{yo}U_{fo}G_{yo}U_{fo}$ $A_{yo}G_{yo}C_{yo}U_{yo}U_{ys}A_{es}A_{e}$, wherein:
  A=an adenine nucleobase,
  C=a cytosine nucleobase,
  G=a guanine nucleobase,
  T=a thymine nucleobase,
  U=a uracil nucleobase,
  d=a 2-β-D-deoxyribosyl sugar moiety,
  e=a 2'-MOE sugar moiety,
  f=a 2'-fluoro sugar moiety,
  y=a 2'-OMe sugar moiety,
  o=a phosphodiester internucleoside linkage,
  s=a phosphorothioate internucleoside linkage, and
  vP=a 5' vinyl phosphonate moiety.

Embodiment A207

An oligomeric compound comprising a modified oligonucleotide according to the following chemical notation:

(SEQ ID NO: 1029)

$A_{es}A_{es}G_{yo}C_{yo}U_{yo}A_{yo}C_{yo}A_{yo}G_{yo}A_{fo}A_{fo}U_{yo}C_{yo}U_{yo}A_{yo}U_{yo}$ $U_{yo}U_{yo}A_{ys}T_{es}A_{e}$;

wherein:
  A=an adenine nucleobase,
  C=a cytosine nucleobase,
  G=a guanine nucleobase,
  T=a thymine nucleobase,
  U=a uracil nucleobase,
  e=a 2'-MOE sugar moiety,
  f=a 2'-fluoro sugar moiety,
  y=a 2'-OMe sugar moiety,
  o=a phosphodiester internucleoside linkage, and
  s=a phosphorothioate internucleoside linkage.

Embodiment A208

An oligomeric compound comprising a conjugated modified oligonucleotide according to the following chemical notation:

(SEQ ID NOS 1295 and 1041)

[Ac-C P [HyP] D A Y L G C [tBuGly] S Y C E P W

[K(N₃)]-NH₂]-[6-(BCN-carbamate)hexyl]$_o$A$_{es}$A$_{es}$G$_{yo}$ $C_{yo}U_{yo}A_{yo}C_{yo}A_{yo}G_{yo}A_{fo}A_{fo}U_{yo}C_{yo}U_{yo}A_{yo}U_{yo}U_{yo}U_{yo}A_{ys}$ $T_{es}A_{e}$, wherein:
  Ac=acetyl, C=cysteine, [HyP]=trans-4-hydroxy-L-proline, D=aspartate, A=alanine, Y=tyrosine, L=leucine, G=glycine, [tBuGly]=t-butyl-glycine, S=serine, E=glutamate, P=proline, W=tryptophan, [K(N₃)]=6-azido lysine, NH₂=amino, BCN=(bicyclo[6.1.0]non-yne)-formyl, C=a cytosine nucleobase, A=an adenine nucleobase, G=a guanine nucleobase, T=a thymine nucleobase, U=a uracil nucleobase, e=a 2-MOE sugar moiety, f=a 2'-fluoro sugar moiety, y=a 2'-OMe sugar moiety, o=a phosphodiester internucleoside linkage, and s=a phosphorothioate internucleoside linkage; and wherein each cysteine of the peptide forms a covalent bond with a molecular scaffold of 1,1',1''-(1,3,5-triazinane-1,3,5-triyl)tris(2-bromoethanone) (TATB).

Embodiment A209

An oligomeric duplex comprising an oligomeric compound of embodiment A205 and an oligomeric compound of embodiment A206.

Embodiment A210

An oligomeric compound comprising an oligomeric compound of embodiment A205 and an oligomeric compound of embodiment A207.

Embodiment A211

An oligomeric compound comprising a modified oligonucleotide according to the following chemical notation:

(SEQ ID NO: 1036)

$vPT_{es}A_{fs}U_{yo}A_{yo}A_{do}A_{yo}T_{do}A_{yo}G_{yo}A_{yo}U_{yo}U_{yo}C_{yo}U_{fo}G_{yo}U_{fo}$ $A_{yo}G_{yo}C_{yo}U_{yo}U_{ys}A_{es}A_{e}$, wherein:
  A=an adenine nucleobase,
  C=a cytosine nucleobase,
  G=a guanine nucleobase,
  T=a thymine nucleobase,
  U=a uracil nucleobase,
  d=a 2-β-D-deoxyribosyl sugar moiety,
  e=a 2'-MOE sugar moiety,
  f=a 2'-fluoro sugar moiety,
  y=a 2'-OMe sugar moiety,
  o=a phosphodiester internucleoside linkage,
  s=a phosphorothioate internucleoside linkage, and
  vP=a 5' vinyl phosphonate moiety.

Embodiment A212

An oligomeric compound comprising a modified oligonucleotide according to the following chemical notation:

(SEQ ID NO: 1030)

$A_{es}A_{es}G_{yo}C_{yo}U_{yo}A_{yo}C_{fo}A_{yo}G_{fo}A_{yo}A_{fo}U_{yo}C_{yo}U_{yo}A_{yo}U_{yo}$ $U_{yo}U_{yo}A_{ys}U_{es}A_{e}$, wherein:
  A=an adenine nucleobase,
  C=a cytosine nucleobase,
  G=a guanine nucleobase,
  U=a uracil nucleobase,
  e=a 2'-MOE sugar moiety,
  f=a 2'-fluoro sugar moiety,
  y=a 2'-OMe sugar moiety,
  o=a phosphodiester internucleoside linkage, and
  S=a phosphorothioate internucleoside linkage.

Embodiment A213

An oligomeric compound comprising a conjugated modified oligonucleotide conjugate according to the following chemical notation:

(SEQ ID NOS 1296 and 1042)

[Ac-C P [HyP] D A Y L G C [tBuGly] S Y C E P W

[K(N₃)]-NH₂]-[6-(BCN-carbamate)hexyl]ₒAₑₛAₑₛGᵧₒ

CᵧₒUᵧₒAᵧₒCᵩₒAᵧₒGᵣₒAᵧₒAᵩₒUᵧₒCᵧₒUᵧₒAᵧₒUᵧₒUᵧₒUᵧₒAᵧₛ

UₑₛAₑ, wherein:

Ac=acetyl, C=cysteine, [HyP]=trans-4-hydroxy-L-proline, D=aspartate, A=alanine, Y=tyrosine, L-leucine, G-glycine, [tBuGly]=t-butyl-glycine, S=serine, E=glutamate, P=proline, W=tryptophan, [K(N₃)]=6-azido lysine, NH₂=amino, BCN=(bicyclo[6.1.0]nonyne)-formyl, C=a cytosine nucleobase, A=an adenine nucleobase, G=a guanine nucleobase, U=a uracil nucleobase, e=a 2'-MOE sugar moiety, f=a 2'-fluoro sugar moiety, y=a 2'-OMe sugar moiety, o=a phosphodiester internucleoside linkage, and s=a phosphorothioate internucleoside linkage;

and wherein each cysteine of the peptide forms a covalent bond with a molecular scaffold of 1,1',1"-(1,3,5-triazinane-1,3,5-triyl)tris(2-bromoethanone) (TATB).

Embodiment A214

An oligomeric duplex comprising an oligomeric compound of embodiment A210 and an oligomeric compound of embodiment A211.

Embodiment A215

An oligomeric duplex comprising an oligomeric compound of embodiment A210 and an oligomeric compound of embodiment A212.

Embodiment A216

An oligomeric compound comprising a modified oligonucleotide according to the following chemical notation:

(SEQ ID NO: 1037)

vPTₑₛUₔₛAᵧₒAᵧₒGᵧₒTₔₒUᵧₒUᵧₒUᵧₒAᵧₒGᵧₒUᵧₒCᵧₒUᵩₒUᵧₒAᵩₒ

AᵧₒUᵧₒCᵧₒUᵧₒUᵧₛAₑₛAₑ, wherein:

A=an adenine nucleobase,
C=a cytosine nucleobase,
G=a guanine nucleobase,
T=a thymine nucleobase,
U=a uracil nucleobase,
d=a 2'-β-D-deoxyribosyl sugar moiety,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage, and
vP=a 5' vinyl phosphonate moiety.

Embodiment A217

An oligomeric compound comprising a modified oligonucleotide according to the following chemical notation:

(SEQ ID NO: 1031)

AₑₛAₑₛGᵧₒAᵧₒUᵧₒUᵧₒAᵧₒAᵧₒGᵧₒAᵩₒCᵩₒUᵧₒAᵧₒAᵧₒAᵧₒAᵧₒ

CᵧₒUᵧₒUᵧₛAₑₛAₑ;

wherein:

A=an adenine nucleobase,
C=a cytosine nucleobase,
G=a guanine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage, and
s=a phosphorothioate internucleoside linkage.

Embodiment A218

An oligomeric compound comprising a conjugated modified oligonucleotide according to the following chemical notation:

(SEQ ID NOS 1297 and 1043)

[Ac-C P [HyP] D A Y L G C [tBuGly] S Y C E P W

[K(N₃)]-NH₂]-[6-(BCN-carbamate)hexyl]ₒAₑₛAₑₛGᵧₒ

AᵧₒUᵧₒUᵧₒAᵧₒAᵧₒGᵧₒAᵩₒCᵩₒUᵧₒAᵧₒAᵧₒAᵧₒAᵧₒCᵧₒUᵧₒUᵧₛ

AₑₛAₑ, wherein:

Ac=acetyl, C=cysteine, [HyP]=trans-4-hydroxy-L-proline, D=aspartate, A=alanine, Y=tyrosine, L=leucine, G=glycine, [tBuGly]=t-butyl-glycine, S=serine, E=glutamate, P=proline, W=tryptophan, [K(N₃)]=6-azido lysine, NH₂=amino, BCN=(bicyclo[6.1.0]nonyne)-formyl, C=a cytosine nucleobase, A=an adenine nucleobase, G=a guanine nucleobase, U=a uracil nucleobase, e=a 2'-MOE sugar moiety, f=a 2'-fluoro sugar moiety, y=a 2'-OMe sugar moiety, o=a phosphodiester internucleoside linkage, and s=a phosphorothioate internucleoside linkage;

and wherein each cysteine of the peptide forms a covalent bond with a molecular scaffold of 1,1',1"-(1,3,5-triazinane-1,3,5-triyl)tris(2-bromoethanone) (TATB).

Embodiment A219

An oligomeric duplex comprising the modified oligonucleotide according to embodiment A215 and the modified oligonucleotide according to embodiment A216.

Embodiment A220

An oligomeric duplex comprising the modified oligonucleotide according to embodiment A215 and the conjugate according to embodiment A217.

Embodiment A221

An oligomeric compound comprising a modified oligonucleotide according to the following chemical notation:

(SEQ ID NO: 1038)

vPTₑₛUₔₛAᵧₒAᵧₒGₔₒUᵧₒTₔₒUᵧₒUᵧₒAᵧₒGᵧₒUᵧₒCᵧₒUᵩₒUᵧₒAᵩₒ

AᵧₒUᵧₒCᵧₒUᵧₒUᵧₛAₑₛAₑ, wherein:

A=an adenine nucleobase,
C=a cytosine nucleobase,

G=a guanine nucleobase,

T=a thymine nucleobase,

U=a uracil nucleobase, d=a 2-β-D-deoxyribosyl sugar moiety, e=a 2'-MOE sugar moiety, f=a 2'-fluoro sugar moiety, y=a 2'-OMe sugar moiety, o=a phosphodiester internucleoside linkage, s=a phosphorothioate internucleoside linkage, and vP=a 5' vinyl phosphonate moiety.

Embodiment A222

An oligomeric compound comprising a modified oligo-nucleotide according to the following chemical notation:

(SEQ ID NO: 1032)

$A_{es}A_{es}G_{yo}A_{yo}U_{yo}U_{yo}A_{fo}A_{yo}G_{fo}A_{yo}C_{fo}U_{yo}A_{yo}A_{yo}A_{yo}A_{yo}$ $C_{yo}U_{yo}U_{ys}A_{es}A_{e}$, wherein:

A=an adenine nucleobase,

C=a cytosine nucleobase,

G=a guanine nucleobase,

U=a uracil nucleobase, e=a 2'-MOE sugar moiety, f=a 2'-fluoro sugar moiety, y=a 2'-OMe sugar moiety, o=a phosphodiester internucleoside linkage, and s=a phosphorothioate internucleoside linkage.

Embodiment A223

An oligomeric compound comprising a conjugated modi-fied oligonucleotide according to the following chemical notation:

(SEQ ID NOS 1298 and 1044)

[Ac-C P [HyP] D A Y L G C [tBuGly] S Y C E P W

[K(N₃)]-NH₂]-[6-(BCN-carbamate)hexyl]₀A_{es}A_{es}G_{yo}

$A_{yo}U_{yo}U_{yo}A_{fo}A_{yo}G_{ro}A_{yo}C_{fo}U_{yo}A_{yo}A_{yo}A_{yo}A_{yo}A_{yo}C_{yo}U_{yo}U_{ys}$ $A_{es}A_{e}$, wherein:

Ac=acetyl, C=cysteine, [HyP]=trans-4-hydroxy-L-pro-line, D=aspartate, A=alanine, Y=tyrosine, L=leucine, G-glycine, [tBuGly]=t-butyl-glycine, S=serine, E=glutamate, P=proline, W=tryptophan, [K(N₃)]=6-azido lysine, NH₂=amino, BCN=(bicyclo[6.1.0]non-yne)-formyl, C=a cytosine nucleobase, A=an adenine nucleobase, G=a guanine nucleobase, U=a uracil nucle-obase, e=a 2'-MOE sugar moiety, f=a 2'-fluoro sugar moiety, y=a 2'-OMe sugar moiety, o=a phosphodiester internucleoside linkage, and s=a phosphorothioate internucleoside linkage;

and wherein each cysteine of the peptide forms a covalent bond with a molecular scaffold of 1,1',1"-(1,3,5-triazinane-1,3,5-triyl)tris(2-bromoethanone) (TATB).

Embodiment A224

An oligomeric duplex comprising an oligomeric com-pound of embodiment A220 and an oligomeric compound of embodiment A221.

Embodiment A225

An oligomeric duplex comprising an oligomeric com-pound of embodiment A220 and an oligomeric compound of embodiment A222.

A268. A population of oligomeric duplexed or oligomeric compounds of any of embodiments A1-A225, wherein the population is enriched for first and/or second modified oligonucleotides comprising at least one particular phospho-rothioate internucleoside linkage having a particular stereo-chemical configuration

Embodiment A269

The population of embodiment A267, wherein the popu-lation is enriched for first and/or second modified oligo-nucleotides comprising at least one particular phosphoroth-ioate internucleoside linkage having the (Sp) or (Rp) configuration.

Embodiment A270

The oligomeric duplex or oligomeric compound of any one of embodiments A1-A225, wherein the first modified oligonucleotide consists of 23 linked nucleosides and the second modified oligonucleotide consists of 21 linked nucleosides.

Embodiment A271

An antisense compound comprising or consisting of an oligomeric duplex or oligomeric compound of any one of embodiments A1-A225.

Embodiment A272

The antisense compound of embodiment A270, wherein the antisense compound is an RNAi agent capable of reduc-ing the amount of PLN nucleic acid through the activation of RISC/Ago2.

Embodiment A273

A pharmaceutical composition comprising the oligomeric duplex or oligomeric compound of any one of embodiments A1-A225 or A269, the population of any one of embodi-ments A267-A268, or the antisense compound of embodi-ment A270 or embodiment A271, and a pharmaceutically acceptable diluent or carrier.

Embodiment A274

The pharmaceutical composition of embodiment A272, wherein the pharmaceutically acceptable diluent is water or phosphate-buffered saline.

Embodiment A275

The pharmaceutical composition of embodiment A273, wherein the pharmaceutical composition consists essentially of the oligomeric duplex, oligomeric compound or the antisense compound, and water or phosphate-buffered saline.

Embodiment A276

A method of decreasing the amount of PLN RNA or PLN protein in a cell, tissue, organ or subject, comprising contacting the cell, tissue, organ or subject with the oligomeric duplex or oligomeric compound of any one of embodiments A1-A225 or A269, the population of any one of embodiments A267-A268, the antisense compound of embodiment A270 or embodiment A271, or the pharmaceutical composition of any one of embodiments A272-A274.

Embodiment A277

The method of embodiment A275, wherein the cell is a muscle cell and/or a cardiac cell.

Embodiment A278

A method comprising administering to a subject the oligomeric duplex or oligomeric compound of any one of embodiments A1-A225 or A269, the population of any one of embodiments A267-A268, the antisense compound of embodiment A270 or embodiment A271, or the pharmaceutical composition of any one of embodiments A272-A274; wherein the subject has or is at risk for developing a cardiovascular or cardiac injury, disease, condition or disorder, cardiomyopathy, cardiac arrythmia, and/or heart failure.

Embodiment A279

A method of preventing or treating a disease, disorder, condition or injury associated with cardiac calcium misregulation, or postponing a symptom of a disease, disorder or condition associated with a damaged, weakened and/or overworked heart, comprising administering to a subject having, or at risk of having, a disease, disorder or condition associated with cardiac calcium misregulation a therapeutically effective amount of the oligomeric duplex or oligomeric compound of any one of embodiments A1-A225 or A269, the population of any one of embodiments A267-A268, the antisense compound of embodiment A270 or embodiment A271, or the pharmaceutical composition of any one of embodiments A272-A274; wherein the disease, disorder, condition or injury is selected from a cardiac or cardiovascular disease, disorder, condition or injury, a cardiomyopathy, cardiac arrythmia, and/or heart failure.

Embodiment A280

A method of preventing or treating a cardiac or cardiovascular disease, disorder, condition or injury associated with heart failure, or postponing a symptom of heart failure, comprising administering to a subject having, or at risk of having, a cardiac or cardiovascular disease, disorder, condition or injury a therapeutically effective amount of the oligomeric duplex or oligomeric compound of any one of embodiments A1-A225 or A269, the population of any one of embodiments A267-A268, the antisense compound of embodiment A270 or embodiment A271, or the pharmaceutical composition of any one of embodiments A272-A274; wherein the disease, disorder, condition or injury is a cardiomyopathy, cardiac arrythmia, and/or heart failure.

Embodiment A281

A method of decreasing the amount of PLN RNA and/or PLN protein in the heart of a subject having or at risk of developing a disease, disorder or condition associated with a damaged, weakened and/or overworked heart, comprising administering to a subject having, or at risk of having, a disease, disorder or condition associated with a damaged, weakened and/or overworked heart a therapeutically effective amount of the oligomeric duplex or oligomeric compound of any one of embodiments A1-A225 or A269, the population of any one of embodiments A267-A268, the antisense compound of embodiment A270 or embodiment A271, or the pharmaceutical composition of any one of embodiments A272-A274; wherein the disease, disorder, condition or injury is a cardiomyopathy, cardiac arrythmia, and/or heart failure.

Embodiment A282

The method of any one of embodiments A275-A280, wherein the amount of PLN RNA and/or PLN protein in cardiac muscle of the subject is decreased.

Embodiment A283

The method of any one of embodiments A276-A281, wherein the disease, disorder or condition is cardiomyopathy or arrhythmia.

Embodiment A284

The method of embodiment A282, wherein the cardiomyopathy is genetic cardiomyopathy.

Embodiment A285

The method of embodiment A283, wherein the genetic cardiomyopathy is associated with p.Arg14del, Arg9Cys (R9C), or Arg25Cys (R25C) genetic mutations.

Embodiment A286

The method of embodiment A282, wherein the cardiomyopathy is dilated cardiomyopathy (DCM).

Embodiment A287

The method of embodiment A285 wherein the DCM is genetic DCM.

Embodiment A288

The method of embodiment A286, wherein the genetic DCM is associated with TTN, LMNA, RBM20, SCN5A, MYH7, TNNT2, and TPM1 mutations.

Embodiment A289

The method of embodiment A285, wherein the DCM is arrhythmogenic DCM.

Embodiment A290

The method of any one of embodiments A277-A281, wherein the heart failure is heart failure with preserved ejection fraction (HFpEF), heart failure with reduced ejection fraction (HFrEF), acute heart failure, or worsening of chronic heart failure.

Embodiment A291

The method of embodiment A282, wherein the arrhythmia is ventricular tachycardia (vtac) or ventricular fibrillation (vfib).

Embodiment A292

The method of embodiment A278, wherein the symptom of a disease, disorder or condition associated with a damaged, weakened and/or overworked heart, or heart failure is reduced myocardial contractile function and/or impaired relaxation of the heart.

Embodiment A293

The method of any one or embodiments A277A-291, wherein the method prevents or slows progression of damage, weakening and/or overworked heart effects and/or heart failure.

Embodiment A294

The method of any one of embodiments A277-A291, wherein administering of the oligomeric duplex or oligomeric compound of any one of embodiments A1-A225 or A269, the population of any one of embodiments A267-A268, the antisense compound of embodiment A270 or embodiment A271, or the pharmaceutical composition of any one of embodiments A272-A274 improves cardiac function, cardiovascular death, cardiac dilation, cardiac fibrosis, low voltage ECG, diastolic calcium uptake, ejection fraction (EF), left ventricular ejection fraction (LVEF), left ventricular end systolic volume (LVESV), left ventricular end diastolic volume (LVEDV), mitral valve flow profile, left ventricle (LV) strain, left ventricle (LV) strain rate, infarct size, heart failure hospitalization, 6 minute walk test (6MWT), the Kansas City Cardiomyopathy Questionnaire Score (KCCQS), heart rate, or heart rhythm in the subject.

Embodiment A295

The method of any one of embodiments A275-A293, wherein the oligomeric duplex or oligomeric compound of any one of embodiments A1-A225 or A269, the population of any one of embodiments A267-A268, the antisense compound of embodiment A270 or embodiment A271, or the pharmaceutical composition of any one of embodiments A272-A274 comprises a conjugate moiety having affinity for a transferrin receptor.

Embodiment A296

The method any one of embodiments A275-A293, wherein the oligomeric duplex or oligomeric compound of any one of embodiments A1-A225 or A269, the population of any one of embodiments A267-A268, the antisense compound of embodiment A270 or embodiment A271, or the pharmaceutical composition of any one of embodiments A272-A274 comprises a bicycle compound having affinity for a transferrin receptor.

Embodiment A297

Use of the oligomeric duplex or oligomeric compound of any one of embodiments A1-A225 or A269, the population of any one of embodiments A267-268, the antisense compound of embodiment A270 or embodiment A271, or the pharmaceutical composition of any one of embodiments A272-A274 for treating or preventing a disease, disorder or condition associated with a damaged, weakened and/or overworked heart or heart failure.

Embodiment A298

Use of the oligomeric duplex or oligomeric compound of any one of embodiments A1-A225 or A269, the population of any one of embodiments A267-A268, the antisense compound of embodiment A270 or embodiment A271, or the pharmaceutical composition of any one of embodiments A272-A274 in the manufacture of a medicament for treating or preventing a disease, disorder or condition associated with a damaged, weakened and/or overworked heart or heart failure.

Embodiment A299

The use of embodiment A296 or A297, wherein the disease, disorder or condition associated with a damaged, weakened and/or overworked heart or associated with heart failure is cardiomyopathy, cardiac arrythmia, and/or heart failure.

Embodiment A300

The use of embodiment A298, wherein the cardiomyopathy is genetic cardiomyopathy.

Embodiment A301

The use of embodiment A299, wherein the genetic cardiomyopathy is associated with p.Arg14del, Arg9Cys (R9C), or Arg25Cys (R25C) genetic mutations.

Embodiment A302

The use of embodiment A298, wherein the cardiomyopathy is dilated cardiomyopathy (DCM).

Embodiment A303

The use of embodiment A301, wherein the DCM is genetic DCM.

Embodiment A304

The use of embodiment A302, wherein the genetic DCM is associated with TTN, LMNA, RBM20, SCN5A, MYH7, TNNT2, and TPM1 mutations.

Embodiment A305

The use of embodiment A301, wherein the DCM is arrhythmogenic DCM.

Embodiment A306

The use of embodiment A298, wherein the heart failure is heart failure with preserved ejection fraction (HFpEF), heart failure with reduced ejection fraction (HFrEF), acute heart failure, or worsening of chronic heart failure.

Embodiment A307

The use of embodiment A298, wherein the arrhythmia is ventricular tachycardia (vtac) or ventricular fibrillation (vfib).

Embodiment B1

An oligomeric duplex comprising a first oligomeric compound and a second oligomeric compound, wherein:

(1) a first oligomeric compound comprises a modified oligonucleotide consisting of 8 to 50 linked nucleosides, wherein the nucleobase sequence of the first modified oligonucleotide comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of the nucleobase sequence of any one of SEQ ID NOs: 3-314, 627-782, 939-976, 1033-1038, or 1254-1255 wherein each of the nucleosides of the first modified oligonucleotide independently comprises a modified sugar moiety or sugar surrogate and wherein at least one modified nucleoside and less than 40% of the nucleosides of the first modified oligonucleotide comprises a fluorine; and (2) a second oligomeric compound comprises a modified oligonucleotide consisting of 8 to 50 contiguous linked nucleosides wherein the nucleobase sequence of the second modified oligonucleotide comprises at least 8, at least 9, at least 10, at least 11, at least 12, at least 13, at least 14, at least 15, at least 16, at least 17, at least 18, at least 19, at least 20, or at least 21 contiguous nucleobases of the nucleobase sequence of any one of SEQ ID NOs: 315-626, 783-938, 977-1016 or 1027-1032, wherein each of the nucleosides of the second modified oligonucleotide independently comprises a modified sugar moiety or sugar surrogate and wherein less than 40% of the nucleosides of the second modified oligonucleotide comprises a fluorine.

Embodiment B2

The oligomeric duplex of embodiment B1, wherein the first modified oligonucleotide is at least 80%, at least 85%, at least 90%, at least 95%, or at least 99% complementary to an equal length portion of a PLN nucleic acid, wherein the PLN nucleic acid has the nucleobase sequence of SEQ ID NO: 1 or SEQ ID NO: 2.

Embodiment B3

The oligomeric duplex of embodiment B1 or embodiment B2, wherein each of the nucleosides of the first modified oligonucleotide independently and the second modified oligonucleotide independently comprises a modified sugar moiety or sugar surrogate independently selected from a 2'-F sugar moiety, 2'-MOE sugar moiety, 2'-OMe sugar moiety, 2'-deoxyribosyl sugar moiety, and 3-fluoro-hexitol sugar moiety.

Embodiment B4

The oligomeric duplex of any one of embodiments B1-B3, wherein fewer than 35%, fewer than 30%, fewer than 25%, fewer than 20%, fewer than 15%, fewer than 14%, fewer than 13%, fewer than 12%, fewer than 10%, fewer than 5%, or fewer than 1% of the nucleosides in the first modified oligonucleotide comprises a fluorine.

Embodiment B5

The oligomeric duplex of any one of embodiments B1-B4, wherein no more than 1 nucleoside, no more than 2 nucleosides, no more than 3 nucleosides, or no more than 4 nucleosides in the first modified oligonucleotide comprise a modified sugar moiety comprising a fluorine or a sugar surrogate comprising a fluorine.

Embodiment B6

The oligomeric duplex of any one of embodiments B1-5, wherein no more than 1 nucleoside, no more than 2 nucleosides, or no more than 3 nucleosides within the sequence of the first modified oligonucleotide between and including the third and twenty-first nucleosides counting from the 5' end of the modified oligonucleotide comprise a modified sugar moiety comprising a fluorine or a sugar surrogate comprising a fluorine.

Embodiment B7

The oligomeric duplex of any one of embodiments B1-6, wherein a nucleoside comprising a modified sugar moiety comprising a fluorine or a sugar surrogate comprising a fluorine of the first modified oligonucleotide is independently selected from:

i. the second nucleoside counting from the 5' end, ii. the fourteenth and sixteenth nucleosides counting from the 5' end, or iii. the second, fourteenth and sixteenth nucleosides counting from the 5' end:

wherein each modified sugar moiety comprising a fluorine or sugar surrogate comprising a fluorine is independently a 2'-fluoro sugar moiety or a 3-fluoro-hexitol sugar moiety.

Embodiment B8

The oligomeric duplex of any one of embodiments B1-B7, wherein no more than one of the modified sugar moiety comprising a fluorine in the first modified oligonucleotide is a 3'-fluoro-hexitol sugar moiety.

Embodiment B9

The oligomeric duplex of any one of embodiments B1-B8, wherein one or more nucleosides of the first modified oligonucleotide is a 2'-deoxynucleoside.

Embodiment B10

The oligomeric duplex of embodiment B9, wherein the one or more 2'-deoxynucleosides is one or more nucleosides in a region of the sequence of the first modified oligonucleotide between and including the fifth nucleoside to the sixteenth nucleoside counting from the 5' end of the first modified oligonucleotide.

Embodiment B11

The oligomeric duplex of embodiment B10, wherein the one or more 2'-deoxynucleosides is in a region of the sequence of the first modified oligonucleotide that is any of the fifth, sixth, and/or seventh nucleosides or that is any of the fourteenth, fifteenth, and/or sixteenth nucleosides counting from the 5' end of the first modified oligonucleotide.

Embodiment B12

The oligomeric duplex of any one of embodiments B9-B11, wherein fewer than 20%, or fewer than 15%, of the nucleosides of the first modified oligonucleotide comprises a fluorine.

Embodiment B13

The oligomeric duplex of any one of embodiments B9-B12, wherein the one or more 2'-deoxynucleosides is the fifth, sixth and/or seventh nucleoside(s) counting from the 5' end of the first modified oligonucleotide.

Embodiment B14

The oligomeric duplex of any one of embodiments B9-B13, wherein only two nucleosides of the first modified oligonucleotide are 2'-deoxynucleosides.

Embodiment B15

The oligomeric duplex of embodiment B14, wherein the two 2'-deoxynucleosides are the fifth and seventh nucleosides, or the fourteenth and sixteenth nucleosides, counting from the 5' end of the first modified oligonucleotide.

Embodiment B16

The oligomeric duplex of embodiment B14, wherein the two 2'-deoxynucleosides are the fifth and seventh nucleosides counting from the 5' end of the first modified oligonucleotide.

Embodiment B17

The oligomeric duplex of any one of embodiments B9-B13, wherein only one of the nucleosides of the first modified oligonucleotide is a 2'-deoxynucleoside.

Embodiment B18

The oligomeric duplex of embodiment B17, wherein the 2'-deoxynucleoside is the sixth or sixteenth nucleoside counting from the 5' end of the first modified oligonucleotide.

Embodiment B19

The oligomeric duplex of embodiment B17, wherein the 2'-deoxynucleoside is the sixth nucleoside counting from the 5' end of the first modified oligonucleotide.

Embodiment B20

The oligomeric duplex of any one of embodiments B1-B19, wherein one or more of the nucleosides of the first modified oligonucleotide independently comprises a sugar surrogate or a bicyclic sugar moiety.

Embodiment B21

The oligomeric duplex of embodiment B20, wherein the bicyclic sugar moiety comprises a 2'-4' bridge selected from —O—CH$_2$—; and —O—CH(CH$_3$)—.

Embodiment B22

The oligomeric duplex of any one of embodiments B1-B21, wherein one or more of the nucleosides of the first modified oligonucleotide comprises a 2'-OMe sugar moiety.

Embodiment B23

The oligomeric duplex of embodiment B22, wherein at least 10%, at least 20%, at least 30%, at least 40%, at least 50% or at least 60% of the nucleosides of the first modified oligonucleotide comprise a 2'-OMe sugar moiety.

Embodiment B24

The oligomeric duplex of embodiment B22 or embodiment B23, wherein the one or more nucleosides comprising a 2'-OMe sugar moiety are in a region of the sequence of the first modified oligonucleotide between and including the third and twenty-first nucleosides counting from the 5' end of the first modified oligonucleotide.

Embodiment B25

The oligomeric duplex of embodiment B22 or embodiment B23, wherein the 3'-terminal nucleoside of the first modified oligonucleotide comprises a 2'-OMe sugar moiety and/or the nucleoside immediately 5' of the 3'-terminal nucleoside of the first modified oligonucleotide comprises a 2'-OMe sugar moiety.

Embodiment B26

The oligomeric duplex of any one of embodiments B1-B25, wherein one or more of the nucleosides of the first modified oligonucleotide comprise a 2'-MOE sugar moiety.

Embodiment B27

The oligomeric duplex of embodiment B26, wherein the 5'- and/or 3'-terminal nucleosides of the first modified oligonucleotide comprise a 2'-MOE sugar moiety.

Embodiment B28

The oligomeric duplex of any one of embodiments B1-B27, wherein the nucleoside immediately 5' of the 3'-terminal nucleoside of the first modified oligonucleotide comprises a 2'-MOE sugar moiety.

Embodiment B29

The oligomeric duplex of any one of embodiments B1-B24 and B26-B28, wherein the 5'- and 3'-terminal nucleosides of the first modified oligonucleotide comprise a 2'-MOE sugar moiety and the nucleoside immediately 5' of the 3'-terminal nucleoside of the first modified oligonucleotide comprises a 2-MOE sugar moiety.

Embodiment B30

The oligomeric duplex of any one of embodiments B1-B29, wherein the first modified oligonucleotide comprises a stabilized phosphate group attached to the 5'-terminal nucleoside.

Embodiment B31

The oligomeric duplex of embodiment B30, wherein the stabilized phosphate group comprises a cyclopropyl phosphonate or a vinyl phosphonate.

Embodiment B32

The oligomeric duplex of any one of embodiments B1-B31, wherein the duplex comprises a conjugate group comprising a conjugate moiety and a conjugate linker.

Embodiment B33

The oligomeric duplex of embodiment B32, wherein the conjugate group comprises a cell-targeting moiety.

Embodiment B34

The oligomeric duplex of embodiment B32, wherein the conjugate moiety comprises an active drug substance, an aliphatic chain, a lipid, a peptide, a protein, a hydrocarbon, a polyamine, a polyamide, a polyether, a thioether, an aptamer, an antibody or antibody fragment, a vitamin, a fatty acid, a carbohydrate, an intercalator or a reporter molecule.

Embodiment B35

The oligomeric duplex of embodiment B32, wherein the conjugate group comprises a C22 alkyl, C20 alkyl, C17 alkyl, C16 alkyl, C10 alkyl, C21 alkyl, C19 alkyl, C18 alkyl, C15 alkyl, C14 alkyl, C13 alkyl, C12 alkyl, C11 alkyl, C9 alkyl, C8 alkyl, C7 alkyl, C6 alkyl, or C5 alkyl, wherein the alkyl chain optionally has one or more unsaturated bonds.

Embodiment B36

The oligomeric duplex of embodiment B32, wherein the conjugate group comprises a 6-palmitamidohexyl moiety or a 2-(hydroxymethyl)-6-palmitamidohexyl moiety.

Embodiment B37

The oligomeric duplex of embodiment B32, wherein the duplex comprises a conjugate moiety that binds type 1 transferrin receptor (TfR1).

Embodiment B38

The oligomeric duplex of embodiment B37, wherein the conjugate moiety is selected from an antibody or fragment thereof, a protein or peptide and an aptamer capable of binding TfR1.

Embodiment B39

The oligomeric duplex of embodiment B38, wherein the conjugate moiety is a cyclic protein or cyclic peptide.

Embodiment B40

The oligomeric duplex of embodiment B37, wherein the conjugate group consists of a bicycle ligand and a conjugate linker.

Embodiment B41

The oligomeric duplex of embodiment B40, wherein the bicycle ligand comprises a peptide consisting of 13-22 linked amino acids or amino acid mimetics and a molecular scaffold, wherein each of a first, a second, and a third amino acid of the peptide comprises a reactive group, each of which separately forms a bond with the molecular scaffold, thereby forming two peptide loops attached to the molecular scaffold.

Embodiment B42

The oligomeric duplex of embodiment B41, wherein the peptide has an amino acid sequence selected from any one of SEQ ID NOs: 1071-1253 and wherein each cysteine forms a covalent bond with the molecular scaffold 1,1',1"-(1,3,5-triazinane-1,3,5-triyl)tris(2-bromoethanone) (TATB) or the molecular scaffold 1,1',1"-(1,3,5-triazinane-1,3,5-triyl)triprop-2-en-1-one (TATA).

Embodiment B43

The oligomeric duplex of embodiment B41, wherein the conjugate group has the structure:

or a salt thereof, wherein Q is N₃ (BCY17901, SEQ ID NO: 1045), NH₂ (BCY21757, SEQ ID NO: 1202), SH (BCY21758, SEQ ID NO: 1203), a conjugate linker, or a conjugate linker covalently connected to an oligonucleotide.

Embodiment B44

The oligomeric duplex of any one of embodiments B32-B43, wherein the conjugate group is conjugated to the second modified oligonucleotide.

Embodiment B45

The oligomeric duplex of any one of embodiments B32-B43, wherein the conjugate group is conjugated to the 5' end or 3' end of the second modified oligonucleotide.

Embodiment B46

The oligomeric duplex of any one of embodiments B32-B43, wherein the conjugate group is attached to the 5'-terminal nucleoside or the 3'-terminal nucleoside of the second modified oligonucleotide.

Embodiment B47

The oligomeric duplex of any one of embodiments B32-B43, wherein the conjugate group is attached to the 5'-terminal nucleoside of the second modified oligonucleotide.

Embodiment B48

The oligomeric duplex of any one of embodiments B32-B43, wherein the conjugate group is attached to the 3'-terminal nucleoside of the second modified oligonucleotide.

Embodiment B49

The oligomeric duplex of any one of embodiments B32-B48, wherein the conjugate linker of the conjugate group consists of a single bond.

Embodiment B50

The oligomeric duplex of any one of embodiments B32-B48, wherein the conjugate linker of the conjugate group is cleavable.

Embodiment B51

The oligomeric duplex of any one of embodiments B32-B50, wherein the conjugate linker comprises 1 to 3 linker-nucleosides.

Embodiment B52

The oligomeric duplex of any one of embodiments B32-B48, wherein the conjugate linker comprises a (bicyclo [6.1.0]nonyne)-formyl (BCN) moiety.

Embodiment B53

The oligomeric duplex of embodiment B52, wherein the conjugate linker comprises a 6-(BCN-carbamate)-2-(hydroxymethyl)hexyl phosphoryl moiety or a 6-(BCN-carbamate) hexyl phosphoryl moiety.

Embodiment B54

The oligomeric duplex of embodiment B41, wherein the conjugate group has the structure (SEQ ID NO: 1291):

Embodiment B55

The oligomeric duplex of embodiment B41, wherein the conjugate group has the structure (SEQ ID NO: 1292):

Embodiment B56

The oligomeric duplex of any one of embodiments B1-B55, wherein, the nucleobase sequence of the first modified oligonucleotide is at least 80%, at least 85%, at least 90%, at least 95%, or 100% complementary to an equal length portion within nucleobases selected from any one of 295-316, 296-317, 297-318, 298-320, 299-320, 300-321, 301-322, 302-324, 303-324, 304-325, 304-326, 305-327, 306-325, 306-328, 307-328, 308-329, 309-330, 310-331, 311-332, 312-333, 313-334, 314-335, 315-336, 316-337, 317-339, 318-339, 319-340, 320-341, 321-342, 322-344, 323-345, 324-345, 324-346, 325-345, 325-347, 326-347, 327-348, 328-349, 329-350, 330-351, 331-352, 332-353, 333-354, 334-355, 505-526, 506-528, 507-529, 508-530, 509-531.510-531.511-532, 512-533, 513-535, 514-535, 514-536, 515-536, 516-535, 516-537.517-538, 518-539, 519-541, 520-541, 521-542, 522-544, 523-544, 524-546, 535-556, 536-557, 537-558, 538-559, 539-560, 540-561, 541-563, 542-563, 543-564, 544-565, 545-566, 546-567, 547-568, 548-570, 549-571, 550-572, 551-572, 552-574, 553-574, 554-575, 555-577, 556-578, 557-579, 558-580, 559-580, 560-581, 561-582, 562-583, 563-584, 595-616, 596-618, 597-618, 598-620, 599-621, 600-622, 601-623, 602-623, 603-624, 604-625, 605-627, 606-628, 607-628, 608-629, 609-630, 610-631, 611-632, 612-633, 613-635, 665-687.666-687.667-689.668-689, 669-690, 670-691.671-692, 672-694, 673-694, 674-695, 675-696, 676-697, 677-698, 678-700, 679-701, 680-702, 681-703, 682-703, 683-704, 684-705, 685-706, 686-708, 687-708, 688-709, 689-710, 690-711, 691-712, 692-714, 693-715, 1675-1696, 1676-1698, 1677-1698, 1678-1699, 1679-1700, 1680-

1702.1681-1702.1682-1703, 1683-1705, 1684-1705, 1685-1706, 1686-1707.1687-1709, 1688-1709, 1689-1710, 1690-1712, 1691-1713, 1692-1714, or 1693-1714 of SEQ ID NO: 1.

Embodiment B57

The oligomeric duplex of any one of embodiments B1-B55, wherein the nucleobase sequence of the first modified oligonucleotide is at least 80%, at least 85%, at least 90%, at least 95%, or 100% complementary to an equal length portion within nucleobases 304-326, 306-325, 324-346, 325-345, 514-536, 516-535 of SEQ ID NO: 1.

Embodiment B58

The oligomeric duplex of any one of embodiments B1-B55, wherein the nucleobase sequence of the first modified oligonucleotide comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of any one of the nucleobase sequences of SEQ ID NOs: 3-314, 627-782.939-976, 1033-1038, or 1254-1255.

Embodiment B59

The oligomeric duplex of any one of embodiments B1-B55, wherein the nucleobase sequence of the first modified oligonucleotide comprises the nucleobase sequence of any one of SEQ ID NOs: 3-314, 627-782, 939-976, 1033-1038, or 1254-1255.

Embodiment B60

The oligomeric duplex of any one of embodiments B1-B55, wherein the nucleobase sequence of the first modified oligonucleotide consists of the nucleobase sequence of any one of SEQ ID NOs: 3-314, 627-782, 939-976, 1033-1038, or 1254-1255.

Embodiment B61

The oligomeric duplex of any one of embodiments B1-B55, wherein the nucleobase sequence of the first modified oligonucleotide comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of any one of the nucleobase sequences of SEQ ID NOs: 29, 171, 176, 967, 968, 971, 972, 974, 975, 1254, 1255, or 1033-1038.

Embodiment B62

The oligomeric duplex of any one of embodiments B1-B55, wherein the nucleobase sequence of the first modified oligonucleotide comprises the nucleobase sequence of any one of SEQ ID NOs: 29, 171, 176, 967, 968, 971, 972, 974, 975, 1254, 1255, or 1033-1038.

Embodiment B63

The oligomeric duplex of any one of embodiments B1-B55, wherein the nucleobase sequence of the first modified oligonucleotide consists of the nucleobase sequence of any one of SEQ ID NOs: 29, 171, 176, 967, 968, 971, 972, 974, 975, 1254, 1255, or 1033-1038.

Embodiment B64

The oligomeric duplex of any one of embodiments B1-B55, wherein the first modified oligonucleotide and the second modified oligonucleotide each independently consist of 18 to 30, 18 to 25, 18 to 24, 18 to 23, 18-22, 18-21, 18-19, 19 to 30, 19 to 25, 19 to 24, 19 to 23, 19-21, 19-20, 20 to 30, to 25, 20 to 24, 20 to 23, 20 to 22, or 20 to 21 linked nucleosides.

Embodiment B65

The oligomeric duplex of any one of embodiments B1-B55, wherein the first modified oligonucleotide consists of 23 nucleosides.

Embodiment B66

The oligomeric duplex of any one of embodiments B1-B65, wherein the first modified oligonucleotide has a sugar motif (5' to 3') selected from among: efyyydyyyyyyfyfyyyyyee, efyyydyyyyyyfyfyyyyyyy, e[FHNA]yyydyyyyyyfyfyyyyyee, e[FHNA] yyydyyyyyyfyfyyyyyyy, efyydydyyyyyfyfyyyyyee, efyydydyyyyyfyfyyyyyyy, e[FHNA] yydydyyyyyfyfyyyyyee, e[FHNA] yydydyyyyyfyfyyyyyyy, efyyyfyyyyyyyfyfyyyyyyy, efyyyfyyyyyyyfyfyyyyyey, efyyyyyyyyyyyyfyfyyyyyee, efyyyfyyyyyyyfyfyyyyyee, efyyyyyyyyyyyyfyyyyyyee, efyyyyyyyyyyyfyyyyyyyy, e[FHNA] yyyfyyyyyyyfyfyyyyyee, e[FHNA] yyyfyyyyyyyfyfyyyyyyy, efyyydyyyyyydydyyyyyee, efyyydyyyyyydydyyyyyyy, efyydydyyyyyfyfyyyyyyy, efyyyfyyyyyyyfyyyyyyyee, efyyyfyyyyyyyfyyyyyyyy, efyyyyyyyyyyyfyfyyyyyee, efyyyyyyyyyyyyfyfyyyyyyy, e[FHNA]yydydyyyyfyfyfyyyyyyy, efyyyfyyyyyyyfydyyyyyyy, efyyyfyyyyyyyfydyyyyee, efyyyfyyyyyyyfyfyyyee, and efyyyfyyyyyyyfyfyyyyy, wherein each "d" represents a 2'-β-D-deoxyribosyl sugar moiety, each "y" represents a 2'-OMe sugar moiety, each "e" represents a 2'-MOE sugar moiety, each "f" represents a 2'-fluoro sugar moiety, and each "[FHNA]" represents a 3-fluoro-hexitol sugar moiety.

Embodiment B67

The oligomeric duplex of any one of embodiments B1-B65, wherein the first modified oligonucleotide has a sugar motif (5' to 3') selected from among: efyydydyyyyyfyfyyyyyee, efyyydyyyyyyfyfyyyyyee, efyydydyyyyyfyfyyyyyyy, e[FHNA] yydydyyyyfyfyfyyyyyyy, efyyyyyyyyyyyyfyfyyyyyee and efyyydyyyyyyfyfyyyyyyy.

Embodiment B68

The oligomeric duplex of any one of embodiments B1-B67, wherein the first modified oligonucleotide comprises at least one modified internucleoside linkage.

Embodiment B69

The oligomeric duplex of embodiment B68, wherein at least one modified internucleoside linkage is a phosphorothioate or mesyl phosphoramidate internucleoside linkage.

Embodiment B70

The oligomeric duplex of embodiment B68, wherein fewer than 50%, fewer than 40%, fewer than 30%, fewer than 20%, or fewer than 10% of the internucleoside linkages of the first modified oligonucleotide are modified internucleoside linkages.

Embodiment B71

The oligomeric duplex of any one of embodiments B1-70, wherein each internucleoside linkage of the first modified oligonucleotide is independently selected from a phosphodiester internucleoside linkage and a phosphorothioate internucleoside linkage.

Embodiment B72

The oligomeric duplex of embodiment B71, wherein the internucleoside linkages between the first and second nucleosides and the second and third nucleosides counting from the 5' end of the first modified oligonucleotide are modified internucleoside linkages.

Embodiment B73

The oligomeric duplex of embodiment B71, wherein the internucleoside linkages between the first and second nucleosides and the second and third nucleosides counting from the 3" end of the first modified oligonucleotide are modified internucleoside linkages.

Embodiment B74

The oligomeric duplex of embodiment B72, wherein the internucleoside linkages between the first and second nucleosides and the second and third nucleosides counting from the 5' end of the first modified oligonucleotide, and the internucleoside linkages between the first and second nucleosides and the second and third nucleosides counting from the 3' end of the first modified oligonucleotide are modified internucleoside linkages.

Embodiment B75

The oligomeric duplex of any one of embodiments B71-B74, wherein the modified internucleoside linkages are phosphorothioate internucleoside linkages.

Embodiment B76

The oligomeric duplex of embodiment B74 or embodiment B75, wherein all other internucleoside linkages in the first modified oligonucleotide are phosphodiester internucleoside linkages.

Embodiment B77

The oligomeric duplex of embodiment B76, wherein the first modified oligonucleotide has an internucleoside linkage motif of ssooooooooooooooooooooss and a sugar motif (5' to 3') selected from among: efyydydyyyyyyfyfyyyyyee, efyyydyyyyyyfyfyyyyyee, efyydydyyyyyyfyfyyyyyy, e[FHNA]yydydyyyyfyfyfyyyyyyy, efyyyyyyyyyyyyfyfyyyyyee and efyyydyyyyyyfyfyyyyyyy; wherein each "d" represents a 2-β-D-deoxyribosyl sugar moiety, each "y" represents a 2'-OMe sugar moiety, each "e" represents a 2'-MOE sugar moiety, each "f" represents a 2'-fluoro sugar moiety, each "[FHNA]" represents a 3"-fluoro-hexitol sugar moiety, each "o" represents a phosphodiester internucleoside linkage and each "s" represents a phosphorothioate internucleoside linkage.

Embodiment B78

The oligomeric duplex of any one of embodiments B1-B77, wherein fewer than 30%, fewer than 25%, fewer than 20%, fewer than 15%, fewer than 14%, fewer than 13%, fewer than 12%, fewer than 10%, or fewer than 5% of the nucleosides in the second modified oligonucleotide comprise a fluorine.

Embodiment B79

The oligomeric duplex of any one of embodiments B1-B77, wherein no more than 4 nucleosides, no more than 3 nucleosides, no more than 2 nucleosides, or no more than 1 nucleoside in the second modified oligonucleotide comprise a modified sugar moiety comprising a fluorine.

Embodiment B80

The oligomeric duplex of any one of embodiments B1-B77, wherein none of the nucleosides before the seventh or after the eleventh nucleoside counting from the 5' end of the second modified oligonucleotide comprise a modified sugar moiety comprising a fluorine.

Embodiment B81

The oligomeric duplex of any one of embodiments B1-B77, wherein one or more of the seventh, ninth and eleventh nucleosides counting from the 5' end of the second modified oligonucleotide comprises a modified sugar moiety comprising a fluorine.

Embodiment B82

The oligomeric duplex embodiment B81, wherein two or more of the seventh, ninth and eleventh nucleosides counting from the 5' end of the second modified oligonucleotide comprise a modified sugar moiety comprising a fluorine.

Embodiment B83

The oligomeric duplex embodiment B81, wherein the seventh, ninth and eleventh nucleosides counting from the 5' end of the second modified oligonucleotide comprise a modified sugar moiety comprising a fluorine.

Embodiment B84

The oligomeric duplex of any one of embodiments B1-B80, wherein one or both of the tenth and eleventh nucleosides counting from the 5' end of the second modified oligonucleotide comprises a modified sugar moiety comprising a fluorine.

Embodiment B85

The oligomeric duplex of any one of embodiments B77-B84, wherein the modified sugar moiety comprising a fluorine is a 2'-fluoro sugar moiety.

Embodiment B86

The oligomeric duplex of any one of embodiments B1-B85, wherein fewer than 30%, fewer than 25%, fewer than 20%, fewer than 15%, fewer than 14%, fewer than 13%, fewer than 12%, fewer than 10%, fewer than 5%, or fewer than 1% of the total nucleosides in the oligomeric duplex comprise a fluorine.

Embodiment B87

The oligomeric duplex of any one of embodiments B1-B86, wherein one or more of the nucleosides of the second modified oligonucleotide independently comprises a sugar surrogate or a bicyclic sugar moiety.

Embodiment B88

The oligomeric duplex of embodiment B87, wherein the bicyclic sugar moiety comprises a 2'4' bridge selected from —O—CH$_2$—; and —O—CH(CH$_3$)—.

Embodiment B89

The oligomeric duplex of any one of embodiments B1-B88, wherein one or more of the nucleosides of the second modified oligonucleotide comprises a 2'-OMe sugar moiety.

Embodiment B90

The oligomeric duplex of embodiment B89, wherein at least 10%, at least 20%, at least 30%, at least 40%, at least 50%, or at least 60%, or at least 65%, or at least 70%, or at least 80%, or at least 85%, or at least 90% of the nucleosides of the second modified oligonucleotide comprise a 2'-OMe sugar moiety.

Embodiment B91

The oligomeric duplex of embodiment B89 or embodiment B90, wherein the one or more nucleosides comprising a 2'-OMe sugar moiety are in a region of the sequence of the second modified oligonucleotide between and including the third and nineteenth nucleosides counting from the 5' end of the second modified oligonucleotide.

Embodiment B92

The oligomeric duplex of embodiment B89 or embodiment B90, wherein the 3'-terminal nucleoside of the second modified oligonucleotide comprises a 2'-OMe sugar moiety and/or the nucleoside immediately 5' of the 3'-terminal nucleoside of the second modified oligonucleotide comprises a 2-OMe sugar moiety.

Embodiment B93

The oligomeric duplex of any one of embodiments B89, B90 and B92, wherein the 5'-terminal nucleoside of the second modified oligonucleotide comprises a 2'-OMe sugar moiety and/or the nucleoside immediately 3' of the 5'-terminal nucleoside of the second modified oligonucleotide comprises a 2-OMe sugar moiety.

Embodiment B94

The oligomeric duplex of embodiment B89 or embodiment B90, wherein the 5'-terminal nucleoside, the nucleoside immediately 3' of the 5'-terminal nucleoside, the 3'-terminal nucleoside, and the nucleoside immediately 5' of the 3'-terminal nucleoside of the second modified oligonucleotide comprises a 2'-OMe sugar moiety.

Embodiment B95

The oligomeric duplex of any one of embodiments B1-B94, wherein one or more of the nucleosides of the second modified oligonucleotide comprise a 2'-MOE sugar moiety.

Embodiment B96

The oligomeric duplex of any one of embodiments B1-B93, wherein the 3'-terminal nucleoside of the second modified oligonucleotide comprises a 2"-MOE sugar moiety and/or the nucleoside immediately 5' of the 3'-terminal nucleoside of the second modified oligonucleotide comprises a 2'-MOE sugar moiety.

Embodiment B97

The oligomeric duplex of any one of embodiments B1-B93, B95 and B96, wherein the 5'-terminal nucleoside of the second modified oligonucleotide comprises a 2'-MOE sugar moiety and/or the nucleoside immediately 3' of the 5'-terminal nucleoside of the second modified oligonucleotide comprises a 2'-MOE sugar moiety.

Embodiment B98

The oligomeric duplex of any one of embodiments B1-B91, wherein the 5'-terminal nucleoside, the nucleoside immediately 3' of the 5'-terminal nucleoside, the 3'-terminal nucleoside, and the nucleoside immediately 5' of the 3'-terminal nucleoside of the second modified oligonucleotide comprises a 2'-MOE sugar moiety.

Embodiment B99

The oligomeric duplex of any one of embodiments B1-B98, wherein the second modified oligonucleotide has a sugar motif (5' to 3") selected from among: eeyyyyfyfyfyyyyyyyyee, eeyyyyfyfyfyyyyyyyyyy, yyyyyyfyfyfyyyyyyyyee, yyyyyyfyfyfyyyyyyyyyy, eeyyyyfyfffyyyyyyyyee, eeyyyyfyfffyyyyyyyyyy, yyyyyyfyfffyyyyyyyyee, yyyyyyfyfffyyyyyyyyyy, eeyyyyyyyffyyyyyyyyee, eeyyyyyyyffyyyyyyyyyy, yyyyyyyyyffyyyyyyyyee, yyyyyyyyyffyyyyyyyyyy, eeyyyyffyyyyyyyyee, eeyyyyffyyyyyyyyyy, yyyyyyyffyyyyyyyyee, yyyyyyyffyyyyyyyyyy, yyyyyyfyfffyyyyyyyy, eeyyyyfyfffyyyyyyee, eeyyyyfyfffyyyyyyyy, yyyyyyfyfffyyyyyyee, eeyyfyfffyyyyyyyyee, eeyyfyfffyyyyyyyyyy, yyyyfyfffyyyyyyyyee, yyyyfyfffyyyyyyyyyy, eeyyyyyyyydyyyyyyyyee, eeyyyyyyyydyyyyyyyyyy, yyyyyyyyyydyyyyyyyyee, yyyyyyyyyydyyyyyyyyyy, eeyyyyyyyyyyyyyyyyee, eeyyyyyyyyyyyyyyyyyy, yyyyyyyyyyyyyyyyyyee, and yyyyyyyyyyyyyyyyyyyy wherein each "y" represents a 2'-OMe sugar moiety, each "e" represents a 2'-MOE sugar moiety, each "f" represents a 2'-fluoro sugar moiety, and each "d" represents a 2-β-D-deoxyribosyl sugar moiety.

Embodiment B100

The oligomeric duplex of any one of embodiments B1-B98, wherein the second modified oligonucleotide has a sugar motif (5' to 3') selected from among: eeyyyyyyyffyyyyyyyyee, eeyyyyfyfyfyyyyyyyyee, yyyyyyyyyffyyyyyyyyyy, and yyyyyyyyfyfyyyyyyyyyy, wherein each "y" represents a 2'-OMe sugar moiety, each "e" represents a 2'-MOE sugar moiety, and each "f" represents a 2'-fluoro sugar moiety.

Embodiment B101

The oligomeric duplex of any one of embodiments B1-B100, wherein the nucleobase of the 3'-terminal nucleoside and/or of the nucleoside immediately 5' of the 3'-terminal nucleoside of the second modified oligonucleotide is an adenine.

Embodiment B102

The oligomeric duplex of any one of embodiments B1-B100, wherein the nucleobase of the 3'-terminal nucleoside is an adenine and the nucleobase of the nucleoside immediately 5' of the 3'-terminal nucleoside of the second modified oligonucleotide is a thymine or uracil.

Embodiment B103

The oligomeric duplex of any one of embodiments B1-B100, wherein the second modified oligonucleotide comprises at least one modified internucleoside linkage.

Embodiment B104

The oligomeric duplex of embodiment B103, wherein at least one modified internucleoside linkage is a phosphorothioate or mesyl phosphoramidate internucleoside linkage.

Embodiment B105

The oligomeric duplex of embodiment B103, wherein fewer than 50%, fewer than 40%, fewer than 30%, fewer than 20%, or fewer than 10% of the internucleoside linkages of the second modified oligonucleotide are modified internucleoside linkages.

Embodiment B106

The oligomeric duplex of any one of embodiments B103-B105, wherein each internucleoside linkage of the second modified oligonucleotide is independently selected from a phosphodiester internucleoside linkage and a phosphorothioate internucleoside linkage.

Embodiment B107

The oligomeric duplex of any one of embodiments B103-B105, wherein the internucleoside linkages between the first and second nucleosides and the second and third nucleosides counting from the 5' end of the second modified oligonucleotide are modified internucleoside linkages.

Embodiment B108

The oligomeric duplex of any one of embodiments B103-B105 and B107, wherein the internucleoside linkages between the first and second nucleosides and the second and third nucleosides counting from the 3' end of the second modified oligonucleotide are modified internucleoside linkages.

Embodiment B109

The oligomeric duplex of any one of embodiments B103-B105, wherein the internucleoside linkages between the first and second nucleosides and the second and third nucleosides counting from the 5' end of the second modified oligonucleotide, and the internucleoside linkages between the first and second nucleosides and the second and third nucleosides counting from the 3' end of the second modified oligonucleotide are modified internucleoside linkages.

Embodiment B110

The oligomeric duplex of any one of embodiments B103-B109, wherein the modified internucleoside linkages are phosphorothioate internucleoside linkages.

Embodiment B111

The oligomeric duplex of embodiment B110, wherein all other internucleoside linkages in the second modified oligonucleotide are phosphodiester internucleoside linkages.

Embodiment B112

The oligomeric duplex of embodiment B111, wherein the second modified oligonucleotide has an internucleoside linkage motif of ssooooooooooooooooss and a sugar motif (5' to 3') selected from among: eeyyyyyyyffyyyyyyyyyee, eeyyyyfyfyfyyyyyyyyee, yyyyyyyyyffyyyyyyyyyy, and yyyyyyfyfyfyyyyyyyyyy; wherein each "y" represents a 2'-OMe sugar moiety, each "e" represents a 2'-MOE sugar moiety, each "f" represents a 2'-fluoro sugar moiety, each "o" represents a phosphodiester internucleoside linkage and each "s" represents a phosphorothioate internucleoside linkage.

Embodiment B113

The oligomeric duplex of any one of embodiments B1-B112, wherein the nucleobase sequence of the second modified oligonucleotide comprises least 8, at least 9, at least 10, at least 11, at least 12, at least 13, at least 14, at least 15, at least 16, at least 17, at least 18, at least 19, at least 20, or at least 21 contiguous nucleobases of any one of the nucleobase sequences of SEQ ID NOs: 315-626, 783-938, 977-1016, or 1027-1032.

Embodiment B114

The oligomeric duplex of any one of embodiments B1-B112, wherein the nucleobase sequence of the second modified oligonucleotide comprises the nucleobase sequence of any one of SEQ ID NOs: 315-626.783-938, 977-1016, or 1027-1032.

Embodiment B115

The oligomeric duplex of any one of embodiments B1-B112, wherein the nucleobase sequence of the second modified oligonucleotide consists of the nucleobase sequence of any one of SEQ ID NOs: 315-626, 783-938, 977-1016, or 1027-1032.

Embodiment B116

The oligomeric duplex of any one of embodiments B1-B112, wherein the nucleobase sequence of the second modified oligonucleotide comprises at least 8, at least 9, at least 10, at least 11, at least 12, at least 13, at least 14, at least 15, or at least 16 contiguous nucleobases of any one of the nucleobase sequences of SEQ ID NOs: 341, 483, 488, 1011-1016, or 1027-1032.

Embodiment B117

The oligomeric duplex of any one of embodiments B1-B112, wherein the nucleobase sequence of the second modified oligonucleotide comprises the nucleobase sequence of any one of SEQ ID NOs: 341, 483, 488, 1011-1016, or 1027-1032.

Embodiment B118

The oligomeric duplex of any one of embodiments B1-B112, wherein the nucleobase sequence of the second modified oligonucleotide consists of the nucleobase sequence of any one of SEQ ID NOs: 341, 483, 488, 1011-1016, or 1027-1032.

Embodiment B119

An oligomeric duplex comprising:
(1) a first oligomeric compound comprising a first modified oligonucleotide consisting of 18 to 30 contiguous linked nucleosides that is at least 80%, at least 85%, at least 90%, at least 95% or at least 95% complementary or 100% complementary to an equal length portion within nucleobases selected from any one of 295-316, 296-317, 297-318, 298-320, 299-320, 300-321, 301-322, 302-324, 303-324, 304-325, 304-326, 305-327, 306-325, 306-328, 307-328, 308-329, 309-330, 310-331, 311-332, 312-333, 313-334, 314-335, 315-336, 316-337, 317-339, 318-339, 319-340, 320-341, 321-342, 322-344, 323-345, 324-345, 324-346, 325-345, 325-347, 326-347, 327-348, 328-345, 328-349, 329-350, 330-351, 331-352, 332-353, 333-354, 334-355, 505-526, 506-528, 507-529, 508-530, 509-531, 510-531, 511-532, 512-533, 513-535, 514-535, 514-536, 515-536, 516-535, 516-537, 517-538, 518-539, 519-541, 520-541, 521-542, 522-544, 523-544, 524-546, 535-556, 536-557, 537-558, 538-559, 539-560, 540-561, 541-563, 542-563, 543-564, 544-565, 545-566, 546-567, 547-568, 548-570, 549-571, 550-572, 551-572, 552-574, 553-574, 554-575, 555-577, 556-578, 557-579, 558-580, 559-580, 560-581, 561-582, 562-583, 563-584, 595-616, 596-618, 597-618, 598-620, 599-621, 600-622, 601-623, 602-623, 603-624, 604-625, 605-627, 606-628, 607-628, 608-629, 609-630, 610-631, 611-632, 612-633, 613-635, 665-687, 666-687, 667-689, 668-689, 669-690, 670-691, 671-692, 672-694, 673-694, 674-695, 675-696, 676-697, 677-698, 678-700, 679-701, 680-702, 681-703, 682-703, 683-704, 684-705, 685-706, 686-708, 687-708, 688-709, 689-710, 690-711, 691-712, 692-714, 693-715, 1675-1696, 1676-1698, 1677-1698, 1678-1699, 1679-1700, 1680-1702, 1681-1702, 1682-1703, 1683-1705, 1684-1705, 1685-1706, 1686-1707, 1687-1709, 1688-1709, 1689-1710, 1690-1712, 1691-1713, 1692-1714, or 1693-1714 of SEQ ID NO: 1, and (2) a second oligomeric compound comprising a second modified oligonucleotide consisting of 16 to 28 contiguous linked nucleosides that is at least 90% complementary to an equal length portion of the first modified oligonucleotide:

wherein:

(a) each of the nucleosides of the first modified oligonucleotide and each of the nucleosides of the second modified oligonucleotide comprise a modified sugar moiety or a sugar surrogate, (b) at least one of the modified sugar moiety or sugar surrogate of the first modified oligonucleotide comprises a fluorine, and (c) fewer than 40% of the nucleosides of the first modified oligonucleotide comprise a fluorine.

Embodiment B120

An oligomeric duplex comprising. (1) a first oligomeric compound comprising a first modified oligonucleotide consisting of 18 to 30 contiguous linked nucleosides, wherein the nucleobase sequence of the first modified oligonucleotide comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of any one of the nucleobase sequences of SEQ ID NOs: 3-314, 627-782, 939-976, 1033-1038 or 1254-1255; and (2) a second oligomeric compound comprising a second modified oligonucleotide consisting of 16 to 28 contiguous linked nucleosides that is at least 90% complementary to an equal length portion of the first modified oligonucleotide; wherein: (a)

each of the nucleosides of the first modified oligonucleotide and each of the nucleosides of the second modified oligonucleotide comprise a modified sugar moiety or a sugar surrogate, (b) at least one of the modified sugar moiety or sugar surrogate of the first modified oligonucleotide comprises a fluorine, and (c) fewer than 40% of the nucleosides of the first modified oligonucleotide comprise a fluorine.

Embodiment B121

The oligomeric duplex of embodiment B120, wherein the nucleobase sequence of the first modified oligonucleotide comprises the nucleobase sequence of any one of SEQ ID NOs: 3-314, 627-782, 939-976, 1033-1038, or 1254-1255.

Embodiment B122

The oligomeric duplex of embodiment B120, wherein the nucleobase sequence of the first modified oligonucleotide consists of the nucleobase sequence of any one of SEQ ID NOs: 3-314, 627-782, 939-976, 1033-1038, or 1254-1255.

Embodiment B123

The oligomeric duplex of embodiment B120, wherein the nucleobase sequence of the first modified oligonucleotide comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of any one of the nucleobase sequences of SEQ ID NOs: 29, 171, 176, 967, 968, 971, 972, 974, 975, 1254, 1255, or 1033-1038.

Embodiment B124

The oligomeric duplex of embodiment B120, wherein the nucleobase sequence of the first modified oligonucleotide comprises the nucleobase sequence of any one of SEQ ID NOs: 29, 171, 176, 967, 968, 971, 972, 974, 975, 1254, 1255, or 1033-1038.

Embodiment B125

The oligomeric duplex of embodiment B120, wherein the nucleobase sequence of the first modified oligonucleotide consists of the nucleobase sequence of any one of SEQ ID NOs: 29, 171, 176, 967, 968, 971, 972, 974, 975, 1254, 1255, or 1033-1038.

Embodiment B126

The oligomeric duplex of embodiment B120, wherein the nucleobase sequence of the second modified oligonucleotide comprises least 8, at least 9, at least 10, at least 11, at least 12, at least 13, at least 14, at least 15, at least 16, at least 17, at least 18, at least 19, at least 20, or at least 21 contiguous nucleobases of any one of the nucleobase sequences of SEQ ID NOs: 315-626, 783-938, 977-1016, or 1027-1032.

Embodiment B127

The oligomeric duplex of embodiment B121, wherein the nucleobase sequence of the second modified oligonucleotide comprises the nucleobase sequence of any one of SEQ ID NOs: 315-626, 783-938, 977-1016, or 1027-1032.

Embodiment B128

The oligomeric duplex of embodiment B122, wherein the nucleobase sequence of the second modified oligonucleotide consists of the nucleobase sequence of any one of SEQ ID NOs: 315-626, 783-938, 977-1016, or 1027-1032.

Embodiment B129

The oligomeric duplex of embodiment B123, wherein the nucleobase sequence of the second modified oligonucleotide comprises at least 8, at least 9, at least 10, at least 11, at least 12, at least 13, at least 14, at least 15, at least 16, at least 17, at least 18, at least 19, at least 20, or at least 21 contiguous nucleobases of any one of the nucleobase sequences of SEQ ID NOs: 341, 483, 488, 1011-1016, or 1027-1032.

Embodiment B130

The oligomeric duplex of embodiment B124, wherein the nucleobase sequence of the second modified oligonucleotide comprises the nucleobase sequence of any one of SEQ ID NOs: 341, 483, 488, 1011-1016, or 1027-1032.

Embodiment B131

The oligomeric duplex of embodiment B125, wherein the nucleobase sequence of the second modified oligonucleotide consists of the nucleobase sequence of any one of SEQ ID NOs: 341, 483, 488, 1011-1016, or 1027-1032.

Embodiment B132

The oligomeric duplex of any one of embodiments B119-B131, wherein none of the modified sugar moieties or sugar surrogates of the nucleosides of the second modified oligonucleotide comprises a fluorine.

Embodiment B133

The oligomeric duplex of any one of embodiments B119-B131, wherein at least one of the modified sugar moieties or sugar surrogates of the second modified oligonucleotide comprises a fluorine and wherein fewer than 40% of the nucleosides of the second modified oligonucleotide comprises a fluorine.

Embodiment B134

The oligomeric duplex of any one of embodiments B119-B131, wherein two, three or four of the nucleosides of the second modified oligonucleotide independently comprise a modified sugar moiety comprising a fluorine or a sugar surrogate comprising a fluorine.

Embodiment B135

The oligomeric duplex of any one of embodiments B119-B134, wherein two, three or four of the nucleosides of the first modified oligonucleotide independently comprise a modified sugar moiety comprising a fluorine or a sugar surrogate comprising a fluorine.

Embodiment B136

The oligomeric duplex of any one of embodiments B119-B135 wherein none of the nucleosides of the second modified oligonucleotide is a 2'-deoxynucleoside and/or none of the nucleosides of the first modified oligonucleotide is a 2-deoxynucleoside.

Embodiment B137

The oligomeric duplex of any one of embodiments B119-B136 wherein all of the nucleosides of the second modified oligonucleotide comprise a modified ribosyl sugar moiety.

Embodiment B138

The oligomeric duplex of any one of embodiments B119-B137, wherein one, two or three of the nucleosides of the first modified oligonucleotide is/are a 2-deoxynucleoside.

Embodiment B139

The oligomeric duplex of any one of embodiments B119-B138, wherein:
(a) the 5'- and 3'-terminal nucleosides, the nucleoside immediately adjacent to the 5'-terminal nucleoside, and the nucleoside immediately adjacent to the 3'-terminal nucleoside of the second modified oligonucleotide comprise a 2'-MOE sugar moiety,
(b) the 5'- and 3'-terminal nucleosides and the nucleoside immediately 5' of the 3'-terminal nucleoside of the first modified oligonucleotide comprise a 2-MOE sugar moiety, and/or
(c) any nucleoside in the first and second modified oligonucleotides that does not comprise a fluorine or a 2'-MOE sugar moiety comprises a 2'-OMe sugar moiety.

Embodiment B140

The oligomeric duplex of any one of embodiments B119-B139, wherein no more than four of the nucleosides of the first modified oligonucleotide comprise a modified sugar moiety comprising a fluorine or a sugar surrogate comprising a fluorine.

Embodiment B141

The oligomeric duplex of embodiment B140, wherein the first modified oligonucleotide has a sugar motif (5' to 3') selected from among: efyyyfyyyyyyyyfyfyyyyyee, efyyyfyyyyyyyyfyfyyyyyyy, e[FHNA] yyyfyyyyyyyyfyfyyyyyee, e[FHNA] yyyfyyyyyyyyfyfyyyyyyy, efyyyfyyyyyyyyfyfyyyyyey, e[FHNA]yydydyyyyfyfyfyyyyyyy and efyyyfyyyyyyyyfyfyyyyee; wherein each "d" represents a 2"-β-D-deoxyribosyl sugar moiety, each "y" represents a 2'-OMe sugar moiety, each "e" represents a 2'-MOE sugar moiety, each "f" represents a 2'-fluoro sugar moiety, and each "[FHNA]" represents a 3-fluoro-hexitol sugar moiety.

Embodiment B142

The oligomeric duplex of any one of embodiments B119-B139, wherein no more than three of the nucleosides of the first modified oligonucleotide comprise a modified sugar moiety comprising a fluorine or a sugar surrogate comprising a fluorine.

Embodiment B143

The oligomeric duplex of embodiment B142 wherein the first modified oligonucleotide has a sugar motif (5' to 3") selected from among: efyyydyyyyyyyfyfyyyyyee, efyyydyyyyyyyyfyfyyyyyyy, e[FHNA]

yyydyyyyyyyfyfyyyyyee, e[FHNA]
yyydyyyyyyyfyfyyyyyyy, efyyydydyyyyyyfyfyyyyyee,
efyyydydyyyyyyfyfyyyyyyy, e[FHNA]
yyydyyyyyyyfyfyyyyyee, e[FHNA]
yyydyyyyyyyfyfyyyyyyy, efyyyyyyyyyyyyfyfyyyyyee,
efyyyfyyyyyyyfyyyyyyyyy, efyyyfyyyyyyyfydyyyyyee,
efyyyfyyyyyyyfydyyyyyyy, efyyyfyyyyyyyfydyyyyyee,
efyyyfyyyyyyyfydyyyyyyy; wherein each "d" represents a
2-β-D-deoxyribosyl sugar moiety, each "y" represents a
2'-OMe sugar moiety, each "e" represents a 2'-MOE sugar
moiety, each "f" represents a 2'-fluoro sugar moiety, and
each "[FHNA]" represents a 3-fluoro-hexitol sugar moiety.

Embodiment B144

The oligomeric duplex of any one of embodiments B119-B139, wherein no more than two of the nucleosides of the first modified oligonucleotide comprise a modified sugar moiety comprising a fluorine or a sugar surrogate comprising a fluorine.

Embodiment B145

The oligomeric duplex of embodiment B144 wherein the first modified oligonucleotide has a sugar motif (5' to 3") selected from among: efyyyyyyyyyyyyfyyyyyyyee, efyyyyyyyyyyyyfyyyyyyyyy, e[FHNA]yyyyyyyyyy[FHNA]yyyyyyyee, and e[FHNA]yyyyyyyyyyy[FHNA]yyyyyyyyyy; wherein each "y" represents a 2'-OMe sugar moiety, each "c" represents a 2'-MOE sugar moiety, each "f" represents a 2'-fluoro sugar moiety, and each "[FHNA]" represents a 3-fluoro-hexitol sugar moiety.

Embodiment B146

The oligomeric duplex of any one of embodiments B119-B139, wherein only one of the nucleosides of the first modified oligonucleotide comprises a modified sugar moiety comprising a fluorine or a sugar surrogate comprising a fluorine.

Embodiment B147

The oligomeric duplex of embodiment B146 wherein the first modified oligonucleotide has a sugar motif (5' to 3') selected from among: efyyydyyyyyyydydyyyyyyy, efyyydyyyyyyydydyyyyyee, e[FHNA] yyydyyyyyyydydyyyyyyy, and e[FHNA] yyydyyyyyyydydyyyyyyy; wherein each "d" represents a 2"-β-D-deoxyribosyl sugar moiety, each "y" represents a 2'-OMe sugar moiety, each "e" represents a 2'-MOE sugar moiety, each "f" represents a 2'-fluoro sugar moiety, and each "[FHNA]" represents a 3'-fluoro-hexitol sugar moiety.

Embodiment B148

The oligomeric duplex of any one of embodiments B119-B144 and B146, wherein no more than two of the nucleosides of the first modified oligonucleotide are 2"-deoxynucleosides.

Embodiment B149

The oligomeric duplex of embodiment B148 wherein the first modified oligonucleotide has a sugar motif (5' to 3") selected from among: efyyydydyyyyyyfyfyyyyyee, efyyydydyyyyyyfyfyyyyyyy, e[FHNA]

yydydyyyyyyfyfyyyyyee, and e[FHNA]
yydydyyyyyyfyfyyyyyyy; wherein each "d" represents a
2"-β-D-deoxyribosyl sugar moiety, each "y" represents a
2'-OMe sugar moiety, each "e" represents a 2'-MOE sugar
moiety, each "f" represents a 2'-fluoro sugar moiety, and
each "[FHNA]" represents a 3-fluoro-hexitol sugar moiety.

Embodiment B150

The oligomeric duplex of any one of embodiments B119-B140, B143 and B146, wherein only one of the nucleosides of the first modified oligonucleotide is a 2-deoxynucleoside.

Embodiment B151

The oligomeric duplex of embodiment B150, wherein the first modified oligonucleotide has a sugar motif (5' to 3') selected from among: efyyydyyyyyyyfyfyyyyyee, efyyydyyyyyyyfyfyyyyyyy, e[FHNA] yyydyyyyyyyfyfyyyyyee, e[FHNA] yyydyyyyyyyfyfyyyyyyy, eyyyfyyyyyyyfydyyyyyyy, efyyyfyyyyyyyfydyyyyyee, eyyy[FHNA] yyyyyyyfydyyyyyyy, and e[FHNA] yyyfyyyyyyyfydyyyyyee; wherein each "d" represents a 2-β-D-deoxyribosyl sugar moiety, each "y" represents a 2'-OMe sugar moiety, each "e" represents a 2'-MOE sugar moiety, each "f" represents a 2'-fluoro sugar moiety, and each "[FHNA]" represents a 3'-fluoro-hexitol sugar moiety.

Embodiment B152

The oligomeric duplex of any one of embodiments B119-B151, wherein no more than four of the nucleosides of the second modified oligonucleotide comprise a modified sugar moiety comprising a fluorine or a sugar surrogate comprising a fluorine.

Embodiment B153

The oligomeric duplex of embodiment B152, wherein the second modified oligonucleotide has a sugar motif (5' to 3") selected from among: yyyyyyfyfffyyyyyyyyyyy, eeyyyyfyfffyyyyyyyyyee, yyyyyyfyfffyyyyyyyyy, eeyyyyfyfffyyyyyyyee, yyyyfyfffyyyyyyyyyyy, and eeyyfyfffyyyyyyyyyee; wherein each "y" represents a 2'-OMe sugar moiety, each "c" represents a 2'-MOE sugar moiety, and each "f" represents a 2'-fluoro sugar moiety.

Embodiment B154

The oligomeric duplex of any one of embodiments B119-B151, wherein no more than three of the nucleosides of the second modified oligonucleotide comprise a modified sugar moiety comprising a fluorine or a sugar surrogate comprising a fluorine.

Embodiment B155

The oligomeric duplex of embodiment B154, wherein the second modified oligonucleotide has a sugar motif (5' to 3') selected from among: eeyyyyfyfyfyyyyyyyyee and yyyyyyfyfyfyyyyyyyyyyy; wherein each "y" represents a 2'-OMe sugar moiety, each "e" represents a 2"-MOE sugar moiety, and each "f" represents a 2'-fluoro sugar moiety.

Embodiment B156

The oligomeric duplex of any one of embodiments B119-B151, wherein no more than two of the nucleosides of the second modified oligonucleotide comprise a modified sugar moiety comprising a fluorine or a sugar surrogate comprising a fluorine.

Embodiment B157

The oligomeric duplex of embodiment B156, wherein the second modified oligonucleotide has a sugar motif (5' to 3') selected from among: eeyyyyyyyyffyyyyyyyyee, yyyyyyyyyffyyyyyyyyyy, eeyyyyyffyyyyyyyyee, and yyyyyyyffyyyyyyyyyy; wherein each "y" represents a 2'-OMe sugar moiety, each "e" represents a 2'-MOE sugar moiety, and each "f" represents a 2'-fluoro sugar moiety.

Embodiment B158

The oligomeric duplex of any one of embodiments B119-B151, wherein none of the nucleosides of the second modified oligonucleotide comprises a modified sugar moiety comprising a fluorine or a sugar surrogate comprising a fluorine.

Embodiment B159

The oligomeric duplex of embodiment B158, wherein the second modified oligonucleotide has a sugar motif (5' to 3') selected from among: yyyyyyyyyyyyyyyyyyyyyy, eeyyyyyyyyyyyyyyyyyyee, yyyyyyyyyydyyyyyyyyyy, and eeyyyyyyyyydyyyyyyyee; wherein each "y" represents a 2'-OMe sugar moiety, each "e" represents a 2'-MOE sugar moiety, and each "d" represents a 2'-β-D-deoxyribosyl sugar moiety.

Embodiment B160

The oligomeric duplex of any one of embodiments B119-B159, wherein fewer than 50%, fewer than 40%, fewer than 30%, fewer than 20%, or fewer than 10% of the internucleoside linkages of the first modified oligonucleotide are modified internucleoside linkages.

Embodiment B161

The oligomeric duplex of any one of embodiments B119-B160, wherein the internucleoside linkages between the first and second nucleosides and the second and third nucleosides counting from the 5' end of the first modified oligonucleotide, and the internucleoside linkages between the first and second nucleosides and the second and third nucleosides counting from the 3' end of the first modified oligonucleotide are phosphorothioate internucleoside linkages.

Embodiment B162

The oligomeric duplex of any one of embodiments B119-B161, wherein the first modified oligonucleotide has an internucleoside linkage motif (5' to 3') selected from among: ssooooooooooooooooooss, ssoooosooooooooooooooss, ssoososooooooooooooooss, and ssooooooooooooooooooss; wherein each "o" represents a phosphodiester internucleoside linkage and each "s" represents a phosphorothioate internucleoside linkage.

Embodiment B163

The oligomeric duplex of any one of embodiments B119-B162, wherein fewer than 50%, fewer than 40%, fewer than 30%, fewer than 20%, or fewer than 10% of the internucleoside linkages of the second modified oligonucleotide are modified internucleoside linkages.

Embodiment B164

The oligomeric duplex of any one of embodiments B119-B163, wherein the internucleoside linkages between the first and second nucleosides and the second and third nucleosides counting from the 5' end of the second modified oligonucleotide, and the internucleoside linkages between the first and second nucleosides and the second and third nucleosides counting from the 3' end of the second modified oligonucleotide are phosphorothioate internucleoside linkages.

Embodiment B165

The oligomeric duplex of any one of embodiments B119-B164, wherein the second modified oligonucleotide has an internucleoside linkage motif (5' to 3") selected from among: wherein each "o" represents a phosphodiester internucleoside linkage, each "s" represents a phosphorothioate internucleoside linkage, and each 'z' represents a mesyl phosphoramidate internucleoside linkage.

Embodiment B166

The oligomeric duplex of any one of embodiments B1-B165, wherein the first modified oligonucleotide has a first sugar motif ($1^{st}$) and the second modified oligonucleotide has a second sugar motif ($2^{nd}$) and the first and second sugar motifs are selected from among the following combinations (5' to 3"); $1^{st}$: efyydydyyyyyyfyfyyyyyee and $2^{nd}$: eeyyyyfyfyfYyyyyyyyyee; $1^{st}$: efyydydyyyyyyfyfyyyyyyy and $2^{nd}$: yyyyyyfffyyyyyyyyyy; $1^{st}$: efyydydyyyyyyfyfyyyyyee and $2^{nd}$: yyyyyyfyfyfyyyyyyyyyy; $1^{st}$: efyydydyyyyyyfyfyyyyyyy and $2^{nd}$: eeyyyyfyfyfyyyyyyyyyee; $1^{st}$: efyyyyyyyyyyyyfyfyyyyyee and $2^{nd}$: eeyyyyyyyffyyyyyyyyee; $1^{st}$: efyyyyyyyyyyyyfyfyyyyyyy and $2^{nd}$: yyyyyyyyyffyyyyyyyyyy; $1^{st}$: efyyyyyyyyyyyyfyfyyyyyee and $2^{nd}$: yyyyyyyyyffyyyyyyyyyy $1^{st}$: efyyyyyyyyyyyyfyfyyyyyyy and $2^{nd}$: eeyyyyyyyffyyyyyyyyee; $1^{st}$: efyyydyyyyyyfyfyyyyyee and $2^{nd}$: eeyyyyyyyffyyyyyyyyee; $1^{st}$: efyyydyyyyyyfyfyyyyyyy and $2^{nd}$: yyyyyyyyyffyyyyyyyyyy; $1^{st}$: efyyydyyyyyyfyfyyyyyee and $2^{nd}$: yyyyyyyyyffyyyyyyyyyy; $1^{st}$: efyyydyyyyyyfyfyyyyyyy and $2^{nd}$: eeyyyyyyyffyyyyyyyyee; $1^{st}$: efyydydyyyyyyfyfyyyyyee and $2^{nd}$: eeyyyyyyyffyyyyyyyyee; $1^{st}$: efyydydyyyyyyfyfyyyyyyy and $2^{nd}$: yyyyyyyyyffyyyyyyyyyy; $1^{st}$: efyydydyyyyyyfyfyyyyyee and $2^{nd}$: yyyyyyyyyffyyyyyyyyyy; $1^{st}$t: efyydydyyyyyyfyfyyyyyyy and $2^{nd}$: eeyyyyyyyffyyyyyyyyee; $1^{st}$: efyyydyyyyyyfyfyyyyyee and $2^{nd}$: eeyyyyfyfyfyyyyyyyyyee; $1^{st}$: efyyydyyyyyyfyfyyyyyyy and $2^{nd}$: yyyyyyfyfyfyyyyyyyyyy; $1^{st}$: efyyydyyyyyyfyfyyyyyee and $2^{nd}$: yyyyyyfyfyfyyyyyyyyyy; and $1^{st}$t: efyyydyyyyyyfyfyyyyyyy and $2^{nd}$: eeyyyyfyfyfyyyyyyyyyee, wherein each "y" represents a 2'-OMe sugar moiety, each "e" represents a 2"-MOE sugar moiety, each "f" represents a 2-fluoro sugar moiety, and each "d" represents a 2-β-D-deoxyribosyl sugar moiety.

Embodiment B167

The oligomeric duplex of any one of embodiments B1-B165, wherein the first modified oligonucleotide has a first sugar motif ($1^{st}$) and the second modified oligonucleotide has a second sugar motif ($2^{nd}$) and the first and second sugar motifs are selected from among the following combinations (5' to 3'); $1^{st}$: efyydydyyyyyyfyfyyyyyee and $2^{nd}$: eeyyyyyfyfffyyyyyyyyee; $1^{st}$: efyydydyyyyyyfyfyyyyyy and $2^{nd}$: yyyyyyfyfffyyyyyyyyyy; $1^{st}$: efyydydyyyyyyfyfyyyyyee and $2^{nd}$: yyyyyyfyfffyyyyyyyyyy; $1^{st}$: efyydydyyyyyyfyfyyyyyy and $2^{nd}$: eeyyyyyfyfffyyyyyyyyee; $1^{st}$: efyyyyyyyyyyyyfyfyyyyyee and $2^{nd}$: eeyyyyyfyfffyyyyyyyyee; $1^{st}$: efyyyyyyyyyyyyfyfyyyyyy and $2^{nd}$: yyyyyyfyfffyyyyyyyyyy; $1^{st}$: efyyyyyyyyyyyyfyfyyyyyee and $2^{nd}$: yyyyyyfyfffyyyyyyyyyy; $1^{st}$: efyyyyyyyyyyyyfyfyyyyyy and $2^{nd}$: eeyyyyyfyfffyyyyyyyyee; $1^{st}$: efyyyyyyyyyyyyfyfyyyyyee and $2^{nd}$: eeyyyyyyyffyyyyyyyyee; $1^{st}$: efyyyyyyyyyyyyfyfyyyyyy and $2^{nd}$: yyyyyyyyyffyyyyyyyyyy; $1^{st}$: efyyyyyyyyyyyyfyfyyyyyee and $2^{nd}$: yyyyyyyyyffyyyyyyyyyy; $1^{st}$: efyyyyyyyyyyyyfyfyyyyyy and $2^{nd}$: eeyyyyyyyffyyyyyyyyee; $1^{st}$: efyyyyyyyyyyyyfyfyyyyyee and $2^{nd}$: eeyyyyfyfyfyyyyyyyyee; $1^{st}$: efyyyyyyyyyyyyfyfyyyyyy and $2^{nd}$: yyyyyyfyfyfyyyyyyyyyy; It: efyyyyyyyyyyyyfyfyyyyyee and $2^{nd}$: yyyyyyfyfyfyyyyyyyyyy; $1^{st}$: efyyyyyyyyyyyyfyfyyyyyy and $2^{nd}$: eeyyyyfyfyfyyyyyyyyee; $1^{st}$: efyyyfyyyyyyfyfyyyyyy and $2^{nd}$: yyyyyyyyffYYYyyyyyy; $1^{st}$: efyyyfyyyyyyfyfyyyyyee and $2^{nd}$: eeyyyyyyffyyyyyyyyee; $1^{st}$: efyyyfyyyyyyfyfyyyyyy and $2^{nd}$: eeyyyyyyffyyyyyyyyee; $1^{st}$: efyyyfyyyyyyfyfyyyyyee and $2^{nd}$: yyyyyyyyffyyyyyyyyyy; $1^{st}$: efyyyfyyyyyyfyfyyyyyy and $2^{nd}$: yyyyyyfyfyfyyyyyyyyY; $1^{st}$: efyyyfyyyyyyfyfyyyyyee and $2^{nd}$: eeyyyyfyfyfyyyyyyyyee; $1^{st}$ efyyyfyyyyyyfyfyyyyyy and $2^{nd}$: eeyyyyfyfyfyyyyyyyyee; $1^{st}$: efyyyfyyyyyyfyfyyyyyee and $2^{nd}$: yyyyyyfyfyfyyyyyyyyY; $1^{st}$: efyyyfyyyyyyfyfyyyyee and $2^{nd}$: eeyyyyfyfffyyyyyyyee; $1^{st}$: efyyyfyyyyyyfyfyyyyy and $2^{nd}$: yyyyyyfyfffyyyyyyyyy; $1^{st}$: efyyyfyyyyyyfyfyyyyee and $2^{nd}$: yyyyyyfyfffyyyyyyyyy; $1^{st}$: efyyyfyyyyyyfyfyyyyy and $2^{nd}$: eeyyyyyfyfffyyyyyyyee; $1^{st}$: efyyyfyyyyyyfyfyyyee and $2^{nd}$: eeyyyyyffyyyyyyyee; $1^{st}$: efyyyfyyyyyyfyfyyyyy and $2^{nd}$: yyyyyyffyyyyyyyyyy; $1^{st}$: efyyyfyyyyyyfyfyyyee and $2^{nd}$: yyyyyyffyyyyyyyyyy; $1^{st}$: efyyyfyyyyyyfyfyyyyy and $2^{nd}$: eeyyyyyffyyyyyyyyee; $1^{st}$: e[FHNA]yydydyyyyfyfyfyyyyyee and $2^{nd}$ eeyyyyyfyfffyyyyyyyyee; $1^{st}$: efyyyfyyyyyyyfyfyyyyyey and $2^{nd}$: eeyyyyyfyfffyyyyyyyyee; $1^{st}$: efyyyfyyyyyyyfyfyyyyyey and $2^{nd}$: yyyyyyfyfffyyyyyyyyyy; $1^{st}$: e[FHNA] yydydyyyyfyfyfyyyyyy and $2^{nd}$: yyyyyyfyfffyyyyyyyyyy; $1^{st}$: e[FHNA]yydydyyyyfyfyfYyyyyee and $2^{nd}$: yyyyyyfyfffyyyyyyyyyy; 1st e[FHNA] yydydyyyyfyfyfyyyyyy and $2^{nd}$: eeyyyyyfyfffyyyyyyyyyee; $1^{st}$: e[FHNA]yydydyyyyfyfyfyyyyyee and $2^{nd}$: eeyyyyyfyfyfyyyyyyyyee; $1^{st}$: e[FHNA] yydydyyyyfyfyfyyyyyy and $2^{nd}$: yyyyyyfyfyfyyyyyyyyyy; $1^{st}$: e[FHNA]yydydyyyyfyfyfyyyyyee and $2^{nd}$: yyyyyyfyfyfyyyyyyyyyy; and $1^{st}$: e[FHNA] yydydyyyyfyfyfyyyyyy and $2^{nd}$: eeyyyyyfyfyfyyyyyyyyee, wherein each "y" represents a 2'-OMe sugar moiety, each "e" represents a 2'-MOE sugar moiety, each "f" represents a 2'-fluoro sugar moiety, each "[FHNA]" represents a 3'-fluoro-hexitol sugar moiety, and each "d" represents a 2'-β-D-deoxyribosyl sugar moiety.

Embodiment B168

The oligomeric duplex of any one of embodiments B1-B165, wherein the first modified oligonucleotide has a first sugar motif ($1^{st}$) and the second modified oligonucleotide has a second sugar motif ($2^{nd}$) and the first and second sugar motifs are selected from among the following combinations (5' to 3'); $1^{st}$: efyyyfyyyyyyyfyfyyyyyy and $2^{nd}$: yyyyyyfyfffyyyyyyyyyy; $1^{st}$: efyyyfyyyyyyyfyfyyyyyee and $2^{nd}$: eeyyyyyfyfffyyyyyyyyee; $1^{st}$: efyyyfyyyyyyyfyfyyyyyee and $2^{nd}$: yyyyyyfyfffyyyyyyyyyy; and $1^{st}$: efyyyfyyyyyyyfyfyyyyyy and $2^{nd}$: eeyyyyyfyfffyyyyyyyyee, wherein each "y" represents a 2'-OMe sugar moiety, each "e" represents a 2'-MOE sugar moiety, and each "f" represents a 2'-fluoro sugar moiety.

Embodiment B169

The oligomeric duplex of any one of embodiments B1-B165, wherein the first modified oligonucleotide has a first sugar motif ($1^{st}$) and the second modified oligonucleotide has a second sugar motif ($2^{nd}$) and the first and second sugar motifs are selected from among the following combinations (5' to 3'); $1^{st}$: efyyyfyyyyyyyfyfyyyyyy and $2^{nd}$: yyyyyyyyyyyyyyyyyyyy; $1^{st}$: efyyyfyyyyyyyfyfyyyyyee and $2^{nd}$: eeyyyyyyyyyyyyyyyyyyee; $1^{st}$: efyyyfyyyyyyyfyfyyyyyy and $2^{nd}$: eeyyyyyyyyyyyyyyyyyyee; $1^{st}$: efyyyfyyyyyyyfyfyyyyyee and $2^{nd}$: yyyyyyyyyyyyyyyyyyyy; $1^{st}$: efyyyfyyyyyyyfyfyyyyyy and $2^{nd}$: yyyyyyyyydyyyyyyyyyy; $1^{st}$: efyyyfyyyyyyyfyfyyyyyee and $2^{nd}$: eeyyyyyyyydyyyyyyyyee; $1^{st}$: efyyyfyyyyyyyfyfyyyyyy and $2^{nd}$: eeyyyyyyyydyyyyyyyyee; $1^{st}$: efyyyfyyyyyyyfyfyyyyyee and $2^{nd}$: yyyyyyyyydyyyyyyyyyy; $1^{st}$: efyyyyyyyyyyfyyyyyyee and $2^{nd}$: eeyyyyfyfffyyyyyyyyee; $1^{st}$: efyyyyyyyyyyyyfyyyyyyyy and $2^{nd}$: yyyyyyfyfffyyyyyyyyyy; $1^{st}$ efyyyyyyyyyyyyfyyyyyyyee and $2^{nd}$: eeyyyyfyfffyyyyyyyyee; $1^{st}$: efyyyyyyyyyyyyfyyyyyyyy and $2^{nd}$: yyyyyyfyfffyyyyyyyyyy; $1^{st}$: efyyyyyyyyyyfyfyyyyyyyyy and $2^{nd}$: eeyyyyfyfyfyyyyyyyyee; $1^{st}$: efyyyyyyyyyyfyyyyyyyy and $2^{nd}$: yyyyyyfyfyfyyyyyyyyyy; $1^{st}$: efyyyyyyyyyyfyyyyyyyyyY; $1^{st}$: efyyyyyyyyyyyyfyyyyyyyyy and $2^{nd}$: eeyyyyfyfyfyyyyyyyyee; $1^{st}$: efyydyyyyyyfyfyyyyyee and $2^{nd}$: eeyyyyyfyfffyyyyyyyyee; $1^{st}$: efyydyyyyyyfyfyyyyyy and $2^{nd}$: yyyyyyfyfffyyyyyyyyyy; $1^{st}$: efyydyyyyyyfyfyyyyyee and $2^{nd}$: yyyyyyfyfffyyyyyyyyyy; $1^{st}$: efyydyyyyyyfyfyyyyyy and $2^{nd}$: eeyyyyyfyfffyyyyyyyyee; $1^{st}$: efyyyfyyyyyyfyfyyyee and $2^{nd}$: eeyyfyfffyyyyyyyyee; $1^{st}$: efyyyfyyyyyyyfyfyyyyyy and $2^{nd}$: yyyyfyfffyyyyyyyyyy; $1^{st}$: efyyyfyyyyyyyfyfyyyyee and $2^{nd}$: yyyyfyfffyyyyyyyyyy; $1^{st}$: efyyyfyyyyyyyfyfyyyyyy and $2^{nd}$: eeyyfyfffyyyyyyyyee; $1^{st}$: efyyyyyyyyyfydyyyyee and $2^{nd}$: eeyyyyyfyfffyyyyyyyyee; $1^{st}$: efyyyfyyyyyyyfydyyyyyy and $2^{nd}$: yyyyyyfyfffyyyyyyyyyy; $1^{st}$: efyyyfyyyyyyyfydyyyyyee and $2^{nd}$: yyyyyyfyfffyyyyyyyyyy; $1^{st}$: efyyyfyyyyyyyfydyyyyyy and 2$^{nd}$: eeyyyyfyfffyyyyyyyyee; 1$^{st}$: e[FHNA]yyyfyyyyyyyyfyfyyyyyee and 2$^{nd}$: eeyyyyfyfffyyyyyyyyee; 1$^{st}$: e[FHNA]yyyfyyyyyyyyfyfyyyyyyy and 2$^{nd}$: yyyyyyfyfffyyyyyyyyyy; 1$^{st}$: e[FHNA]yyyfyyyyyyyyfyfyyyyyee and 2$^{nd}$: yyyyyyfyfffyyyyyyyyyy; and 1$^{st}$: e[FHNA]yyyfyyyyyyyyfyfyyyyyyy and 2$^{nd}$: eeyyyyfyfffyyyyyyyyee, wherein each "y" represents a 2'-OMe sugar moiety, each "e" represents a 2'-MOE sugar moiety, each "f" represents a 2'-fluoro sugar moiety, each "[FHNA]" represents a 3'-fluoro-hexitol sugar moiety, and each "d" represents a 2'-β-D-deoxyribosyl sugar moiety.

Embodiment B170

The oligomeric duplex of any one of embodiments B1-B165, wherein the first modified oligonucleotide has a first sugar motif (1$^{st}$) and the second modified oligonucleotide has a second sugar motif (2$^{nd}$) and the first and second sugar motifs are selected from among the following combinations (5' to 3'); 1$^{st}$: efyyyyyyyyyyyyfyyyyyyyee and 2$^{nd}$: eeyyyyyyyffyyyyyyyyee; 1$^{st}$: efyyyyyyyyyyyyfyyyyyyyyy and 2$^{nd}$: yyyyyyyyyffyyyyyyyyyy; 1$^{st}$: efyyyyyyyyyyyyfyyyyyyyee and 2$^{nd}$: yyyyyyyyyffyyyyyyyyyy; 1$^{st}$: efYyyyyyyyyyyyfyyyyyyyyy and 2$^{nd}$: eeyyyyyyyffyyyyyyyyee; 1$^{st}$: efyyyfyyyyyyyfyyyyyyyee and 2$^{nd}$: eeyyyyfyfffyyyyyyyyee; 1$^{st}$: efyyyfyyyyyyyfyyyyyyyyy and 2$^{nd}$: yyyyyyfyfffyyyyyyyyyy; 1$^{st}$: efyyyfyyyyyyyfyyyyyyyee and 2$^{nd}$: yyyyyyfyfffyyyyyyyyyy; 1$^{st}$: efyyyfyyyyyyyfyyyyyyyyy and 2$^{nd}$: eeyyyyfyfffyyyyyyyyee; 1$^{st}$: efyyyfyyyyyyyfyyyyyyyee and 2$^{nd}$: eeyyyyyyyffyyyyyyyyee; 1$^{st}$: efyyyfyyyyyyyfyyyyyyyyy and 2$^{nd}$: yyyyyyyyyffyyyyyyyyyy; 1$^{st}$: efyyyfyyyyyyyfyyyyyyyee and 2$^{nd}$: yyyyyyfyfffyyyyyyyyyy; and 1$^{st}$: efyyyfyyyyyyyfyyyyyyyyy and 2$^{nd}$: eeyyyyfyfffyyyyyyyyee, wherein each "y" represents a 2'-OMe sugar moiety, each "e" represents a 2'-MOE sugar moiety, and each "f" represents a 2'-fluoro sugar moiety.

Embodiment B171

The oligomeric duplex of any one of embodiments B119-B170, wherein the internucleoside linkages between the first and second nucleosides and the second and third nucleosides counting from the 5' end of the first modified oligonucleotide, and the internucleoside linkages between the first and second nucleosides and the second and third nucleosides counting from the 3' end of the first modified oligonucleotide are phosphorothioate internucleoside linkages and wherein all other internucleoside linkages of the first modified oligonucleotide are phosphodiester internucleoside linkages.

Embodiment B172

The oligomeric duplex of any one of embodiments B119-B171, wherein the internucleoside linkages between the first and second nucleosides and the second and third nucleosides counting from the 5' end of the second modified oligonucleotide, and the internucleoside linkages between the first and second nucleosides and the second and third nucleosides counting from the 3' end of the second modified oligonucleotide are phosphorothioate internucleoside linkages and wherein all other internucleoside linkages of the second modified oligonucleotide are phosphodiester internucleoside linkages.

Embodiment B173

The oligomeric duplex of any one of embodiments B119-B172, wherein the nucleobase sequence of the first modified oligonucleotide comprises or consists of the nucleobase sequence of any one of SEQ ID NOs: 967, 968, 971, 972, 974, 975, 1254, 1255, or 1033-1038.

Embodiment B174

The oligomeric duplex of any one of embodiments B1-B172, wherein a cytosine nucleobase in the first and/or second modified oligonucleotide is optionally 5-methylcytosine.

Embodiment B175

The oligomeric duplex of any one of embodiments B119-B174, wherein the duplex comprises a conjugate group comprising a conjugate moiety and a conjugate linker.

Embodiment B176

The oligomeric duplex of embodiment B175, wherein the conjugate moiety comprises an active drug substance, an aliphatic chain, a lipid, a peptide, a protein, a hydrocarbon, a polyamine, a polyamide, a polyether, a thioether, an aptamer, an antibody or antibody fragment, a vitamin, a fatty acid, a carbohydrate, an intercalator or a reporter molecule.

Embodiment B177

The oligomeric duplex of embodiment B175, wherein the conjugate group comprises a C22 alkyl, C20 alkyl, C17 alkyl, C16 alkyl, C10 alkyl, C21 alkyl, C19 alkyl, C18 alkyl, C15 alkyl, C14 alkyl, C13 alkyl, C12 alkyl, C11 alkyl, C9 alkyl, C8 alkyl, C7 alkyl, C6 alkyl, or C5 alkyl, wherein the alkyl chain optionally has one or more unsaturated bonds.

Embodiment B178

The oligomeric duplex of embodiment B175, wherein the conjugate group comprises a 6-palmitamidohexyl moiety or a 2-(hydroxymethyl)-6-palmitamidohexyl moiety.

Embodiment B179

The oligomeric duplex of embodiment B175, wherein the duplex comprises a conjugate moiety that binds type 1 transferrin receptor (TfR1).

Embodiment B180

The oligomeric duplex of embodiment B179, wherein the conjugate moiety is selected from an antibody or fragment thereof, a protein or peptide, and an aptamer capable of binding TfR1.

Embodiment B181

The oligomeric duplex of embodiment B180, wherein the conjugate moiety is a cyclic protein or cyclic peptide.

Embodiment B182

The oligomeric duplex of embodiment B181, wherein the conjugate group consists of a bicycle ligand and a conjugate linker.

Embodiment B183

The oligomeric duplex of embodiment B182, wherein the bicycle ligand comprises a peptide consisting of 13-22 linked amino acids or amino acid mimetics and a molecular scaffold, wherein each of a first, a second, and a third amino acid of the peptide comprises a reactive group, each of which separately forms a bond with the molecular scaffold, thereby forming two peptide loops attached to the molecular scaffold.

Embodiment B184

The oligomeric duplex of embodiment B183 wherein the bicycle ligand comprises an amino acid sequence selected from any one of SEQ ID NO: 1071-1253.

Embodiment B185

The oligomeric duplex of any one of embodiments B182-B184, wherein the conjugate linker comprises a (bicyclo [6.1.0]nonyne)-formyl (BCN) moiety.

Embodiment B186

The oligomeric duplex of embodiment B185, wherein the conjugate linker comprises a 6-(BCN-carbamate)-2-(hydroxymethyl)hexyl phosphoryl moiety or a 6-(BCN-carbamate)hexyl phosphoryl moiety.

Embodiment B187

The oligomeric duplex of any one of embodiments B119-B174, comprising a conjugate group consisting of a conjugate moiety and a conjugate linker wherein the conjugate linker comprises a 6-(BCN-carbamate)-2-(hydroxymethyl) hexyl phosphoryl moiety or a 6-(BCN-carbamate)hexyl phosphoryl moiety.

Embodiment B188

The oligomeric duplex of any one of embodiments B119-B174, comprising a bicycle ligand comprising a peptide having an amino acid sequence selected from any one of SEQ ID NOs: 1071-1253 and wherein each cysteine forms a covalent bond with the molecular scaffold 1,1',1"-(1,3,5-triazinane-1,3,5-triyl)tris(2-bromoethanone) (TATB) or the molecular scaffold is 1,1',1"-(1,3,5-triazinane-1,3,5-triyl) triprop-2-en-1-one (TATA).

Embodiment B189

The oligomeric duplex of any one of embodiments B119-B174, or the oligomeric compound of any one of embodiments B198, B203, B208, B213, B218, B223, or B310, comprising a bicycle ligand having the following structure:

or a salt thereof, wherein Q is $N_3$ (BCY17901, SEQ ID NO: 1045), $NH_2$ (BCY21757, SEQ ID NO: 1202), SH (BCY21758, SEQ ID NO:1203), a conjugate linker, or a conjugate linker covalently connected to an oligonucleotide.

Embodiment B190

The oligomeric duplex of embodiment B189, wherein Q is $N_3$.

Embodiment B191

The oligomeric duplex of any one of embodiments B119-B174, or the oligomeric compound of any one of embodiments B198, 203, 208, 213, 218, 223, or 310, comprising a conjugate group having the following structure (SEQ ID NO: 1291):

Embodiment B192

The oligomeric duplex of any one of embodiments B119-B174, or the oligomeric compound of any one of embodiments B198, B203, B208, B213, B218, B223, or B310, comprising a conjugate group having the following structure (SEQ ID NO: 1292):

Embodiment B193

The oligomeric duplex of any one of embodiments B175-B192, wherein the bicycle ligand or conjugate group is attached to the second modified oligonucleotide.

Embodiment B194

The oligomeric duplex of any one of embodiments B175-B192, wherein the bicycle ligand or conjugate group is attached to the 5'- or 3'-end of the second modified oligonucleotide.

Embodiment B195

The oligomeric duplex of any one of embodiments B175-B192, or the oligomeric compound of any one of embodiments B198, B203, B208, B213, B218, B223, or B310, wherein the bicycle ligand or conjugate group is attached to the 5'-terminal nucleoside of the second modified oligonucleotide.

Embodiment B196

An oligomeric compound comprising a modified oligonucleotide according to the following chemical notation:

(SEQ ID NO: 1033)

$vPT_{es}U_{fs}U_{yo}A_{yo}A_{yo}G_{do}A_{yo}U_{yo}G_{yo}A_{yo}G_{yo}A_{yo}C_{yo}A_{fo}G_{yo}$ $A_{fo}A_{yo}A_{yo}U_{y}U_{yo}G_{ys}A_{es}A_{e}$, wherein:
A=an adenine nucleobase,
C=a cytosine nucleobase,
G=a guanine nucleobase,
T=a thymine nucleobase,
U=a uracil nucleobase,
d=a 2'-β-D-deoxyribosyl sugar moiety,
e=a 2'-MOE sugar moiety, f=a 2'-fluoro sugar moiety,
y=a 2'-OMe sugar moiety,
o=a phosphodiester internucleoside linkage,
s=a phosphorothioate internucleoside linkage, and
vP=a 5' vinyl phosphonate moiety.

Embodiment B197

An oligomeric compound comprising a modified oligonucleotide according to the following chemical notation:

(SEQ ID NO: 1027)

$mC_{es}A_{es}A_{yo}U_{yo}U_{yo}U_{yo}C_{yo}U_{yo}G_{yo}U_{fo}C_{fo}U_{yo}C_{yo}A_{yo}U_{yo}C_{yo}$ $U_{y}U_{yo}A_{ys}A_{es}A_{e}$, wherein:
A=an adenine nucleobase,
$^{m}$C=a 5-methyl cytosine nucleobase,
C=a cytosine nucleobase,
G=a guanine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage, and
s=a phosphorothioate internucleoside linkage.

Embodiment B198

An oligomeric compound comprising a conjugated modified oligonucleotide according to the following chemical notation:

(SEQ ID NO: 1039)

$[X]_{1}-mC_{es}A_{es}A_{yo}U_{yo}U_{yo}U_{yo}C_{yo}U_{yo}G_{yo}U_{fo}C_{fo}U_{yo}C_{yo}A_{yo}$ $U_{yo}C_{yo}U_{yo}U_{yo}A_{ys}A_{es}A_{e}$, wherein:

$^mC$=a 5-methyl cytosine nucleobase,

C=a cytosine nucleobase,

A=an adenine nucleobase,

G=a guanine nucleobase,

U=a uracil nucleobase, e=a 2'-MOE sugar moiety, f=a 2'-fluoro sugar moiety, y=a 2'-OMe sugar moiety, o=a phosphodiester internucleoside linkage, s=a phosphorothioate internucleoside linkage,

[X]=a conjugate group comprising a bicycle ligand, and n and k are 0 or 1, wherein if n=1 then k=0, and if n=0 then k=1.

Embodiment B199

An oligomeric duplex comprising the oligomeric compound according to embodiment B196 and the oligomeric compound according to embodiment B197.

Embodiment B200

An oligomeric duplex comprising the oligomeric compound according to embodiment B196 and the oligomeric compound according to embodiment B198.

Embodiment B201

An oligomeric compound comprising a modified oligonucleotide according to the following chemical notation:

(SEQ ID NO: 1034)

$vPT_{es}U_{fs}U_{yo}A_{yo}A_{do}G_{yo}A_{do}U_{yo}G_{yo}A_{yo}G_{yo}A_{yo}C_{yo}A_{ro}G_{yo}$ $A_{ro}A_{yo}A_{yo}U_{yo}U_{yo}G_{ys}A_{es}A_e,$ wherein:

A=an adenine nucleobase,

C=a cytosine nucleobase,

G=a guanine nucleobase,

T=a thymine nucleobase,

U=a uracil nucleobase, d=a 2'-β-D-deoxyribosyl sugar moiety, e=a 2'-MOE sugar moiety, f=a 2'-fluoro sugar moiety, y=a 2'-OMe sugar moiety, o=a phosphodiester internucleoside linkage, s=a phosphorothioate internucleoside linkage, and vP=a 5' vinyl phosphonate moiety.

Embodiment B202

An oligomeric compound comprising a modified oligonucleotide according to the following chemical notation:

(SEQ ID NO: 1028)

$C_{es}A_{es}A_{yo}U_{yo}U_{yo}U_{yo}C_{fo}U_{yo}G_{fo}U_{yo}C_{fo}U_{yo}C_{yo}A_{yo}U_{yo}C_{yo}$ $U_{yo}U_{yo}A_{ys}A_{es}A_e,$ wherein:

A=an adenine nucleobase,

C=a cytosine nucleobase,

G=a guanine nucleobase,

U=a uracil nucleobase, e=a 2'-MOE sugar moiety, f=a 2'-fluoro sugar moiety, y=a 2'-Ome sugar moiety, o=a phosphodiester internucleoside linkage, and s=a phosphorothioate internucleoside linkage.

Embodiment B203

An oligomeric compound comprising a conjugated modified oligonucleotide according to the following chemical notation:

(SEQ ID NO: 1040)

$[X]_n\text{-}C_{es}A_{es}A_{yo}U_{yo}U_{yo}U_{yo}C_{fo}U_{yo}G_{ro}U_{yo}C_{fo}U_{yo}C_{yo}A_{yo}$ $U_{yo}C_{yo}U_{yo}U_{yo}A_{ys}A_{es}A_e\text{-}[X]_k,$ wherein:

C=a cytosine nucleobase,

A=an adenine nucleobase,

G=a guanine nucleobase,

U=a uracil nucleobase, e=a 2'-MOE sugar moiety, f=a 2'-fluoro sugar moiety, y=a 2'-Ome sugar moiety, o=a phosphodiester internucleoside linkage, s=a phosphorothioate internucleoside linkage,

[X]=a conjugate group comprising a bicycle ligand, and n and k are 0 or 1, wherein if n=1 then k=0, and if n=0 then k=1.

Embodiment B204

An oligomeric duplex comprising an oligomeric compound of embodiment B201 and an oligomeric compound of embodiment B202.

Embodiment B205

An oligomeric duplex comprising an oligomeric compound of embodiment B201 and an oligomeric compound of embodiment B203.

Embodiment B206

An oligomeric compound comprising a modified oligonucleotide according to the following chemical notation:

(SEQ ID NO: 1035)

$vPT_{es}A_{fs}U_{yo}A_{yo}A_{yo}A_{do}U_{yo}A_{yo}G_{yo}A_{yo}U_{yo}U_{yo}C_{yo}U_{fo}G_{yo}$ $U_{fo}A_{yo}G_{yo}C_{yo}U_{yo}U_{ys}A_{es}A_e,$ wherein:

A=an adenine nucleobase,

C=a cytosine nucleobase,

G=a guanine nucleobase,

T=a thymine nucleobase,

U=a uracil nucleobase, d=a 2'-β-D-deoxyribosyl sugar moiety, e=a 2'-MOE sugar moiety, f=a 2'-fluoro sugar moiety, y=a 2'-OMe sugar moiety, o=a phosphodiester internucleoside linkage, s=a phosphorothioate internucleoside linkage, and vP=a 5' vinyl phosphonate moiety.

Embodiment B207

An oligomeric compound comprising a modified oligonucleotide according to the following chemical notation:

(SEQ ID NO: 1029)

$A_{es}A_{es}G_{yo}C_{yo}U_{yo}A_{yo}C_{yo}A_{yo}G_{yo}A_{fo}A_{fo}U_{yo}C_{yo}U_{yo}A_{yo}U_{yo}$ $U_{yo}U_{yo}A_{ys}T_{es}A_{e}$, wherein:
 A=an adenine nucleobase,
 C=a cytosine nucleobase,
 G=a guanine nucleobase,
 T=a thymine nucleobase,
 U=a uracil nucleobase,
 e=a 2'-MOE sugar moiety,
 f=a 2'-fluoro sugar moiety,
 y=a 2'-OMe sugar moiety,
 o=a phosphodiester internucleoside linkage, and
 s=a phosphorothioate internucleoside linkage.

Embodiment B208

An oligomeric compound comprising a conjugated modified oligonucleotide according to the following chemical notation:

(SEQ ID NO: 1041)

$[X]_{1}\text{-}A_{es}A_{es}G_{yo}C_{yo}U_{yo}A_{yo}C_{yo}A_{yo}G_{yo}A_{fo}A_{fo}U_{yo}C_{yo}U_{yo}$ $A_{yo}U_{yo}U_{yo}U_{yo}A_{ys}T_{es}A_{e}$, wherein:
 C=a cytosine nucleobase,
 A=an adenine nucleobase,
 G=a guanine nucleobase,
 T=a thymine nucleobase,
 U=a uracil nucleobase,
 e=a 2'-MOE sugar moiety,
 f=a 2'-fluoro sugar moiety,
 y=a 2'-OMe sugar moiety,
 o=a phosphodiester internucleoside linkage,
 s=a phosphorothioate internucleoside linkage,
 [X]=a conjugate group comprising a bicycle ligand, and
 n and k are 0 or 1, wherein if n=1 then k=0, and if n=0 then k=1.

Embodiment B209

An oligomeric duplex comprising an oligomeric compound of embodiment B206 and an oligomeric compound of embodiment B207.

Embodiment B210

An oligomeric compound comprising an oligomeric compound of embodiment B206 and an oligomeric compound of embodiment B208.

Embodiment B211

An oligomeric compound comprising a modified oligonucleotide according to the following chemical notation:

(SEQ ID NO: 1036)

$vPT_{es}A_{fs}U_{yo}A_{yo}A_{do}A_{yo}T_{do}A_{yo}G_{yo}A_{yo}U_{yo}U_{yo}C_{yo}U_{fo}G_{yo}U_{fo}$ $A_{yo}G_{yo}C_{yo}U_{yo}U_{ys}A_{es}A_{e}$, wherein:
 A=an adenine nucleobase,
 C=a cytosine nucleobase,
 G=a guanine nucleobase,
 T=a thymine nucleobase,
 U=a uracil nucleobase,
 d=a 2'-β-D-deoxyribosyl sugar moiety,
 e=a 2'-MOE sugar moiety,
 f=a 2'-fluoro sugar moiety,
 y=a 2'-OMe sugar moiety,
 o=a phosphodiester internucleoside linkage,
 S=a phosphorothioate internucleoside linkage, and
 vP=a 5' vinyl phosphonate moiety.

Embodiment B212

An oligomeric compound comprising a modified oligonucleotide according to the following chemical notation:

(SEQ ID NO: 1030)

$A_{es}A_{es}G_{yo}C_{yo}U_{yo}A_{yo}C_{fo}A_{yo}G_{fo}A_{yo}A_{fo}U_{yo}C_{yo}U_{yo}A_{yo}U_{yo}$ $U_{yo}U_{yo}A_{ys}U_{es}A_{e}$, wherein:
 A=an adenine nucleobase,
 C=a cytosine nucleobase,
 G=a guanine nucleobase,
 U=a uracil nucleobase,
 e=a 2'-MOE sugar moiety,
 f=a 2'-fluoro sugar moiety,
 y=a 2'-OMe sugar moiety,
 o=a phosphodiester internucleoside linkage, and
 s=a phosphorothioate internucleoside linkage.

Embodiment B213

An oligomeric compound comprising a conjugated modified oligonucleotide according to the following chemical notation:

(SEQ ID NO: 1042)

$[X]_{n}\text{-}A_{es}A_{es}G_{yo}C_{yo}U_{yo}A_{yo}C_{fo}A_{yo}G_{fo}A_{yo}A_{yo}U_{yo}C_{yo}U_{yo}$ $A_{yo}U_{yo}U_{yo}U_{yo}A_{ys}U_{es}A_{e}\text{-}[X]_{k}$, wherein:
 C=a cytosine nucleobase,
 A=an adenine nucleobase,
 G=a guanine nucleobase,
 U=a uracil nucleobase,
 e=a 2'-MOE sugar moiety,
 f=a 2'-fluoro sugar moiety,
 y=a 2'-OMe sugar moiety,
 o=a phosphodiester internucleoside linkage,
 s=a phosphorothioate internucleoside linkage,
 [X]=a conjugate group comprising a bicycle ligand, and
 n and k are 0 or 1, wherein if n=1 then k=0, and if n=0 then k=1.

Embodiment B214

An oligomeric duplex comprising an oligomeric compound of embodiment B211 and an oligomeric compound of embodiment B212.

Embodiment B215

An oligomeric duplex comprising an oligomeric compound of embodiment B211 and an oligomeric compound of embodiment B213.

Embodiment B216

An oligomeric compound comprising a modified oligonucleotide according to the following chemical notation:

(SEQ ID NO: 1037)
$$vPT_{es}U_{fs}A_{yo}A_{yo}G_{yo}T_{do}U_{yo}U_{yo}U_{yo}A_{yo}G_{yo}U_{yo}C_{yo}U_{fo}U_{yo}A_{yo}$$
$$A_{yo}U_{yo}C_{yo}U_{yo}U_{ys}A_{es}A_{e},$$

wherein:
A=an adenine nucleobase,
C=a cytosine nucleobase,
G=a guanine nucleobase,
T=a thymine nucleobase,
U=a uracil nucleobase,
d=a 2'-β-D-deoxyribosyl sugar moiety,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage, and
vP=a 5' vinyl phosphonate moiety.

Embodiment B217

An oligomeric compound comprising a modified oligonucleotide according to the following chemical notation:

(SEQ ID NO: 1031)
$$A_{es}A_{es}G_{yo}A_{yo}U_{yo}U_{yo}A_{yo}A_{yo}G_{yo}A_{fo}C_{fo}U_{yo}A_{yo}A_{yo}A_{yo}A_{yo}$$
$$C_{yo}U_{yo}U_{ys}A_{es}A_{e},$$

wherein:
A=an adenine nucleobase,
C=a cytosine nucleobase,
G=a guanine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage, and
s=a phosphorothioate internucleoside linkage.

Embodiment B218

An oligomeric compound comprising a conjugated modified oligonucleotide according to the following chemical notation:

(SEQ ID NO: 1043)
$$[X]_1\text{-}A_{es}A_{es}G_{yo}A_{yo}U_{yo}U_{yo}A_{yo}A_{yo}G_{yo}A_{fo}C_{fo}U_{yo}A_{yo}A_{yo}$$
$$A_{yo}A_{yo}C_{yo}U_{yo}U_{ys}A_{es}A_{e},$$

wherein:
C=a cytosine nucleobase,
A=an adenine nucleobase,
G=a guanine nucleobase,
U=a uracil nucleobase, e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage,
[X]=a conjugate group comprising a bicycle ligand, and
n and k are 0 or 1, wherein if n=1 then k=0, and if n=0 then k=1.

Embodiment B219

An oligomeric duplex comprising the modified oligonucleotide according to embodiment B216 and the modified oligonucleotide according to embodiment B217.

Embodiment B220

An oligomeric duplex comprising the modified oligonucleotide according to embodiment B216 and the conjugate according to embodiment B218.

Embodiment B221

An oligomeric compound comprising a modified oligonucleotide according to the following chemical notation:

(SEQ ID NO: 1038)
$$vPT_{es}U_{fs}A_{yo}A_{yo}G_{do}U_{yo}T_{do}U_{yo}U_{yo}A_{yo}G_{yo}U_{yo}C_{yo}U_{fo}U_{yo}A_{yo}$$
$$A_{yo}U_{yo}C_{yo}U_{yo}U_{ys}A_{es}A_{e},$$

wherein:
A=an adenine nucleobase,
C=a cytosine nucleobase,
G=a guanine nucleobase,
T=a thymine nucleobase,
U=a uracil nucleobase,
d=a 2'-β-D-deoxyribosyl sugar moiety,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage, and
vP=a 5' vinyl phosphonate moiety.

Embodiment B222

An oligomeric compound comprising a modified oligonucleotide according to the following chemical notation:

(SEQ ID NO: 1038)
$$vPT_{es}U_{fs}A_{yo}A_{yo}G_{do}U_{yo}T_{do}U_{yo}U_{yo}A_{yo}G_{yo}U_{yo}C_{yo}U_{fo}U_{yo}A_{yo}$$
$$A_{yo}U_{yo}C_{yo}U_{yo}U_{ys}A_{es}A_{e},$$

wherein:
A=an adenine nucleobase,
C=a cytosine nucleobase,
G=a guanine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage, and
s=a phosphorothioate internucleoside linkage.

Embodiment B223

An oligomeric compound comprising a conjugated modified oligonucleotide according to the following chemical notation:

(SEQ ID NO: 1044)

[X]₁-A_{es}A_{es}G_{yo}A_{yo}U_{yo}U_{yo}A_{fo}A_{yo}G_{fo}A_{yo}C_{fo}U_{yo}A_{yo}A_{yo}

A_{yo}A_{yo}C_{yo}U_{yo}U_{ys}A_{es}A_{e}, wherein:
C=a cytosine nucleobase,
A=an adenine nucleobase,
G=a guanine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage,
[X]=a conjugate group comprising a bicycle ligand, and
n and k are 0 or 1, wherein if n=1 then k=0, and if n=0 then k=1.

Embodiment B224

An oligomeric duplex comprising an oligomeric compound of embodiment B221 and an oligomeric compound of embodiment B222.

Embodiment B225

An oligomeric duplex comprising an oligomeric compound of embodiment B221 and an oligomeric compound of embodiment B223.

Embodiment B268

A population of oligomeric duplexes or oligomeric compounds of any one of embodiments B1-B225, wherein the population is enriched for first and/or second modified oligonucleotides comprising at least one particular phosphorothioate internucleoside linkage having a particular stereochemical configuration.

Embodiment B269

The population of embodiment B268, wherein the population is enriched for first and/or second modified oligonucleotides comprising at least one particular phosphorothioate internucleoside linkage having the (Sp) or (Rp) configuration.

Embodiment B270

The oligomeric duplex or oligomeric compound of any one of embodiments B1-B225, wherein the first modified oligonucleotide consists of 23 linked nucleosides and the second modified oligonucleotide consists of 21 linked nucleosides.

Embodiment B271

An antisense compound comprising or consisting of an oligomeric duplex or oligomeric compound of any one of embodiments B1-B225.

Embodiment B272

The antisense compound of embodiment B271, wherein the antisense compound is an RNAi agent capable of reducing the amount of PLN nucleic acid through the activation of RISC/Ago2.

Embodiment B273

A pharmaceutical composition comprising the oligomeric duplex or oligomeric compound of any one of embodiments B1-B225 or B270, the population of any one of embodiments B268-269, or the antisense compound of embodiment B271 or embodiment B272, and a pharmaceutically acceptable diluent or carrier.

Embodiment B274

The pharmaceutical composition of embodiment B273, wherein the pharmaceutically acceptable diluent is water or phosphate-buffered saline.

Embodiment B275

The pharmaceutical composition of embodiment B274, wherein the pharmaceutical composition consists essentially of the oligomeric duplex, oligomeric compound or the antisense compound, and water or phosphate-buffered saline.

Embodiment B276

A method of decreasing the amount of PLN RNA or PLN protein in a cell, tissue, organ or subject, comprising contacting the cell, tissue, organ or subject with the oligomeric duplex or oligomeric compound of any one of embodiments B1-B225 or B270, the population of any one of embodiments B268-B269, the antisense compound of embodiment B271 or embodiment B272, or the pharmaceutical composition of any one of embodiments B273-B275.

Embodiment B277

The method of embodiment B276, wherein the cell is a muscle cell and/or a cardiac cell.

Embodiment B278

A method comprising administering to a subject the oligomeric duplex or oligomeric compound of any one of embodiments B1-B225 or B270, the population of any one of embodiments B268-B269, the antisense compound of embodiment B271 or embodiment B272, or the pharmaceutical composition of any one of embodiments B273-B275; wherein the subject has or is at risk for developing a cardiovascular or cardiac injury, disease, condition or disorder, cardiomyopathy, cardiac arrythmia, and/or heart failure.

Embodiment B279

A method of preventing or treating a disease, disorder, condition or injury associated with cardiac calcium misregulation, or postponing a symptom of a disease, disorder or condition associated with a damaged, weakened and/or overworked heart, comprising administering to a subject having, or at risk of having, a disease, disorder or condition associated with cardiac calcium misregulation a therapeutically effective amount of the oligomeric duplex or oligomeric compound of any one of embodiments B1-B225 or B270, the population of any one of embodiments B268-B269, the antisense compound of embodiment B271 or embodiment B272, or the pharmaceutical composition of any one of embodiments B273-B275; wherein the disease, disorder, condition or injury is selected from a cardiac or cardiovascular disease, disorder, condition or injury, a cardiomyopathy, cardiac arrythmia, and/or heart failure.

Embodiment B280

A method of preventing or treating a cardiac or cardiovascular disease, disorder, condition or injury associated with heart failure, or postponing a symptom of heart failure, comprising administering to a subject having, or at risk of having, a cardiac or cardiovascular disease, disorder, condition or injury a therapeutically effective amount of the oligomeric duplex or oligomeric compound of any one of embodiments B1-B225 or B270, the population of any one of embodiments B268-B269, the antisense compound of embodiment B271 or embodiment B272, or the pharmaceutical composition of any one of embodiments B273-B275; wherein the disease, disorder, condition or injury is a cardiomyopathy, cardiac arrythmia, and/or heart failure.

Embodiment B281

A method of decreasing the amount of PLN RNA and/or PLN protein in the heart of a subject having or at risk of developing a disease, disorder or condition associated with a damaged, weakened and/or overworked heart, comprising administering to a subject having, or at risk of having, a disease, disorder or condition associated with a damaged, weakened and/or overworked heart a therapeutically effective amount of the oligomeric duplex or oligomeric compound of any one of embodiments B1-B225 or B270, the population of any one of embodiments B268-B269, the antisense compound of embodiment B271 or embodiment B272, or the pharmaceutical composition of any one of embodiments B273-B275; wherein the disease, disorder, condition or injury is a cardiomyopathy, cardiac arrythmia, and/or heart failure.

Embodiment B282

The method of any one of embodiments B276-B281, wherein the amount of PLN RNA and/or PLN protein in cardiac muscle of the subject is decreased.

Embodiment B283

The method of any one of embodiments B276-B281, wherein the disease, disorder or condition is cardiomyopathy or arrhythmia.

Embodiment B284

The method of embodiment B283, wherein the cardiomyopathy is genetic cardiomyopathy.

Embodiment B285

The method of embodiment B284, wherein the genetic cardiomyopathy is associated with PLN p.Arg14del, Arg9Cys (R9C), or Arg25Cys (R25C) genetic mutations.

Embodiment B286

The method of embodiment B283, wherein the cardiomyopathy is dilated cardiomyopathy (DCM).

Embodiment B287

The method of embodiment B286 wherein the DCM is genetic DCM.

Embodiment B288

The method of embodiment B287, wherein the genetic DCM is associated with TTN, LMNA, RBM20, SCN5A, MYH7, TNNT2, and TPM1 mutations.

Embodiment B289

The method of embodiment B286, wherein the DCM is arrhythmogenic DCM.

Embodiment B290

The method of any one of embodiments B278-B282, wherein the heart failure is heart failure with preserved ejection fraction (HFpEF), heart failure with reduced ejection fraction (HFrEF), acute heart failure, or worsening of chronic heart failure.

Embodiment B291

The method of embodiment B283, wherein the arrhythmia is ventricular tachycardia (vtac) or ventricular fibrillation (vfib).

Embodiment B292

The method of embodiment B279, wherein the symptom of a disease, disorder or condition associated with a damaged, weakened and/or overworked heart, or heart failure is reduced myocardial contractile function and/or impaired relaxation of the heart.

Embodiment B293

The method of any one of embodiments B278-B292, wherein the method prevents or slows progression of damage, weakening and/or overworked heart effects and/or heart failure.

Embodiment B294

The method of any one of embodiments B278-B292, wherein administering of the oligomeric duplex or oligomeric compound of any one of embodiments B1-B225 or B270, the population of any one of embodiments B268-B269, the antisense compound of embodiment B271 or embodiment B272, or the pharmaceutical composition of any one of embodiments B273-B275 improves cardiac function, cardiovascular death, cardiac dilation, cardiac fibrosis, low voltage ECG, diastolic calcium uptake, ejection fraction (EF), left ventricular ejection fraction (LVEF), left ventricular end systolic volume (LVESV), left ventricular end diastolic volume (LVEDV), mitral valve flow profile, left ventricle (LV) strain, left ventricle (LV) strain rate, infarct size, heart failure hospitalization, 6 minute walk test (6MWT), the Kansas City Cardiomyopathy Questionnaire Score (KCCQS), heart rate, or heart rhythm in the subject.

Embodiment B295

The method of any one of embodiments B276-B294, wherein the oligomeric duplex or oligomeric compound of any one of embodiments B1-B225 or B270, the population of any one of embodiments B268-B269, the antisense compound of embodiment B271 or embodiment B272, or the pharmaceutical composition of any one of embodiments B273-B275 comprises a conjugate moiety having affinity for a transferrin receptor.

Embodiment B296

The method any one of embodiments B276-B294, wherein the oligomeric duplex or oligomeric compound of any one of embodiments B1-B225 or B270, the population of any one of embodiments B268-B269, the antisense compound of embodiment B271 or embodiment B272, or the pharmaceutical composition of any one of embodiments B273-B275 comprises a bicycle ligand having affinity for a transferrin receptor.

Embodiment B297

Use of the oligomeric duplex or oligomeric compound of any one of embodiments B1-B225 or B270, the population of any one of embodiments B268-B269, the antisense compound of embodiment B271 or embodiment B272, or the pharmaceutical composition of any one of embodiments B273-B275 for treating or preventing a disease, disorder or condition associated with a damaged, weakened and/or overworked heart or heart failure.

Embodiment B298

Use of the oligomeric duplex or oligomeric compound of any one of embodiments B1-B225 or B270, the population of any one of embodiments B268-269, the antisense compound of embodiment B271 or embodiment B272, or the pharmaceutical composition of any one of embodiments B273-B275 in the manufacture of a medicament for treating or preventing a disease, disorder or condition associated with a damaged, weakened and/or overworked heart or heart failure.

Embodiment B299

The use of embodiment B297 or B298, wherein the disease, disorder or Embodiment B299, condition associated with a damaged, weakened and/or overworked heart or associated with heart failure is cardiomyopathy, cardiac arrythmia, and/or heart failure.

328

Embodiment B300

The use of embodiment B299, wherein the cardiomyopathy is genetic cardiomyopathy.

Embodiment B301

The use of embodiment B300, wherein the genetic cardiomyopathy is associated with PLN p.Arg14del, Arg9Cys (R9C), or Arg25Cys (R25C) genetic mutations.

Embodiment B302

The use of embodiment B299, wherein the cardiomyopathy is dilated cardiomyopathy (DCM).

Embodiment B303

The use of embodiment B302, wherein the DCM is genetic DCM.

Embodiment B304

The use of embodiment B303, wherein the genetic DCM is associated with TTN, LMNA, RBM20, SCN5A, MYH7, TNNT2, and TPM1 mutations.

Embodiment B305

The use of embodiment B302, wherein the DCM is arrhythmogenic DCM.

Embodiment B306

The use of embodiment B299, wherein the heart failure is heart failure with preserved ejection fraction (HFpEF), heart failure with reduced ejection fraction (HFrEF), acute heart failure, or worsening of chronic heart failure.

Embodiment B307

The use of embodiment B299, wherein the arrhythmia is ventricular tachycardia (vtac) or ventricular fibrillation (vfib).

Embodiment B308

An oligomeric compound comprising a modified oligonucleotide according to the following chemical notation:

$$\text{(SEQ ID NO: 1255)}$$
$$vPT_{es}A_{fs}U_{yo}A_{yo}A_{yo}A_{yo}U_{yo}A_{yo}G_{yo}A_{yo}U_{yo}U_{yo}C_{yo}U_{fo}G_{yo}U_{fo}$$
$$A_{yo}G_{yo}C_{yo}U_{yo}U_{ys}A_{e}sA_{e},$$

wherein:
A=an adenine nucleobase,
C=a cytosine nucleobase,
G=a guanine nucleobase,
T=a thymine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage, and
vP=a 5' vinyl phosphonate moiety.

Embodiment B309

An oligomeric compound comprising a modified oligo-nucleotide according to the following chemical notation:

(SEQ ID NO: 1029)

$A_{es}A_{es}G_{yo}C_{yo}U_{yo}A_{yo}C_{yo}A_{yo}G_{yo}A_{fo}A_{fo}U_{yo}C_{yo}U_{yo}A_{yo}U_{yo}$ $U_{yo}U_{yo}A_{ys}T_{es}A_{e};$ wherein:
A=an adenine nucleobase,
C=a cytosine nucleobase,
G=a guanine nucleobase,
U=a uracil nucleobase,
T=a thymine nucleobase,
e=a 2'-MOE sugar moiety,
f=a 2'-fluoro sugar moiety,
y=a 2'-OMe sugar moiety,
o=a phosphodiester internucleoside linkage, and
s=a phosphorothioate internucleoside linkage.

Embodiment B310

An oligomeric compound comprising a conjugated modi-fied oligonucleotide according to the following chemical notation:

(SEQ ID NO: 1041)

$[X]_n$—$A_{es}A_{es}G_{yo}C_{yo}U_{yo}A_{yo}C_{yo}A_{yo}G_{yo}A_{fo}A_{fo}U_{yo}C_{yo}U_{yo}A_{yo}U_{yo}U_{yo}U_{yo}A_{ys}T_{es}A_e$—$[X]_k,$

C=a cytosine nucleobase,
A=an adenine nucleobase,
G=a guanine nucleobase,
U=a uracil nucleobase,
T=a thymine nucleobase,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage,
[X]=a conjugate group comprising a bicycle ligand, and
n and k are 0 or 1, wherein if n=1 then k=0, and if n=0 then k=1.

Embodiment B311

An oligomeric duplex comprising the oligomeric com-pound according to embodiment B308 and the oligomeric compound according to embodiment B309.

Embodiment B312

An oligomeric duplex comprising the oligomeric com-pound according to embodiment B308 and the oligomeric compound according to embodiment B310.

I. Oligonucleotides

In certain embodiments, provided herein are oligomeric compounds and oligomeric duplexes comprising a modified antisense oligonucleotide complementary to PLN RNA and a modified sense oligonucleotide complementary to an anti-sense oligonucleotide. Also provided herein in certain embodiments are oligomeric compounds comprising or con-sisting of a modified oligonucleotide, e.g., a modified anti-sense oligonucleotide complementary to PLN RNA or a modified sense oligonucleotide complementary to an anti-sense oligonucleotide that is complementary to PLN RNA. Modified antisense and/or sense oligonucleotides comprise at least one modified nucleoside (comprising a modified sugar moiety or sugar surrogate and/or a modified nucle-obase) and/or at least one modified internucleoside linkage. Examples of certain modified nucleosides and modified internucleoside linkages suitable for use in modified anti-sense and/or sense oligonucleotides are described herein.

A. Modified Nucleosides

Modified nucleosides comprise a modified sugar moiety or sugar surrogate or a modified nucleobase or both a modified sugar moiety (or sugar surrogate) and a modified nucleobase. In certain embodiments, modified nucleosides comprising the following modified sugar moieties or sugar surrogates and/or the following modified nucleobases may be incorporated into modified antisense and/or sense oligo-nucleotides of the invention.

1. Modified Sugar Moieties and Sugar Surrogates

In certain embodiments, modified sugar moieties are non-bicyclic modified sugar moieties. In certain embodi-ments, modified sugar moieties are bicyclic or tricyclic sugar moieties. In certain embodiments, a modified sugar moiety is a modified ribosyl sugar moiety. In some embodi-ments, a modified sugar moiety is a 2'-deoxyfuranosyl sugar moiety, e.g., a 2'-deoxy sugar moiety.

In certain embodiments, modified sugar moieties are non-bicyclic modified furanosyl sugar moieties comprising one or more substituent groups including, but not limited to, substituents at the 2'. 3'. 4', and/or 5' positions. In certain embodiments, the furanosyl sugar moiety is a ribosyl sugar moiety. In certain embodiments one or more non-bridging substituent of non-bicyclic modified sugar moieties is branched.

In certain embodiments, non-bicyclic modified sugar moi-eties comprise a substituent group at the 2'-position. Examples of substituent groups suitable for the 2'-position of modified sugar moieties include but are not limited to: 2'-F, 2'-OCH; ("OMe" or "O-methyl"), and 2'-O(CH$_2$): OCH$_3$ ("MOE" or "O-methoxyethyl"). In certain embodiments, 2-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alk-enyl, S-alkenyl, N(R$_m$)-alkenyl, O-alkynyl, S-alkynyl, N(R$_m$)-alkynyl, O-alkylenyl-O-alkyl, alkynyl, alkaryl, aral-kyl, O-alkaryl, O-aralkyl, O(CH$_2$)$_2$SCH$_3$, O(CH$_2$)$_2$ON(R$_m$) (R$_n$) or OCH$_2$C(=O)—N(R$_m$)(R$_n$), where each R$_m$ and R$_n$ is, independently, H, an amino protecting group, or substi-tuted or unsubstituted C$_1$-C$_{10}$ alkyl, —O(CH$_2$)$_2$ON(CH$_3$)$_2$ ("DMAOE"), or 2'-O(CH$_2$)$_2$O(CH$_2$)$_2$N(CH$_3$)$_2$ ("DMAEOE"). Synthetic methods for some of these 2'-sub-stituent groups can be found, e.g., in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl.

In certain embodiments, a 2'-substituted non-bicyclic modified nucleoside comprises a sugar moiety comprising a non-bridging 2'-substituent group selected from: F, $NH_2$, $N_3$, $OCF_3$, $OCH_3$, $O(CH_2)_2NH_2$, $CH_2CH=CH_2$, $OCH_2CH=CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide $(OCH_2C(=O)—N(R_m)(R_n))$, where each $R_m$ and $R_n$ is, independently. H, an amino protecting group, or substituted or unsubstituted $C_1$-$C_{10}$ alkyl.

In certain embodiments, a 2'-substituted sugar moiety of a modified nucleoside comprises a non-bridging 2'-substituent group selected from: F, $OCF_3$, $OCH_3$, $OCH_2CH_2OCH_3$, $O(CH_2)_2SCH_3$, $O(CH_2)_2ON(CH_2)_2$, $O(CH_2)_2O(CH_2)_2N$ $(CH_3)_2$, $O(CH_2)_2ON(CH_3)_2$ ("DMAOE"), $O(CH_2)_2$ $O(CH_2)_2N(CH_3)_2$ ("DMAEOE"), and $OCH_2C(=O)—N(H)$ $CH_3$ ("NMA").

In certain embodiments, a 2'-substituted non-bicyclic modified nucleoside comprises a sugar moiety comprising a non-bridging 2-substituent group selected from: F, $OCF_3$, $OCH_3$, $OCH_2CH_2OCH_3$, $O(CH_2)_2SCH_3$, $O(CH_2)_2$ $ON(CH_3)_2$, $O(CH_2)_2O(CH_2)_2N(CH_3)_2$, and $OCH_2C$ $(=O)—N(H)CH_2$ ("NMA").

In certain embodiments, a 2'-substituted sugar moiety of a modified nucleoside comprises a 2'-substituent group selected from: F. $OCH_3$, and $OCH_2CH_2OCH_3$.

In certain embodiments, modified furanosyl sugar moieties and nucleosides incorporating such modified furanosyl sugar moieties are further defined by isomeric configuration. For example, a 2'-deoxyfuranosyl sugar moiety (i.e., 2'-(H)H furanosyl sugar moiety) may be in seven isomeric configurations other than the naturally occurring β-D-deoxyribosyl configuration. Such modified sugar moieties are described in, e.g., WO2020/072991, incorporated by reference herein. A 2'-modified sugar moiety has an additional stereocenter at the 2'-position relative to a 2'-deoxyfuranosyl sugar moiety: therefore, such sugar moieties have a total of sixteen possible isomeric configurations. Modified furanosyl sugar moieties described herein are in the β-D-ribosyl isomeric configuration unless otherwise specified.

In certain embodiments, non-bicyclic modified sugar moieties comprise a substituent group at the 4'-position. Examples of substituent groups suitable for the 4-position of modified sugar moieties include, but are not limited to, alkoxy (e.g., methoxy), alkyl, and those described in Manoharan et al., WO 2015/106128.

In certain embodiments, non-bicyclic modified sugar moieties comprise a substituent group at the 3'-position. Examples of substituent groups suitable for the 3"-position of modified sugar moieties include, but are not limited to, alkoxy (e.g., methoxy), alkyl (e.g., methyl, ethyl).

In certain embodiments, non-bicyclic modified sugar moieties comprise a substituent group at the 5'-position. Examples of substituent groups suitable for the 5'-position of modified sugar moieties include, but are not limited to, allyl (e.g., vinyl), alkoxy (e.g., methoxy), alkynyl, and alkyl (e.g., methyl (R or S), ethyl (R or S)).

In certain embodiments, non-bicyclic modified sugar moieties comprise more than one non-bridging sugar substituent, for example, 2'-F-5'-methyl sugar moieties, such as described in Migawa et al., US2010/0190837, or alternative 2'- and 5'-modified sugar moieties as described in Rajeev et al., US2013/0203836.

In naturally occurring nucleic acids, sugars are linked to one another 3' to 5'. In certain embodiments, oligonucleotides include one or more nucleoside or sugar moiety linked at an alternative position, for example at the 2' or inverted 5' to 3'. For example, where the linkage is at the 2' position, the 2"-substituent groups may instead be at the 3'-position. As used herein. "inverted nucleoside" means a nucleotide having a non-natural linkage, e.g., a 3' to 3' and/or 5' to 5' internucleoside linkage, as shown herein. An "inverted sugar moiety" means the sugar moiety of an inverted nucleoside or an abasic sugar moiety, e.g., having a 3' to 3' and/or 5' to 5' internucleoside linkage.

Certain modified sugar moieties comprise a substituent that bridges two atoms of the furanosyl ring to form a second ring, resulting in a bicyclic sugar moiety. In certain embodiments, the bicyclic sugar moiety comprises a bridge between the 4' and the 2' furanose ring atoms. Examples of such 4' to 2' bridging sugar substituents include, but are not limited to: $4'-CH_2-2',4'-(CH_2)_2-2',4'-(CH_2)$ $3-2',4'-CH_2—O-2'$ ("LNA"), $4'-CH_2—S-2',4'-(CH_2)_2—O-2'$ ("ENA"), $4'-CH$ $(CH_3)—O-2'$ (referred to as "constrained ethyl" or "cEt" when in the S configuration), $4-CH_2—O—CH_2-2',4'-CH_2—$ $N(R)-2',4'-CH(CH_2OCH_3)—O-2'$ ("constrained MOE" or "cMOE") and analogs thereof, $4'-C(CH_3)(CH_3)—O-2'$ and analogs thereof, $4'-CH_2—N(OCH_3)-2'$ and analogs thereof, $4'-CH_2—O—N(CH_3)-2',4'-CH_2—C(H)(CH_3)-2',4'-CH_2—C$ $(=CH_2)-2'$ and analogs thereof, $4-C(R_aR_b)—N(R)—O-2'$, $4'-C(R_aR_b)—O—N(R)-2',4'-CH—O—N(R)-2'$, and $4'-CH_2—N(R)—O-2'$, wherein each R, $R_a$, and $R_b$ is, independently, H, a protecting group, or C1-$C_{12}$ alkyl. Representative U.S. patents that teach the preparation of such bicyclic sugar moieties include, but are not limited to: Imanishi et al., U.S. Pat. No. 7,427,672: Swayze et al., U.S. Pat. No. 7,741,457, and Swayze et al., U.S. Pat. No. 8,022, 193; Seth et al., U.S. Pat. No. 8,278,283; Prakash et al., U.S. Pat. No. 8,278,425; Seth et al., U.S. Pat. No. 8,278,426.

In certain embodiments, such 4' to 2' bridges independently comprise from 1 to 4 linked groups independently selected from: —[C(Ra)(Rb)]n-, —[C(Ra)(Rb)]n-O—, C(Ra)=C(Rb)-, C(Ra)=N—, C(=NRa)-, —C(=O)—, —C(=S)—, —O—, —Si(Ra)_2—, —S(=O)x-, and N(Ra)-:

wherein:

x is 0, 1, or 2:

n is 1, 2, 3, or 4;

each Ra and Rb is, independently, H, a protecting group, hydroxyl, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, heterocycle radical, substituted heterocycle radical, heteroaryl, substituted heteroaryl, C5-C7 alicyclic radical, substituted C5-C7 alicyclic radical, halogen, OJ1, NJ1J2, SJ1, $N_3$, COOJ1, acyl (C(=O)—H), substituted acyl, CN, sulfonyl (S(=O) $_2$-J1), or sulfoxyl (S(=O)-J1); and each J1 and J2 is, independently, H, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, acyl (C(=O)—H), substituted acyl, a heterocycle radical, a substituted heterocycle radical, C1-C12 aminoalkyl, substituted C1-C12 aminoalkyl, or a protecting group.

Additional bicyclic sugar moieties are known in the art, see, for example: Wan, et al., *J. Medicinal Chemistry.* 2016, 59, 9645-9667: Wengel et al., U.S. Pat. No. 8,080,644; Ramasamy et al., U.S. Pat. No. 6,525,191: Seth et al., U.S. Pat. No. 7,547,684; and Seth et al., U.S. Pat. No. 7,666,854.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

LNA (β-D-configuration)
bridge = 4'-CH₂-O-2'

LNA (α-L-configuration)
bridge = 4'-CH₂-O-2'

α-L-methyleneoxy (4'-CH₂—O-2') or α-L-LNA bicyclic nucleosides have been incorporated into oligonucleotides that showed antisense activity (Frieden et al., *Nucleic Acids Research*. 2003, 21, 6365-6372). The addition of locked nucleic acids to siRNAs has been shown to increase siRNA stability in serum, and to reduce off-target effects (Elmen, J, et al., (2005) *Nucleic Acids Research* 33 (1): 439-447; Mook, O R, et al., (2007) *Mol Canc Ther* 6 (3): 833-843; Grunweller, A, et al., (2003) *Nucleic Acids Research* 31 (12): 3185-3193). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, a modified nucleoside comprises a sugar surrogate. In certain such embodiments, the oxygen atom of the sugar moiety is replaced, e.g., with a sulfur, carbon or nitrogen atom. In certain such embodiments, such sugar surrogates also comprise bridging and/or non-bridging substituents as described herein. For example, certain sugar surrogates comprise a 4'-sulfur atom and a substitution at the 2'-position and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), altritol nucleic acid ("ANA"), manitol nucleic acid ("MNA"), fluoro HNA:

FHNA ("FHNA", see e.g., Egli, et, al., *J Am Chem Soc* (2011) 133 (41): 16642-16649, Swayze et al., U.S. Pat. No. 8,088,904; and Swayze et al., U.S. Pat. No. 8,440,803); FHNA can also be referred to as a F-THP or 3'-fluoro tetrahydropyran or 3'-FHNA), and nucleosides comprising additional modified THP compounds having the formula:

wherein, independently, for each of said modified THP nucleoside:

Bx is a nucleobase moiety:

$T_3$ and $T_4$ are each, independently, an internucleoside linkage, linking the modified THP nucleoside to the remainder of an oligonucleotide or one of $T_3$ and $T_4$ is an internucleoside linkage, linking the modified THP nucleoside to the remainder of an oligonucleotide and the other of $T_3$ and $T_4$ is H, a hydroxyl protecting group, a linked conjugate group, or a 5' or 3'-terminal group:

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q+$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported. As used here, the term "morpholino" means a sugar surrogate having the following structure:

In certain embodiments, a morpholino is modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid, and nucleosides and oligonucleotides described in Manoharan et al., U.S. Pat. No. 10,913,767. Representative U.S. patents that teach the preparation of PNA compounds include, but are not limited to, U.S. Pat. Nos. 5,539,082; 5,714,331; and 5,719,262.

In certain embodiments, sugar surrogates are the "unlocked" sugar structure of UNA (unlocked nucleic acid) nucleosides. UNA is an unlocked acyclic nucleic acid, wherein any of the bonds of the sugar has been removed, forming an unlocked sugar surrogate. Representative U.S. publications that teach the preparation of UNA include, but are not limited to, US Patent Publication No. 2011/0313020.

In certain embodiments, sugar surrogates are the glycerol as found in GNA (glycol nucleic acid) nucleosides as depicted below:

(S)-GNA where Bx represents any nucleobase.

Many other bicyclic and tricyclic sugar and sugar surrogates are known in the art that can be used in modified nucleosides. In certain embodiments, the modified oligonucleotide comprises a modification disclosed in U.S. Pat. No. 10,233,448 or 11,504,391.

2. Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside. In certain embodiments, modified oligonucleotides contain no abasic nucleosides. In certain embodiments, modified oligonucleotides comprise one or more inosine nucleosides (i.e., nucleosides comprising a hypoxanthine nucleobase). An "unmodified nucleobase" is unmodified adenine (A), unmodified thymine (T), unmodified cytosine (C), unmodified uracil (U), or unmodified guanine (G). A modified nucleobase is a group of atoms other than unmodified A, T, C, U, or G capable of pairing with at least one other nucleobase. 5-methylcytosine and hypoxanthine are examples of modified nucleobases.

Unless otherwise indicated, modified adenine has structure (I):

wherein: $R^{1A}$ is absent or H; $R^{2A}$ is H, $C_1$-$C_6$ alkyl, substituted $C_1$-$C_6$ alkyl, $C_1$-$C_6$ thioalkyl, or substituted $C_1$-$C_6$ thioalkyl, $C_1$-$C_6$ alkyloxy, or substituted $C_1$-$C_6$ alkyloxy; $R^{6A}$ is H, $N(R^a)(R^b)$, oxo, acetyl, formyl, or O-phenyl; $Y^{7A}$ is N and $R^{7A}$ is absent or is $C_1$-$C_6$ alkyl; or $Y^{7A}$ is C and $R^{7A}$ is selected from H, $C_1$-$C_6$ alkyl, or $N(R^a)(R^b)$; $Y^{8A}$ is N and $R^{8A}$ is absent, or $Y^{8A}$ is C and $R^{8A}$ is selected from H, a halogen, OH, $C_1$-$C_6$ alkyl, or substituted $C_1$-$C_6$ alkyl; $R^a$ and $R^b$ are independently selected from H, $C_1$-$C_6$ alkyl, substituted $C_1$-$C_6$ alkyl, $C_1$-$C_6$ alkenyl, substituted $C_1$-$C_6$ alkenyl, acetyl, or formyl, or together form a 5-7-membered heterocycle; excluding where $Y^{7A}$ is N and $R^{7A}$ is absent; $Y^{8A}$ is C, $R^{8A}$ is H, $R^{2A}$ is H, and $R^{6A}$ is $NH_2$ (unmodified adenine).

Hypoxanthine has Structure (Ia):

Ia

Hypoxanthine is considered a modified adenine, where $Y^{7A}$ is N and $R^{7A}$ is absent; $Y^{8A}$ is C, $R^{8A}$ is H, $R^{1A}$ is H, $R^{2A}$ is H, and $R^{6A}$ is oxo.

Unless otherwise indicated, modified guanine has structure (II):

II wherein: $R^{2G}$ is $N(R^a)(R^b)$; $R^{6G}$ is oxo and $R^{1G}$ is H, or $R^{6G}$ is selected from O—$C_1$-$C_6$ alkyl or S—$C_1$-$C_6$ alkyl and RIG is absent: $Y^{7G}$ is N and $R^{7G}$ is absent or is $C_1$-$C_6$ alkyl; or $Y^{1G}$ is C and $R^{7G}$ is selected from H, $C_1$-$C_6$ alkyl, or $N(R^a)(R^b)$; $Y^{8G}$ is N and $R^{8G}$ is absent, or $Y^{8G}$ is C and $R^{8G}$ is selected from H, a halogen, OH, $C_1$-$C_6$ alkyl, or substituted $C_1$-$C_6$ alkyl; $R^a$ and $R^b$ are independently selected from H, $C_1$-$C_6$ alkyl, substituted $C_1$-$C_6$ alkyl, $C_1$-$C_6$ alkenyl, substituted $C_1$-$C_6$ alkenyl, acetyl, or formyl, or together form a 5-7-membered heterocycle; excluding where $Y^{7G}$ is N and $R^{7G}$ is absent; $Y^{8G}$ is C, $R^{8G}$ is H, $R^{2G}$ is $NH_2$, and $R^{6G}$ is =O, and $R^{1G}$ is H (unmodified guanosine).

Unless otherwise indicated, modified thymine or modified uracil has structure (III):

III $$R^{5G}$$

wherein: each X is independently O or S and $R^{5U}$ is selected from H, OH, halogen, O—$C_1$-$C_{20}$ alkyl, O—$C_1$-$C_{12}$ substituted alkyl, $C_1$-$C_{12}$ alkyl, substituted $C_1$-$C_{12}$ alkyl, $C_1$-$C_{12}$ alkenyl, substituted $C_1$-C12 alkenyl, $C_1$-$C_{12}$ alkynyl, substituted $C_1$-$C_{12}$ alkynyl; wherein if each X is O, $R^{5U}$ is not H or $CH_3$ (unmodified uracil and unmodified thymine, respectively).

Unless otherwise indicated, modified cytosine has structure (IV):

IV $$R^{5G}$$

wherein: X is selected from O or S, $R^{4C}$ is $N(R^a)(R^b)$; $R^{5C}$ is selected from H, OH, halogen, O—$C_1$-$C_{12}$ alkyl, O—$C_1$-$C_{12}$ substituted alkyl, $C_1$-$C_{12}$ alkyl, substituted $C_1$-$C_{12}$ alkyl, $C_1$-$C_{12}$ alkenyl, substituted $C_1$-$C_{12}$ alkenyl: $R^a$ and $R^b$ are independently selected from H, $C_1$-$C_6$ alkyl, substituted $C_1$-$C_6$ alkyl, $C_1$-$C_6$ alkenyl, substituted $C_1$-$C_6$ alkenyl, $C_1$-$C_{12}$ alkynyl, substituted $C_1$-$C_{12}$ alkynyl: acetyl, or formyl, or together form a 5-7-membered heterocycle: excluding where X is O, $R^{4C}$ is $NH_2$ and $R^{5C}$ is H (unmodified cytosine).

In certain embodiments, modified nucleobases of a modified oligonucleotide are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 5-methylcytosine, 1-methylpsuedouridine, 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—$CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo (particularly 5-bromo), 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Englisch et al., Angewandte Chemie, International Edition, 1991, 30, 613: Sanghvi, Y. S., Chapter 15, Antisense Research and Applications, Crooke, S. T, and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases, as well as other modified nucleobases include without limitation, Rogers et al., U.S. Pat. No. 5,134,066: Benner et al., U.S. Pat. No. 5,432,272: Matteucci et al., U.S. Pat. No. 5,502,177: Frochler et al., U.S. Pat. No. 5,594,121; and Cook et al., U.S. Pat. No. 5,681,941.

In certain embodiments, at least one nucleobase of a modified oligonucleotide is a modified nucleobase selected from modified adenine (A) having a structure represented by structure I, modified guanine (G) having a structure represented by structure II, modified thymine (T) or modified uracil (U) having a structure represented by structure III, and modified cytosine (C) having a structure represented by structure IV.

In certain embodiments, each nucleobase of a modified oligonucleotide is selected from unmodified A, unmodified G, unmodified C, unmodified T, unmodified U, and 5-methylcytosine ($^mC$). 5-methylcytosine is a modified nucleobase having structure IV, where X is O, $R^{4C}$ is $NH_2$, and $R^{5C}$ is $CH_3$.

In certain embodiments, each nucleobase of a modified oligonucleotide is selected from unmodified A, unmodified G, unmodified C, unmodified T, unmodified U, $^mC$ and hypoxanthine. Hypoxanthine is a modified nucleobase having structure Ia and is also a modified A represented by structure I, where $Y^{7A}$ is N and $R^{7A}$ is absent; $Y^{8A}$ is C, $R^{8A}$ is H, $R^{1A}$ is H, $R^{2A}$ is H, and $R^{6A}$ is oxo.

In certain embodiments, there are no modified nucleobases in a modified oligonucleotide and each nucleobase of a modified oligonucleotide is selected from unmodified A, unmodified G, unmodified C, unmodified T, and unmodified U.

3. Modified Internucleoside Linkages

In certain embodiments, oligomeric compounds provided herein comprise or consist of a modified oligonucleotide comprising at least one modified internucleoside linkage. The naturally occurring internucleoside linkage of RNA and DNA is a 3' to 5' phosphodiester linkage. In certain embodiments, nucleosides of modified oligonucleotides are linked together using one or more modified internucleoside linkages. The two main classes of internucleoside linkages are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linkages include but are not limited to methylenemethylimino (—$CH_2$—$N(CH_3)$—O—$CH_2$—), thiodiester, thionocarbamate (—O—C(=O)(NH)—S—); siloxane (—O—$SiH_2$—O—); and N,N'-dimethylhydrazine (—$CH_2$—$N(CH_3)$—$N(CH_3)$—). Modified internucleoside linkages, compared to naturally occurring phosphate linkages, can be used to alter, typically increase, nuclease resistance of the oligonucleotide.

In certain embodiments, a modified internucleoside linkage is any of those described in WO/2021/030778, incorporated by reference herein. In certain embodiments, a modified internucleoside linkage comprises the formula:

$$X=P-N-T$$

with $O$ above and $O$, $R_1$ below P and N respectively.

wherein independently for each internucleoside linkage of the modified oligonucleotide:

X is selected from O or S;

$R_1$ is selected from H, $C_1$-$C_6$ alkyl, and substituted $C_1$-$C_6$ alkyl; and T is selected from $SO_2R_2$, $C(=O)R_3$, and $P(=O)R_4R_5$, wherein:

$R_2$ is selected from an aryl, a substituted aryl, a heterocycle, a substituted heterocycle, an aromatic heterocycle, a substituted aromatic heterocycle, a diazole, a substituted diazole, a $C_1$-$C_6$ alkoxy, $C_1$-$C_6$ alkyl, $C_1$-$C_6$ alkenyl, $C_1$-$C_6$ alkynyl, substituted $C_1$-$C_6$ alkyl, substituted $C_1$-$C_6$ alkenyl, substituted $C_1$-$C_6$ alkynyl, and a conjugate group;

$R_3$ is selected from an aryl, a substituted aryl, $CH_3$, $N(CH_3)_2$, $OCH_3$ and a conjugate group;

$R_4$ is selected from $OCH_3$, OH, $C_1$-$C_6$ alkyl, substituted $C_1$-$C_6$ alkyl and a conjugate group; and $R_5$ is selected from $OCH_3$, OH, $C_1$-$C_6$ alkyl, and substituted $C_1$-$C_6$ alkyl.

In certain embodiments, a modified internucleoside linkage comprises a mesyl phosphoramidate linkage having a formula:

$$O=P-N(H)-S$$

with O above and O below P, H on N, and two O on S.

Certain internucleoside linkages having reduced charge (referred to as "neutral internucleoside linkages") have been described. Such neutral internucleoside linkages include, without limitation, phosphotriesters, methylphosphonates, MMI (3'-$CH_2$—$N(CH_3)$—O-5'), amide-3 (3'-$CH_2$—C(=O)—N(H)-5'), amide-4 (3'-$CH_2$—N(H)—C(=O)-5'), formacetal (3'-O—$CH_2$—O-5'), methoxypropyl (MOP) (see, e.g., U.S. Pat. No. 9,926,556), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, modified oligonucleotides comprise one or more inverted nucleoside, as shown below:

340 wherein each Bx independently represents any nucleobase.

In certain embodiments, an inverted nucleoside is terminal (i.e., the last nucleoside on one end of an oligonucleotide) and so only one internucleoside linkage depicted above will be present. In certain embodiments, additional features (e.g., a conjugate group) are attached to the inverted nucleoside. Such terminal inverted nucleosides can be attached to either or both ends of an oligonucleotide.

In certain embodiments, inverted nucleosides lack a nucleobase and are referred to herein as inverted sugar moieties. In certain embodiments, an inverted sugar moiety is terminal (i.e., attached to the last nucleoside on one end of an oligonucleotide) and so only one internucleoside linkage above will be present. In certain such embodiments, additional features (e.g., a conjugate group) are attached to the inverted sugar moiety. A terminal inverted sugar moiety can be attached to either or both ends of an oligonucleotide.

In certain embodiments, nucleosides are linked 2' to 5' rather than the standard 3' to 5' linkage. Such a linkage is illustrated below.

wherein each Bx represents any nucleobase.

In certain embodiments, internucleoside linkages have at least one chiral center. In such embodiments, a chiral atom can be prepared as a racemic mixture, or as separate enantiomers. Representative internucleoside linkages having a chiral center include but are not limited to alkylphosphonates, mesyl phosphoramidates, and phosphorothioates.

The mesyl phosphoramidate internucleoside linkage comprises a chiral center. In certain embodiments, modified oligonucleotides comprising (Rp) and/or (Sp) mesyl phosphoramidates comprise one or more of the following formulas, respectively, wherein "Bx" indicates a nucleobase:

(S$_p$)

(R$_p$)

The phosphorothioate internucleoside linkage comprises a chiral center. In certain embodiments, modified oligonucleotides comprising (Rp) and/or (Sp) phosphorothioates comprise one or more of the following formulas, respectively, wherein "Bx" indicates a nucleobase:

(R$_p$)

-continued (S$_p$)

Modified oligonucleotides comprising internucleoside linkages having a chiral center can be prepared as populations of modified oligonucleotides comprising stereorandom internucleoside linkages, or as populations of modified oligonucleotides comprising internucleoside linkages containing chiral centers in particular stereochemical configurations. In certain embodiments, populations of modified oligonucleotides comprise one or more phosphorothioate internucleoside linkages wherein all of the phosphorothioate internucleoside linkages are stereorandom. In certain embodiments, populations of modified oligonucleotides comprise one or more mesyl phosphoramidate internucleoside linkages wherein all of the mesyl phosphoramidate internucleoside linkages are stereorandom. Such modified oligonucleotides can be generated using synthetic methods that result in random selection of the stereochemical configuration of each phosphorothioate and/or mesyl phosphoramidate linkage. Nonetheless, each individual phosphorothioate and/or mesyl phosphoramidate of each individual oligonucleotide molecule has a defined stereoconfiguration. In certain embodiments, populations of modified oligonucleotides are enriched for modified oligonucleotides comprising one or more particular phosphorothioate and/or mesyl phosphoramidate internucleoside linkages in a particular, independently selected stereochemical configuration (e.g., Rp or Sp). In certain embodiments, the particular configuration of the particular phosphorothioate and/or mesyl phosphoramidate linkage is present in at least 65% of the molecules in the population. In certain embodiments, the particular configuration of the particular phosphorothioate and/or mesyl phosphoramidate linkage is present in at least 70% of the molecules in the population. In certain embodiments, the particular configuration of the particular phosphorothioate and/or mesyl phosphoramidate linkage is present in at least 80% of the molecules in the population. In certain embodiments, the particular configuration of the particular phosphorothioate and/or mesyl phosphoramidate linkage is present in at least 90% of the molecules in the population. In certain embodiments, the particular configuration of the particular phosphorothioate and/or mesyl phosphoramidate linkage is present in at least 99% of the molecules in the population. Such chirally enriched populations of modified oligonucleotides can be generated using synthetic methods known in the art, e.g., methods described in Oka et al., *J. Am. Chem. Soc.* 125.8307-8317 (2003). Wan et al. *Nuc. Acid. Res.* 42.13456 (2014), and WO 2017/015555.

As used herein. "chirally enriched" in reference to a population means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom as defined herein. Chirally enriched populations of molecules having multiple chiral centers within each molecule may contain one or more stereorandom chiral centers. In certain embodiments, the molecules are modified oligonucleotides. In certain embodiments, the molecules are oligomeric compounds comprising modified oligonucleotides. In certain embodiments, the chiral center is at the phosphorous atom of a phosphorothioate internucleoside linkage. In certain embodiments, the chiral center is at the phosphorous atom of a mesyl phosphoramidate internucleoside linkage. In certain embodiments, a population of modified oligonucleotides is enriched for modified oligonucleotides having at least one indicated phosphorothioate and/or mesyl phosphoramidate in the (Sp) configuration. In certain embodiments, a population of modified oligonucleotides is enriched for modified oligonucleotides having at least one phosphorothioate and/or mesyl phosphoramidate in the (Rp) configuration. Unless otherwise indicated, chiral internucleoside linkages of modified oligonucleotides described herein can be stereorandom or in a particular stereochemical configuration. In certain embodiments, modified oligonucleotides of a chirally enriched population are enriched for β-D ribosyl sugar moieties, and all of the phosphorothioate internucleoside linkages are stereorandom and all of the mesyl phosphoramidate internucleoside linkages are stereorandom. In certain embodiments, modified oligonucleotides of a chirally enriched population are enriched for β-D ribosyl sugar moieties, at least one particular phosphorothioate internucleoside linkage in a particular stereochemical configuration is enriched, and all of the mesyl phosphoramidate internucleoside linkages are stereorandom. In certain embodiments, modified oligonucleotides of a chirally enriched population are enriched for β-D ribosyl sugar moieties, at least one particular mesyl phosphoramidate internucleoside linkage in a particular stereochemical configuration is enriched, and all of the phosphorothioate internucleoside linkages are stereorandom. In certain embodiments, modified oligonucleotides of a chirally enriched population are enriched for both β-D ribosyl sugar moieties and at least one, particular phosphorothioate internucleoside linkage in a particular stereochemical configuration and at least one particular mesyl phosphoramidate internucleoside linkage in a particular stereochemical configuration is enriched.

B. Motifs

In certain embodiments, modified oligonucleotides comprise one or more modified nucleosides comprising a modified sugar moiety or sugar surrogate. In certain embodiments, modified oligonucleotides comprise one or more modified nucleosides comprising a modified nucleobase. In certain embodiments, modified oligonucleotides comprise one or more modified internucleoside linkage. In certain such embodiments, the modified, unmodified, and differently modified sugar moieties, sugar surrogates, nucleobases, and/or internucleoside linkages of a modified oligonucleotide define a pattern or motif. In certain embodiments, the patterns of sugar moieties, sugar surrogates, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the nucleobase sequence).

1. Sugar Motifs

In certain embodiments, oligonucleotides comprise one or more type of modified sugar, sugar surrogate, and/or unmodified sugar moiety arranged along the oligonucleotide or portion thereof in a defined pattern or sugar motif. In certain instances, such sugar motifs include but are not limited to any of the sugar modifications and sugar surrogates discussed herein. In certain embodiments, the sugar moiety of at least one nucleoside of an antisense oligonucleotide is a modified sugar moiety or sugar surrogate. In certain embodiments, the sugar moiety of at least one nucleoside of a sense oligonucleotide is a modified sugar moiety or sugar surrogate.

In certain embodiments, modified oligonucleotides comprise or consist of a region having a fully modified sugar motif. In such embodiments, each nucleoside of the fully modified region of the modified oligonucleotide comprises a modified sugar moiety or sugar surrogate. In certain embodiments, each nucleoside of the entire modified oligonucleotide comprises a modified sugar moiety or sugar surrogate and the oligonucleotide is referred to as a fully modified oligonucleotide. In certain embodiments, modified oligonucleotides comprise or consist of a region having a fully modified sugar motif, wherein each nucleoside within the fully modified region comprises the same modified sugar moiety or sugar surrogate, referred to herein as a uniformly modified sugar motif. In certain embodiments, a fully modified oligonucleotide is a uniformly modified oligonucleotide. In certain embodiments, each nucleoside of a uniformly modified oligonucleotide comprises the same 2'-modification. In certain embodiments, every other nucleoside of a uniformly modified oligonucleotide comprises the same 2'-modification, resulting in an alternating 2'-modifications. In certain embodiments, neighboring nucleosides comprise different 2'-modification, and every other nucleoside of a uniformly modified oligonucleotide comprises the same 2'-modification, resulting in a uniform, alternating 2'-modification motif.

In certain embodiments, at least one nucleoside of a modified oligonucleotide comprises a 2'-OMe sugar moiety (i.e., a 2'-OMe modified nucleoside). In certain embodiments, at least 2 nucleosides comprise 2'-OMe sugar moieties. In certain embodiments, at least 5 nucleosides comprise 2'-OMe sugar moieties. In certain embodiments, at least 8 nucleosides comprise 2'-OMe sugar moieties. In certain embodiments, at least nucleosides comprise 2'-OMe sugar moieties. In certain embodiments, at least 12 nucleosides comprise 2'-OMe sugar moieties. In certain embodiments, at least 13 nucleosides comprise 2'-OMe sugar moieties. In certain embodiments, at least 14 nucleosides comprise 2'-OMe sugar moieties. In certain embodiments, at least 15 nucleosides comprise 2'-OMe sugar moieties. In certain embodiments, at least 16 nucleosides comprise 2'-OMe sugar moieties. In certain embodiments, at least 17 nucleosides comprise 2'-OMc sugar moieties. In certain such embodiments, at least 18 nucleosides comprise 2'-OMe sugar moieties. In certain such embodiments, at least 20 nucleosides comprise 2'-OMe sugar moieties. In certain such embodiments, at least 21 nucleosides comprise 2'-OMe sugar moietics.

In certain embodiments, at least one nucleoside of a modified oligonucleotide comprises a 2'-F sugar moiety (i.e., a 2'-F modified nucleoside). In certain embodiments, at least 2 nucleosides comprise 2'-F sugar moieties. In certain embodiments, at least 3 nucleosides comprise 2'-F sugar moieties. In certain embodiments, at least 4 nucleosides comprise 2'-F sugar moieties. In certain embodiments, at least 6 nucleosides comprise 2'-F sugar moieties. In certain embodiments, at least 8 nucleosides comprise 2-F sugar moieties. In certain embodiments, at least 10 nucleosides comprise 2'-F sugar moieties. In certain embodiments, at least 11 nucleosides comprise 2-F sugar moieties. In certain embodiments, one, but not more than one nucleoside comprises a 2-F sugar moiety. In certain embodiments, 1 or 2 nucleosides comprise 2'-F sugar moieties. In certain embodiments, 1-3 nucleosides comprise 2-F sugar moieties. In certain embodiments, at least 1-4 nucleosides comprise 2'-F sugar moieties. In certain embodiments, antisense oligonucleotides have a block of 2-4 contiguous 2'-F modified nucleosides. In certain embodiments. 4 nucleosides of an antisense oligonucleotide are 2'-F modified nucleosides and 2 or 3 of those 2'-F modified nucleosides are contiguous. In certain embodiments, 1, 2, 3, or 4 nucleosides of an antisense oligonucleotide are 2'-F modified nucleosides and each of those 2'-F modified nucleosides are non-contiguous. In certain such embodiments the remainder of the nucleosides are 2'-OMe modified nucleosides.

In certain embodiments, at least one nucleoside of a modified oligonucleotide comprises a 2'-deoxy sugar moiety that has no additional modifications. In certain embodiments, at least one nucleoside comprises a 2'-deoxy sugar moiety. In certain embodiments, at least 2 nucleosides comprise a 2'-deoxy sugar moiety. In certain embodiments, at least 3 nucleosides comprise a 2-deoxy sugar moiety. In certain embodiments, at least 4 nucleosides comprise a 2'-deoxy sugar moiety. In certain embodiments, one, but not more than one nucleoside comprises a 2'-deoxy sugar moiety. In certain embodiments, 1 or 2 nucleosides comprise a 2'-deoxy sugar moiety. In certain embodiments, 1-3 nucleosides comprise a 2'-deoxy sugar moiety. In certain embodiments, at least 1-4 nucleosides comprise a 2'-deoxy sugar moiety. In certain embodiments, 1, 2, 3, or 4 nucleosides of an antisense oligonucleotide is/are a 2'-deoxynucleoside and each 2-deoxynucleoside is not immediately adjacent to another 2'-deoxynucleoside. In certain embodiments, 1, or 2 nucleosides of an antisense oligonucleotide are a 2'-deoxy nucleoside and each 2'-deoxynucleoside is not immediately adjacent to another 2'-deoxynucleoside. In certain embodiments, 1, or 2 nucleosides of a sense oligonucleotide are a 2'-deoxynucleoside and each 2'-deoxy nucleoside is not immediately adjacent to another 2'-deoxynucleoside.

In certain embodiments, 2 nucleosides of an antisense oligonucleotide are 2'-deoxynucleosides and one nucleoside of a sense oligonucleotide is a 2-deoxynucleoside. In certain embodiments, 2 nucleosides of an antisense oligonucleotide are 2'-deoxynucleosides and no nucleoside of a sense oligonucleotide is a 2'-deoxynucleoside. In certain embodiments, 2 nucleosides of an antisense oligonucleotide are 2'-deoxynucleosides.

In certain embodiments, at least one nucleoside of an antisense oligonucleotide and/or a sense oligonucleotide comprises a modified sugar moiety and/or sugar surrogate. In certain embodiments, a sugar moiety of an antisense oligonucleotide is modified, wherein the modified sugar modifications and/or sugar surrogate is selected from 2'-F, 2'-MOE, 2'-OMe, 2'-deoxy, and FHNA. In certain embodiments, a sugar motif (from 5' to 3') of the antisense oligonucleotide is selected from yfyyyfyyyyyyyfyfyyyyyyy, efyyyfyyyyyyyfyfyyyyyee, efyyyyyyyyyyyyfyyyyyyee, efyyydyyyyyyyfyfyyyyyee, efyyydyyyyyyydydyyyyyyy, efyyydyyyyyyyfyfyyyyyyy, efyydydyyyyyyyfyfyyyyyyy, efyyyfyyyyyyyfyyyyyyyee, efyyyyyyyyyyyyfyfyyyyyee, efyyyfyyyyyyyfyyyyyyyyy, efyyyyyyyyyyyyfyfyyyyyyy, efyyyfyyyyyyyfyfyyyyyey, efyyyfyyyyyyyfydyyyyyee, efyyyfyyyyyyyfydyyyyyyy, efyydydyyyyyyyfyfyyyyyee, efyyyfyyyyyyyfyfyyyee, e[FHNA] yydydyyyyfyfyfyyyyyyy, e[FHNA] yyyfyyyyyyyfyfyyyyyyy, e[FHNA] yyyfyyyyyyyfyfyyyyyee, and e[FHNA]yyyyyyyyyyy [FHNA]yyyyyyyee, wherein each 'y' represents a 2'-OMe sugar moiety, each 'f' represents a 2'-F sugar moiety, each '[FHNA]' represents a 3'-fluoro-hexitol sugar moiety, each 'd' represents a 2'-deoxy sugar moiety, and each 'e' represents a 2'-MOE sugar moiety. In certain embodiments, a sugar moiety of a sense oligonucleotide is modified, wherein the modified sugar moiety is selected from 2'-F, 2'-MOE, 2'-OMe, and 2'-deoxy. In certain embodiments, a sugar motif (from 5' to 3') of a sense oligonucleotide is selected from among: yyyyyyfyfffyyyyyyyyyyy, yyyyyyyyyyyyyyyyyyyyyy, yyyyyyyyyffyyyyyyyyyyy, yyyyyyfyfyfyyyyyyyyy, yyyyyyyyyydyyyyyyyyyy, eeyyyyfyfffyyyyyyyyee, eeyyyyyyyffyyyyyyyyee, and eeyyyyfyfyfyyyyyyyyee, wherein each 'y' represents a 2'-OMe sugar moiety, each 'f' represents a 2'-F sugar moiety, each 'd' represents a 2'-deoxy sugar moiety, and each 'e' represents a 2'-MOE sugar moiety.

2. Nucleobase Motifs

In certain embodiments, oligonucleotides comprise modified and/or unmodified nucleobases arranged along the oligonucleotide or portion thereof in a defined pattern or motif. In certain embodiments, at least one nucleobase is modified. In certain embodiments, none of the nucleobases are modified. In certain embodiments, at least one purine and/or at least pyrimidine is modified. In certain embodiments, at least one adenine is modified. In certain embodiments, at least one guanine is modified. In certain embodiments, at least one thymine is modified. In certain embodiments, at least one uracil is modified. In certain embodiments, at least one cytosine is modified. In certain embodiments, at least one of the cytosine nucleobases in a modified oligonucleotide is 5-methylcytosine. In certain embodiments, all of the cytosine nucleobases are 5-methylcytosines and all of the other nucleobases of the modified oligonucleotide are unmodified nucleobases. In certain embodiments, one or two of the cytosine nucleobases are 5-methylcytosine and all of the other nucleobases of the modified oligonucleotide are unmodified nucleobases. In certain embodiments, each nucleobase is selected from 5-methylcytosine, unmodified cytosine, unmodified thymine, unmodified uracil, unmodified adenine, and unmodified guanine, hypoxanthine, and xanthine. In certain embodiments, each nucleobase is selected from 5-methylcytosine, unmodified cytosine, unmodified thymine, unmodified adenine, and unmodified guanine. In certain embodiments, each nucleobase is selected from unmodified cytosine, unmodified thymine, unmodified uracil, unmodified adenine, and unmodified guanine and hypoxanthine. In certain embodiments, each nucleobase is selected from unmodified cytosine, unmodified thymine, unmodified adenine, and unmodified guanine and hypoxanthine. In certain embodiments, each nucleobase is selected from unmodified cytosine, unmodified thymine, unmodified uracil, unmodified adenine, and unmodified guanine. In certain embodiments, each nucleobase is selected from unmodified cytosine, unmodified thymine, unmodified adenine, and unmodified guanine.

3. Internucleoside Linkage Motifs

In certain embodiments, oligonucleotides comprise modified and unmodified internucleoside linkages arranged along the oligonucleotide or portion thereof in a defined pattern or motif. In certain embodiments, each internucleoside linkage is a phosphodiester internucleoside linkage (P=O). In certain embodiments, each internucleoside linkage of a modified oligonucleotide is a phosphorothioate internucleoside linkage (P=S). In certain embodiments, each internucleoside linkage of a modified oligonucleotide is independently selected from a phosphorothioate internucleoside linkage, a mesyl phosphoramidate internucleoside linkage, and phosphodiester internucleoside linkage. In certain embodiments, each internucleoside linkage of a modified oligonucleotide is independently selected from a phosphorothioate internucleoside linkage and a phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, each mesyl phosphoramidate internucleoside linkage is independently selected from a stereorandom mesyl phosphoramidate, a (Sp) mesyl phosphoramidate, and a (Rp) mesyl phosphoramidate.

In certain embodiments, at least one internucleoside linkage of the antisense oligonucleotide is a modified internucleoside linkage. In certain embodiments, the 5'-most internucleoside linkage (i.e., linking the first nucleoside from the 5'-end to the second nucleoside from the 5'-end) is modified. In certain embodiments, the two 5'-most internucleoside linkages are modified. In certain embodiments, the first one or 2 internucleoside linkages from the 3'-end are modified. In certain embodiments, the modified internucleoside linkage is a phosphorothioate internucleoside linkage. In certain embodiments, the modified internucleoside linkage is a mesyl phosphoramidate internucleoside linkage. In certain embodiments, the remaining internucleoside linkages are all unmodified phosphodiester internucleoside linkages. In certain embodiments an antisense oligonucleotide has an internucleoside linkage motif (from 5' to 3) of: ssooooooooooooooooooss, wherein each 'o' represents a phosphodiester internucleoside linkage and each 's' represents a phosphorothioate internucleoside linkage. In certain embodiments an antisense oligonucleotide has an internucleoside linkage motif (from 5' to 3") of: ssoooosoooooooooooooooss, wherein each 'o' represents a phosphodiester internucleoside linkage and each 's' represents a phosphorothioate internucleoside linkage. In certain embodiments an antisense oligonucleotide has an internucleoside linkage motif (from 5' to 3') of: ssooso-sooooooooooooooss, wherein each 'o' represents a phosphodiester internucleoside linkage and each 's' represents a phosphorothioate internucleoside linkage. In certain embodiments an antisense oligonucleotide has an internucleoside linkage motif (from 5' to 3') of: ssoooooooooooooooooooss, wherein each 'o' represents a phosphodiester internucleoside linkage and each 's' represents a phosphorothioate internucleoside linkage. In certain embodiments an antisense oligonucleotide has an internucleoside linkage motif (from 5' to 3') of: ss (o) n-sss, wherein each 'o' represents a phosphodiester internucleoside linkage and each 's' represents a phosphorothioate internucleoside linkage, and wherein n represents the number of nucleobases in the oligonucleotide.

In certain embodiments, at least one internucleoside linkage of the sense oligonucleotide is a modified internucleoside linkage. In certain embodiments, the 5'-most internucleoside linkage (i.e., linking the first nucleoside from the 5'-end to the second nucleoside from the 5'-end) is modified. In certain embodiments, the two 5-most internucleoside linkages are modified. In certain embodiments, the first one or 2 internucleoside linkages from the 3'-end are modified. In certain embodiments, the modified internucleoside linkage is a phosphorothioate internucleoside linkage. In certain embodiments, the modified internucleoside linkage is a mesyl phosphoramidate internucleoside linkage. In certain embodiments, the remaining internucleoside linkages are all unmodified phosphodiester linkages. In certain embodiments a sense oligonucleotide has an internucleoside linkage motif (from 5' to 3') of: ssoooooooooooooooooss, wherein each 'o' represents a phosphodiester internucleoside linkage and each 's' represents a phosphorothioate internucleoside linkage. In certain embodiments a sense oligonucleotide has an internucleoside linkage motif (from 5' to 3') of: ssoooooo-zozoooooooss, wherein each 'o' represents a phosphodiester internucleoside linkage and each 's' represents a phosphorothioate internucleoside linkage and each 'z' represents a mesyl phosphoramidate internucleoside linkage. In certain embodiments a sense oligonucleotide has an internucleoside linkage motif (from 5' to 3") of: ssooooooosooooooooss, wherein each 'o' represents a phosphodiester internucleoside linkage and each 's' represents a phosphorothioate internucleoside linkage. In certain embodiments a sense oligonucleotide has an internucleoside linkage motif (from 5' to 3') of: ssoooooooooooooooss, wherein each 'o' represents a phosphodiester internucleoside linkage and each 's' represents a phosphorothioate internucleoside linkage. In certain embodiments a sense oligonucleotide has an internucleoside linkage motif (from 5' to 3") of: ss (o) n-sss, wherein each 'o' represents a phosphodiester internucleoside linkage and each 's' represents a phosphorothioate internucleoside linkage, and wherein n represents the number of nucleobases in the oligonucleotide.

C. Lengths

It is possible to increase or decrease the length of an oligonucleotide without eliminating activity. For example, in Woolf et al. (Proc. Natl. Acad. Sci. USA 89:7305-7309, 1992), a series of oligonucleotides 13-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target RNA, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (e.g., modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 27, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, to 28.25 to 29.25 to 30.26 to 27.26 to 28.26 to 29.26 to 30, 27 to 28, 27 to 29, 27 to 30, 28 to 29.28 to 30, or 29 to 30 linked nucleosides.

In certain embodiments, modified oligonucleotides (including, e.g., antisense oligonucleotides, sense oligonucleotides) comprise 16 linked nucleosides having no more than 1 to 3 mismatches to a target sequence. In certain embodiments, modified oligonucleotides (including, e.g., antisense oligonucleotides, sense oligonucleotides) comprise 17 linked nucleosides having no more than 1 to 3 mismatches to a target sequence. In certain embodiments, modified oligonucleotides (including, e.g., antisense oligonucleotides, sense oligonucleotides) comprise 18 linked nucleosides having no more than 1 to 3 mismatches to a target sequence. In certain embodiments, modified oligonucleotides (including, e.g., antisense oligonucleotides, sense oligonucleotides) comprise 19 linked nucleosides having no more than 1 to 3 mismatches to a target sequence. In certain embodiments, modified oligonucleotides (including, e.g., antisense oligonucleotides, sense oligonucleotides) comprise 20 linked nucleosides having no more than 1 to 3 mismatches to a target sequence. In certain embodiments, modified oligonucleotides (including, e.g., antisense oligonucleotides, sense oligonucleotides) comprise 21 linked nucleosides having no more than 1 to 3 mismatches to a target sequence. In certain embodiments, modified oligonucleotides (including, e.g., antisense oligonucleotides, sense oligonucleotides) comprise 22 linked nucleosides having no more than 1 to 3 mismatches to a target sequence. In certain embodiments, modified oligonucleotides (including, e.g., antisense oligonucleotides, sense oligonucleotides) comprise 23 linked nucleosides having no more than 1 to 3 mismatches to a target sequence.

In certain embodiments, modified oligonucleotides (including, e.g., antisense oligonucleotides, sense oligonucleotides) consist of 16 linked nucleosides. In certain embodiments, modified oligonucleotides (including antisense oligonucleotides) consist of 17 linked nucleosides. In certain embodiments, modified oligonucleotides (including, e.g., antisense oligonucleotides, sense oligonucleotides) consist of 18 linked nucleosides. In certain embodiments, modified oligonucleotides (including, e.g., antisense oligonucleotides, sense oligonucleotides) consist of 19 linked nucleosides. In certain embodiments, modified oligonucleotides (including, e.g., antisense oligonucleotides, sense oligonucleotides) consist of 20 linked nucleosides. In certain embodiments, modified oligonucleotides (including, e.g., antisense oligonucleotides, sense oligonucleotides) consist of 21 linked nucleosides. In certain embodiments, modified oligonucleotides (including, e.g., antisense oligonucleotides, sense oligonucleotides) consist of 22 linked nucleosides. In certain embodiments, modified oligonucleotides (including, e.g., antisense oligonucleotides, sense oligonucleotides) consist of 23 linked nucleosides.

In certain embodiments, antisense oligonucleotides consist of 12-30 linked nucleosides. In certain embodiments, antisense oligonucleotides consist of 17-25 linked nucleosides. In certain embodiments, antisense oligonucleotides consist of 17-23 linked nucleosides. In certain embodiments, antisense oligonucleotides consist of 17-21 linked nucleosides. In certain embodiments, antisense oligonucleotides consist of 18-30 linked nucleosides. In certain embodiments, antisense oligonucleotides consist of 20-30 linked nucleosides. In certain embodiments, antisense oligonucleotides consist of 21-30 linked nucleosides. In certain embodiments, antisense oligonucleotides consist of 23-30 linked nucleosides. In certain embodiments, antisense oligonucleotides consist of 18-25 linked nucleosides. In certain embodiments, antisense oligonucleotides consist of 20-22 linked nucleosides. In certain embodiments, antisense oligonucleotides consist of 21-23 linked nucleosides. In certain embodiments, antisense oligonucleotides consist of 23-24 linked nucleosides. In certain embodiments, antisense oligonucleotides consist of 20 linked nucleosides. In certain embodiments, antisense oligonucleotides consist of 21 linked nucleosides. In certain embodiments, antisense oligonucleotides consist of 22 linked nucleosides. In certain embodiments, antisense oligonucleotides consist of 23 linked nucleosides. In certain embodiments, antisense oligonucleotides consist of 20 linked nucleosides having no more than 1 to 3 mismatches to a target sequence. In certain embodiments, antisense oligonucleotides consist of 21 linked nucleosides having no more than 1 to 3 mismatches to a target sequence. In certain embodiments, antisense oligonucleotides consist of 22 linked nucleosides having no more than 1 to 3 mismatches to a target sequence. In certain embodiments, antisense oligonucleotides consist of 23 linked nucleosides having no more than 1 to 3 mismatches to a target sequence.

In certain embodiments, sense oligonucleotides consist of 12-30 linked nucleosides. In certain embodiments, sense oligonucleotides consist of 16-25 linked nucleosides. In certain embodiments, sense oligonucleotides consist of 16-23 linked nucleosides. In certain embodiments, sense oligonucleotides consist of 16-21 linked nucleosides. In certain embodiments, sense oligonucleotides consist of 16-30 linked nucleosides. In certain embodiments, sense oligonucleotides consist of 18-30 linked nucleosides. In certain embodiments, sense oligonucleotides consist of 19-30 linked nucleosides. In certain embodiments, sense oligonucleotides consist of 19-25 linked nucleosides. In certain embodiments, sense oligonucleotides consist of 18-25 linked nucleosides. In certain embodiments, sense oligonucleotides consist of 18-20 linked nucleosides. In certain embodiments, sense oligonucleotides consist of 19-21 linked nucleosides. In certain embodiments, sense oligonucleotides consist of 18 linked nucleosides. In certain embodiments, sense oligonucleotides consist of 19 linked nucleosides. In certain embodiments, sense oligonucleotides consist of linked nucleosides. In certain embodiments, sense oligonucleotides consist of 21 linked nucleosides. In certain embodiments, sense oligonucleotides consist of 18 linked nucleosides having no more than 1 to 3 mismatches to a target sequence. In certain embodiments, sense oligonucleotides consist of 19 linked nucleosides having no more than 1 to 3 mismatches to a target sequence. In certain embodiments, sense oligonucleotides consist of 20 linked nucleosides having no more than 1 to 3 mismatches to a target sequence. In certain embodiments, sense oligonucleotides consist of 21 linked nucleosides having no more than 1 to 3 mismatches to a target sequence.

D. Oligomeric Modifications

Provided oligomeric compounds comprise one or more modifications, e.g., sugar, nucleobase, internucleoside linkage, and/or combinations thereof, incorporated into a modified oligonucleotide. In certain embodiments, a modified oligonucleotide is characterized by modification motif(s) and overall length. In certain embodiments, such parameters are each independent of one another. Thus, unless otherwise indicated, each internucleoside linkage of an oligonucleotide having one or more modified sugar moiety or sugar surrogate and/or sugar motif, independently, is modified or unmodified and may or may not follow the modification pattern of the sugar modifications. For example, internucleoside linkages within regions of an oligonucleotide comprising certain sugar modifications may be the same or different from one another and may be the same or different from the internucleoside linkages of the region of the oligonucleotide comprising different sugar modifications. Likewise, such modified oligonucleotides may comprise one or more modified nucleobase independent of the pattern of the sugar modifications and independent of the internucleoside linkages. Unless specifically indicated, all modifications are independent of nucleobase sequence. Furthermore, each modification, whether internucleoside linkage, modified sugar moiety, sugar surrogate, modified nucleobase, of an antisense oligonucleotide is independent of each modification of a sense oligonucleotide binding partner unless specifically indicated otherwise.

E. Nucleobase Sequence

In certain embodiments, oligonucleotides (unmodified or modified oligonucleotides) are further described by their nucleobase sequence. In certain embodiments oligonucleotides have a nucleobase sequence that is complementary to a nucleobase sequence of a second oligonucleotide or an identified reference nucleic acid, such as a target nucleic acid or portion thereof. In certain such embodiments, a region of an oligonucleotide has a nucleobase sequence that is complementary to a nucleobase sequence of a second oligonucleotide or an identified reference nucleic acid, such as a target nucleic acid or portion thereof. In certain embodiments, the nucleobase sequence of a region or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid or portion thereof.

II. Oligomeric Duplexes

In certain embodiments, an oligomeric compound provided herein comprises a first modified oligonucleotide having a nucleobase sequence complementary to a sequence in a PLN target nucleic acid paired with a second modified oligonucleotide to form an oligomeric duplex. Such oligomeric duplex comprises a first oligomeric compound comprising a modified oligonucleotide having a portion complementary to a sequence in a PLN target nucleic acid and a second oligomeric compound comprising a modified oligonucleotide having a portion complementary to the first modified oligonucleotide. In certain embodiments, the first oligomeric compound of an oligomeric duplex comprises or consists of a first modified oligonucleotide and optionally a conjugate group and/or terminal group; and the second oligomeric compound of the oligomeric duplex comprises or consists of a second modified oligonucleotide and optionally a terminal group and/or a conjugate group. Either or both oligomeric compounds of an oligomeric duplex may comprise a conjugate group. In certain embodiments the sense oligomeric compound of an oligomeric duplex comprises a conjugate group attached at the 5' or 3' end of the sense oligomeric compound. Either or both oligomeric compounds of an oligomeric duplex may comprise a terminal group. In certain embodiments the antisense oligomeric compound of an oligomeric duplex comprises a 5'-terminal group. One or both oligonucleotides of each oligomeric compound of an oligomeric duplex may include one or more (e.g., one, two, three, or more) terminal nucleosides that form an overhang at one (i.e., the 5' end or 3' end) or both ends of the oligomeric duplex. In certain embodiments an overhang is one or two nucleosides (e.g., of an antisense oligomeric compound, sense oligomeric compound, antisense oligonucleotide, sense oligonucleotide) of an oligomeric duplex. In certain embodiments the terminal one or two nucleosides at the 3' end or at the 5' end of an antisense or sense oligomeric compound or an antisense or sense oligonucleotide are overhang nucleosides of an oligomeric duplex. In certain embodiments the overhang nucleosides are adenosine, inosine, or thymidine. In certain embodiments one or both ends of the oligomeric duplex are blunt ends. In certain embodiments, the two oligonucleotides have at least one mismatch relative to one another. In certain embodiments, the oligomeric duplex is an antisense compound.

In certain embodiments, an overhang is one or two nucleosides of a first oligomeric compound or first modified oligonucleotide of an oligomeric duplex. In certain embodiments the last two 3'-nucleosides (i.e., the 3'-terminal nucleoside and the nucleoside immediately 5' of the 3'-terminal nucleoside) of a first oligomeric compound or first modified oligonucleotide of an oligomeric duplex are overhang nucleosides. In certain embodiments, a 3' overhang nucleoside of a first oligomeric compound or first modified oligonucleotide of an oligomeric duplex comprises an unmodified adenine, unmodified thymine, unmodified uracil or hypoxanthine nucleobase. In certain embodiments, a 3' overhang of a first oligomeric compound or first modified oligonucleotide of an oligomeric duplex comprises two nucleosides, each comprising a nucleobase independently selected from an unmodified adenine, an unmodified thymine, an unmodified uracil and a hypoxanthine. In certain embodiments, the last two nucleosides at the 3' end of a first oligomeric compound or first modified oligonucleotide of an oligomeric duplex having a 3' overhang each comprise a nucleobase independently selected from an unmodified adenine, unmodified thymine, unmodified uracil and hypoxanthine. In certain embodiments, a 3'-overhang nucleoside of a first oligomeric compound or first modified oligonucleotide of an oligomeric duplex comprises an unmodified adenine nucleobase or hypoxanthine nucleobase. In certain embodiments, a 3' overhang of a first oligomeric compound or first modified oligonucleotide of an oligomeric duplex comprises two nucleosides, each comprising a nucleobase independently selected from an unmodified adenine nucleobase or a hypoxanthine nucleobase. In certain embodiments, the last two terminal nucleosides at the 3' end of a first oligomeric compound or first modified oligonucleotide of an oligomeric duplex having a 3' overhang each independently comprise an unmodified adenine nucleobase or a hypoxanthine nucleobase. In certain embodiments, the last two terminal nucleosides at the 3' end of a first oligomeric compound or first modified oligonucleotide of an oligomeric duplex having a 3' overhang comprise an unmodified adenine nucleobase. In certain embodiments, the last two terminal nucleosides at the 3' end of a first oligomeric compound or first modified oligonucleotide of an oligomeric duplex having a 3' overhang each comprise a hypoxanthine nucleobase. In certain embodiments, the 3'-terminal nucleo- side and the nucleoside immediately 5' of the 3'-terminal nucleoside of a first oligomeric compound or first modified oligonucleotide of an oligomeric duplex having a 3' over- hang comprise an unmodified adenine nucleobase and a hypoxanthine nucleobase, respectively. In certain embodi- ments, the 3'-terminal nucleoside and the nucleoside imme- diately 5' of the 3'-terminal nucleoside of a first oligomeric compound or first modified oligonucleotide of an oligomeric duplex having a 3' overhang comprise a hypoxanthine nucleobase and an unmodified adenine nucleobase, respec- tively.

In certain embodiments an overhang of an oligomeric duplex is the 3'-terminal nucleoside of a first oligomeric compound or first modified oligonucleotide of the oligo- meric duplex. In certain embodiments the 3'-terminal nucleoside of a first oligomeric compound or first modified oligonucleotide of the oligomeric duplex having a 3' over- hang comprises an unmodified adenine, unmodified thy- mine, unmodified uracil or hypoxanthine nucleobase. In certain embodiments the 3'-terminal nucleoside of a first oligomeric compound or first modified oligonucleotide of the oligomeric duplex having a 3' overhang comprises an unmodified adenine nucleobase or hypoxanthine nucle- obase. In certain embodiments the 3'-terminal nucleoside of a first oligomeric compound or first modified oligonucle- otide of the oligomeric duplex having a 3' overhang com- prises an unmodified adenine nucleobase. In certain embodi- ments the 3'-terminal nucleoside of a first oligomeric compound or first modified oligonucleotide of the oligo- meric duplex having a 3' overhang comprises a hypoxan- thine nucleobase.

In certain embodiments, one or both ends of an oligomeric duplex are blunt ends. In certain embodiments, one end of an oligomeric duplex is blunt. In certain embodiments, both ends of an oligomeric duplex are blunt. In certain embodi- ments, the 5'-terminal nucleoside of a first oligomeric com- pound or a first modified oligonucleotide of an oligomeric duplex having at least one blunt end comprises an unmodi- fied thymine nucleobase. In certain embodiments, the 3'-ter- minal nucleoside of a first oligomeric compound or a first modified oligonucleotide of an oligomeric duplex having at least one blunt end comprises an unmodified guanine or unmodified uracil nucleobase. In certain embodiments, the 5'-terminal nucleoside of a first oligomeric compound or a first modified oligonucleotide of an oligomeric duplex hav- ing two blunt ends comprises an unmodified thymine nucle- obase and the 3'-terminal nucleoside of the first oligomeric compound or first modified oligonucleotide comprises an unmodified guanine or unmodified uracil nucleobase.

In certain embodiments, an oligomeric duplex comprises a first oligomeric compound/second oligomeric compound pair in which the nucleobase sequence of the first modified oligonucleotide and the nucleobase sequence of the second modified oligonucleotide are a duplex comprising any one of the following pairs of SEQ ID NOS: 1033/1039, 1034/1040, 1035/1041, 1036/1042, 1037/1043, 1038/1044, 1036/1288, 1255/1041, 1265/1288, 1265/1042, 1259/1012, 1262/1013, 1268/1015, 1271/1016, 1264/1288, 1264/1042, 1258/1012, 1261/1013, 1267/1015, 1270/1046, 1260/1012, 1263/1013, 1266/1014, 1269/1015, 1272/1016, 1279/1288, 1273/1012, 1276/1013, 1282/1015, 1285/1016, 1280/1288, 1274/1012, 1277/1013, 1283/1015, and 1286/1016, 1275/1012, 1278/ 1013, 1281/1014, 1284/1015, and 1287/1016.

In certain embodiments, an oligomeric duplex comprises: a first oligomeric compound comprising a first modified oligonucleotide consisting of 12 to 50 linked nucleosides, wherein the first modified oligonucleotide comprises a region having a nucleobase sequence comprising at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of the nucleobase sequence of any one of SEQ ID Nos: 3-314.627-782.939-976.1033- 1038.1254-1255, and 1258-1287; and a second oligomeric compound comprising a second modified oligonucleotide consisting of 12 to 50 linked nucleosides that contains a region of at least 12 contiguous nucleosides, wherein the nucleobase sequence of the region of at least 12 contiguous nucleosides is at least 80%, at least 90%, at least 95%, or at least 99% or 100% complementary to the nucleobase sequence of an equal length region of the first modified oligonucleotide. In certain embodiments, the nucleobase sequence of the region of the first modified oligonucleotide having a nucleobase sequence comprising at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of the nucleobase sequence of any one of SEQ ID Nos: 3-314, 627-782, 939-976, 1033-1038, 1254-1255, and 1258-1287 is at least 80% complementary to the nucle- obase sequence of an equal length region of a PLN nucleic acid. In certain embodiments, the nucleobase sequence of the second modified oligonucleotide comprises at least 8, at least 9, at least 10, at least 11, at least 12, at least 13, at least 14, at least 15, at least 16, at least 17, at least 18, at least 19, at least 20, or at least 21 contiguous nucleobases of the nucleobase sequence of any one of SEQ ID Nos: 315-626, 783-938, 977-1016, 1027-1032, 1256-1257, and 1288-1290. In certain embodiments, the first oligomeric compound of the oligomeric duplex is an antisense compound, wherein the first modified oligonucleotide is an antisense oligonucle- otide. In certain embodiments, the second oligomeric com- pound of the oligomeric duplex is a sense compound, wherein the second modified oligonucleotide is a sense oligonucleotide. In certain embodiments, the first modified oligonucleotide is an antisense RNAi oligonucleotide. In certain embodiments, the second modified oligonucleotide is a sense RNAi oligonucleotide.

In certain embodiments, an oligomeric duplex comprises: a first oligomeric compound comprising a first modified oligonucleotide consisting of 15 to 30 linked nucleosides, wherein the nucleobase sequence of the first modified oli- gonucleotide comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of the nucleobase sequence of any one of SEQ ID Nos: 3-314, 627-782, 939-976, 1033-1038, 1254-1255, and 1258-1287; and a second oligomeric compound comprising a second modified oligonucleotide consisting of 15 to 29 linked nucleosides, wherein the nucleobase sequence of the second modified oligonucleotide comprises at least 8, at least 9, at least 10, at least 11, at least 12, at least 13, at least 14, at least 15, at least 16, at least 17, at least 18, at least 19, at least 20, or at least 21 contiguous nucleobases of the nucleobase sequence of any one of SEQ ID Nos: 315-626, 783-938, 977-1016, 1027-1032, 1256-1257, and 1288-1290. In cer- tain embodiments, the oligomeric duplex is an antisense compound. In certain embodiments, the first oligomeric compound of the oligomeric duplex is an antisense com- pound, wherein the first modified oligonucleotide is an antisense oligonucleotide. In certain embodiments, the sec- ond oligomeric compound of the oligomeric duplex is a sense compound, wherein the second modified oligonucle-
otide is a sense oligonucleotide. In certain embodiments, the
first modified oligonucleotide is an antisense RNAi oligo-
nucleotide. In certain embodiments, the second modified
oligonucleotide is a sense RNAi oligonucleotide. In certain
embodiments, the nucleobase sequence of the second modi-
fied oligonucleotide is at least 90%, 95% or 100% comple-
mentary to the nucleobase sequence of an equal length
portion of the first modified oligonucleotide.

In certain embodiments, an oligomeric duplex comprises
a first oligomeric compound comprising a first modified
oligonucleotide consisting of 18 to 30 linked nucleosides,
wherein the nucleobase sequence of the first modified oli-
gonucleotide comprises at least 12, at least 13, at least 14, at
least 15, at least 16, at least 17, at least 18, at least 19, at least
20, at least 21, at least 22, or 23 contiguous nucleobases of
the nucleobase sequence of any one of SEQ ID NO: 3-314,
627-782, 939-976, 1033-1038, 1254-1255, and 1258-1287,
and a second oligomeric compound comprising a second
modified oligonucleotide consisting of 15 to 29 linked
nucleosides, wherein the nucleobase sequence of the second
modified oligonucleotide comprises at least 12, at least 13,
at least 14, at least 15, at least 16, at least 17, at least 18, at
least 19, at least 20, or at least 21 contiguous nucleobases of
the nucleobase sequence of any one of SEQ ID Nos:
315-626, 783-938, 977-1016, 1027-1032, 1256-1257, and
1288-1290. In certain embodiments, the first oligomeric
compound is an antisense compound, wherein the first
modified oligonucleotide is an antisense oligonucleotide. In
certain embodiments, the second oligomeric compound is a
sense compound, wherein the second modified oligonucle-
otide is a sense oligonucleotide. In certain embodiments, the
first modified oligonucleotide is an antisense RNAi oligo-
nucleotide. In certain embodiments, the second modified
oligonucleotide is a sense RNAi oligonucleotide. In certain
embodiments, the nucleobase sequence of the second modi-
fied oligonucleotide comprises a complementary region of at
least 9, at least 10, at least 11, at least 12, at least 13, at least
14, at least 15, at least 16, at least 17, at least 18, at least 19,
at least 20, or 21 contiguous nucleobases that is 100%
complementary to the nucleobase sequence of an equal
length portion of the first modified oligonucleotide. In
certain embodiments, the nucleobase sequence of the second
modified oligonucleotide is at least 80%, at least 85%, at
least 90%, at least 95%, at least 98%, at least 99%, or 100%
complementary to the nucleobase sequence of an equal
length portion of the first modified oligonucleotide. In
certain embodiments, the oligomeric duplex is an antisense
compound. In certain embodiments, the nucleobase
sequence of the second modified oligonucleotide comprises
a complementary region of at least 9, at least 10, at least 11,
at least 12, at least 13, at least 14, at least 15, at least 16, at
least 17, at least 18, at least 19, at least 20, or 21 contiguous
nucleobases that is 100% complementary to the nucleobase
sequence of an equal length portion of the first modified
oligonucleotide; and the nucleobase sequence of the second
modified oligonucleotide is at least 80%, at least 85%, at
least 90%, at least 95%, at least 98%, at least 99%, or 100%
complementary to the nucleobase sequence of an equal
length portion of the first modified oligonucleotide. In
certain embodiments, the oligomeric duplex is an antisense
compound.

In certain embodiments, an oligomeric duplex comprises
a first oligomeric compound comprising a first modified
oligonucleotide consisting of 19 to 25 linked nucleosides,
wherein the nucleobase sequence of the first modified oli-
gonucleotide comprises at least 10, at least 11, at least 12, at least 13, at least 14, at least 15, at least 16, at least 17, at least
18, at least 19, at least 20, or at least 21 contiguous
nucleobases of the nucleobase sequence of any one of SEQ
ID NO: 3-314, 627-782, 939-976, 1033-1038, 1254-1255,
and 1258-1287; and a second oligomeric compound com-
prising a second modified oligonucleotide consisting of 16
to 24 linked nucleosides, wherein the nucleobase sequence
of the second modified oligonucleotide comprises at least 9,
at least 10, at least 11, at least 12, at least 13, at least 14, at
least 15, at least 16, at least 17, at least 18, at least 19, or at
least 20 contiguous nucleobases of the nucleobase sequence
of any one of SEQ ID NO: 315-626.783-938.977-
1016.1027-1032.1256-1257, and 1288-1290. In certain
embodiments, the first oligomeric compound is an antisense
compound, wherein the first modified oligonucleotide is an
antisense oligonucleotide. In certain embodiments, the sec-
ond oligomeric compound is a sense compound, wherein the
second modified oligonucleotide is a sense oligonucleotide.
In certain embodiments, the first modified oligonucleotide is
an antisense RNAi oligonucleotide, and the second modified
oligonucleotide is a sense RNAi oligonucleotide. In certain
embodiments, the nucleobase sequence of the second modi-
fied oligonucleotide is at least 95% or 100% complementary
to the nucleobase sequence of an equal length portion of the
first modified oligonucleotide. In certain embodiments, the
oligomeric duplex is an antisense compound.

In certain embodiments, an oligomeric duplex comprises
a first oligomeric compound comprising a first modified
oligonucleotide, wherein the first modified oligonucleotide
consists of 23.22 or 21 linked nucleosides and has nucle-
obase sequence comprising at least a 19-bp nucleobase
sequence of any one of SEQ ID Nos: 3-314, 627-782,
939-976, 1033-1038, 1254-1255, and 1258-1287 having 0,
1, 2 or 3 nucleobases that are different from the correspond-
ing nucleotide in any of SEQ ID Nos: 3-314, 627-782,
939-976, 1033-1038, 1254-1255, and 1258-1287; and a
second oligomeric compound comprising a second modified
oligonucleotide wherein the second modified oligonucle-
otide consists of 21 linked nucleosides and has a nucleobase
sequence comprising at least a 16-bp nucleobase sequence
of any one of SEQ ID Nos: 315-626, 783-938, 977-1016,
1027-1032, 1256-1257, and 1288-1290 having 0, 1, 2 or 3
nucleobases that are different from the corresponding
nucleotide in any of SEQ ID Nos: 315-626, 783-938,
977-1016, 1027-1032, 1256-1257, and 1288-1290. In cer-
tain embodiments, the first oligomeric compound is an
antisense compound, wherein the first modified oligonucle-
otide is an antisense oligonucleotide. In certain embodi-
ments, the second oligomeric compound is a sense com-
pound, wherein the second modified oligonucleotide is a
sense oligonucleotide. In certain embodiments, the first
modified oligonucleotide is an antisense RNAi oligonucle-
otide and the second modified oligonucleotide is a sense
RNAi oligonucleotide. In certain embodiments, the nucle-
obase sequence of the second modified oligonucleotide is at
least 95% or 100% complementary to the nucleobase
sequence of an equal length portion of the first modified
oligonucleotide. In certain embodiments, the oligomeric
duplex is an antisense compound. In certain embodiments,
the oligomeric duplex comprises one or two unpaired
nucleosides at either or both ends, forming one or two
overhang ends. In certain embodiments an overhang end is
one or two nucleosides of the antisense oligonucleotide. In
certain embodiments an overhang end is one or two
3'-nucleosides of the antisense oligonucleotide. In certain
embodiments the last two 3'-nucleosides of the antisense
oligonucleotide are overhang nucleosides not paired with the sense oligonucleotide. In certain embodiments the last one or two 3'-unpaired overhang nucleosides comprise an adenine nucleobase. In certain embodiments the last one or two 3'-unpaired overhang nucleosides comprise a hypoxanthine nucleobase. In certain embodiments the last one or two 3'-unpaired overhang nucleosides comprise a thymine nucleobase.

In certain embodiments, an oligomeric duplex comprises a first oligomeric compound comprising a first modified oligonucleotide, wherein the first modified oligonucleotide consists of 21, 20 or 19 linked nucleosides and has a nucleobase sequence comprising at least a 19-bp nucleobase sequence of any one of SEQ ID Nos: 3-314, 627-782, 939-976, 1033-1038, 1254-1255, and 1258-1287 having 0.1.2 or 3 mismatches with a sequence in a target PLN nucleic acid sequence; and a second oligomeric compound comprising a second modified oligonucleotide wherein the second modified oligonucleotide consists of 19 linked nucleosides, comprising at least a 19-bp nucleobase sequence of any one of SEQ ID Nos: 315-626, 783-938, 977-1016, 1027-1032, 1256-1257, and 1288-1290 having 0, 1, 2 or 3 mismatches to the first modified oligonucleotide. In certain embodiments, the first oligomeric compound is an antisense compound, wherein the first modified oligonucleotide is an antisense oligonucleotide. In certain embodiments, the second oligomeric compound is a sense compound, wherein the second modified oligonucleotide is a sense oligonucleotide. In certain embodiments, the first modified oligonucleotide is an antisense RNAi oligonucleotide and the second modified oligonucleotide is a sense RNAi oligonucleotide. In certain embodiments, the nucleobase sequence of the second modified oligonucleotide is at least 95% or 100% complementary to the nucleobase sequence of an equal length portion of the first modified oligonucleotide. In certain embodiments, the oligomeric duplex is an antisense compound. In certain embodiments, the oligomeric duplex comprises one or two unpaired nucleosides at either or both ends, forming one or two overhang ends. In certain embodiments an overhang end is one or two nucleosides of the antisense oligonucleotide. In certain embodiments an overhang end is one or two 3'-nucleosides of the antisense oligonucleotide. In certain embodiments the last two 3'-nucleosides of the antisense oligonucleotide are overhang nucleosides not paired with the sense oligonucleotide. In certain embodiments the last one or two 3'-unpaired overhang nucleosides comprise an adenine nucleobase. In certain embodiments the last one or two 3'-unpaired overhang nucleosides comprise a hypoxanthine nucleobase. In certain embodiments the last one or two 3'-unpaired overhang nucleosides comprise a thymine nucleobase.

In certain embodiments, an oligomeric duplex comprises a first oligomeric compound comprising a first modified oligonucleotide, wherein the first modified oligonucleotide consists of 23, 22 or 21 linked nucleosides and has a nucleobase sequence comprising at least a 19-bp nucleobase sequence of any one of SEQ ID Nos: 3-314, 627-782, 939-976, 1033-1038, 1254-1255, and 1258-1287; and a second oligomeric compound comprising a second modified oligonucleotide wherein the second modified oligonucleotide consists of 21 linked nucleosides and has a nucleobase sequence comprising at least a 19-bp nucleobase sequence of any one of SEQ ID Nos: 315-626, 783-938, 977-1016, 1027-1032, 1256-1257, and 1288-1290. In certain embodiments, the first oligomeric compound is an antisense compound, wherein the first modified oligonucleotide is an antisense oligonucleotide. In certain embodiments, the second oligomeric compound is a sense compound, wherein the second modified oligonucleotide is a sense oligonucleotide. In certain embodiments, the first modified oligonucleotide is an antisense RNAi oligonucleotide and the second modified oligonucleotide is a sense RNAi oligonucleotide. In certain embodiments, the nucleobase sequence of the second modified oligonucleotide is at least 95% or 100% complementary to the nucleobase sequence of an equal length portion of the first modified oligonucleotide. In certain embodiments, the oligomeric duplex is an antisense compound. In certain embodiments, the oligomeric duplex comprises one or two unpaired nucleosides at either or both ends, forming one or two overhang ends. In certain embodiments an overhang end is one or two nucleosides of the antisense oligonucleotide. In certain embodiments an overhang end is one or two 3'-nucleosides of the antisense oligonucleotide. In certain embodiments the last two 3'-nucleosides of the antisense oligonucleotide are overhang nucleosides not paired with the sense oligonucleotide. In certain embodiments the last one or two 3'-unpaired overhang nucleosides comprise an adenine nucleobase. In certain embodiments the last one or two 3'-unpaired overhang nucleosides comprise a hypoxanthine nucleobase. In certain embodiments the last one or two 3'-unpaired overhang nucleosides comprise a thymine nucleobase.

In certain embodiments, an oligomeric duplex comprises a first oligomeric compound comprising a first modified oligonucleotide, wherein the first modified oligonucleotide consists of 21 linked nucleosides and has a nucleobase sequence comprising at least a 19-bp nucleobase sequence of any one of SEQ ID Nos: 3-314, 627-782, 939-976, 1033-1038, 1254-1255, and 1258-1287; and a second oligomeric compound comprising a second modified oligonucleotide wherein the second modified oligonucleotide consists of 19 linked nucleosides and has a nucleobase sequence comprising at least a 16-bp nucleobase sequence of any one of SEQ ID Nos: 315-626, 783-938, 977-1016, 1027-1032, 1256-1257, and 1288-1290, wherein the nucleobase sequence of the second modified oligonucleotide is at least 90% complementary to the nucleobase sequence of an equal length portion of the first modified oligonucleotide. In certain embodiments, the first oligomeric compound is an antisense compound, wherein the first modified oligonucleotide is an antisense oligonucleotide. In certain embodiments, the second oligomeric compound is a sense compound, wherein the second modified oligonucleotide is a sense oligonucleotide. In certain embodiments, the first modified oligonucleotide is an antisense RNAi oligonucleotide and the second modified oligonucleotide is a sense RNAi oligonucleotide. In certain embodiments, the nucleobase sequence of the second modified oligonucleotide is at least 95% or 100% complementary to the nucleobase sequence of an equal length portion of the first modified oligonucleotide. In certain embodiments, the oligomeric duplex is an antisense compound. In certain embodiments, the oligomeric duplex comprises one or two unpaired nucleosides at either or both ends, forming one or two overhang ends. In certain embodiments an overhang end is one or two nucleosides of the antisense oligonucleotide. In certain embodiments an overhang end is one or two 3'-nucleosides of the antisense oligonucleotide. In certain embodiments the last two 3'-nucleosides of the antisense oligonucleotide are overhang nucleosides not paired with the sense oligonucleotide. In certain embodiments the last one or two 3'-unpaired overhang nucleosides comprise an adenine nucleobase. In certain embodiments the last one or two 3'-unpaired overhang nucleosides comprise a hypoxanthine nucleobase. In certain embodiments the last one or two 3'-unpaired overhang nucleosides comprise a thymine nucleobase.

In certain embodiments, an oligomeric duplex comprises a first oligomeric compound comprising a first modified oligonucleotide consisting of 19 to 25 linked nucleosides and a second oligomeric compound comprising a second modified oligonucleotide consisting of 16 to 24 linked nucleosides, wherein the nucleobase sequence of the first modified oligonucleotide and the nucleobase sequence of the second modified oligonucleotide each comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of any of the following pairs of nucleobase sequences recited in SEQ ID Nos: 939/978, 939/1001, 941/979, 941/1003, 942/980, 942/1004, 943/981, 943/1005, 944/982, 944/1006, 945/983, 945/1007, 946/984, 946/1008, 947/985, 947/1009, 940/977, 940/1002, 967/1011, 968/1012, 974/1013, 975/1014, 971/1015, 972/1016, 1254/1013, 1033/1039, 1034/1040, 1035/1041, 1036/1042, 1037/1043, 1038/1044, 1036/1288, and 1255/1041, 1265/1288, 1265/1042, 1259/1012, 1262/1013, 1268/1015, 1271/1016, 1264/1288, 1264/1042, 1258/1012, 1261/1013, 1267/1015, 1270/1046, 1260/1012, 1263/1013, 1266/1014, 1269/1015, 1272/1016, 1279/1288, 1273/1012, 1276/1013, 1282/1015, 1285/1016, 1280/1288, 1274/1012, 1277/1013, 1283/1015, 1286/1016, 1275/1012, 1278/1013, 1281/1014, 1284/1015, and 1287/1016, wherein the nucleobase sequence of the first modified oligonucleotide comprises a sequence of contiguous nucleobases of the nucleobase sequence of the first SEQ ID NO recited in the pair and the nucleobase sequence of the second modified oligonucleotide comprises a sequence of contiguous nucleobases of the nucleobase sequence of the second SEQ ID NO recited in the pair. In certain embodiments, the first oligomeric compound is an antisense compound. In certain embodiments, the first modified oligonucleotide is an antisense oligonucleotide. In certain embodiments, the second oligomeric compound is a sense compound. In certain embodiments, the second modified oligonucleotide is a sense oligonucleotide. In certain embodiments, the first modified oligonucleotide is an antisense RNAi oligonucleotide. In certain embodiments, the second oligomeric compound is a sense compound. In certain embodiments, the second modified oligonucleotide is a sense RNAi oligonucleotide. In certain embodiments, the oligomeric duplex comprises one or two unpaired nucleosides at either or both ends, forming one or two overhang ends. In certain embodiments an overhang end is one or two 3'-nucleosides of the antisense oligonucleotide. In certain embodiments the last two 3'-nucleosides of the antisense oligonucleotide are overhang nucleosides not paired with the sense oligonucleotide. In certain embodiments the last one or two 3'-unpaired overhang nucleosides comprise an adenine nucleobase. In certain embodiments the last one or two 3'-unpaired overhang nucleosides comprise a hypoxanthine nucleobase. In certain embodiments the last one or two 3'-unpaired overhang nucleosides comprise a thymine nucleobase.

In certain embodiments, an oligomeric duplex comprises a first oligomeric compound comprising a first modified oligonucleotide consisting of 21 or 23 linked nucleosides and a second oligomeric compound comprising a second modified oligonucleotide consisting of 19 or 21 linked nucleosides, wherein the nucleobase sequences of the first modified oligonucleotide and second modified oligonucleotide consist of any of the following pairs of nucleobase sequences recited in SEQ ID Nos: 939/978, 939/1001, 941/979, 941/1003, 942/980, 942/1004, 943/981, 943/1005, 944/982, 944/1006, 945/983, 945/1007, 946/984, 946/1008, 947/985, 947/1009, 940/977, 940/1002, 967/1011, 968/1012, 974/1013, 975/1014, 971/1015, 972/1016, 1254/1013, 1033/1039, 1034/1040, 1035/1041, 1036/1042, 1037/1043, 1038/1044, 1036/1288, and 1255/1041, 1265/1288, 1265/1042, 1259/1012, 1262/1013, 1268/1015, 1271/1016, 1264/1288, 1264/1042, 1258/1012, 1261/1013, 1267/1015, 1270/1046, 1260/1012, 1263/1013, 1266/1014, 1269/1015, 1272/1016, 1279/1288, 1273/1012, 1276/1013, 1282/1015, 1285/1016, 1280/1288, 1274/1012, 1277/1013, 1283/1015, 1286/1016, 1275/1012, 1278/1013, 1281/1014, 1284/1015, and 1287/1016, wherein the nucleobase sequence of the first modified oligonucleotide comprises the nucleobase sequence of the first SEQ ID NO recited in the pair and the nucleobase sequence of the second modified oligonucleotide comprises the nucleobase sequence of the second SEQ ID NO recited in the pair. In certain embodiments, the first oligomeric compound is an antisense compound. In certain embodiments, the first modified oligonucleotide is an antisense oligonucleotide. In certain embodiments, the second Oligomeric compound is a sense compound. In certain embodiments, the second modified oligonucleotide is a sense oligonucleotide. In certain embodiments, the first modified oligonucleotide is an antisense RNAi oligonucleotide. In certain embodiments, the second oligomeric compound is a sense compound. In certain embodiments, the second modified oligonucleotide is a sense RNAi oligonucleotide. In certain embodiments, the oligomeric duplex comprises one or two unpaired nucleosides at either or both ends, forming one or two overhang ends. In certain embodiments an overhang end is one or two 3'-nucleosides of the antisense oligonucleotide. In certain embodiments the last two 3'-nucleosides of the antisense oligonucleotide are overhang nucleosides not paired with the sense oligonucleotide. In certain embodiments the last one or two 3'-unpaired overhang nucleosides comprise an adenine nucleobase. In certain embodiments the last one or two 3'-unpaired overhang nucleosides comprise a hypoxanthine nucleobase. In certain embodiments the last one or two 3'-unpaired overhang nucleosides comprise a thymine nucleobase. In certain embodiments, the oligomeric duplex comprises one blunt end at cither end, or two blunt ends.

In any of the oligomeric duplexes described herein, at least one nucleoside of the first modified oligonucleotide and/or the second modified oligonucleotide comprises a modified sugar moiety. Examples of suitable modified sugar moieties include, but are not limited to, a bicyclic sugar moiety, e.g., a modified furanosyl sugar moiety containing a 2'-4' bridge selected from —O—CH$_2$—; and —O—CH(CH$_2$)—, and a non-bicyclic sugar moiety, e.g., a 2'-MOE sugar moiety, a 2'-F sugar moiety, a 2'-OMe sugar moiety, or a 2'-NMA sugar moiety. In certain embodiments, at least one nucleoside of the first modified oligonucleotide and/or the second modified oligonucleotide comprises a modified 2'-deoxy sugar moiety. In certain embodiments, at least 80%, at least 90%, or 100% of the nucleosides of the first modified oligonucleotide and/or the second modified oligonucleotide comprises a modified sugar moiety independently selected from 2'-F, 2'-MOE, 2'-OMc, and 2'-deoxy. In certain embodiments, at least 80%, at least 90%, or 100% of the nucleosides of the first modified oligonucleotide and the second modified oligonucleotide comprises a modified sugar moiety independently selected from 2'-F, 2'-MOE, 2'-OMc, and 2'-deoxy.

In certain embodiments, in an oligomeric duplex provided herein, at least one nucleoside of the first modified oligonucleotide and/or the second modified oligonucleotide comprises a sugar surrogate. Examples of suitable sugar surrogates include, but are not limited to, morpholino, hexitol nucleic acid (HNA), fluoro-hexitol nucleic acid (FHNA), the sugar surrogates of glycol nucleic acid (GNA), and unlocked nucleic acid (UNA). In certain embodiments, at least one nucleoside of the first modified oligonucleotide comprises a sugar surrogate, which is FHNA. In certain embodiments, at least 80%, at least 90%, or 100% of the nucleosides of the first modified oligonucleotide and/or the second modified oligonucleotide comprises a modified sugar moiety and/or sugar surrogate independently selected from 2'-F, 2'-MOE, 2'-OMe, 2"-deoxy, and FHNA. In certain embodiments, at least 80%, at least 90%, or 100% of the nucleosides of the first modified oligonucleotide and the second modified oligonucleotide comprises a modified sugar moiety and/or sugar surrogate independently selected from 2'-F, 2'-MOE, 2'-OMc, 2'-deoxy, and FHNA.

In certain embodiments, in an oligomeric duplex provided herein, at least one nucleoside of the first modified oligonucleotide and/or the second modified oligonucleotide comprises a modified sugar moiety and/or sugar surrogate. In certain embodiments, in an oligomeric duplex provided herein, a sugar moiety of the first modified oligonucleotide is modified, wherein the modified sugar moiety and/or sugar surrogate is selected from 2'-F, 2'-MOE, 2'-OMe, 2'-deoxy, and FHNA. In certain embodiments, in an oligomeric duplex provided herein, a sugar motif (from 5' to 3') of the first modified oligonucleotide is selected from yfyyyfyyyyyyyfyfyyyyyyy, efyyyfyyyyyyyfyfyyyyyee, efyyyyyyyyyyyyfyyyyyyyee, efyyydyyyyyyyfyfyyyyyee, efyyydyyyyyyydydyyyyyy, efyyydyyyyyyyfyfyyyyyyy, efyydydyyyyyyfyfyyyyyyy, efyyyfyyyyyyyfyyyyyyyee, efyyyyyyyyyyyyfyfyyyyyee, efyyyfyyyyyyyfyyyyyyyyy, efyyyyyyyyyyyyfyfyyyyyyy, efyyyfyyyyyyyfyfyyyyyey, efyyyfyyyyyyyfydyyyyyee, efyyyfyyyyyyyfydyyyyyyy, efyydydyyyyyyfyfyyyyyee, efyyyfyyyyyyyfyfyyyee, e[FHNA]yydydyyyyfyfyfyyyyyyy, e[FHNA]yyyfyyyyyyyfyfyyyyyyy, e[FHNA]yyyfyyyyyyyfyfyyyyyee, and e[FHNA]yyyyyyyyyyy[FHNA]yyyyyyyee, wherein each 'y' represents a 2'-OMe sugar moiety, each 'f' represents a 2'-F sugar moiety, each [FHNA]' represents a 3"-fluoro-hexitol sugar moiety, each 'd' represents a 2'-deoxy sugar moiety, and each 'c' represents a 2'-MOE sugar moiety. In certain embodiments, in an oligomeric duplex provided herein, a sugar moiety of the second modified oligonucleotide is modified, wherein the modified sugar moiety is selected from 2'-F, 2'-MOE, 2'-OMc, and 2'-deoxy. In certain embodiments, in an oligomeric duplex provided herein, a sugar motif (from 5' to 3') of the second modified oligonucleotide is selected from among: yyyyyyfyfffyyyyyyyyyy, yyyyyyyyyyyyyyyyyyyy, yyyyyyyyyfffyyyyyyyyyy, yyyyyyfyfyfyyyyyyyyyy, yyyyyyyyyydyyyyyyyyyy, eeyyyyfyfffyyyyyyyyee, eeyyyyyyyffyyyyyyyyee, and eeyyyyfyfyfyyyyyyyyee, wherein each 'y' represents a 2'-OMe sugar moiety, each 'f' represents a 2'-F sugar moiety, each 'd' represents a 2'-deoxy sugar moiety, and each 'c' represents a 2'-MOE sugar moiety.

In certain embodiments, in an oligomeric duplex provided herein, at least one internucleoside linkage of the first modified oligonucleotide and/or the second modified oligonucleotide comprises a modified internucleoside linkage. In certain embodiments, the modified internucleoside linkage is a phosphorothioate internucleoside linkage. In certain embodiments, at least one of the first, second, or third internucleoside linkages from the 5' end and/or the 3' end of the first modified oligonucleotide comprises a phosphorothioate linkage. In certain embodiments, at least one of the first, second, or third internucleoside linkages from the 5' end and/or the 3' end of the second modified oligonucleotide comprises a phosphorothioate linkage. In certain embodiments, the modified internucleoside linkage is a mesyl phosphoramidate internucleoside linkage. In certain embodiments, at least one of the internucleoside linkages of the first modified oligonucleotide comprises a mesyl phosphoramidate internucleoside linkage. In certain embodiments, at least one of the internucleoside linkages of the second modified oligonucleotide comprises a mesyl phosphoramidate internucleoside linkage.

In certain embodiments, in an oligomeric duplex provided herein, each internucleoside linkage of the first modified oligonucleotide is independently selected from a phosphodiester, a phosphorothioate, or a mesyl phosphoramidate internucleoside linkage, and each internucleoside linkage of the second modified oligonucleotide is independently selected from a phosphodiester, a phosphorothioate, or a mesyl phosphoramidate internucleoside linkage.

In certain embodiments, in an oligomeric duplex provided herein, each internucleoside linkage of the first modified oligonucleotide is independently selected from a phosphodiester or a phosphorothioate internucleoside linkage and each internucleoside linkage of the second modified oligonucleotide is independently selected from a phosphodiester or a phosphorothioate internucleoside linkage.

In certain embodiments, in an oligomeric duplex provided herein, at least one internucleoside linkage of the first modified oligonucleotide (e.g., antisense oligonucleotide) is a modified internucleoside linkage. In certain embodiments, in an oligomeric duplex provided herein, an internucleoside linkage of the first modified oligonucleotide is modified, wherein the 5'-most internucleoside linkage (i.e., linking the first nucleoside from the 5'-end to the second nucleoside from the 5'-end) is modified. In certain embodiments, in an oligomeric duplex provided herein, the internucleoside linkage motif (from 5' to 3') of the first modified oligonucleotide is selected from 5'-ssooooooooooooooooooss-3',5'-ssooooooooooooooooss-3',5'-ssooosooooooooooooss-3', 5'-ssoosossooooooooooooss-3', wherein each "s" is a phosphorothioate internucleoside linkage and each "o" is a phosphodiester internucleoside linkage. In certain embodiments, in an oligomeric duplex provided herein, an internucleoside linkage of the second modified oligonucleotide is modified, wherein the 5'-most internucleoside linkage (i.e., linking the first nucleoside from the 5'-end to the second nucleoside from the 5'-end) is modified. In certain embodiments, in an oligomeric duplex provided herein, the internucleoside linkage motif (from 5' to 3') of the second modified oligonucleotide is selected from (from 5' to 3') of: ssooooooooooooooooss, ssooooooozozooooooooss, ssooooooosoooooooooss, ssooooooooooooooooss, wherein each 'o' represents a phosphodiester internucleoside linkage and each 's' represents a phosphorothioate internucleoside linkage and each 'z' represents a mesyl phosphoramidate internucleoside linkage. In certain embodiments, the two 5'-most internucleoside linkages of a first modified oligonucleotide and/or second modified oligonucleotide of an oligomeric duplex are modified. In certain embodiments, the first one or 2 internucleoside linkages from the 3'-end of a first modified oligonucleotide and/or second modified oligonucleotide of an oligomeric duplex are modified. In certain embodiments, the two 5'-most internucleoside linkages of a first modified oligonucleotide and/or second modified oligonucleotide of an oligomeric duplex are modified and the first two internucleoside linkages from the 3'-end of the first modified oligonucleotide and/or second modified oligonucleotide are modified. In certain embodiments, the modified internucleoside linkage is a phosphorothioate linkage. In certain embodiments, the modified internucleoside linkage is a mesyl phosphoramidate linkage.

In certain embodiments, in an oligomeric duplex provided herein, at least one nucleobase of the first modified oligonucleotide and/or at least one nucleobase of the second modified oligonucleotide is a modified nucleobase. In certain embodiments, the modified nucleobase is 5-methylcytosine. In certain embodiments, the modified nucleobase is hypoxanthine.

In certain embodiments, in an oligomeric duplex provided herein, the first modified oligonucleotide is attached to a terminal group comprising a stabilized phosphate group attached to the 5' position of the 5'-most nucleoside. In certain embodiments, the stabilized phosphate group comprises a cyclopropyl phosphonate or an (E)-vinyl phosphonate. In certain particular embodiments, the stabilized phosphate group is an (E)-vinyl phosphonate.

In certain embodiments, in an oligomeric duplex provided herein, the first modified oligonucleotide is attached to a conjugate group. In certain embodiments, the conjugate group comprises a conjugate linker and a conjugate moiety. In certain embodiments, the conjugate group is attached to the first modified oligonucleotide at the 5'-end of the first modified oligonucleotide. In certain embodiments, the conjugate group is attached to the first modified oligonucleotide at the 3'-end of the modified oligonucleotide. In certain embodiments, the conjugate group is attached to the first modified oligonucleotide at an internal position. In certain embodiments, the conjugate group is attached to the first modified oligonucleotide through a 2'-modification of a furanosyl sugar moiety. In certain embodiments, the conjugate group is attached to the first modified oligonucleotide through a modified internucleoside linkage. In certain embodiments, the conjugate group comprises N-acetyl galactosamine. In certain embodiments, the conjugate group comprises a cell-targeting moiety having an affinity for transferrin receptor (TfR), TfR1, also known as CD71, TFRC. In certain embodiments, the conjugate group comprises a TfR1 targeting peptide or polypeptide, targeting protein, or targeting low molecular weight molecule. In certain embodiments the conjugate group comprises a TfR1 targeting antibody or fragment thereof. In certain embodiments, the conjugate group comprises a protein or peptide capable of binding TfR1. In certain embodiments, the conjugate group comprises an aptamer capable of binding TfR1. In certain embodiments the conjugate group comprises a bicycle ligand that binds a transferrin receptor. In certain embodiments a conjugate group comprises BCY17901 as further described herein. In certain embodiments, a conjugate group comprises a moiety selected from any of a C22 alkyl, C20 alkyl, C16 alkyl, C10 alkyl, C21 alkyl, C19 alkyl, C18 alkyl, C17 alkyl, C15 alkyl, C14 alkyl, C13 alkyl, C12 alkyl, C11 alkyl, C9 alkyl, C8 alkyl, C7 alkyl, C6 alkyl, C5 alkyl, C22 alkenyl. C20 alkenyl. C16 alkenyl. C10 alkenyl. C21 alkenyl. C19 alkenyl. C18 alkenyl. C17 alkenyl. C15 alkenyl. C14 alkenyl. C13 alkenyl. C12 alkenyl. C11 alkenyl. C9 alkenyl. C8 alkenyl. C7 alkenyl. C6 alkenyl, or C5 alkenyl. In certain embodiments, a conjugate group comprises a moiety selected from any of C22 alkyl, C20 alkyl, C16 alkyl. C10 alkyl, C21 alkyl, C19 alkyl, C18 alkyl, C17 alkyl, C15 alkyl, C14 alkyl, C13 alkyl, C12 alkyl, C11 alkyl.

C9 alkyl, C8 alkyl, C7 alkyl, C6 alkyl, and C5 alkyl, where the alkyl chain optionally has one or more unsaturated bonds.

In any of the oligomeric duplexes described herein, the second modified oligonucleotide optionally is attached to a conjugate group. In certain embodiments, the conjugate group comprises a conjugate linker and a conjugate moiety. In certain embodiments, the conjugate group is attached to the second modified oligonucleotide at the 5'-end of the second modified oligonucleotide. In certain embodiments, the conjugate group is attached to the second modified oligonucleotide at the 3'-end of the modified oligonucleotide. In certain embodiments, the conjugate group is attached to the second modified oligonucleotide at an internal position. In certain embodiments, the conjugate group is attached to the second modified oligonucleotide through a 2-modification of a furanosyl sugar moiety. In certain embodiments, the conjugate group is attached to the second modified oligonucleotide through a modified internucleoside linkage. In certain embodiments, the conjugate group comprises N-acetyl galactosamine. In certain embodiments, the conjugate group comprises a cell-targeting moiety having an affinity for transferrin receptor (TfR). TfR1, also known as CD71. TFRC. In certain embodiments, the conjugate group comprises a TfR1 targeting peptide or polypeptide, targeting protein, or targeting low molecular weight molecule. In certain embodiments the conjugate group comprises an anti-TfR1 targeting antibody or fragment thereof. In certain embodiments, the conjugate group comprises a protein or peptide capable of binding TfR1. In certain embodiments, the conjugate group comprises an aptamer capable of binding TfR1. In certain embodiments the conjugate group comprises a bicycle ligand that binds a transferrin receptor. In certain embodiments the conjugate group comprises BCY17901 as further described herein. In certain embodiments, a conjugate group comprises a moiety selected from any of a C22 alkyl, C20 alkyl, C16 alkyl, C10 alkyl, C21 alkyl, C19 alkyl, C18 alkyl. C17 alkyl, C15 alkyl, C14 alkyl, C13 alkyl, C12 alkyl, C11 alkyl, C9 alkyl, C8 alkyl, C7 alkyl, C6 alkyl, C5 alkyl, C22 alkenyl. C20 alkenyl. C16 alkenyl. C10 alkenyl. C21 alkenyl. C19 alkenyl. C18 alkenyl. C17 alkenyl. C15 alkenyl. C14 alkenyl. C13 alkenyl. C12 alkenyl. C11 alkenyl. C9 alkenyl. C8 alkenyl. C7 alkenyl. C6 alkenyl, or C5 alkenyl. In certain embodiments, a conjugate group comprises a moiety selected from any of C22 alkyl, C20 alkyl, C16 alkyl, C10 alkyl, C21 alkyl, C19 alkyl, C18 alkyl, C17 alkyl, C15 alkyl, C14 alkyl, C13 alkyl, C12 alkyl, C11 alkyl, C9 alkyl, C8 alkyl, C7 alkyl, C6 alkyl, and C5 alkyl, where the alkyl chain optionally has one or more unsaturated bonds.

In certain embodiments, an oligomeric compound comprises an antisense compound, which comprises an oligomeric duplex described herein. In certain embodiments, an antisense compound, which comprises an oligomeric duplex described herein, is an RNAi agent capable of reducing the amount of PLN RNA through the activation of RISC/Ago2.

In certain embodiments, an oligomeric compound comprises at least two oligomeric duplexes linked together. In certain embodiments, an oligomeric compound comprises two oligomeric duplexes wherein at least one oligomeric duplex comprises an oligonucleotide comprising a portion having a nucleobase sequence complementary to a nucleobase sequence in a PLN nucleic acid (i.e., is targeted to PLN RNA) as described herein. In certain embodiments, an oligomeric compound comprises two or more of the same oligomeric duplex, which is any of the oligomeric duplexes described herein. In certain embodiments, the two or more oligomeric duplexes are covalently linked together. In certain embodiments, the second modified oligonucleotides of the two or more oligomeric duplexes are covalently linked together. In certain embodiments, the second modified oligonucleotides of two or more oligomeric duplexes are covalently linked together at their 3' ends. In certain embodiments, the second modified oligonucleotides of two or more oligomeric duplexes are covalently linked together at the 3' end of one to the 5' end of the other. In certain embodiments, the two or more oligomeric duplexes are covalently linked together by a glycol linker, e.g., a tetraethylene glycol linker. A structure of oligomeric duplexes covalently linked by a glycol linker is described in, e.g., Alterman, et al., *Nature Biotech.* 37:844-894.2019. In some embodiments, an oligomeric compound comprises two or more oligomeric duplexes linked, e.g., covalently linked, together in a branched structure, e.g., a di-branched, tri-branched or tetra-branched structure (see, e.g., WO2022/256565). In some such embodiments, the structure contains a linker (e.g., one or more subunits of an ethylene glycol, alkyl, carbohydrate, block copolymer, peptide, ester, amide, carbamate, triazole) and optionally one or more branch point moieties (e.g., phosphoroamidite, tosylated solketal, 1,3-diaminopropanol, pentaerythritol).

In certain embodiments, an oligomeric duplex comprises two or more regions each of which has a nucleobase sequence complementary to the nucleobase sequence of a different target region of the same nucleic acid target (PLN nucleic acid), or one of which has a nucleobase sequence complementary to the nucleobase sequence of a target region of a PLN nucleic acid (e.g., a PLN RNA such as described herein) and the other having a nucleobase sequence complementary to the nucleobase sequence of a target region of a different nucleic acid target (i.e., other than a PLN nucleic acid target). In some embodiments, the nucleobase sequence(s) complementary to a target region of a PLN nucleic acid targets a PLN nucleic acid region as described herein and/or comprises at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases of the nucleobase sequence of any one of SEQ ID NOs: 3-314.627-782.939-976.1033-1038.1254-1255, or 1258-1287. In certain embodiments, such an oligomeric duplex comprises a first modified oligonucleotide comprising (1) a first region having a nucleobase sequence complementary to a first sequence in a PLN target nucleic acid and (2) a second region having a nucleobase sequence complementary to (a) a different (i.e., second) sequence in a PLN target nucleic acid, or (b) a sequence in a target nucleic acid other than a PLN nucleic acid. In some such embodiments, the second modified oligonucleotide of the oligomeric duplex comprises (1) a region having a nucleobase sequence complementary to the first region of the first modified oligonucleotide and (2) a region having a nucleobase sequence complementary to the second region of the first modified oligonucleotide. In certain embodiments, an oligomeric duplex comprises a first modified oligonucleotide comprising a first region having a nucleobase sequence complementary to a first sequence in a PLN target nucleic acid and a second modified oligonucleotide comprising a second region having a nucleobase sequence complementary to: (a) the nucleobase sequence of a different (i.e., second) sequence in a PLN target nucleic acid, or (b) a sequence in a target nucleic acid other than a PLN nucleic acid. In some such embodiments, the first modified oligonucleotide further comprises a region having a nucleobase sequence complementary to the nucleobase sequence of the second region in the second modified oligonucleotide. In some such embodiments, the second modified oligonucleotide further comprises a region having a nucleobase sequence complementary to the nucleobase sequence of the first region in the first modified oligonucleotide (sec, e.g., PCT International Patent Application Publication WO2020/065602).

III. Conjugates

In certain embodiments, provided herein are oligomeric compounds comprising one or more modified oligonucleotide and one or more conjugate groups. In certain embodiments, an oligomeric compound optionally further comprises one or more terminal groups. In certain embodiments, oligomeric compounds comprise an oligonucleotide, a cell-targeting moiety, and a conjugate linker. In certain embodiments, oligomeric compounds comprise an oligonucleotide, a transferrin receptor ligand, and a conjugate linker. In certain embodiments, oligomeric compounds comprise an oligonucleotide, a bicycle ligand, and a conjugate linker. In certain embodiments, oligomeric compounds comprise an oligonucleotide, a peptide or polypeptide, a conjugate linker, and optionally N-terminal or C-terminal modifications to the peptide or polypeptide. In certain embodiments, oligomeric compounds comprise an oligonucleotide, two or more peptides or polypeptides, a branching group, a conjugate linker, and optionally N-terminal or C-terminal modifications to the peptides or polypeptides. In certain embodiments, a conjugate linker connects a peptide or polypeptide and/or a bicycle ligand to an oligonucleotide.

In certain embodiments, the N-terminus of a bicycle ligand is covalently connected to a conjugate linker, and the conjugate linker is covalently connected to the 3' end of an oligonucleotide. In certain embodiments, the C-terminus of a bicycle ligand is covalently connected to a conjugate linker, and the conjugate linker is covalently connected to the 3' end of an oligonucleotide. In certain embodiments, an internal amino acid of a bicycle ligand is covalently connected to a conjugate linker, and the conjugate linker is covalently connected to the 3' end of an oligonucleotide. In certain embodiments, the N-terminus of a bicycle ligand is covalently connected to a conjugate linker, and the conjugate linker is covalently connected to the 5' end of an oligonucleotide. In certain embodiments, the C-terminus of a bicycle ligand is covalently connected to a conjugate linker, and the conjugate linker is covalently connected to the 5' end of an oligonucleotide. In certain embodiments, an internal amino acid of a bicycle ligand is covalently connected to a conjugate linker, and the conjugate linker is covalently connected to the 5' end of an oligonucleotide. In certain embodiments, the N-terminus of a bicycle ligand is covalently connected to a conjugate linker, and the conjugate linker is covalently connected at an internal position of an oligonucleotide. In certain embodiments, the C-terminus of a bicycle ligand is covalently connected to a conjugate linker, and the conjugate linker is covalently connected at an internal position of an oligonucleotide. In certain embodiments, an internal amino acid of a bicycle ligand is covalently connected to a conjugate linker, and the conjugate linker is covalently connected at an internal position of an oligonucleotide. In certain embodiments, an internal position of an oligonucleotide is a 2'-position of a modified sugar moiety of a nucleoside within the internal region of an oligonucleotide that is not the 5' terminal nucleoside or the 3' terminal nucleoside. In certain embodiments, an internal position of an oligonucleotide is a modified internucleoside linkage of the oligonucleotide.

A. Conjugate Groups

In certain embodiments, a conjugate moiety modifies one or more properties of an attached oligonucleotide, including but not limited to pharmacodynamics, pharmacokinetics, stability, binding, absorption, tissue distribution, cellular distribution, cellular uptake, charge and clearance. In certain embodiments, a conjugate moiety imparts a new property on the attached oligonucleotide.

In certain embodiments, a conjugate group comprises a conjugate moiety and a conjugate linker. In certain embodiments, a conjugate moiety comprises or consists of a cell-targeting moiety. In certain embodiments, a cell-targeting moiety is capable of binding the cell-surface receptor or the cell-surface moiety. In certain embodiments, a compound comprising a cell-targeting moiety is capable of being internalized when it interacts with or binds the cell-surface receptor or the cell-surface moiety. In certain embodiments, a cell-targeting moiety comprises a bicyclic peptide or polypeptide or a bicycle ligand. In certain embodiments, a cell-targeting moiety consists of a bicyclic peptide or polypeptide or a bicycle ligand.

In certain embodiments, a bicycle ligand comprises a bicyclic peptide ligand including those previously described in International Patent Application Publication No. WO2022/101633, which is incorporated herein by reference, and those previously described in International Patent Application Publication No. WO2023/056388, which is hereby incorporated by reference.

In certain embodiments, a bicycle ligand comprises a peptide or polypeptide or peptidomimetic comprising at least three reactive groups, separated by at least two loop sequences, and a molecular scaffold. A molecular scaffold is a chemical group which forms covalent bonds with reactive groups of a peptide. Through such bonding, at least two peptide loops are formed on the molecular scaffold. In certain embodiments, the molecular scaffold is 1,1',1"-(1,3, 5-triazinane-1,3,5-triyl)triprop-2-en-1-one (TATA). In certain embodiments, the molecular scaffold is 1,1',1"-(1,3,5-triazinane-1,3,5-triyl)tris(2-bromoethanone) (TATB).

TATA

-continued

TATB

In certain embodiments, a bicycle ligand peptide or peptidomimetic comprises natural amino acids, non-natural amino acids and/or amino acid mimetics. In certain embodiments, reactive groups of a bicycle ligand peptide are cysteines. In certain embodiments, loop sequences comprise 2, 3, 4, 5, 6, 7, 8, or 9 amino acids. In certain embodiments, a bicycle ligand peptide comprises three cysteine residues separated by two loop sequences, the first of which consists of 2 amino acids and the second of which consists of 9 amino acids. In certain embodiments, a bicycle ligand peptide comprises three cysteine residues separated by two loop sequences both of which consist of 6 amino acids. In certain embodiments, a bicycle ligand peptide comprises three cysteine residues separated by two loop sequences the first of which consists of 3 amino acids and the second of which consists of 8 amino acids. In certain embodiments, a bicycle ligand peptide comprises three cysteine residues separated by two loop sequences the first of which consists of 7 amino acids and the second of which consists of 3 amino acids.

In certain embodiments, a bicycle ligand comprises an amino acid sequence selected from:

$$C_iXXC_{ii}XXXXXXXXXXC_{iii},$$

$$C_iXXXXXXC_{ii}XXXXXXC_{iii},$$

$$C_iXXXC_{ii}XXXXXXXXXC_{iii},$$
or $$C_iXXXXXXXC_{ii}XXXC_{iii};$$

wherein $C_i$, $C_{ii}$ and $C_{iii}$ represent first, second and third cysteine residues, respectively, and each "X" represents an independently selected natural or non-natural amino acid, or a pharmaceutically acceptable salt thereof. In certain embodiments, a bicycle ligand further comprises an N-terminal extension and/or a C-terminal extension.

In certain embodiments, a bicycle ligand comprises an amino acid sequence at least 80%, 85%, 90%, 95%, or 100% identical to any of the following sequences:

(SEQ ID NO: 1062)
$$C_iSPDAHLGC_{ii}ISYC_{iii};$$

(SEQ ID NO: 1063)
$$C_iSPDAYLGC_{ii}ISYC_{iii};$$

(SEQ ID NO: 1064)
$$C_iP[HyP]DAYLGC_{ii}ISYC_{iii};$$

(SEQ ID NO: 1065)
$$C_iS[HyP]DAHLGC_{ii}ISYC_{iii};$$

-continued (SEQ ID NO: 1066)
$C_iS[Aze]DAHLGC_{ii}ISYC_{iii}$;

(SEQ ID NO: 1067)
$C_iP[HyP]DAYLGC_{ii}[tBuGly]SYC_{iii}$;

(SEQ ID NO: 1068)
$C_i[K(N_3)]PDAHLGC_{ii}ISYC_{iii}$;

(SEQ ID NO: 1069)
$C_iS[K(N_3)]DAHLGC_{ii}ISYC_{iii}$;
or (SEQ ID NO: 1070)
$C_iSPD[K(N_3)]HLGC_{ii}ISYC_{iii}$;

$C_i$, $C_{ii}$ and $C_{iii}$ represent first, second and third cysteines, respectively: [HyP] represents 4-trans-hydroxy-L-proline: [Aze] represents azetidine: [tBuGly] represents t-butyl glycine; and [$K(N_3)$] represents 6-azido lysine. In certain embodiments, a bicycle ligand further comprises an N-terminal extension and/or a C-terminal extension.

In certain embodiments, a bicycle ligand comprises an amino acid sequence of: $C_iXXDXXXGC_{ii}ISYC_{iii}$ (SEQ ID NO: 1026); wherein each X is independently selected from natural or non-natural amino acid, or a pharmaceutically acceptable salt thereof. In certain embodiments, a bicycle ligand further comprises an N-terminal extension and/or a C-terminal extension.

In certain embodiments, an oligomeric compound comprises two or more bicyclic ligands attached through a conjugate linker including a bivalent linker including a branching group. In certain embodiments, a bivalent linker comprises one or more PEG repeats. In certain embodiments, the bivalent linker is shown in the structure below:

bladder, pancreas, pituitary, prostate, skin, adrenal gland, and thyroid. By way of non-limiting example, the cell of interest may be any one or more of a myocyte, adipocyte, hepatocyte, cardiomyocyte, vascular smooth muscle cell, endothelial cell, neuron, blood cell, macrophage, lymphocyte, cancer cell, and immune cell.

In certain embodiments, a bicycle ligand is capable of interacting with or binding a cell surface receptor. In certain embodiments, the cell surface receptor is capable of internalizing the bicycle ligand. In certain embodiments, the cell surface receptor is capable of internalizing an oligonucleotide, oligomeric compound or oligomeric duplex connected to the bicycle ligand via a conjugate linker. In certain embodiments, the cell surface receptor is a human transferrin receptor.

In certain embodiments, a bicycle ligand is represented by the formula $[B]_n-[Z_i]-[J]_m-[Z_{ii}]-[O]_o-[Z_{iii}]-[U]_p$, wherein:

$Z_i$, $Z_{ii}$, and $Z_{iii}$ are the first, second, and third amino acids comprising a reactive group;

each B, J, O, and U is independently selected amino acids or amino acid mimetics;

n is from 0 to 5;

m is from 3 to 7;

is from 3 to 7;

p is from 0 to 5;

wherein the sum of m+o is less than 12.

In particular embodiments, m is 7 and o is 3.

In certain embodiments, a bicycle ligand comprises the following structure,

In certain embodiments, a bicycle ligand is capable of interacting with a cell surface receptor on a cell. In certain embodiments, a bicycle ligand is capable of interacting with a cell surface moiety on a cell. In certain embodiments, a bicycle ligand is capable of binding a cell surface receptor on a cell. In certain embodiments, a bicycle ligand is capable of binding a cell surface moiety on a cell. In certain embodiments, a bicycle ligand is capable of being internalized by the cell when it interacts with and/or binds a cell surface receptor and/or cell surface moiety. In certain embodiments, a cell surface receptor is not expressed ubiquitously (e.g., the cell surface receptor is undetectable in at least one tissue of a human subject), and a bicycle ligand selectively delivers an oligonucleotide, oligomeric compound or oligomeric duplex to a tissue of interest or a cell of interest. By way of non-limiting example, tissue of interest may be any one or more of brain, spinal cord, retina, heart, kidney, liver, lung, skeletal muscle, cardiac muscle, smooth muscle, adipose, white adipose, brown adipose, spleen, bone, intestine, colon, testes, breast, ovary, placenta, uterus, N-terminal C-terminal Bicycle ligand wherein each Xaa is an independently selected amino acid side chain;

each Baa is an independently selected amino acid or amino acid mimetic;

n is from 0 to 5;

m is from 3 to 7;

is from 3 to 7;

p is from 0 to 5;

wherein the sum of m+o is less than 12.

In particular embodiments, m is 7 and o is 3.

In certain embodiments, the conjugate linker is attached through the N-terminus, the C-terminus, or through one of the loop amino acids.

In certain embodiments, a bicycle ligand comprises the formula $[Z_i]-[J]_m-[Z_{ii}]-[O]_o-[Z_{iii}]$. In certain embodiments, a bicycle ligand comprises the following structure:

Loop polypeptide wherein each Xaa is an independently selected amino acid side chain, each Baa is an independently selected amino acid or amino acid mimetic;

m is from 3 to 7 and;

is from 3 to 7.

In certain embodiments, a bicycle ligand further comprises an N-terminal extension and/or a C-terminal extension.

In certain embodiments, a conjugate linker is attached through the N-terminus, the C-terminus, or through one of the loop amino acids.

In certain embodiments, a bicycle ligand comprises or consists of a sequence selected from Table D:

TABLE D

| Bicycle ligands | | | |
|---|---|---|---|
| Bicycle Number | N-terminal Mod. | Sequence | SEQ ID NO: |
| BCY13983 | none | ACSADDWLGCISWCA | 1071 |
| BCY14474 | none | ACSADDWLGCISWCA[Sar]$_6$[K-F1] | 1072 |
| BCY13986 | none | ACSSDAYLGCISWCA | 1073 |
| BCY14475 | none | ACSSDAYLGCISWCA[Sar]$_6$[K-F1] | 1074 |
| BCY15466 | none | ACPPDAHLGCISWCA | 1075 |
| BCY15889 | Ac | CPPDAHLGCISWC | 1076 |
| BCY15467 | none | ACPQDAYLGCISWCA | 1077 |
| BCY15890 | Ac | CPQDAYLGCISWC | 1078 |
| BCY13989 | none | ACPPDSWQGCISYCA | 1079 |
| BCY14476 | none | ACPPDSWQGCISYCA[Sar]$_6$[K-F1] | 1080 |
| BCY15468 | none | ACSPDAHLGCISYCA | 1081 |
| BCY15768 | none | ACSPDAHLGCISYCA[Sar]$_6$[K-F1] | 1082 |
| BCY15934 | none | CSPDAHLGCISYC[Sar]$_6$[K-F1] | 1083 |

TABLE D-continued

Bicycle ligands

| Bicycle Number | N-terminal Mod. | Sequence | SEQ ID NO: |
|---|---|---|---|
| BCY15937 | Ac | CSPDAHLGCISYCA[Sar]$_6$[K-F1] | 1084 |
| BCY15938 | Ac | CSPDAHLGCISYC[Sar]$_6$[K-F1] | 1085 |
| BCY15940 | none | [Fl-G][Sar]$_5$ACSPDAHLGCISYCA | 1086 |
| BCY18030 | none | N[1Nal]NCSPDAHLGCISYC | 1087 |
| BCY18039 | Ac | CSPDAHLGCISYCE[Pip]W | 1088 |
| BCY17994 | Ac | CSPDAHLGCISYCEPW | 1089 |
| BCY18029 | none | NWNCSPDAHLGCISYC | 1090 |
| BCY17109 | none | NWNCSPDAHLGCISYCA | 1091 |
| BCY18037 | Ac | CSPDAHLGCISYCE[Aze]W | 1092 |
| BCY17992 | Ac | NWNCSPDAHLGCISYC | 1093 |
| BCY18038 | Ac | CSPDAHLGCISYCE[dP]W | 1094 |
| BCY18034 | Ac | N[1Nal]NCSPDAHLGCISYC | 1095 |
| BCY18031 | none | N[dW]NCSPDAHLGCISYC | 1096 |
| BCY18035 | Ac | N[dW]NCSPDAHLGCISYC | 1097 |
| BCY17110 | none | HWMCSPDAHLGCISYCA | 1098 |
| BCY17115 | none | ACSPDAHLGCISYCPHP | 1099 |
| BCY17114 | none | ACSPDAHLGCISYCEPW | 1100 |
| BCY17112 | none | NEVCSPDAHLGCISYCA | 1101 |
| BCY17120 | none | ACSPDAHLGCISYCPIVH | 1102 |
| BCY15891 | Ac | CSPDAHLGCISYC | 1103 |
| BCY17111 | none | HTSCSPDAHLGCISYCA | 1104 |
| BCY18036 | Ac | N[NMeTrp]NCSPDAHLGCISYC | 1105 |
| BCY18032 | none | N[NMeTrp]NCSPDAHLGCISYC | 1106 |
| BCY15939 | Ac | ACSPDAHLGCISYCA | 1107 |
| BCY17119 | none | ACSPDAHLGCISYCEHQE | 1108 |
| BCY17113 | none | ESFCSPDAHLGCISYCA | 1109 |
| BCY17870 | none | NWNCSPDAHLGCISYC[K(N$_3$)] | 1110 |
| BCY17871 | Ac | NWNCSPDAHLGCISYC[K(N$_3$)] | 1111 |
| BCY17872 | AzPro | NWNCSPDAHLGCISYC | 1112 |
| BCY17873 | Ac | CSPDAHLGCISYCEPW[K(N$_3$)] | 1113 |
| BCY17874 | AzPro | CSPDAHLGCISYCEPW | 1114 |
| BCY17868 | Ac | CSPDAHLGCISYC[K(N$_3$)] | 1115 |
| BCY17869 | AzPro | CSPDAHLGCISYC | 1116 |
| BCY17882 | Ac | N[dY]NCSPDAHLGCISYC[K(N$_3$)] | 1117 |
| BCY17890 | Ac | CSPDAHLGCISYCE-[dP]W[K(N$_3$)] | 1118 |
| BCY17892 | Ac | CSPDAHLGCISYCE-[Aze]W[K(N$_3$)] | 1119 |
| BCY17894 | Ac | CSPDAHLGCISYCE-[Pip]W[K(N$_3$)] | 1120 |

TABLE D-continued

Bicycle ligands

| Bicycle Number | N-terminal Mod. | Sequence | SEQ ID NO: |
|---|---|---|---|
| BCY17906 | Ac | CSPDAHLGCISYC[K(N$_3$)(PYA-maleimide)] | 1121 |
| BCY19405 | Ac | CSPDAHLGCISYCEPW[PEG10][K(N$_3$)] | 1122 |
| BCY19406 | Ac | CSPDAHLGCISYCEPW[PEG24][K(N$_3$)] | 1123 |
| BCY19407 | Ac | CSPDAHLGCISYCEPWGGSGGS[K(N$_3$)] | 1124 |
| BCY15469 | none | ACPGDAHLGCISYCA | 1125 |
| BCY15892 | Ac | CPGDAHLGCISYC | 1126 |
| BCY15470 | none | ACPPDSHLGCISYCA | 1127 |
| BCY15893 | Ac | CPPDSHLGCISYC | 1128 |
| BCY15471 | none | ACSADDWLGCISYCA | 1129 |
| BCY15894 | Ac | CSADDWLGCISYC | 1130 |
| BCY17991 | Ac | CP[HyP]DAYLGC[tBuGly]SYC | 1131 |
| BCY17995 | Ac | CP[HyP]DAYLGC[tBuGly]SYCEPW | 1132 |
| BCY17993 | Ac | NWNCP[HyP]DAYLGC[tBuGly]SYC | 1133 |
| BCY16754 | none | ACP[HyP]DAYLGC[tBuGly]SYCA | 1134 |
| BCY18033 | none | NWNCP[HyP]DAYLGC[tBuGly]SYC | 1135 |
| BCY17896 | Ac | CP[HyP]DAYLGC[tBuGly]SYC[K(N$_3$)] | 1136 |
| BCY17899 | Ac | NWNCP[HyP]DAYLGC[tBuGly]SYC[K(N$_3$)] | 1137 |
| BCY17901 | Ac | CP[HyP]DAYLGC[tBuGly]SYCEPW[K(N$_3$)] | 1253 |
| BCY17990 | Ac | CP[HyP]DAYLGCISYC | 1138 |
| BCY17875 | Ac | CP[HyP]DAYLGCISYC[K(N$_3$)] | 1139 |
| BCY17876 | AzPro | CP[HyP]DAYLGCISYC | 1140 |
| BCY17989 | Ac | CS[HyP]DAHLGCISYC | 1141 |
| BCY16047 | none | ACS[HyP]DAHLGCISYCA | 1142 |
| BCY17877 | Ac | CS[HyP]DAHLGCISYC[K(N$_3$)] | 1143 |
| BCY17878 | AzPro | CS[HyP]DAHLGCISYC | 1144 |
| BCY16962 | none | ACP[Aib]DAHLGC[tBuGly]SYCA | 1145 |
| BCY17117 | none | TYMNCPPDAHLGCISYCA | 1146 |
| BCY16048 | none | ACPPDAHLGCISYCA | 1147 |
| BCY16963 | none | ACP[Aib]DAYLGC[tBuGly]SYCA | 1148 |
| BCY17987 | Ac | CSADAHLGCISYC | 1149 |
| BCY16753 | none | ACS[Aib]DAHLGC[tBuGly]SYCA | 1150 |
| BCY16046 | none | ACSPDAHLGC[EPA]SYCA | 1151 |
| BCY16964 | none | ACPPDAYLGC[tBuGly]SYCA | 1152 |
| BCY16965 | none | ACS[Aib]DAYLGC[tBuGly]SYCA | 1153 |
| BCY17986 | Ac | CAPDAHLGCISYC | 1154 |
| BCY16550 | none | ACP[Aib]DAHLGCISYCA | 1155 |
| BCY16966 | none | ACSPDAYLGC[tBuGly]SYCA | 1156 |
| BCY16051 | none | ACSPDAHLGC[tBuGly]SYCA | 1157 |

TABLE D-continued

Bicycle ligands

| Bicycle Number | N-terminal Mod. | Sequence | SEQ ID NO: |
|---|---|---|---|
| BCY17118 | none | IDSNCPNDAHLGCISYCA | 1158 |
| BCY17116 | none | WGKSCPIDAHLGCISYCA | 1159 |
| BCY16053 | none | ACSPDAYLGCISYCA | 1160 |
| BCY16557 | none | ACPPDAYLGCISYCA | 1161 |
| BCY16035 | none | ACS[Aib]DAHLGCISYCA | 1162 |
| BCY16043 | none | ACSPDAHLGC[Chg]SYCA | 1163 |
| BCY15769 | none | ACAPDAHLGCISYCA[Sar]$_6$[K-F1] | 1164 |
| BCY15648 | none | ACYLPDW[tBuAla]CGDEYCA | 1165 |
| BCY16031 | none | ACSPDAHLGCIS[2Nal]CA | 1166 |
| BCY16079 | none | ACSPDAHLGCIS[$_3$tBuTyr]CA | 1167 |
| BCY16036 | none | ACSPD[Aib]HLGCISYCA | 1168 |
| BCY16029 | none | ACSPDAHLGCIS[1Nal]CA | 1169 |
| BCY16089 | none | ACSPDAH[tBuAla]GCISYCA | 1170 |
| BCY16088 | none | ACSPDAH[Cba]GCISYCA | 1171 |
| BCY16052 | none | ACSPDAHLGCISWCA | 1172 |
| BCY16033 | none | ACSPD[Abu]HLGCISYCA | 1173 |
| BCY16039 | none | ACS[Aze]DAHLGCISYCA | 1174 |
| BCY17988 | Ac | CS[Aze]DAHLGCISYC | 1175 |
| BCY17879 | Ac | CS[Aze]DAHLGCISYC[K(N$_3$)] | 1176 |
| BCY17880 | AzPro | CS[Aze]DAHLGCISYC | 1177 |
| BCY16038 | none | ACSPDDHLGCISYCA | 1178 |
| BCY16050 | none | ACSPDSHLGCISYCA | 1179 |
| BCY16034 | none | ACSPDAH[Abu]GCISYCA | 1180 |
| BCY16032 | none | ACSPDAHLGCIS[4Pal]CA | 1181 |
| BCY16049 | none | ACP[dA]DAHLGCISYCA | 1182 |
| BCY16558 | none | ACSPDAYLGC[tBuAla]SYCA | 1183 |
| BCY16041 | none | ACSPDAHLGC[C5g]SYCA | 1184 |
| BCY16042 | none | ACSPDAHLGC[Cbg]SYCA | 1185 |
| BCY16045 | none | ACSPDAHL[dA]CISYCA | 1186 |
| BCY16037 | none | ACSPDAH[Aib]GCISYCA | 1187 |
| BCY16044 | none | ACSPDAHLGC[Cpg]SYCA | 1188 |
| BCY16040 | none | ACSPDAHLGC[B-Melle]SYCA | 1189 |
| BCY15771 | none | ACSADAHLGCISYCA[Sar]$_6$[K-F1] | 1190 |
| BCY15772 | none | ACSPAAHLGCISYCA[Sar]$_6$[K-F1] | 1191 |
| BCY15773 | none | ACSPDAALGCISYCA[Sar]$_6$[K-F1] | 1192 |
| BCY15774 | none | ACSPDAHAGCISYCA[Sar]$_6$[K-F1] | 1193 |
| BCY15775 | none | ACSPDAHLACISYCA[Sar]$_6$[K-F1] | 1194 |

TABLE D-continued

Bicycle ligands

| Bicycle Number | N-terminal Mod. | Sequence | SEQ ID NO: |
|---|---|---|---|
| BCY15776 | none | ACSPDAHLGCASYCA[Sar]$_6$[K-F1] | 1195 |
| BCY15777 | none | ACSPDAHLGCIAYCA[Sar]$_6$[K-F1] | 1196 |
| BCY15770 | none | ACSPDAHLGCISACA[Sar]$_6$[K-F1] | 1197 |
| BCY17903 | Ac | C[K(N$_3$)]PDAHLGCISYC | 1198 |
| BCY17904 | Ac | CS[K(N$_3$)]DAHLGCISYC | 1199 |
| BCY17905 | Ac | CSPD[K(N$_3$)]HLGCISYC | 1200 |
| BCY23180 | none | C[HyP][HyP]DAYLGC[tBuGly]SYCEPW | 1201 |
| BCY21757 | Ac | CP[HyP]DAYLGC[tBuGly]SYCEPWK | 1202 |
| BCY21758 | Ac | CP[HyP]DAYLGC[tBuGly]SYCEPWC | 1203 |
| BCY23181 | none | C[Oxa][HyP]DAYLGC[tBuGly]SYCEPW | 1204 |
| BCY23182 | none | C[Cis-HyP][HyP]DAYLGC[tBuGly]SYCEPW | 1205 |
| BCY23183 | none | CP[Oxa]DAYLGC[tBuGly]SYCEPW | 1206 |
| BCY23184 | none | CP[Cis-HyP]DAYLGC[tBuGly]SYCEPW | 1207 |
| BCY23185 | none | CP[HyP]DA[DOPA]LGC[tBuGly]SYCEPW | 1208 |
| BCY23186 | none | CP[HyP]DA[pCaPhe]LGC[tBuGly]SYCEPW | 1209 |
| BCY23187 | none | CP[HyP]DA[pCoPhe]LGC[tBuGly]SYCEPW | 1210 |
| BCY23188 | none | CP[HyP]DA[hTyr]LGC[tBuGly]SYCEPW | 1211 |
| BCY23189 | none | CP[HyP]DAYL[dS]C[tBuGly]SYCEPW | 1212 |
| BCY23190 | none | CP[HyP]DAYL[dT]C[tBuGly]SYCEPW | 1213 |
| BCY23191 | none | CP[HyP]DAYL[dD]C[tBuGly]SYCEPW | 1214 |
| BCY23192 | none | CP[HyP]DAYL[dE]C[tBuGly]SYCEPW | 1215 |
| BCY23193 | none | CP[HyP]DAYL[dN]C[tBuGly]SYCEPW | 1216 |
| BCY23194 | none | CP[HyP]DAYL[dQ]C[tBuGly]SYCEPW | 1217 |
| BCY23195 | none | CP[HyP]DAYL[dY]C[tBuGly]SYCEPW | 1218 |
| BCY23196 | none | CP[HyP]DAYLSC[tBuGly]SYCEPW | 1219 |
| BCY23197 | none | CP[HyP]DAYLDC[tBuGly]SYCEPW | 1220 |
| BCY23198 | none | CP[HyP]DAYLYC[tBuGly]SYCEPW | 1221 |
| BCY23199 | none | CP[HyP]DAYLNC[tBuGly]SYCEPW | 1222 |
| BCY23200 | none | CP[HyP]DAYLGC[tBuGly]S[DOPA]CEPW | 1223 |
| BCY23201 | none | CP[HyP]DAYLGC[tBuGly]S[pCaPhe]CEPW | 1224 |
| BCY23202 | none | CP[HyP]DAYLGC[tBuGly]S[pCoPhe]CEPW | 1225 |
| BCY23203 | none | CP[HyP]DAYLGC[tBuGly]S[hTyr]CEPW | 1226 |
| BCY23204 | none | CP[HyP]DAYLGC[tBuGly]SYCE[HyP]W | 1227 |
| BCY23205 | none | CP[HyP]DAYLGC[tBuGly]SYCE[Oxa]W | 1228 |
| BCY23206 | none | CP[HyP]DAYLGC[tBuGly]SYCE[Cis-HyP]W | 1229 |

TABLE D-continued

Bicycle ligands

| Bicycle Number | N-terminal Mod. | Sequence | SEQ ID NO: |
|---|---|---|---|
| BCY23207 | none | CP[HyP]DAYLGC[tBuGly]SYCEPY | 1230 |
| BCY23208 | none | CP[HyP]DAYLGC[tBuGly]SYCEP[DOPA] | 1231 |
| BCY23209 | none | CP[HyP]DAYLGC[tBuGly]SYCEP[pCaPhe] | 1232 |
| BCY23210 | none | CP[HyP]DAYLGC[tBuGly]SYCEP[pCoPhe] | 1233 |
| BCY23211 | none | CP[HyP]DAYLGC[tBuGly]SYCEP[hTyr] | 1234 |
| BCY23216 | none | CP[HyP]EAYLGC[tBuGly]SYCEPW | 1235 |
| BCY23217 | none | CP[HyP][Gla]AYLGC[tBuGly]SYCEPW | 1236 |
| BCY23218 | none | CP[HyP]DAYSGC[tBuGly]SYCEPW | 1237 |
| BCY23219 | none | CP[HyP]DAYTGC[tBuGly]SYCEPW | 1238 |
| BCY23220 | none | CP[HyP]DAYDGC[tBuGly]SYCEPW | 1239 |
| BCY23221 | none | CP[HyP]DAYEGC[tBuGly]SYCEPW | 1240 |
| BCY23222 | none | CP[HyP]DAYNGC[tBuGly]SYCEPW | 1241 |
| BCY23223 | none | CP[HyP]DAYQGC[tBuGly]SYCEPW | 1242 |
| BCY23224 | none | CP[HyP]DAYLGC[tBuGly][HSer]YCEPW | 1243 |
| BCY23225 | none | CP[HyP]DAYLGC[tBuGly]TYCEPW | 1244 |
| BCY23226 | none | CP[HyP]DAYLGC[tBuGly]DYCEPW | 1245 |
| BCY23227 | none | CP[HyP]DAYLGC[tBuGly]EYCEPW | 1246 |
| BCY23228 | none | CP[HyP]DAYLGC[tBuGly]NYCEPW | 1247 |
| BCY23229 | none | CP[HyP]DAYLGC[tBuGly]QYCEPW | 1248 |
| BCY23230 | none | CP[HyP]DAYLGC[tBuGly]SYCDPW | 1249 |
| BCY23231 | none | CP[HyP]DAYLGC[tBuGly]SYC[Gla]PW | 1250 |
| BCY23514 | none | CP[HyP]DAYLGCYSYCEPW | 1251 |
| BCY23515 | none | CP[HyP]DAYLGC[3HyV]SYCEPW | 1252 | wherein Ac represents acetyl, AzPro represents azidopropyl, Abu represents aminobutyric acid, Aib represents aminoisobutyric acid, Aze represents azetidine, B-MeIle represents beta-methyl isoleucine, C5g represents cyclopentyl glycine, Cba represents β-cyclobutylalanine, Cbg represents cyclobutyl glycine, Chg represents cyclohexyl glycine, Cpg represents cyclopropyl glycine, EPA represents 2-amino-3-ethyl-pentanoic acid, HyP represents trans-4-hydroxy-L-proline, K(N$_3$) represents 6-azido lysine, 1Nal represents 1-naphthylalanine, 2Nal represents 2-naphthylalanine, 4Pal represents 4-pyridylalanine, Pip represents pipecolic acid; tBuAla represents t-butyl-alanine, tBuGly represents t-butyl-glycine, 3tBuTyr represents 3-t-Butyl-Tyrosine, Sar represents sarcosine, K—Fl represents fluorescein attached at the 6-position of a lysine, Fl-G represents fluorescein attached at the N-terminus of a glycine, NMeTrp represents N-methyl tryptophan, dP represents D-proline, dA represents $_D$-alanine, dW represents $_D$-tryptophan, dS represents $_D$-serine, dT represents D-threonine, dD represents $_D$-aspartic acid, dE represents $_D$-glutamic acid, dN represents $_D$-asparagine, dQ represents $_D$-glutamine, dY represents $_D$-tyrosine, Cis-HyP represents cis-L-4-hydroxyproline, DOPA represents 3,4-dihydroxy-phenylalanine, Gla represents L-γ-carboxyglutamic acid, HSer represents homoserine, hTyr represents homo-tyrosine, 3HyV represents 3-hydroxy-L-valine, Oxa represents oxazolidine-4-carboxylic acid, pCaPhe represents L-4-carbamoylphenylalanine, pCoPhe represents 4-carboxy-L-phenylalanine, and [K(N$_3$)(PYA-Maleimide)] represents a modified lysine having the following structure:

In certain embodiments, a bicycle ligand, or a conjugate group comprising a bicycle ligand, has the structure:

or a salt thereof, wherein Q is $N_3$ (BCY17901, SEQ ID NO: 1045), $NH_2$ (BCY21757, SEQ ID NO: 1202), SH (BCY21758, SEQ ID NO: 1203), a conjugate linker, or a conjugate linker covalently connected to an oligonucleotide.

In certain embodiments, a bicycle ligand comprises an amino acid sequence which is selected from CP[HyP]DAY-LGC[tBuGly]SYCEPWK (SEQ ID NO: 1202, herein referred to as BCY21757) and CP[HyP]DAYLGC[tBuGly] SYCEPWC (SEQ ID NO: 1203, herein referred to as BCY21758), wherein HyP represents trans-4-hydroxy-L-proline and tBuGly represents t-butyl-glycine. In certain embodiments, the bicycle ligand comprises an N-terminal acetyl group and a C-terminal $CONH_2$ group. In certain embodiments, the first, second, and third cysteine residues within the bicycle ligand are covalently bonded to a molecular scaffold such that two peptide loops are formed on the molecular scaffold. In certain embodiments, the molecular scaffold is 1,1',1"-(1,3,5-triazinane-1,3,5-triyl)triprop-2-en-1-one (TATA). In certain embodiments, the molecular scaffold is 1,1',1"-(1,3,5-triazinane-1,3,5-triyl)tris(2-bromoethanone) (TATB).

Transferrin Receptor

In certain embodiments, a bicycle ligand is capable of interacting with the type 1 transferrin receptor (e.g., a human type 1 transferrin receptor). In certain embodiments, a bicycle ligand is capable of binding the type 1 transferrin receptor. In certain embodiments, a bicycle ligand is capable of binding the type 1 transferrin receptor while not interfering with the binding of the natural ligand transferrin. In certain embodiments, a bicycle ligand inhibits the binding of the natural ligand transferrin.

Alternative Transferrin Receptor Ligands

Alternative cell-targeting moieties that have affinity for transferrin receptor (TfR1), including antibodies and antibody fragments, proteins, peptides, and aptamers, have been described. Such moietics may replace a bicycle ligand conjugate moiety described herein for targeting an oligomeric compound to cardiac cells (e.g., cardiac muscle cells)/tissue/heart. Thus, in certain embodiments, a conjugate group comprises a cell-targeting moiety that binds transferrin receptor (TfR). In certain embodiments, a conjugate group described herein comprises an anti-TfR1 antibody or fragment thereof. In certain embodiments, the conjugate group comprises a protein or peptide capable of binding TfR1. In certain embodiments, the conjugate group comprises an aptamer capable of binding TfR1. In certain embodiments, the anti-TfR1 antibody or fragment thereof is any known in the art including but not limited to those described in WO1991/004753: WO2013/103800: WO2014/144060: WO2016/081643: WO2016/179257: WO2016/207240: WO2017/221883: WO2018/129384: WO2018/124121: WO2019/151539; WO2020/132584: WO2020/028864; U.S. Pat. Nos. 7,208,174; 9,034,329; 10,550,188; and 11,512,136. In certain embodiments, a fragment of an anti-TfR1 antibody is F(ab')2. Fab. Fab'. Fv, scFv. VHH, or VNAR. In certain embodiments, an antibody binds to TfR1 through an engineered Fc domain rather than through the antigen-binding portion, as described in, e.g., US 2020/0223935. In certain embodiments, the conjugate group comprises a protein or peptide capable of binding TfR1. In certain embodiments, the protein or peptide capable of binding TfR1 is any known in the art including but not limited to those described in WO2019/140050: WO2020/037150: WO2020/124032: WO 2022/026555; and U.S. Pat. No. 10,138,483. In certain embodiments, the peptide is a cyclic peptide, as described in WO 2021/167107. In certain embodiments, the conjugate group comprises an aptamer capable of binding TfR1. In certain embodiments, the aptamer capable of binding TfR1 is any known in the art including but not limited to those described in WO2013/163303: WO2019/033051; and WO2020/245198. In certain embodiments, the conjugate group comprises a peptide, including but not limited to a cyclic peptide, capable of binding TfR1. In certain embodiments, the peptide capable of binding TfR1 is any known in the art including but not limited to those described in EP4108676: WO2023/027125; and WO2023/022234.

Conjugate Linkers

In certain embodiments, oligomeric compounds comprise an oligonucleotide and a conjugate group, wherein the conjugate group comprises or consists of a conjugate moiety and a conjugate linker. In certain embodiments, the conjugate linker links the conjugate moiety to the oligonucleotide. In certain embodiments, the conjugate linker is a single chemical bond (i.e., the conjugate moiety is attached directly to an oligonucleotide through a single bond). In certain embodiments, the conjugate linker comprises one or more atoms. In certain embodiments, the conjugate linker comprises a chemical group. In certain embodiments, the conjugate linker comprises a chain structure, such as a hydrocarbyl chain, or an oligomer of repeating units such as ethylene glycol, nucleosides, or amino acid units. In certain embodiments, the oligonucleotide is a modified oligonucleotide. In certain embodiments, the conjugate moiety is a bicycle ligand. In certain embodiments, the conjugate moiety comprises two peptide loops attached to a molecular scaffold.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises one or more groups selected from alkyl, amino, oxo, amide and other groups. In certain embodiments, the conjugate linker comprises one or more groups selected from alkyl and amide groups. In certain embodiments, the conjugate linker comprises one or more groups selected from alkyl and other groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described herein, are bifunctional linking moieties, e.g., those known in the art to be useful for attaching conjugate moieties to parent compounds, such as the oligonucleotides provided herein. In general, a bifunctional linking moiety comprises at least two functional groups. One of the functional groups is selected to react with a particular site on a parent compound and the other is selected to react with a conjugate moiety. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkonyl, and alkynyl.

In certain embodiments, conjugate linkers comprise chemical groups that are formed upon a reaction between a first functional group and a second functional group. In certain embodiments, a modified oligonucleotide is attached to the first functional group during synthesis, and a conjugate moiety is attached to a second functional group during synthesis. Then, the two compounds are mixed under specific conditions to yield the oligomeric compound. In certain embodiments, the conjugate moiety is a bicycle ligand. In certain embodiments, the conjugate moiety comprises two peptide loops attached to a molecular scaffold. Such reactions that are compatible with both oligonucleotide and peptide chemistry have been previously described and are often called "bioconjugation" reactions. These reactions include strain promoted azido-alkyne cycloaddition (SPAAC), copper-catalyzed click reaction (CuAAC), active ester conjugation to an amino modified oligonucleotide, maleimide-thiol Michael addition, ketol/hydroxylamine ligation, the Staudinger ligation, reductive amination, thio ether formation, disulfide formation, reductive alkylation, catalyst-free N-arylation, sulfur fluoride exchange click reaction (SuFEx), and inverse demand Diels Alder reaction. Certain such reactions are described in, e.g., Jbara, et al., "Oligonucleotide Bioconjugation with Bifunctional Palladium Reagents", *Angew. Chem. Int. Ed.* 2021, 60(21)12109-12115: Dong, et al., "Sulfur (VI) Fluoride Exchange (SuFEx): Another Good Reaction for Click Chemistry." *Angew. Chem. Int. Ed.* 2014, 53(36):9430-9448.4: Zhang, et al., "Arylation Chemistry for Bioconjugation." *Angew. Chem. Int. Ed. Engl.* 2019; 58(15): 4810-4839; Walsh, et al., "Site-selective modification strategies in antibody-drug conjugates" Chem. Soc. Rev., 2021, 50: 1305-1353: Tiefenbrunn, et al., "Chemoselective ligation techniques: modern applications of time-honored chemistry", *Biopolymers.* 2010.94 (1): 95-106: Drake, et al., *Bioconjug. Chem.* 2014, 25(7):1331-1341: Bode, *Acc. Chem. Res.* 2017, 50, 9, 2104-2115: J. Magano. B. Bock, et al. *Org. Proc. Res. Dev.* 2014, 18:142-151; Craig S. Mckay and M. G. Finn, *Chem. Biol.* 2014, 21 (9), 1075-1101: Mitchell P. Christy et al., *Org. Lett.* 2020, 22: 2365; Ren et al., *Angew. Chem. Int. Ed. Engl.* 2009, 48, 9658-9662; Rohrbacher. F, et al., *Helv. Chim. Acta.* 2018, 101 (5), e1800039; Baalmaan, et al. "A Bioorthogonal Click Chemistry Toolbox for Targeted Synthesis of Branched and Well-Defined Protein-Protein Conjugates", *Angew. Chem. Int. Ed.* 2020 (59): 12885-12893: Lang, et al. "Biorthogonal Reactions for Labeling Proteins", *J. Am. Chem. Soc.* 2014, 9(1): 16-20; Nair, et al., "The Thiol-Michael Addition Click Reaction: A Powerful and Widely Used Tool in Materials Chemistry", *Chem. Mater.* 2013 26 (1): 724-744: Kalia and Raines. "Hydrolytic Stability of Hydrazones and Oximes", *Angew. Chem. Int. Ed.,* 2008, 47:7523-7526.

Examples of conjugate linkers include but are not limited to pyrrolidine, 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, the bicycle ligand comprises an N-terminal or a C-terminal extension azide group, which optionally may be joined with an oligonucleotide or oligomeric compound by cycloaddition with bicycle[6.1.0]non-4-yn-9-ylmethyl carbamate-oligo or 2-(cyclooct-2-yn-1-yloxy) acetamide-oligo. In certain embodiments, the bicycle ligand comprises an N-terminal or a C-terminal extension amide group which optionally may be joined with an oligonucleotide or oligomeric compound by coupling with oligo-7-amido-7-oxoheptanoic acid. In certain embodiments, the bicycle ligand comprises an N-terminal or a C-terminal extension 2-(aminooxy) acetamide group which optionally may be joined with an oligonucleotide or oligomeric compound by condensation with 5-oxo-5-(4-oxopiperidin-1-yl) pentanamide-oligo. In certain embodiments, the bicycle ligand comprises an N-terminal or a C-terminal extension thiol group which optionally may be joined with an oligonucleotide or oligomeric compound by addition to 3-(2,5-dioxo-2,5-dihydro-1H-pyrrol-1-yl) propenamide-oligo.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a sugar surrogate. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) an oligonucleotide consisting of 8-30 nucleosides and (2) a conjugate linker comprising 1-10 linker-nucleosides that are contiguous with the nucleosides of the oligonucleotide. The total number of contiguous linked nucleosides in such an oligomeric compound is more than 30. Alternatively, an oligomeric compound may comprise an oligonucleotide consisting of 8-30 nucleosides and no conjugate linker. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate moiety to be cleaved from the oligonucleotide. For example, in certain circumstances oligomeric compounds comprising a particular conjugate moiety are better taken up by a particular cell type, but once the oligomeric compound has been taken up, it is desirable that the conjugate moiety be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphodiester linkage between an oligonucleotide and a conjugate moiety.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphodiester internucleoside linkage and covalently attached to the remainder of the conjugate linker or conjugate moiety by a phosphodiester or phosphorothioate linkage. In certain such embodiments, the cleavable moiety comprises or is a 2'-deoxyadenosine.

In certain embodiments, oligomeric compounds described herein comprise an oligonucleotide linked to a conjugate moiety by a conjugate linker, wherein the oligomeric compound is prepared using Click chemistry known in the art. Compounds have been prepared using Click chemistry wherein alkynyl phosphonate internucleoside linkages on an oligomeric compound attached to a solid support are converted into the 1,2,3-triazolylphosphonate internucleoside linkages and then cleaved from the solid support (Krishna et al., *J. Am. Chem. Soc.* 2012, 134 (28), 11618-11631), which is incorporated by reference herein in its entirety. Additional conjugate linkers suitable for use in several embodiments are prepared by Click chemistry described in "Click Chemistry for Biotechnology and Materials Science" Ed. Joerg Laham, Wiley 2009, which is incorporated by reference herein in its entirety. Further examples of linking chemistry include an inverse electron demand Diels-Alder reaction, e.g., as described in Argamunt et al., *J. Org. Chem.* 2020, 85.10, 6593-6604, Sarrett et al., *Nat. Protocols* 2021, 16, 3348-3381; Handula et al., *Molecules,* 2021, 26 (15), 4640, Wiessler et al., *Int. J. Med. Sci.* 2010, 7 (1), 19-28: copper-catalyzed azide-alkyne cycloaddition (CuAAC) see, e.g., S. I. Presolski, et al., *J. Am. Chem. Soc.* 2010, 132, 14570-14576: D. Soriano Del Amo, et al., *J. Am. Chem. Soc.,* 2010, 132.16893-16899; Staudinger reaction, see, e.g., Saxon and C. R. Bertozzi, *Science,* 2000, 287.2007-2010; B. L. Nilsson, et al., *Org. Lett.,* 2000, 2, 1939-1941, E. Saxon, et al., *Org. Lett.* 2000, 2, 2141-2143; formation of hydrazones and oximes, see, e.g., J. Y. Axup, et al., *Proc. Natl. Acad. Sci. U.S.A,* 2012, 109, 16101-16106: photoclick reactions, see, e.g., W. Song, et al., *Angew. Chem., Int. Ed.,* 2008, 47, 2832-2835, A. Herner and Q. Lin, *Top. Curr. Chem.,* 2016, 374, 1: strain-promoted alkyne-nitrone cycloaddition (SPANC) reactions, see, e.g., D. A. Mackenzie, et al., *Curr. Opin. Chem. Biol.,* 2014, 21, 81-88; transition metal catalyzed cross coupling, see, e.g., M. Chalker, et al., *J. Am. Chem. Soc.,* 2009, 131, 16346-16347: nucleophilic additions, in particular, of a thiol to a maleimide, see, e.g., Kang et al., *Chem. Sci.,* 2021, 12, 13613-13647, Bernardim et al.,

*Nat. Comm.* 2016, 7, 13128, Jain et al., *Pharm. Res.* 2015, 32(11), 3526-3540, each of which is incorporated by reference herein in its entirety.

In certain embodiments, the conjugate linker is prepared by reaction of a first reactive moiety with a second reactive moiety, wherein the first reactive moiety is attached to the oligonucleotide and the second reactive moiety is attached to the conjugate moiety, or a precursor thereof. In certain embodiments, the conjugate linker is prepared by reaction of a dipolarophile (e.g., a triple bonded moiety such as an alkyne or nitrile) with a 1,3-dipole (e.g., an azide, a nitrone, an isocyanate, or a thioisocyanate):

wherein each Q is independently a carbon atom or a heteroatom, one of X and Y is attached to an oligonucleotide, and the other of X and Y is attached to a conjugate moiety. The conjugate linker thus prepared may comprise a five-membered unsaturated heterocyclic ring such as a triazole.

In certain embodiments, the conjugate linker is prepared by reaction of a dieneophile (e.g., an electron rich double bond such as a furan or derivative thereof) with an electron poor diene (e.g., a tetrazine):

wherein each Q is independently a carbon atom or a heteroatom, one of X and Y is attached to an oligonucleotide, and the other of X and Y is attached to a conjugate moiety. The conjugate linker thus prepared may comprise a six-membered unsaturated heterocyclic ring such as a dihydropyrazine.

In certain embodiments, the conjugate linker is prepared by reaction of a nucleophile (e.g., a thiol or amine) with an electrophile (e.g., an electron-poor carbonyl or carbonyl-conjugated alkene or alkyne):

wherein each Q is independently a carbon atom or a heteroatom, one of X and Y is attached to an oligonucleotide, and the other of X and Y is attached to a conjugate moiety. The conjugate linker thus prepared may comprise a thioether, hydrazone, oxime, or amide.

Each of the first reactive moiety and the second reactive moiety may attach at any suitable position of the oligonucleotide and the conjugate moiety, for example, at a position described herein. In certain embodiments, the conjugate moiety comprises a peptide or polypeptide. In certain embodiments, the second reactive moiety is attached to an amino-acid side chain of a peptide or polypeptide. In certain embodiments, the second reactive moiety is attached to the N-terminus of the peptide or polypeptide. In certain embodiments, the second reactive moiety is attached to the C-terminus of a peptide or polypeptide. In certain embodiments, the second reactive moiety replaces the amino group of a lysine of a peptide or polypeptide.

In certain embodiments, a Click reaction is used to link a conjugate moiety and an oligonucleotide by reacting:

with an oligonucleotide having a terminal amine, including but not limited to the following compound:

wherein Y is the oligonucleotide, to yield:

which is reacted with a conjugate moiety having an azide to yield:

wherein N—N=N is formed from an azido group of the conjugate moiety, and wherein X represents the remainder of the conjugate moiety. In certain embodiments, the conjugate moiety comprises a bicycle ligand. In certain embodiments, the conjugate moiety comprises a peptide or polypeptide. In certain embodiments, the azido group is attached to an amino-acid side chain of the peptide or polypeptide. In certain embodiments, the azido group is attached to the N-terminus of the peptide or polypeptide. In certain embodiments, the azido group is attached to the C-terminus of the peptide or polypeptide. In certain embodiments, the azido group replaces the amino group of a lysine of the peptide or polypeptide.

In certain embodiments, an oligomeric compound comprises an oligonucleotide linked to a conjugate moiety by a conjugate linker, wherein the conjugate linker is prepared from the following compound:

In certain embodiments, an oligomeric compound comprises an oligonucleotide linked to a conjugate moiety by a conjugate linker, wherein the conjugate linker comprises:

In certain embodiments, an oligomeric compound comprises an oligonucleotide linked to a conjugate moiety by a conjugate linker, wherein the conjugate linker comprises:

In certain embodiments, an oligomeric compound comprises an oligonucleotide linked to a conjugate moiety by a conjugate linker, wherein the compound comprises:

Wherein N—N=N is formed from an azido group of the conjugate moiety; X represents the remainder of the conjugate moiety; and Y represents a portion of the oligomeric compound comprising the oligonucleotide. In certain embodiments, the conjugate moiety comprises a bicycle ligand. In certain embodiments, the conjugate moiety comprises a peptide or polypeptide. In certain embodiments, the azido group is attached to an amino-acid side chain of the peptide or polypeptide. In certain embodiments, the azido group is attached to the N-terminus of the peptide or polypeptide. In certain embodiments, the azido group is attached to the C-terminus of the peptide or polypeptide. In certain embodiments, the azido group replaces the amino group of a lysine of the peptide or polypeptide.

In certain embodiments, an oligomeric compound comprises an oligonucleotide linked to a conjugate moiety by a conjugate linker, wherein the oligomeric compound comprises:

wherein N—N=N is formed from an azido group of the conjugate moiety; X represents the remainder of the conjugate moiety; and Y represents the oligonucleotide. In certain embodiments, the conjugate moiety comprises a bicycle ligand. In certain embodiments, the conjugate moiety comprises a peptide or polypeptide. In certain embodiments, the azido group is attached to an amino-acid side chain of the peptide or polypeptide. In certain embodiments, the azido group is attached to the N-terminus of the peptide or peptide or polypeptide. In certain embodiments, the azido group is attached to the C-terminus of the peptide or polypeptide. In certain embodiments, the azido group replaces the amino group of a lysine of the peptide or polypeptide.

In certain embodiments, an oligomeric compound comprises an oligonucleotide linked to a conjugate moiety by a conjugate linker, wherein the oligomeric compound comprises:

wherein N—N=N is formed from an azido group of the conjugate moiety; X represents the remainder of the conjugate moiety; and Y represents the oligonucleotide. In certain embodiments, the conjugate moiety comprises a bicycle ligand. In certain embodiments, the conjugate moiety comprises a peptide or polypeptide. In certain embodiments, the azido group is attached to an amino-acid side chain of the peptide or polypeptide. In certain embodiments, the azido group is attached to the N-terminus of the peptide or polypeptide. In certain embodiments, the azido group is attached to the C-terminus of the peptide or polypeptide. In certain embodiments, the azido group replaces the amino group of a lysine of the peptide or polypeptide.

In certain embodiments, a Click reaction is used to link a conjugate moiety and an oligonucleotide by reacting:

393

-continued in solution together with an oligonucleotide having a terminal amine, including but not limited to the following compound:

wherein Y is the oligonucleotide, to yield:

which is reacted with a conjugate moiety having an azide to yield:

wherein N—N=N is formed from an azido group of the conjugate moiety, and wherein X represents the remainder of the conjugate moiety. In certain embodiments, the conjugate moiety comprises a bicycle ligand. In certain embodiments, the conjugate moiety comprises a peptide or polypeptide. In certain embodiments, the azido group is attached to an amino-acid side chain of the peptide or polypeptide. In certain embodiments, the azido group is attached to the N-terminus of the peptide or polypeptide. In certain embodiments, the azido group is attached to the C-terminus of the peptide or polypeptide. In certain embodiments, the azido group replaces the amino group of a lysine of the peptide or polypeptide.

In certain embodiments, an oligomeric compound comprises an oligonucleotide linked to a conjugate moiety by a conjugate linker, wherein the conjugate linker is prepared from the following compound:

In certain embodiments, an oligomeric compound comprises an oligonucleotide linked to a conjugate moiety by a conjugate linker, wherein the conjugate linker comprises:

394

In certain embodiments, an oligomeric compound comprises an oligonucleotide linked to a conjugate moiety by a conjugate linker, wherein the conjugate linker comprises:

In certain embodiments, an oligomeric compound comprises an oligonucleotide linked to a conjugate moiety by a conjugate linker, wherein the compound comprises:

wherein N—N=N is formed from an azido group of the conjugate moiety; X represents the remainder of the conjugate moiety; and Y represents a portion of the oligomeric compound comprising the oligonucleotide. In certain embodiments, the conjugate moiety comprises a bicycle ligand. In certain embodiments, the conjugate moiety comprises a peptide or polypeptide. In certain embodiments, the azido group is attached to an amino-acid side chain of the peptide or polypeptide. In certain embodiments, the azido group is attached to the N-terminus of the peptide or polypeptide. In certain embodiments, the azido group is attached to the C-terminus of the peptide or polypeptide. In certain embodiments, the azido group replaces the amino group of a lysine of the peptide or polypeptide.

In certain embodiments, an oligomeric compound comprises an oligonucleotide linked to a conjugate moiety by a conjugate linker, wherein the oligomeric compound comprises:

wherein N—N=N is formed from an azido group of the conjugate moiety; X represents the remainder of the conjugate moiety; and Y represents the oligonucleotide. In certain embodiments, the conjugate moiety comprises a bicycle ligand. In certain embodiments, the conjugate moiety comprises a peptide or polypeptide. In certain embodiments, the azido group is attached to an amino-acid side chain of the peptide or polypeptide. In certain embodiments, the azido group is attached to the N-terminus of the peptide or polypeptide. In certain embodiments, the azido group is attached to the C-terminus of the peptide or polypeptide. In certain embodiments, the azido group replaces the amino group of a lysine of the peptide or polypeptide.

In certain embodiments, an oligomeric compound comprises an oligonucleotide linked to a conjugate moiety by a conjugate linker, wherein the oligomeric compound comprises:

wherein N—N═N is formed from an azido group of the conjugate moiety; X represents the remainder of the conjugate moiety; and Y represents the oligonucleotide. In certain embodiments, the conjugate moiety comprises a bicycle ligand. In certain embodiments, the conjugate moiety comprises a peptide or polypeptide. In certain embodiments, the azido group is attached to an amino-acid side chain of the peptide or polypeptide. In certain embodiments, the azido group is attached to the N-terminus of the peptide or polypeptide. In certain embodiments, the azido group is attached to the C-terminus of the peptide or polypeptide. In certain embodiments, the azido group replaces the amino group of a lysine of the peptide or polypeptide.

In certain embodiments, an oligomeric compound comprises an oligonucleotide linked to a conjugate moiety by a conjugate linker, wherein the oligomeric compound comprises:

wherein X comprises the conjugate moiety; and Y comprises the oligonucleotide.

In certain embodiments, an oligomeric compound comprises an oligonucleotide linked to a conjugate moiety by a conjugate linker, wherein the oligomeric compound comprises:

wherein X comprises the oligonucleotide; and Y comprises the conjugate moiety.

In certain embodiments, an oligomeric compound comprises an oligonucleotide linked to a conjugate moiety by a conjugate linker, wherein the conjugate linker comprises:

In certain embodiments, an oligomeric compound comprises an oligonucleotide linked to a conjugate moiety by a conjugate linker, wherein the conjugate linker comprises:

In certain embodiments, an oligomeric compound comprises an oligonucleotide linked to a conjugate moiety by a conjugate linker, wherein the conjugate linker comprises:

In certain embodiments, an oligomeric compound comprises an oligonucleotide linked to a conjugate moiety by a conjugate linker, wherein the conjugate linker comprises:

In certain embodiments, an oligomeric compound comprises an oligonucleotide linked to a conjugate moiety by a conjugate linker, wherein the conjugate linker comprises:

In certain embodiments, a Click reaction is used to link a conjugate moiety and an oligonucleotide by reacting:

with wherein one of Y and Y' is attached to the conjugate moiety and X is attached to the oligonucleotide, to yield:

Synthetic methods describing preparation of the above starting materials and intermediates can be found in one or more of the following: Agard, N. J., et al. "A Strain-Promoted [3+2] Azide-Alkyne Cycloaddition for Covalent Modification of Biomolecules in Living Systems." *J. Am. Chem. Soc.* 2004, 126, 15046-15047; Lang, K., and Chin, J. W. "Biorthogonal Reactions for Labeling Proteins." *ACS Chem. Biol.* 2014, 9 (1), 16-20; Nair, D. P, et al. "The Thiol-Michael Addition Click Reaction: A Powerful and Widely Used Tool in Materials Chemistry." *Chem. Mater.* 2013 26 (1), 724-744; WO2011/136645; Kölmel, D. K, and Kool, E. T. "Oximes and Hydrazones in Bioconjugation: Mechanism and Catalysis." *Chem. Rev.* 2017, 117, 10358-10376; Wang, J, et al. "Polyfluorophenyl Ester-Terminated Homobifunctional Cross-Linkers for Protein Conjugation." *Synlett,* 2017, 28 (15), 1934-1938; Kishimoto, S, et al. "Site-Specific Chemical Conjugation of Antibodies by Using Affinity Peptide for the Development of Therapeutic Antibody Format." *Bioconjugate Chem.* 2019.30 (3), 698-702. Wu and Devaraj. "Inverse Electron-Demand Diels-Alder Bioorthogonal Reactions." *Top. Curr. Chem.* 2016, 374.3. Oliveira et al., "Inverse electron demand Diels-Alder reactions in chemical biology." *Chem. Soc. Rev.* 2017, 46, 4895-4950.

Synthetic methods describing preparation of conjugated bicycle peptide ligands can be found in one or more of the following: International Patent Application Publication No. WO2022/101633. International Patent Application Publication No. WO2023/056388, each of which is hereby incorporated by reference. Bicycle peptides are synthesized by standard techniques, followed by reaction with a molecular scaffold using standard chemistry to form bicycle compound. See also, e.g., Timmerman et al., *Chembiochem,* 2005, 6:821-824: Heinis et al., *Angewandte Chemie.* International Edition 2014, 53:1602-1606; van de Langemheen et al., *Chembiochem,* 2017, 18: 387-395. Standard bio-conjugation, chemistry, and/or coupling techniques may be used to introduce, e.g., activated or activatable N- and/or C-terminal groups, or through side chains, including utilizing linkers described herein, to introduce additional components to conjugate compounds herein.

B. Certain Terminal Groups

As used herein. "terminal group" means a chemical group or group of atoms that is covalently linked to a terminus of an oligonucleotide. Examples of a terminal group include, but are not limited to, a capping group, a phosphate moiety, a stabilized phosphate group, a protecting group, a modified or unmodified nucleoside, and two or more nucleosides that are independently modified or unmodified, wherein one or more groups is attached to either or both ends of an oligonucleotide. In certain embodiments, one or more terminal groups is attached to cither or both ends of an oligonucleotide. In certain embodiments, one or more terminal groups is attached at the 3' and/or 5'-end of the oligonucleotide. In certain embodiments, one or more terminal groups is attached at the 3'-end of the oligonucleotide. In certain embodiments, one or more terminal groups is attached at the 5'-end of the oligonucleotide. In certain embodiments, one or more terminal groups is attached at the 3'-end of the oligonucleotide and one or more terminal groups is attached at the 5'-end of the oligonucleotide. In certain embodiments, a terminal group is attached at the 3' and/or 5'-end of the oligonucleotide. In certain embodiments, a terminal group is attached at the 3'-end of the oligonucleotide. In certain embodiments, a terminal group is attached near the 3'-end of the oligonucleotide. In certain embodiments, a terminal group is attached at the 5'-end of the oligonucleotide. In certain embodiments, a terminal group is attached near the 5'-end of the oligonucleotide. In certain embodiments, a terminal group is attached at the 3'-end of the oligonucleotide and a terminal group is attached at the 5'-end of the oligonucleotide.

In certain embodiments, an oligomeric compound comprises one or more terminal groups. In certain embodiments, an oligomeric compound comprises a terminal group comprising a stabilized 5'-phosphate. In certain embodiments, a stabilized phosphate group results in stabilization of a 5'-phosphate moiety of the 5'-terminal nucleoside of an oligonucleotide, relative to the stability of an unmodified 5'-phosphate of a nucleoside under biologic conditions. Such stabilization of a 5'-phosphate group includes but is not limited to resistance to removal by phosphatases. Stabilized 5'-phosphates include, but are not limited to 5'-phosphonates, including, but not limited to 5-vinylphosphonate, 5'-methylphosphonate, and 5'-cyclopropyl phosphonate. In certain embodiments, the stabilized phosphate group is a cyclopropyl phosphonate or an (I)-vinyl phosphonate. In certain embodiments, a terminal group comprises one or more abasic sugar moietics. In certain embodiments, a terminal group comprises one or more inverted sugar moieties and/or inverted nucleosides. In certain embodiments, a terminal group comprises one or more 2'-linked nucleosides or sugar moietics. In certain embodiments, the 2'-linked terminal group is an abasic sugar moiety. In certain embodiments, an antisense oligonucleotide has a vinylphosphonate group on the 5'-end (5'-vP). In certain particular embodiments, each antisense oligonucleotide has a vinyl phosphonate group on the 5'-end (5'-vP).

IV. Target Nucleic Acids

A. PLN

In certain embodiments, oligomeric compounds comprise or consist of an oligonucleotide comprising or consisting of a region that is complementary to an equal-length target region of a target nucleic acid, wherein the target nucleic acid is PLN. In certain embodiments, PLN nucleic acid has the sequence set forth in SEQ ID NO: 1 (GENBANK Accession No. NM_002667.4) or SEQ ID NO: 2 (GEN-BANK Accession No. NC_000006.12, truncated from nucleosides 118545001 to 118565000). In certain embodiments, contacting a cell with an oligomeric compound (e.g., a single-stranded oligomeric compound or a paired oligomeric compound e.g., an oligomeric duplex) comprising an oligonucleotide comprising or consisting of a region that is complementary to an equal-length target region of SEQ ID NOs: 1 or 2 reduces the amount of PLN RNA in the cell, and in certain embodiments reduces the amount of phospholamban protein in the cell. In certain embodiments, the oligomeric compound consists of a modified oligonucleotide. In certain embodiments, the oligomeric compound consists of a modified oligonucleotide and a conjugate group. In certain embodiments, the oligomeric compound consists of a modified oligonucleotide and one or more terminal group(s). In certain embodiments, the oligomeric compound consists of a modified oligonucleotide and a conjugate group and one or more terminal group(s).

In certain embodiments, oligomeric compounds comprise an antisense oligonucleotide comprising or consisting of a region that is complementary to a nucleobase sequence of an equal-length target region of a target PLN nucleic acid. In certain embodiments, oligomeric compounds comprise an antisense oligonucleotide comprising a region that is complementary to a nucleobase sequence of a target PLN nucleic acid, and a sense oligonucleotide comprising a region that is complementary to the nucleobase sequence of the antisense oligonucleotide or a region thereof. In certain embodiments, the target nucleic acid is an endogenous PLN RNA molecule. In certain embodiments, the target PLN nucleic acid encodes phospholamban. In certain embodiments, the target PLN nucleic acid is a precursor to a nucleic acid that encodes phospholamban. In certain such embodiments, the target PLN nucleic acid is selected from: a mature mRNA and a pre-mRNA, including intronic, exonic and untranslated regions. In certain embodiments, the target PLN RNA is a mature mRNA. In certain embodiments, the target nucleic acid is a pre-mRNA. In certain embodiments, the oligomeric compound or oligomeric duplex is an RNAi agent. In certain embodiments, antisense compounds comprise an antisense oligonucleotide comprising or consisting of a region that is complementary to a nucleobase sequence of a target PLN nucleic acid.

In certain embodiments, antisense oligonucleotides of the invention are complementary to a nucleobase sequence in a target PLN nucleic acid over the entire length of the modified oligonucleotide. In certain embodiments, antisense oligonucleotides are at least 99%, at least 95%, at least 90%, at least 85%, or at least 80% complementary to an equal length portion of the target PLN nucleic acid. In certain embodiments, antisense oligonucleotides are at least 80% complementary to a nucleobase sequence of an equal length portion of the target PLN nucleic acid over the entire length of the oligonucleotide and comprise a region that is 100% or fully complementary to a sequence in the target PLN nucleic acid.

In certain embodiments, a region of full complementarity is from 6 to 20, 10 to 18, 14 to 18.16 to 20, or 18 to 20 nucleobases in length. In certain embodiments, the complementary region comprises or consists of at least 8, at least 9, at least 10, at least 11, at least 12, at least 13, at least 14, at least 15, at least 16, at least 17, at least 18, at least 19, at least 20, at least 21, at least 22, or at least 23 contiguous nucleobases. In certain embodiments, the complementary region comprises or consists of at least 8, at least 9, at least 10, at least 11, at least 12, at least 13, at least 14, at least 15, at least 16, at least 17, at least 18, at least 19, at least 20, at least 21, at least 22, or 23 contiguous nucleobases. In certain embodiments, the complementary region constitutes at least 75%, at least 80%, at least 85%, at least 90%, or at least 95% of the nucleosides of the antisense oligonucleotide. In certain embodiments, the complementary region constitutes all of the nucleosides of the antisense oligonucleotide. In certain embodiments, the complementary region of the antisense oligonucleotide is at least 99%, at least 95%, at least 90%, at least 85%, or at least 80% complementary to a nucleobase sequence in the target PLN nucleic acid. In certain embodiments, the complementary region of the antisense oligonucleotide is 100% complementary to a nucleobase sequence in the target PLN nucleic acid.

In certain embodiments, antisense oligonucleotides comprise one or more mismatched nucleobases relative to the target PLN nucleic acid or portion thereof. In certain embodiments, antisense activity against the target is reduced by such mismatch, but activity against a non-target is reduced by a greater amount. Thus, in certain embodiments selectivity of the antisense oligonucleotides is improved. In certain embodiments, antisense oligonucleotides are at least 80% complementary to a nucleobase sequence of an equal length portion of the target PLN nucleic acid over the entire length of the oligonucleotide and comprise no more than one to three mismatches with the equal length portion of the target PLN nucleic acid. In certain embodiments, antisense oligonucleotides are at least 80% complementary to a nucleobase sequence in the target PLN nucleic acid over the entire length of the oligonucleotide and comprise no more than one to three mismatches with target nucleic acid, not inclusive of terminal nucleobases of the antisense oligonucleotide. In certain embodiments, antisense oligonucleotides comprise a region that is at least 80% complementary to a nucleobase sequence of an equal length portion of the target PLN nucleic acid and the region comprises no more than one to three mismatches with the equal length portion of the target PLN nucleic acid. In certain embodiments, antisense oligonucleotides are at least 80%, at least 85%, at least 90%, at least 95%, or 100% complementary to an equal length portion of the target PLN nucleic acid over the entire length of the oligonucleotide sequence. In certain embodiments, a mismatch is specifically positioned within an antisense oligonucleotide. In certain embodiments, a mismatch is at position 3, 4, 5, 6, 7, 8, 9, 10, 11, or 12 from the 5'-end of the antisense oligonucleotide. In certain embodiments, a mismatch is at position 11, 10, 9, 8, 7, 6, 5, 4, 3, or 2 from the 3'-end of the antisense oligonucleotide. In certain embodiments, a mismatch is at position 1, 2, 3, or 4 from the 5'-end of the antisense oligonucleotide. In certain embodiments, a mismatch is at position 1 and/or 2 from the 5'-end of the antisense oligonucleotide. In certain embodiments, a mismatch is at position 4, 3, 2, or 1 from the 3'-end of the antisense oligonucleotide. In certain embodiments, a mismatch is at position 1 and/or 2 from the 3'-end of the antisense oligonucleotide. In certain embodiments, 1-2 additional mismatches may be present at a terminus or at both termini of the antisense oligonucleotide.

B. Target Nucleic Acids in Certain Tissues

In certain embodiments, oligomeric compounds comprise or consist of an oligonucleotide comprising a region that is complementary to a nucleobase sequence of an equal length portion of a PLN target nucleic acid, wherein the PLN target nucleic acid is expressed in a pharmacologically relevant tissue. In certain embodiments, the PLN target nucleic acid is expressed in the heart cells and cardiac tissues, e.g., cardiomyocytes, cardiac muscle.

C. Oligonucleotide Sequences

Provided herein are oligomeric compounds comprising modified oligonucleotides comprising a region that is complementary to a sequence of nucleobases in a PLN nucleic acid, such as, for example, a human PLN nucleic acid, such as SEQ ID NO: 1 (GENBANK Accession No. NM_002667.4), and/or SEQ ID NO: 2 (GENBANK Accession No. NC_000006.12, truncated from nucleosides 118545001 to 118565000) and compositions comprising such oligomeric compounds. In certain embodiments, a modified oligonucleotide of the invention comprises or consists of a region having a nucleobase sequence that is at least 80%, at least 85%, at least 90%, at least 95%, or at least 99% complementary to a sequence of nucleobases in SEQ ID NOs: 1 or 2. In certain embodiments, a modified oligonucleotide of the invention comprises or consists of a region having a nucleobase sequence that is at least 80%, at least 85%, at least 90%, at least 95%, or at least 99% complementary to a nucleobase sequence comprising or consisting of a nucleobase sequence that is at least 80%, at least 85%, at least 90%, at least 95%, or at least 99% complementary to a sequence of nucleobases in SEQ ID NOs: 1 or 2. In certain embodiments, a modified oligonucleotide comprises or consists of a region having a nucleobase sequence that is 100% complementary to a sequence of nucleobases in SEQ ID NOs: 1 or 2. In certain embodiments, a modified oligonucleotide of the invention has a nucleobase sequence comprising or consisting of a nucleobase sequence that is at least 80%, at least 85%, at least 90%, at least 95%, or at least 99% complementary to a nucleobase sequence comprising or consisting of a nucleobase sequence that is 100% complementary to a sequence of nucleobases in SEQ ID NOs: 1 or 2. In certain embodiments, a modified oligonucleotide has a nucleobase sequence comprising or consisting of a nucleobase sequence that is selected from among the sequences provided in Table A, Tables B1-B2. Table B1a or B1b, Tables 1-21, Table 23, or SEQ ID NOS: 3-1016, 1027-1044, 1254-1290.

V. Methods and Uses

A. Antisense Activity

In certain embodiments, oligomeric compounds of the invention are capable of hybridizing to a target nucleic acid, resulting in at least one antisense activity: such oligomeric compounds and oligomeric duplexes are antisense compounds.

In certain antisense activities, hybridization of an antisense oligonucleotide to a target nucleic acid results in recruitment of a protein that cleaves the target nucleic acid. For example, in certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi agents. RNAi agents may be double-stranded (siRNA or dsRNAi) or single-stranded (ssRNA). In certain embodiments, RNAi agents are capable of RISC-mediated modulation of a target nucleic acid in a cell. In certain embodiments, such compounds reduce or inhibit the amount or activity of a target nucleic acid by 25% or more in the standard in vitro assay. In certain embodiments, RNAi agents selectively affect one or more target nucleic acid. Such RNAi agents comprise an oligonucleotide sequence having a nucleobase sequence that hybridizes to one or more target nucleic acid, resulting in one or more desired antisense activity. In certain embodiments, an RNAi agent does not hybridize to one or more non-target nucleic acid or does not hybridize to one or more non-target nucleic acid in such a way that results in significant undesired antisense activity.

In certain embodiments, provided herein are methods of decreasing, reducing and/or inhibiting PLN expression, PLN RNA levels and/or phospholamban levels and/or activity, in a cell, tissue, and/or animal (e.g., human subject) comprising contacting the cell, tissue or subject with an oligomeric compound (e.g., an oligomeric duplex) comprising or consisting of a modified antisense oligonucleotide comprising or consisting of a region having a nucleobase sequence complementary to sequence in a PLN nucleic acid (e.g., a nucleobase sequence in SEQ ID NO: 1 or SEQ ID NO: 2). In certain embodiments, the cell is a cardiac cell, cardiomyocyte, or cardiovascular smooth muscle cell. In certain embodiments, the tissue is heart, muscle (e.g., cardiac muscle). In certain embodiments, such oligomeric compound (e.g., oligomeric duplex) reduces and/or inhibits PLN expression, PLN RNA levels and/or phospholamban levels and/or activity in the heart, plasma, serum, blood or other fluid of the subject.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or animal (e.g., a human). In certain embodiments, the detectable amount of the PLN RNA may be reduced or decreased by at least 10%, at least 20%, at least 30%, at least 40%, at least 50%, at least 60%, at least 70%, at least 80%, or at least 90%, for example, compared to the amount of PLN RNA prior to contacting a cell, tissue, or animal with the oligomeric compound (e.g., an oligomeric duplex) comprising or consisting of a modified antisense oligonucleotide comprising or consisting of linked nucleosides comprising a region having a nucleobase sequence complementary to sequence in a PLN nucleic acid or compared to the amount of PLN RNA in a cell, tissue, or animal that has not been contacted with the oligomeric compound (e.g., an oligomeric duplex), e.g., a control cell, tissue or animal.

B. Treatment, Prophylaxis

In certain embodiments, provided herein are methods of decreasing, reducing and/or inhibiting PLN expression. PLN RNA levels and/or phospholamban levels and/or activity, in a subject having, or at risk of having, a disease, disorder, condition or injury associated with PLN and/or phospholamban, such as, for example, a disease, disorder, condition or injury associated with cardiac calcium misregulation, wherein the method includes administering to the subject an oligomeric compound, modified antisense oligonucleotide, or oligomeric duplex comprising or consisting of a modified oligonucleotide comprising or consisting of a region having a nucleobase sequence complementary to a nucleobase sequence in a PLN nucleic acid, thereby inhibiting or reducing. PLN expression. PLN RNA levels and/or phospholamban levels and/or activity in the subject. In certain embodiments, administering such oligomeric compound or oligomeric duplex reduces and/or inhibits PLN expression. PLN RNA levels and/or phospholamban levels and/or activity in the heart, plasma, serum, blood and/or other body fluid of the subject. In certain embodiments, administering such oligomeric compound or oligomeric duplex reduces and/or inhibits PLN expression. PLN RNA levels and/or phospholamban levels and/or activity in the muscle, e.g., cardiac muscle, of the subject. In some instances, such oligomeric compound or oligomeric duplex is administered parenterally. In some instances, an oligomeric compound or oligomeric duplex is administered intravenously, intramuscularly, or subcutaneously. In certain embodiments, the detectable amount of the PLN RNA may be reduced by at least 10%, at least 20%, at least 30%, at least 40%, at least 50%, at least 60%, at least 70%, at least 75%, at least 80%, at least 85%, or at least 90%, for example, compared to the amount of PLN RNA prior to administering the oligomeric compound (e.g., an antisense oligonucleotide, oligomeric duplex) to the subject or compared to the amount of PLN RNA in a subject to whom the oligomeric compound has not been administered. In certain embodiments, the detectable amount of PLN RNA may be reduced by about 70% to about 85%, or about 75% to about 85%, or up to about 90%, or up to about 85%. In certain embodiments, an oligomeric compound comprising or consisting of, or an oligomeric duplex comprising, a modified antisense oligonucleotide comprising or consisting of a region having a nucleobase sequence complementary to a nucleobase sequence in SEQ ID NO: 1 or SEQ ID NO: 2 is capable of decreasing or reducing a detectable amount of a phospholamban protein in a cell, organ, e.g., the heart, tissue (e.g., muscle, e.g., cardiac muscle), plasma, scrum, blood, or other fluid of the subject, when the oligomeric compound or oligomeric duplex is administered to the cell, a tissue, and/or subject. In certain embodiments, the detectable amount of the phospholamban protein may be reduced by at least 10%, at least 20%, at least 30%, at least 40%, at least 50%, at least 60%, at least 70%, at least 75%, at least 80%, at least 85%, or at least 90%, for example, compared to the amount of phospholamban protein prior to administering the oligomeric compound (e.g., an antisense oligonucleotide, oligomeric duplex) to the cell, tissue and/or subject or compared to the amount of PLN RNA in a cell, tissue, and/or subject to whom the oligomeric compound has not been administered. In certain embodiments, the detectable amount of the phospholamban protein may be reduced by about 70% to about 85%, or about 75% to about 85%, or up to about 90%, or up to about 85%.

In certain embodiments, provided herein are methods for preventing, treating, or delaying or preventing the development or progression of, diseases, disorders, conditions or injuries associated with PLN and/or phospholamban, such as, for example, a disease, disorder, condition or injury associated with cardiac calcium misregulation, wherein the method comprises administering to a subject an oligomeric compound or oligomeric duplex of the invention (e.g., a modified antisense oligonucleotide, an antisense compound) comprising or consisting of a modified oligonucleotide comprising or consisting of a region having a nucleobase sequence complementary to a nucleobase sequence in a PLN nucleic acid. Also provided are methods of ameliorating, preventing, or delaying the onset of, one or more symptoms associated with diseases, disorders, conditions or injuries associated with PLN or phospholamban, such as, for example, a disease, disorder, condition or injury associated with cardiac calcium misregulation, wherein the method comprises administering to a subject an oligomeric compound comprising or consisting of, or an oligomeric duplex comprising, a modified antisense oligonucleotide comprising or consisting of a region having a nucleobase sequence complementary to a nucleobase sequence in a PLN nucleic acid. Examples of diseases, disorders or conditions associated with PLN and/or phospholamban treatable with the compounds, compositions, and methods provided herein include, for example, a disease, disorder or condition associated with cardiac calcium misregulation (e.g., cardiovascular/cardiac injury, disease, disorder or condition as further described herein). In certain embodiments, the disease, disorder, condition or injury associated with cardiac calcium misregulation, for example, a cardiac or cardiovascular disease, disorder, condition or injury, is cardiomyopathy, arrythmia, and/or heart failure. In certain embodiments, cardiomyopathy is genetic, including PLN p.Arg14del, Arg9Cys (R9C), and Arg25Cys (R25C) mutations. In certain embodiments, cardiomyopathy is dilated cardiomyopathy (DCM). In certain embodiments, DCM is genetic, including TTN, LMNA, RBM20, SCN5A, MYH7, TNNT2, and TPM1 mutations. In certain embodiments, DCM is arrhythmogenic DCM. In certain embodiments, heart failure is heart failure with preserved ejection fraction (HFpEF), heart failure with reduced ejection fraction (HFrEF), acute heart failure, or worsening of chronic heart failure. In certain embodiments, arrhythmia is ventricular tachycardia (vtac) or ventricular fibrillation (vfib).

Cardiac dysfunction associated with cardiac calcium misregulation is associated with cardiovascular and cardiac diseases and disorders, conditions and/or injuries such as, for example, cardiomyopathy, cardiac arrythmia and heart failure. Symptoms of a cardiac disease, disorder, condition or injury include pain, hypokalemia, heart palpitations (e.g., irregular tempo, fast heartbeat, forceful heartbeat, or fluttering), chest pain, fatigue, shortness of breath, weakness, lightheadedness, dizziness, fainting episode(s), nausea, confusion, intolerance to exertion, blood clots, or a combination thereof. In certain embodiments, the cardiac disorder or cardiac injury is heart failure, a cardiomyopathy, or a cardiac arrythmia. Cardiomyopathy may be, for example, hypertrophic cardiomyopathy, dilated cardiomyopathy, restrictive cardiomyopathy, arrhythmogenic right ventricular dysplasia, or Takotsubo cardiomyopathy (broken heart syndrome). Cardiac arrythmias may include, but are not limited to, atrial or ventricular arrythmia, for example, atrial fibrillation (afib), ventricular fibrillation (vfib), or ventricular tachycardia (vtac). In some embodiments, compounds, compositions, materials and methods provided herein improve one or more indices of heart function, e.g., cardiovascular death, cardiac dilation, cardiac fibrosis, low voltage ECG, diastolic calcium uptake, ejection fraction (EF), left ventricular ejection fraction (LVEF), left ventricular end systolic volume (LVESV), left ventricular end diastolic volume (LVEDV), mitral valve flow profile, left ventricle (LV) strain, left ventricle (LV) strain rate, infarct size, heart failure hospitalization, 6 minute walk test (6MWT), the Kansas City Cardiomyopathy Questionnaire Score (KCCQS), heart rate, and heart rhythm in the subject. In certain embodiments, the compounds, methods, and pharmaceutical compositions are useful in reducing a progression of heart failure. Progression of heart failure may be classified according to the New York Heart Association classification, the American College of Cardiology/American Heart Association guidelines, and/or another method known in the art.

Thus, in certain embodiments, a method comprises administering to a subject an oligomeric compound provided herein comprising or consisting of an oligomeric duplex comprising a modified antisense oligonucleotide comprising or consisting of a region having a nucleobase sequence complementary to a sequence in a PLN nucleic acid. In certain embodiments, the subject has or is at risk for developing a cardiovascular or cardiac injury, disease, condition or disorder. In certain embodiments, the subject has or is at risk for developing cardiomyopathy, cardiac arrythmia, and/or heart failure. In certain embodiments, cardiomyopathy is genetic, including PLN p.Arg14del, Arg9Cys (R9C), and Arg25Cys (R25C) mutations. In certain embodiments, cardiomyopathy is dilated cardiomyopathy (DCM). In certain embodiments, DCM is genetic, including TTN, LMNA, RBM20, SCN5A, MYH7, TNNT2, and TPM1 mutations. In certain embodiments. DCM is arrhythmogenic DCM. In certain embodiments, heart failure is heart failure with preserved ejection fraction (HFpEF), heart failure with reduced ejection fraction (HFrEF), acute heart failure, or worsening of chronic heart failure. In certain embodiments, arrhythmia is ventricular tachycardia (vtac) or ventricular fibrillation (vfib). In certain embodiments, at least one symptom of the cardiovascular/cardiac injury, disease, condition, or disorder is ameliorated. In certain embodiments, the at least one symptom is selected from pain, hypokalemia, heart palpitations (e.g., irregular tempo, fast heartbeat, forceful heartbeat, or fluttering), chest pain, fatigue, shortness of breath, weakness, lightheadedness, dizziness, fainting episode(s), nausea, confusion, intolerance to exertion, blood clots, or a combination thereof. In certain embodiments, administration of the compound of the invention (e.g., an oligomeric compound, modified antisense oligonucleotide, or oligomeric duplex) to the subject reduces or delays the onset or progression of at least one of pain, hypokalemia, heart palpitations (e.g., irregular tempo, fast heartbeat, forceful heartbeat, or fluttering), chest pain, fatigue, shortness of breath, weakness, lightheadedness, dizziness, fainting episode(s), nausea, confusion, intolerance to exertion, or blood clots, or a combination thereof.

In certain embodiments, a method of treating cardiomyopathy, heart failure, or arrhythmia in a subject comprises administering to the subject an oligomeric compound provided herein, e.g., a modified antisense oligonucleotide, or oligomeric duplex, comprising or consisting of a modified oligonucleotide comprising or consisting of a region having a nucleobase sequence complementary to a sequence in a PLN nucleic acid, thereby treating the subject. In certain embodiments, the subject has or is at risk for developing cardiomyopathy, cardiac arrythmia, and/or heart failure. In certain embodiments, cardiomyopathy is genetic, including PLN p.Arg14del, Arg9Cys (R9C), and Arg25Cys (R25C) mutations. In certain embodiments, cardiomyopathy is dilated cardiomyopathy (DCM). In certain embodiments, DCM is genetic, including TTN, LMNA, RBM20, SCN5A, MYH7, TNNT2, and TPM1 mutations. In certain embodiments, DCM is arrhythmogenic DCM. In certain embodiments, heart failure is heart failure with preserved ejection fraction (HFpEF), heart failure with reduced ejection fraction (HFrEF), acute heart failure, or worsening of chronic heart failure. In certain embodiments, arrhythmia is ventricular tachycardia (vtac) or ventricular fibrillation (vfib). In certain embodiments, administering the oligomeric compound, modified antisense oligonucleotide, or oligomeric duplex (e.g., a therapeutically effective amount of the oligomeric compound, modified antisense oligonucleotide, or oligomeric duplex) improves cardiac function, cardiovascular death, cardiac dilation, cardiac fibrosis, low voltage ECG, diastolic calcium uptake, ejection fraction (EF), left ventricular ejection fraction (LVEF), left ventricular end systolic volume (LVESV), left ventricular end diastolic volume (LVEDV), mitral valve flow profile, left ventricle (LV) strain, left ventricle (LV) strain rate, infarct size, heart failure hospitalization, 6 minute walk test (6MWT), the Kansas City Cardiomyopathy Questionnaire Score (KCCQS), heart rate, or heart rhythm in the subject. In certain embodiments, at least one symptom of the cardiomyopathy, cardiac arrythmia and/or heart failure is ameliorated. In certain embodiments, the at least one symptom is selected from pain, hypokalemia, heart palpitations (e.g., irregular tempo, fast heartbeat, forceful heartbeat, or fluttering), chest pain, fatigue, shortness of breath, weakness, lightheadedness, dizziness, fainting episode(s), nausea, confusion, intolerance to exertion, blood clots, or a combination thereof. In certain embodiments, administration of a pharmaceutical composition comprising a compound of the invention (e.g., an oligomeric compound, modified antisense oligonucleotide, or oligomeric duplex) to the subject reduces or delays the onset or progression of at least one of pain, hypokalemia, heart palpitations (e.g., irregular tempo, fast heartbeat, forceful heartbeat, or fluttering), chest pain, fatigue, shortness of breath, weakness, lightheadedness, dizziness, fainting episode(s), nausea, confusion, intolerance to exertion, or blood clots, or a combination thereof.

In certain embodiments, a method of inhibiting expression of, or decreasing or reducing the amount of, PLN nucleic acid, such as RNA, and/or phospholamban in a subject having or at risk of a disease, injury, condition or disorder associated with PLN comprises administering to the subject an oligomeric compound, modified antisense oligonucleotide, or oligomeric duplex, any of which comprising a modified oligonucleotide comprising or consisting of a region having a nucleobase sequence complementary to a sequence of nucleobases in a PLN nucleic acid, thereby inhibiting expression of, or decreasing or reducing the amount of PLN nucleic acid and/or PLN protein in the subject. In certain embodiments, administering the oligomeric compound, modified oligonucleotide, or oligomeric duplex inhibits expression of, or decreases or reduces the amount of PLN nucleic acid and/or PLN protein in the heart. In certain embodiments, the subject has, or is at risk of having, cardiomyopathy, heart failure, or arrhythmia. In certain embodiments, cardiomyopathy is genetic, including PLN p.Arg14del, Arg9Cys (R9C), and Arg25Cys (R25C) mutations. In certain embodiments, cardiomyopathy is dilated cardiomyopathy (DCM). In certain embodiments, DCM is genetic, including TTN, LMNA, RBM20, SCN5A, MYH7, TNNT2, and TPM1 mutations. In certain embodiments. DCM is arrhythmogenic DCM. In certain embodiments, heart failure is heart failure with preserved ejection fraction (HFpEF), heart failure with reduced ejection fraction (HFrEF), acute heart failure, or worsening of chronic heart failure. In certain embodiments, arrhythmia is ventricular tachycardia (vtac) or ventricular fibrillation (vfib). In certain embodiments, administering the oligomeric compound, modified antisense oligonucleotide, or oligomeric duplex improves cardiac function, cardiovascular death, cardiac dilation, cardiac fibrosis, low voltage ECG, diastolic calcium uptake, ejection fraction (EF), left ventricular ejection fraction (LVEF), left ventricular end systolic volume (LVESV), left ventricular end diastolic volume (LVEDV), mitral valve flow profile, left ventricle (LV) strain, left ventricle (LV) strain rate, infarct size, heart failure hospitalization, 6 minute walk test (6MWT), the Kansas City Cardiomyopathy Questionnaire Score (KCCQS), heart rate, or heart rhythm in the subject. In certain embodiments, at least one symptom of the cardiomyopathy, cardiac arrythmia and/or heart failure is ameliorated. In certain embodiments, the at least one symptom is selected from pain, hypokalemia, heart palpitations (e.g., irregular tempo, fast heartbeat, forceful heartbeat, or fluttering), chest pain, fatigue, shortness of breath, weakness, lightheadedness, dizziness, fainting episode(s), nausea, confusion, intolerance to exertion, blood clots, or a combination thereof. In certain embodiments, administration of a pharmaceutical composition comprising a compound of the invention (e.g., a an oligomeric compound, modified antisense oligonucleotide, or oligomeric duplex) to the subject reduces or delays the onset or progression of at least one of pain, hypokalemia, heart palpitations (e.g., irregular tempo, fast heartbeat, forceful heartbeat, or fluttering), chest pain, fatigue, shortness of breath, weakness, lightheadedness, dizziness, fainting episode(s), nausea, confusion, intolerance to exertion, or blood clots, or a combination thereof.

Certain embodiments are drawn to an oligomeric compound, modified oligonucleotide, or oligomeric duplex, any of which comprising a modified antisense oligonucleotide comprising or consisting of a region having a nucleobase sequence complementary to a nucleobase sequence in a PLN nucleic acid, for use in treating a disease, disorder, condition or injury associated with PLN and/or phospholamban. In certain embodiments, the disease, disorder, condition or injury is associated with cardiac calcium misregulation, for example, a cardiac or cardiovascular disease, disorder, condition or injury (e.g., cardiomyopathy, cardiac arrythmia, heart failure). Certain embodiments provided herein are drawn to an oligomeric compound, modified oligonucleotide, or oligomeric duplex, any of which comprising a modified antisense oligonucleotide comprising or consisting of a region having a nucleobase sequence complementary to a nucleobase sequence in a PLN nucleic acid, for use in treating a disease, disorder, condition or injury associated with cardiac calcium misregulation, for example, a cardiac or cardiovascular disease, disorder, condition or injury (e.g., cardiomyopathy, cardiac arrythmia, heart failure). In certain embodiments, the disease, disorder, condition or injury is cardiomyopathy, heart failure, or arrhythmia. In certain embodiments, cardiomyopathy is genetic, including PLN p.Arg14del, Arg9Cys (R9C), and Arg25Cys (R25C) mutations. In certain embodiments, cardiomyopathy is dilated cardiomyopathy (DCM). In certain embodiments, DCM is genetic, including TTN. LMNA, RBM20, SCN5A. MYH7. TNNT2, and TPM1 mutations. In certain embodiments, DCM is arrhythmogenic DCM. In certain embodiments, heart failure is heart failure with preserved ejection fraction (HFpEF), heart failure with reduced ejection fraction (HFrEF), acute heart failure, or worsening of chronic heart failure. In certain embodiments, arrhythmia is ventricular tachycardia (vtac) or ventricular fibrillation (vfib). In certain embodiments, an oligomeric compound, modified oligonucleotide, or oligomeric duplex is for use in improving cardiac function, cardiovascular death, cardiac dilation, cardiac fibrosis, low voltage ECG, diastolic calcium uptake, ejection fraction (EF), left ventricular ejection fraction (LVEF), left ventricular end systolic volume (LVESV), left ventricular end diastolic volume (LVEDV), mitral valve flow profile, left ventricle (LV) strain, left ventricle (LV) strain rate, infarct size, heart failure hospitalization, 6 minute walk test (6MWT), the Kansas City Cardiomyopathy Questionnaire Score (KCCQS), heart rate, or heart rhythm associated with cardiomyopathy, heart failure, or arrhythmia.

Certain embodiments are drawn to an oligomeric compound, modified oligonucleotide, or oligomeric duplex, any of which comprising a modified antisense oligonucleotide comprising or consisting of a region having a nucleobase sequence complementary to a nucleobase sequence in a PLN nucleic acid, for the manufacture or preparation of a medicament for ameliorating, or delaying or preventing development or progression of a disease, disorder, condition or injury and/or for ameliorating, preventing or delaying the onset of one or more symptoms of a disease, disorder, condition or injury, wherein the disease, disorder, condition or injury is associated with cardiac calcium misregulation, for example, a cardiac or cardiovascular disease, disorder, condition or injury (e.g., cardiomyopathy, cardiac arrythmia, heart failure). In certain embodiments, the disease is cardiomyopathy, heart failure, or arrhythmia. In certain embodiments, an oligomeric compound, modified oligonucleotide, or oligomeric duplex is for the manufacture or preparation of a medicament for improving cardiac function, cardiovascular death, cardiac dilation, cardiac fibrosis, low voltage ECG, diastolic calcium uptake, ejection fraction (EF), left ventricular ejection fraction (LVEF), left ventricular end systolic volume (LVESV), left ventricular end diastolic volume (LVEDV), mitral valve flow profile, left ventricle (LV) strain, left ventricle (LV) strain rate, infarct size, heart failure hospitalization, 6 minute walk test (6MWT), the Kansas City Cardiomyopathy Questionnaire Score (KCCQS), heart rate, or heart rhythm associated with cardiomyopathy, heart failure, or arrhythmia. In certain embodiments, cardiomyopathy is genetic, including p.Arg14del, Arg9Cys (R9C), and Arg25Cys (R25C) mutations. In certain embodiments, cardiomyopathy is dilated cardiomyopathy (DCM). In certain embodiments, DCM is genetic, including TTN, LMNA, RBM20, SCN5A, MYH7, TNNT2, and TPM1 mutations. In certain embodiments, DCM is arrhythmogenic DCM. In certain embodiments, heart failure is heart failure with preserved ejection fraction (HFpEF), heart failure with reduced ejection fraction (HFrEF), acute heart failure, or worsening of chronic heart failure. In certain embodiments, arrhythmia is ventricular tachycardia (vtac) or ventricular fibrillation (vfib).

Certain embodiments are drawn to an oligomeric compound, modified oligonucleotide, or oligomeric duplex, any of which comprising a modified antisense oligonucleotide comprising or consisting of a region having a nucleobase sequence complementary to a nucleobase sequence in a PLN nucleic acid, for the manufacture or preparation of a medicament for treating a disease, disorder, condition or injury associated with cardiac calcium misregulation, for example, a cardiac or cardiovascular disease, disorder, condition or injury (e.g., cardiomyopathy, cardiac arrythmia, heart failure). In certain embodiments, cardiomyopathy is genEtic, including PLN p.Arg14del, Arg9Cys (R9C), and Arg25Cys (R25C) mutations. In certain embodiments, cardiomyopathy is dilated cardiomyopathy (DCM). In certain embodiments, DCM is genetic, including TTN, LMNA, RBM20, SCN5A, MYH7, TNNT2, and TPM1 mutations. In certain embodiments, DCM is arrhythmogenic DCM. In certain embodiments, heart failure is heart failure with preserved ejection fraction (HFpEF), heart failure with reduced ejection fraction (HFrEF), acute heart failure, or worsening of chronic heart failure. In certain embodiments, arrhythmia is ventricular tachycardia (vtac) or ventricular fibrillation (vfib).

In certain embodiments, prophylactic administration of an oligomeric compound, modified antisense oligonucleotide, or oligomeric duplex or composition provided herein to a subject at risk for cardiomyopathy, heart failure, or arrhythmia, is able to prevent, ameliorate, postpone or delay a symptom and/or development or progression of cardiomyopathy progression and/or heart failure. In certain embodiments, an oligomeric compound, modified oligonucleotide, or oligomeric duplex is for the manufacture or preparation of a medicament for improving cardiac function, cardiovascular death, cardiac dilation, cardiac fibrosis, low voltage ECG, diastolic calcium uptake, ejection fraction (EF), left ventricular ejection fraction (LVEF), left ventricular end systolic volume (LVESV), left ventricular end diastolic volume (LVEDV), mitral valve flow profile, left ventricle (LV) strain, left ventricle (LV) strain rate, infarct size, heart failure hospitalization, 6 minute walk test (6MWT), the Kansas City Cardiomyopathy Questionnaire Score (KCCQS), heart rate, or heart rhythm associated with cardiomyopathy, heart failure, or arrhythmia.

In any of the methods or uses described herein, the oligomeric compound, modified oligonucleotide, oligomeric duplex or antisense compound can be any described herein.

In some embodiments an oligomeric compound or oligomeric duplex of the invention has PLN RNA and/or protein reduction activity, and, in particular embodiments, cardiac PLN RNA and/or protein reduction activity, that is comparable to or greater than the PLN RNA and/or protein reduction activity of a comparator compound, e.g., having one or two modified oligonucleotides having the same or similar nucleobase sequence as the oligonucleotide(s) of the oligomeric compound or oligomeric duplex provided herein but having different modifications and/or motifs (e.g., sugar motif, internucleoside linkage motif). In certain embodiments, the comparator compound comprises a modified oligonucleotide that is complementary to the same or a similar PLN target region as the modified oligonucleotide of an oligomeric compound or oligomeric duplex provided herein. In certain embodiments, the comparator compound comprises a modified oligonucleotide that is complementary to a target region that is different from the target region to which a modified oligonucleotide of the oligomeric compound or oligomeric duplex provided herein is complementary. In certain embodiments, a comparator compound lacks a conjugate group or includes a different conjugate group compared to an oligomeric compound or oligomeric duplex provided herein but is otherwise the same (or includes additional differences, e.g., modifications and/or motifs). In certain embodiments, a comparator compound lacks a terminal group or includes a different terminal group compared to an oligomeric compound or oligomeric duplex provided herein but is otherwise the same (or includes additional differences, e.g., modifications and/or motifs). In certain embodiments an oligomeric compound or oligomeric duplex of the invention has cardiomyocyte PLN RNA and/or protein reduction activity that is comparable to, or greater than the cardiomyocyte PLN RNA and/or protein reduction activity of a comparator compound, e.g., having the same or similar nucleobase sequence and different modifications.

Methods of detecting the level of and/or measuring the amount of PLN RNA and/or protein in a cell, organ, tissue, system or subject (e.g., animal) are described herein and/or known in the art. In some embodiments, the amount of PLN RNA is reduced by at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% in a cell (e.g., cardiomyocyte), organ (e.g., heart), tissue, system or subject (e.g., animal) that has been contacted with or administered an oligomeric compound or oligomeric duplex of the invention provided herein (or a composition comprising such oligomeric compound or oligomeric duplex) compared to a control (e.g., a cell, organ, tissue, system or subject that had not been contacted with or administered the oligomeric compound or duplex, or was contacted with or administered a control substance (e.g., PBS)). In certain embodiments, the detectable amount of PLN RNA may be reduced by about 70% to about 85%, or about 75% to about 85%, or up to about 90%, or up to about 85%. In some embodiments, the percentage of PLN RNA decrease or reduction in a cell (e.g., a cardiomyocyte), organ (e.g., a heart), tissue (e.g., muscle, cardiac muscle), system or subject (e.g., animal) contacted with or administered an oligomeric compound, oligomeric duplex or composition provided herein is 0.1% to 30% greater or less than, 0.1% to 25% greater or less than, 0.1% to 20% greater or less than, 0.1% to 15% greater or less than, 0.1% to 10% greater or less than, or 0.1% to 5% greater or less than, 0.1% to 1% greater or less than, 5% to 40% greater or less than, 5% to 35% greater or less than, 10% to 40% greater or less than, at least 5% greater than, at least 10% greater than, at least 15% greater than, at least 20% greater than, at least 25% greater than, or at least 30% greater than the percentage of PLN RNA decrease or reduction in a cell (e.g., a cardiomyocyte), organ (e.g., a heart), tissue (e.g., muscle, cardiac muscle), system or subject (e.g., animal) contacted with or administered the same concentration or dose of a comparator compound, e.g., having the same or similar nucleobase sequence and different modifications.

In certain embodiments an oligomeric compound or oligomeric duplex of the invention has greater PLN RNA and/or protein reduction activity (i.e., greater specificity of action) in a target cell/organ/tissue/system (e.g., muscle, cardiac muscle cell or cardiac cell/organ/tissue/system) than in a non-target or off-target (e.g., liver or kidney) cell/organ/tissue/system. For example, in some embodiments administration of an oligomeric compound of the invention reduces the amount or activity of target cell/organ/tissue/system (e.g., cardiac cell/organ/tissue/system) PLN RNA and/or protein at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% compared to a control and has no, or a non-significant, effect, or significantly less effect on (e.g., reduction in) the amount or activity of PLN RNA and/or protein in a different or non- or off-target cell/organ/tissue/system, e.g., liver and/or kidney cells/tissue. In certain embodiments, the detectable amount of PLN RNA and/or PLN protein may be decreased by about 70% to about 85%, or about 75% to about 85%, or up to about 90%, or up to about 85%. In some embodiments administration of an oligomeric compound of the invention reduces the amount or activity of target cell/organ/tissue/system (e.g., muscle or cardiac cell/organ/tissue/system) PLN RNA and/or protein 15%-90%, or at least 20%, or at least 25%, or at least 30%, or at least 40%, or at least 50%, or at least 60%, or at least 70%, or at least 80%, or at least 90% more than it reduces the amount or activity of PLN RNA and/or protein in liver and/or kidney cells/tissue.

In some embodiments an oligomeric compound or oligomeric duplex of the invention has PLN RNA and/or PLN protein reduction activity, and, in particular embodiments, cardiac PLN RNA and/or PLN protein reduction activity, that is comparable to or greater than the PLN RNA and/or PLN protein reduction activity of a comparator compound, e.g., having one or two modified oligonucleotides having the same or similar nucleobase sequence as the oligonucleotide (s) of the oligomeric compound or oligomeric duplex provided herein but having different modifications and/or motifs (e.g., sugar motif, internucleoside linkage motif), and/or conjugate group but that has a longer duration of action in a subject than the comparator compound. In such cases, the oligomeric compound or oligomeric duplex may be administered less frequently and/or at lower doses than a comparator compound. In some embodiments, the amount of PLN RNA and/or PLN protein is reduced by at least 10%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% in a cell (e.g., cardiomyocyte), organ (e.g., heart), tissue, system or subject (e.g., animal) that has been contacted with or administered an oligomeric compound or oligomeric duplex of the invention provided herein (or a composition comprising such oligomeric compound or oligomeric duplex) compared to a control (e.g., a cell, organ, tissue, system or subject that had not been contacted with or administered the oligomeric compound or duplex, or was contacted with or administered a control substance (e.g., PBS)). In certain embodiments, the detectable amount of PLN RNA and/or PLN protein may be reduced by about 70% to about 85%, or about 75% to about 85%, or up to about 90%, or up to about 85%.

VI. Pharmaceutical Compositions

In certain embodiments, described herein are pharmaceutical compositions comprising one or more oligomeric compounds or oligomeric duplexes of the invention, wherein each oligomeric compound or duplex comprises or consists of a modified oligonucleotide. In certain embodiments, the one or more oligomeric compounds or oligomeric duplex each consists of or comprises an antisense compound. In certain embodiments, a pharmaceutical composition comprises a pharmaceutically acceptable diluent or carrier. In certain embodiments, a pharmaceutical composition comprises or consists of a sterile saline solution and one or more compound or duplex of the invention. In certain embodiments, the sterile saline is pharmaceutical grade saline. In certain embodiments, a pharmaceutical composition comprises or consists of one or more compound or duplex of the invention and sterile water. In certain embodiments, the sterile water is pharmaceutical grade water. In certain embodiments, a pharmaceutical composition comprises or consists of one or more compound or duplex of the invention and phosphate-buffered saline (PBS). In certain embodiments, sterile PBS is pharmaceutical grade PBS.

In certain embodiments, a pharmaceutical composition comprises an oligomeric compound or oligomeric duplex comprising or consisting of a modified oligonucleotide; and sterile saline. In certain such embodiments, a pharmaceutical composition consists of such oligomeric compound or oligomeric duplex and sterile saline. In certain embodiments, a pharmaceutical composition consists essentially of such oligomeric compound or oligomeric duplex and sterile saline. In certain embodiments, the sterile saline is sterile PBS. In certain embodiments, the sterile saline is pharmaceutical grade.

In certain embodiments, a pharmaceutical composition comprises an oligomeric compound or oligomeric duplex comprising or consisting of a modified oligonucleotide; and sterile saline. In certain such embodiments, a pharmaceutical composition consists of such modified oligonucleotide or oligomeric duplex and sterile saline. In certain embodiments, a pharmaceutical composition consists essentially of such modified oligonucleotide and sterile saline. In certain embodiments, the sterile saline is sterile PBS. In certain embodiments, the sterile saline is pharmaceutical grade.

In certain embodiments, a pharmaceutical composition comprises an oligomeric compound or oligomeric duplex comprising or consisting of a modified oligonucleotide and sterile saline. In certain embodiments, a pharmaceutical composition consists of an oligomeric compound or oligomeric duplex comprising or consisting of a modified oligonucleotide and sterile saline. In certain embodiments, a pharmaceutical composition consists essentially of an oligomeric compound or oligomeric duplex comprising or consisting of a modified oligonucleotide and sterile saline. In certain embodiments, the sterile saline is sterile PBS. In certain embodiments, the sterile saline is pharmaceutical grade.

In certain embodiments, pharmaceutical compositions comprise one or more oligomeric compound or oligomeric duplex of the invention and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, an oligomeric compound or oligomeric duplex of the invention may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound or oligomeric duplex of the invention encompass any pharmaceutically acceptable salts of the compound or duplex, esters of the compound or duplex, or salts of such esters. As used herein "pharmaceutically acceptable salts" means physiologically and pharmaceutically acceptable salts of compounds. Pharmaceutically acceptable salts retain the desired biological activity of the parent compound and do not impart undesired toxicological effects thereto. In certain embodiments, pharmaceutical compositions comprising an oligomeric compound or oligomeric duplex of the invention comprising one or more oligonucleotide, upon administration to a subject, including a human, are capable of providing (directly or indirectly) the biologically active metabolite or residue thereof. Accordingly, for example, the disclosure is also drawn to pharmaceutically acceptable salts of oligomeric compounds or oligomeric duplexes of the invention, prodrugs, pharmaceutically acceptable salts of such prodrugs, and other bioequivalents. In certain embodiments, pharmaceutically acceptable salts comprise inorganic salts, such as monovalent or divalent inorganic salts. Suitable pharmaceutically acceptable salts include, but are not limited to, sodium, potassium, calcium, and magnesium salts.

In certain embodiments, oligomeric compounds or oligomeric duplexes of the invention are lyophilized and isolated, e.g., as sodium salts. In certain embodiments, a sodium salt of a compound or duplex of the invention is mixed with a pharmaceutically acceptable diluent. In certain embodiments, the pharmaceutically acceptable diluent comprises sterile saline, sterile water, or PBS. In certain embodiments, a sodium salt of an oligomeric compound or oligomeric duplex of the invention is mixed with PBS.

Lipid moieties have been used in nucleic acid therapies in a variety of methods. In certain methods, a nucleic acid, such as an oligomeric compound or oligomeric duplex of the invention comprising a nucleic acid, is introduced into preformed liposomes or lipoplexes made of mixtures of cationic lipids and neutral lipids. In certain methods, nucleic acid complexes with mono- or poly-cationic lipids are formed without the presence of a neutral lipid. In certain embodiments, a lipid moiety is selected to increase distribution of a pharmaceutical compound to a particular cell or tissue. In certain embodiments, a lipid moiety is selected to increase distribution of a pharmaceutical compound to fat tissue. In certain embodiments, a lipid moiety is selected to increase distribution of a pharmaceutical compound to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more compounds of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™: the fraction size of polyethylene glycol may be varied: other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), etc.). In certain of such embodiments, a pharmaceutical composition comprises a carrier or diluent and is formulated in aqueous solution, such as water or physiologically compatible buffers such as Hanks's solution. Ringer's solution, or physiological saline buffer. In certain embodiments, other ingredients are included (e.g., ingredients that aid in solubility or serve as preservatives). In certain embodiments, injectable suspensions are prepared using appropriate liquid carriers, diluents, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Under certain conditions, certain compounds disclosed herein act as acids. Although such compounds may be drawn or described in protonated (free acid) form, or ionized and in association with a cation (salt) form, aqueous solutions of such compounds exist in equilibrium among such forms. For example, a phosphodiester linkage of an oligonucleotide in aqueous solution exists in equilibrium among free acid, anion and salt forms. Unless otherwise indicated, compounds described herein are intended to include all such forms. Moreover, certain oligonucleotides have several such linkages, each of which is in equilibrium. Thus, oligonucleotides in solution exist in an ensemble of forms at multiple positions all at equilibrium. The term "oligonucleotide" herein is intended to include all such forms. Drawn structures necessarily depict a single form. Nevertheless, unless otherwise indicated, such drawings are likewise intended to include corresponding forms. Herein, a structure depicting the free acid of a compound followed by the term "or a pharmaceutically acceptable salt thereof" expressly includes all such forms that may be fully or partially protonated/de-protonated/in association with a cation or a combination of cations. In certain embodiments, one or more specific cation is identified. The cations include, but are not limited to, sodium, potassium, calcium, and magnesium. In certain embodiments, a structure depicting the free acid of a compound followed by the term "or a pharmaceutically acceptable salt thereof" expressly includes all such forms that may be fully or partially protonated/de-protonated/in association with one or more cations selected from sodium, potassium, calcium, and magnesium.

In certain embodiments, oligomeric compounds, modified oligonucleotides, or oligomeric duplexes of the invention are in aqueous solution with sodium. In certain embodiments, oligomeric compounds, modified oligonucleotides or oligomeric duplexes of the invention are in aqueous solution with potassium. In certain embodiments, oligomeric compounds, modified oligonucleotides or oligomeric duplexes of the invention are in PBS. In certain embodiments, oligomeric compounds, modified oligonucleotides or oligomeric duplexes of the invention are in water. In certain such embodiments, the pH of a solution is adjusted with NaOH and/or HCl to achieve a desired pH.

Herein, certain specific doses are described. A dose may be in the form of a dosage unit. For clarity, a dose (or dosage unit) of a compound of the invention (e.g., modified oligonucleotide, oligomeric duplex, antisense compound) in milligrams indicates the mass of the free acid form of the compound. As described herein, in aqueous solution, the free acid is in equilibrium with anionic and salt forms. However, for the purpose of calculating dose, it is assumed that the compound of the invention (e.g., modified oligonucleotide, oligomeric duplex, antisense compound) exists as a solvent-free, sodium-acetate free, anhydrous, free acid. In certain embodiments, where a compound of the invention (e.g., modified oligonucleotide, oligomeric duplex, antisense compound) is in solution comprising sodium (e.g., saline), the compound may be partially or fully de-protonated and in association with sodium ions. However, the mass of the protons is nevertheless counted toward the weight of the dose, and the mass of the sodium ions is not counted toward the weight of the dose. When a compound of the invention comprises a conjugate group, the mass of the conjugate group is included in calculating the dose of such compound. If the conjugate group also has an acid, the conjugate group is likewise assumed to be fully protonated for the purpose of calculating dose.

VII. Compounds

Table A includes nucleobase sequences for oligomeric compounds and oligomeric duplexes that were previously described in International Patent Application Publication No. WO/2022/173976. Each of those oligomeric duplexes contains an antisense sequence that is complementary to a sequence in a human PLN nucleic acid and a sense sequence that is complementary to the antisense sequence. Each of the antisense oligonucleotides having the nucleobase sequences listed in Table A is described in International Patent Application Publication No. WO/2022/173976 as having a sugar motif (from 5' to 3') of: yfyfyfyfyfyfyfyfyfyvy, and each of the sense oligonucleotides having the nucleobase sequences listed in Table A is described in International Patent Application Publication No. WO/2022/173976 as having a sugar motif (from 5' to 3') of: fyfyfyfyfyfyfyfyfyf, wherein each "y" represents a 2'-OMe sugar moiety and each "f" represents a 2-fluoro ribosyl moiety.

In certain embodiments, provided herein are reduced fluorine content oligomeric compounds and oligomeric duplexes. In some embodiments, a reduced fluorine content oligomeric compound comprises an oligonucleotide (e.g., an antisense oligonucleotide) which has a nucleobase sequence complementary to a sequence in a PLN nucleic acid, e.g., a human PLN nucleic acid, or an oligonucleotide (e.g., a sense oligonucleotide) which has a nucleobase sequence complementary to a sequence of an oligonucleotide which has a nucleobase sequence complementary to a sequence in a PLN nucleic acid, e.g., a human PLN nucleic acid. In some embodiments, a reduced fluorine content oligomeric duplex comprises a first modified oligonucleotide (e.g., an antisense oligonucleotide), which has a nucleobase sequence complementary to a sequence of a PLN nucleic acid (e.g., human PLN nucleic acid), and a second modified oligonucleotide (e.g., a sense oligonucleotide), which has a nucleobase sequence complementary to a sequence of the first modified oligonucleotide. In some embodiments, the reduced fluorine content oligomeric compounds and oligomeric duplexes provided herein, which may be preferable to compounds containing more fluorine atoms due to improved properties, e.g., decreased off-target actions and/or improved tolerability, have PLN RNA and/or protein reduction activity that is comparable to or greater than that of a comparator compound containing more fluorine atoms (e.g., a compound having 50% or more, 45% or more, or 40% or more fluorine-containing nucleosides). In some embodiments, an oligomeric compound or oligomeric duplex having reduced fluorine content provided herein comprises a modified oligonucleotide or a first modified oligonucleotide (e.g., antisense oligonucleotide) which has a nucleobase sequence complementary to a sequence in a PLN nucleic acid, having reduced fluorine content (e.g., fewer than 45%, fewer than 40%, fewer than 35%, fewer than 30%, fewer than 25%, fewer than 20%, fewer than 15%, or fewer than 10% of nucleosides comprising a fluorine atom, e.g., a modified sugar moiety containing fluorine) of nucleosides comprising a fluorine atom, such as e.g., a modified sugar moiety containing fluorine) and/or a modified oligonucleotide or a second modified oligonucleotide (e.g., sense oligonucleotide) comprising or consisting of a region that has a nucleobase sequence complementary to the first oligonucleotide, or to a sequence that is complementary to a sequence in a PLN nucleic acid, having reduced fluorine content (e.g., fewer than 45%, fewer than 40%, fewer than 35%, fewer than 30%, fewer than 25%, fewer than 20%, fewer than 15%, or fewer than 10% of nucleosides comprising a fluorine atom, e.g., a modified sugar moiety containing fluoric).

In certain embodiments, an oligomeric compound or oligomeric duplex having reduced fluorine content provided herein comprises a modified oligonucleotide or first modified oligonucleotide (e.g., antisense oligonucleotide) having reduced fluorine content (e.g., fewer than 45%, fewer than 40%, fewer than 35%, fewer than 30%, fewer than 25%, fewer than 20%, or fewer than 15% of nucleosides comprising a fluorine atom, e.g., a modified sugar moiety containing fluorine). In certain such embodiments, the second modified oligonucleotide (e.g., sense oligonucleotide) of such oligomeric duplexes has a reduced fluorine content (e.g., fewer than 45%, fewer than 40%, fewer than 35%, fewer than 30%, fewer than 25%, fewer than 20%, fewer than 15%, or fewer than 10% of nucleosides comprising a fluorine atom, e.g., a modified sugar moiety containing fluorine). In certain embodiments, an oligomeric compound or oligomeric duplex provided herein comprises an oligonucleotide or first modified oligonucleotide (e.g., an antisense oligonucleotide) having reduced fluorine content (e.g., fewer than 45%, fewer than 40%, fewer than 35%, fewer than 30%, fewer than 25%, fewer than 20%, fewer than 15%, or fewer than 10% of nucleosides comprising a fluorine atom, e.g., a modified sugar moiety containing fluorine) comprising or consisting of a region having a nucleobase sequence that is at least 85%, at least 90%, at least 95%, or at least 99% complementary to an equal length portion of a PLN nucleic acid (e.g., a sequence in SEQ ID NO: 1). In certain embodiments, an oligomeric compound or oligomeric duplex provided herein comprises an oligonucleotide or a first modified oligonucleotide (e.g., an antisense oligonucleotide) having reduced fluorine content (e.g., fewer than 45%, fewer than 40%, fewer than 35%, fewer than 30%, fewer than 25%, fewer than 20%, fewer than 15%, or fewer than 10% of nucleosides comprising a fluorine atom, e.g., a modified sugar moiety containing fluorine) and having a nucleobase sequence selected from among the sequences provided in Table A, Table B1 or SEQ ID NOS: 3-314, 627-782, 939-976, 1033-1038, 1254-1255, and 1258-1287. In particular embodiments, such oligomeric compounds or oligomeric duplexes comprise an oligonucleotide or second modified oligonucleotide (e.g., a sense oligonucleotide), comprising or consisting of a region having a nucleobase sequence, e.g., a sequence complementary to the first modified oligonucleotide, selected from among the sequences provided in Table A, Table B2 or SEQ ID NOS: 315-626, 783-938, 977-1016, 1027-1032, 1256-1257, and 1288-1290. In some such embodiments, the modified oligonucleotide or second modified oligonucleotide has a reduced fluorine content (e.g., fewer than 40%, fewer than 35%, fewer than 30%, fewer than 25%, fewer than 20%, fewer than 15%, or fewer than 10% of nucleosides comprising a fluorine atom, e.g., a modified sugar moiety containing fluorine). In certain embodiments, an oligomeric compound or oligomeric duplex provided herein comprises an oligonucleotide or a first modified oligonucleotide (e.g., an antisense oligonucleotide) having reduced fluorine content (e.g., fewer than 45%, fewer than 40%, fewer than 35%, fewer than 30%, fewer than 25%, fewer than 20%, fewer than 15%, or fewer than 10% of nucleosides comprising a fluorine atom, e.g., a modified sugar moiety containing fluorine) and having a nucleobase sequence selected from among the sequences of SEQ ID NOS: 29, 171, 176, 967, 968, 971, 972, 974, 975, 1033-1038, 1254, 1255, and 1258-1287. In particular embodiments, such oligomeric compounds or oligomeric duplexes comprise an oligonucleotide or second modified oligonucleotide (e.g., a sense oligonucleotide), comprising or consisting of a region having a nucleobase sequence, e.g., a sequence complementary to the first modified oligonucle-otide, selected from among the sequences of SEQ ID NOS: 341, 483, 488, 1011-1016, 1027-1032, 1256-1257, and 1288-1290. In some such embodiments, the modified oligonucleotide or second modified oligonucleotide has a reduced fluorine content (e.g., fewer than 40%, fewer than 35%, fewer than 30%, fewer than 25%, fewer than 20%, fewer than 15%, or fewer than 10% of nucleosides comprising a fluorine atom, e.g., a modified sugar moiety containing fluorine).

In some embodiments, an oligomeric compound or oligomeric duplex having reduced fluorine content provided herein comprises a conjugate group. In some such embodiments of oligomeric duplexes provided herein, the conjugate group is attached to the first (e.g., antisense) or second (e.g., sense) modified oligonucleotide of the oligomeric duplex. In some embodiments, the conjugate group is attached to the 5'- or 3'-end of the modified oligonucleotide of an oligomeric compound or of the first or second modified oligonucleotide of an oligomeric duplex, or the 5'- or 3'-terminal nucleoside of the modified oligonucleotide of an oligomeric compound or of the first or second modified oligonucleotide of an oligomeric duplex. In particular embodiments, the conjugate group is attached to the second modified oligonucleotide (e.g., sense oligonucleotide), for example, the 5'- or 3'-terminal nucleoside of the second modified oligonucleotide, of an oligomeric duplex. In particular embodiments, the conjugate group is attached to the 5'-terminal nucleoside of the alkyl, C11 alkyl. C9 alkyl, C8 alkyl, C7 alkyl, C6 alkyl, or C5 alkyl, wherein the alkyl chain optionally has one or more unsaturated bonds. In some embodiments, the conjugate group comprises a 6-palmitamidohexyl moiety, 6-amino-hexyl, or a 2-(hydroxymethyl)-6-palmitamidohexyl moiety. In some embodiments, the conjugate moiety of the conjugate group has affinity for a transferrin receptor, e.g., a type 1 transferrin receptor, e.g., a peptide, polypeptide, protein, and low molecular weight molecule. Examples of such conjugate moieties include, but are not limited to, a transferrin receptor ligand, an antibody, a fragment of an antibody, and a drug, any of which recognizes and/or binds to a transferrin receptor. In some embodiments, the conjugate moiety is a bicycle peptide compound, such as, for example, a bicycle ligand that binds to a transferrin receptor, e.g., a type 1 transferrin receptor, including those previously described in International Patent Application Publication No. WO2022/101633, which is incorporated herein by reference, and those previously described in International Patent Application Publication No. WO2023/056388, which is hereby incorporated by reference. In some embodiments, the bicycle ligand comprises an amino acid sequence of SEQ ID NO: 1045, wherein each cysteine forms a covalent bond with the molecular scaffold 1,1',1''-(1,3,5-triazinane-1,3,5-triyl)tris(2-bromoethanone) (TATB). In some embodiments, a bicycle ligand or a conjugate group comprising a bicycle ligand has the following structure:

second modified oligonucleotide. In some embodiments, the conjugate group comprises an active drug substance, a small molecule drug, an aliphatic chain, a lipid, a peptide, a protein, a hydrocarbon, a polyamine, a polyamide, a polyether, a thioether, an aptamer, an antibody, an antibody fragment, a vitamin, a fatty acid, a carbohydrate, an intercalator, a reporter molecule, or an alkyl moiety, e.g., a C22 alkyl, C20 alkyl, C17 alkyl. C16 alkyl, C10 alkyl, C21 alkyl, C19 alkyl, C18 alkyl, C15 alkyl, C14 alkyl, C13 alkyl, C12 or a salt thereof, wherein Q is $N_3$ (BCY17901, SEQ ID NO: 1045), $NH_2$ (BCY21757, SEQ ID NO: 1202), SH (BCY21758, SEQ ID NO: 1203), a conjugate linker, or a conjugate linker covalently connected to the modified oligonucleotide or the first modified oligonucleotide (e.g., antisense oligonucleotide) or second modified oligonucleotide (e.g., sense oligonucleotide). In some embodiments, the conjugate group has the following structure (SEQ ID NO: 1291):

and is attached to the modified oligonucleotide of the oligomeric compound or the first modified oligonucleotide (e.g., antisense oligonucleotide) or the second modified oligonucleotide (e.g., sense oligonucleotide) of the oligomeric duplex through a phosphodiester bond, e.g., through a phosphodiester bond with the 5'-terminal nucleoside of the modified oligonucleotide of the oligomeric compound or the second modified oligonucleotide of the oligomeric duplex. In some embodiments, the conjugate group has the following structure (SEQ ID NO: 1292):

and is attached to the modified oligonucleotide of the oligomeric compound or the first modified oligonucleotide (e.g., antisense oligonucleotide) or the second modified oligonucleotide (e.g., sense oligonucleotide) of the oligomeric duplex through a phosphodiester bond, e.g., through a phosphodiester bond with the 3'-terminal nucleoside of the modified oligonucleotide of the oligomeric compound or the second modified oligonucleotide of the oligomeric duplex.

As noted herein, in certain embodiments, an oligomeric compound or oligomeric duplex provided herein contains a modified oligonucleotide or a first modified oligonucleotide (e.g., antisense oligonucleotide) comprising or consisting of a sequence of linked nucleosides having reduced fluorine content. In some embodiments, fewer than 40% of the nucleosides of the modified oligonucleotide or first modified oligonucleotide (e.g., antisense oligonucleotide) contain a fluorine atom, e.g., a modified sugar moiety containing fluorine. In certain embodiments, fewer than 35%, fewer than 30%, fewer than 25%, fewer than 20%, fewer than 15%, fewer than 14%, fewer than 13%, fewer than 12%, fewer than 10%, fewer than 5%, or fewer than 1% of the nucleosides in the modified oligonucleotide or first modified oligonucleotide (e.g., antisense oligonucleotide) contain a fluorine atom (e.g., a modified sugar moiety containing fluorine). In certain embodiments, such an oligomeric compound or oligomeric duplex provided herein contains a second modified oligonucleotide, or a second modified sense oligonucleotide (e.g., sense oligonucleotide) comprising or consisting of linked nucleosides having reduced fluorine content. In some embodiments, fewer than 40% of the nucleosides of the modified oligonucleotide or second modified oligonucleotide contain a fluorine atom, e.g., a modified sugar moiety containing fluorine. In certain embodiments, fewer than 35%, fewer than 30%, fewer than 25%, fewer than 20%, fewer than 15%, fewer than 14%, fewer than 13%, fewer than 12%, fewer than 10%, fewer than 5%, or fewer than 1% of the nucleosides in the second modified oligonucleotide or sense modified oligonucleotide contain a fluorine atom (e.g., a modified sugar moiety containing fluorine). In particular embodiments, the total fluorine content of the oligomeric compound or oligomeric duplex is reduced (e.g., less than 40% of the total nucleobases in the compound comprising a fluorine atom, a modified sugar moiety containing fluorine). In certain embodiments, less than 35%, less than 30%, less than 25%, less than 20%, less than 15%, less than 14%, less than 13%, less than 12%, less than 10%, less than 5%, or less than 1% of the nucleosides in the oligomeric compound or oligomeric duplex having a reduced fluorine content contain a fluorine atom (e.g., a modified sugar moiety containing fluorine). In some embodiments, no more than 8, no more than 7, no more than 6, no more than 5, no more than 4, no more than 2 or no more than 1 nucleoside(s) in an oligomeric compound or oligomeric duplex having reduced fluorine content provided herein contain a fluorine atom, e.g., a modified sugar moiety containing fluorine.

In some embodiments, an oligomeric compound or oligomeric duplex having a reduced fluorine content provided herein has a modified oligonucleotide or a first modified oligonucleotide (e.g., antisense oligonucleotide) containing one or more nucleosides containing a fluorine atom (e.g., a modified sugar moiety containing fluorine). In some embodiments, such an oligomeric compound or oligomeric duplex provided herein has a modified oligonucleotide or a first modified oligonucleotide (e.g., antisense oligonucleotide) containing one, two, three or four nucleosides containing a fluorine atom. In some embodiments, the nucleosides of the modified oligonucleotide or a first modified oligonucleotide that contain a fluorine atom contain a modified sugar moiety containing a fluorine atom, e.g., a 2'-fluoro sugar moiety, or sugar surrogate containing a fluorine atom, e.g., a 3-fluoro-hexitol sugar moiety. In some embodiments, the modified oligonucleotide or first modified oligonucleotide (e.g., antisense oligonucleotide) of an oligomeric compound or oligomeric duplex having reduced fluorine content provided herein does not contain any fluorine atoms. In certain embodiments, no more than three nucleosides, or no more than two nucleosides, in the modified oligonucleotide or first modified oligonucleotide (e.g., antisense oligonucleotide) contain a fluorine atom (e.g., a modified sugar moiety containing fluorine). In certain embodiments, no more than three nucleosides in the modified oligonucleotide or first modified oligonucleotide (e.g., antisense oligonucleotide) between and including the second and twenty-first nucleosides counting from the 5' terminus of the modified oligonucleotide or first modified oligonucleotide contain a fluorine atom (e.g., a modified sugar moiety containing fluorine). In particular embodiments, no more than two nucleosides in the modified oligonucleotide or first modified oligonucleotide (e.g., antisense oligonucleotide) between and including the third and twenty-first nucleosides counting from the 5' terminus of the modified oligonucleotide or first modified oligonucleotide contain a fluorine atom (e.g., a modified sugar moiety containing fluorine). In some embodiments, at least 85%, or at least 90%, or at least 95%, or at least 99%, or all of the nucleosides of the modified oligonucleotide or first modified oligonucleotide (e.g., antisense oligonucleotide) contain a 2'-modified sugar moiety and one or more of the nucleosides contain a fluorine atom (e.g., a 2-fluoro sugar moiety). In some such embodiments, one or more of the nucleosides contain a 2'-OMe sugar moiety or a 2'-MOE sugar moiety. In some embodiments, any of the nucleosides that do not contain a fluorine atom independently contain a 2'-OMe sugar moiety or a 2'-MOE sugar moiety. In some embodiments, the 5'- and/or 3'-terminal nucleosides of the modified oligonucleotide or first modified oligonucleotide (e.g., antisense oligonucleotide) comprise a 2'-MOE sugar moiety. In some embodiments, the nucleoside immediately 5' of the 3'-terminal nucleoside of the modified oligonucleotide or first modified oligonucleotide (e.g., antisense oligonucleotide) comprises a 2-MOE sugar moiety. In particular embodiments, the 5'- and 3'-terminal nucleosides of the modified oligonucleotide or first modified oligonucleotide comprise a 2'-MOE sugar moiety and the nucleoside immediately 5' of the 3'-terminal nucleoside of the modified oligonucleotide or first modified oligonucleotide comprises a 2'-MOE sugar moiety. In some embodiments, at least 10%, at least 20%, at least 30%, at least 40%, at least 50% or at least 60%, or more of the nucleosides of the modified oligonucleotide or first modified oligonucleotide (e.g., antisense oligonucleotide) comprise a 2'-OMe sugar moiety. In particular embodiments, the 3'-terminal nucleoside of the modified oligonucleotide or first modified oligonucleotide (e.g., antisense oligonucleotide) comprises a 2'-OMe sugar moiety and/or the nucleoside immediately 5' of the 3'-terminal nucleoside of the modified oligonucleotide or first modified oligonucleotide comprises a 2'-OMe sugar moiety.

In some embodiments, an oligomeric compound or oligomeric duplex having a reduced fluorine content provided herein has a modified oligonucleotide or first modified oligonucleotide (e.g., antisense oligonucleotide) containing no more than four nucleosides containing a fluorine atom (e.g., a modified sugar moiety containing fluorine). In some such embodiments, the number of nucleosides in the modified oligonucleotide or first modified oligonucleotide is 23, 22, or 21. In some such embodiments, the nucleobase sequence of the modified oligonucleotide or first modified oligonucleotide (e.g., antisense oligonucleotide) comprises or consists of a nucleobase sequence selected from among the sequences provided in Table A. Table B1 or SEQ ID NOS: 3-314, 627-782, 939-976, 1033-1038, 1254-1255, and 1258-1287. Examples of sugar motifs for such a modified oligonucleotide or first modified oligonucleotide (e.g., antisense oligonucleotide) of an oligomeric compound or oligomeric duplex provided herein include, but are not limited to (from 5' to 3'): efyyyfyyyyyyyfyfyyyyyee, efyyyfyyyyyyyfyfyyyyyyy, efyyyfyyyyyyyfyfyyyyye, e[FHNA]yyyfyyyyyyyfyfyyyyyee, e[FHNA]yyyfyyyyyyyfyfyyyyyyy, e[FHNA]yyyfyyyyyyyfyfyyyyye, e[FHNA]yyyfyyyyyyyfyfyyyyy, efyyyfyyyyyyyfyfyyyyyey, efyyyfyyyyyyyfyfyyyyye, efyyyfyyyyyyyfyfyyyee, and efyyyfyyyyyyyfyfyyyyy, wherein each "y" represents a 2'-OMe sugar moiety, each "c" represents a 2'-MOE sugar moiety, each "f" represents a 2'-fluoro sugar moiety, and each "[FHNA]" represents a 3'-fluoro-hexitol sugar moiety. In some embodiments, an oligomeric compound or oligomeric duplex having a reduced fluorine content provided herein has a modified oligonucleotide or first modified oligonucleotide (e.g., antisense oligonucleotide) containing no more than three nucleosides containing a fluorine atom (e.g., a modified sugar moiety containing fluorine). In some such embodiments, the number of nucleosides in the modified oligonucleotide or first modified oligonucleotide is 23, 22, or 21. In some such embodiments, the nucleobase sequence of the modified oligonucleotide or first modified oligonucleotide (e.g., antisense oligonucleotide) comprises or consists of a nucleobase sequence selected from among the sequences provided in Table A. Table B1 or SEQ ID NOS: 3-314, 627-782, 939-976, 1033-1038, 1254-1255, and 1258-1287. In some such embodiments, the nucleobase sequence of the modified oligonucleotide or first modified oligonucleotide (e.g., antisense oligonucleotide) comprises or consists of a nucleobase sequence selected from among the nucleobase sequences of SEQ ID NOS: 29, 171, 176, 967, 968, 971, 972, 974, 975, 1033-1038, 1254, 1255, and 1258-1287. Examples of sugar motifs for such a modified oligonucleotide or first modified oligonucleotide of an oligomeric compound or oligomeric duplex provided herein include, but are not limited to, (from 5' to 3'): efyyyyyyyyyyyyfyfyyyyyee, efyyyyyyyyyyyyfyfyyyyyyy, efyyyyyyyyyyyyfyfyyyyye, efyyyyyyyyyyyyfyfyyyyyy, efyyyfyyyyyyyfyyyyyyyyy, and efyyyfyyyyyyyfyyyyyyyee, wherein each "y" represents a 2'-OMe sugar moiety, each "c" represents a 2'-MOE sugar moiety, and each "f" represents a 2'-fluoro sugar moiety. In some embodiments, an oligomeric compound or oligomeric duplex having a reduced fluorine content provided herein has a modified oligonucleotide or first modified oligonucleotide (e.g., antisense oligonucleotide) containing no more than two nucleosides containing a fluorine atom (e.g., a modified sugar moiety containing fluorine). In some such embodiments, the number of nucleosides in the modified oligonucleotide or first modified oligonucleotide is 23, 22, or 21. In some such embodiments, the nucleobase sequence of the modified oligonucleotide or first modified oligonucleotide (e.g., antisense oligonucleotide) comprises or consists of a nucleobase sequence selected from among the sequences provided in Table A. Table B1 or SEQ ID NOS: 3-314, 627-782, 939-976, 1033-1038, 1254-1255, and 1258-1287. In some such embodiments, the nucleobase sequence of the modified oligonucleotide or first modified oligonucleotide (e.g., antisense oligonucleotide) comprises or consists of a nucleobase sequence selected from among the nucleobase sequences of SEQ ID NOS: 29, 171, 176, 967, 968, 971, 972, 974, 975, 1033-1038, 1254, 1255, and 1258-1287. Examples of sugar motifs for such a modified oligonucleotide or first modified oligonucleotide of an oligomeric compound or oligomeric duplex provided herein include, but are not limited to, (from 5' to 3'): efyyyyyyyyyyyyfyyyyyyyee, efyyyyyyyyyyyyfyyyyyyyyy, efyyyyyyyyyyyyfyyyyyye, efyyyyyyyyyyyyfyyyyyyyy, e[FHNA]yyyyyyyyyyyy[FHNA]yyyyyyyee, e[FHNA]yyyyyyyyyyyy[FHNA]yyyyyyyyy, e[FHNA]yyyyyyyyyyyy[FHNA]yyyyyyyye, and e[FHNA]yyyyyyyyyyyy[FHNA]yyyyyyy; wherein each "y" represents a 2'-OMe sugar moiety, each "c" represents a 2'-MOE sugar moiety, each "f" represents a 2'-fluoro sugar moiety, and each "[FHNA]" represents a 3-fluoro-hexitol sugar moiety. In some embodiments, an oligomeric compound or oligomeric duplex provided herein comprises a modified oligonucleotide or first modified oligonucleotide (e.g., antisense oligonucleotide) comprising or consisting of a sequence of linked nucleosides having reduced fluorine content, such as, for example, any such sugar motifs set out herein, and having an internucleoside linkage motif containing one or more modified internucleoside linkages. In some such embodiments, the modified oligonucleotide or first modified oligonucleotide (e.g., antisense oligonucleotide) contains one or more phosphorothioate internucleoside linkages, such as, for example, 1, 2, 3, 4, 5 or 6 phosphorothioate internucleoside linkages. In some such embodiments, all the internucleoside linkages that are not phosphorothioate internucleoside linkages are phosphodiester internucleoside linkages.

In some such embodiments, the number of nucleosides in the modified oligonucleotide or first modified oligonucleotide (e.g., antisense oligonucleotide) is 23.22 or 21. Examples of internucleoside linkage motifs for a first modified oligonucleotide of an oligomeric compound provided herein include, but are not limited to ssooooooooooooooooooooss, ssoooosoooooooooooooooss, ssoosososooooooooooooooss, ssoooooooooooooooooooos, ssooooooooooooooooooo, and ssoooooooooooooooooooss.

In certain embodiments, a modified oligonucleotide or first modified oligonucleotide (e.g., antisense oligonucleotide) of an oligomeric compound or oligomeric duplex having a reduced fluorine content provided herein contains one or more 2-deoxynucleosides. In some embodiments, the one or more 2'-deoxynucleosides is/are in a region of the sequence of the modified oligonucleotide or first modified oligonucleotide (e.g., antisense oligonucleotide) that is between and includes the fifth and sixteenth, or the fifth and seventh, nucleosides counting from the 5' terminus of the modified oligonucleotide or first modified oligonucleotide. In particular embodiments, the one or more 2'-deoxynucleosides is one or more of the fifth, sixth and/or seventh nucleoside(s) counting from the 5' terminus of the modified oligonucleotide or first modified oligonucleotide (e.g., antisense oligonucleotide). In some embodiments, an oligomeric compound or oligomeric duplex having a reduced fluorine content provided herein has a modified oligonucleotide or first modified oligonucleotide (e.g., antisense oligonucleotide) containing no more than three 2'-deoxynucleosides. In particular embodiments, the modified oligonucleotide or first modified oligonucleotide (e.g., antisense oligonucleotide) contains no more than two 2'-deoxynucleosides. In some embodiments, the modified oligonucleotide or first modified oligonucleotide (e.g., antisense oligonucleotide) contains only one 2'-deoxynucleoside. In some embodiments, the modified oligonucleotide or first modified oligonucleotide (e.g., antisense oligonucleotide) does not contain any 2'-deoxynucleosides. In some embodiments, an oligomeric compound or oligomeric duplex having a reduced fluorine content provided herein has a modified oligonucleotide or first modified oligonucleotide (e.g., antisense oligonucleotide) containing one or more 2'-deoxy-nucleosides and one or more nucleosides containing a fluorine atom (e.g., a fluorine-containing modified sugar moiety e.g., a 2'-F sugar moiety). In some such embodiments, fewer than 20%, or fewer than 15%, of the nucleosides of the modified oligonucleotide or first modified oligonucleotide (e.g., antisense oligonucleotide) contain a fluorine atom. In particular embodiments, an oligomeric compound or oligomeric duplex having a reduced fluorine content provided herein has a modified oligonucleotide or first modified oligonucleotide (e.g., antisense oligonucleotide) containing one, two or three 2'-deoxynucleosides and one, two, or three nucleosides containing fluorine atom (e.g., a fluorine-containing modified sugar moiety e.g., a 2'-F sugar moiety). For example, in some embodiments, the modified oligonucleotide or first modified oligonucleotide (e.g., antisense oligonucleotide) contains one 2'-deoxynucleoside and three nucleosides containing a modified sugar moiety having a fluorine atom (e.g., a fluorine-containing modified sugar moiety e.g., a 2-F sugar moiety). In some such embodiments, the number of nucleosides in the modified oligonucleotide or first modified oligonucleotide (e.g., antisense oligonucleotide) is 23, 22, or 21. In some such embodiments, the nucleobase sequence of the modified oligonucleotide or first modified oligonucleotide (e.g., antisense oligonucleotide) comprises or consists of a nucleobase sequence selected from among the sequences provided in Table A. Table B1 or SEQ ID NOS: 3-314, 627-782, 939-976, 1033-1038, 1254-1255, and 1258-1287. In some such embodiments, the nucleobase sequence of the modified oligonucleotide or first modified oligonucleotide (e.g., antisense oligonucleotide) comprises or consists of a nucleobase sequence selected from among the nucleobase sequences of SEQ ID NOS: 29, 171, 176, 967, 968, 971, 972, 974, 975, 1033-1038, 1254, 1255, and 1258-1287. Examples of sugar motifs for such a modified oligonucleotide or first modified oligonucleotide (e.g., antisense oligonucleotide) of an oligomeric compound or oligomeric duplex provided herein include, but are not limited to, (from 5' to 3'): efyyydyyyyyyyfyfyyyyyee, efyyydyyyyyyyfyfyyyyyyy, efyyydyyyyyyyfyfyyyyye, efyyydyyyyyyyfyfyyyyy, efyyyfyyyyyyyfydyyyyyee, efyyyfyyyyyyyfydyyyyyyy, efyyyfyyyyyyyfydyyyyye, and efyyyfyyyyyyyfydyyyyy; wherein each "y" represents a 2'-OMe sugar moiety, each "c" represents a 2'-MOE sugar moiety, each "f" represents a 2'-fluoro sugar moiety and each "d" represents a 2'-deoxy sugar moiety. In some embodiments, the modified oligo-nucleotide or first modified oligonucleotide (e.g., antisense oligonucleotide) contains two 2'-deoxynucleosides and three nucleosides containing a modified sugar moiety having a fluorine atom (e.g., a fluorine-containing modified sugar moiety e.g., a 2'-F sugar moiety). In some such embodiments, the number of nucleosides in the modified oligo-nucleotide or first modified oligonucleotide (e.g., antisense oligonucleotide) is 23.22 or 21. In some such embodiments, the nucleobase sequence of the modified oligonucleotide or first modified oligonucleotide (e.g., antisense oligonucleotide) comprises or consists of a nucleobase sequence selected from among the sequences provided in Table A. Table B1 or SEQ ID NOS: 3-314, 627-782, 939-976, 1033-

1038, 1254-1255, and 1258-1287. In some such embodiments, the nucleobase sequence of the modified oligonucle-otide or first modified oligonucleotide (e.g., antisense oligonucleotide) comprises or consists of a nucleobase sequence selected from among the nucleobase sequences of SEQ ID NOS: 29, 171, 176, 967, 968, 971, 972, 974, 975, 1033-1038, 1254, 1255, and 1258-1287. Examples of sugar motifs for such a modified oligonucleotide or first modified oligonucleotide (e.g., antisense oligonucleotide) of an oligomeric compound or oligomeric duplex provided herein include, but are not limited to, (from 5' to 3): efyydydyyyyyyfyfyyyyyee, efyydydyyyyyyfyfyyyyyyy, efyydydyyyyyyfyfyyyyye, and efyydydyyyyyyfyfyyyyy, wherein each "y" represents a 2'-OMe sugar moiety, each "e" represents a 2'-MOE sugar moiety, each "f" represents a 2"-fluoro sugar moiety and each "d" represents a 2'-deoxy sugar moiety. In some embodiments, the modified oligo-nucleotide or first modified oligonucleotide (e.g., antisense oligonucleotide) contains three 2'-deoxynucleosides and one nucleoside containing a modified sugar moiety having a fluorine atom (e.g., a fluorine-containing modified sugar moiety e.g., a 2'-F sugar moiety). In some such embodi-ments, the number of nucleosides in the modified oligo-nucleotide or first modified oligonucleotide (e.g., antisense oligonucleotide) is 23, 22, or 21. In some such embodi-ments, the nucleobase sequence of the modified oligonucle-otide or first modified oligonucleotide (e.g., antisense oli-gonucleotide) comprises or consists of a nucleobase sequence selected from among the sequences provided in Table A. Table B1 or SEQ ID NOS: 3-314, 627-782, 939-976, 1033-1038, 1254-1255, 1258-1287. In some such embodiments, the nucleobase sequence of the modified oligonucleotide or first modified oligonucleotide (e.g., anti-sense oligonucleotide) comprises or consists of a nucleobase sequence selected from among the nucleobase sequences of SEQ ID NOS: 29, 171, 176, 967, 968, 971, 972, 974, 975, 1033-1038, 1254, 1255, and 1258-1287. Examples of sugar motifs for such a modified oligonucleotide or first modified oligonucleotide (e.g., antisense oligonucleotide) of an oli-gomeric compound or oligomeric duplex provided herein include, but are not limited to, (from 5' to 3'): efyyydyyyyyyydydyyyyyee, efyyydyyyyyyydydyyyyyyy, efyyydyyyyyyydydyyyyye, and efyyydyyyyyyydydyyyyy, wherein each "y" represents a 2'-OMe sugar moiety, each "c" represents a 2'-MOE sugar moiety, each "f" represents a 2'-fluoro sugar moiety and each "d" represents a 2'-deoxy sugar moiety. In some such embodiments, the modified oligonucleotide or first modified oligonucleotide (e.g., anti-sense oligonucleotide) contains one or more phosphoroth-ioate internucleoside linkages, such as, for example, 1, 2, 3, 4, 5 or 6 phosphorothioate internucleoside linkages. In some embodiments, an oligomeric compound or oligomeric duplex provided herein comprises a modified oligonucle-otide or first modified oligonucleotide (e.g., antisense oli-gonucleotide) comprising or consisting of a contiguous sequence of linked nucleosides having reduced fluorine content, such as, for example, any such sugar motifs set out herein, and having an internucleoside linkage motif com-prising one or more modified internucleoside linkages. In some embodiments, the modified oligonucleotide or first modified oligonucleotide (e.g., antisense oligonucleotide) contains one or more phosphorothioate internucleoside link-ages. In some such embodiments, all the internucleoside linkages that are not phosphorothioate internucleoside link-ages are phosphodiester linkages. In some such embodi-ments, the number of nucleosides in the modified oligo-nucleotide or first modified oligonucleotide (e.g., antisense oligonucleotide) is 23.22 or 21. Examples of internucleoside linkage motifs for a modified oligonucleotide or first modified oligonucleotide (e.g., antisense oligonucleotide) of an oligomeric compound or oligomeric duplex provided herein include, but are not limited to, (from 5' to 3'): ssooooooooooooooooooss, ssooosooooooooooooooss, ssoosososooooooooooooss, ssooooooooooooooooooos, ssooooooooooooooooooo, and ssooooooooooooooooooss, wherein each "o" represents a phosphodiester linkage and each "s" represents a phosphorothioate linkage.

In some embodiments, an oligomeric compound having a reduced fluorine content provided herein contains a modified oligonucleotide having reduced fluorine content (e.g., fewer than 40% or fewer than 35% of the nucleosides of the modified oligonucleotide comprises a fluorine atom) which comprises or consists of a region having a nucleobase sequence complementary to a sequence that is complementary to a sequence in a PLN nucleic acid. In some embodiments, an oligomeric duplex having a reduced fluorine content provided herein contains a second modified oligonucleotide (e.g., sense oligonucleotide) having reduced fluorine content (e.g., fewer than 40% of the nucleosides of the modified oligonucleotide or second modified oligonucleotide comprising a fluorine atom) which comprises or consists of a region having a nucleobase sequence complementary to a first oligonucleotide (e.g., antisense oligonucleotide) comprising or consisting of a region having a nucleobase sequence complementary to a sequence in a PLN nucleic acid. In some such embodiments, fewer than 30%, fewer than 25%, fewer than 20%, fewer than 15%, fewer than 14%, fewer than 13%, fewer than 12%, fewer than 10%, fewer than 5%, or fewer than 1% of the nucleosides in the modified oligonucleotide or second modified oligonucleotide (e.g., sense oligonucleotide) contain a fluorine atom, e.g., a 2-F sugar moiety. In particular embodiments, no more than 3, or no more than 2, nucleosides in the modified oligonucleotide or second modified oligonucleotide (e.g., sense oligonucleotide) contain a fluorine atom (e.g., a fluorine-containing modified sugar moiety e.g., a 2'-F sugar moiety). In some embodiments, only one or no nucleosides in the modified oligonucleotide or second modified oligonucleotide (e.g., sense oligonucleotide) contain a fluorine atom (e.g., a fluorine-containing modified sugar moiety e.g., a 2'-F sugar moiety). In certain embodiments, none of the nucleosides before the seventh or after the eleventh nucleoside counting from the 5' terminus of the modified oligonucleotide or second modified oligonucleotide (e.g., sense oligonucleotide) contain a fluorine atom (e.g., a fluorine-containing modified sugar moiety e.g., a 2'-F sugar moiety). In certain embodiments, none of the nucleosides before the tenth or after the eleventh nucleoside counting from the 5' terminus of the modified oligonucleotide or second modified oligonucleotide (e.g., sense oligonucleotide) contain a fluorine atom (e.g., a fluorine-containing modified sugar moiety e.g., a 2'-F sugar moiety). In certain embodiments, an oligomeric duplex containing a second modified oligonucleotide (e.g., sense oligonucleotide) that has a sequence of linked nucleosides having reduced fluorine content provided herein contains a first modified oligonucleotide (e.g., antisense oligonucleotide) having a reduced fluorine content. In certain such embodiments, the first modified oligonucleotide (e.g., antisense oligonucleotide) of such an oligomeric duplex is a first modified oligonucleotide having reduced fluorine content as described herein, including, for example, a first modified oligonucleotide having a sugar motif as described herein. In some embodiments, the nucleobase sequence of the first modified oligonucleotide (e.g., antisense oligonucleotide) comprises or consists of a nucleobase sequence selected from among the sequences provided in Table A. Table B1 or SEQ ID NOS: 3-314, 627-782, 939-976, 1033-1038, 1254-1255, and 1258-1287. In some such embodiments, the nucleobase sequence of the first modified oligonucleotide (e.g., antisense oligonucleotide) comprises or consists of a nucleobase sequence selected from among the nucleobase sequences of SEQ ID NOS: 29, 171, 176, 967, 968, 971, 972, 974, 975, 1033-1038, 1254, 1255, and 1258-1287. In particular embodiments, the total fluorine content of the oligomeric compound or oligomeric duplex is reduced (e.g., fewer than 40% of the total nucleosides in the compound or duplex comprising a fluorine atom). In some embodiments, a modified oligonucleotide, which comprises or consists of a region having a nucleobase sequence complementary to a nucleobase sequence complementary to a sequence in a PLN nucleic acid, of an oligomeric compound provided herein, or a second modified oligonucleotide (e.g., sense oligonucleotide) of an oligomeric duplex provided herein, contains one or more nucleosides containing a fluorine atom (e.g., a fluorine-containing modified sugar moiety e.g., a 2'-F sugar moiety). In some embodiments, the modified oligonucleotide or second modified oligonucleotide (e.g., sense oligonucleotide) contains one, two, three or four nucleosides containing a fluorine atom (e.g., a fluorine-containing modified sugar moiety e.g., a 2"-F sugar moiety). In some embodiments, the number of nucleosides in the modified oligonucleotide or second modified oligonucleotide (e.g., sense oligonucleotide) is 21, 20 or 19. In particular embodiments, one or more, or two or more, of the seventh, ninth and eleventh nucleosides counting from the 5' terminus of the modified oligonucleotide or second modified oligonucleotide (e.g., sense oligonucleotide) contains a fluorine atom (e.g., a fluorine-containing modified sugar moiety e.g., a 2-F sugar moiety). In particular embodiments, the seventh, ninth and eleventh nucleosides counting from the 5' terminus of the modified oligonucleotide or second modified oligonucleotide (e.g., sense oligonucleotide) contain a fluorine atom (e.g., a fluorine-containing modified sugar moiety e.g., a 2'-F sugar moiety). In some embodiments, the tenth and eleventh nucleosides counting from the 5' terminus of the modified oligonucleotide or second modified oligonucleotide (e.g., sense oligonucleotide) contain a fluorine atom (e.g., a fluorine-containing modified sugar moiety e.g., a 2'-F sugar moiety). In some embodiments, the modified oligonucleotide of an oligomeric compound or the second modified oligonucleotide (e.g., sense oligonucleotide) of an oligomeric duplex provided herein does not contain any fluorine atoms. In some such embodiments, one or more of the nucleosides contain a 2'-OMe sugar moiety or a 2'-MOE sugar moiety. In some embodiments, any of the nucleosides that do not contain a fluorine atom contain a 2'-OMe sugar moiety or a 2-MOE sugar moiety. In some embodiments, at least 10%, at least 20%, at least 30%, at least 40%, at least 50%, or at least 60%, or at least 65%, or at least 70%, or at least 80%, or at least 85%, or at least 90% of the nucleosides of the modified oligonucleotide or second modified oligonucleotide contain a 2'-OMe sugar moiety. In particular embodiments, the one or more nucleosides comprising a 2'-OMe sugar moiety are in a region of the sequence of the modified oligonucleotide or second modified oligonucleotide (e.g., sense oligonucleotide) between and including the third and nineteenth nucleosides counting from the 5' terminus of the modified oligonucleotide or second modified oligonucleotide. In some embodiments, the 3'-terminal nucleoside of the modified oligonucleotide or second modified oligonucleotide (e.g., sense oligonucleotide) contains a 2'-OMe sugar moiety and/or the nucleoside immediately 5' of the 3'-terminal nucleoside of the modified oligonucleotide or second modified oligonucleotide contains a 2'-OMe sugar moiety. In some embodiments, the 5'-terminal nucleoside of the modified oligonucleotide or second modified oligonucleotide (e.g., sense oligonucleotide) comprises a 2'-OMe sugar moiety and/or the nucleoside immediately 3' of the 5'-terminal nucleoside of the modified oligonucleotide or second modified oligonucleotide comprises a 2'-OMe sugar moiety. In some embodiments, all of the nucleosides contain a 2'-OMe sugar moiety. In some embodiments, one or more of the nucleosides of the modified oligonucleotide or second modified oligonucleotide (e.g., sense oligonucleotide) contain a 2'-MOE sugar moiety. In certain embodiments, the 3'-terminal nucleoside of the modified oligonucleotide or second modified oligonucleotide (e.g., sense oligonucleotide) contains a 2'-MOE sugar moiety and/or the nucleoside immediately 5' of the 3'-terminal nucleoside of the modified oligonucleotide or second modified oligonucleotide contains a 2'-MOE sugar moiety. In certain embodiments, the 5'-terminal nucleoside of the modified oligonucleotide or second modified oligonucleotide (e.g., sense oligonucleotide) contains a 2'-MOE sugar moiety and/or the nucleoside immediately 3' of the 5'-terminal nucleoside of the modified oligonucleotide or second modified oligonucleotide contains a 2'-MOE sugar moiety. In particular embodiments, the 5'-terminal nucleoside, the nucleoside immediately 3' of the 5'-terminal nucleoside, the 3'-terminal nucleoside, and the nucleoside immediately 5' of the 3'-terminal nucleoside of the modified oligonucleotide or second modified oligonucleotide (e.g., sense oligonucleotide) contains a 2-MOE sugar moiety.

In some embodiments, an oligomeric compound having reduced fluorine content provided herein contains a modified oligonucleotide comprising or consisting of a region having a nucleobase sequence complementary to a nucleobase sequence that is complementary to a sequence in a PLN nucleic acid wherein the modified oligonucleotide contains no more than four nucleosides containing a fluorine atom (e.g., a fluorine-containing modified sugar moiety, e.g., a 2'-fluoro sugar moiety). In some embodiments, an oligomeric duplex having reduced fluorine content provided herein contains a second modified oligonucleotide (e.g., a sense oligonucleotide) containing no more than four nucleosides containing a fluorine atom (e.g., a fluorine-containing modified sugar moiety e.g., a 2'-F sugar moiety). For example, in some embodiments, the modified oligonucleotide or second modified oligonucleotide (e.g., a sense oligonucleotide) contains four nucleosides containing a modified sugar moiety having a fluorine atom. In some such embodiments, the number of nucleosides in the modified oligonucleotide or second modified oligonucleotide is 21, 20 or 19. In some such embodiments, the nucleobase sequence of the modified oligonucleotide or second modified oligonucleotide (e.g., a sense oligonucleotide) comprises or consists of a nucleobase sequence selected from among the sequences provided in Table A. Table B2 or SEQ ID NOS: 315-626, 783-938, 977-1016, 1027-1032, 1256-1257, and 1288-1290. In some such embodiments, the nucleobase sequence of the modified oligonucleotide or second modified oligonucleotide (e.g., a sense oligonucleotide) comprises or consists of a nucleobase sequence selected from among the nucleobase sequences of SEQ ID NOS: 341, 483, 488, 1011-1016, 1027-1032, 1256-1257, and 1288-1290. Examples of sugar motifs for such a modified oligonucleotide or second modified oligonucleotide (e.g., a sense oligonucleotide) of an oligomeric compound or oligomeric duplex provided herein include, but are not limited to, (from 5' to 3'): eeyyyyfyfffyyyyyyyyee, eeyyyyfyfffyyyyyyyyyy, yyyyyyfyfffyyyyyyyyee, yyyyyyfyfffyyyyyyyyyy, eeyyyyfyfffyyyyyyee, eeyyyyfyfffyyyyyyyyy, yyyyyyfyfffyyyyyyee, yyyyyyfyfffyyyyyyyyy, eeyyfyfffyyyyyyyyee, eeyyfyfffyyyyyyyyyy, yyyyfyfffyyyyyyyyee, and yyyyfyfffyyyyyyyyyy, wherein each "y" represents a 2'-OMe sugar moiety, each "e" represents a 2'-MOE sugar moiety, and each "f" represents a 2'-fluoro sugar. In some embodiments, an oligomeric compound or oligomeric duplex provided herein has a modified oligonucleotide or second modified oligonucleotide (e.g., sense oligonucleotide) containing no more than three nucleosides containing a fluorine atom (e.g., a fluorine-containing modified sugar moiety). For example, in some embodiments, the modified oligonucleotide or second modified oligonucleotide (e.g., a sense oligonucleotide) contains three nucleosides containing a modified sugar moiety having a fluorine atom. In some such embodiments, the number of nucleosides in the modified oligonucleotide or second modified oligonucleotide is independently 21, 20 or 19. In some such embodiments, the nucleobase sequence of the modified oligonucleotide or second modified oligonucleotide (e.g., a sense oligonucleotide) comprises or consists of a nucleobase sequence selected from among the sequences provided in Table A. Table B2 or SEQ ID NOS: 315-626, 783-938, 977-1016, 1027-1032, 1256-1257, and 1288-1290. In some such embodiments, the nucleobase sequence of the modified oligonucleotide or second modified oligonucleotide (e.g., a sense oligonucleotide) comprises or consists of a nucleobase sequence selected from among the nucleobase sequences of SEQ ID NOS: 341, 483, 488, 1011-1016, 1027-1032, 1256-1257, and 1288-1290. Examples of sugar motifs for such a modified oligonucleotide or second modified oligonucleotide (e.g., a sense oligonucleotide) of an oligomeric compound or oligomeric duplex provided herein include, but are not limited to, (from 5' to 3'): eeyyyyfyfyfyyyyyyyyee, eeyyyyfyfyfyyyyyyyyyy, yyyyyyfyfyfyyyyyyyyee, and yyyyyyfyfyfyyyyyyyyyy, wherein each "y" represents a 2'-OMe sugar moiety, each "c" represents a 2'-MOE sugar moiety, and each "f" represents a 2'-fluoro sugar moiety. In some embodiments, an oligomeric compound or oligomeric duplex provided herein has a modified oligonucleotide or second modified oligonucleotide (e.g., a sense oligonucleotide) containing no more than two nucleosides containing a fluorine atom (e.g., a fluorine-containing modified sugar moiety e.g., a 2-F sugar moiety). For example, in some embodiments, the modified oligonucleotide or second modified oligonucleotide (e.g., a sense oligonucleotide) contains two nucleosides containing a modified sugar moiety having a fluorine atom. In some such embodiments, the number of nucleosides in the second modified oligonucleotide is 21, 20, or 19. In some such embodiments, the nucleobase sequence of the modified oligonucleotide or second modified oligonucleotide (e.g., a sense oligonucleotide) comprises or consists of a nucleobase sequence selected from among the sequences provided in Table A. Table B2 or SEQ ID NOS: 315-626, 783-938, 977-1016, 1027-1032, 1256-1257, and 1288-1290. In some such embodiments, the nucleobase sequence of the modified oligonucleotide or second modified oligonucleotide (e.g., a sense oligonucleotide) comprises or consists of a nucleobase sequence selected from among the nucleobase sequences of SEQ ID NOS: 341, 483, 488, 1011-1016, 1027-1032, 1256-1257, and 1288-1290. Examples of sugar motifs for such a modified oligonucleotide or second modified oligonucleotide of an oligomeric compound or oligomeric duplex provided herein include, but are not limited to, (from 5' to 3'): eeyyyyyyyffyyyyyyyyee, eeyyyyyyyffyyyyyyyyyy, yyyyyyyyyffyyyyyyyyee, yyyyyyyyyffyyyyyyyyyy, eeyyyyyffyyyyyyyyee, eeyyyyyffyyyyyyyyyy, yyyyyyyffyyyyyyyyee, and yyyyyyyffyyyyyyyyyy, wherein each "y" represents a 2'-OMe sugar moiety, each "c" represents a 2'-MOE sugar moiety, and each "f" represents a 2'-fluoro sugar moiety. In some embodiments, the modified oligonucleotide or second modified oligonucleotide (e.g., a sense oligonucleotide) of an oligomeric compound or oligomeric duplex provided herein does not contain any fluorine atoms. In some such embodiments, the modified oligonucleotide or second modified oligonucleotide may contain one or more 2'-deoxynucleosides. In particular such embodiments, the modified oligonucleotide or second modified oligonucleotide (e.g., a sense oligonucleotide) contains only one 2'-deoxynucleoside. In some such embodiments, the number of nucleosides in the modified oligonucleotide or second modified oligonucleotide is 21, 20, or 19. In some such embodiments, the nucleobase sequence of the modified oligonucleotide or second modified oligonucleotide (e.g., a sense oligonucleotide) comprises or consists of a nucleobase sequence selected from among the sequences provided in Table A, Table B2 or SEQ ID NOS: 315-626, 783-938, 977-1016, 1027-1032, 1256-1257, and 1288-1290. In some such embodiments, the nucleobase sequence of the modified oligonucleotide or second modified oligonucleotide (e.g., a sense oligonucleotide) comprises or consists of a nucleobase sequence selected from among the nucleobase sequences of SEQ ID NOS: 341, 483, 488, 1011-1016, 1027-1032, 1256-1257, and 1288-1290. Examples of a sugar motif for such a modified oligonucleotide or second modified oligonucleotide (e.g., a sense oligonucleotide) of an oligomeric compound or oligomeric duplex provided herein include, but are not limited to, (from 5' to 3'): eeyyyyyyyyydyyyyyyyyee, eeyyyyyyyyydyyyyyyyyyy, yyyyyyyyyyydyyyyyyyyee, and yyyyyyyyyyydyyyyyyyyyy, wherein each "y" represents a 2'-OMe sugar moiety, each "c" represents a 2'-MOE sugar moiety, and each "d" represents a 2'-deoxy sugar moiety. In some embodiments, all of the nucleosides of the modified oligonucleotide or second modified oligonucleotide (e.g., a sense oligonucleotide) contain a 2'-modified sugar moiety and none of the nucleosides contain a fluorine atom. In particular such embodiments, none of the modified sugar moieties is a 2'-deoxynucleoside. In some embodiments, the number of nucleosides in the modified oligonucleotide or second modified oligonucleotide is 21, 20, or 19. In some such embodiments, the nucleobase sequence of the modified oligonucleotide or second modified (e.g., a sense oligonucleotide) oligonucleotide comprises or consists of a nucleobase sequence selected from among the sequences provided in Table A, Table B2 or SEQ ID NOS: 315-626, 783-938, 977-1016, 1027-1032, 1256-1257, and 1288-1290. In some such embodiments, the nucleobase sequence of the modified oligonucleotide or second modified oligonucleotide (e.g., a sense oligonucleotide) comprises or consists of a nucleobase sequence selected from among the nucleobase sequences of SEQ ID NOS: 341, 483, 488, 1011-1016, 1027-1032, 1256-1257, and 1288-1290. Examples of a sugar motif for a modified oligonucleotide or second modified oligonucleotide (e.g., a sense oligonucleotide) of an oligomeric compound or oligomeric duplex provided herein that does not contain a fluorine atom include, but are not limited to, (from 5' to 3'): eeyyyyyyyyyyyyyyyyyyee, eeyyyyyyyyyyyyyyyyyyyy, yyyyyyyyyyyyyyyyyyyyee, and yyyyyyyyyyyyyyyyyyyyyy, wherein each "y" represents a 2'-OMe sugar moiety and each "c" represents a 2'-MOE sugar moiety. In some embodiments, an oligomeric compound or oligomeric duplex provided herein comprises a modified oligonucleotide or second modified oligonucleotide (e.g., a sense oligonucleotide) containing a sequence of linked nucleosides having reduced fluorine content, such as, for example, any such sugar motifs set out herein, and having an internucleoside linkage motif comprising one or more modified internucleoside linkages. In such embodiments, the modified oligonucleotide or second modified oligonucleotide (e.g., a sense oligonucleotide) may contain one or more mesyl phosphoramidate internucleoside linkages and/or one or more phosphorothioate internucleoside linkages, such as, for example, 1, 2, 3, 4, 5, or 6 phosphorothioate internucleoside linkages. In some embodiments, no more than 4 of the internucleoside linkages of the modified oligonucleotide or second modified oligonucleotide (e.g., a sense oligonucleotide) are phosphorothioate internucleoside linkages. In some such embodiments, all the internucleoside linkages that are not phosphorothioate internucleoside linkages are phosphodiester internucleoside linkages. Examples of internucleoside linkage motifs for a modified oligonucleotide or second modified oligonucleotide (e.g., a sense oligonucleotide) of an oligomeric compound or oligomeric duplex provided herein include, but are not limited to, (from 5' to 3"): ssooooooooooooooooss, ssooooooosooooooooss, ssooooooooooooooss, and ssoooooozozoooooooss, wherein each "o" represents a phosphodiester linkage, each "z" represents a mesyl phosphoramidate linkage, and each "s" represents a phosphorothioate linkage.

In some embodiments, oligomeric duplexes having reduced fluorine content provided herein contain a first modified oligonucleotide (e.g., an antisense oligonucleotide) having a reduced fluorine content and a second modified oligonucleotide (e.g., a sense oligonucleotide) having a reduced fluorine content. In some such embodiments, the number of nucleosides in the first modified oligonucleotide is 23, 22, or 21 and the number of nucleosides in the second modified oligonucleotide is 21, 20, or 19. In some such embodiments, the number of nucleosides in the first modified oligonucleotide is 23 and the number of nucleosides in the second modified oligonucleotide is 21. In some embodiments, the number of nucleosides in the first modified oligonucleotide is 21 and the number of nucleosides in the second modified oligonucleotide is 19. In some embodiments, the nucleobase sequence of the first modified oligonucleotide (e.g., an antisense oligonucleotide) comprises or consists of a nucleobase sequence selected from among the sequences provided in Table A, Table B1 or SEQ ID NOS: 3-314, 627-782, 939-976, 1033-1038, 1254-1255, and 1258-1287. In some embodiments, the nucleobase sequence of the first modified oligonucleotide comprises or consists of a nucleobase sequence selected from among the nucleobase sequences of SEQ ID NOS: 29, 171, 176, 967, 968, 971, 972, 974, 975, 1033-1038, 1254, 1255, and 1258-1287. In some such embodiments, the nucleobase sequence of the second modified oligonucleotide (e.g., a sense oligonucleotide) comprises or consists of a nucleobase sequence complementary to a sequence in the nucleobase sequence of the first modified oligonucleotide, or of a nucleobase sequence selected from among the sequences provided in Table A, Table B2 or SEQ ID NOS: 315-626, 783-938, 977-1016, 1027-1032, 1256-1257, and 1288-1290. In some embodiments, an oligomeric duplex having a reduced fluorine content provided herein has a first modified oligonucleotide (e.g., antisense oligonucleotide) having a reduced fluorine content containing one or more nucleosides containing a fluorine atom and/or a second modified oligonucleotide (e.g., a sense oligonucleotide) having a reduced fluorine content containing one or more nucleosides containing a fluorine atom (e.g., a fluorine-containing modified sugar moiety e.g., a 2'-F sugar moiety). In some such embodiments, the first modified oligonucleotide and the second modified oligonucleotide each independently contain none or one, two, three, or four nucleosides containing a fluorine atom. In some such embodiments, the first and/or second modified oligonucleotide contains no 2-deoxynucleosides or contains one or more 2'-deoxynucleosides. In some such embodiments, the first modified oligonucleotide (e.g., an antisense oligonucleotide) contains one or more 2'-deoxynucleosides and one or more nucleosides containing a fluorine atom (e.g., a fluorine-containing modified sugar moiety e.g., a 2'-F sugar moiety). In particular embodiments, the first modified oligonucleotide (e.g., an antisense oligonucleotide) contains one, two or three 2'-deoxynucleosides and one, two, or three nucleosides containing fluorine atom (e.g., a fluorine-containing modified sugar moiety, e.g., a 2'-F sugar moiety). For example, in some embodiments, the first modified oligonucleotide (e.g., an antisense oligonucleotide) contains only one 2'-deoxynucleoside and three nucleosides containing a sugar moiety having a fluorine atom (e.g., a fluorine-containing modified sugar moiety e.g., a 2'-F sugar moiety). In some embodiments, the first modified oligonucleotide (e.g., an antisense oligonucleotide) contains no more than three 2'-deoxynucleosides or no more than two 2'-deoxynucleosides. In some such embodiments, the first modified oligonucleotide or the second modified nucleotide contains only one 2'-deoxynucleoside. In some embodiments, all of the nucleosides of the first modified oligonucleotide and of the second modified oligonucleotide contain a 2-modified sugar moiety and one or more of the nucleosides contain a fluorine atom (e.g., a fluorine-containing modified sugar moiety e.g., a 2'-F sugar moiety). In some such embodiments, one or more of the nucleosides contain a 2'-OMe sugar moiety or a 2'-MOE sugar moiety. In some embodiments, any of the nucleosides in the first modified oligonucleotide or the second modified oligonucleotide that do not contain a fluorine atom contain a 2'-OMe sugar moiety or a 2-MOE sugar moiety.

In some embodiments, oligomeric duplexes having reduced fluorine content provided herein contain a first modified oligonucleotide (e.g., an antisense oligonucleotide) having a reduced fluorine content and a second modified oligonucleotide (e.g., a sense oligonucleotide) having a reduced fluorine content and each of the first modified oligonucleotide and the second modified oligonucleotide contain no more than four nucleosides containing a fluorine atom. For example, in some such embodiments, the first modified oligonucleotide contains four nucleosides containing a fluorine atom and the second modified oligonucleotide contains four, three, two, one, or no nucleosides containing a fluorine atom, or the first modified oligonucleotide contains four, three, two, one, or no nucleosides containing a fluorine atom, and the second modified oligonucleotide contains four nucleosides containing a fluorine atom. In some such embodiments, the number of nucleosides in the first modified oligonucleotide is 23, 22, or 21 and the number of nucleosides in the second modified oligonucleotide is 21, 20, or 19. In some such embodiments, the number of nucleosides in the first modified oligonucleotide is 23 and the number of nucleosides in the second modified oligonucleotide is 21. In some embodiments, the number of nucleosides in the first modified oligonucleotide is 21 and the number of nucleosides in the second modified oligonucleotide is 19. In some embodiments, the nucleobase sequence of the first modified oligonucleotide (e.g., an antisense oligonucleotide) comprises or consists of a nucleobase sequence selected from among the sequences provided in Table A. Table B1 or SEQ ID NOS: 3-314, 627-782, 939-976, 1033-1038, 1254-1255, and 1258-1287. In some embodiments, the nucleobase sequence of the first modified oligonucleotide (e.g., an antisense oligonucleotide) comprises or consists of a nucleobase sequence selected from among the nucleobase sequences of SEQ ID NOS: 29, 171, 176, 967, 968, 971, 972, 974, 975, 1033-1038, 1254, 1255, and 1258-1287. In some such embodiments, the nucleobase sequence of the second modified oligonucleotide (e.g., a sense oligonucleotide) comprises or consists of a nucleobase sequence complementary to a sequence in the nucleobase sequence of the first modified oligonucleotide, or of a nucleobase sequence selected from among the sequences provided in Table A. Table B2 or SEQ ID NOS: 315-626, 783-938, 977-1016, 1027-1032, 1256-1257, and 1288-1290. In some such embodiments, the nucleobase sequence of the second modified oligonucleotide (e.g., a sense oligonucleotide) comprises or consists of a nucleobase sequence selected from among the nucleobase sequences of SEQ ID NOS: 341, 483, 488, 1011-1016, 1027-1032, 1256-1257, and 1288-1290. In some embodiments, each of the first modified oligonucleotide and the second modified oligonucleotide contains no more than three nucleosides containing a fluorine atom. For example, in some such embodiments, the first modified oligonucleotide contains three nucleosides containing a fluorine atom and the second modified oligonucleotide contains three, two, one, or no nucleosides containing a fluorine atom, or the first modified oligonucleotide contains three, two, one, or no nucleosides containing a fluorine atom, and the second modified oligonucleotide contains three nucleosides containing a fluorine atom. In particular such embodiments, the first modified oligonucleotide has three nucleosides comprising a fluorine and the second modified oligonucleotide has two or three nucleosides comprising a fluorine. In some such embodiments, the number of nucleosides in the first modified oligonucleotide is 23, 22, or 21 and the number of nucleosides in the second modified oligonucleotide is 21, 20 or 19. In some such embodiments, the number of nucleosides in the first modified oligonucleotide is 23 and the number of nucleosides in the second modified oligonucleotide is 21. In some embodiments, the number of nucleosides in the first modified oligonucleotide is 21 and the number of nucleosides in the second modified oligonucleotide is 19. In some embodiments, the nucleobase sequence of the first modified oligonucleotide (e.g., an antisense oligonucleotide) comprises or consists of a nucleobase sequence selected from among the sequences provided in Table A. Table B1 or SEQ ID NOS: 3-314, 627-782, 939-976, 1033-1038, 1254-1255, and 1258-1287. In some embodiments, the nucleobase sequence of the first modified oligonucleotide (e.g., an antisense oligonucleotide) comprises or consists of a nucleobase sequence selected from among the nucleobase sequences of SEQ ID NOS: 29, 171, 176, 967, 968, 971, 972, 974, 975, 1033-1038, 1254, 1255, and 1258-1287. In some such embodiments, the nucleobase sequence of the second modified oligonucleotide (e.g., a sense oligonucleotide) comprises or consists of a nucleobase sequence complementary to a sequence in the nucleobase sequence of the first modified oligonucleotide, or of a nucleobase sequence selected from among the sequences provided in Table A. Table B2 or SEQ ID NOS: 315-626, 783-938, 977-1016, 1027-1032, 1256-1257, and 1288-1290. In some such embodiments, the nucleobase sequence of the second modified oligonucleotide (e.g., a sense oligonucleotide) comprises or consists of a nucleobase sequence selected from among the nucleobase sequences of SEQ ID NOS: 341, 483, 488, 1011-1016, 1027-1032, 1256-1257, and 1288-1290. In some embodiments, each of the first modified oligonucleotide and the second modified oligonucleotide contains no more than two nucleosides containing a fluorine atom. For example, in some such embodiments, the first modified oligonucleotide (e.g., an antisense oligonucleotide) contains two nucleosides containing a fluorine atom and the second modified oligonucleotide (e.g., a sense oligonucleotide) contains two, one, or no nucleosides containing a fluorine atom, or the first modified oligonucleotide contains two, one, or no nucleosides containing a fluorine atom, and the second modified oligonucleotide contains two nucleosides containing a fluorine atom. In some such embodiments, the number of nucleosides in the first modified oligonucleotide is 23, 22, or 21 and the number of nucleosides in the second modified oligonucleotide is 21, or 19. In some such embodiments, the number of nucleosides in the first modified oligonucleotide is 23 and the number of nucleosides in the second modified oligonucleotide is 21. In some embodiments, the number of nucleosides in the first modified oligonucleotide is 21 and the number of nucleosides in the second modified oligonucleotide is 19. In some embodiments, the nucleobase sequence of the first modified oligonucleotide (e.g., an antisense oligonucleotide) comprises or consists of a nucleobase sequence selected from among the sequences provided in Table A, Table B1 or SEQ ID NOS: 3-314, 627-782, 939-976, and 1033-1038, 1254-1255, and 1258-1287. In some embodiments, the nucleobase sequence of the first modified oligonucleotide (e.g., an antisense oligonucleotide) comprises or consists of a nucleobase sequence selected from among the nucleobase sequences of SEQ ID NOS: 29, 171, 176, 967, 968, 971, 972, 974, 975, 1033-1038, 1254, 1255, and 1258-1287. In some such embodiments, the nucleobase sequence of the second modified oligonucleotide (e.g., a sense oligonucleotide) comprises or consists of a nucleobase sequence complementary to a sequence in the nucleobase sequence of the first modified oligonucleotide, or of a nucleobase sequence selected from among the sequences provided in Table A, Table B2 or SEQ ID NOS: 315-626, 783-938, 977-1016, 1027-1032, 1256-1257, and 1288-1290. In some such embodiments, the nucleobase sequence of the second modified oligonucleotide (e.g., a sense oligonucleotide) comprises or consists of a nucleobase sequence selected from among the nucleobase sequences of SEQ ID NOS: 341, 483, 488, 1011-1016, 1027-1032, 1256-1257, and 1288-1290.

In some embodiments, an oligomeric duplex having a reduced fluorine content provided herein contains a first modified oligonucleotide (e.g., an antisense oligonucleotide) having a reduced fluorine content having a first sugar motif ($1^{st}$) and a second modified oligonucleotide (e.g., a sense oligonucleotide) having a reduced fluorine content having a second sugar motif ($2^{nd}$) and the first and second sugar motifs are independently selected from among the first and second sugar motifs provided in Table C. In some embodiments, an oligomeric duplex having a reduced fluorine content provided herein comprises a first modified oligonucleotide (e.g., an antisense oligonucleotide) having a reduced fluorine content having a first sugar motif ($1^{st}$) and a second modified oligonucleotide (e.g., a sense oligonucleotide) having a reduced fluorine content having a second sugar motif ($2^{nd}$) and the first and second sugar motifs are any one of the exemplary combinations of first and second sugar motifs set out in Table C. In Table C, each "y" represents a 2'-OMe sugar moiety, each "c" represents a 2'-MOE sugar moiety, each "f" represents a 2'-fluoro sugar moiety, each "[FHNA]" represents a 3"-fluoro-hexitol sugar moiety, and each "d" represents a 2'-deoxy sugar moiety.

TABLE C

| Exemplary Modified Oligonucleotide Sugar Motifs | | |
|---|---|---|
| Exemplary Combination Number | First Sugar Motif | Second Sugar Motif |
| 1 | efyydydyyyyyyfyfyyyyyee | eeyyyyfyfyfyyyyyyyyee |
| 2 | efyydydyyyyyyfyfyyyyyy | yyyyyyfyfyfyyyyyyyyyy |
| 3 | efyydydyyyyyyfyfyyyyyee | yyyyyyfyfyfyyyyyyyyyy |
| 4 | efyydydyyyyyyfyfyyyyyy | eeyyyyfyfyfyyyyyyyyee |
| 5 | efyyydyyyyyyfyfyyyyyee | eeyyyyyyyffyyyyyyyyee |
| 6 | efyyydyyyyyyfyfyyyyyy | yyyyyyyyyffyyyyyyyyyy |
| 7 | efyyydyyyyyyfyfyyyyyee | yyyyyyyyyffyyyyyyyyyy |
| 8 | efyyydyyyyyyfyfyyyyyy | eeyyyyyyyffyyyyyyyyee |
| 9 | efyydydyyyyyyfyfyyyyyee | eeyyyyyyyffyyyyyyyyee |
| 10 | efyydydyyyyyyfyfyyyyyy | yyyyyyyyyffyyyyyyyyyy |
| 11 | efyydydyyyyyyfyfyyyyyee | yyyyyyyyyffyyyyyyyyyy |
| 12 | efyydydyyyyyyfyfyyyyyy | eeyyyyyyyffyyyyyyyyee |
| 13 | efyyydyyyyyyfyfyyyyyee | eeyyyyfyfyfyyyyyyyyee |
| 14 | efyyydyyyyyyfyfyyyyyy | yyyyyyfyfyfyyyyyyyyyy |

TABLE C-continued

Exemplary Modified Oligonucleotide Sugar Motifs

| Exemplary Combination Number | First Sugar Motif | Second Sugar Motif |
|---|---|---|
| 15 | efyyydyyyyyyyfyfyyyyyee | yyyyyyfyfyfyyyyyyyyyy |
| 16 | efyyydyyyyyyyfyfyyyyyyy | eeyyyyfyfyfyyyyyyyyee |
| 17 | efyydydyyyyyyfyfyyyyyee | eeyyyyfyfffyyyyyyyyee |
| 18 | efyydydyyyyyyfyfyyyyyyy | yyyyyyfyfffyyyyyyyyyy |
| 19 | efyydydyyyyyyfyfyyyyyee | yyyyyyfyfffyyyyyyyyyy |
| 20 | efyydydyyyyyyfyfyyyyyyy | eeyyyyfyfffyyyyyyyyee |
| 21 | efyyyyyyyyyyyfyfyyyyyee | eeyyyyfyfffyyyyyyyyee |
| 22 | efyyyyyyyyyyyfyfyyyyyyy | yyyyyyfyfffyyyyyyyyyy |
| 23 | efyyyyyyyyyyyfyfyyyyyee | yyyyyyfyfffyyyyyyyyyy |
| 24 | efyyyyyyyyyyyfyfyyyyyyy | eeyyyyfyfffyyyyyyyyee |
| 25 | efyyyyyyyyyyyfyfyyyyyee | eeyyyyyyyffyyyyyyyyee |
| 26 | efyyyyyyyyyyyfyfyyyyyyy | yyyyyyyyyffyyyyyyyyyy |
| 27 | efyyyyyyyyyyyfyfyyyyyee | yyyyyyyyyffyyyyyyyyyy |
| 28 | efyyyyyyyyyyyfyfyyyyyyy | eeyyyyyyyffyyyyyyyyee |
| 29 | efyyyyyyyyyyyfyfyyyyyee | eeyyyyfyfyfyyyyyyyyee |
| 30 | efyyyyyyyyyyyfyfyyyyyyy | yyyyyyfyfyfyyyyyyyyyy |
| 31 | efyyyyyyyyyyyfyfyyyyyee | yyyyyyfyfyfyyyyyyyyyy |
| 32 | efyyyyyyyyyyyfyfyyyyyyy | eeyyyyfyfyfyyyyyyyyee |
| 33 | efyyyfyyyyyyyfyfyyyyyyy | yyyyyyyyyffyyyyyyyyyy |
| 34 | efyyyfyyyyyyyfyfyyyyyee | eeyyyyyyyffyyyyyyyyee |
| 35 | efyyyfyyyyyyyfyfyyyyyyy | eeyyyyyyyffyyyyyyyyee |
| 36 | efyyyfyyyyyyyfyfyyyyyee | yyyyyyyyyffyyyyyyyyyy |
| 37 | efyyyfyyyyyyyfyfyyyyyyy | yyyyyyfyfyfyyyyyyyyyy |
| 38 | efyyyfyyyyyyyfyfyyyyyee | eeyyyyfyfyfyyyyyyyyee |
| 39 | efyyyfyyyyyyyfyfyyyyyyy | eeyyyyfyfyfyyyyyyyyee |
| 40 | efyyyfyyyyyyyfyfyyyyyee | yyyyyyfyfyfyyyyyyyyyy |
| 41 | efyyyfyyyyyyyyfyfyyyee | eeyyyyfyfffyyyyyyee |
| 42 | efyyyfyyyyyyyyfyfyyyyy | yyyyyyfyfffyyyyyyyy |
| 43 | efyyyfyyyyyyyyfyfyyyee | yyyyyyfyfffyyyyyyyy |
| 44 | efyyyfyyyyyyyyfyfyyyyy | eeyyyyfyfffyyyyyyee |
| 45 | efyyyfyyyyyyyyfyfyyyee | eeyyyyffyyyyyyyyee |
| 46 | efyyyfyyyyyyyyfyfyyyyy | yyyyyyffyyyyyyyyyy |
| 47 | efyyyfyyyyyyyyfyfyyyee | yyyyyyffyyyyyyyyyy |
| 48 | efyyyfyyyyyyyyfyfyyyyy | eeyyyyffyyyyyyyyee |
| 49 | e[FHNA]yydydyyyyfyfyfyyyyyee | eeyyyyfyfffyyyyyyyyee |
| 50 | efyyyfyyyyyyyyyfyfyyyyyey | eeyyyyfyfffyyyyyyyyee |
| 51 | efyyyfyyyyyyyfyfyyyyyey | yyyyyyfyfffyyyyyyyyyy |

TABLE C-continued

Exemplary Modified Oligonucleotide Sugar Motifs

| Exemplary Combination Number | First Sugar Motif | Second Sugar Motif |
|---|---|---|
| 52 | e[FHNA]yydydyyyyfyfyfyyyyyyy | yyyyyyfyfffyyyyyyyyyy |
| 53 | e[FHNA]yydydyyyyfyfyfyyyyyee | yyyyyyfyfffyyyyyyyyyy |
| 54 | e[FHNA]yydydyyyyfyfyfyyyyyyy | eeyyyyfyfffyyyyyyyyee |
| 55 | e[FHNA]yydydyyyyfyfyfyyyyyee | eeyyyyfyfyfyyyyyyyyee |
| 56 | e[FHNA]yydydyyyyfyfyfyyyyyyy | yyyyyyfyfyfyyyyyyyyyy |
| 57 | e[FHNA]yydydyyyyfyfyfyyyyyee | yyyyyyfyfyfyyyyyyyyyy |
| 58 | e[FHNA]yydydyyyyfyfyfyyyyyyy | eeyyyyfyfyfyyyyyyyyee |
| 59 | efyyyfyyyyyyyyfyfyyyyyyy | yyyyyyfyfffyyyyyyyyyy |
| 60 | efyyyfyyyyyyyyfyfyyyyyee | eeyyyyfyfffyyyyyyyyee |
| 61 | efyyyfyyyyyyyyfyfyyyyyee | yyyyyyfyfffyyyyyyyyyy |
| 62 | efyyyfyyyyyyyyfyfyyyyyyy | eeyyyyfyfffyyyyyyyyee |
| 63 | efyyyfyyyyyyyyfyfyyyyyyy | yyyyyyyyyyyyyyyyyyyy |
| 64 | efyyyfyyyyyyyyfyfyyyyyee | eeyyyyyyyyyyyyyyyyee |
| 65 | efyyyfyyyyyyyyfyfyyyyyyy | eeyyyyyyyyyyyyyyyyee |
| 66 | efyyyfyyyyyyyyfyfyyyyyee | yyyyyyyyyyyyyyyyyyyy |
| 67 | efyyyfyyyyyyyyfyfyyyyyyy | yyyyyyyyyydyyyyyyyyy |
| 68 | efyyyfyyyyyyyyfyfyyyyyee | eeyyyyyyyydyyyyyyyee |
| 69 | efyyyfyyyyyyyyfyfyyyyyyy | eeyyyyyyyydyyyyyyyee |
| 70 | efyyyfyyyyyyyyfyfyyyyyee | yyyyyyyyyydyyyyyyyyy |
| 71 | efyyyyyyyyyyyyfyyyyyyyee | eeyyyyfyfffyyyyyyyyee |
| 72 | efyyyyyyyyyyyyfyyyyyyyyy | yyyyyyfyfffyyyyyyyyyy |
| 73 | efyyyyyyyyyyyyfyyyyyyyee | yyyyyyfyfffyyyyyyyyyy |
| 74 | efyyyyyyyyyyyyfyyyyyyyyy | eeyyyyfyfffyyyyyyyyee |
| 75 | efyyyyyyyyyyyyfyyyyyyyee | eeyyyyfyfyfyyyyyyyyee |
| 76 | efyyyyyyyyyyyyfyyyyyyyyy | yyyyyyfyfyfyyyyyyyyyy |
| 77 | efyyyyyyyyyyyyfyyyyyyyee | yyyyyyfyfyfyyyyyyyyyy |
| 78 | efyyyyyyyyyyyyfyyyyyyyyy | eeyyyyfyfyfyyyyyyyyee |
| 79 | efyyydyyyyyyyyfyfyyyyyee | eeyyyyfyfffyyyyyyyyee |
| 80 | efyyydyyyyyyyyfyfyyyyyyy | yyyyyyfyfffyyyyyyyyyy |
| 81 | efyyydyyyyyyyyfyfyyyyyee | yyyyyyfyfffyyyyyyyyyy |
| 82 | efyyydyyyyyyyyfyfyyyyyyy | eeyyyyfyfffyyyyyyyyee |
| 83 | efyyyfyyyyyyyyfyfyyyee | eeyyfyfffyyyyyyyyyee |
| 84 | efyyyfyyyyyyyyfyfyyyyy | yyyyfyfffyyyyyyyyyy |
| 85 | efyyyfyyyyyyyyfyfyyyee | yyyyfyfffyyyyyyyyyy |
| 86 | efyyyfyyyyyyyyfyfyyyyy | eeyyfyfffyyyyyyyyyee |
| 87 | efyyyfyyyyyyyyfydyyyyee | eeyyyyfyfffyyyyyyyyee |
| 88 | efyyyfyyyyyyyyfydyyyyyy | yyyyyyfyfffyyyyyyyyyy |

TABLE C-continued

Exemplary Modified Oligonucleotide Sugar Motifs

| Exemplary Combination Number | First Sugar Motif | Second Sugar Motif |
|---|---|---|
| 89 | efyyyfyyyyyyyfydyyyyyee | yyyyyyfyfffyyyyyyyyyy |
| 90 | efyyyfyyyyyyyfydyyyyyy | eeyyyyfyfffyyyyyyyyee |
| 91 | e[FHNA]yyyfyyyyyyyfyfyyyyyee | eeyyyyfyfffyyyyyyyyee |
| 92 | e[FHNA]yyyfyyyyyyyfyfyyyyyyy | yyyyyyfyfffyyyyyyyyyy |
| 93 | e[FHNA]yyyfyyyyyyyfyfyyyyyee | yyyyyyfyfffyyyyyyyyyy |
| 94 | e[FHNA]yyyfyyyyyyyfyfyyyyyyy | eeyyyyfyfffyyyyyyyyee |
| 95 | efyyyyyyyyyyyfyyyyyyyee | eeyyyyyyyyffyyyyyyyyee |
| 96 | efyyyyyyyyyyyfyyyyyyyyy | yyyyyyyyyyffyyyyyyyyyy |
| 97 | efyyyyyyyyyyyfyyyyyyyee | yyyyyyyyyyffyyyyyyyyyy |
| 98 | efyyyyyyyyyyyfyyyyyyyyy | eeyyyyyyyyffyyyyyyyyee |
| 99 | efyyyfyyyyyyyfyyyyyyyee | eeyyyyyfyfffyyyyyyyyee |
| 100 | efyyyfyyyyyyyfyyyyyyyyy | yyyyyyfyfffyyyyyyyyyy |
| 101 | efyyyfyyyyyyyfyyyyyyyee | yyyyyyfyfffyyyyyyyyyy |
| 102 | efyyyfyyyyyyyfyyyyyyyyy | eeyyyyfyfffyyyyyyyyee |
| 103 | efyyyfyyyyyyyfyyyyyyyee | eeyyyyyyyyffyyyyyyyyee |
| 104 | efyyyfyyyyyyyfyyyyyyyyy | yyyyyyyyyyffyyyyyyyyyy |
| 105 | efyyyfyyyyyyyfyyyyyyyee | yyyyyyfyfffyyyyyyyyyy |
| 106 | efyyyfyyyyyyyfyyyyyyyyy | eeyyyyfyfffyyyyyyyyee |
| 107 | efyyyyyyyyyyyyfyfyyyyye | eeyyyyyyyyffyyyyyyyyee |
| 108 | efyyyyyyyyyyyyfyfyyyyyy | yyyyyyyyyyffyyyyyyyyyy |
| 109 | efyyyyyyyyyyyyfyfyyyyye | yyyyyyyyyyffyyyyyyyyyy |
| 110 | efyyyyyyyyyyyyfyfyyyyyy | eeyyyyyyyyffyyyyyyyyee |
| 111 | efyyyyyyyyyyyyfyfyyyyye | eeyyyyfyfyfyyyyyyyyee |
| 112 | efyyyyyyyyyyyyfyfyyyyyy | yyyyyyfyfyfyyyyyyyyyy |
| 113 | efyyyyyyyyyyyyfyfyyyyye | yyyyyyfyfyfyyyyyyyyyy |
| 114 | efyyyyyyyyyyyyfyfyyyyyy | eeyyyyfyfyfyyyyyyyyee |
| 115 | efyyyyyyyyyyyyfyfyyyyy | eeyyyyyyyyffyyyyyyyyee |
| 116 | efyyyyyyyyyyyyfyfyyyyy | yyyyyyyyyyffyyyyyyyyyy |
| 117 | efyyyyyyyyyyyyfyfyyyyy | eeyyyyfyfyfyyyyyyyyee |
| 118 | efyyyyyyyyyyyyfyfyyyyy | yyyyyyfyfyfyyyyyyyyyy |
| 119 | efyyyfyyyyyyyfyyyyyyye | eeyyyyfyfffyyyyyyyyee |
| 120 | efyyyfyyyyyyyfyyyyyyyy | yyyyyyfyfffyyyyyyyyyy |
| 121 | efyyyfyyyyyyyfyyyyyyye | yyyyyyfyfffyyyyyyyyyy |
| 122 | efyyyfyyyyyyyfyyyyyyyy | eeyyyyfyfffyyyyyyyyee |
| 123 | efyydydyyyyyyfyfyyyyye | eeyyyyfyfyfyyyyyyyyee |
| 124 | efyydydyyyyyyfyfyyyyyy | yyyyyyfyfyfyyyyyyyyyy |
| 125 | efyydydyyyyyyfyfyyyyye | yyyyyyfyfyfyyyyyyyyyy |

TABLE C-continued

Exemplary Modified Oligonucleotide Sugar Motifs

| Exemplary Combination Number | First Sugar Motif | Second Sugar Motif |
|---|---|---|
| 126 | efyydydyyyyyyfyfyyyyyy | eeyyyyfyfyfyyyyyyyyee |
| 127 | efyydydyyyyyyfyfyyyyy | eeyyyyfyfyfyyyyyyyyee |
| 128 | efyydydyyyyyyfyfyyyyy | yyyyyyfyfyfyyyyyyyyyy |
| 129 | efyydydyyyyyyfyfyyyyye | eeyyyyyyyyffyyyyyyyyee |
| 130 | efyydydyyyyyyfyfyyyyyy | yyyyyyyyyyffyyyyyyyyyy |
| 131 | efyydydyyyyyyfyfyyyyye | yyyyyyyyyyffyyyyyyyyyy |
| 132 | efyydydyyyyyyfyfyyyyyy | eeyyyyyyyyffyyyyyyyyee |
| 133 | efyydydyyyyyyfyfyyyyy | eeyyyyyyyyffyyyyyyyyee |
| 134 | efyydydyyyyyyfyfyyyyy | yyyyyyyyyyffyyyyyyyyyy |
| 135 | efyydydyyyyyyfyfyyyyye | eeyyyyfyfffyyyyyyyyee |
| 136 | efyydydyyyyyyfyfyyyyyy | yyyyyyfyfffyyyyyyyyyy |
| 137 | efyydydyyyyyyfyfyyyyye | yyyyyyfyfffyyyyyyyyyy |
| 138 | efyydydyyyyyyfyfyyyyyy | eeyyyyfyfffyyyyyyyyee |
| 139 | efyydydyyyyyyfyfyyyyy | eeyyyyfyfffyyyyyyyyee |
| 140 | efyydydyyyyyyfyfyyyyy | yyyyyyfyfffyyyyyyyyyy |
| 141 | efyyydyyyyyyyfyfyyyyye | eeyyyyyyyyffyyyyyyyyee |
| 142 | efyyydyyyyyyyfyfyyyyyy | yyyyyyyyyyffyyyyyyyyyy |
| 143 | efyyydyyyyyyyfyfyyyyye | yyyyyyyyyyffyyyyyyyyyy |
| 144 | efyyydyyyyyyyfyfyyyyyy | eeyyyyyyyyffyyyyyyyyee |
| 145 | efyyydyyyyyyyfyfyyyyy | eeyyyyyyyyffyyyyyyyyee |
| 146 | efyyydyyyyyyyfyfyyyyy | yyyyyyyyyyffyyyyyyyyyy |
| 147 | efyyydyyyyyyyfyfyyyyye | eeyyyyfyfyfyyyyyyyyee |
| 148 | efyyydyyyyyyyfyfyyyyyy | yyyyyyfyfyfyyyyyyyyyy |
| 149 | efyyydyyyyyyyfyfyyyyye | yyyyyyfyfyfyyyyyyyyyy |
| 150 | efyyydyyyyyyyfyfyyyyyy | eeyyyyfyfyfyyyyyyyyee |
| 151 | efyyydyyyyyyyfyfyyyyy | eeyyyyfyfyfyyyyyyyyee |
| 152 | efyyydyyyyyyyfyfyyyyy | yyyyyyfyfyfyyyyyyyyyy |
| 153 | efyyydyyyyyyyfyfyyyyye | eeyyyyfyfffyyyyyyyyee |
| 154 | efyyydyyyyyyyfyfyyyyyy | yyyyyyfyfffyyyyyyyyyy |
| 155 | efyyydyyyyyyyfyfyyyyye | yyyyyyfyfffyyyyyyyyyy |
| 156 | efyyydyyyyyyyfyfyyyyyy | eeyyyyfyfffyyyyyyyyee |
| 157 | efyyydyyyyyyyfyfyyyyy | eeyyyyfyfffyyyyyyyyee |
| 158 | efyyydyyyyyyyfyfyyyyy | yyyyyyfyfffyyyyyyyyyy |

In some embodiments, an oligomeric duplex having a reduced fluorine content provided herein contains a first modified oligonucleotide (e.g., an antisense oligonucleotide) having a reduced fluorine content having a first sugar motif (1st) and a second modified oligonucleotide (e.g., a sense oligonucleotide) having a reduced fluorine content having a second sugar motif ($2^{nd}$) and the first and second sugar motifs are independently selected from among the first and second sugar motifs provided in Table C. In some such embodiments, the number of nucleosides in the first modified oligonucleotide is 23, 22, or 21 and the number of nucleosides in the second modified oligonucleotide is 21, 20, or 19. In some such embodiments, the number of nucleosides in the first modified oligonucleotide is 23 and the number of nucleosides in the second modified oligonucleotide is 21. In some embodiments, the number of nucleosides in the first modified oligonucleotide is 21 and the number of nucleosides in the second modified oligonucleotide is 19. In some such embodiments, the first modified oligonucleotide (e.g., an antisense oligonucleotide) comprises or consists of a nucleobase sequence selected from among the sequences provided in Table A. Table B1 or SEQ ID NOS: 3-314, 627-782, 939-976, 1033-1038, 1254-1255, and 1258-1287 (or at least 21 contiguous nucleosides of any one of the sequences provided in Table A, Table B1 or SEQ ID NOS: 3-314, 627-782, 939-976, 1033-1038, 1254-1255, and 1258-1287) and/or the nucleobase sequence of the second modified oligonucleotide (e.g., a sense oligonucleotide) comprises or consists of a nucleobase sequence complementary to a sequence in the nucleobase sequence of the first modified oligonucleotide, or of a nucleobase sequence selected from among the sequences provided in Table A. Table B2 or SEQ ID NOS: 315-626, 783-938, 977-1016, 1027-1032, 1256-1257, and 1288-1290 (or at least 19 contiguous nucleosides of any one of the sequences provided in Table A. Table B2 or SEQ ID NOS: 315-626, 783-938, 977-1016, 1027-1032, 1256-1257, and 1288-1290). In some such embodiments, the first modified oligonucleotide (e.g., an antisense oligonucleotide) comprises or consists of a nucleobase sequence selected from among SEQ ID NOS: 29, 171, 176, 967, 968, 971, 972, 974, 975, 1033-1038, 1254-1255, and 1258-1287 (or at least 21 contiguous nucleosides of any one of SEQ ID NOS: 29, 171, 176, 967, 968, 971, 972, 974, 975, 1033-1038, 1254-1255, and 1258-1287) and/or the nucleobase sequence of the second modified oligonucleotide (e.g., a sense oligonucleotide) comprises or consists of a nucleobase sequence selected from among SEQ ID NOS: 341, 483, 488, 1011-1016, 1027-1032, 1256-1257, and 1288-1290 (or at least 19 contiguous nucleosides of any one of SEQ ID NOS: 341, 483, 488, 1011-1016, 1027-1032, 1256-1257, and 1288-1290). In some such embodiments, the first modified oligonucleotide comprises one or more modified internucleoside linkages. For example, the first modified oligonucleotide (e.g., an antisense oligonucleotide) may contain one or more phosphorothioate internucleoside linkages, such as, for example, 1, 2, 3, 4, 5 or 6 phosphorothioate internucleoside linkages. In some embodiments, no more than 4 of the internucleoside linkages of the first modified oligonucleotide are phosphorothioate internucleoside linkages. In some embodiments, all the internucleoside linkages that are not phosphorothioate internucleoside linkages are phosphodiester internucleoside linkages. Examples of internucleoside linkage motifs for a first modified oligonucleotide (e.g., an antisense oligonucleotide) having a first sugar motif selected from among the first sugar motifs provided in Table C include, but are not limited to, (from 5' to 3"): ssooooooooooooooooooss, ssooosooooooooooooooss, ssoosososoooooooooooooss, ssooooooooooooooooooos, ssooooooooooooooooooo, and ssooooooooooooooooooss, wherein each "o" represents a phosphodiester internucleoside linkage and each "s" represents a phosphorothioate internucleoside linkage. In some such embodiments, the second modified oligonucleotide (e.g., a sense oligonucleotide) comprises one or more modified internucleoside linkages. In such embodiments, the second modified oligonucleotide may contain one or more mesyl phosphoramidate internucleoside linkages and/or one or more phosphorothioate internucleoside linkages, such as, for example, 1, 2, 3, 4, 5, or 6 phosphorothioate internucleoside linkages. In some embodiments, no more than 4 of the internucleoside linkages of the second modified oligonucleotide are phosphorothioate internucleoside linkages. In some embodiments, all the internucleoside linkages that are not phosphorothioate internucleoside linkages are phosphodiester internucleoside linkages. Examples of internucleoside linkage motifs for a second modified oligonucleotide (e.g., a sense oligonucleotide) having a second sugar motif selected from among the second sugar motifs provided in Table C include, but are not limited to, (from 5' to 3'): ssooooooooooooooooss, ssoooooooosooooooooss, ssooooooooooooooooss, and ssooooooozozooooooooss, wherein each "o" represents a phosphodiester linkage, each "z" represents a mesyl phosphoramidate linkage, and each "s" represents a phosphorothioate linkage. In particular embodiments, the first modified oligonucleotide has an internucleoside linkage motif of ssoooooooooooooooooooss and the second modified oligonucleotide has an internucleoside linkage motif of ssoooooooooooooooooss.

In some embodiments, an oligomeric duplex having a reduced fluorine content provided herein contains a first modified oligonucleotide (e.g., an antisense oligonucleotide) having a reduced fluorine content having a first sugar motif ($1^{st}$) and a second modified oligonucleotide (e.g., a sense oligonucleotide) having a reduced fluorine content having a second sugar motif ($2^{nd}$) and the first and second sugar motifs are any one of the exemplary combinations of first and second sugar motifs set out in Table C. In some such embodiments, the number of nucleosides in the first modified oligonucleotide is 23, 22, or 21 and the number of nucleosides in the second modified oligonucleotide is 21, 20, or 19. In some such embodiments, the number of nucleosides in the first modified oligonucleotide is 23 and the number of nucleosides in the second modified oligonucleotide is 21. In some embodiments, the number of nucleosides in the first modified oligonucleotide is 21 and the number of nucleosides in the second modified oligonucleotide is 19. In some embodiments, the first modified oligonucleotide (e.g., an antisense oligonucleotide) comprises or consists of a nucleobase sequence selected from among the sequences provided in Table A. Table B1 or SEQ ID NOS: 3-314, 627-782, 939-976, 1033-1038, 1254-1255, and 1258-1287 (or at least 21 contiguous nucleosides of any one of the sequences provided in Table A. Table B1 or SEQ ID NOS: 3-314, 627-782, 939-976, 1033-1038, 1254-1255, and 1258-1287) and/or the nucleobase sequence of the second modified oligonucleotide (e.g., a sense oligonucleotide) comprises or consists of a nucleobase sequence complementary to a sequence in the nucleobase sequence of the first modified oligonucleotide, or of a nucleobase sequence selected from among the sequences provided in Table A. Table B2 or SEQ ID NOS: 315-626, 783-938, 977-1016, 1027-1032, 1256-1257, and 1288-1290 (or at least 19 contiguous nucleosides of any one of the sequences provided in Table A. Table B2 or SEQ ID NOS: 315-626, 783-938, 977-1016, 1027-1032, 1256-1257, and 1288-1290). In some such embodiments, the nucleobase sequence of the first modified oligonucleotide (e.g., an antisense oligonucleotide) comprises or consists of a nucleobase sequence selected from among SEQ ID NOS: 29, 171, 176, 967, 968, 971, 972, 974, 975, 1033-1038, 1254-1255, and 1258-1287 (or at least 21 contiguous nucleosides of any one of SEQ ID NOS: 29, 171, 176, 967, 968, 971, 972, 974, 975, 1033-1038, 1254-1255, and 1258-1287) and/or the nucleobase sequence of the second modified oligonucleotide (e.g., a sense oligonucleotide) comprises or consists of a nucleobase sequence selected from among SEQ ID NOS: 341, 483, 488, 1011-1016, 1027-1032, 1256-1257, and 1288-1290 (or at least 19 contiguous nucleosides of any one of SEQ ID NOS: 341, 483, 488, 1011-1016, 1027-1032, 1256-1257, and 1288-

1290). In some such embodiments, the first modified oligo-nucleotide comprises one or more modified internucleoside linkages. For example, the first modified oligonucleotide may contain one or more phosphorothioate internucleoside linkages, such as, for example, 1, 2, 3, 4, 5 or 6 phospho-rothioate internucleoside linkages. In some embodiments, no more than 4 of the internucleoside linkages of the first modified oligonucleotide are phosphorothioate internucleo-side linkages. In some embodiments, all the internucleoside linkages that are not phosphorothioate internucleoside link-ages are phosphodiester internucleoside linkages. Examples of internucleoside linkage motifs for a first modified oligo-nucleotide (e.g., an antisense oligonucleotide) having a first sugar motif in a combination of first and second sugar motifs selected from among the combinations provided in Table C include, but are not limited to, (from 5' to 3"): ssoooooooooooooooooooss, ssooosooooooooooooooss, ssoosososooooooooooooss, ssooooooooooooooooooos, ssooooooooooooooooooo, and ssooooooooooooooooooss, wherein each "o" represents a phosphodiester internucleo-side linkage and each "s" represents a phosphorothioate internucleoside linkage. In some such embodiments, the second modified oligonucleotide (e.g., a sense oligonucle-otide) comprises one or more modified internucleoside link-ages. In such embodiments, the second modified oligonucle-otide may contain one or more mesyl phosphoramidate internucleoside linkages and/or one or more phosphoroth-ioate internucleoside linkages, such as, for example, 1, 2, 3, 4, 5, or 6 phosphorothioate internucleoside linkages. In some embodiments, no more than 4 of the internucleoside linkages of the second modified oligonucleotide are phos-phorothioate internucleoside linkages. In some embodi-ments, all the internucleoside linkages that are not phospho-rothioate internucleoside linkages are phosphodiester internucleoside linkages. Examples of internucleoside link-age motifs for a second modified oligonucleotide (e.g., a sense oligonucleotide) having a second sugar motif in a combination of first and second sugar motifs selected from among the combinations provided in Table C include, but are not limited to, (from 5' to 3"): ssooooooooooooooooooss, ssoooooooosoooooooooss, ssooooooooooooooooooss, and ssooooooozozoooooooooss, wherein each "o" represents a phosphodiester linkage, each "z" represents a mesyl phos-phoramidate linkage, and each "s" represents a phosphoro-thioate linkage. In particular embodiments, the first modified oligonucleotide has an internucleoside linkage motif of ssooooooooooooooooooooss and the second modified oligo-nucleotide has an internucleoside linkage motif of ssooooooooooooooooooss.

a. Compound No. 1757465

Provided herein is Compound No. 1757465, which is an oligomeric duplex that consists of a first oligomeric com-pound containing a first modified oligonucleotide and a second oligomeric compound containing a second modified oligonucleotide attached to a conjugate group as follows. First Oligomeric Compound of Compound No. 1757465:

The first oligomeric compound of Compound no. 1757465, which is Compound No. 1746643, has a first modified oligonucleotide having a nucleobase sequence of (from 5' to 3") TUUAAGAUGAGACAGAAAUUGAA (SEQ ID NO: 967), wherein each of nucleosides 1, 22 and 23 (from 5' to 3) comprises a 2'-MOE modified sugar moiety, each of nucleosides 2, 14 and 16 (from 5' to 3') comprises a 2'-fluoro modified sugar moiety, each of nucleosides 3-5, 7-13, 15 and 17-21 (from 5' to 3') comprises a 2-OMe modified sugar moiety, and nucleoside 6 (from 5' to 3') is a 2'-deoxynucleoside, wherein each of the internucleoside linkages linking nucleosides 1 to 2, 2 to 3, 21 to 22, and 22 to 23 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, to 16, 16 to 17, 17 to 18, 18 to 19, 19 to 20, and 20 to 21 (from 5' to 3') is a phosphodiester linkage, and wherein nucleoside 1 (from 5' to 3') is attached to a vinyl phosphonate group.

The first oligomeric compound of Compound 1757465 is represented by the following chemical notation:

(SEQ ID NO: 1033)

$$vPT_{es}U_{fs}U_{yo}A_{yo}A_{yo}G_{do}A_{yo}U_{yo}G_{yo}A_{yo}G_{yo}A_{yo}C_{yo}A_{fo}G_{yo}$$

$$A_{fo}A_{yo}A_{yo}U_{yo}U_{yo}G_{ys}A_{es}A_e;$$

wherein
- A=an adenine nucleobase,
- C=a cytosine nucleobase,
- G=a guanine nucleobase,
- T=a thymine nucleobase,
- U=a uracil nucleobase,
- d=a 2'-deoxy sugar moiety,
- e=a 2'-MOE sugar moiety,
- f=a 2'-fluoro sugar moiety,
- y=a 2'-OMe sugar moiety,
- o=a phosphodiester internucleoside linkage,
- s=a phosphorothioate internucleoside linkage, and
- vP=a 5' vinyl phosphonate group.

Second Oligomeric Compound of Compound No. 1757465:

The second oligomeric compound of Compound No. 1757465, which is Compound No. 1757454, has a second modified oligonucleotide having a nucleobase sequence of (from 5' to 3') CAAUUUCUGUCUCAUCUUAAA (SEQ ID NO: 1011), wherein each of nucleosides 1, 2, 20 and 21 (from 5' to 3') comprises a 2'-MOE modified sugar moiety, each of nucleosides 10 and 11 (from 5' to 3') comprises a 2'-fluoro modified sugar moiety, and each of nucleosides 3-9, and 12-19 (from 5' to 3') comprises a 2'-OMe modified sugar moiety, wherein each of the internucleoside linkages linking nucleosides 1 to 2, 2 to 3, 19 to 20, and 20 to 21 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 (from 5' to 3') is a phosphodiester linkage, and wherein nucleoside 1 (from 5' to 3') is a 5-methylcyto-sine attached through a 5'-phosphodiester linkage and a 6-(BCN-carbamate)hexyl conjugate linker to a conjugate moiety comprising the amino acid sequence of bicycle compound BCY17901 (SEQ ID NO: 1045) wherein each cysteine forms a covalent bond with the molecular scaffold 1,1',1"-(1,3,5-triazinane-1,3,5-triyl)tris(2-bromoethanone) (TATB).

The second oligomeric compound of Compound 1757465 is represented by the following chemical notation:

(SEQ ID NO: 1039)

$[X]_1$-mC$_{es}$A$_{es}$A$_{yo}$U$_{yo}$U$_{yo}$U$_{yo}$C$_{yo}$U$_{yo}$G$_{yo}$U$_{fo}$C$_{fo}$U$_{yo}$C$_{yo}$A$_{yo}$

U$_{yo}$C$_{yo}$U$_{yo}$U$_{yo}$A$_{ys}$A$_{es}$A$_e$;

wherein:

$^m$C=a 5-methyl cytosine nucleobase,

C=a cytosine nucleobase,

A=an adenine nucleobase,

G=a guanine nucleobase, U=a uracil nucleobase, e=a 2'-MOE sugar moiety, f=a 2'-fluoro sugar moiety, y=a 2'-OMe sugar moiety, o=a phosphodiester internucleoside linkage, s=a phosphorothioate internucleoside linkage, and $[X]_1$=a conjugate group having the following structure (SEQ ID NO: 1299):

The following chemical structure is one structural representation of Compound No. 1757465:

451                                                                                                      452

(SEQ ID NO: 1033 and SEQ ID NO: 1039; peptide sequence disclosed as SEQ ID NO: 1293)

-continued

-continued or a salt thereof.

In certain embodiments, Compound No. 1757465 is in the form of an anion or a salt thereof, for example, a sodium salt. In certain embodiments, the oligomeric duplex is in anionic form in a solution. In certain embodiments. Compound No. 1757465 is a sodium salt or a potassium salt.

The following chemical structure represents Compound No. 1757465 in sodium solution:

457                                                                                              458

(SEQ ID NO: 1033 and SEQ ID NO: 1039; peptide sequence disclosed as SEQ ID NO: 1293)

459 460

-continued

-continued

In certain embodiments, provided herein are oligomeric duplexes comprising or consisting of a first oligomeric compound containing a first modified oligonucleotide and a second oligomeric compound containing a second modified oligonucleotide as follows.

First Oligomeric Compound:

The first modified oligonucleotide has a nucleobase sequence of (from 5' to 3') TUUAAGAUGA-GACAGAAAUUGAA (SEQ ID NO: 967), wherein each of nucleosides 1, 22 and 23 (from 5' to 3') comprises a 2'-MOE modified sugar moiety, each of nucleosides 2, 14 and 16

(from 5' to 3') comprises a 2'-fluoro modified sugar moiety, each of nucleosides 3-5, 7-13, 15 and 17-21 (from 5' to 3') comprises a 2'-OMe modified sugar moiety, and nucleoside 6 (from 5' to 3') is a 2-deoxynucleoside, wherein each of the internucleoside linkages linking nucleosides 1 to 2, 2 to 3, 21 to 22, and 22 to 23 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, to 16, 16 to 17, 17 to 18, 18 to 19, 19 to 20, and 20 to 21 (from 5' to 3') is a phosphodiester linkage, and wherein nucleoside 1 (from 5' to 3') is attached to a vinyl phosphonate group.

The first oligomeric compound is represented by the following chemical notation:

(SEQ ID NO: 1033)

$vPT_{es}U_{fs}U_{yo}A_{yo}A_{yo}G_{do}A_{yo}U_{yo}G_{yo}A_{yo}G_{yo}A_{yo}C_{yo}A_{fo}G_{yo}$ $A_{fo}A_{yo}A_{yo}U_{y}U_{yo}G_{yo}A_{es}A_{e};$ wherein A=an adenine nucleobase, C=a cytosine nucleobase, G=a guanine nucleobase, T=a thymine nucleobase, U=a uracil nucleobase, d=a 2'-deoxy sugar moiety, e=a 2'-MOE sugar moiety, f=a 2'-fluoro sugar moiety, y=a 2'-OMe sugar moiety, o=a phosphodiester internucleoside linkage, s=a phosphorothioate internucleoside linkage, and vP=a 5' vinyl phosphonate group.

Second Oligomeric Compound:

The second modified oligonucleotide has a nucleobase sequence of (from 5' to 3') CAAUUUCUGUCUCAUC-UUAAA (SEQ ID NO: 1011), wherein each of nucleosides 1, 2, 20 and 21 (from 5' to 3') comprises a 2'-MOE modified sugar moiety, each of nucleosides 10 and 11 (from 5' to 3') comprises a 2'-fluoro modified sugar moiety, and each of nucleosides 3-9, and 12-19 (from 5' to 3') comprises a 2'-OMe modified sugar moiety, wherein each of the inter-nucleoside linkages linking nucleosides 1 to 2, 2 to 3, 19 to 20, and 20 to 21 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 (from 5' to 3') is a phosphodiester linkage.

The second modified oligonucleotide is represented by the following chemical notation:

(SEQ ID NO: 1027)

$mC_{es}A_{es}A_{yo}U_{yo}U_{yo}U_{yo}C_{yo}U_{yo}G_{yo}U_{fo}C_{fo}U_{yo}C_{yo}A_{yo}U_{yo}C_{yo}$ $U_{y}U_{yo}A_{ys}A_{es}A_{e};$

A=an adenine nucleobase,

C=a 5-methyl cytosine nucleobase,

C=a cytosine nucleobase,

G=a guanine nucleobase,

U=a uracil nucleobase, e=a 2'-MOE sugar moiety, f=a2'-fluoro sugar moiety, y=a 2'-OMe sugar moiety, o=a phosphodiester internucleoside linkage, and s=a phosphorothioate internucleoside linkage.

In particular embodiments, such an oligomeric duplex is represented by the following chemical structure:

465

466

(SEQ ID NO: 1033 and SEQ ID NO: 1027)

-continued

-continued or a salt thereof.

In certain embodiments, such an oligomeric duplex is in the form of an anion or a salt thereof, for example, a sodium salt. In certain embodiments, the oligomeric duplex is in anionic form in a solution. In certain embodiments, the oligomeric duplex is a sodium salt or a potassium salt.

The following chemical structure represents such an oligomeric duplex in sodium solution:

471 472

(SEQ ID NO: 1033 and SEQ ID NO: 1027)

-continued

-continued

A, b. Compound No. 1757468

Provided herein is Compound No. 1757468, which is an oligomeric duplex that consists of a first oligomeric compound containing a first modified oligonucleotide and a second oligomeric compound containing a second modified oligonucleotide attached to a conjugate group as follows.

First Oligomeric Compound of Compound No. 1757468:

The first oligomeric compound of Compound No. 1757468, which is Compound No. 1746644, has a first modified oligonucleotide having a nucleobase sequence of (from 5' to 3') TUUAAGAUGAGACAGAAAUUGAA (SEQ ID NO: 968), wherein each of nucleosides 1, 22 and 23 (from 5' to 3') comprises a 2'-MOE modified sugar moiety, each of nucleosides 2, 14 and 16 (from 5' to 3') comprises a 2'-fluoro modified sugar moiety, each of nucleosides 3, 4, 6, 8-13, 15 and 17-21 (from 5' to 3') comprises a 2'-OMe modified sugar moiety, and each of nucleosides 5 and 7 (from 5' to 3') is a 2'-deoxynucleoside, wherein each of the internucleoside linkages linking nucleosides 1 to 2, 2 to 3, 21 to 22, and 22 to 23 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, and 20 to 21 (from 5' to 3') is a phosphodiester linkage, and wherein nucleoside 1 (from 5' to 3') is attached to a vinyl phosphonate group.

The first modified oligonucleotide of Compound 1757468 is represented by the following chemical (SEQ ID NO: 1034)

$vPT_{es}U_{fs}U_{yo}A_{yo}A_{do}G_{yo}A_{do}U_{yo}G_{yo}A_{yo}G_{yo}A_{yo}C_{yo}A_{ro}G_{yo}$ $A_{ro}A_{yo}A_{yo}U_{yo}U_{yo}G_{ys}A_{es}A_{e};$ wherein
  A=an adenine nucleobase,
  C=a cytosine nucleobase,
  G=a guanine nucleobase,
  T=a thymine nucleobase,
  U=a uracil nucleobase,
  d=a 2'-deoxy sugar moiety,
  e=a 2'-MOE sugar moiety, f=a 2'-fluoro sugar moiety,
y=a 2'-OMe sugar moiety,
o=a phosphodiester internucleoside linkage,
s=a phosphorothioate internucleoside linkage, and
vP=a 5' vinyl phosphonate group.

Second Oligomeric Compound of Compound No. 1757468:

The second oligomeric compound of Compound No. 1757468, which is Compound No. 1753740, has a second modified oligonucleotide having a nucleobase sequence of (from 5' to 3') CAAUUUCUGUCUCAUCUUAAA (SEQ ID NO: 1012), wherein each of nucleosides 1, 2, 20 and 21 (from 5' to 3') comprises a 2'-MOE modified sugar moiety, each of nucleosides 7, 9, and 11 (from 5' to 3') comprises a 2'-fluoro modified sugar moiety, and each of nucleosides 3-6, 8, 10, and 12-19 (from 5' to 3') comprises a 2'-OMe modified sugar moiety, wherein each of the internucleoside linkages linking nucleosides 1 to 2, 2 to 3, 19 to 20, and 20 to 21 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 (from 5' to 3') is a phosphodiester linkage, and wherein nucleoside 1 (from 5' to 3') is attached through a 5'-phosphodiester linkage and a 6-(BCN-carbamate)hexyl conjugate linker to a conjugate moiety comprising the amino acid sequence of bicycle compound BCY17901 (SEQ ID NO: 1045) wherein each cysteine forms a covalent bond with the molecular scaffold 1,1',1"-(1,3,5-triazinane-1,3,5-triyl)tris(2-bromoethanone) (TATB).

The second oligomeric compound of Compound 1757468 is represented by the following chemical (SEQ ID NO: 1040)

$[X]_1 - C_{es}A_{es}A_{yo}U_{yo}U_{yo}U_{yo}C_{fo}U_{yo}G_{ro}U_{yo}C_{fo}U_{yo}C_{yo}A_{yo}$ $U_{yo}C_{yo}U_{yo}U_{yo}A_{ys}A_{es}A_{e};$ wherein:
  C=a cytosine nucleobase,
  A=an adenine nucleobase,
  G=a guanine nucleobase,
  U=a uracil nucleobase, e=a 2'-MOE sugar moiety,
f=a 2'-fluoro sugar moiety,
y=a 2'-OMe sugar moiety,
o=a phosphodiester internucleoside linkage, s=a phosphorothioate internucleoside linkage, and

[X]₁=a conjugate group having the following structure (SEQ ID NO: 1300):

(SEQ ID NO: 1034 and SEQ ID NO: 1040; peptide sequence disclosed as SEQ ID NO: 1294)

The following chemical structure is one structural representation of Compound No. 1757468:

481                                                              482

-continued

-continued or a salt thereof.

In certain embodiments, Compound No. 1757468 is in the form of an anion or a salt thereof, for example, a sodium salt. In certain embodiments, the oligomeric duplex is in anionic form in a solution. In certain embodiments, Compound No. 1757468 is a sodium salt or a potassium salt.

The following chemical structure represents Compound No. 1757468 in sodium solution:

(SEQ ID NO: 1034 and SEQ ID NO: 1040; peptide sequence disclosed as SEQ ID NO: 1294)

-continued 491 492

-continued

-continued

In certain embodiments, provided herein are oligomeric duplexes comprising or consisting of a first oligomeric compound containing a first modified oligonucleotide and a second oligomeric compound containing a second modified oligonucleotide as follows.

First Oligomeric Compound:

The first modified oligonucleotide has a nucleobase sequence of (from 5' to 3') TUUAAGAUGA-GACAGAAAUUGAA (SEQ ID NO: 968), wherein each of nucleosides 1, 22 and 23 (from 5' to 3') comprises a 2'-MOE modified sugar moiety, each of nucleosides 2, 14 and 16 (from 5' to 3') comprises a 2'-fluoro modified sugar moiety, each of nucleosides 3, 4, 6, 8-13, 15 and 17-21 (from 5' to 3') comprises a 2'-OMe modified sugar moiety, and each of nucleosides 5 and 7 (from 5' to 3') is a 2'-deoxynucleoside, wherein each of the internucleoside linkages linking nucleosides 1 to 2, 2 to 3, 21 to 22, and 22 to 23 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, and 20 to 21 (from 5' to 3') is a phosphodiester linkage, and wherein nucleoside 1 (from 5' to 3') is attached to a vinyl phosphonate group.

The first oligomeric compound is represented by the following chemical notation:

(SEQ ID NO: 1034)

vPT$_{es}$U$_{fs}$U$_{yo}$A$_{yo}$A$_{do}$G$_{yo}$A$_{do}$U$_{yo}$G$_{yo}$A$_{yo}$G$_{yo}$A$_{yo}$C$_{yo}$A$_{fo}$G$_{yo}$

A$_{fo}$A$_{yo}$A$_{yo}$U$_{yo}$U$_{yo}$G$_{ys}$A$_{es}$A$_{e}$;

wherein

A=an adenine nucleobase,
C=a cytosine nucleobase,
G=a guanine nucleobase,
T=a thymine nucleobase,
U=a uracil nucleobase,
d=a 2'-deoxy sugar moiety, e=a 2'-MOE sugar moiety,
f=a 2-fluoro sugar moiety,
y=a 2'-OMe sugar moiety,
o=a phosphodiester internucleoside linkage,
s=a phosphorothioate internucleoside linkage, and
vP=a 5' vinyl phosphonate group.

Second Oligomeric Compound:

The second modified oligonucleotide has a nucleobase sequence of (from 5' to 3") CAAUUUCUGUCUCAUC-UUAAA (SEQ ID NO: 1012), wherein each of nucleosides 1, 2, 20 and 21 (from 5' to 3') comprises a 2'-MOE modified sugar moiety, each of nucleosides 7, 9, and 11 (from 5' to 3') comprises a 2'-fluoro modified sugar moiety, and each of nucleosides 3-6, 8, 10, and 12-19 (from 5' to 3') comprises a 2'-OMe modified sugar moiety, wherein each of the internucleoside linkages linking nucleosides 1 to 2, 2 to 3, 19 to 20, and 20 to 21 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 (from 5' to 3') is a phosphodiester linkage.

The second oligomeric compound is represented by the following chemical notation:

(SEQ ID NO: 1028)

C$_{es}$A$_{es}$A$_{yo}$U$_{yo}$U$_{yo}$U$_{yo}$C$_{fo}$U$_{yo}$G$_{ro}$U$_{yo}$C$_{fo}$U$_{yo}$C$_{yo}$A$_{yo}$U$_{yo}$C$_{yo}$

U$_{yo}$U$_{yo}$A$_{ys}$A$_{es}$A$_{e}$,

A=an adenine nucleobase,
C=a cytosine nucleobase,
G=a guanine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage, and
s=a phosphorothioate internucleoside linkage.

In particular embodiments, such an oligomeric duplex is represented by the following chemical structure:

(SEQ ID NO: 1034 and SEQ ID NO: 1028)

-continued

-continued or a salt thereof.

In certain embodiments, such an oligomeric duplex is in the form of an anion or a salt thereof, for example, a sodium salt. In certain embodiments, the oligomeric duplex is in anionic form in a solution. In certain embodiments, the oligomeric duplex is a sodium salt or a potassium salt.

The following chemical structure represents such an oligomeric duplex in sodium solution:

(SEQ ID NO: 1034 and SEQ ID NO: 1028)

-continued

-continued

A, c. Compound No. 1757471

Provided herein is Compound No. 1757471, which is an oligomeric duplex that consists of a first oligomeric compound containing a first modified oligonucleotide and a second oligomeric compound containing a second modified oligonucleotide attached to a conjugate group as follows. First Oligomeric Compound of Compound No. 1757471;

The first modified oligonucleotide of Compound no. 1757471, which is Compound No. 1753975, has a nucleobase sequence of (from 5' to 3') TAUAAAUAGAUUCU-GUAGCUUAA (SEQ ID NO: 974), wherein each of nucleosides 1, 22 and 23 (from 5' to 3') comprises a 2'-MOE modified sugar moiety, each of nucleosides 2, 14 and 16 (from 5' to 3') comprises a 2'-fluoro modified sugar moiety, each of nucleosides 3-5, 7-13, 15 and 17-21 (from 5' to 3') comprises a 2'-OMe modified sugar moiety, and nucleoside 6 (from 5' to 3') is a 2'-deoxynucleoside, wherein each of the internucleoside linkages linking nucleosides 1 to 2, 2 to 3, 21 to 22, and 22 to 23 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, and 20 to 21 (from 5' to 3') is a phosphodiester linkage, and wherein nucleoside 1 (from 5' to 3') is attached to a vinyl phosphonate group.

The first oligomeric compound of Compound 1757471 is represented by the following chemical notation:

(SEQ ID NO: 1035)

$$vPT_{es}A_{fs}U_{yo}A_{yo}A_{yo}A_{do}U_{yo}A_{yo}G_{yo}A_{yo}U_{yo}U_{yo}C_{yo}U_{fo}G_{yo}$$

$$U_{fo}A_{yo}G_{yo}C_{yo}U_{yo}U_{ys}A_{es}A_{e};$$

wherein
A=an adenine nucleobase,
C=a cytosine nucleobase,
G=a guanine nucleobase,
T=a thymine nucleobase,
U=a uracil nucleobase,
d=a 2'-deoxy sugar moiety,
e=a 2'-MOE sugar moiety, f=a 2'-fluoro sugar moiety,
y=a 2'-OMe sugar moiety,
o=a phosphodiester internucleoside linkage,
s=a phosphorothioate internucleoside linkage, and
vP=a 5' vinyl phosphonate group.
Second Oligomeric Compound of Compound No. 1757471:

The second modified oligonucleotide of Compound No. 1757471, which is Compound No. 1757456, has a nucleobase sequence of (from 5' to 3') AAGCUACAGAAUC-UAUUUATA (SEQ ID NO: 1013), wherein each of nucleosides 1, 2, 20 and 21 (from 5' to 3') comprises a 2'-MOE modified sugar moiety, each of nucleosides 10 and 11 (from 5' to 3') comprises a 2'-fluoro modified sugar moiety, and each of nucleosides 3-9, and 12-19 (from 5' to 3') comprises a 2'-OMe modified sugar moiety, wherein each of the internucleoside linkages linking nucleosides 1 to 2, 2 to 3, 19 to 20, and 20 to 21 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 (from 5' to 3') is a phosphodiester linkage, and wherein nucleoside 1 (from 5' to 3') is attached through a 5'-phosphodiester linkage and a 6-(BCN-carbamate)hexyl conjugate linker to a conjugate moiety comprising the amino acid sequence of bicycle compound BCY17901 (SEQ ID NO: 1045) wherein each cysteine forms a covalent bond with the molecular scaffold 1,1',1"-(1,3,5-triazinane-1,3,5-triyl)tris(2-bromoethanone) (TATB).

The second oligomeric compound of Compound 1757471 is represented by the following chemical notation:

(SEQ ID NO: 1041)

$$[X]_1\text{-}A_{es}A_{es}G_{yo}C_{yo}U_{yo}A_{yo}C_{yo}A_{yo}G_{yo}A_{fo}A_{fo}U_{yo}C_{yo}U_{yo}$$

$$A_{yo}U_{yo}U_{yo}U_{yo}A_{ys}T_{es}A_{e};$$

wherein:
C=a cytosine nucleobase,
A=an adenine nucleobase,
G=a guanine nucleobase,
T=a thymine nucleobase, U=a uracil nucleobase,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage,
[X]₁=a conjugate group having the following structure
(SEQ ID NO: 1301):

The following chemical structure is one structural representation of Compound No. 1757471:

(SEQ ID NO: 1035 and SEQ ID NO: 1041; peptide sequence disclosed as SEQ ID NO: 1295)

-continued

-continued or a salt thereof.

In certain embodiments, Compound No. 1757471 is in the form of an anion or a salt thereof, for example, the oligomeric duplex may be in the form of a sodium salt. In certain embodiments, the oligomeric duplex is in anionic form in a solution. In certain embodiments, Compound No. 1757471 is a sodium salt or a potassium salt.

The following chemical structure represents Compound
No. 1757471 in sodium solution:

(SEQ ID NO: 1035 and SEQ ID NO: 1041; peptide sequence disclosed as SEQ ID NO: 1295)

-continued

-continued

-continued

In certain embodiments, provided herein are oligomeric duplexes comprising or consisting of a first oligomeric compound containing a first modified oligonucleotide and a second oligomeric compound containing a second modified oligonucleotide as follows.

First Oligomeric Compound:

The first modified oligonucleotide has a nucleobase sequence of (from 5' to 3') TAUAAAUAGAUUCU-GUAGCUUAA (SEQ ID NO: 974), wherein each of nucleosides 1, 22 and 23 (from 5' to 3') comprises a 2'-MOE modified sugar moiety, each of nucleosides 2, 14 and 16 (from 5' to 3') comprises a 2'-fluoro modified sugar moiety, each of nucleosides 3-5, 7-13, 15 and 17-21 (from 5' to 3') comprises a 2'-OMe modified sugar moiety, and nucleoside 6 (from 5' to 3') is a 2'-deoxynucleoside, wherein each of the internucleoside linkages linking nucleosides 1 to 2, 2 to 3, 21 to 22, and 22 to 23 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, to 16, 16 to 17, 17 to 18, 18 to 19, 19 to 20, and 20 to 21 (from 5' to 3') is a phosphodiester linkage, and wherein nucleoside 1 (from 5' to 3') is attached to a vinyl phosphonate group.

The first oligomeric compound is represented by the following chemical notation:

(SEQ ID NO: 1035)
vPT$_{es}$A$_{fs}$U$_{yo}$A$_{yo}$A$_{yo}$A$_{do}$U$_{yo}$A$_{yo}$G$_{yo}$A$_{yo}$U$_{yo}$U$_{yo}$C$_{yo}$U$_{fo}$G$_{yo}$

U$_{fo}$A$_{yo}$G$_{yo}$C$_{yo}$U$_{yo}$U$_{ys}$A$_{es}$A$_{e}$ ;

A=an adenine nucleobase,
C=a cytosine nucleobase,
G=a guanine nucleobase,
T=a thymine nucleobase, U=a uracil nucleobase,
d=a 2'-deoxy sugar moiety,
e=a 2'-MOE sugar moiety,
f=a 2-fluoro sugar moiety,
y=a 2'-OMe sugar moiety,
o=a phosphodiester internucleoside linkage,
s=a phosphorothioate internucleoside linkage, and
vP=a 5' vinyl phosphonate group.

Second Oligomeric Compound:

The second modified oligonucleotide has a nucleobase sequence of (from 5' to 3") AAGCUACAGAAUC-UAUUUATA (SEQ ID NO: 1013), wherein each of nucleosides 1, 2, 20 and 21 (from 5' to 3') comprises a 2'-MOE modified sugar moiety, each of nucleosides 10 and 11 (from 5' to 3') comprises a 2'-fluoro modified sugar moiety, and each of nucleosides 3-9, and 12-19 (from 5' to 3') comprises a 2'-OMe modified sugar moiety, wherein each of the internucleoside linkages linking nucleosides 1 to 2, 2 to 3, 19 to 20, and 20 to 21 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 (from 5' to 3') is a phosphodiester linkage.

The second oligomeric compound is represented by the following chemical notation:

(SEQ ID NO: 1029)
A$_{es}$A$_{es}$G$_{yo}$C$_{yo}$U$_{yo}$A$_{yo}$C$_{yo}$A$_{yo}$G$_{yo}$A$_{fo}$A$_{fo}$U$_{yo}$C$_{yo}$U$_{yo}$A$_{yo}$U$_{yo}$

U$_{yo}$U$_{yo}$A$_{ys}$T$_{es}$A$_{e}$ ;

A=an adenine nucleobase,
C=a cytosine nucleobase,
G=a guanine nucleobase,
T=a thymine nucleobase,

525

U=a uracil nucleobase,
e=a2'-MOE sugar moiety,
f=a2'-fluoro sugar moiety,
y=a 2'-OMe sugar moiety,

526 o=a phosphodiester internucleoside linkage, and
s=a phosphorothioate internucleoside linkage.

In particular embodiments, such an oligomeric duplex is represented by the following chemical structure:

(SEQ ID NO: 1035 and SEQ ID NO: 1029)

-continued

-continued

-continued or a salt thereof.

In certain embodiments, such an oligomeric duplex is in the form of an anion or a salt thereof, for example, a sodium salt. In certain embodiments, the oligomeric duplex is in anionic form in a solution. In certain embodiments, the oligomeric duplex is a sodium salt or a potassium salt.

The following chemical structure represents such an oligomeric duplex in sodium solution:

(SEQ ID NO: 1035 and SEQ ID NO: 1029)

-continued

-continued d. Compound No. 1757474

Provided herein is Compound No. 1757474, which is an oligomeric duplex that consists of a first oligomeric compound containing a first modified oligonucleotide and a second oligomeric compound containing a second modified oligonucleotide attached to a conjugate group as follows.

First Oligomeric Compound of Compound No. 1757474;

The first modified oligonucleotide of Compound No. 1757474, which is Compound No. 1753976, has a nucleobase sequence of (from 5' to 3') TAUAAATAGAUUCU-GUAGCUUAA (SEQ ID NO: 975), wherein each of nucleosides 1, 22 and 23 (from 5' to 3') comprises a 2'-MOE modified sugar moiety, each of nucleosides 2, 14 and 16 (from 5' to 3') comprises a 2'-fluoro modified sugar moiety, each of nucleosides 3, 4, 6, 8-13, 15 and 17-21 (from 5' to 3') comprises a 2'-OMe modified sugar moiety, and each of nucleosides and 7 (from 5' to 3') is a 2'-deoxynucleoside, wherein each of the internucleoside linkages linking nucleosides 1 to 2, 2 to 3, 21 to 22, and 22 to 23 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, to 11, 11 to 12, 12 to 13, 13 to 14, 14 to 15, 15 to 16, 16 to 17, 17 to 18, 18 to 19, 19 to 20, and 20 to 21 (from 5' to 3') is a phosphodiester linkage, and wherein nucleoside 1 (from 5' to 3') is attached to a vinyl phosphonate group.

The first oligomeric compound of Compound 1757474 is represented by the following chemical notation:

(SEQ ID NO: 1036)

$\text{vPT}_{es}\text{A}_{fs}\text{U}_{yo}\text{A}_{yo}\text{A}_{do}\text{A}_{yo}\text{T}_{do}\text{A}_{yo}\text{G}_{yo}\text{A}_{yo}\text{U}_{yo}\text{U}_{yo}\text{C}_{yo}\text{U}_{fo}\text{G}_{yo}\text{U}_{fo}$ $\text{A}_{yo}\text{G}_{yo}\text{C}_{yo}\text{U}_{yo}\text{U}_{ys}\text{A}_{es}\text{A}_{e};$ wherein
   A=an adenine nucleobase,
   C=a cytosine nucleobase,
   G=a guanine nucleobase,
   T=a thymine nucleobase,
   U=a uracil nucleobase, d=a 2'-deoxy sugar moiety,
   e=a 2'-MOE sugar moiety,
   f=a 2'-fluoro sugar moiety,
   y=a 2'-OMe sugar moiety,
   o=a phosphodiester internucleoside linkage,
   s=a phosphorothioate internucleoside linkage, and
   vP=a 5' vinyl phosphonate group.

Second Oligomeric Compound of Compound No. 1757474:

The second modified oligonucleotide of Compound No. 1757474, which is Compound No. 1757458, has a nucleobase sequence of (from 5' to 3') AAGCUACAGAAUC-UAUUUAUA (SEQ ID NO: 1014), wherein each of nucleosides 1, 2, 20 and 21 (from 5' to 3') comprises a 2'-MOE modified sugar moiety, each of nucleosides 7, 9, and 11 (from 5' to 3') comprises a 2'-fluoro modified sugar moiety, and each of nucleosides 3-6, 8, 10, and 12-19 (from 5' to 3') comprises a 2'-OMe modified sugar moiety, wherein each of the internucleoside linkages linking nucleosides 1 to 2, 2 to 3, 19 to 20, and 20 to 21 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 (from 5' to 3') is a phosphodiester linkage, and wherein nucleoside 1 (from 5' to 3') is attached through a 5'-phosphodiester linkage and a 6-(BCN-carbamate)hexyl conjugate linker to a conjugate moiety comprising the amino acid sequence of bicycle compound BCY17901 (SEQ ID NO: 1045) wherein each cysteine forms a covalent bond with the molecular scaffold 1,1',1"-(1,3,5-triazinane-1,3,5-triyl) tris(2-bromo-ethanone) (TATB).

The second oligomeric compound of Compound 1757474 is represented by the following chemical (SEQ ID NO: 1042)

$[\text{X}]_1\text{-A}_{es}\text{A}_{es}\text{G}_{yo}\text{C}_{yo}\text{U}_{yo}\text{A}_{yo}\text{C}_{fe}\text{A}_{yo}\text{G}_{ro}\text{A}_{yo}\text{A}_{fo}\text{U}_{yo}\text{C}_{yo}\text{U}_{yo}$ $\text{A}_{yo}\text{U}_{yo}\text{U}_{yo}\text{U}_{yo}\text{A}_{ys}\text{U}_{es}\text{A}_{e};$

541

542 wherein:
    C=a cytosine nucleobase,
    A=an adenine nucleobase,
    G=a guanine nucleobase,
    U=a uracil nucleobase,
    e=a 2'-MOE sugar moiety,
    f=a 2'-fluoro sugar moiety,
    y=a 2'-OMe sugar moiety,
    o=a phosphodiester internucleoside linkage,
    s=a phosphorothioate internucleoside linkage, and
    [X]₁=a conjugate group having the following structure
        (SEQ ID NO: 1302):

The following chemical structure is one structural repre-
sentation of Compound No. 1757474:

(SEQ ID NO: 1036 and SEQ ID NO: 1042; peptide sequence disclosed as SEQ ID NO: 1296)

-continued

-continued or a salt thereof.

In certain embodiments, Compound No. 1757474 is in the form of an anion or a salt thereof, for example, a sodium salt.

In certain embodiments, the oligomeric duplex is in anionic form in a solution. In certain embodiments, Compound No. 1757474 is a sodium salt or a potassium salt.

The following chemical structure represents Compound
No. 1757474 in sodium solution:

(SEQ ID NO: 1036 and SEQ ID NO: 1042; peptide sequence disclosed as SEQ ID NO: 1296)

-continued

-continued

In certain embodiments, provided herein are oligomeric duplexes comprising or consisting of a first oligomeric compound containing a first modified oligonucleotide and a second oligomeric compound containing a second modified oligonucleotide as follows.

First Oligomeric Compound:

The first modified oligonucleotide has a nucleobase sequence of (from 5' to 3') TAUAAATAGAUUCU-GUAGCUUAA (SEQ ID NO: 975), wherein each of nucleosides 1, 22 and 23 (from 5' to 3') comprises a 2'-MOE modified sugar moiety, each of nucleosides 2, 14 and 16 (from 5' to 3') comprises a 2'-fluoro modified sugar moiety, each of nucleosides 3, 4, 6, 8-13, 15 and 17-21 (from 5' to 3') comprises a 2'-OMe modified sugar moiety, and each of nucleosides 5 and 7 (from 5' to 3') is a 2'-deoxynucleoside, wherein each of the internucleoside linkages linking nucleosides 1 to 2, 2 to 3, 21 to 22, and 22 to 23 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, and 20 to 21 (from 5' to 3') is a phosphodiester linkage, and wherein nucleoside 1 (from 5' to 3') is attached to a vinyl phosphonate group.

The first oligomeric compound is represented by the following chemical notation:

(SEQ ID NO: 1036)

$$\text{vPT}_{es}\text{A}_{fs}\text{U}_{yo}\text{A}_{yo}\text{A}_{do}\text{A}_{yo}\text{T}_{do}\text{A}_{yo}\text{G}_{yo}\text{A}_{yo}\text{U}_{yo}\text{U}_{yo}\text{C}_{yo}\text{U}_{fo}\text{G}_{yo}\text{U}_{fo}$$

$$\text{A}_{yo}\text{G}_{yo}\text{C}_{yo}\text{U}_{yo}\text{U}_{ys}\text{A}_{es}\text{A}_e;$$

A=an adenine nucleobase,

C=a cytosine nucleobase,

G=a guanine nucleobase,

T=a thymine nucleobase,

U=a uracil nucleobase, d=a 2'-deoxy sugar moiety, e=a 2'-MOE sugar moiety, f=a 2'-fluoro sugar moiety, y=a 2'-OMe sugar moiety, o=a phosphodiester internucleoside linkage, s=a phosphorothioate internucleoside linkage, and vP=a 5' vinyl phosphonate group.

Second Oligomeric Compound:

The second modified oligonucleotide has a nucleobase sequence of (from 5' to 3") AAGCUACAGAAUC-UAUUUAUA (SEQ ID NO: 1014), wherein each of nucleosides 1, 2, 20 and 21 (from 5' to 3') comprises a 2'-MOE modified sugar moiety, each of nucleosides 7, 9, and 11 (from 5' to 3") comprises a 2'-fluoro modified sugar moiety, and each of nucleosides 3-6, 8, 10, and 12-19 (from 5' to 3') comprises a 2'-OMe modified sugar moiety, wherein each of the internucleoside linkages linking nucleosides 1 to 2, 2 to 3, 19 to 20, and 20 to 21 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 (from 5' to 3') is a phosphodiester linkage.

The second oligomeric compound is represented by the following chemical notation:

(SEQ ID NO: 1030)

$$\text{A}_{es}\text{A}_{es}\text{G}_{yo}\text{C}_{yo}\text{U}_{yo}\text{A}_{yo}\text{C}_{fo}\text{A}_{yo}\text{G}_{fo}\text{A}_{yo}\text{A}_{fo}\text{U}_{yo}\text{C}_{yo}\text{U}_{yo}\text{A}_{yo}\text{U}_{yo}$$

$$\text{U}_{yo}\text{U}_{yo}\text{A}_{ys}\text{U}_{es}\text{A}_e,$$

wherein

A=an adenine nucleobase,

C=a cytosine nucleobase.

G=a guanine nucleobase.

U=a uracil nucleobase, c=a 2'-MOE sugar moiety, f=a 2-fluoro sugar moiety.

y=a 2-OMe sugar moiety.

o=a phosphodiester internucleoside linkage, and

S=a phosphorothioate internucleoside linkage.

In particular embodiments, such an oligomeric duplex is represented by the following chemical structure:

(SEQ ID NO: 1036 and SEQ ID NO: 1030)

-continued

-continued or a salt thereof.

In certain embodiments, such an oligomeric duplex is in the form of an anion or a salt thereof, for example, a sodium salt. In certain embodiments, the oligomeric duplex is in anionic form in a solution. In certain embodiments, the oligomeric duplex is a sodium salt or a potassium salt.

The following chemical structure represents such an oligomeric duplex in sodium solution:

(SEQ ID NO: 1036 and SEQ ID NO: 1030)

-continued e. Compound No. 1757477

Provided herein is Compound No. 1757477, which is an oligomeric duplex that consists of a first oligomeric compound containing a first modified oligonucleotide and a second oligomeric compound containing a second modified oligonucleotide attached to a conjugate group as follows.

First Oligomeric Compound of Compound No. 1757477:

The first modified oligonucleotide of compound no. 1757477, which is Compound No. 1753977, has a nucleobase sequence of (from 5' to 3') TUAAGTUUUAGUC-UUAAUCUUAA (SEQ ID NO: 971), wherein each of nucleosides 1, 22 and 23 (from 5' to 3') comprises a 2'-MOE modified sugar moiety, each of nucleosides 2, 14 and 16 (from 5' to 3') comprises a 2-fluoro modified sugar moiety, each of nucleosides 3-5, 7-13, 15 and 17-21 (from 5' to 3') comprises a 2'-OMe modified sugar moiety, and nucleoside 6 (from 5' to 3') is a 2'-deoxynucleoside, wherein each of the internucleoside linkages linking nucleosides 1 to 2, 2 to 3, 21 to 22, and 22 to 23 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, and 20 to 21 (from 5' to 3') is a phosphodiester linkage, and wherein nucleoside 1 (from 5' to 3') is attached to a vinyl phosphonate group.

The first oligomeric compound of Compound 1757477 is represented by the following chemical notation:

(SEQ ID NO: 1037)

$vPT_{es}U_{fs}A_{yo}A_{yo}G_{yo}T_{do}U_{yo}U_{yo}U_{yo}A_{yo}G_{yo}U_{yo}C_{yo}U_{fo}U_{yo}A_{fo}$ $A_{yo}U_{yo}C_{yo}U_{yo}U_{ys}A_{es}A_{e}$;

wherein

A=an adenine nucleobase,

C=a cytosine nucleobase,

G=a guanine nucleobase,

T=a thymine nucleobase,

U=a uracil nucleobase, d=a 2'-deoxy sugar moiety, e=a 2'-MOE sugar moiety, f=a 2'-fluoro sugar moiety, y=a 2'-OMe sugar moiety, o=a phosphodiester internucleoside linkage, s=a phosphorothioate internucleoside linkage, and vP=a 5' vinyl phosphonate group.

Second Oligomeric Compound of Compound No. 1757477:

The second modified oligonucleotide of Compound No. 1757477, which is Compound No. 1757460, has a nucleobase sequence of (from 5' to 3') AAGAUUAAGAC-UAAAACUUAA (SEQ ID NO: 1015), wherein each of nucleosides 1, 2, 20 and 21 (from 5' to 3') comprises a 2'-MOE modified sugar moiety, each of nucleosides 10 and 11 (from 5' to 3') comprises a 2'-fluoro modified sugar moiety, and each of nucleosides 3-9, and 12-19 (from 5' to 3') comprises a 2'-OMe modified sugar moiety, wherein each of the internucleoside linkages linking nucleosides 1 to 2, 2 to 3, 19 to 20, and 20 to 21 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 (from 5' to 3') is a phosphodiester linkage, and wherein nucleoside 1 (from 5' to 3') is attached through a 5'-phosphodiester linkage and a 6-(BCN-carbamate)hexyl conjugate linker to a conjugate moiety comprising the amino acid sequence of bicycle compound BCY17901 (SEQ ID NO: 1045) wherein each cysteine forms a covalent bond with the molecular scaffold 1,1',1''-(1,3,5-triazinane-1,3,5-triyl)tris(2-bromo-ethanone) (TATB).

The second oligomeric compound of Compound 1757477 is represented by the following chemical notation:

(SEQ ID NO: 1043)

$[X]_1$-$A_{es}A_{es}G_{yo}A_{yo}U_{yo}U_{yo}A_{yo}A_{yo}G_{yo}A_{fo}C_{fo}U_{yo}A_{yo}A_{yo}$ $A_{yo}A_{yo}C_{yo}U_{yo}U_{ys}A_{es}A_{e}$;

wherein:

C=a cytosine nucleobase,

A=an adenine nucleobase,

G=a guanine nucleobase,

U=a uracil nucleobase, e=a 2'-MOE sugar moiety, f=a 2'-fluoro sugar moiety, y=a 2'-OMe sugar moiety, o=a phosphodiester internucleoside linkage, s=a phosphorothioate internucleoside linkage, and $[X]_1$=a conjugate group having the following structure (SEQ ID NO: 1303):

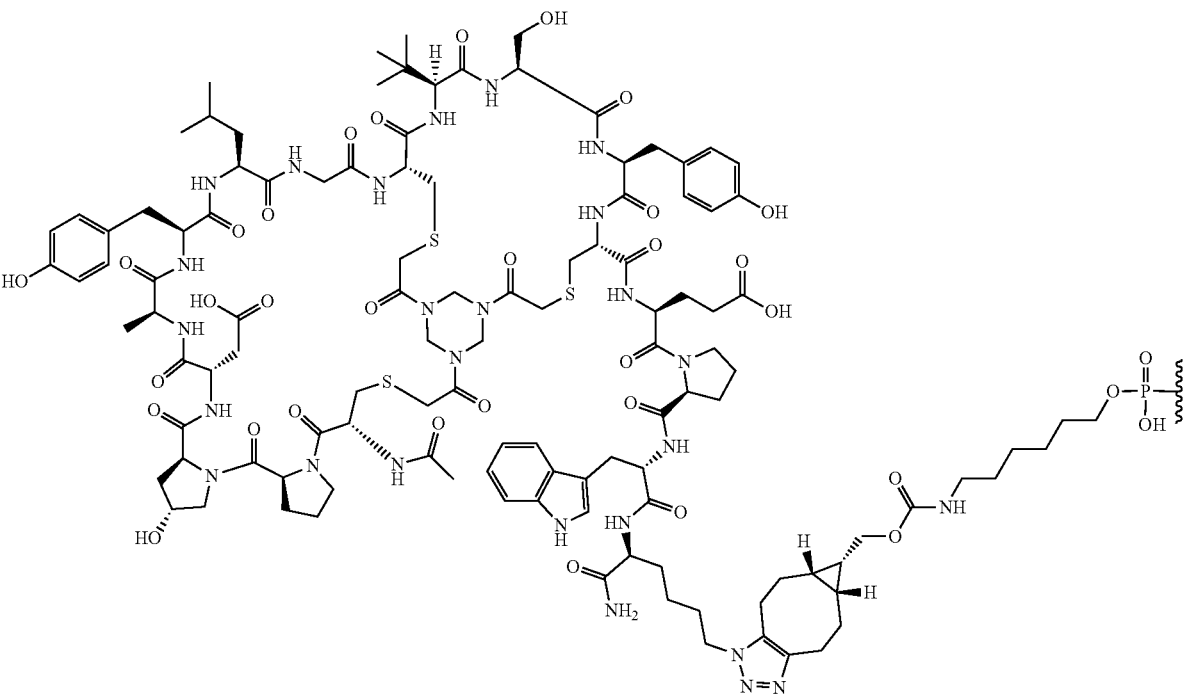 [SMILES: *P(=O)(O)OCCCCCCNC(=O)OC[C@@H]1[C@@H]2CCc3nnn(CCCC[C@H](NC(=O)[C@H](Cc4c[nH]c5ccccc45)NC(=O)[C@@H]4CCCN4C(=O)[C@H](CCC(=O)O)NC(=O)[C@@H]4CSCC(=O)N5CN6CN(C5)C(=O)CSC[C@H](NC(C)=O)C(=O)N5CCC[C@H]5C(=O)N5C[C@H](O)C[C@H]5C(=O)N[C@@H](CC(=O)O)C(=O)N[C@@H](C)C(=O)N[C@@H](Cc5ccc(O)cc5)C(=O)N[C@@H](CC(C)C)C(=O)NCC(=O)N[C@@H](CSCC6=O)C(=O)N[C@@H](C(C)(C)C)C(=O)N[C@@H](CO)C(=O)N[C@@H](Cc5ccc(O)cc5)C(=O)N4)C(N)=O)c3CC[C@@H]21]

The following chemical structure is one structural repre-
sentation of Compound No. 1757477:

(SEQ ID NO: 1037 and SEQ ID NO: 1043; peptide sequence disclosed as SEQ ID NO: 1297)

-continued

-continued or a salt thereof.

In certain embodiments, Compound No. 1757477 is in the form of an anion or a salt thereof, for example, a sodium salt. In certain embodiments, the oligomeric duplex is in anionic form in a solution. In certain embodiments, Compound No. 1757477 is a sodium salt or a potassium salt.

The following chemical structure represents Compound No. 1757477 in sodium solution:

(SEQ ID NO: 1037 and SEQ ID NO: 1043; peptide sequence disclosed as SEQ ID NO: 1297)

-continued

-continued

-continued

In certain embodiments, provided herein are oligomeric duplexes comprising or consisting of a first oligomeric compound containing a first modified oligonucleotide and a second oligomeric compound containing a second modified oligonucleotide as follows.

First Oligomeric Compound:

The first modified oligonucleotide has a nucleobase sequence of (from 5' to 3') TUAAGTUUUAGUC- UUAAUCUUAA (SEQ ID NO: 971), wherein each of nucleosides 1, 22 and 23 (from 5' to 3') comprises a 2'-MOE modified sugar moiety, each of nucleosides 2, 14 and 16 (from 5' to 3') comprises a 2'-fluoro modified sugar moiety, each of nucleosides 3-5, 7-13, 15 and 17-21 (from 5' to 3') comprises a 2'-OMe modified sugar moiety, and nucleoside 6 (from 5' to 3') is a 2'-deoxynucleoside, wherein each of the internucleoside linkages linking nucleosides 1 to 2, 2 to 3, 21 to 22, and 22 to 23 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, to 16, 16 to 17, 17 to 18, 18 to 19, 19 to 20, and 20 to 21 (from 5' to 3') is a phosphodiester linkage, and wherein nucleoside 1 (from 5' to 3') is attached to a vinyl phosphonate group.

The first oligomeric compound is represented by the following chemical notation:

(SEQ ID NO: 1037)
$$\text{vPT}_{es}\text{U}_{fs}\text{A}_{yo}\text{A}_{yo}\text{G}_{yo}\text{T}_{do}\text{U}_{yo}\text{U}_{yo}\text{U}_{yo}\text{A}_{yo}\text{G}_{yo}\text{U}_{yo}\text{C}_{yo}\text{U}_{fo}\text{U}_{yo}\text{A}_{fo}$$

$$\text{A}_{yo}\text{U}_{yo}\text{C}_{yo}\text{U}_{yo}\text{U}_{ys}\text{A}_{es}\text{A}_{e};$$

A=an adenine nucleobase,
C=a cytosine nucleobase,
G=a guanine nucleobase,
T=a thymine nucleobase,
U=a uracil nucleobase,
d=a 2'-deoxy sugar moiety,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage, and
vP=a 5' vinyl phosphonate group.

Second Oligomeric Compound:

The second modified oligonucleotide has a nucleobase sequence of (from 5' to 3") AAGAUUAAGACUAAAAC-UUAA (SEQ ID NO: 1015), wherein each of nucleosides 1, 2, 20 and 21 (from 5' to 3') comprises a 2'-MOE modified sugar moiety, each of nucleosides 10 and 11 (from 5' to 3') comprises a 2'-fluoro modified sugar moiety, and each of nucleosides 3-9, and 12-19 (from 5' to 3') comprises a 2'-OMe modified sugar moiety, wherein each of the internucleoside linkages linking nucleosides 1 to 2, 2 to 3, 19 to 20, and 20 to 21 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 (from 5' to 3') is a phosphodiester linkage.

The second oligomeric compound is represented by the following chemical notation:

(SEQ ID NO: 1031)
$$\text{A}_{es}\text{A}_{es}\text{G}_{yo}\text{A}_{yo}\text{U}_{yo}\text{U}_{yo}\text{A}_{yo}\text{A}_{yo}\text{G}_{yo}\text{A}_{fo}\text{C}_{fo}\text{U}_{yo}\text{A}_{yo}\text{A}_{yo}\text{A}_{yo}\text{A}_{yo}$$

$$\text{C}_{yo}\text{U}_{yo}\text{U}_{ys}\text{A}_{es}\text{A}_{e};$$

A=an adenine nucleobase,
C=a cytosine nucleobase,
G=a guanine nucleobase.
U=a uracil nucleobase,
c=a 2-MOE sugar moiety,
f=a 2-fluoro sugar moiety.
y=a 2-OMe sugar moiety.
o=a phosphodiester internucleoside linkage, and
s=a phosphorothioate internucleoside linkage.

In particular embodiments, such an oligomeric duplex is represented by the following chemical structure:

587

588

(SEQ ID NO: 1037 and SEQ ID NO: 1031)

-continued

-continued or a salt thereof.

In certain embodiments, such an oligomeric duplex is in the form of an anion or a salt thereof, for example, a sodium salt. In certain embodiments, the oligomeric duplex is in anionic form in a solution. In certain embodiments, the oligomeric duplex is a sodium salt or a potassium salt.

The following chemical structure represents such an oligomeric duplex in sodium solution:

(SEQ ID NO: 1037 and SEQ ID NO: 1031)

-continued

-continued f. Compound No. 1757480

Provided herein is Compound No. 1757480, which is an oligomeric duplex that consists of a first oligomeric compound containing a first modified oligonucleotide and a second oligomeric compound containing a second modified oligonucleotide attached to a conjugate group as follows. First Oligomeric Compound of Compound No. 1757480;

The first modified oligonucleotide of Compound No. 1757480, which is Compound No. 1753978, has a nucleobase sequence of (from 5' to 3') TUAAGUTUUAGUC-UUAAUCUUAA (SEQ ID NO: 972), wherein each of nucleosides 1, 22 and 23 (from 5' to 3") comprises a 2'-MOE modified sugar moiety, each of nucleosides 2, 14 and 16

(from 5' to 3') comprises a 2'-fluoro modified sugar moiety, each of nucleosides 3, 4, 6, 8-13, 15 and 17-21 (from 5' to 3') comprises a 2'-OMe modified sugar moiety, and each of nucleosides and 7 (from 5' to 3') is a 2'-deoxynucleoside, wherein each of the internucleoside linkages linking nucleosides 1 to 2, 2 to 3, 21 to 22, and 22 to 23 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, to 11, 11 to 12, 12 to 13, 13 to 14, 14 to 15, 15 to 16, 16 to 17, 17 to 18, 18 to 19, 19 to 20, and 20 to 21 (from 5' to 3') is a phosphodiester linkage, and wherein nucleoside 1 (from 5' to 3') is attached to a vinyl phosphonate group.

The first oligomeric compound of Compound 1757480 is represented by the following chemical notation:

(SEQ ID NO: 1038)

$$vPT_{es}U_{fs}A_{yo}A_{yo}G_{do}U_{yo}T_{do}U_{yo}U_{yo}A_{yo}G_{yo}U_{yo}C_{yo}U_{fo}U_{yo}A_{fo}$$

$$A_{yo}U_{yo}C_{yo}U_{yo}U_{ys}A_{es}A_e;$$

wherein

A=an adenine nucleobase,
C=a cytosine nucleobase,
G=a guanine nucleobase,
T=a thymine nucleobase,
U=a uracil nucleobase,
d=a 2'-deoxy sugar moiety,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage, and
vP=a 5' vinyl phosphonate group.

Second Oligomeric Compound of Compound No. 1757480:

The second modified oligonucleotide of Compound No. 1757480, which is Compound No. 1757462, has a nucleobase sequence of (from 5' to 3') AAGAUUAAGAC-UAAAACUUAA (SEQ ID NO: 1016), wherein each of nucleosides 1, 2, 20 and 21 (from 5' to 3') comprises a 2'-MOE modified sugar moiety, each of nucleosides 7, 9, and 11 (from 5' to 3') comprises a 2'-fluoro modified sugar moiety, and each of nucleosides 3-6, 8, 10, and 12-19 (from 5' to 3') comprises a 2'-OMe modified sugar moiety, wherein each of the internucleoside linkages linking nucleosides 1 to 2, 2 to 3, 19 to 20, and 20 to 21 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 (from 5' to 3') is a phosphodiester linkage, and wherein nucleoside 1 (from 5' to 3') is attached through a 5'-phosphodiester linkage and a 6-(BCN-carbamate)hexyl conjugate linker to a conjugate moiety comprising the amino acid sequence of bicycle compound BCY17901 (SEQ ID NO: 1045) wherein each cysteine forms a covalent bond with the molecular scaffold 1,1',1''-(1,3,5-triazinane-1,3,5-triyl) tris (2-bromoethanone) (TATB).

The second oligomeric compound of Compound 1757480 is represented by the following chemical notation:

(SEQ ID NO: 1044)

$$[X]_1-A_{es}A_{es}G_{yo}A_{yo}U_{yo}U_{yo}A_{fo}A_{yo}G_{fo}A_{yo}C_{fo}U_{yo}A_{yo}A_{yo}$$

$$A_{yo}A_{yo}C_{yo}U_{yo}U_{ys}A_{es}A_e;$$

wherein:

C=a cytosine nucleobase,
A=an adenine nucleobase,
G=a guanine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage, and
[X]₁=a conjugate group having the following structure (SEQ ID NO: 1304):

The following chemical structure is one structural repre-
sentation of Compound No. 1757480:

(SEQ ID NO: 1038 and SEQ ID NO: 1044; peptide sequence disclosed as SEQ ID NO: 1298)

-continued

-continued or a salt thereof.

In certain embodiments, Compound No. 1757480 is in the form of an anion or a salt thereof, for example, a sodium salt. In certain embodiments, the oligomeric duplex is in anionic form in a solution. In certain embodiments, Compound No. 1757480 is a sodium salt or a potassium salt.

The following chemical structure represents Compound No. 1757480 in sodium solution can be represented by the following chemical structure:

(SEQ ID NO: 1038 and SEQ ID NO: 1044; peptide sequence disclosed as SEQ ID NO: 1298)

-continued

611

612

In certain embodiments, provided herein are oligomeric duplexes comprising or consisting of a first oligomeric compound containing a first modified oligonucleotide and a second oligomeric compound containing a second modified oligonucleotide as follows.

First Oligomeric Compound:

The first modified oligonucleotide has a nucleobase sequence of (from 5' to 3') TUAAGUTUUAGUC-UUAAUCUUAA (SEQ ID NO: 972), wherein each of nucleosides 1, 22 and 23 (from 5' to 3) comprises a 2'-MOE modified sugar moiety, each of nucleosides 2, 14 and 16 (from 5' to 3') comprises a 2'-fluoro modified sugar moiety, each of nucleosides 3, 4, 6, 8-13, 15 and 17-21 (from 5' to 3') comprises a 2'-OMe modified sugar moiety, and each of nucleosides 5 and 7 (from 5' to 3') is a 2'-deoxynucleoside, wherein each of the internucleoside linkages linking nucleosides 1 to 2, 2 to 3, 21 to 22, and 22 to 23 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, and 20 to 21 (from 5' to 3') is a phosphodiester linkage, and wherein nucleoside 1 (from 5' to 3') is attached to a vinyl phosphonate group.

The first oligomeric compound is represented by the following chemical notation:

(SEQ ID NO: 1038)

$$vPT_{es}U_{fs}A_{yo}A_{yo}G_{do}U_{yo}T_{do}U_{yo}U_{yo}A_{yo}G_{yo}U_{yo}C_{yo}U_{fo}U_{yo}A_{fo}$$

$$A_{yo}U_{yo}C_{yo}U_{yo}U_{ys}A_{es}A_e;$$

wherein

A=an adenine nucleobase,

C=a cytosine nucleobase,

G=a guanine nucleobase,

T=a thymine nucleobase,

U=a uracil nucleobase, d=a 2'-deoxy sugar moiety, e=a 2'-MOE sugar moiety, f=a 2'-fluoro sugar moiety, y=a 2'-OMe sugar moiety, o=a phosphodiester internucleoside linkage, s=a phosphorothioate internucleoside linkage, and vP=a 5' vinyl phosphonate group.

Second Oligomeric Compound:

The second modified oligonucleotide has a nucleobase sequence of (from 5' to 3') AAGAUUAAGACUAAAAC-UUAA (SEQ ID NO: 1016), wherein each of nucleosides 1, 2, 20 and 21 (from 5' to 3') comprises a 2'-MOE modified sugar moiety, each of nucleosides 7, 9, and 11 (from 5' to 3") comprises a 2'-fluoro modified sugar moiety, and each of nucleosides 3-6, 8, 10, and 12-19 (from 5' to 3') comprises a 2'-OMe modified sugar moiety, wherein each of the internucleoside linkages linking nucleosides 1 to 2, 2 to 3, 19 to 20, and 20 to 21 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 (from 5' to 3') is a phosphodiester linkage.

The second oligomeric compound is represented by the following chemical notation:

(SEQ ID NO: 1032)

$$A_{es}A_{es}G_{yo}A_{yo}U_{yo}U_{yo}A_{fo}A_{yo}G_{fo}A_{yo}C_{fo}U_{yo}A_{yo}A_{yo}A_{yo}A_{yo}$$

$$C_{yo}U_{yo}U_{ys}A_{es}A_e,$$

wherein
  A=an adenine nucleobase,
  C=a cytosine nucleobase,
  G=a guanine nucleobase,
  U=a uracil nucleobase,
  c=a2'-MOE sugar moiety, f=a2'-fluoro sugar moiety,
  y=a 2'-OMe sugar moiety,
  o=a phosphodiester internucleoside linkage, and
  s=a phosphorothioate internucleoside linkage.

In particular embodiments, such an oligomeric duplex is represented by the following chemical structure:

(SEQ ID NO: 1038 and SEQ ID NO: 1032)

617                                                              618

-continued or a salt thereof.

In certain embodiments, such an oligomeric duplex is in the form of an anion or a salt thereof, for example, a sodium salt. In certain embodiments, the oligomeric duplex is in anionic form in a solution. In certain embodiments, the oligomeric duplex is a sodium salt or a potassium salt.

The following chemical structure represents such an oligomeric duplex in sodium solution:

621

622

(SEQ ID NO: 1038 and SEQ ID NO: 1032)

623 624

-continued

-continued g. Compound No. 1779744

Provided herein is Compound No. 1779744, which is an oligomeric duplex that consists of a first oligomeric compound containing a first modified oligonucleotide and a second oligomeric compound containing a second modified oligonucleotide attached to a conjugate group as follows.

First Oligomeric Compound of Compound No. 1779744;

The first modified oligonucleotide of Compound no. 1779744, which is Compound No. 1753981, has a nucleobase sequence of (from 5' to 3') TAUAAAUAGAUUCU-GUAGCUUAA (SEQ ID NO: 1254), wherein each of nucleosides 1, 22 and 23 (from 5' to 3') comprises a 2'-MOE modified sugar moiety, each of nucleosides 2, 14 and 16 (from 5' to 3') comprises a 2'-fluoro modified sugar moiety, and each of nucleosides 3-13, 15 and 17-21 (from 5' to 3') comprises a 2'-OMe modified sugar moiety, wherein each of the internucleoside linkages linking nucleosides 1 to 2, 2 to 3, 21 to 22, and 22 to 23 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, and 20 to 21 (from 5' to 3') is a phosphodiester linkage, and wherein nucleoside 1 (from 5' to 3') is attached to a vinyl phosphonate group.

The first oligomeric compound of Compound 1779744 is represented by the following chemical notation:

(SEQ ID NO: 1255)

vPT$_{es}$A$_{fs}$U$_{yo}$A$_{yo}$A$_{yo}$A$_{yo}$U$_{yo}$A$_{yo}$G$_{yo}$A$_{yo}$U$_{yo}$U$_{yo}$C$_{yo}$U$_{fo}$G$_{yo}$U$_{fo}$

A$_{yo}$G$_{yo}$C$_{yo}$U$_{yo}$U$_{ys}$A$_e$sA$_e$;

wherein

A=an adenine nucleobase,
C=a cytosine nucleobase,
G=a guanine nucleobase,
T=a thymine nucleobase,
U=a uracil nucleobase,
e=a 2'-MOE sugar moiety,
f=a 2-fluoro sugar moiety,
y=a 2'-OMe sugar moiety,
o=a phosphodiester internucleoside linkage,
s=a phosphorothioate internucleoside linkage, and
vP=a 5' vinyl phosphonate group.

Second Oligomeric Compound of Compound No. 1779744:

The second modified oligonucleotide of Compound No. 1779744, which is Compound No. 1757456, has a nucleobase sequence of (from 5' to 3') AAGCUACAGAAUCUAUUUATA (SEQ ID NO: 1013), wherein each of nucleosides 1, 2, 20 and 21 (from 5' to 3') comprises a 2'-MOE modified sugar moiety, each of nucleosides 10 and 11 (from 5' to 3') comprises a 2'-fluoro modified sugar moiety, and each of nucleosides 3-9 and 12-19 (from 5' to 3') comprises a 2'-OMe modified sugar moiety, wherein each of the internucleoside linkages linking nucleosides 1 to 2, 2 to 3, 19 to 20, and 20 to 21 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 (from 5' to 3') is a phosphodiester linkage, and wherein nucleoside 1 (from 5' to 3') is attached through a 5'-phosphodiester linkage and a 6-(BCN-carbamate)hexyl conjugate linker to a conjugate moiety comprising the amino acid sequence of bicycle compound BCY17901 (SEQ ID NO: 1045) wherein each cysteine forms a covalent bond with the molecular scaffold 1,1',1''-(1,3,5-triazinane-1,3,5-triyl)tris(2-bromoethanone) (TATB).

The second oligomeric compound of Compound 1779744 is represented by the following chemical notation:

(SEQ ID NO: 1041)

[X]$_1$-A$_{es}$A$_{es}$G$_{yo}$C$_{yo}$U$_{yo}$A$_{yo}$C$_{yo}$A$_{yo}$G$_{yo}$A$_{fo}$A$_{fo}$U$_{yo}$C$_{yo}$U$_{yo}$

A$_{yo}$U$_{yo}$U$_{yo}$U$_{yo}$A$_{ys}$T$_{es}$A$_e$;

wherein:

C=a cytosine nucleobase,
A=an adenine nucleobase,
G=a guanine nucleobase,
T=a thymine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage, and
[X]$_1$=a conjugate group having the following structure (SEQ ID NO: 1305):

The following chemical structure is one structural representation of Compound No. 1779744:

(SEQ ID NO: 1255 and SEQ ID NO: 1041; peptide sequence disclosed as SEQ ID NO: 1295)

631                                                                                      632 or a salt thereof.

In certain embodiments, Compound No. 1779744 is in the form of an anion or a salt thereof, for example, a sodium salt. In certain embodiments, the oligomeric duplex is in anionic form in a solution. In certain embodiments, Compound No. 1779744 is a sodium salt or a potassium salt. The following chemical structure represents Compound No. 1779744 in sodium solution:

(SEQ ID NO: 1255 and SEQ ID NO: 1041; peptide sequence disclosed as SEQ ID NO: 1295)

-continued

-continued

In certain embodiments, provided herein are oligomeric duplexes comprising or consisting of a first oligomeric compound containing a first modified oligonucleotide and a second oligomeric compound containing a second modified oligonucleotide as follows.

First Oligomeric Compound:

The first modified oligonucleotide has a nucleobase sequence of (from 5' to 3') TAUAAAUAGAUUCU-GUAGCUUAA (SEQ ID NO: 1254), wherein each of nucleosides 1, 22 and 23 (from 5' to 3') comprises a 2'-MOE modified sugar moiety, each of nucleosides 2, 14 and 16 (from 5' to 3') comprises a 2'-fluoro modified sugar moiety, and each of nucleosides 3-13, 15 and 17-21 (from 5' to 3') comprises a 2'-OMe modified sugar moiety, wherein each of the internucleoside linkages linking nucleosides 1 to 2, 2 to 3, 21 to 22, and 22 to 23 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, 18 to 19, 19 to 20, and 20 to 21 (from 5' to 3') is a phosphodiester linkage, and wherein nucleoside 1 (from 5' to 3') is attached to a vinyl phosphonate group.

The first oligomeric compound is represented by the following chemical notation:

(SEQ ID NO: 1255)
$\text{vPT}_{es}\text{A}_{fs}\text{U}_{yo}\text{A}_{yo}\text{A}_{yo}\text{A}_{yo}\text{U}_{yo}\text{A}_{yo}\text{G}_{yo}\text{A}_{yo}\text{U}_{yo}\text{U}_{yo}\text{C}_{yo}\text{U}_{fo}\text{G}_{yo}\text{U}_{fo}$ $\text{A}_{yo}\text{G}_{yo}\text{C}_{yo}\text{U}_{yo}\text{U}_{ys}\text{A}_{e}\text{sA}_{e}\text{;}$ wherein A=an adenine nucleobase,
C=a cytosine nucleobase,
G=a guanine nucleobase,
T=a thymine nucleobase,
U=a uracil nucleobase,
e=a 2'-MOE sugar moiety,
f=a 2'-fluoro sugar moiety,
y=a 2'-OMe sugar moiety,
o=a phosphodiester internucleoside linkage,
s=a phosphorothioate internucleoside linkage, and
vP=a 5' vinyl phosphonate group.

Second Oligomeric Compound:

The second modified oligonucleotide has a nucleobase sequence of (from 5' to 3') AAGCUACAGAAUC-UAUUUATA (SEQ ID NO: 1013), wherein each of nucleosides 1, 2, 20 and 21 (from 5' to 3') comprises a 2'-MOE modified sugar moiety, each of nucleosides 10 and 11 (from 5' to 3') comprises a 2'-fluoro modified sugar moiety, and each of nucleosides 3-9 and 12-19 (from 5' to 3') comprises a 2'-OMe modified sugar moiety, wherein each of the internucleoside linkages linking nucleosides 1 to 2, 2 to 3, 19 to 20, and 20 to 21 (from 5' to 3') is a phosphorothioate internucleoside linkage and each of the internucleoside linkages linking nucleosides 3 to 4, 4 to 5, 5 to 6, 6 to 7, 7 to 8, 8 to 9, 9 to 10, 10 to 11, 11 to 12, 12 to 13, 13 to 14, 14 to 15, 15 to 16, 16 to 17, 17 to 18, and 18 to 19 (from 5' to 3') is a phosphodiester linkage.

The second oligomeric compound is represented by the following chemical notation:

(SEQ ID NO: 1029)
$\text{A}_{es}\text{A}_{es}\text{G}_{yo}\text{C}_{yo}\text{U}_{yo}\text{A}_{yo}\text{C}_{yo}\text{A}_{yo}\text{G}_{yo}\text{A}_{fo}\text{A}_{fo}\text{U}_{yo}\text{C}_{yo}\text{U}_{yo}\text{A}_{yo}\text{U}_{yo}$ $\text{U}_{yo}\text{U}_{yo}\text{A}_{ys}\text{T}_{es}\text{A}_{e}\text{;}$ A=an adenine nucleobase, C=a cytosine nucleobase, G=a guanine nucleobase, T=a thymine nucleobase, U=a uracil nucleobase, e=a 2'-MOE sugar moiety, f=a 2'-fluoro sugar moiety, y=a 2'-OMe sugar moiety, o=a phosphodiester internucleoside linkage, and s=a phosphorothioate internucleoside linkage.

In particular embodiments, such an oligomeric duplex is represented by the following chemical structure:

(SEQ ID NO: 1255 and SEQ ID NO: 1029)

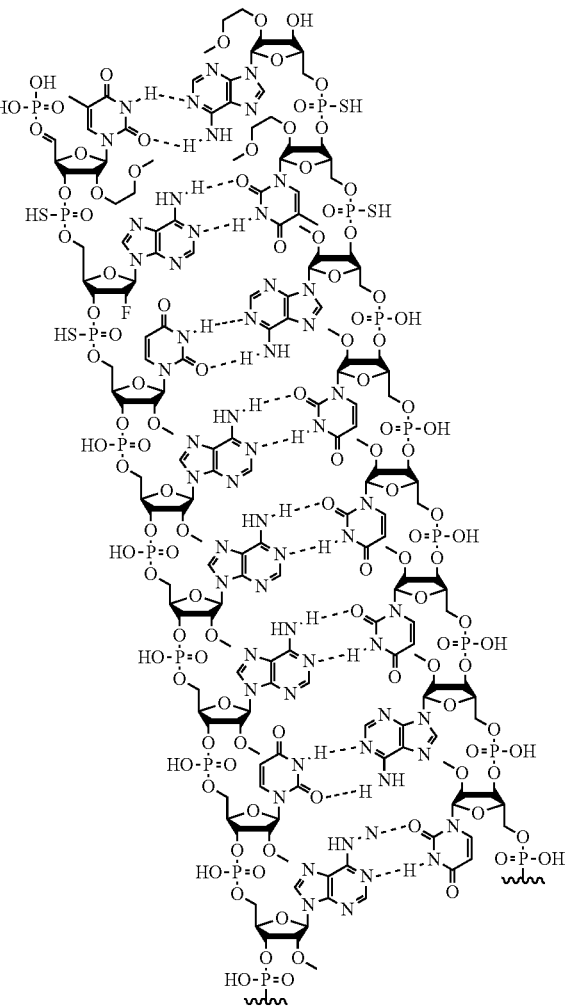

643

-continued

644

-continued

55 or a salt thereof.

In certain embodiments, such an oligomeric duplex is in the form of an anion or a salt thereof, for example, a sodium salt. In certain embodiments, the oligomeric duplex is in anionic form in a solution. In certain embodiments, the oligomeric duplex is a sodium salt or a potassium salt.

The following chemical structure represents such an oligomeric duplex in sodium solution:

645

646

(SEQ ID NO: 1255 and SEQ ID NO: 1029)

-continued

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references. GenBank accession numbers. ENSEMBL identifiers, and the like recited in the present application is incorporated herein by reference in its entirety.

The sequence listing accompanying this filing identifies each sequence as either "RNA" or "DNA" as required: however, one of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (5-methyl uracil) in place of an uracil of RNA).

Herein, the description of compounds as having "the nucleobase sequence of" a SEQ ID NO, describes only the nucleobase sequence. Accordingly, absent additional description, such description of compounds by reference to a nucleobase sequence of a SEQ ID NO, does not limit sugar or internucleoside linkage modifications or presence or absence of additional substituents such as a conjugate group. Herein, the description of compounds by chemical notation (subscripts and/or superscripts to indicate chemical modifications) without reference to a specific Compound No, include only each noted modification, but may include additional substituents, such as a conjugate group, unless otherwise indicated. For example, the chemical notation of "$A_{cs}T_{ko}{}^mC_{ez}G_{ds}C_d$" indicates a compound wherein the first nucleoside comprises a 2'-MOE sugar moiety (indicated by the "c" subscript) and an unmodified adenine nucleobase linked to the second nucleoside via a phosphorothioate linkage (indicated by the "s" subscript): the second nucleoside comprises a cEt sugar moiety (indicated by the "k" subscript) and an unmodified thymine nucleobase linked to the third nucleoside via a phosphodiester linkage (indicated by the "o" subscript): the third nucleoside comprises a 2-MOE sugar moiety and a 5-methyl modified cytosine nucleobase (indicated by the "m" superscript) linked to the fourth nucleoside via a mesyl phosphoramidate linkage (indicated by the "z" subscript): the fourth nucleoside comprises a 2'-deoxy sugar moiety (indicated by the "d" subscript) and an unmodified guanine nucleobase linked to the fifth nucleoside with a phosphorothioate linkage; and the fifth nucleoside comprises a 2'-deoxy sugar moiety and an unmodified cytosine nucleobase; and the compound may include additional substituents, such as a conjugate group. Herein, where a specific compound (e.g., with reference to a Compound No.) is described (as in the examples) by chemical notation, each nucleobase, sugar, and internucleoside linkage of such specific compound is modified only as indicated. Accordingly, in the context of a description of a specific compound having a particular Compound No., "$A_{cs}T_{ko}{}^mC_{ez}G_{ds}C_d$" indicates a compound wherein the nucleosides comprise the indicated sugar moieties and nucleobases and are linked by the indicated internucleoside linkages and the compound does not include additional substituents unless specifically indicated otherwise.

Herein, sugar, internucleoside linkage, and nucleobase modifications may be indicated within a nucleotide or nucleobase sequence (e.g., by superscript or subscript, as shown above) or may be indicated in text accompanying a sequence (e.g., in separate text that appears within or above or below a table of compounds).

Where a specific compound is described herein by way of a drawn chemical structure, each nucleobase, sugar, and internucleoside linkage of such a specific compound includes only the modifications indicated in the drawn chemical structure. One of skill will appreciate, however, that drawn compounds may exist in equilibrium between tautomeric forms and/or as salts in equilibrium with protonated or ionic forms. Drawn structures are intended to capture all such forms of such compounds. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^3$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXEMPLIFICATION

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example A: Oligomeric Compounds that Target Human PLN

Oligomeric compounds comprising antisense oligonucleotides complementary to a human PLN nucleic acid and sense oligonucleotides complementary to the antisense oligonucleotides were previously described in International publication no. WO2022173976, filed Feb. 10, 2022, published Aug. 18, 2022, the entire contents of which is incorporated herein by reference. Oligomeric compounds were described having an antisense oligonucleotide 23 nucleosides in length: a sugar motif (from 5' to 3') of: yfyfyfyfyfyfyfyfyfyvv, wherein each "y" represents a 2'-OMe sugar moiety, and each "f" represents a 2'-fluoro sugar moiety; and has an internucleoside linkage motif (from 5' to 3') of: ssooooooooooooooooooss, wherein each "o" represents a phosphodiester internucleoside linkage, and each "s" represents a phosphorothioate internucleoside linkage. Sense oligonucleotide in each case is 21 nucleosides in length: has a sugar motif (from 5' to 3') of: fyfyfyfyfyfyfyfyfyfyf, wherein each "y" represents a 2'-OMe sugar moiety, and each "f" represents a 2'-fluoro sugar moiety; and has an internucleoside linkage motif (from 5' to 3') of: ssooooooooooooooooss, wherein each "o" represents a phosphodiester internucleoside linkage, and each "s" represents a phosphorothioate internucleoside linkage. Each antisense oligonucleotide having the nucleobase sequence in Table A is complementary to the target nucleic acid (PLN), and each sense oligonucleotide having the nucleobase sequence in Table A is complementary to the first of the 21 nucleosides of the antisense oligonucleotide (from 5' to 3') wherein the last two 3'-nucleosides of the antisense oligonucleotides are not paired with the sense oligonucleotide (are overhanging nucleosides). "Start site" indicates the 5'-most nucleoside to which the antisense oligonucleotide is complementary in the human PLN sequence. "Stop site" indicates the 3'-most nucleoside to which the antisense oligonucleotide is complementary in the human PLN sequence. Each modified antisense oligonucleotide listed in Table A is 100% complementary to SEQ ID NO: 1 (GENBANK Accession No. NM_002667.4), with the exception of Compound No. 1564340 which is 100% complementary to SEQ ID NO: 2 (GENBANK Accession No. NC_000006.12, truncated from nucleosides 118545001 to 118565000) from nucleosides 16694 to 16716.

TABLE A

| | | | | SEQ ID NO: 1 Anti- | SEQ ID NO: 1 Anti- | | | |
| Compound Number | Anti- sense ID | Antisense Sequence (5' to 3') | SEQ ID NO. | sense Start Site | sense Stop Site | Sense ID | Sense Sequence (5' to 3') | SEQ ID NO. |
|---|---|---|---|---|---|---|---|---|
| 1563877 | 1563889 | UCAUCACAGUAU AGAGUAUUGUG | 3 | 94 | 116 | 1563885 | CAAUACUCUAU ACUGUGAUGA | 315 |
| 1563878 | 1563891 | GGUGUUUAGCUG GGGAGUUUUCU | 4 | 54 | 76 | 1563883 | AAAACUCCCCA GCUAAACACC | 316 |
| 1563874 | 1563886 | UCUGACUCUGUC ACCCAGUUUAU | 5 | 34 | 56 | 1563880 | AAACUGGGUGA CAGAGUCAGA | 317 |
| 1563875 | 1563887 | GGUAGCCUUGGC AGCUGUGAUCA | 6 | 114 | 136 | 1563881 | AUCACAGCUGC CAAGGCUACC | 318 |
| 1563876 | 1563890 | GUGUUGUAUGAA GUCUUACGGGU | 7 | 74 | 96 | 1563882 | CCGUAAGACUU CAUACAACAC | 319 |
| 1563879 | 1563888 | GAGAUAACUGUC UUCUUUUAGGU | 8 | 134 | 156 | 1563884 | CUAAAAGAAGA CAGUUAUCUC | 320 |
| 1563894 | 1563905 | UUUCUCCAUGAU ACCAGCAGGAC | 9 | 214 | 236 | 1563900 | CCUGCUGGUAU CAUGGAGAAA | 321 |
| 1563897 | 1563909 | AAAAGCUGGCAG CCAAAUAUGAG | 10 | 154 | 176 | 1563903 | CAUAUUUGGCU GCCAGCUUUU | 322 |
| 1563892 | 1563906 | AAGUGGUCGAGA GAAAGAUAAAA | 11 | 174 | 196 | 1563899 | UUAUCUUUCUC UCGACCACUU | 323 |
| 1563896 | 1563908 | GACAGGAAGUCU GAAGUUUUAAG | 12 | 194 | 216 | 1563902 | UAAAACUUCAG ACUUCCUGUC | 324 |
| 1563893 | 1563907 | UUGAGGCUCUUC UUAUAGCUGAG | 13 | 254 | 276 | 1563901 | CAGCUAUAAGA AGAGCCUCAA | 325 |
| 1563895 | 1563904 | GAGCGAGUGAGG UAUUGGACUUU | 14 | 234 | 256 | 1563898 | AGUCCAAUACC UCACUCGCUC | 326 |
| 1563910 | 1563925 | UUGUUGAGGCAU UUCAAUGGUUG | 15 | 274 | 296 | 1563919 | ACCAUUGAAAU GCCUCAACAA | 327 |
| 1563915 | 1563926 | UUCUGUAGCUUU UGACGUGCUUG | 16 | 294 | 316 | 1563920 | AGCACGUCAAA AGCUACAGAA | 328 |
| 1563911 | 1563924 | UAGCAGAACUUC AGAGAAGCAUC | 17 | 374 | 396 | 1563918 | UGCUUCUCUGA AGUUCUGCUA | 329 |
| 1563913 | 1563922 | AUCACGAUGAUA CAGAUCAGCAA | 18 | 354 | 376 | 1563917 | GCUGAUCUGUA UCAUCGUGAU | 330 |
| 1563914 | 1563927 | GACAGAAAUUGA UAAAUAGAUUC | 19 | 314 | 336 | 1563921 | AUCUAUUUAUC AAUUUCUGUC | 331 |
| 1563912 | 1563923 | CAAGAGACAUAU UAAGAUGAGAC | 20 | 334 | 356 | 1563916 | CUCAUCUUAAU AUGUCUCUUG | 332 |
| 1563928 | 1563945 | AGCUGCAGAUCU AGAGGUUGUAG | 21 | 394 | 416 | 1563939 | ACAACCUCUAG AUCUGCAGCU | 333 |
| 1563931 | 1563942 | CUGUUAUACAAU AUUGUUUUCCU | 22 | 454 | 476 | 1563934 | GAAAACAAUAU UGUAUAACAG | 334 |
| 1563933 | 1563940 | GAUUUUAAGCUG AUGUGGCAAGC | 23 | 414 | 436 | 1563936 | UUGCCACAUCA GCUUAAAAUC | 335 |
| 1563932 | 1563943 | CCUGUCUGCAUG GGAUGACAGAU | 24 | 434 | 456 | 1563937 | CUGUCAUCCCA UGCAGACAGG | 336 |
| 1563930 | 1563941 | UCUUCUACUCAG GAAGUGGUCUG | 25 | 474 | 496 | 1563935 | GACCACUUCCU GAGUAGAAGA | 337 |
| 1563929 | 1563944 | UGACCUUUUCAC AAAGAAACUCU | 26 | 494 | 516 | 1563938 | AGUUUCUUUGU GAAAAGGUCA | 338 |

TABLE A-continued

| | | | | SEQ ID NO: 1 Anti-sense Start Site | SEQ ID NO: 1 Anti-sense Stop Site | | | |
|---|---|---|---|---|---|---|---|---|
| Compound Number | Anti-sense ID | Antisense Sequence (5' to 3') | SEQ ID NO. | | | Sense ID | Sense Sequence (5' to 3') | SEQ ID NO. |
| 1563947 | 1563960 | AUCAACAGUUGC AUUUUAUACAC | 27 | 614 | 636 | 1563954 | GUAUAAAAUGC AACUGUUGAU | 339 |
| 1563948 | 1563958 | CACUUAUUUUGA AGUUAAUUUUU | 28 | 594 | 616 | 1563953 | AAAUUAACUUC AAAAUAAGUG | 340 |
| 1563951 | 1563962 | AUAAGUUUUAGU CUUAAUCUUGA | 29 | 514 | 536 | 1563956 | AAGAUUAAGAC UAAAACUUAU | 341 |
| 1563950 | 1563963 | CAUGUUUACAAG AUCCAACAGAU | 30 | 554 | 576 | 1563957 | CUGUUGGAUCU UGUAAACAUG | 342 |
| 1563946 | 1563959 | GAUGAAUACAUA UGGUAACAAUA | 31 | 534 | 556 | 1563955 | UUGUUACCAUA UGUAUUCAUC | 343 |
| 1563949 | 1563961 | UUUGAAAAUAAA GCCCUUUUCAU | 32 | 574 | 596 | 1563952 | GAAAAGGGCUU UAUUUUCAAA | 344 |
| 1563964 | 1563976 | ACUAAACUCUUC AUCUUCAGAAA | 33 | 674 | 696 | 1563973 | UCUGAAGAUGA AGAGUUUAGU | 345 |
| 1563965 | 1563977 | CAAAAGAGUAAA AAUAAUGCUUU | 34 | 734 | 756 | 1563972 | AGCAUUAUUUU UACUCUUUUG | 346 |
| 1563969 | 1563980 | UUGUGAGCCAUG UUGAGGAAAUC | 35 | 634 | 656 | 1563974 | UUUCCUCAACA UGGCUCACAA | 347 |
| 1563967 | 1563975 | GUUGGCAGUGCA GUUUUAAAACU | 36 | 694 | 716 | 1563970 | UUUUAAAACUG CACUGCCAAC | 348 |
| 1563966 | 1563979 | UUUAUAUAUGAA GUGAACUUGUU | 37 | 714 | 736 | 1563971 | CAAGUUCACUU CAUAUAUAAA | 349 |
| 1563968 | 1563981 | AAAAGAUUUGGG AUAGAAAUUUG | 38 | 654 | 676 | 1563978 | AAUUUCUAUCC CAAAUCUUUU | 350 |
| 1563985 | 1563996 | UACUUUGAUACU UGGUGAAGACC | 39 | 814 | 836 | 1563988 | UCUUCACCAAG UAUCAAGUA | 351 |
| 1563983 | 1563994 | UGACACUUCAUU UGUGUUAUUAC | 40 | 834 | 856 | 1563990 | AAUAACACAAA UGAAGUGUCA | 352 |
| 1563982 | 1563997 | AAUAUAAAUUAU AUUCACCUCAA | 41 | 754 | 776 | 1563991 | GAGGUGAAUAU AAUUUAUAUU | 353 |
| 1563986 | 1563998 | ACCUGAAAAAUA CUUAGUAUUAA | 42 | 794 | 816 | 1563993 | AAUACUAAGUA UUUUUCAGGU | 354 |
| 1563987 | 1563999 | UAAAGAAGCUUU UACAUUGUAAU | 43 | 774 | 796 | 1563992 | UACAAUGUAAA AGCUUCUUUA | 355 |
| 1563984 | 1563995 | GUUAUUACUUUG AUACUUGGUGA | 44 | 819 | 841 | 1563989 | ACCAAGUAUCA AAGUAAUAAC | 356 |
| 1564003 | 1564015 | UGUAGAUUCUGA UAGUUACUACA | 45 | 914 | 936 | 1564006 | UAGUAACUAUC AGAAUCUACA | 357 |
| 1564000 | 1564012 | CAGUGGACUAUU UUGAAUAAUGA | 46 | 854 | 876 | 1564009 | AUUAUUCAAAA UAGUCCACUG | 358 |
| 1564005 | 1564017 | AGAUAACAGAUG UGAGGAGUCAG | 47 | 874 | 896 | 1564010 | GACUCCUCACA UCUGUUAUCU | 359 |
| 1564002 | 1564013 | AUACAAUUUCUG UUUUAGAAUGU | 48 | 934 | 956 | 1564007 | AUUCUAAAACA GAAAUUGUAU | 360 |
| 1564004 | 1564016 | ACAAAUAGUUCU UUAUAAUAAGA | 49 | 894 | 916 | 1564011 | UUAUUAUAAAG AACUAUUUGU | 361 |
| 1564001 | 1564014 | GUUAAUGUGGCA UAGAAAAAAUA | 50 | 954 | 976 | 1564008 | UUUUUUCUAUG CCACAUUAAC | 362 |

TABLE A-continued

| | | | | SEQ ID NO: 1 Anti-sense Start Site | SEQ ID NO: 1 Anti-sense Stop Site | | | |
|---|---|---|---|---|---|---|---|---|
| Compound Number | Anti-sense ID | Antisense Sequence (5' to 3') | SEQ ID NO. | | | Sense ID | Sense Sequence (5' to 3') | SEQ ID NO. |
| 1564021 | 1564029 | CUUACUUUUCCA UACUUGAUUCU | 51 | 994 | 1016 | 1564025 | AAUCAAGUAUG GAAAAGUAAG | 363 |
| 1564022 | 1564034 | UUAUUAUGUAAG AGUAUGGCCUU | 52 | 1014 | 1036 | 1564028 | GGCCAUACUCU UACAUAAUAA | 364 |
| 1564018 | 1564030 | UCUCAUCAACUU UAAAAGAUGUU | 53 | 974 | 996 | 1564026 | CAUCUUUUAAA GUUGAUGAGA | 365 |
| 1564023 | 1564035 | CAUACUUGAUUC UCAUCAACUUU | 54 | 984 | 1006 | 1564033 | AGUUGAUGAGA AUCAAGUAUG | 366 |
| 1564020 | 1564031 | AAAAUUACUUAA AAGGAAUUUUA | 55 | 1034 | 1056 | 1564024 | AAAUUCCUUUU AAGUAAUUUU | 367 |
| 1564019 | 1564032 | GAAUUCUGUGAU UCUUUGAAAAA | 56 | 1054 | 1076 | 1564027 | UUUCAAAGAAU CACAGAAUUC | 368 |
| 1564036 | 1564051 | UAUGUCUUAGAA CAGAUUUAUGA | 57 | 1094 | 1116 | 1564045 | AUAAAUCUGUU CUAAGACAUA | 369 |
| 1564038 | 1564047 | AUUAGUGAUAUG ACUAAUCUCAC | 58 | 1154 | 1176 | 1564043 | GAGAUUAGUCA UAUCACUAAU | 370 |
| 1564040 | 1564053 | CACUGUCACAUA UUAACCACCAG | 59 | 1134 | 1156 | 1564048 | GGUGGUUAAUA UGUGACAGUG | 371 |
| 1564037 | 1564050 | UUAGAUUCUGUU GUUAGUAUAUU | 60 | 1174 | 1196 | 1564044 | UAUACUAACAA CAGAAUCUAA | 372 |
| 1564039 | 1564049 | CAGUUCUCAUCU GUUGAUCAUAU | 61 | 1114 | 1136 | 1564042 | AUGAUCAACAG AUGAGAACUG | 373 |
| 1564041 | 1564052 | UGAUUUACCUAC AUGUACUAGAA | 62 | 1074 | 1096 | 1564046 | CUAGUACAUGU AGGUAAAUCA | 374 |
| 1564058 | 1564071 | UAGUAUGGUAAG CUAGGUAACUC | 63 | 1234 | 1256 | 1564065 | GUUACCUAGCU UACCAUACUA | 375 |
| 1564054 | 1564067 | UACAGUGCCUUA AAUGAAGAUUA | 64 | 1194 | 1216 | 1564063 | AUCUUCAUUUA AGGCACUGUA | 376 |
| 1564059 | 1564070 | CUCUAGCUCAGA UAAUUCACUAC | 65 | 1214 | 1236 | 1564064 | AGUGAAUUAUC UGAGCUAGAG | 377 |
| 1564057 | 1564069 | GAUAUAGUAUGG UAAGCUAGGUA | 66 | 1238 | 1260 | 1564061 | CCUAGCUUACC AUACUAUAUC | 378 |
| 1564055 | 1564068 | UGAUUCCAAAGA UAUAGUAUGGU | 67 | 1248 | 1270 | 1564062 | CAUACUAUAUC UUUGGAAUCA | 379 |
| 1564056 | 1564066 | CCAAAGAUAUAG UAUGGUAAGCU | 68 | 1243 | 1265 | 1564060 | CUUACCAUACU AUAUCUUUGG | 380 |
| 1564074 | 1564081 | CUGCAUUGGAUG UUAGGCUGGAA | 69 | 1314 | 1336 | 1564078 | CCAGCCUAACA UCCAAUGCAG | 381 |
| 1564072 | 1564082 | GUUUCAUGAUUC CAAAGAUAUAG | 70 | 1254 | 1276 | 1564077 | AUAUCUUUGGA AUCAUGAAAC | 382 |
| 1564084 | 1564088 | AAAUCUUUUAUU UUCCUUGCCUG | 71 | 1334 | 1356 | 1564086 | GGCAAGGAAAA UAAAAGAUUU | 383 |
| 1564073 | 1564080 | GAAUGGAAGACA ACCUGCAAAAU | 72 | 1294 | 1316 | 1564076 | UUUGCAGGUUG UCUUCCAUUC | 384 |
| 1564085 | 1564089 | AUAUAUUUUUCU GUCACUGGAAA | 73 | 1354 | 1376 | 1564087 | UCCAGUGACAG AAAAAUAUAU | 385 |
| 1564075 | 1564083 | AAUCAUUCUGAA GUCUUAAGGUU | 74 | 1274 | 1296 | 1564079 | CCUUAAGACUU CAGAAUGAUU | 386 |

TABLE A-continued

Oligomeric compounds targeting human PLN

| Compound Number | Anti-sense ID | Antisense Sequence (5' to 3') | SEQ ID NO. | SEQ ID NO: 1 Anti-sense Start Site | SEQ ID NO: 1 Anti-sense Stop Site | Sense ID | Sense Sequence (5' to 3') | SEQ ID NO. |
|---|---|---|---|---|---|---|---|---|
| 1564090 | 1564104 | UUUAAAAAAUAC UUGAGAUAAUA | 75 | 1374 | 1396 | 1564101 | UUAUCUCAAGU AUUUUUUAAA | 387 |
| 1564093 | 1564105 | CUAAUAAUUAGU UAAUAUUUGGA | 76 | 1414 | 1436 | 1564100 | CAAAUAUUAAC UAAUUAUUAG | 388 |
| 1564094 | 1564102 | GGAGAGAGAAUU CAUAUAUUUUU | 77 | 1394 | 1416 | 1564097 | AAAUAUAUGAA UUCUCUCUCC | 389 |
| 1564092 | 1564103 | AUGUAAUAGAUG GGCCAACAAGU | 78 | 1454 | 1476 | 1564099 | UUGUUGGCCCA UCUAUUACAU | 390 |
| 1564091 | 1564107 | UGUUCAAGGGUC AGCUGUAGAUG | 79 | 1474 | 1496 | 1564096 | UCUACAGCUGA CCCUUGAACA | 391 |
| 1564095 | 1564106 | AGUUCAUUUCAA AAUAUAAUCUA | 80 | 1434 | 1456 | 1564098 | GAUUAUAUUUU GAAAUGAACU | 392 |
| 1564113 | 1564122 | GUCAGCUCCCCU AACCCCCAUGU | 81 | 1494 | 1516 | 1564118 | AUGGGGGUUAG GGGAGCUGAC | 393 |
| 1564111 | 1564124 | UAGUUAAGAUUU UGCGGACCCAC | 82 | 1522 | 1544 | 1564116 | GGGUCCGCAAA AUCUUAACUA | 394 |
| 1564110 | 1564120 | AUUUACUGUUUA UGUUAUCAGUA | 83 | 1574 | 1596 | 1564114 | CUGAUAACAUA AACAGUAAAU | 395 |
| 1564109 | 1564121 | GUAAGGUUUAUG GUCAAUAGUAG | 84 | 1554 | 1576 | 1564115 | ACUAUUGACCA UAAACCUUAC | 396 |
| 1564112 | 1564123 | UAGGCUAUUAGG UAGUUAAGAUU | 85 | 1534 | 1556 | 1564119 | UCUUAACUACC UAAUAGCCUA | 397 |
| 1564108 | 1564125 | AUUUUGCGGACC CACGAAUUGUC | 86 | 1514 | 1536 | 1564117 | CAAUUCGUGGG UCCGCAAAAU | 398 |
| 1564127 | 1564139 | UAUUUUCUCUUU CUUAUGAUUUU | 87 | 1674 | 1696 | 1564134 | AAUCAUAAGAA AGAGAAAAUA | 399 |
| 1564129 | 1564142 | UAGCUUACUUUA UUGUAGGAAUA | 88 | 1634 | 1656 | 1564137 | UUCCUACAAUA AAGUAAGCUA | 400 |
| 1564128 | 1564140 | CAUUUAAUGAAU AGUAAAUAUAU | 89 | 1694 | 1716 | 1564132 | AUAUUUACUAU UCAUUAAAUG | 401 |
| 1564131 | 1564138 | AACACGCAAAAU AUGUGUUAAUU | 90 | 1594 | 1616 | 1564133 | UUAACACAUAU UUUGCGUGUU | 402 |
| 1564130 | 1564141 | UUUCUAAAUAAC AUUUUCUCUAG | 91 | 1654 | 1676 | 1564136 | AGAGAAAAUGU UAUUUAGAAA | 403 |
| 1564126 | 1564143 | AUAUAGUGUAUA AUACAUAUAAC | 92 | 1614 | 1636 | 1564135 | UAUAUGUAUUA UACACUAUAU | 404 |
| 1564146 | 1564157 | CUCCUCUGCCUA CUCAAUGUGAA | 93 | 1754 | 1776 | 1564152 | CACAUUGAGUA GGCAGAGGAG | 405 |
| 1564145 | 1564159 | CCCCACACCCCU AAGACAAGACU | 94 | 1814 | 1836 | 1564153 | UCUUGUCUUAG GGGUGUGGGG | 406 |
| 1564147 | 1564158 | UCUUCCUCCCCA UCUUUCUCCUC | 95 | 1774 | 1796 | 1564150 | GGAGAAAGAUG GGGAGGAAGA | 407 |
| 1564149 | 1564160 | CUUUUAUGUUGA CCCACUUCCAU | 96 | 1714 | 1736 | 1564155 | GGAAGUGGGUC AACAUAAAAG | 408 |
| 1564148 | 1564161 | GAAGACAAUGAG AAUGAAGACUU | 97 | 1734 | 1756 | 1564154 | GUCUUCAUUCU CAUUGUCUUC | 409 |

TABLE A-continued

| | | | | SEQ ID NO: 1 Anti- | SEQ ID NO: 1 Anti- | | | |
|---|---|---|---|---|---|---|---|---|
| Compound Number | Anti- sense ID | Antisense Sequence (5' to 3') | SEQ ID NO. | sense Start Site | sense Stop Site | Sense ID | Sense Sequence (5' to 3') | SEQ ID NO. |
| 1564144 | 1564156 | ACUGCAAGACCA ACGCCUUCUCU | 98 | 1794 | 1816 | 1564151 | AGAAGGCGUUG GUCUUGCAGU | 410 |
| 1564167 | 1564178 | UGAAUAUUCUUU CCCCCACUCCC | 99 | 1834 | 1856 | 1564169 | GAGUGGGGGAA AGAAUAUUCA | 411 |
| 1564162 | 1564174 | UGCAAGGGUCCA CUUAUACAUGA | 100 | 1854 | 1876 | 1564170 | AUGUAUAAGUG GACCCUUGCA | 412 |
| 1564166 | 1564175 | AUCCUAUUACAG UUGACCCUUGA | 101 | 1894 | 1916 | 1564168 | AAGGGUCAACU GUAAUAGGAU | 413 |
| 1564163 | 1564176 | AGAGGAAGAAAA AUAGCUAUAUC | 102 | 1914 | 1936 | 1564172 | UAUAGCUAUUU UUCUUCCUCU | 414 |
| 1564164 | 1564177 | AUGCUUACCAUU UGGUUGAUAGA | 103 | 1934 | 1956 | 1564173 | UAUCAACCAAA UGGUAAGCAU | 415 |
| 1564165 | 1564179 | UGAACAACAAGG GCUUGAAUUGC | 104 | 1874 | 1896 | 1564171 | AAUUCAAGCCC UUGUUGUUCA | 416 |
| 1564184 | 1564195 | AAAUUUAUUCAU CAAGAAAAUAA | 105 | 2014 | 2036 | 1564188 | AUUUUCUUGAU GAAUAAAUUU | 417 |
| 1564181 | 1564194 | UUAUUGGAAGAU GUUCUGAAAUG | 106 | 2054 | 2076 | 1564189 | UUUCAGAACAU CUUCCAAUAA | 418 |
| 1564180 | 1564192 | GGAUCUAUAAUU UAGCUCAGUAG | 107 | 1974 | 1996 | 1564191 | ACUGAGCUAAA UUAUAGAUCC | 419 |
| 1564183 | 1564193 | UAAUUAUAAAUA GCAUAGCUGGA | 108 | 1994 | 2016 | 1564190 | CAGCUAUGCUA UUUAUAAUUA | 420 |
| 1564182 | 1564197 | AUGGUCAGAGGA GAAAUUGAAAA | 109 | 2034 | 2056 | 1564186 | UUCAAUUUCUC CUCUGACCAU | 421 |
| 1564185 | 1564196 | UAGAGUGGACUG CAAAAUAGAUG | 110 | 1954 | 1976 | 1564187 | UCUAUUUUGCA GUCCACUCUA | 422 |
| 1564202 | 1564215 | UUACCAAAGUUU GGUGAAUAUAU | 111 | 2114 | 2136 | 1564205 | AUAUUCACCAA ACUUUGGUAA | 423 |
| 1564199 | 1564210 | GAUUAUGCAGUA UAGGUGUAAAC | 112 | 2174 | 2196 | 1564204 | UUACACCUAUA CUGCAUAAUC | 424 |
| 1564198 | 1564212 | UAUUUUCCAGCA CUCAAUUUUAC | 113 | 2094 | 2116 | 1564209 | AAAAUUGAGUG CUGGAAAAUA | 425 |
| 1564200 | 1564214 | AACUAUUUUAGA CUUAAUUUUAA | 114 | 2154 | 2176 | 1564208 | AAAAUUAAGUC UAAAAUAGUU | 426 |
| 1564201 | 1564211 | UAAACUUUAGUC AACUUAAAUUA | 115 | 2134 | 2156 | 1564206 | AUUUAAGUUGA CUAAAGUUUA | 427 |
| 1564203 | 1564213 | UACUUCAGUUGU UUUAUGAGUUA | 116 | 2074 | 2096 | 1564207 | ACUCAUAAAAC AACUGAAGUA | 428 |
| 1564216 | 1564228 | AACUGAAAUUAA AAUUGUUGGAU | 117 | 2194 | 2216 | 1564222 | CCAACAAUUUU AAUUUCAGUU | 429 |
| 1564221 | 1564229 | UAUAUUAGUAAC AUGUCUUCAAC | 118 | 2214 | 2236 | 1564227 | UGAAGACAUGU ACUAAUAUA | 430 |
| 1564217 | 1564231 | UAGUAACCAUGU UUUAGAAGAUA | 119 | 2274 | 2296 | 1564224 | UCUUCUAAAAC AUGGUUACUA | 431 |
| 1564220 | 1564233 | AUAUGGUUAAUU ACACAUCCUCU | 120 | 2254 | 2276 | 1564223 | AGGAUGUGUAA UUAACCAUAU | 432 |
| 1564218 | 1564232 | AUUGAUGUUACA UAUUCUUUUAG | 121 | 2294 | 2316 | 1564225 | AAAAGAAUAUG UAACAUCAAU | 433 |

TABLE A-continued

| | | | | SEQ ID NO: 1 Anti- | SEQ ID NO: 1 Anti- | | | |
|---|---|---|---|---|---|---|---|---|
| Compound Number | Anti- sense ID | Antisense Sequence (5' to 3') | SEQ ID NO. | sense Start Site | sense Stop Site | Sense ID | Sense Sequence (5' to 3') | SEQ ID NO. |
| 1564219 | 1564230 | UCUACUCUUUA AUAAUAGUUAU | 122 | 2234 | 2256 | 1564226 | AACUAUUAUUA AAAGAGUAGA | 434 |
| 1564235 | 1564247 | UAUCCCUGAACC AAACACUUUCC | 123 | 2414 | 2436 | 1564241 | AAAGUGUUUGG UUCAGGGAUA | 435 |
| 1564237 | 1564248 | UCUCUCAUGGGU UCAGAAAAUUU | 124 | 2374 | 2396 | 1564242 | AUUUUCUGAAC CCAUGAGAGA | 436 |
| 1564234 | 1564249 | UAUUGAGUUAGC AACACUUGUGU | 125 | 2334 | 2356 | 1564244 | ACAAGUGUUGC UAACUCAAUA | 437 |
| 1564238 | 1564250 | UGUAAGAAACCA AGGUCAAUAUU | 126 | 2314 | 2336 | 1564243 | UAUUGACCUUG GUUUCUUACA | 438 |
| 1564256 | 1564265 | GAAUUUCCAGCU UGUAGAUGAGG | 127 | 2474 | 2496 | 1564261 | UCAUCUACAAG CUGGAAAUUC | 439 |
| 1564236 | 1564246 | UUUAAUAGUGUC UCCUUCACUAU | 128 | 2354 | 2376 | 1564240 | AGUGAAGGAGA CACUAUUAAA | 440 |
| 1564239 | 1564251 | UCCACUCCCCAU CUCUAGUAUCU | 129 | 2394 | 2416 | 1564245 | AUACUAGAGAU GGGGAGUGGA | 441 |
| 1564253 | 1564269 | ACUAAAACCAGU GAGGUGAGUGU | 130 | 2534 | 2556 | 1564258 | ACUCACCUCAC UGGUUUUAGU | 442 |
| 1564257 | 1564268 | AGGCGUCACUUA AGAAAUCUCUG | 131 | 2454 | 2476 | 1564263 | GAGAUUUCUUA AGUGACGCCU | 443 |
| 1564254 | 1564267 | UGUAUCACCUGU UGUUUAUAAGC | 132 | 2514 | 2536 | 1564259 | UUAUAAACAAC AGGUGAUACA | 444 |
| 1564252 | 1564266 | CUGCCCUUCUGU UCUUCAGAUAU | 133 | 2434 | 2456 | 1564260 | AUCUGAAGAAC AGAAGGGCAG | 445 |
| 1564255 | 1564264 | AGCUUUCUACUU GUUUUUAGGAA | 134 | 2494 | 2516 | 1564262 | CCUAAAAACAA GUAGAAAGCU | 446 |
| 1564270 | 1564283 | ACUUUCUGUAUU GGUAAUUUACU | 135 | 2554 | 2576 | 1564280 | UAAAUUACCAA UACAGAAAGU | 447 |
| 1564274 | 1564284 | AAUCAGUUCAAA UUUUCCACUUG | 136 | 2594 | 2616 | 1564278 | AGUGGAAAAUU UGAACUGAUU | 448 |
| 1564271 | 1564285 | AAAAUAUUGUAA CAAACAGUGUA | 137 | 2634 | 2656 | 1564277 | CACUGUUUGUU ACAAUAUUUU | 449 |
| 1564275 | 1564286 | GUUAUUUCUGUU UACUGAGAAAA | 138 | 2654 | 2676 | 1564276 | UUCUCAGUAAA CAGAAAUAAC | 450 |
| 1564272 | 1564282 | UUGUUUUUAAGA CUAGGGAUACU | 139 | 2574 | 2596 | 1564279 | UAUCCCUAGUC UUAAAAACAA | 451 |
| 1564273 | 1564287 | GUAAUCAAAGGA AUAUGACUAAU | 140 | 2614 | 2636 | 1564281 | UAGUCAUAUUC CUUUGAUUAC | 452 |
| 1564292 | 1564304 | AAUGAAGAACAA AAAAAUUAGUU | 141 | 2674 | 2696 | 1564299 | CUAAUUUUUUU GUUCUUCAUU | 453 |
| 1564293 | 1564305 | UAUGAUGAAGAA UAAUUAUUUAA | 142 | 2774 | 2796 | 1564298 | AAAUAAUUAUU CUUCAUCAUA | 454 |
| 1564288 | 1564300 | UAAAGAGUUUAU UCUACUUUAUA | 143 | 2754 | 2776 | 1564294 | UAAAGUAGAAU AAACUCUUUA | 455 |
| 1564291 | 1564302 | GAUUUUAAUUUC UAUCAAAGAAU | 144 | 2694 | 2716 | 1564297 | UCUUUGAUAGA AAUUAAAAUC | 456 |

TABLE A-continued

Oligomeric compounds targeting human PLN

| Compound Number | Anti-sense ID | Antisense Sequence (5' to 3') | SEQ ID NO. | SEQ ID NO: 1 Anti-sense Start Site | SEQ ID NO: 1 Anti-sense Stop Site | Sense ID | Sense Sequence (5' to 3') | SEQ ID NO. |
|---|---|---|---|---|---|---|---|---|
| 1564289 | 1564301 | AUAAUUUGAGUU AUAGUAUUCUG | 145 | 2734 | 2756 | 1564296 | GAAUACUAUAA CUCAAAUUAU | 457 |
| 1564290 | 1564303 | CUGUAAUCCUCA CAGAAUAAGAU | 146 | 2714 | 2736 | 1564295 | CUUAUUCUGUG AGGAUUACAG | 458 |
| 1564308 | 1564319 | AUUGUUUUUAGU GCCCUGUAAAU | 147 | 2894 | 2916 | 1564316 | UUACAGGGCAC UAAAAACAAU | 459 |
| 1564310 | 1564320 | CUAUAGUAGAAC AUAUUUGAGCA | 148 | 2854 | 2876 | 1564313 | CUCAAAUAUGU UCUACUAUAG | 460 |
| 1564307 | 1564321 | AAUUAAGAUAAG AACUUAUUCUA | 149 | 2874 | 2896 | 1564317 | GAAUAAGUUCU UAUCUUAAUU | 461 |
| 1564311 | 1564323 | AUAUCUUAUUCU UUACACUUUAU | 150 | 2794 | 2816 | 1564314 | AAAGUGUAAAG AAUAAGAUAU | 462 |
| 1564309 | 1564318 | GCAUUUAGUAUA UUAAAUUUUAA | 151 | 2834 | 2856 | 1564312 | AAAAUUUAAUA UACUAAAUGC | 463 |
| 1564306 | 1564322 | UAAAAAUAAAUU GUUUUCUUAUA | 152 | 2814 | 2836 | 1564315 | UAAGAAAACAA UUUAUUUUUA | 464 |
| 1564328 | 1564336 | UUAAACAAAUAU AUAUUCUUAAC | 153 | 2954 | 2976 | 1564332 | UAAGAUAUAU AUUUGUUUAA | 465 |
| 1564325 | 1564340 | UGAGUUUUCAAG AACAUUCAUUU | 154 | N/A | N/A | 1564335 | AUGAAUGUUCU UGAAAACUCA | 466 |
| 1564324 | 1564339 | AACCAAUUAAAA UAUAAAAGGCA | 155 | 2934 | 2956 | 1564333 | CCUUUUAUAUU UUAAUUGGUU | 467 |
| 1564329 | 1564341 | GCAACAUUAAGC AUUUUAAAAUU | 156 | 2914 | 2936 | 1564334 | UUUUAAAAUGC UUAAUGUUGC | 468 |
| 1564326 | 1564337 | ACAUUCAUUUUA AUAUAGUGAUU | 157 | 2987 | 3009 | 1564330 | UCACUAUAUUA AAAUGAAUGU | 469 |
| 1564327 | 1564338 | UAUAGUGAUUCU GAUUUGCAUUA | 158 | 2974 | 2996 | 1564331 | AUGCAAAUCAG AAUCACUAUA | 470 |
| 1576614 | 1576627 | AUAGAGUAUUGU GUUGUAUGAAG | 159 | 84 | 106 | 1576620 | UCAUACAACAC AAUACUCUAU | 471 |
| 1576613 | 1576624 | GCAGCUGUGAUC AUCACAGUAUA | 160 | 104 | 126 | 1576618 | UACUGUGAUGA UCACAGCUGC | 472 |
| 1576616 | 1576629 | AAGUCUUACGGG UGUUUAGCUGG | 161 | 64 | 86 | 1576622 | AGCUAAACACC CGUAAGACUU | 473 |
| 1576617 | 1576628 | AGCCAAAUAUGA GAUAACUGUCU | 162 | 144 | 166 | 1576623 | ACAGUUAUCUC AUAUUUGGCU | 474 |
| 1576615 | 1576626 | UCUUCUUUUAGG UAGCCUUGGCA | 163 | 124 | 146 | 1576619 | CCAAGGCUACC UAAAAGAAGA | 475 |
| 1576612 | 1576625 | UGGGGAGUUUUC UGACUCUGUCA | 164 | 44 | 66 | 1576621 | ACAGAGUCAGA AAACUCCCCA | 476 |
| 1576632 | 1576643 | AUUUCAAUGGUU GAGGCUCUUCU | 165 | 264 | 286 | 1576640 | AAGAGCCUCAA CCAUUGAAAU | 477 |
| 1576634 | 1576645 | CUGAAGUUUUAA GUGGUCGAGAG | 166 | 184 | 206 | 1576639 | CUCGACCACUU AAAACUUCAG | 478 |
| 1576635 | 1576646 | AUACCAGCAGGA CAGGAAGUCUG | 167 | 204 | 226 | 1576637 | GACUUCCUGUC CUGCUGGUAU | 479 |
| 1576630 | 1576647 | GAGAAAGAUAAA AAGCUGGCAGC | 168 | 164 | 186 | 1576636 | UGCCAGCUUUU UAUCUUUCUC | 480 |

TABLE A-continued

| | | | | | | | | |
|---|---|---|---|---|---|---|---|---|

Oligomeric compounds targeting human PLN

| Compound Number | Anti-sense ID | Antisense Sequence (5' to 3') | SEQ ID NO. | SEQ ID NO: 1 Anti-sense Start Site | SEQ ID NO: 1 Anti-sense Stop Site | Sense ID | Sense Sequence (5' to 3') | SEQ ID NO. |
|---|---|---|---|---|---|---|---|---|
| 1576633 | 1576644 | GGUAUUGGACUU UCUCCAUGAUA | 169 | 224 | 246 | 1576638 | UCAUGGAGAAA GUCCAAUACC | 481 |
| 1576631 | 1576642 | UCUUAUAGCUGA GCGAGUGAGGU | 170 | 244 | 266 | 1576641 | CUCACUCGCUC AGCUAUAAGA | 482 |
| 1576652 | 1576664 | AUUAAGAUGAGA CAGAAAUUGAU | 171 | 324 | 346 | 1576659 | CAAUUUCUGUC UCAUCUUAAU | 483 |
| 1576651 | 1576663 | UACAGAUCAGCA AGAGACAUAUU | 172 | 344 | 366 | 1576654 | UAUGUCUCUUG CUGAUCUGUA | 484 |
| 1576648 | 1576661 | UUUGACGUGCUU GUUGAGGCAUU | 173 | 284 | 306 | 1576657 | UGCCUCAACAA GCACGUCAAA | 485 |
| 1576649 | 1576660 | CUAGAGGUUGUA GCAGAACUUCA | 174 | 384 | 406 | 1576656 | AAGUUCUGCUA CAACCUCUAG | 486 |
| 1576650 | 1576662 | UCAGAGAAGCAU CACGAUGAUAC | 175 | 364 | 386 | 1576655 | AUCAUCGUGAU GCUUCUCUGA | 487 |
| 1576653 | 1576665 | GAUAAAUAGAUU CUGUAGCUUUU | 176 | 304 | 326 | 1576658 | AAGCUACAGAA UCUAUUUAUC | 488 |
| 1576667 | 1576678 | ACAAAGAAACUC UUCUACUCAGG | 177 | 484 | 506 | 1576674 | UGAGUAGAAGA GUUUCUUUGU | 489 |
| 1576666 | 1576677 | UGAUGUGGCAAG CUGCAGAUCUA | 178 | 404 | 426 | 1576673 | GAUCUGCAGCU UGCCACAUCA | 490 |
| 1576671 | 1576683 | GUCUUAAUCUUG ACCUUUUCACA | 179 | 504 | 526 | 1576679 | UGAAAAGGUCA AGAUUAAGAC | 491 |
| 1576669 | 1576681 | AUAUUGUUUUCC UGUCUGCAUGG | 180 | 444 | 466 | 1576676 | AUGCAGACAGG AAAACAAUAU | 492 |
| 1576668 | 1576680 | AGGAAGUGGUCU GUUAUACAAUA | 181 | 464 | 486 | 1576672 | UUGUAUAACAG ACCACUUCCU | 493 |
| 1576670 | 1576682 | UGGGAUGACAGA UUUUAAGCUGA | 182 | 424 | 446 | 1576675 | AGCUUAAAAUC UGUCAUCCCA | 494 |
| 1576684 | 1576697 | UAUGGUAACAAU AAGUUUUAGUC | 183 | 524 | 546 | 1576693 | CUAAAACUUAU UGUUACCAUA | 495 |
| 1576686 | 1576694 | GCAUUUUAUACA CUUAUUUUGAA | 184 | 604 | 626 | 1576692 | CAAAAUAAGUG UAUAAAAUGC | 496 |
| 1576689 | 1576701 | AGAUCCAACAGA UGAAUACAUAU | 185 | 544 | 566 | 1576696 | AUGUAUUCAUC UGUUGGAUCU | 497 |
| 1576688 | 1576700 | AAGCCCUUUUCA UGUUUACAAGA | 186 | 564 | 586 | 1576695 | UUGUAAACAUG AAAAGGGCUU | 498 |
| 1576687 | 1576699 | GAAGUUAAUUUU UGAAAAUAAAG | 187 | 584 | 606 | 1576690 | UUAUUUUCAAA AAUUAACUUC | 499 |
| 1576685 | 1576698 | UGUUGAGGAAAU CAACAGUUGCA | 188 | 624 | 646 | 1576691 | CAACUGUUGAU UUCCUCAACA | 500 |
| 1576705 | 1576716 | AAGUGAACUUGU UGGCAGUGCAG | 189 | 704 | 726 | 1576708 | GCACUGCCAAC AAGUUCACUU | 501 |
| 1576706 | 1576719 | CAGUUUUAAAAC UAAACUCUUCA | 190 | 684 | 706 | 1576713 | AAGAGUUUAGU UUUAAAACUG | 502 |
| 1576704 | 1576714 | AAAAUAAUGCUU UAUAUAUGAAG | 191 | 724 | 746 | 1576709 | UCAUAUAUAAA GCAUUAUUUU | 503 |

TABLE A-continued

Oligomeric compounds targeting human PLN

| Compound Number | Anti-sense ID | Antisense Sequence (5' to 3') | SEQ ID NO. | SEQ ID NO: 1 Anti-sense Start Site | SEQ ID NO: 1 Anti-sense Stop Site | Sense ID | Sense Sequence (5' to 3') | SEQ ID NO. |
|---|---|---|---|---|---|---|---|---|
| 1576703 | 1576717 | AUAUUCACCUCA AAAGAGUAAAA | 192 | 744 | 766 | 1576711 | UUACUCUUUUG AGGUGAAUAU | 504 |
| 1576702 | 1576715 | GGAUAGAAAUUU GUGAGCCAUGU | 193 | 644 | 666 | 1576710 | AUGGCUCACAA AUUUCUAUCC | 505 |
| 1576707 | 1576718 | UCAUCUUCAGAA AAGAUUUGGGA | 194 | 664 | 686 | 1576712 | CCAAAUCUUUU CUGAAGAUGA | 506 |
| 1576725 | 1576737 | UACUUAGUAUUA AAGAAGCUUUU | 195 | 784 | 806 | 1576730 | AAGCUUCUUUA AUACUAAGUA | 507 |
| 1576723 | 1576734 | UUUUGAAUAAUG ACACUUCAUUU | 196 | 844 | 866 | 1576726 | AUGAAGUGUCA UUAUUCAAAA | 508 |
| 1576722 | 1576733 | UGUGAGGAGUCA GUGGACUAUUU | 197 | 864 | 886 | 1576727 | AUAGUCCACUG ACUCCUCACA | 509 |
| 1576724 | 1576736 | CUUGGUGAAGAC CUGAAAAAUAC | 198 | 804 | 826 | 1576731 | AUUUUUCAGGU CUUCACCAAG | 510 |
| 1576721 | 1576732 | CUUUAUAAUAAG AUAACAGAUGU | 199 | 884 | 906 | 1576729 | AUCUGUUAUCU UAUUAUAAAG | 511 |
| 1576720 | 1576735 | UUUACAUUGUAA UAUAAAUUAUA | 200 | 764 | 786 | 1576728 | UAAUUUAUAUU ACAAUGUAAA | 512 |
| 1576742 | 1576754 | CAUAGAAAAAU ACAAUUUCUGU | 201 | 944 | 966 | 1576749 | AGAAAUUGUAU UUUUUCUAUG | 513 |
| 1576743 | 1576755 | UGUUUUAGAAUG UAGAUUCUGAU | 202 | 924 | 946 | 1576748 | CAGAAUCUACA UUCUAAAACA | 514 |
| 1576741 | 1576751 | UUUAAAAGAUGU UAAUGUGGCAU | 203 | 964 | 986 | 1576744 | GCCACAUUAAC AUCUUUUAAA | 515 |
| 1576740 | 1576750 | AGAGUAUGGCCU UACUUUUCCAU | 204 | 1004 | 1026 | 1576745 | GGAAAGUAAG GCCAUACUCU | 516 |
| 1576738 | 1576753 | GAUAGUUACUAC AAAUAGUUCUU | 205 | 904 | 926 | 1576747 | GAACUAUUUGU AGUAACUAUC | 517 |
| 1576739 | 1576752 | AAAAGGAAUUUU AUUAUGUAAGA | 206 | 1024 | 1046 | 1576746 | UUACAUAAUAA AAUUCCUUUU | 518 |
| 1576760 | 1576773 | AACAGAUUUAUG AUUUACCUACA | 207 | 1084 | 1106 | 1576770 | UAGGUAAAUCA UAAAUCUGUU | 519 |
| 1576759 | 1576771 | UAUUAACCACCA GUUCUCAUCUG | 208 | 1124 | 1146 | 1576763 | GAUGAGAACUG GUGGUUAAUA | 520 |
| 1576761 | 1576772 | AUUCUUUGAAAA AAUUACUAAA | 209 | 1044 | 1066 | 1576766 | UAAGUAAUUUU UUCAAAGAAU | 521 |
| 1576758 | 1576767 | CUGUUGAUCAUA UGUCUUAGAAC | 210 | 1104 | 1126 | 1576762 | UCUAAGACAUA UGAUCAACAG | 522 |
| 1576757 | 1576769 | UGACUAAUCUCA CUGUCACAUAU | 211 | 1144 | 1166 | 1576765 | AUGUGACAGUG AGAUUAGUCA | 523 |
| 1576756 | 1576768 | ACAUGUACUAGA AUUCUGUGAUU | 212 | 1064 | 1086 | 1576764 | UCACAGAAUUC UAGUACAUGU | 524 |
| 1576777 | 1576786 | AAGUCUUAAGGU UUCAUGAUUCC | 213 | 1264 | 1286 | 1576781 | AAUCAUGAAAC CUUAAGACUU | 525 |
| 1576778 | 1576791 | GAUAAUUCACUA CAGUGCCUUAA | 214 | 1204 | 1226 | 1576785 | AAGGCACUGUA GUGAAUUAUC | 526 |
| 1576779 | 1576790 | UAAAUGAAGAUU AGAUUCUGUUG | 215 | 1184 | 1206 | 1576784 | ACAGAAUCUAA UCUUCAUUUA | 527 |

TABLE A-continued

| | | | | | | | | |
|---|---|---|---|---|---|---|---|---|
Oligomeric compounds targeting human PLN

| Compound Number | Anti- sense ID | Antisense Sequence (5' to 3') | SEQ ID NO. | SEQ ID NO: 1 Anti- sense Start Site | SEQ ID NO: 1 Anti- sense Stop Site | Sense ID | Sense Sequence (5' to 3') | SEQ ID NO. |
|---|---|---|---|---|---|---|---|---|
| 1576776 | 1576787 | AGCUAGGUAACU CUAGCUCAGAU | 216 | 1224 | 1246 | 1576780 | CUGAGCUAGAG UUACCUAGCU | 528 |
| 1576775 | 1576789 | UGCAAAAUCAUU CUGAAGUCUUA | 217 | 1279 | 1301 | 1576782 | AGACUUCAGAA UGAUUUUGCA | 529 |
| 1576774 | 1576788 | UUGUUAGUAUAU UAGUGAUAUGA | 218 | 1164 | 1186 | 1576783 | AUAUCACUAAU AUACUAACAA | 530 |
| 1576796 | 1576809 | UUUUCCUUGCCU GCAUUGGAUGU | 219 | 1324 | 1346 | 1576806 | AUCCAAUGCAG GCAAGGAAAA | 531 |
| 1576793 | 1576803 | UUCAUAUAUUUU UAAAAAAUACU | 220 | 1384 | 1406 | 1576801 | UAUUUUUUAAA AAUAUAUGAA | 532 |
| 1576797 | 1576808 | UGUUAGGCUGGA AUGGAAGACAA | 221 | 1304 | 1326 | 1576802 | GUCUUCCAUUC CAGCCUAACA | 533 |
| 1576792 | 1576804 | CAACCUGCAAAA UCAUUCUGAAG | 222 | 1284 | 1306 | 1576800 | UCAGAAUGAUU UUGCAGGUUG | 534 |
| 1576794 | 1576807 | ACUUGAGAUAAU AUAUUUUUCUG | 223 | 1364 | 1386 | 1576799 | GAAAAAUAUAU UAUCUCAAGU | 535 |
| 1576795 | 1576805 | CUGUCACUGGAA AUCUUUUAUUU | 224 | 1344 | 1366 | 1576798 | AUAAAAGAUUU CCAGUGACAG | 536 |
| 1576813 | 1576825 | UGGGCCAACAAG UUCAUUUCAAA | 225 | 1444 | 1466 | 1576819 | UGAAAUGAACU UGUUGGCCCA | 537 |
| 1576810 | 1576821 | GUUAAUAUUUGG AGAGAGAAUUC | 226 | 1404 | 1426 | 1576817 | AUUCUCUCUCC AAAUAUUAAC | 538 |
| 1576812 | 1576826 | CUAACCCCCAUG UUCAAGGGUCA | 227 | 1484 | 1506 | 1576820 | ACCCUUGAACA UGGGGGUUAG | 539 |
| 1576814 | 1576824 | AAAAUAUAAUCU AAUAAUUAGUU | 228 | 1424 | 1446 | 1576818 | CUAAUUAUUAG AUUAUAUUUU | 540 |
| 1576815 | 1576827 | GAAUUGUCAGCU CCCCUAACCCC | 229 | 1499 | 1521 | 1576822 | GGUUAGGGGAG CUGACAAUUC | 541 |
| 1576811 | 1576823 | UCAGCUGUAGAU GUAAUAGAUGG | 230 | 1464 | 1486 | 1576816 | AUCUAUUACAU CUACAGCUGA | 542 |
| 1576829 | 1576845 | UAAUACAUAUAA CACGCAAAAUA | 231 | 1604 | 1626 | 1576838 | UUUUGCGUGUU AUAUGUAUUA | 543 |
| 1576830 | 1576840 | AUAUGUGUUAAU UUACUGUUUAU | 232 | 1584 | 1606 | 1576837 | AAACAGUAAAU UAACACAUAU | 544 |
| 1576828 | 1576842 | UAUUGUAGGAAU AUAGUGUAUAA | 233 | 1624 | 1646 | 1576839 | AUACACUAUAU UCCUACAAUA | 545 |
| 1576831 | 1576844 | UAUGUUAUCAGU AAGGUUUAUGG | 234 | 1564 | 1586 | 1576834 | AUAAACCUUAC UGAUAACAUA | 546 |
| 1576833 | 1576841 | CCCACGAAUUGU CAGCUCCCCUA | 235 | 1504 | 1526 | 1576836 | GGGGAGCUGAC AAUUCGUGGG | 547 |
| 1576832 | 1576843 | UGGUCAAUAGUA GGCUAUUAGGU | 236 | 1544 | 1566 | 1576835 | CUAAUAGCCUA CUAUUGACCA | 548 |
| 1576848 | 1576859 | AGAAUGAAGACU UUUAUGUUGAC | 237 | 1724 | 1746 | 1576853 | CAACAUAAAAG UCUUCAUUCU | 549 |
| 1576850 | 1576863 | AUAGUAAAUAUA UUUUCUCUUUC | 238 | 1684 | 1706 | 1576860 | AAGAGAAAAUA UAUUUACUAU | 550 |
| 1576851 | 1576862 | UUCUUAUGAUUU UCUAAAUAACA | 239 | 1664 | 1686 | 1576856 | UUAUUUAGAAA AUCAUAAGAA | 551 |

TABLE A-continued

| | | | | SEQ ID NO: 1 Anti- | SEQ ID NO: 1 Anti- | | | |
| Compound Number | Anti- sense ID | Antisense Sequence (5' to 3') | SEQ ID NO. | sense Start Site | sense Stop Site | Sense ID | Sense Sequence (5' to 3') | SEQ ID NO. |
| --- | --- | --- | --- | --- | --- | --- | --- | --- |
| 1576849 | 1576857 | GACCCACUUCCA UUUAAUGAAUA | 240 | 1704 | 1726 | 1576852 | UUCAUUAAAUG GAAGUGGGUC | 552 |
| 1576847 | 1576858 | UACUCAAUGUGA AGACAAUGAGA | 241 | 1744 | 1766 | 1576854 | UCAUUGUCUUC ACAUUGAGUA | 553 |
| 1576846 | 1576861 | ACAUUUUCUCUA GCUUACUUUAU | 242 | 1644 | 1666 | 1576855 | AAAGUAAGCUA GAGAAAAUGU | 554 |
| 1576869 | 1576881 | GGGCUUGAAUUG CAAGGGUCCAC | 243 | 1864 | 1886 | 1576876 | GGACCCUUGCA AUUCAAGCCC | 555 |
| 1576868 | 1576879 | CAUCUUUCUCCU CCUCUGCCUAC | 244 | 1764 | 1786 | 1576873 | AGGCAGAGGAG GAGAAAGAUG | 556 |
| 1576864 | 1576877 | CUAAGACAAGAC UGCAAGACCAA | 245 | 1804 | 1826 | 1576871 | GGUCUUGCAGU CUUGUCUUAG | 557 |
| 1576865 | 1576875 | UUCCCCCACUCC CCACACCCUA | 246 | 1824 | 1846 | 1576872 | GGGGUGUGGGG AGUGGGGGAA | 558 |
| 1576866 | 1576874 | CACUUAUACAUG AAUAUUCUUUC | 247 | 1844 | 1866 | 1576870 | AAGAAUAUUCA UGUAUAAGUG | 559 |
| 1576867 | 1576880 | CAACGCCUUCUC UUCCUCCCCAU | 248 | 1784 | 1806 | 1576878 | GGGGAGGAAGA GAAGGCGUUG | 560 |
| 1576882 | 1576895 | AGUUGACCCUUG AACAACAAGGG | 249 | 1884 | 1906 | 1576889 | CUUGUUGUUCA AGGGUCAACU | 561 |
| 1576884 | 1576894 | UUUAGCUCAGUA GAGUGGACUGC | 250 | 1964 | 1986 | 1576888 | AGUCCACUCUA CUGAGCUAAA | 562 |
| 1576883 | 1576896 | UAGCAUAGCUGG AUCUAUAAUUU | 251 | 1984 | 2006 | 1576890 | AUUAUAGAUCC AGCUAUGCUA | 563 |
| 1576887 | 1576897 | AAAUAGCUAUAU CCUAUUACAGU | 252 | 1904 | 1926 | 1576891 | UGUAAUAGGAU AUAGCUAUUU | 564 |
| 1576885 | 1576899 | UUUGGUUGAUAG AGGAAGAAAAA | 253 | 1924 | 1946 | 1576892 | UUUCUUCCUCU AUCAACCAAA | 565 |
| 1576886 | 1576898 | UGCAAAAUAGAU GCUUACCAUUU | 254 | 1944 | 1966 | 1576893 | AUGGUAAGCAU CUAUUUUGCA | 566 |
| 1576901 | 1576912 | CACUCAAUUUUA CUUCAGUUGUU | 255 | 2084 | 2106 | 1576909 | CAACUGAAGUA AAAUUGAGUG | 567 |
| 1576903 | 1576913 | AUGUUCUGAAAU GGUCAGAGGAG | 256 | 2044 | 2066 | 1576907 | CCUCUGACCAU UUCAGAACAU | 568 |
| 1576902 | 1576911 | GUUUUAUGAGUU AUUGGAAGAUG | 257 | 2064 | 2086 | 1576906 | UCUUCCAAUAA CUCAUAAAAC | 569 |
| 1576900 | 1576915 | AUCAAGAAAAUA AUUAUAAAUAG | 258 | 2004 | 2026 | 1576908 | AUUUAUAAUUA UUUUCUUGAU | 570 |
| 1576905 | 1576916 | AUUGAAAAUUUA UUCAUCAAGAA | 259 | 2019 | 2041 | 1576910 | CUUGAUGAAUA AAUUUUCAAU | 571 |
| 1576904 | 1576917 | GAGAAAUUGAAA AUUUAUUCAUC | 260 | 2024 | 2046 | 1576914 | UGAAUAAAUUU UCAUUUCUC | 572 |
| 1576919 | 1576933 | ACAUGUCUUCAA CUGAAAUUAAA | 261 | 2204 | 2226 | 1576926 | UAAUUUCAGUU GAAGACAUGU | 573 |
| 1576920 | 1576929 | AAAAUUGUUGGA UUAUGCAGUAU | 262 | 2184 | 2206 | 1576925 | ACUGCAUAAUC CAACAAUUUU | 574 |

TABLE A-continued

| | | | | SEQ ID NO: 1 Anti- | SEQ ID NO: 1 Anti- | | | |
|---|---|---|---|---|---|---|---|---|
| Compound Number | Anti- sense ID | Antisense Sequence (5' to 3') | SEQ ID NO. | sense Start Site | sense Stop Site | Sense ID | Sense Sequence (5' to 3') | SEQ ID NO. |
| 1576923 | 1576934 | UCAACUUAAAUU ACCAAAGUUUG | 263 | 2124 | 2146 | 1576928 | AACUUUGGUAA UUUAAGUUGA | 575 |
| 1576922 | 1576935 | GACUUAAUUUUA AACUUUAGUCA | 264 | 2144 | 2166 | 1576931 | ACUAAAGUUUA AAAUUAAGUC | 576 |
| 1576921 | 1576930 | UAUAGGUGUAAA CUAUUUUAGAC | 265 | 2164 | 2186 | 1576924 | CUAAAAUAGUU UACACCUAUA | 577 |
| 1576918 | 1576932 | UUGGUGAAUAUA UUUUCCAGCAC | 266 | 2104 | 2126 | 1576927 | GCUGGAAAAUA UAUUCACCAA | 578 |
| 1576937 | 1576950 | CAAGGUCAAUAU UGAUGUUACAU | 267 | 2304 | 2326 | 1576945 | GUAACAUCAAU AUUGACCUUG | 579 |
| 1576938 | 1576947 | CAUAUUCUUUUA GUAACCAUGUU | 268 | 2284 | 2306 | 1576943 | CAUGGUUACUA AAAGAAUAUG | 580 |
| 1576939 | 1576949 | GUUUUAGAAGAU AUGGUUAAUUA | 269 | 2264 | 2286 | 1576942 | AUUAACCAUAU CUUCUAAAAC | 581 |
| 1576936 | 1576951 | AUAGUUAUAUUA GUAACAUGUCU | 270 | 2219 | 2241 | 1576944 | ACAUGUUACUA AUAUAACUAU | 582 |
| 1576941 | 1576952 | UUACACAUCCUC UACUCUUUUAA | 271 | 2244 | 2266 | 1576946 | AAAAGAGUAGA GGAUGUGUAA | 583 |
| 1576940 | 1576953 | UAAUAAUAGUUA UAUUAGUAACA | 272 | 2224 | 2246 | 1576948 | UUACUAAUAUA ACUAUUAUUA | 584 |
| 1576956 | 1576966 | AUCUCUAGUAUC UCUCAUGGGUU | 273 | 2384 | 2406 | 1576961 | CCCAUGAGAGA UACUAGAGAU | 585 |
| 1576957 | 1576967 | UAGUAUCUCUCA UGGGUUCAGAA | 274 | 2379 | 2401 | 1576960 | CUGAACCCAUG AGAGAUACUA | 586 |
| 1576959 | 1576970 | UCUCCUUCACUA UUGAGUUAGCA | 275 | 2344 | 2366 | 1576964 | CUAACUCAAUA GUGAAGGAGA | 587 |
| 1576955 | 1576968 | CCAAACACUUUC CACUCCCCAUC | 276 | 2404 | 2426 | 1576963 | UGGGGAGUGGA AAGUGUUUGG | 588 |
| 1576958 | 1576971 | GUUCAGAAAAUU UAAUAGUGUCU | 277 | 2364 | 2386 | 1576965 | ACACUAUUAAA UUUUCUGAAC | 589 |
| 1576954 | 1576969 | GCAACACUUGUG UAAGAAACCAA | 278 | 2324 | 2346 | 1576962 | GGUUUCUUACA CAAGUGUUGC | 590 |
| 1576974 | 1576985 | UUGUUUUUAGGA AUUUCCAGCUU | 279 | 2484 | 2506 | 1576979 | GCUGGAAAUUC CUAAAAACAA | 591 |
| 1576976 | 1576988 | CUUGUAGAUGAG GCGUCACUUAA | 280 | 2464 | 2486 | 1576984 | AAGUGACGCCU CAUCUACAAG | 592 |
| 1576977 | 1576989 | UAAGAAAUCUCU GCCCUUCUGUU | 281 | 2444 | 2466 | 1576982 | CAGAAGGGCAG AGAUUUCUUA | 593 |
| 1576975 | 1576983 | UUUAGGAAUUUC CAGCUUGUAGA | 282 | 2479 | 2501 | 1576978 | UACAAGCUGGA AAUUCCUAAA | 594 |
| 1576972 | 1576986 | GUUCUUCAGAUA UCCCUGAACCA | 283 | 2424 | 2446 | 1576981 | GUUCAGGGAUA UCUGAAGAAC | 595 |
| 1576973 | 1576987 | GUUGUUUAUAAG CUUUCUACUUG | 284 | 2504 | 2526 | 1576980 | AGUAGAAAGCU UAUAAACAAC | 596 |
| 1576993 | 1577004 | GAAUAUGACUAA UCAGUUCAAAU | 285 | 2604 | 2626 | 1576996 | UUGAACUGAUU AGUCAUAUUC | 597 |
| 1576995 | 1577006 | GACUAGGGAUAC UUUCUGUAUUG | 286 | 2564 | 2586 | 1577000 | AUACAGAAAGU AUCCCUAGUC | 598 |

TABLE A-continued

Oligomeric compounds targeting human PLN

| Compound Number | Anti-sense ID | Antisense Sequence (5' to 3') | SEQ ID NO. | SEQ ID NO: 1 Anti-sense Start Site | SEQ ID NO: 1 Anti-sense Stop Site | Sense ID | Sense Sequence (5' to 3') | SEQ ID NO. |
|---|---|---|---|---|---|---|---|---|
| 1576992 | 1577002 | ACAGUGUAAUCA AAGGAAUAUGA | 287 | 2619 | 2641 | 1576998 | AUAUUCCUUUG AUUACACUGU | 599 |
| 1576994 | 1577007 | UUGGUAAUUUAC UAAAACCAGUG | 288 | 2544 | 2566 | 1577001 | CUGGUUUUAGU AAAUUACCAA | 600 |
| 1576990 | 1577005 | GUGAGGUGAGUG UAUCACCUGUU | 289 | 2524 | 2546 | 1576999 | CAGGUGAUACA CUCACCUCAC | 601 |
| 1576991 | 1577003 | AAUUUUCCACUU GUUUUUAAGAC | 290 | 2584 | 2606 | 1576997 | CUUAAAAACAA GUGGAAAAUU | 602 |
| 1577013 | 1577024 | UUUACUGAGAAA AAUAUUGUAAC | 291 | 2644 | 2666 | 1577018 | UACAAUAUUUU UCUCAGUAAA | 603 |
| 1577008 | 1577022 | AACAAACAGUGU AAUCAAAGGAA | 292 | 2624 | 2646 | 1577016 | CCUUUGAUUAC ACUGUUUGUU | 604 |
| 1577011 | 1577021 | UCUAUCAAAGAA UGAAGAACAAA | 293 | 2684 | 2706 | 1577014 | UGUUCUUCAUU CUUUGAUAGA | 605 |
| 1577010 | 1577020 | AAUAAGAUUUUA AUUUCUAUCAA | 294 | 2699 | 2721 | 1577015 | GAUAGAAAUUA AAAUCUUAUU | 606 |
| 1577012 | 1577025 | AAAAAAAUUAGU UAUUUCUGUUU | 295 | 2664 | 2686 | 1577019 | ACAGAAAUAAC UAAUUUUUUU | 607 |
| 1577009 | 1577023 | CACAGAAUAAGA UUUUAAUUUCU | 296 | 2704 | 2726 | 1577017 | AAAUUAAAAUC UUAUUCUGUG | 608 |
| 1577028 | 1577041 | UUAUUUAAAGAG UUUAUUCUACU | 297 | 2759 | 2781 | 1577038 | UAGAAUAAACU CUUUAAAUAA | 609 |
| 1577026 | 1577037 | UUAUAGUAUUCU GUAAUCCUCAC | 298 | 2724 | 2746 | 1577032 | GAGGAUUACAG AAUACUAUAA | 610 |
| 1577030 | 1577043 | UUGUUUUCUUAU AUCUUAUUCUU | 299 | 2804 | 2826 | 1577039 | GAAUAAGAUAU AAGAAACAA | 611 |
| 1577027 | 1577035 | AAUAAUUAUUUA AAGAGUUUAUU | 300 | 2764 | 2786 | 1577033 | UAAACUCUUUA AAUAAUUAUU | 612 |
| 1577031 | 1577042 | AUUCUACUUUAU AAUUUGAGUUA | 301 | 2744 | 2766 | 1577036 | ACUCAAAUUAU AAAGUAGAAU | 613 |
| 1577029 | 1577040 | CUUUACACUUUA UGAUGAAGAAU | 302 | 2784 | 2806 | 1577034 | UCUUCAUCAUA AAGUGUAAAG | 614 |
| 1577045 | 1577058 | GCAUUUUAAAAU UGUUUUUAGUG | 303 | 2904 | 2926 | 1577052 | CUAAAAACAAU UUUAAAAUGC | 615 |
| 1577049 | 1577060 | AGAACUUAUUCU AUAGUAGAACA | 304 | 2864 | 2886 | 1577054 | UUCUACUAUAG AAUAAGUUCU | 616 |
| 1577046 | 1577057 | CUGUAAAUUAAG AUAAGAACUUA | 305 | 2879 | 2901 | 1577050 | AGUUCUUAUCU UAAUUUACAG | 617 |
| 1577047 | 1577056 | GUGCCCUGUAAA UUAAGAUAAGA | 306 | 2884 | 2906 | 1577051 | UUAUCUUAAUU UACAGGGCAC | 618 |
| 1577048 | 1577061 | ACAUAUUUGAGC AUUUAGUAUAU | 307 | 2844 | 2866 | 1577055 | AUACUAAAUGC UCAAAUAUGU | 619 |

TABLE A-continued

Oligomeric compounds targeting human PLN

| Compound Number | Anti-sense ID | Antisense Sequence (5' to 3') | SEQ ID NO. | SEQ ID NO: 1 Anti-sense Start Site | SEQ ID NO: 1 Anti-sense Stop Site | Sense ID | Sense Sequence (5' to 3') | SEQ ID NO. |
|---|---|---|---|---|---|---|---|---|
| 1577044 | 1577059 | UAUUAAAUUUUA AAAAUAAAUUG | 308 | 2824 | 2846 | 1577053 | AUUUAUUUUUA AAAUUUAAUA | 620 |
| 1577066 | 1577075 | AAUAUAAAAGGC AACAUUAAGCA | 309 | 2924 | 2946 | 1577071 | CUUAAUGUUGC CUUUUAUAUU | 621 |
| 1577067 | 1577079 | UUCAAGAACAUU CAUUUUAAUAU | 310 | 2994 | 3016 | 1577073 | AUUAAAAUGAA UGUUCUUGAA | 622 |
| 1577065 | 1577078 | AUAUAUUCUUAA CCAAUUAAAAU | 311 | 2944 | 2966 | 1577072 | UUUAAUUGGUU AAGAAUAUAU | 623 |
| 1577064 | 1577077 | CUGAUUUGCAUU AAACAAAUAUA | 312 | 2964 | 2986 | 1577069 | UAUUUGUUUAA UGCAAAUCAG | 624 |
| 1577063 | 1577076 | AUUUUAAUAUAG UGAUUCUGAUU | 313 | 2981 | 3003 | 1577068 | UCAGAAUCACU AUAUUAAAAU | 625 |
| 1577062 | 1577074 | AAAAGGCAACAU UAAGCAUUUUA | 314 | 2919 | 2941 | 1577070 | AAAUGCUUAAU GUUGCCUUUU | 626 |

Oligomeric duplexes described above were shown to reduce PLN RNA in single dose as well as in a dose dependent effect in cultured cells. We have found modification of oligomeric duplex compounds directed to PLN, as well as conjugated compounds comprising an oligomeric duplex conjugated to a cell targeting moiety, e.g., a transferrin receptor ligand (e.g., a bicycle peptide compound targeting TfrR1) improves activity and/or other properties, such as pharmacokinetic and/or pharmacodynamic (e.g., duration of action, specificity of action, tolerability) of PLN-targeted compounds. Modifications provided herein may be applied to any one of the oligomeric compounds previously described. For example, improved modifications to oligomeric antisense and sense oligonucleotides, including specific modified sugar, nucleobase and/or internucleoside linkages, or motifs comprising any one or more of such modifications, may be incorporated into the nucleobase sequences previously described. Further, conjugation to cell targeting moieties as provided herein may be applied to previously described antisense and/or sense oligonucleotide nucleobase sequences to confer improved compounds.

Compound Nos. 1343077 (Table A1) and 1436542 (Table A2) are comparator compounds previously disclosed in International publication no. WO2022173976. Compound 1436542 is conjugated to a 6-palmitamidohexyl phosphoryl conjugate group attached to the 5'-OH of the oligonucleotide. The structure for the conjugate group 5'-C16 is depicted in Example 1.

TABLE A1

Modified oligonucleotide comparator targeted to human PLN

| Compound No. | SEQ ID No: 2 Start Site | SEQ ID No: 2 Stop Site | Sequence (5' to 3') | Sugar Motif (5' to 3') | Internucleoside Linkage (5' to 3') | SEQ ID NO |
|---|---|---|---|---|---|---|
| 1343077 | 5501 | 5516 | ACACGAGTATATTAGG | kkkddddddddddddkkk | ssssssssssssssss | 1024 |

TABLE A2

5' 6-palmitamidohexyl conjugated modified oligonucleotide comparator targeted to human PLN

| Compound No. | SEQ ID No: 2 Start Site | SEQ ID No: 2 Stop Site | Sequence (5' to 3') | Sugar Motif (5' to 3') | Internucleoside Linkage (5' to 3') | SEQ ID NO |
|---|---|---|---|---|---|---|
| 1436542 | 5501 | 5516 | ACACGAGTATATTAGG | kkkddddddddddddkkk | ssssssssssssssss | 1025 |

Example B: Oligomeric Compounds that Target Human PLN

Design of Antisense Oligonucleotides that Target Human PLN

Oligomeric compounds comprising antisense oligonucleotides complementary to a human PLN nucleic acid, and sense oligonucleotides complementary to the antisense oligonucleotides were designed having nucleobase sequences as shown in Table B1 (including Table B1a and Table B1b) and Table B2, respectively. Each antisense oligonucleotide in Table B1 is 23 nucleosides in length having the nucleobase sequence in Table B1: has a sugar motif (from 5' to 3') of: yfyyyfyyyyyyfyfyyyyyy; wherein 'y' represents a 2'-OMe sugar moiety and 'f represents a 2'-fluoro sugar moiety; and an internucleoside linkage motif (from 5' to 3') of: ssooooooooooooooooooss; wherein 'o' represents a phosphodiester internucleoside linkage and 's' represents a phosphorothioate internucleoside linkage. Each cytosine residue is a non-methylated cytosine. Each antisense oligonucleotide has a terminal phosphate at the 5'-end. "Start site" indicates the 5'-most nucleoside to which the antisense oligonucleotide is complementary in the target nucleic acid sequence. "Stop site" indicates the 3'-most nucleoside to which the antisense oligonucleotide is complementary in the target nucleic acid sequence. Each antisense oligonucleotide is 100% complementary to SEQ ID NO: 1 (GenBank Accession NM_002667.4), to SEQ ID NO: 2 (GenBank Accession NC_000006.12 truncated from nucleosides 118545001 to 118565000), or to both, with the exception of a single mismatch at the 5' end for certain sequences.

TABLE B1

Antisense oligonucleotides (antisense oligo.) targeted to human PLN

| Antisense Oligo. Compound No. | SEQ ID NO: 1 Antisense Oligo. Start Site | SEQ ID NO: 1 Antisense Oligo. Stop Site | SEQ ID NO: 2 Antisense Oligo. Start Site | SEQ ID NO: 2 Antisense Oligo. Stop Site | Antisense Strand Sequence (5' to 3') | SEQ ID NO |
|---|---|---|---|---|---|---|
| 1716582 | 298 | 320 | 13992 | 14014 | UAGAUUCUGUAGCUUUUGACGUG | 627 |
| 1716594 | 302 | 324 | 13996 | 14018 | UAAAUAGAUUCUGUAGCUUUUGA | 628 |
| 1716603 | 305 | 327 | 13999 | 14021 | UGAUAAAUAGAUUCUGUAGCUUU | 629 |
| 1716606 | 306 | 328 | 14000 | 14022 | UUGAUAAAUAGAUUCUGUAGCUU | 630 |
| 1716639 | 317 | 339 | 14011 | 14033 | UGAGACAGAAAUUGAUAAAUAGA | 631 |
| 1716654 | 322 | 344 | 14016 | 14038 | UAAGAUGAGACAGAAAUUGAUAA | 632 |
| 1716657 | 323 | 345 | 14017 | 14039 | UUAAGAUGAGACAGAAAUUGAUA | 633 |
| 1716663 | 325 | 347 | 14019 | 14041 | UAUUAAGAUGAGACAGAAAUUGA | 634 |
| 1716696 | 506 | 528 | 14200 | 14222 | UAGUCUUAAUCUUGACCUUUUCA | 635 |
| 1716699 | 507 | 529 | 14201 | 14223 | UUAGUCUUAAUCUUGACCUUUUC | 636 |
| 1716702 | 508 | 530 | 14202 | 14224 | UUUAGUCUUAAUCUUGACCUUUU | 637 |
| 1716705 | 509 | 531 | 14203 | 14225 | UUUUAGUCUUAAUCUUGACCUUU | 638 |
| 1716717 | 513 | 535 | 14207 | 14229 | UAAGUUUUAGUCUUAAUCUUGAC | 639 |
| 1716735 | 519 | 541 | 14213 | 14235 | UAACAAUAAGUUUUAGUCUUAAU | 640 |
| 1716744 | 522 | 544 | 14216 | 14238 | UGGUAACAAUAAGUUUUAGUCUU | 641 |
| 1716750 | 524 | 546 | 14218 | 14240 | UAUGGUAACAAUAAGUUUUAGUC | 642 |
| 1716771 | 541 | 563 | 14235 | 14257 | UCCAACAGAUGAAUACAUAUGGU | 643 |
| 1716795 | 548 | 570 | 14242 | 14264 | UACAAGAUCCAACAGAUGAAUAC | 644 |
| 1716798 | 549 | 571 | 14243 | 14265 | UUACAAGAUCCAACAGAUGAAUA | 645 |
| 1716801 | 550 | 572 | 14244 | 14266 | UUUACAAGAUCCAACAGAUGAAU | 646 |
| 1716807 | 552 | 574 | 14246 | 14268 | UGUUUACAAGAUCCAACAGAUGA | 647 |
| 1716816 | 555 | 577 | 14249 | 14271 | UCAUGUUUACAAGAUCCAACAGA | 648 |
| 1716819 | 556 | 578 | 14250 | 14272 | UUCAUGUUUACAAGAUCCAACAG | 649 |
| 1716822 | 557 | 579 | 14251 | 14273 | UUUCAUGUUUACAAGAUCCAACA | 650 |
| 1716825 | 558 | 580 | 14252 | 14274 | UUUUCAUGUUUACAAGAUCCAAC | 651 |
| 1716846 | 596 | 618 | 14290 | 14312 | UACACUUAUUUUGAAGUUAAUUU | 652 |

TABLE B1-continued

Antisense oligonucleotides (antisense oligo.) targeted to human PLN

| Antisense Oligo. Compound No. | SEQ ID NO: 1 Antisense Oligo. Start Site | SEQ ID NO: 1 Antisense Oligo. Stop Site | SEQ ID NO: 2 Antisense Oligo. Start Site | SEQ ID NO: 2 Antisense Oligo. Stop Site | Antisense Strand Sequence (5' to 3') | SEQ ID NO |
|---|---|---|---|---|---|---|
| 1716855 | 598 | 620 | 14292 | 14314 | UAUACACUUAUUUUGAAGUUAAU | 653 |
| 1716858 | 599 | 621 | 14293 | 14315 | UUAUACACUUAUUUUGAAGUUAA | 654 |
| 1716861 | 600 | 622 | 14294 | 14316 | UUUAUACACUUAUUUUGAAGUUA | 655 |
| 1716864 | 601 | 623 | 14295 | 14317 | UUUUAUACACUUAUUUUGAAGUU | 656 |
| 1716876 | 605 | 627 | 14299 | 14321 | UGCAUUUUAUACACUUAUUUUGA | 657 |
| 1716879 | 606 | 628 | 14300 | 14322 | UUGCAUUUUAUACACUUAUUUUG | 658 |
| 1716900 | 613 | 635 | 14307 | 14329 | UCAACAGUUGCAUUUUAUACACU | 659 |
| 1716903 | 665 | 687 | 14359 | 14381 | UUCAUCUUCAGAAAAGAUUUGGG | 660 |
| 1716909 | 667 | 689 | 14361 | 14383 | UCUUCAUCUUCAGAAAAGAUUUG | 661 |
| 1716927 | 672 | 694 | 14366 | 14388 | UAAACUCUUCAUCUUCAGAAAAG | 662 |
| 1716945 | 678 | 700 | 14372 | 14394 | UAAAACUAAACUCUUCAUCUUCA | 663 |
| 1716948 | 679 | 701 | 14373 | 14395 | UUAAAACUAAACUCUUCAUCUUC | 664 |
| 1716951 | 680 | 702 | 14374 | 14396 | UUUAAAACUAAACUCUUCAUCUU | 665 |
| 1716954 | 681 | 703 | 14375 | 14397 | UUUUAAAACUAAACUCUUCAUCU | 666 |
| 1716969 | 686 | 708 | 14380 | 14402 | UGCAGUUUUAAAACUAAACUCUU | 667 |
| 1716987 | 692 | 714 | 14386 | 14408 | UGGCAGUGCAGUUUUAAAACUAA | 668 |
| 1716990 | 693 | 715 | 14387 | 14409 | UUGGCAGUGCAGUUUUAAAACUA | 669 |
| 1716996 | 1676 | 1698 | 15370 | 15392 | UAUAUUUUCUCUUUCUUAUGAUU | 670 |
| 1717008 | 1680 | 1702 | 15374 | 15396 | UAAAUAUAUUUUCUCUUUCUUAU | 671 |
| 1717017 | 1683 | 1705 | 15377 | 15399 | UAGUAAAUAUAUUUUCUCUUUCU | 672 |
| 1717029 | 1687 | 1709 | 15381 | 15403 | UGAAUAGUAAAUAUAUUUUCUCU | 673 |
| 1717038 | 1690 | 1712 | 15384 | 15406 | UAAUGAAUAGUAAAUAUAUUUUC | 674 |
| 1717041 | 1691 | 1713 | 15385 | 15407 | UUAAUGAAUAGUAAAUAUAUUUU | 675 |
| 1717044 | 1692 | 1714 | 15386 | 15408 | UUUAAUGAAUAGUAAAUAUAUUU | 676 |
| 1716573 | 295 | 316 | 13989 | 14010 | UUUCUGUAGCUUUUGACGUGCUU | 677 |
| 1716576 | 296 | 317 | 13990 | 14011 | UAUUCUGUAGCUUUUGACGUGCU | 678 |
| 1716579 | 297 | 318 | 13991 | 14012 | UGAUUCUGUAGCUUUUGACGUGC | 679 |
| 1716585 | 299 | 320 | 13993 | 14014 | UUAGAUUCUGUAGCUUUUGACGU | 680 |
| 1716588 | 300 | 321 | 13994 | 14015 | UAUAGAUUCUGUAGCUUUUGACG | 681 |
| 1716591 | 301 | 322 | 13995 | 14016 | UAAUAGAUUCUGUAGCUUUUGAC | 682 |
| 1716597 | 303 | 324 | 13997 | 14018 | UUAAAUAGAUUCUGUAGCUUUUG | 683 |
| 1716600 | 304 | 325 | 13998 | 14019 | UAUAAAUAGAUUCUGUAGCUUUU | 684 |
| 1716609 | 307 | 328 | 14001 | 14022 | UUUGAUAAAUAGAUUCUGUAGCU | 685 |
| 1716612 | 308 | 329 | 14002 | 14023 | UAUUGAUAAAUAGAUUCUGUAGC | 686 |
| 1716615 | 309 | 330 | 14003 | 14024 | UAAUUGAUAAAUAGAUUCUGUAG | 687 |
| 1716618 | 310 | 331 | 14004 | 14025 | UAAAUUGAUAAAUAGAUUCUGUA | 688 |

TABLE B1-continued

| | | | | | | |
|---|---|---|---|---|---|---|
| | Antisense oligonucleotides (antisense oligo.) targeted to human PLN | | | | | |
| Antisense Oligo. Compound No. | SEQ ID NO: 1 Antisense Oligo. Start Site | SEQ ID NO: 1 Antisense Oligo. Stop Site | SEQ ID NO: 2 Antisense Oligo. Start Site | SEQ ID NO: 2 Antisense Oligo. Stop Site | Antisense Strand Sequence (5' to 3') | SEQ ID NO |
| 1716621 | 311 | 332 | 14005 | 14026 | UGAAAUUGAUAAAUAGAUUCUGU | 689 |
| 1716624 | 312 | 333 | 14006 | 14027 | UAGAAAUUGAUAAAUAGAUUCUG | 690 |
| 1716627 | 313 | 334 | 14007 | 14028 | UCAGAAAUUGAUAAAUAGAUUCU | 691 |
| 1716630 | 314 | 335 | 14008 | 14029 | UACAGAAAUUGAUAAAUAGAUUC | 692 |
| 1716633 | 315 | 336 | 14009 | 14030 | UGACAGAAAUUGAUAAAUAGAUU | 693 |
| 1716636 | 316 | 337 | 14010 | 14031 | UAGACAGAAAUUGAUAAAUAGAU | 694 |
| 1716642 | 318 | 339 | 14012 | 14033 | UUGAGACAGAAAUUGAUAAAUAG | 695 |
| 1716645 | 319 | 340 | 14013 | 14034 | UAUGAGACAGAAAUUGAUAAAUA | 696 |
| 1716648 | 320 | 341 | 14014 | 14035 | UGAUGAGACAGAAAUUGAUAAAU | 697 |
| 1716651 | 321 | 342 | 14015 | 14036 | UAGAUGAGACAGAAAUUGAUAAA | 698 |
| 1716660 | 324 | 345 | 14018 | 14039 | UUUAAGAUGAGACAGAAAUUGAU | 699 |
| 1716666 | 326 | 347 | 14020 | 14041 | UUAUUAAGAUGAGACAGAAAUUG | 700 |
| 1716669 | 327 | 348 | 14021 | 14042 | UAUAUUAAGAUGAGACAGAAAUU | 701 |
| 1716672 | 328 | 349 | 14022 | 14043 | UCAUAUUAAGAUGAGACAGAAAU | 702 |
| 1716675 | 329 | 350 | 14023 | 14044 | UACAUAUUAAGAUGAGACAGAAA | 703 |
| 1716678 | 330 | 351 | 14024 | 14045 | UGACAUAUUAAGAUGAGACAGAA | 704 |
| 1716681 | 331 | 352 | 14025 | 14046 | UAGACAUAUUAAGAUGAGACAGA | 705 |
| 1716684 | 332 | 353 | 14026 | 14047 | UGAGACAUAUUAAGAUGAGACAG | 706 |
| 1716687 | 333 | 354 | 14027 | 14048 | UAGAGACAUAUUAAGAUGAGACA | 707 |
| 1716690 | 334 | 355 | 14028 | 14049 | UAAGAGACAUAUUAAGAUGAGAC | 708 |
| 1716693 | 505 | 526 | 14199 | 14220 | UGUCUUAAUCUUGACCUUUUCAC | 709 |
| 1716708 | 510 | 531 | 14204 | 14225 | UUUUUAGUCUUAAUCUUGACCUU | 710 |
| 1716711 | 511 | 532 | 14205 | 14226 | UGUUUUAGUCUUAAUCUUGACCU | 711 |
| 1716714 | 512 | 533 | 14206 | 14227 | UAGUUUUAGUCUUAAUCUUGACC | 712 |
| 1716720 | 514 | 535 | 14208 | 14229 | UUAAGUUUUAGUCUUAAUCUUGA | 713 |
| 1716723 | 515 | 536 | 14209 | 14230 | UAUAAGUUUUAGUCUUAAUCUUG | 714 |
| 1716726 | 516 | 537 | 14210 | 14231 | UAAUAAGUUUUAGUCUUAAUCUU | 715 |
| 1716729 | 517 | 538 | 14211 | 14232 | UCAAUAAGUUUUAGUCUUAAUCU | 716 |
| 1716732 | 518 | 539 | 14212 | 14233 | UACAAUAAGUUUUAGUCUUAAUC | 717 |
| 1716738 | 520 | 541 | 14214 | 14235 | UUAACAAUAAGUUUUAGUCUUAA | 718 |
| 1716741 | 521 | 542 | 14215 | 14236 | UGUAACAAUAAGUUUUAGUCUUA | 719 |
| 1716747 | 523 | 544 | 14217 | 14238 | UUGGUAACAAUAAGUUUUAGUCU | 720 |
| 1716753 | 535 | 556 | 14229 | 14250 | UGAUGAAUACAUAUGGUAACAAU | 721 |
| 1716756 | 536 | 557 | 14230 | 14251 | UAGAUGAAUACAUAUGGUAACAA | 722 |
| 1716759 | 537 | 558 | 14231 | 14252 | UCAGAUGAAUACAUAUGGUAACA | 723 |
| 1716762 | 538 | 559 | 14232 | 14253 | UACAGAUGAAUACAUAUGGUAAC | 724 |

TABLE B1-continued

| | | | | | | |
|---|---|---|---|---|---|---|
| | Antisense oligonucleotides (antisense oligo.) targeted to human PLN | | | | | |
| Antisense Oligo. Compound No. | SEQ ID NO: 1 Antisense Oligo. Start Site | SEQ ID NO: 1 Antisense Oligo. Stop Site | SEQ ID NO: 2 Antisense Oligo. Start Site | SEQ ID NO: 2 Antisense Oligo. Stop Site | Antisense Strand Sequence (5' to 3') | SEQ ID NO |
| 1716765 | 539 | 560 | 14233 | 14254 | UAACAGAUGAAUACAUAUGGUAA | 725 |
| 1716768 | 540 | 561 | 14234 | 14255 | UCAACAGAUGAAUACAUAUGGUA | 726 |
| 1716774 | 542 | 563 | 14236 | 14257 | UUCCAACAGAUGAAUACAUAUGG | 727 |
| 1716777 | 543 | 564 | 14237 | 14258 | UAUCCAACAGAUGAAUACAUAUG | 728 |
| 1716780 | 544 | 565 | 14238 | 14259 | UGAUCCAACAGAUGAAUACAUAU | 729 |
| 1716783 | 545 | 566 | 14239 | 14260 | UAGAUCCAACAGAUGAAUACAUA | 730 |
| 1716786 | 546 | 567 | 14240 | 14261 | UAAGAUCCAACAGAUGAAUACAU | 731 |
| 1716792 | 547 | 568 | 14241 | 14262 | UCAAGAUCCAACAGAUGAAUACA | 732 |
| 1716804 | 551 | 572 | 14245 | 14266 | UUUUACAAGAUCCAACAGAUGAA | 733 |
| 1716810 | 553 | 574 | 14247 | 14268 | UUGUUUACAAGAUCCAACAGAUG | 734 |
| 1716813 | 554 | 575 | 14248 | 14269 | UAUGUUUACAAGAUCCAACAGAU | 735 |
| 1716828 | 559 | 580 | 14253 | 14274 | UUUUUCAUGUUUACAAGAUCCAA | 736 |
| 1716831 | 560 | 581 | 14254 | 14275 | UCUUUUCAUGUUUACAAGAUCCA | 737 |
| 1716834 | 561 | 582 | 14255 | 14276 | UCCUUUUCAUGUUUACAAGAUCC | 738 |
| 1716837 | 562 | 583 | 14256 | 14277 | UCCCUUUUCAUGUUUACAAGAUC | 739 |
| 1716840 | 563 | 584 | 14257 | 14278 | UGCCCUUUUCAUGUUUACAAGAU | 740 |
| 1716843 | 595 | 616 | 14289 | 14310 | UCACUUAUUUGAAGUUAAUUUU | 741 |
| 1716849 | 597 | 618 | 14291 | 14312 | UUACACUUAUUUGAAGUUAAUU | 742 |
| 1716867 | 602 | 623 | 14296 | 14317 | UUUUUAUACACUUAUUUGAAGU | 743 |
| 1716870 | 603 | 624 | 14297 | 14318 | UAUUUUAUACACUUAUUUGAAG | 744 |
| 1716873 | 604 | 625 | 14298 | 14319 | UCAUUUUAUACACUUAUUUGAA | 745 |
| 1716882 | 607 | 628 | 14301 | 14322 | UUUGCAUUUUAUACACUUAUUUU | 746 |
| 1716885 | 608 | 629 | 14302 | 14323 | UGUUGCAUUUUAUACACUUAUUU | 747 |
| 1716888 | 609 | 630 | 14303 | 14324 | UAGUUGCAUUUUAUACACUUAUU | 748 |
| 1716891 | 610 | 631 | 14304 | 14325 | UCAGUUGCAUUUUAUACACUUAU | 749 |
| 1716894 | 611 | 632 | 14305 | 14326 | UACAGUUGCAUUUUAUACACUUA | 750 |
| 1716897 | 612 | 633 | 14306 | 14327 | UAACAGUUGCAUUUUAUACACUU | 751 |
| 1716906 | 666 | 687 | 14360 | 14381 | UUUCAUCUUCAGAAAAGAUUUGG | 752 |
| 1716915 | 668 | 689 | 14362 | 14383 | UUCUUCAUCUUCAGAAAAGAUUU | 753 |
| 1716918 | 669 | 690 | 14363 | 14384 | UCUCUUCAUCUUCAGAAAAGAUU | 754 |
| 1716921 | 670 | 691 | 14364 | 14385 | UACUCUUCAUCUUCAGAAAAGAU | 755 |
| 1716924 | 671 | 692 | 14365 | 14386 | UAACUCUUCAUCUUCAGAAAAGA | 756 |
| 1716930 | 673 | 694 | 14367 | 14388 | UUAAACUCUUCAUCUUCAGAAAA | 757 |
| 1716933 | 674 | 695 | 14368 | 14389 | UCUAAACUCUUCAUCUUCAGAAA | 758 |
| 1716936 | 675 | 696 | 14369 | 14390 | UACUAAACUCUUCAUCUUCAGAA | 759 |
| 1716939 | 676 | 697 | 14370 | 14391 | UAACUAAACUCUUCAUCUUCAGA | 760 |

TABLE B1-continued

| Antisense oligonucleotides (antisense oligo.) targeted to human PLN | | | | | | |
|---|---|---|---|---|---|---|
| Antisense Oligo. Compound No. | SEQ ID NO: 1 Antisense Oligo. Start Site | SEQ ID NO: 1 Antisense Oligo. Stop Site | SEQ ID NO: 2 Antisense Oligo. Start Site | SEQ ID NO: 2 Antisense Oligo. Stop Site | Antisense Strand Sequence (5' to 3') | SEQ ID NO |
| 1716942 | 677 | 698 | 14371 | 14392 | UAAACUAAACUCUUCAUCUUCAG | 761 |
| 1716957 | 682 | 703 | 14376 | 14397 | UUUUUAAAACUAAACUCUUCAUC | 762 |
| 1716960 | 683 | 704 | 14377 | 14398 | UGUUUUAAAACUAAACUCUUCAU | 763 |
| 1716963 | 684 | 705 | 14378 | 14399 | UAGUUUUAAAACUAAACUCUUCA | 764 |
| 1716966 | 685 | 706 | 14379 | 14400 | UCAGUUUUAAAACUAAACUCUUC | 765 |
| 1716972 | 687 | 708 | 14381 | 14402 | UUGCAGUUUUAAAACUAAACUCU | 766 |
| 1716975 | 688 | 709 | 14382 | 14403 | UGUGCAGUUUUAAAACUAAACUC | 767 |
| 1716978 | 689 | 710 | 14383 | 14404 | UAGUGCAGUUUUAAAACUAAACU | 768 |
| 1716981 | 690 | 711 | 14384 | 14405 | UCAGUGCAGUUUUAAAACUAAAC | 769 |
| 1716984 | 691 | 712 | 14385 | 14406 | UGCAGUGCAGUUUUAAAACUAAA | 770 |
| 1716993 | 1675 | 1696 | 15369 | 15390 | UUAUUUUCUCUUUCUUAUGAUUU | 771 |
| 1716999 | 1677 | 1698 | 15371 | 15392 | UUAUAUUUCUCUUUCUUAUGAU | 772 |
| 1717002 | 1678 | 1699 | 15372 | 15393 | UAUAUAUUUCUCUUUCUUAUGA | 773 |
| 1717005 | 1679 | 1700 | 15373 | 15394 | UAAUAUAUUUCUCUUUCUUAUG | 774 |
| 1717011 | 1681 | 1702 | 15375 | 15396 | UUAAAUAUAUUUCUCUUUCUUA | 775 |
| 1717014 | 1682 | 1703 | 15376 | 15397 | UGUAAAUAUAUUUCUCUUUCUU | 776 |
| 1717020 | 1684 | 1705 | 15378 | 15399 | UUAGUAAAUAUAUUUCUCUUUC | 777 |
| 1717023 | 1685 | 1706 | 15379 | 15400 | UAUAGUAAAUAUAUUUCUCUUU | 778 |
| 1717026 | 1686 | 1707 | 15380 | 15401 | UAAUAGUAAAUAUAUUUCUCUU | 779 |
| 1717032 | 1688 | 1709 | 15382 | 15403 | UUGAAUAGUAAAUAUAUUUCUC | 780 |
| 1717035 | 1689 | 1710 | 15383 | 15404 | UAUGAAUAGUAAAUAUAUUUCU | 781 |
| 1717047 | 1693 | 1714 | 15387 | 15408 | UUUUAAUGAAUAGUAAAUAUAUU | 782 |

Antisense oligonucleotides having the nucleobase sequences in Table B1, however, differing in the 3'terminal nucleoside or two 3'terminal nucleosides may also be prepared and used in the duplexes herein. For example, one or both of the 3' terminal nucleoside is an inosine (having the nucleobase hypoxanthine designated as "I" in Table B1a). In another example, one or both of the 3'terminal nucleosides of the sequences in Table B1 is removed. Exemplary nucleobase sequences are depicted in Tables B1a and B1b:

TABLE B1a

| Antisense oligonucleotides (antisense oligo) targeted to human PLN | |
|---|---|
| SEQ ID NO: | NUCLEOBASE SEQUENCE |
| 1258 | TUUAAGAUGAGACAGAAAUUGAI |
| 1259 | TUUAAGAUGAGACAGAAAUUGII |
| 1260 | TUUAAGAUGAGACAGAAAUUGIA |

TABLE B1a-continued

| Antisense oligonucleotides (antisense oligo) targeted to human PLN | |
|---|---|
| SEQ ID NO: | NUCLEOBASE SEQUENCE |
| 1261 | TAUAAAUAGAUUCUGUAGCUUAI |
| 1262 | TAUAAAUAGAUUCUGUAGCUUII |
| 1263 | TAUAAAUAGAUUCUGUAGCUUIA |
| 1264 | TAUAAATAGAUUCUGUAGCUUAI |
| 1265 | TAUAAATAGAUUCUGUAGCUUII |
| 1266 | TAUAAATAGAUUCUGUAGCUUIA |
| 1267 | TUAAGTUUUAGUCUUAAUCUUAI |
| 1268 | TUAAGTUUUAGUCUUAAUCUUII |

TABLE B1a-continued

Antisense oligonucleotides (antisense oligo) targeted to human PLN

| SEQ ID NO: | NUCLEOBASE SEQUENCE |
|---|---|
| 1269 | TUAAGTUUUAGUCUUAAUCUUIA |
| 1270 | TUAAGUTUUAGUCUUAAUCUUAI |
| 1271 | TUAAGUTUUAGUCUUAAUCUUII |
| 1272 | TUAAGUTUUAGUCUUAAUCUUIA |
| 1273 | TUUAAGAUGAGACAGAAAUUGA |
| 1274 | TUUAAGAUGAGACAGAAAUUGI |
| 1276 | TAUAAAUAGAUUCUGUAGCUUA |
| 1277 | TAUAAAUAGAUUCUGUAGCUUI |
| 1279 | TAUAAATAGAUUCUGUAGCUUA |
| 1280 | TAUAAATAGAUUCUGUAGCUUI |
| 1282 | TUAAGTUUUAGUCUUAAUCUUA |
| 1283 | TUAAGTUUUAGUCUUAAUCUUI |
| 1285 | TUAAGUTUUAGUCUUAAUCUUA |
| 1286 | TUAAGUTUUAGUCUUAAUCUUI |

TABLE B1b

Antisense oligonucleotides (antisense oligo) targeted to human PLN

| SEQ ID NO: | NUCLEOBASE SEQUENCE |
|---|---|
| 1275 | TUUAAGAUGAGACAGAAAUUG |
| 1278 | TAUAAAUAGAUUCUGUAGCUU |
| 1281 | TAUAAATAGAUUCUGUAGCUU |
| 1284 | TUAAGTUUUAGUCUUAAUCUU |
| 1287 | TUAAGUTUUAGUCUUAAUCUU |

Design of Sense Oligonucleotides and Oligomeric Duplex Compounds that Target Human PLN Sense oligonucleotides are listed in Table B2. Each sense oligonucleotide is 21 nucleosides in length having the nucleobase sequence in Table B2; has a sugar motif (from 5' to 3') of: yyyyyyfyfffyyyyyyyyyy; wherein 'y' represents a 2'-OMe sugar moiety and the 'f' represents a 2'-fluoro sugar moiety; and an internucleoside linkage motif (from 5' to 3') of: ssooooooooooooooooss; wherein 'o' represents a phosphodiester internucleoside linkage and 's' represents a phosphorothioate internucleoside linkage. Each antisense oligonucleotide in Table B1 is complementary to target nucleic acid PLN, and each sense oligonucleotide in Table B2 is complementary to the first 21 nucleosides of an antisense oligonucleotide (from 5' to 3') in Table B1 wherein the last two 3'-nucleosides of the antisense oligonucleotides are not paired with the sense oligonucleotide (are overhanging nucleosides). The oligomeric duplex compound with corresponding sense oligonucleotide (sense oligo.) compound and antisense oligonucleotide (antisense oligo.) compound are indicated by compound numbers, together with the sense oligonucleotide sequences in Table B2.

TABLE B2

Sense oligonucleotides and Duplex compounds targeting human PLN

| Duplex Compound Number | Antisense Oligo. Compound No. | Sense Oligo. Compound No. | Sense Oligo. Sequence (5' to 3') | SEQ ID NO |
|---|---|---|---|---|
| 1716584 | 1716582 | 1716583 | CGUCAAAAGCUACAGAAUCUA | 783 |
| 1716596 | 1716594 | 1716595 | AAAAGCUACAGAAUCUAUUUA | 784 |
| 1716605 | 1716603 | 1716604 | AGCUACAGAAUCUAUUUAUCA | 785 |
| 1716608 | 1716606 | 1716607 | GCUACAGAAUCUAUUUAUCAA | 786 |
| 1716641 | 1716639 | 1716640 | UAUUUAUCAAUUUCUGUCUCA | 787 |
| 1716656 | 1716654 | 1716655 | AUCAAUUUCUGUCUCAUCUUA | 788 |
| 1716659 | 1716657 | 1716658 | UCAAUUUCUGUCUCAUCUUAA | 789 |
| 1716665 | 1716663 | 1716664 | AAUUUCUGUCUCAUCUUAAUA | 790 |
| 1716698 | 1716696 | 1716697 | AAAAGGUCAAGAUUAAGACUA | 791 |
| 1716701 | 1716699 | 1716700 | AAAGGUCAAGAUUAAGACUAA | 792 |
| 1716704 | 1716702 | 1716703 | AAGGUCAAGAUUAAGACUAAA | 793 |
| 1716707 | 1716705 | 1716706 | AGGUCAAGAUUAAGACUAAAA | 794 |
| 1716719 | 1716717 | 1716718 | CAAGAUUAAGACUAAAACUUA | 795 |
| 1716737 | 1716735 | 1716736 | UAAGACUAAAACUUAUUGUUA | 796 |
| 1716746 | 1716744 | 1716745 | GACUAAAACUUAUUGUUACCA | 797 |
| 1716752 | 1716750 | 1716751 | CUAAAACUUAUUGUUACCAUA | 798 |
| 1716773 | 1716771 | 1716772 | CAUAUGUAUUCAUCUGUUGGA | 799 |
| 1716797 | 1716795 | 1716796 | AUUCAUCUGUUGGAUCUUGUA | 800 |
| 1716800 | 1716798 | 1716799 | UUCAUCUGUUGGAUCUUGUAA | 801 |
| 1716803 | 1716801 | 1716802 | UCAUCUGUUGGAUCUUGUAAA | 802 |
| 1716809 | 1716807 | 1716808 | AUCUGUUGGAUCUUGUAAACA | 803 |
| 1716818 | 1716816 | 1716817 | UGUUGGAUCUUGUAAACAUGA | 804 |
| 1716821 | 1716819 | 1716820 | GUUGGAUCUUGUAAACAUGAA | 805 |
| 1716824 | 1716822 | 1716823 | UUGGAUCUUGUAAACAUGAAA | 806 |
| 1716827 | 1716825 | 1716826 | UGGAUCUUGUAAACAUGAAAA | 807 |
| 1716848 | 1716846 | 1716847 | AUUAACUUCAAAAUAAGUGUA | 808 |
| 1716857 | 1716855 | 1716856 | UAACUUCAAAAUAAGUGUAUA | 809 |
| 1716860 | 1716858 | 1716859 | AACUUCAAAAUAAGUGUAUAA | 810 |
| 1716863 | 1716861 | 1716862 | ACUUCAAAAUAAGUGUAUAAA | 811 |
| 1716866 | 1716864 | 1716865 | CUUCAAAAUAAGUGUAUAAAA | 812 |
| 1716878 | 1716876 | 1716877 | AAAAUAAGUGUAUAAAAUGCA | 813 |
| 1716881 | 1716879 | 1716880 | AAAUAAGUGUAUAAAAUGCAA | 814 |
| 1716902 | 1716900 | 1716901 | UGUAUAAAAUGCAACUGUUGA | 815 |
| 1716905 | 1716903 | 1716904 | CAAAUCUUUUCUGAAGAUGAA | 816 |
| 1716911 | 1716909 | 1716910 | AAUCUUUUCUGAAGAUGAAGA | 817 |
| 1716929 | 1716927 | 1716928 | UUUCUGAAGAUGAAGAGUUUA | 818 |

TABLE B2-continued

Sense oligonucleotides and Duplex compounds
targeting human PLN

| Duplex Compound Number | Anti-sense Oligo. Compound No. | Sense Oligo. Compound No. | Sense Oligo. Sequence (5' to 3') | SEQ ID NO |
|---|---|---|---|---|
| 1716947 | 1716945 | 1716946 | AAGAUGAAGAGUUUAGUUUUA | 819 |
| 1716950 | 1716948 | 1716949 | AGAUGAAGAGUUUAGUUUUAA | 820 |
| 1716953 | 1716951 | 1716952 | GAUGAAGAGUUUAGUUUUAAA | 821 |
| 1716956 | 1716954 | 1716955 | AUGAAGAGUUUAGUUUUAAAA | 822 |
| 1716971 | 1716969 | 1716970 | GAGUUUAGUUUUAAAACUGCA | 823 |
| 1716989 | 1716987 | 1716988 | AGUUUUAAAACUGCACUGCCA | 824 |
| 1716992 | 1716990 | 1716991 | GUUUUAAAACUGCACUGCCAA | 825 |
| 1716998 | 1716996 | 1716997 | UCAUAAGAAAGAGAAAAUAUA | 826 |
| 1717010 | 1717008 | 1717009 | AAGAAAGAGAAAAUAUAUUUA | 827 |
| 1717019 | 1717017 | 1717018 | AAAGAGAAAAUAUAUUUACUA | 828 |
| 1717031 | 1717029 | 1717030 | AGAAAAUAUAUUUACUAUUCA | 829 |
| 1717040 | 1717038 | 1717039 | AAAUAUAUUUACUAUUCAUUA | 830 |
| 1717043 | 1717041 | 1717042 | AAUAUAUUUACUAUUCAUUAA | 831 |
| 1717046 | 1717044 | 1717045 | AUAUAUUUACUAUUCAUUAAA | 832 |
| 1716575 | 1716573 | 1716574 | GCACGUCAAAAGCUACAGAAA | 833 |
| 1716578 | 1716576 | 1716577 | CACGUCAAAAGCUACAGAAUA | 834 |
| 1716581 | 1716579 | 1716580 | ACGUCAAAAGCUACAGAAUCA | 835 |
| 1716587 | 1716585 | 1716586 | GUCAAAAGCUACAGAAUCUAA | 836 |
| 1716590 | 1716588 | 1716589 | UCAAAAGCUACAGAAUCUAUA | 837 |
| 1716593 | 1716591 | 1716592 | CAAAAGCUACAGAAUCUAUUA | 838 |
| 1716599 | 1716597 | 1716598 | AAAGCUACAGAAUCUAUUUAA | 839 |
| 1716602 | 1716600 | 1716601 | AAGCUACAGAAUCUAUUUAUA | 840 |
| 1716611 | 1716609 | 1716610 | CUACAGAAUCUAUUUAUCAAA | 841 |
| 1716614 | 1716612 | 1716613 | UACAGAAUCUAUUUAUCAAUA | 842 |
| 1716617 | 1716615 | 1716616 | ACAGAAUCUAUUUAUCAAUUA | 843 |
| 1716620 | 1716618 | 1716619 | CAGAAUCUAUUUAUCAAUUUA | 844 |
| 1716623 | 1716621 | 1716622 | AGAAUCUAUUUAUCAAUUUCA | 845 |
| 1716626 | 1716624 | 1716625 | GAAUCUAUUUAUCAAUUUCUA | 846 |
| 1716629 | 1716627 | 1716628 | AAUCUAUUUAUCAAUUUCUGA | 847 |
| 1716632 | 1716630 | 1716631 | AUCUAUUUAUCAAUUUCUGUA | 848 |
| 1716635 | 1716633 | 1716634 | UCUAUUUAUCAAUUUCUGUCA | 849 |
| 1716638 | 1716636 | 1716637 | CUAUUUAUCAAUUUCUGUCUA | 850 |
| 1716644 | 1716642 | 1716643 | AUUUAUCAAUUUCUGUCUCAA | 851 |
| 1716647 | 1716645 | 1716646 | UUUAUCAAUUUCUGUCUCAUA | 852 |
| 1716650 | 1716648 | 1716649 | UUAUCAAUUUCUGUCUCAUCA | 853 |

TABLE B2-continued

Sense oligonucleotides and Duplex compounds
targeting human PLN

| Duplex Compound Number | Anti-sense Oligo. Compound No. | Sense Oligo. Compound No. | Sense Oligo. Sequence (5' to 3') | SEQ ID NO |
|---|---|---|---|---|
| 1716653 | 1716651 | 1716652 | UAUCAAUUUCUGUCUCAUCUA | 854 |
| 1716662 | 1716660 | 1716661 | CAAUUUCUGUCUCAUCUUAAA | 855 |
| 1716668 | 1716666 | 1716667 | AUUUCUGUCUCAUCUUAAUAA | 856 |
| 1716671 | 1716669 | 1716670 | UUUCUGUCUCAUCUUAAUAUA | 857 |
| 1716674 | 1716672 | 1716673 | UUCUGUCUCAUCUUAAUAUGA | 858 |
| 1716677 | 1716675 | 1716676 | UCUGUCUCAUCUUAAUAUGUA | 859 |
| 1716680 | 1716678 | 1716679 | CUGUCUCAUCUUAAUAUGUCA | 860 |
| 1716683 | 1716681 | 1716682 | UGUCUCAUCUUAAUAUGUCUA | 861 |
| 1716686 | 1716684 | 1716685 | GUCUCAUCUUAAUAUGUCUCA | 862 |
| 1716689 | 1716687 | 1716688 | UCUCAUCUUAAUAUGUCUCUA | 863 |
| 1716692 | 1716690 | 1716691 | CUCAUCUUAAUAUGUCUCUUA | 864 |
| 1716695 | 1716693 | 1716694 | GAAAAGGUCAAGAUUAAGACA | 865 |
| 1716710 | 1716708 | 1716709 | GGUCAAGAUUAAGACUAAAAA | 866 |
| 1716713 | 1716711 | 1716712 | GUCAAGAUUAAGACUAAAACA | 867 |
| 1716716 | 1716714 | 1716715 | UCAAGAUUAAGACUAAAACUA | 868 |
| 1716722 | 1716720 | 1716721 | AAGAUUAAGACUAAAACUUAA | 869 |
| 1716725 | 1716723 | 1716724 | AGAUUAAGACUAAAACUUAUA | 870 |
| 1716728 | 1716726 | 1716727 | GAUUAAGACUAAAACUUAUUA | 871 |
| 1716731 | 1716729 | 1716730 | AUUAAGACUAAAACUUAUUGA | 872 |
| 1716734 | 1716732 | 1716733 | UUAAGACUAAAACUUAUUGUA | 873 |
| 1716740 | 1716738 | 1716739 | AAGACUAAAACUUAUUGUUAA | 874 |
| 1716743 | 1716741 | 1716742 | AGACUAAAACUUAUUGUUACA | 875 |
| 1716749 | 1716747 | 1716748 | ACUAAAACUUAUUGUUACCAA | 876 |
| 1716755 | 1716753 | 1716754 | UGUUACCAUAUGUAUUCAUCA | 877 |
| 1716758 | 1716756 | 1716757 | GUUACCAUAUGUAUUCAUCUA | 878 |
| 1716761 | 1716759 | 1716760 | UUACCAUAUGUAUUCAUCUGA | 879 |
| 1716764 | 1716762 | 1716763 | UACCAUAUGUAUUCAUCUGUA | 880 |
| 1716767 | 1716765 | 1716766 | ACCAUAUGUAUUCAUCUGUUA | 881 |
| 1716770 | 1716768 | 1716769 | CCAUAUGUAUUCAUCUGUUGA | 882 |
| 1716776 | 1716774 | 1716775 | AUAUGUAUUCAUCUGUUGGAA | 883 |
| 1716779 | 1716777 | 1716778 | UAUGUAUUCAUCUGUUGGAUA | 884 |
| 1716782 | 1716780 | 1652838 | AUGUAUUCAUCUGUUGGAUCA | 885 |
| 1716785 | 1716783 | 1716784 | UGUAUUCAUCUGUUGGAUCUA | 886 |
| 1716788 | 1716786 | 1716787 | GUAUUCAUCUGUUGGAUCUUA | 887 |
| 1716794 | 1716792 | 1716793 | UAUUCAUCUGUUGGAUCUUGA | 888 |
| 1716806 | 1716804 | 1716805 | CAUCUGUUGGAUCUUGUAAAA | 889 |

TABLE B2-continued

Sense oligonucleotides and Duplex compounds
targeting human PLN

| Duplex Compound Number | Anti-sense Oligo. Compound No. | Sense Oligo. Compound No. | Sense Oligo. Sequence (5' to 3') | SEQ ID NO |
|---|---|---|---|---|
| 1716812 | 1716810 | 1716811 | UCUGUUGGAUCUUGUAAACAA | 890 |
| 1716815 | 1716813 | 1716814 | CUGUUGGAUCUUGUAAACAUA | 891 |
| 1716830 | 1716828 | 1716829 | GGAUCUUGUAAACAUGAAAAA | 892 |
| 1716833 | 1716831 | 1716832 | GAUCUUGUAAACAUGAAAAGA | 893 |
| 1716836 | 1716834 | 1716835 | AUCUUGUAAACAUGAAAAGGA | 894 |
| 1716839 | 1716837 | 1716838 | UCUUGUAAACAUGAAAAGGGA | 895 |
| 1716842 | 1716840 | 1716841 | CUUGUAAACAUGAAAAGGGCA | 896 |
| 1716845 | 1716843 | 1716844 | AAUUAACUUCAAAAUAAGUGA | 897 |
| 1716851 | 1716849 | 1716850 | UUAACUUCAAAAUAAGUGUAA | 898 |
| 1716869 | 1716867 | 1716868 | UUCAAAAUAAGUGUAUAAAAA | 899 |
| 1716872 | 1716870 | 1716871 | UCAAAAUAAGUGUAUAAAAUA | 900 |
| 1716875 | 1716873 | 1716874 | CAAAAUAAGUGUAUAAAAUGA | 901 |
| 1716884 | 1716882 | 1716883 | AAUAAGUGUAUAAAAUGCAAA | 902 |
| 1716887 | 1716885 | 1716886 | AUAAGUGUAUAAAAUGCAACA | 903 |
| 1716890 | 1716888 | 1716889 | UAAGUGUAUAAAAUGCAACUA | 904 |
| 1716893 | 1716891 | 1716892 | AAGUGUAUAAAAUGCAACUGA | 905 |
| 1716896 | 1716894 | 1716895 | AGUGUAUAAAAUGCAACUGUA | 906 |
| 1716899 | 1716897 | 1716898 | GUGUAUAAAAUGCAACUGUUA | 907 |
| 1716908 | 1716906 | 1716907 | AAAUCUUUUCUGAAGAUGAAA | 908 |
| 1716917 | 1716915 | 1716916 | AUCUUUUCUGAAGAUGAAGAA | 909 |
| 1716920 | 1716918 | 1716919 | UCUUUUCUGAAGAUGAAGAGA | 910 |
| 1716923 | 1716921 | 1716922 | CUUUUCUGAAGAUGAAGAGUA | 911 |
| 1716926 | 1716924 | 1716925 | UUUUCUGAAGAUGAAGAGUUA | 912 |
| 1716932 | 1716930 | 1716931 | UUCUGAAGAUGAAGAGUUUAA | 913 |
| 1716935 | 1716933 | 1716934 | UCUGAAGAUGAAGAGUUUAGA | 914 |
| 1716938 | 1716936 | 1716937 | CUGAAGAUGAAGAGUUUAGUA | 915 |
| 1716941 | 1716939 | 1716940 | UGAAGAUGAAGAGUUUAGUUA | 916 |
| 1716944 | 1716942 | 1716943 | GAAGAUGAAGAGUUUAGUUUA | 917 |
| 1716959 | 1716957 | 1716958 | UGAAGAGUUUAGUUUUAAAA | 918 |
| 1716962 | 1716960 | 1716961 | GAAGAGUUUAGUUUUAAAACA | 919 |
| 1716965 | 1716963 | 1716964 | AAGAGUUUAGUUUUAAAACUA | 920 |
| 1716968 | 1716966 | 1716967 | AGAGUUUAGUUUUAAAACUGA | 921 |
| 1716974 | 1716972 | 1716973 | AGUUUAGUUUUAAAACUGCAA | 922 |
| 1716977 | 1716975 | 1716976 | GUUUAGUUUUAAAACUGCACA | 923 |
| 1716980 | 1716978 | 1716979 | UUUAGUUUUAAAACUGCACUA | 924 |

TABLE B2-continued

Sense oligonucleotides and Duplex compounds
targeting human PLN

| Duplex Compound Number | Anti-sense Oligo. Compound No. | Sense Oligo. Compound No. | Sense Oligo. Sequence (5' to 3') | SEQ ID NO |
|---|---|---|---|---|
| 1716983 | 1716981 | 1716982 | UUAGUUUUAAAACUGCACUGA | 925 |
| 1716986 | 1716984 | 1716985 | UAGUUUUAAAACUGCACUGCA | 926 |
| 1716995 | 1716993 | 1716994 | AUCAUAAGAAAGAGAAAAUAA | 927 |
| 1717001 | 1716999 | 1717000 | CAUAAGAAAGAGAAAAUAUAA | 928 |
| 1717004 | 1717002 | 1717003 | AUAAGAAAGAGAAAAUAUAUA | 929 |
| 1717007 | 1717005 | 1717006 | UAAGAAAGAGAAAAUAUAUUA | 930 |
| 1717013 | 1717011 | 1717012 | AGAAAGAGAAAAUAUAUUUAA | 931 |
| 1717016 | 1717014 | 1717015 | GAAAGAGAAAAUAUAUUUACA | 932 |
| 1717022 | 1717020 | 1717021 | AAGAGAAAAUAUAUUUACUAA | 933 |
| 1717025 | 1717023 | 1717024 | AGAGAAAAUAUAUUUACUAUA | 934 |
| 1717028 | 1717026 | 1717027 | GAGAAAAUAUAUUUACUAUUA | 935 |
| 1717034 | 1717032 | 1717033 | GAAAAUAUAUUUACUAUUCAA | 936 |
| 1717037 | 1717035 | 1717036 | AAAAUAUAUUUACUAUUCAUA | 937 |
| 1717049 | 1717047 | 1717048 | UAUAUUUACUAUUCAUUAAAA | 938 |

Activity of Oligomeric Duplex Compounds Targeting Human PLN

Cultured iCell® cardiomyocytes (FujiFilm Cellular Dynamics, Inc.: Catalog No: R1017) were treated with compound at a concentration of 125 nM using Lipofectamine RNAiMAX at a density of 8,000 cells per well: or cultured A431 cells were treated with compound at a concentration of 100 nM using Lipofectamine RNAiMAX at a density of 10,000 cells per well. After a treatment period of 24 hours (for cardiomyocytes) or 72 hours (for A431 cells), total RNA was isolated from the cells and PLN RNA levels were measured by quantitative real-time RTPCR. PLN RNA levels were measured by human primer-probe set RTS40403 (forward sequence GAAGAACAGAAGGGCAGAGATT, designated herein as SEQ ID NO: 1046; reverse sequence AAACCAGTGAGGTGAGTGTATC, designated herein as SEQ ID NO: 1047: probe sequence TTTCCAGCTTGTA-GATGAGGCGTCAC, designated herein as SEQ ID NO: 1048) and human primer-probe set RTS40407 (forward sequence GCTGCCAAGGCTACCTAAA, designated herein as SEQ ID NO: 1049; reverse sequence GAGT-GAGGTATTGGACTTTCTCC, designated herein as SEQ ID NO: 1050; probe sequence TCA-GACTTCCTGTCCTGCTGGTATCA, designated herein as SEQ ID NO: 1051). PLN RNA levels were normalized to total RNA content, as measured by RIBOGREENR. Reduction of PLN RNA is presented as percent PLN RNA relative to the amount of PLN RNA in untreated control cells (% UTC). Results from various experiments are presented in Table B3.

TABLE B3

Effect of oligomeric duplex compounds
targeting human PLN in Cells

| Compound No. | PLN RNA in IPS derived cardiomyocytes (% UTC) | | PLN RNA in A431 cells (% UTC) | |
|---|---|---|---|---|
| | RTS40403 | RTS40407 | RTS40403 | RTS40407 |
| 1716812 | 6 | 8 | 13 | 12 |
| 1716815 | 4 | 5 | 19 | 13 |
| 1716818 | 5 | 6 | 34 | 28 |
| 1716821 | 12 | 12 | 22 | 19 |
| 1716824 | 5 | 6 | 20 | 18 |
| 1716827 | 5 | 7 | 15 | 12 |
| 1716830 | 6 | 8 | 19 | 17 |
| 1716833 | 6 | 8 | 19 | 16 |
| 1716836 | 5 | 7 | 23 | 21 |
| 1716839 | 5 | 7 | 24 | 23 |
| 1716842 | 6 | 6 | 25 | 19 |
| 1716845 | 7 | 8 | 21 | 20 |
| 1716848 | 4 | 5 | 31 | 28 |
| 1716851 | 8 | 10 | 39 | 35 |
| 1716857 | 5 | 6 | 24 | 21 |
| 1716860 | 6 | 9 | 24 | 23 |
| 1716863 | 9 | 12 | 28 | 29 |
| 1716866 | 4 | 8 | 22 | 24 |
| 1716869 | 6 | 11 | 38 | 42 |
| 1716872 | 5 | 6 | 25 | 24 |
| 1716875 | 3 | 5 | 28 | 23 |
| 1716878 | 11 | 12 | 32 | 27 |
| 1716881 | 6 | 9 | 26 | 25 |
| 1716884 | 12 | 12 | 30 | 24 |
| 1716887 | 9 | 11 | 22 | 22 |
| 1716890 | 9 | 9 | 24 | 18 |
| 1716893 | 8 | 11 | 22 | 22 |
| 1716896 | 7 | 11 | 31 | 31 |
| 1716899 | 9 | 13 | 24 | 28 |
| 1716902 | 5 | 6 | 24 | 20 |
| 1716905 | 9 | 17 | 65 | 69 |
| 1716908 | 8 | 27 | 27 | 37 |
| 1716911 | 9 | 25 | 39 | 48 |
| 1716917 | 8 | 26 | 35 | 57 |
| 1716920 | 7 | 25 | 28 | 43 |
| 1716923 | 12 | 21 | 22 | 30 |
| 1716926 | 5 | 19 | 21 | 37 |
| 1716929 | 11 | 40 | 26 | 43 |
| 1716932 | 22 | 44 | 39 | 62 |
| 1716935 | 5 | 13 | 18 | 28 |
| 1716938 | 4 | 14 | 23 | 35 |
| 1716941 | 4 | 18 | 35 | 51 |
| 1716944 | 7 | 27 | 21 | 35 |
| 1716947 | 5 | 18 | 26 | 43 |
| 1716950 | 6 | 23 | 22 | 41 |
| 1716953 | 7 | 22 | 16 | 25 |
| 1716956 | 9 | 24 | 19 | 32 |
| 1716959 | 7 | 29 | 17 | 30 |
| 1716962 | 6 | 22 | 21 | 28 |
| 1716965 | 7 | 20 | 53 | 56 |
| 1716968 | 7 | 16 | 51 | 58 |
| 1716971 | 13 | 30 | 30 | 41 |
| 1716974 | 26 | 45 | 18 | 30 |
| 1716977 | 40 | 40 | 51 | 65 |
| 1716980 | 12 | 26 | 33 | 39 |
| 1716983 | 10 | 27 | 44 | 59 |
| 1716986 | 15 | 46 | 34 | 48 |
| 1716989 | 15 | 36 | 25 | 36 |
| 1716992 | 42 | 49 | 38 | 41 |
| 1716995 | 6 | 37 | 24 | 45 |
| 1716998 | 8 | 34 | 26 | 42 |
| 1717001 | 8 | 53 | 20 | 48 |
| 1717004 | 9 | 41 | 22 | 39 |
| 1717007 | 9 | 57 | 22 | 42 |
| 1717010 | 10 | 77 | 25 | 44 |
| 1717013 | 5 | 35 | 20 | 37 |
| 1717016 | 8 | 57 | 14 | 34 |
| 1717019 | 8 | 66 | 16 | 39 |
| 1717022 | 7 | 51 | 16 | 34 |
| 1717025 | 5 | 33 | 23 | 47 |
| 1717028 | 7 | 47 | 17 | 34 |
| 1717031 | 8 | 48 | 39 | 48 |

TABLE B3-continued

Effect of oligomeric duplex compounds
targeting human PLN in Cells

| Compound No. | PLN RNA in IPS derived cardiomyocytes (% UTC) | | PLN RNA in A431 cells (% UTC) | |
|---|---|---|---|---|
| | RTS40403 | RTS40407 | RTS40403 | RTS40407 |
| 1717034 | 6 | 36 | 20 | 33 |
| 1717037 | 17 | 52 | 57 | 58 |
| 1717040 | 5 | 36 | 20 | 32 |
| 1717043 | 5 | 46 | 27 | 48 |
| 1717046 | 10 | 38 | 23 | 43 |
| 1717049 | 7 | 46 | 22 | 35 |
| 1716575 | 10 | 10 | 42 | 29 |
| 1716578 | 4 | 3 | 25 | 16 |
| 1716581 | 6 | 2 | 30 | 22 |
| 1716584 | 5 | 3 | 22 | 13 |
| 1716587 | 6 | 4 | 18 | 10 |
| 1716590 | 7 | 5 | 31 | 20 |
| 1716593 | 6 | 5 | 33 | 34 |
| 1716596 | 15 | 13 | 30 | 31 |
| 1716599 | 14 | 12 | 56 | 56 |
| 1716602 | 3 | 2 | 20 | 16 |
| 1716605 | 348 | 3 | 21 | 14 |
| 1716608 | 750085 | 3 | 19 | 11 |
| 1716611 | 5 | 4 | 32 | 24 |
| 1716614 | 4 | 3 | 29 | 21 |
| 1716617 | 6 | 6 | 29 | 25 |
| 1716620 | 9 | 8 | 21 | 16 |
| 1716623 | 5 | 4 | 18 | 12 |
| 1716626 | 4 | 3 | 20 | 13 |
| 1716629 | 10 | 8 | 52 | 57 |
| 1716632 | 5 | 4 | 45 | 37 |
| 1716635 | 4 | 3 | 71 | 68 |
| 1716638 | 7 | 4 | 35 | 22 |
| 1716641 | 5 | 4 | 37 | 35 |
| 1716644 | 6 | 4 | 23 | 17 |
| 1716647 | 6 | 5 | 34 | 28 |
| 1716650 | 6 | 3 | 35 | 26 |
| 1716653 | 17 | 9 | 37 | 37 |
| 1716656 | 11 | 8 | 39 | 39 |
| 1716659 | 11 | 9 | 41 | 35 |
| 1716662 | 3 | 2 | 20 | 15 |
| 1716665 | 12 | 10 | 36 | 37 |
| 1716668 | 16 | 12 | 37 | 24 |
| 1716671 | 8 | 4 | 32 | 24 |
| 1716674 | 11 | 9 | 30 | 19 |
| 1716677 | 10 | 8 | 34 | 29 |
| 1716680 | 8 | 5 | 21 | 15 |
| 1716683 | 113 | 93 | 62 | 63 |
| 1716686 | 41 | 32 | 54 | 57 |
| 1716689 | 10 | 7 | 30 | 21 |
| 1716692 | 6 | 4 | 21 | 13 |
| 1716695 | 5 | 4 | 31 | 25 |
| 1716698 | 13 | 11 | 65 | 58 |
| 1716701 | 8 | 8 | 28 | 20 |
| 1716704 | 5 | 4 | 30 | 21 |
| 1716707 | 22 | 20 | 24 | 20 |
| 1716710 | 8 | 8 | 19 | 14 |
| 1716713 | 7 | 7 | 25 | 21 |
| 1716716 | 8 | 9 | 38 | 33 |
| 1716719 | 7 | 8 | 36 | 33 |
| 1716722 | 6 | 6 | 29 | 19 |
| 1716725 | 5 | 5 | 58 | 60 |
| 1716728 | 11 | 10 | 65 | 65 |
| 1716731 | 5 | 7 | 21 | 15 |
| 1716734 | 8 | 12 | 21 | 17 |
| 1716737 | 7 | 9 | 39 | 31 |
| 1716740 | 9 | 9 | 22 | 18 |
| 1716743 | 8 | 9 | 26 | 19 |
| 1716746 | 8 | 11 | 31 | 22 |
| 1716749 | 10 | 12 | 29 | 18 |
| 1716752 | 5 | 7 | 20 | 15 |
| 1716755 | 8 | 9 | 33 | 19 |
| 1716758 | 11 | 11 | 34 | 25 |
| 1716761 | 23 | 23 | 33 | 26 |
| 1716764 | 9 | 10 | 26 | 17 |
| 1716767 | 9 | 11 | 28 | 23 |
| 1716770 | 9 | 12 | 20 | 15 |

699

TABLE B3-continued

Effect of oligomeric duplex compounds
targeting human PLN in Cells

| Compound | PLN RNA in IPS derived cardiomyocytes (% UTC) | | PLN RNA in A431 cells (% UTC) | |
|---|---|---|---|---|
| No. | RTS40403 | RTS40407 | RTS40403 | RTS40407 |
| 1716773 | 9 | 11 | 19 | 13 |
| 1716776 | 8 | 12 | 21 | 17 |
| 1716779 | 13 | 16 | 25 | 14 |
| 1716782 | 14 | 15 | 35 | 22 |
| 1716785 | 13 | 14 | 22 | 14 |
| 1716788 | 7 | 11 | 22 | 14 |
| 1716794 | 10 | 13 | 24 | 14 |
| 1716797 | 9 | 13 | 36 | 24 |
| 1716800 | 24 | 23 | 31 | 16 |
| 1716803 | 10 | 13 | 29 | 18 |
| 1716806 | 10 | 12 | 22 | 14 |
| 1716809 | 14 | 14 | 21 | 12 |

Transgenic Animals

The following transgenic mice were used to determine effects of the modified oligonucleotides and oligomeric duplex compounds provided herein on human PLN:

hPLN$^{tg/tg}$ knock-in mice (Taconic Biosciences): The human PLN allele (NCBI transcript NM_002667.4) harboring the p.Arg14del mutation was generated by CRISPR/Cas9-mediated gene editing. The mutant human allele was inserted into mouse PLN (NCBI transcript NM_023129.5) to generate constitutive humanization of the Pln gene. The mouse genomic sequence from exon 1 including the 5' UTR to 29 bp downstream of exon 2 including the 3' UTR was replaced with the human counterpart. A plasmid containing homology regions of the mouse PLN gene and the replaced human region including the R14del mutation was co-transfected with a plasmid allowing the expression of Cas9 mRNA, the specific gRNA and puromycin N acetyl transferase (puromycin resistance) into the Taconic C57BL/6N Tac ES cell line. Heterozygous mice generated are called hPLN$^{tg/+}$ herein. Homozygous mice generated are called hPLN$^{tg/tg}$ herein.

hTfR$^{+/-}$ knock-in mice were used to determine effects of the modified oligonucleotides described below on mouse PLN. Human transferrin receptor (hTFR)/CD71 knock-in mice used in these studies have the coding region of mouse exon 2 as well as the splice donor-site of mouse intron 2 replaced with the human TFR open reading frame according to NCBI transcript NM_001128148.2. Humanization of the transferrin receptor gene was done via CRISPR/Cas-9-mediated gene editing, allowing for generation of a model with constitutive expression of humanized transferrin receptor gene. Targeting strategy was based on NCBI transcripts NM_011638.4 (mouse) and NM_001128148.2 (human). A plasmid allowing expression of Cas9 mRNA, specific gRNA, and the puromycin resistance cassette; and a plasmid containing the homology regions of the mouse transferrin receptor gene, an FRT site, and the replaced human region were co-transfected into the Taconic Biosciences C57BL/6N Tac ES cell line. The humanized mice are called hTfR$^{+/-}$ knock-in mice herein. They express one copy of the mouse TFR gene and one copy of the humanized TFR gene under the control of the endogenous mouse promoter.

hTfR$^{tg/+}$/hPLN$^{tg/tg}$ knock-in mice were generated by crossing hTfR$^{tg/+}$ and hPLN$^{tg/tg}$. These mice are heterozygous for hTfr and homozygous for human PLN.

hTfR$^{tg/+}$/hPLN$^{tg/+}$ mice were generated by crossing hTfR$^{tg/+}$, and hPLN$^{tg/+}$ These mice are heterozygous for hTfr and heterozygous for human PLN.

Example 1: Design of Modified Oligomeric Compounds that Target Human PLN

Oligomeric compounds comprising antisense oligonucleotides complementary to a human PLN nucleic acid, and sense oligonucleotides complementary to the antisense oligonucleotides were designed as follows.

Design of Antisense Oligonucleotides

Antisense oligonucleotides having nucleobase sequences in Tables 1-9 below are 23 (Tables 1-6), or 22 (Tables 8 and 9), or 21 (Table 7) nucleosides in length, have a sugar motif as designated in the column labeled "Antisense Strand Sugar Motif (5' to 3')," wherein each 'y' represents a 2'-OMe sugar moiety, each 'f' represents a 2-F sugar moiety, each '[FHNA]' represents a 3'-fluoro-hexitol sugar moiety, each 'd' represents a 2'-deoxy sugar moiety, and each 'c' represents a 2'-MOE sugar moiety. In Table 1, each antisense oligonucleotide has an internucleoside linkage motif (from 5' to 3') of: ssoooooooooooooooooooss, in Table 2 each antisense oligonucleotide has an internucleoside linkage motif (from 5' to 3') of: ssoooosoooooooooooooooss, in Table 3 each antisense oligonucleotide has an internucleoside linkage motif (from 5' to 3') of: ssoooooooooooooooooooss, in Table 4 each antisense oligonucleotide has an internucleoside linkage motif (from 5' to 3') of: ssoooooooooooooooooooss, in Table 5 each antisense oligonucleotide has an internucleoside linkage motif (from 5' to 3') of: ssoosoosooooooooooooooss, in Table 6 each antisense oligonucleotide has an internucleoside linkage motif (from 5' to 3') of: ssoooooooooooooooooooss, in Table 7 each antisense oligonucleotide has an internucleoside linkage motif (from 5' to 3') of: ssoooooooooooooooooooss, in Table 8 each antisense oligonucleotide has an internucleoside linkage motif (from 5' to 3') of ssoooooooooooooooooooss, and in Table 9 each antisense oligonucleotide has an internucleoside linkage motif (from 5' to 3") of: ssoooooooooooooooooooos; wherein each 'o' represents a phosphodiester internucleoside linkage and each 's' represents a phosphorothioate internucleoside linkage. Each cytosine residue is a non-methylated cytosine. Each antisense oligonucleotide has a vinyl phosphonate (vP-) group on the 5'-end.

In each of Tables 1-9, "Start site" indicates the 5'-most nucleoside to which the antisense oligonucleotide is complementary in the target nucleic acid sequence. "Stop site" indicates the 3'-most nucleoside to which the antisense oligonucleotide is complementary in the target nucleic acid sequence.

Each antisense oligonucleotide listed in Tables 1-9 is complementary to SEQ ID NO: 1 (GENBANK Accession No. NM_002667.4), except for a single mismatch at position 1 on the 5' end of the antisense oligonucleotide in each of Tables 1-9; and a second mismatch at position 23 on the 3-end of the antisense oligonucleotides in Table 3, a second mismatch at position 22 on the 3'-end of the antisense oligonucleotides in Table 4, a second mismatch at position 23 on the 3'-end of the antisense oligonucleotides in Table 5, two mismatches at positions 22 and 23 on the 3'-end of the antisense oligonucleotides in Table 6, two mismatches at positions 20 and 21 on the 3'-end of the antisense oligonucleotides in Table 7, and a second mismatch at position 22 on the 3'-end of the antisense oligonucleotides in Table 8.

TABLE 1

Antisense oligonucleotides targeted to human PLN

| Compound No. | SEQ ID NO: 1 Start Site | SEQ ID NO: 1 Stop Site | Antisense Strand Sequence (5' to 3') | Antisense Strand Sugar Motif (5' to 3') | SEQ ID NO |
|---|---|---|---|---|---|
| 1652826 | 324 | 345 | TUUAAGAUGAGACAGAAAUUGAU | efyyyfyyyyyyyyfyfyyyyyyy | 939 |
| 1652709 | 304 | 325 | TAUAAAUAGAUUCUGUAGCUUUU | efyyyfyyyyyyyyfyfyyyyyyy | 940 |
| 1691449 | 1044 | 1065 | TUUCUUUGAAAAAAUUACUUAAA | efyyyfyyyyyyyyfyfyyyyyyy | 941 |
| 1691837 | 514 | 535 | TUAAGUUUUAGUCUUAAUCUUGA | efyyyfyyyyyyyyfyfyyyyyyy | 942 |
| 1692941 | 554 | 575 | TAUGUUUACAAGAUCCAACAGAU | efyyyfyyyyyyyyfyfyyyyyyy | 943 |
| 1692943 | 604 | 625 | TCAUUUUAUACACUUAUUUUGAA | efyyyfyyyyyyyyfyfyyyyyyy | 944 |
| 1692945 | 684 | 705 | TAGUUUUAAAACUAAACUCUUCA | efyyyfyyyyyyyyfyfyyyyyyy | 945 |
| 1692950 | 674 | 695 | TCUAAACUCUUCAUCUUCAGAAA | efyyyfyyyyyyyyfyfyyyyyyy | 946 |
| 1692952 | 1684 | 1705 | TUAGUAAAUAUAUUUCUCUUUC | efyyyfyyyyyyyyfyfyyyyyyy | 947 |
| 1731386 | 324 | 345 | TUUAAGAUGAGACAGAAAUUGAT | efyyyfyyyyyyyyfyfyyyyyee | 948 |
| 1731388 | 324 | 345 | TUUAAGAUGAGACAGAAAUUGAT | e[FHNA]yyyyyyyyyyy[FHNA]yyyyyyyee | 949 |
| 1731387 | 324 | 345 | TUUAAGAUGAGACAGAAAUUGAT | efyyyyyyyyyyyyyfyyyyyyyee | 950 |
| 1731389 | 324 | 345 | TUUAAGAUGAGACAGAAAUUGAT | e[FHNA]yyyfyyyyyyyyfyfyyyyyee | 951 |
| 1731390 | 324 | 345 | TUUAAGAUGAGACAGAAAUUGAT | efyyydyyyyyyyfyfyyyyyee | 952 |
| 1736402 | 324 | 345 | TUUAAGAUGAGACAGAAAUUGAU | e[FHNA]yyyfyyyyyyyyfyfyyyyyyy | 953 |
| 1736403 | 324 | 345 | TUUAAGAUGAGACAGAAAUUGAU | efyyydyyyyyyydydyyyyyyy | 954 |
| 1736404 | 324 | 345 | TUUAAGAUGAGACAGAAAUUGAU | efyyydyyyyyyyfyfyyyyyyy | 955 |
| 1738170 | 324 | 345 | TUUAAGAUGAGACAGAAAUUGAU | efyydydyyyyyyfyfyyyyyyy | 956 |
| 1738171 | 324 | 345 | TUUAAGAUGAGACAGAAAUUGAT | efyyyfyyyyyyyyfyyyyyyyee | 957 |
| 1738172 | 324 | 345 | TUUAAGAUGAGACAGAAAUUGAT | efyyyyyyyyyyyyfyfyyyyyee | 958 |
| 1738173 | 324 | 345 | TUUAAGAUGAGACAGAAAUUGAU | efyyyfyyyyyyyyfyyyyyyyyy | 959 |
| 1738174 | 324 | 345 | TUUAAGAUGAGACAGAAAUUGAU | efyyyyyyyyyyyyfyfyyyyyyy | 960 |
| 1749977 | 324 | 345 | TUUAAGAUGAGACAGAAAUUGAU | e[FHNA]yydydyyyyfyfyfyyyyyyy | 961 |
| 1744533 | 324 | 345 | TUUAAGAUGAGACAGAAAUUGAU | efyyyfyyyyyyyyfydyyyyyyy | 962 |
| 1744534 | 324 | 345 | TUUAAGAUGAGACAGAAAUUGAT | efyyyfyyyyyyyyfydyyyyyee | 963 |
| 1749975 | 324 | 345 | TUUAAGAUGAGACAGAAAUUGAU | efyyyfyyyyyyyyfyfyyyyyey | 964 |
| 1801601 | 304 | 325 | TAUAAATAGAUUCUGUAGCUUII | efyydydyyyyyyfyfyyyyyee | 1265 |

TABLE 2

Antisense oligonucleotide targeted to human PLN

| Compound No. | SEQ ID NO: 1 Start Site | SEQ ID NO: 1 Stop Site | Antisense Strand Sequence (5' to 3') | Antisense Strand Sugar Motif (5' to 3') | SEQ ID NO |
|---|---|---|---|---|---|
| 1731397 | 324 | 345 | TUUAAGAUGAGACAGAAAUUGAT | efyyydyyyyyyyyfyfyyyyyee | 965 |

TABLE 3

Antisense oligonucleotides targeted to human PLN

| Compound No. | SEQ ID NO: 1 Start Site | SEQ ID NO: 1 Stop Site | Antisense Strand Sequence (5' to 3') | Antisense Strand Sugar Motif (5' to 3') | SEQ ID NO |
|---|---|---|---|---|---|
| 1749976 | 325 | 345 | TUUAAGAUGAGACAGAAAUUGAA | efyyyfyyyyyyyyfyfyyyyyey | 966 |
| 1746643 | 325 | 345 | TUUAAGAUGAGACAGAAAUUGAA | efyyydyyyyyyyyfyfyyyyyee | 967 |
| 1746644 | 325 | 345 | TUUAAGAUGAGACAGAAAUUGAA | efyydydyyyyyyfyfyyyyyee | 968 |
| 1749974 | 325 | 345 | TUUAAGAUGAGACAGAAAUUGAA | efyyyyyyyyyyyyfyfyyyyyee | 969 |
| 1736400 | 325 | 345 | TUUAAGAUGAGACAGAAAUUGAA | efyyyfyyyyyyyyfyfyyyyyee | 970 |

TABLE 4

Antisense oligonucleotides targeted to human PLN

| Antisense Oligo. Compound No. | SEQ ID NO: 1 Start Site | SEQ ID NO: 1 Stop Site | Antisense Strand Sequence (5' to 3') | Antisense Strand Sugar Motif (5' to 3') | SEQ ID NO |
|---|---|---|---|---|---|
| 1753977 | 516 | 535 | TUAAGTUUUAGUCUUAAUCUUAA | efyyydyyyyyyyyfyfyyyyyee | 971 |
| 1753978 | 516 | 535 | TUAAGUTUUAGUCUUAAUCUUAA | efyydydyyyyyyfyfyyyyyee | 972 |
| 1801600 | 306 | 325 | TAUAAATAGAUUCUGUAGCUUAI | efyydydyyyyyyfyfyyyyyee | 1264 |

TABLE 5

Antisense oligonucleotide targeted to human PLN

| Compound No. | SEQ ID NO: 1 Start Site | SEQ ID NO: 1 Stop Site | Antisense Strand Sequence (5' to 3') | Antisense Strand Sugar Motif (5' to 3') | SEQ ID NO |
|---|---|---|---|---|---|
| 1746645 | 325 | 345 | TUUAAGAUGAGACAGAAAUUGAA | efyydydyyyyyyfyfyyyyyee | 973 |

TABLE 6

Antisense oligonucleotides targeted to human PLN

| Compound No. | SEQ ID NO: 1 Start Site | SEQ ID NO: 1 Stop Site | Antisense Strand Sequence (5' to 3') | Antisense Strand Sugar Motif (5' to 3') | SEQ ID NO |
|---|---|---|---|---|---|
| 1753975 | 306 | 325 | TAUAAAUAGAUUCUGUAGCUUAA | efyyydyyyyyyyyfyfyyyyyee | 974 |
| 1753976 | 306 | 325 | TAUAAATAGAUUCUGUAGCUUAA | efyydydyyyyyyfyfyyyyyee | 975 |
| 1753981 | 306 | 325 | TAUAAAUAGAUUCUGUAGCUUAA | efyyyyyyyyyyyyyfyfyyyyyee | 1254 |

TABLE 7

| | SEQ ID NO: 1 | SEQ ID NO: 1 | | | |
| Compound No. | Start Site | Stop Site | Antisense Strand Sequence (5' to 3') | Antisense Strand Sugar Motif (5' to 3') | SEQ ID NO |
|---|---|---|---|---|---|
| 1736401 | 328 | 345 | TUUAAGAUGAGACAGAAAUAA | efyyyfyyyyyyyfyfyyyee | 976 |

TABLE 8

| | SEQ ID NO: 1 | SEQ ID NO: 1 | | Antisense Strand | SEQ |
| Compound No. | Start Site | Stop Site | Antisense Strand Sequence (5' to 3') | Sugar Motif (5' to 3') | ID NO |
|---|---|---|---|---|---|
| 1805817 | 306 | 325 | TAUAAATAGAUUCUGUAGCUUA | efyydydyyyyyyfyfyyyyye | 1279 |

TABLE 9

| | SEQ ID NO: 1 | SEQ ID NO: 1 | | Antisense Strand | SEQ |
| Compound No. | Start Site | Stop Site | Antisense Strand Sequence (5' to 3') | Sugar Motif (5' to 3') | ID NO |
|---|---|---|---|---|---|
| 1801602 | 305 | 325 | TAUAAATAGAUUCUGUAGCUUI | efyydydyyyyyyfyfyyyyye | 1280 |

Design of Sense Oligonucleotides

The sense oligonucleotide in each case having the nucleobase sequence in Tables 10-15 below is 19-21 nucleosides in length. Each sense oligonucleotide has a sugar motif as designated in the column labeled "Sense Strand Sugar Motif (5' to 3'); wherein each 'y' represents a 2'-OMe sugar moiety, each 'd' represents a 2'-deoxy sugar moiety, each 'e' represents a 2'-MOE sugar moiety, and each 'f' represents a 2'-F sugar moiety; and an internucleoside linkage motif as designated in the column labeled "Sense Strand Internucleoside Linkage (5' to 3')"; wherein each 'o' represents a phosphodiester internucleoside linkage, each 'z' represents a mesyl phosphoramidate internucleoside linkage, and each 's' represents a phosphorothioate internucleoside linkage. Each cytosine residue is non-methylated unless otherwise indicated, 5-methylcytosines are represented in bold underlined italicized font as "C". Each sense oligonucleotide is complementary to an antisense oligonucleotide in one or more of Tables 1-9.

Each sense oligonucleotide in Table 10 is conjugated to a 2-(hydroxymethyl)-6-palmitamidohexyl phosphoryl conjugate group attached to the 3'-OH of the oligonucleotide. Each sense oligonucleotide in Table 11 and in Table 12 is conjugated to a 6-palmitamidohexyl phosphoryl conjugate group attached to the 5'-OH of the oligonucleotide. Each sense oligonucleotide in Table 13 is conjugated to a 6-aminohexyl phosphoryl conjugate group attached to the 5'-OH of the oligonucleotide. Each sense oligonucleotide in Table 14 is conjugated at the 3'-end of the sense oligonucleotide to a bicycle ligand, BCY17901. Each sense oligonucleotide in Table 15 is conjugated at the 5'-end of the sense oligonucleotide to a bicycle ligand, BCY17901.

In Table 10, the structure for the 6-palmitamidohexyl phosphoryl conjugate group attached to the 3'-OH of the oligonucleotide is:

2-(hydroxymethyl)-6-palmitamidohexyl phosphoryl conjugate (3'-C16)

TABLE 10

3'-2-(hydroxymethyl)-6-palmitamidohexyl phosphoryl conjugated sense oligonucleotides

| Compound No. | Sense Oligo. Sequence (5' to 3') | Sense Strand Sugar Motif (5' to 3') | Sense Strand Internucleoside Linkage (5' to 3') | SEQ ID NO |
|---|---|---|---|---|
| 1652825 | AAGCUACAGAAUCUAUUUAUA | yyyyyyfyfffyyyyyyyyyy | ssooooooooooooooooss | 977 |
| 1652841 | CAAUUUCUGUCUCAUCUUAAA | yyyyyyfyfffyyyyyyyyyy | ssooooooooooooooooss | 978 |
| 1691836 | UAAGUAAUUUUUUCAAAGAAA | yyyyyyfyfffyyyyyyyyyy | ssooooooooooooooooss | 979 |
| 1692947 | AAGAUUAAGACUAAAACUUAA | yyyyyyfyfffyyyyyyyyyy | ssooooooooooooooooss | 980 |
| 1692948 | CUGUUGGAUCUUGUAAACAUA | yyyyyyfyfffyyyyyyyyyy | ssooooooooooooooooss | 981 |
| 1692949 | CAAAAUAAGUGUAUAAAAUGA | yyyyyyfyfffyyyyyyyyyy | ssooooooooooooooooss | 982 |
| 1692946 | AAGAGUUUAGUUUUAAAACUA | yyyyyyfyfffyyyyyyyyyy | ssooooooooooooooooss | 983 |
| 1692951 | UCUGAAGAUGAAGAGUUUAGA | yyyyyyfyfffyyyyyyyyyy | ssooooooooooooooooss | 984 |
| 1692953 | AAGAGAAAAUAUAUUUACUAA | yyyyyyfyfffyyyyyyyyyy | ssooooooooooooooooss | 985 |

In Table II and Table 12, the structure for the 6-palmitamidohexyl phosphoryl conjugate group attached to the 5'-OH of the oligonucleotide is:

6-palmitamidohexyl phosphoryl conjugate (5'-C16)

TABLE 11

5' 6-palmitamidohexyl phosphoryl conjugated sense oligonucleotides

| Compound No. | Sense Oligo. Sequence (5' to 3') | Sense Strand Sugar Motif (5' to 3') | Sense Strand Internucleoside Linkage (5' to 3') | SEQ ID NO |
|---|---|---|---|---|
| 1717680 | CAAUUUCUGUCUCAUCUUAAA | yyyyyyfyfffyyyyyyyyyy | ssooooooooooooooooss | 986 |
| 1731395 | CAAUUUCUGUCUCAUCUUAAA | yyyyyyyyyyyyyyyyyyyyy | ssooooooooooooooooss | 987 |
| 1731393 | CAAUUUCUGUCUCAUCUUAAA | yyyyyyyyyffyyyyyyyyyy | ssooooooooooooooooss | 988 |
| 1731392 | CAAUUUCUGUCUCAUCUUAAA | yyyyyyfyfyfyyyyyyyyyy | ssooooooooooooooooss | 989 |
| 1731394 | CAAUUUCUGUCUCAUCUUAAA | yyyyyyyyyffyyyyyyyyyy | ssooooooozozooooooss | 990 |
| 1731396 | CAAUUUCUGUCUCAUCUUAAA | yyyyyyyyyydyyyyyyyyyy | ssooooooooooooooooss | 991 |
| 1736406 | CAAUUUCUGUCUCAUCUUAAA | eeyyyyyfyfffyyyyyyyyee | ssooooooooooooooooss | 992 |
| 1736407 | CAAUUUCUGUCUCAUCUUAAA | eeyyyyyyyyffyyyyyyyyee | ssooooooooooooooooss | 993 |
| 1738167 | CAAUUUCUGUCUCAUCUUAAA | eeyyyyyfyfyfyyyyyyyyee | ssooooooooooooooooss | 994 |
| 1738168 | CAAUUUCUGUCUCAUCUUAAA | eeyyyyyyyyffyyyyyyyyee | ssooooooooooooooooss | 995 |
| 1738169 | CAAUUUCUGUCUCAUCUUAAA | yyyyyyyyyffyyyyyyyyyy | ssooooooooooooooooss | 996 |
| 1736490 | CAAUUUCUGUCUCAUCUUAAA | eeyyyyyfyfffyyyyyyyyee | ssooooooooooooooooss | 997 |
| 1736405 | AUUUCUGUCUCAUCUUAAA | yyyyyyfyfffyyyyyyyy | ssooooooooooooooooss | 998 |

TABLE 11-continued

| | | | Sense Strand | SEQ |
|---|---|---|---|---|
| Compound No. | Sense Oligo. Sequence (5' to 3') | Sense Strand Sugar Motif (5' to 3') | Internucleoside Linkage (5' to 3') | ID NO |
| 1737448 | AUUUCUGUCUCAUCUUAAA | yyyyfyfffyyyyyyyyyy | ssooooooooooooooooss | 999 |
| 1738166 | AUUUCUGUCUCAUCUUAAA | yyyyyyyffyyyyyyyyyy | ssooooooooooooooooss | 1000 |

TABLE 12

5' 6-palmitamidohexyl phosphoryl conjugated sense oligonucleotides

| | | | Sense Strand | |
|---|---|---|---|---|
| Compound No. | Sense Oligo. Sequence (5' to 3') | Sense Strand Sugar Motif (5' to 3') | Internucleoside Linkage (5' to 3') | SEQ ID NO |
| 1750677 | CAAUUUCUGUCUCAUCUUAAA | eeyyyyyyyffyyyyyyyyee | ssooooooooooooooooss | 1256 |
| 1753984 | AAGCUACAGAAUCUAUUUATA | eeyyyyyyyffyyyyyyyyee | ssooooooooooooooooss | 1257 |

In Table 13, the structure for the 6-aminohexyl phosphoryl conjugate group attached to the 5'-OH of the oligonucleotide is:

TABLE 13

5' 6-aminohexyl phosphoryl conjugated sense oligonucleotides

| | | | Sense Strand | |
|---|---|---|---|---|
| Compound No. | Sense Oligo. Sequence (5' to 3') | Sense Strand Sugar Motif (5' to 3') | Internucleoside Linkage (5' to 3') | SEQ ID NO |
| 1738338 | CAAUUUCUGUCUCAUCUUAAA | eeyyyyfyfyfyyyyyyyyee | ssooooooooooooooooss | 1289 |
| 1753982 | AAGCUACAGAAUCUAUUUAUA | eeyyyyfyfyfyyyyyyyyee | ssooooooooooooooooss | 1288 |
| 1750001 | AAGCUACAGAAUCUAUUUATA | eeyyyyyyyffyyyyyyyyee | ssooooooooooooooooss | 1290 |

In Table 14 a bicycle ligand, BCY17901, is conjugated to the 3' end of the sense oligonucleotide via click reaction to a 6-(BCN-carbamate)-2-(hydroxymethyl)hexyl phosphoryl linker. BCY17901 contains the amino acid sequence CP[HyP]DAYLGC[tBuGly]SYCEPW[K(N₃)] (SEQ ID NO: 1253), wherein [HyP] represents trans-4-hydroxy-L-proline, [tBuGly] represents t-butyl-glycine, and [K(N₃)] represents 6-azido lysine. BCY17901 has an N-terminal acetyl modification and a C-terminal amide modification, and each cysteine forms a covalent bond with the molecular scaffold 1,1',1"-(1,3,5-triazinane-1,3,5-triyl)tris(2-bromoethanone) (TATB). The structure for the 3'-BCY17901 conjugate group is (SEQ ID NO: 1292):

BCY17901 6-(BCN-carbamate)-2-(hydroxymethyl)hexyl phosphoryl conjugate (3'-BCY17901)

TABLE 14

Sense oligonucleotides conjugated to BCY17901 at the 3'-end

| Compound No. | Sense Oligo. Sequence (5' to 3') | Sense Strand Sugar Motif (5' to 3') | Sense Strand Internucleoside Linkage (5' to 3') | SEQ ID NO |
|---|---|---|---|---|
| 1696305 | CAAUUUCUGUCUCAUCUUAAA | yyyyyyfyfffyyyyyyyyyyy | ssoooooooooooooooooss | 1001 |
| 1722764 | AAGCUACAGAAUCUAUUUAUA | yyyyyyfyfffyyyyyyyyyyy | ssoooooooooooooooooss | 1002 |
| 1722765 | UAAGUAAUUUUUUCAAAGAAA | yyyyyyfyfffyyyyyyyyyyy | ssoooooooooooooooooss | 1003 |
| 1722767 | AAGAUUAAGACUAAAACUUAA | yyyyyyfyfffyyyyyyyyyyy | ssoooooooooooooooooss | 1004 |
| 1722768 | CUGUUGGAUCUUGUAAACAUA | yyyyyyfyfffyyyyyyyyyyy | ssoooooooooooooooooss | 1005 |
| 1722770 | CAAAAUAAGUGUAUAAAAUGA | yyyyyyfyfffyyyyyyyyyyy | ssoooooooooooooooooss | 1006 |
| 1722771 | AAGAGUUUAGUUUUAAAACUA | yyyyyyfyfffyyyyyyyyyyy | ssoooooooooooooooooss | 1007 |
| 1722773 | UCUGAAGAUGAAGAGUUUAGA | yyyyyyfyfffyyyyyyyyyyy | ssoooooooooooooooooss | 1008 |
| 1722774 | AAGAGAAAAUAUAUUUACUAA | yyyyyyfyfffyyyyyyyyyyy | ssoooooooooooooooooss | 1009 |

In Table 15 a bicycle ligand, BCY17901, is conjugated at the 5'-end of the sense oligonucleotide via click reaction to a 6-(BCN-carbamate)hexyl phosphoryl linker. BCY17901 contains the amino acid sequence CP[HyP]DAYLGC[tBu-Gly]SYCEPW[K(N₃)] (SEQ ID NO: 1253), wherein [HyP] represents trans-4-hydroxy-L-proline, [tBuGly] represents t-butyl-glycine, and [K(N₃)] represents 6-azido lysine. BCY17901 has an N-terminal acetyl modification and a C-terminal amide modification, and each cysteine forms a covalent bond with the molecular scaffold 1,1',1''-(1,3,5-triazinane-1,3,5-triyl)tris(2-bromoethanone) (TATB). The structure for the 5'-BCY17901 conjugate group is (SEQ ID NO: 1291):

BCY17901 6-(BCN-carbamate) hexyl phosphoryl conjugate (5′-BCY17901)

TABLE 15

Sense oligonucleotides conjugated to BCY17901 at the 5'-end

| Compound No. | Sense Oligo. Sequence (5' to 3') | Sense Strand Sugar Motif (5' to 3') | Sense Strand Internucleoside Linkage (5' to 3') | SEQ ID NO |
|---|---|---|---|---|
| 1719928 | CAAUUUCUGUCUCAUCUUAAA | yyyyyyfyfffyyyyyyyyyy | ssooooooooooooooooss | 1010 |
| 1757454 | CAAUUUCUGUCUCAUCUUAAA | eeyyyyyyyyffyyyyyyyyee | ssooooooooooooooooss | 1011 |
| 1753740 | CAAUUUCUGUCUCAUCUUAAA | eeyyyyyfyfyfyyyyyyyyee | ssooooooooooooooooss | 1012 |
| 1757456 | AAGCUACAGAAUCUAUUUATA | eeyyyyyyyyffyyyyyyyyee | ssooooooooooooooooss | 1013 |
| 1757458 | AAGCUACAGAAUCUAUUUAUA | eeyyyyyfyfyfyyyyyyyyee | ssooooooooooooooooss | 1014 |
| 1757460 | AAGAUUAAGACUAAAACUUAA | eeyyyyyyyyffyyyyyyyyee | ssooooooooooooooooss | 1015 |
| 1757462 | AAGAUUAAGACUAAAACUUAA | eeyyyyyfyfyfyyyyyyyyee | ssooooooooooooooooss | 1016 |

Oligomeric duplexes conjugated to BCY17901 at the end of a sense modified oligonucleotide were prepared following the scheme and general procedures. BCY17901 was synthesized as described in International Patent Application Publication No. WO2022/101633, and International Patent Application Publication No. WO2023/056388.

-continued

5′-BCN Sense Oligonucleotide

5′ Unconjugated Sense Oligonucleotide

3′ Unconjugated Sense Oligonucleotide

BCN-NHS ester

715

-continued

3'-BCN Sense Oligonucleotide

Sense oligonucleotide with a 6-aminohexyl linker attached via a phosphoryl group at the 5' end were synthesized following standard procedure. 25-30 mg, 2.5-3.0 μmol, 1 equiv, sense oligonucleotide was dissolved in 300 μL of 0.1 M borax buffer pH 8.5. BCN-NHS ester (3 equiv.) dissolved in DMF (300 μL) was added to the sense oligonucleotide solution, and the reaction mixture stirred at room temperature. Reaction completion was confirmed after 30-60 min by LCMS. Crude reaction mixtures were purified by strong anion exchange (SAX) HPLC, using a gradient of mobile phase A (100 mM NH$_4$OAc in 3:7 ACN:H$_2$O) and mobile phase B (100 mM NH$_4$OAc, 1.5 M NaBr in 3:7 ACN:H$_2$O). After purification, oligonucleotides were desalted by RP HPLC on a 5g Sep-Pak C18 cartridge, loaded and washed with 1.0 M NaCl, then eluted in 1:1 ACN: H$_2$O. Desalted fractions were lyophilized to yield BCN-conjugated sense oligonucleotide.

5'-BCN Sense Oligonucleotide

BCY17901
SPAAC

5'-BCY17901 Conjugated Sense Oligonucleotide

3'-BCN Sense Oligonucleotide

BCY17901
SPAAC

-continued

3'-BCY17901 Conjugated Sense Oligonucleotide

BCY17901 was conjugated to BCN-sense oligonucleotide using a strain-promoted azide-alkyne click (SPAAC) reaction. BCY17901 (1.5 equiv.) dissolved in DMF (300 µL) was added to a solution of BCN-sense oligonucleotide (~20 mg, 2.5-3.0 µmol, 1 equiv.) dissolved in H₂O (1 mL), stirred at room temperature overnight, and conjugation was confirmed by LCMS. Crude reaction mixtures were purified by SAX HPLC, using a gradient of mobile phase A and mobile phase B (described above). After purification, oligonucleotides were desalted by RP HPLC on a 5g Sep-Pak C18 cartridge. Desalted fractions were lyophilized to yield 5' BCY17901-conjugated sense oligonucleotide.

For synthesis of 3' BCY-conjugated sense oligonucleotide, procedure described above was followed, with the following modification: unconjugated sense oligonucleotide starting material has a 2-(hydroxymethyl)-6-aminohexyl phosphoryl group conjugated to the 3'-OH.

Solutions of individual sense and antisense oligonucleotides were prepared at 2× concentration in Dulbecco's Phosphate Buffered Saline (DPBS, no calcium, no magnesium) and filtered through 0.22 µm filters. The 5'-BCY17901 conjugated sense oligonucleotide and antisense oligonucleotide were mixed 1:1 (v:v) and incubated at room temperature for 1-2 hours to give the final 1× concentration of oligomeric duplex in DPBS. Duplex formation was verified by size-exclusion chromatography (SEC) and masses verified by HPLC-MS. Annealed 5'-BCY17901 conjugated modified oligomeric duplexes were stored at 4° C.

Design of Oligomeric Duplexes

Oligomeric duplex compounds prepared with antisense oligonucleotide compound numbers and corresponding sense oligonucleotide compound numbers are listed in Table 16.

TABLE 16

Oligomeric duplexes targeted to human PLN

| Compound Number | Antisense Compound No. | Sense Compound No. |
|---|---|---|
| 1700644 | 1652826 | 1696305 |
| 1722807 | 1652826 | 1719928 |
| 1726638 | 1652709 | 1722764 |
| 1726639 | 1691449 | 1722765 |
| 1726640 | 1691837 | 1722767 |
| 1726641 | 1692941 | 1722768 |
| 1726645 | 1692943 | 1722770 |

TABLE 16-continued

Oligomeric duplexes targeted to human PLN

| Compound Number | Antisense Compound No. | Sense Compound No. |
|---|---|---|
| 1726646 | 1692945 | 1722771 |
| 1726647 | 1692950 | 1722773 |
| 1726648 | 1692952 | 1722774 |
| 1669056 | 1652709 | 1652825 |
| 1669057 | 1652826 | 1652841 |
| 1703266 | 1691449 | 1691836 |
| 1703330 | 1691837 | 1692947 |
| 1703395 | 1692941 | 1692948 |
| 1703527 | 1692943 | 1692949 |
| 1703530 | 1692945 | 1692946 |
| 1703608 | 1692950 | 1692951 |
| 1703668 | 1692952 | 1692953 |
| 1722804 | 1652826 | 1717680 |
| 1735533 | 1731386 | 1717680 |
| 1735536 | 1731388 | 1717680 |
| 1735539 | 1731387 | 1717680 |
| 1735542 | 1731389 | 1717680 |
| 1735545 | 1731390 | 1717680 |
| 1735551 | 1731397 | 1717680 |
| 1735554 | 1652826 | 1731395 |
| 1735557 | 1652826 | 1731393 |
| 1735560 | 1652826 | 1731392 |
| 1735563 | 1652826 | 1731394 |
| 1735566 | 1652826 | 1731396 |
| 1735569 | 1731387 | 1731393 |
| 1735572 | 1731388 | 1731393 |
| 1735575 | 1731389 | 1731393 |
| 1735578 | 1731390 | 1731393 |
| 1735581 | 1731387 | 1731392 |
| 1735584 | 1731387 | 1731394 |
| 1735587 | 1731387 | 1731396 |
| 1735590 | 1731387 | 1731395 |
| 1739642 | 1736400 | 1717680 |
| 1739646 | 1736401 | 1736405 |
| 1739649 | 1736401 | 1737448 |
| 1739652 | 1736401 | 1738166 |
| 1739655 | 1736402 | 1717680 |
| 1739658 | 1736403 | 1717680 |
| 1739661 | 1736404 | 1717680 |
| 1739664 | 1738170 | 1717680 |
| 1739667 | 1738171 | 1717680 |
| 1739670 | 1738172 | 1717680 |
| 1739673 | 1738173 | 1717680 |
| 1739676 | 1738174 | 1717680 |
| 1739679 | 1652826 | 1736406 |
| 1739682 | 1652826 | 1736407 |
| 1739685 | 1652826 | 1738167 |
| 1739688 | 1652826 | 1738168 |
| 1739691 | 1652826 | 1738169 |

TABLE 16-continued

| Oligomeric duplexes targeted to human PLN | | |
|---|---|---|
| Compound Number | Antisense Compound No. | Sense Compound No. |
| 1739694 | 1736404 | 1736407 |
| 1739697 | 1738172 | 1736407 |
| 1739700 | 1738171 | 1736407 |
| 1750177 | 1736400 | 1736406 |
| 1750180 | 1749976 | 1717680 |
| 1750207 | 1749977 | 1717680 |
| 1750213 | 1744533 | 1717680 |
| 1750219 | 1744534 | 1717680 |
| 1750225 | 1746643 | 1717680 |
| 1750231 | 1746644 | 1717680 |
| 1750237 | 1746645 | 1717680 |
| 1750243 | 1749974 | 1717680 |
| 1750248 | 1749975 | 1717680 |
| 1750254 | 1749974 | 1736407 |
| 1750259 | 1749974 | 1738168 |
| 1750268 | 1749974 | 1738167 |
| 1750274 | 1746643 | 1736407 |
| 1750280 | 1746643 | 1736490 |
| 1750292 | 1746644 | 1736407 |
| 1750301 | 1736402 | 1736407 |
| 1750355 | 1652826 | 1736490 |
| 1750676 | 1749977 | 1738167 |
| 1750683 | 1738170 | 1736407 |
| 1755748 | 1746643 | 1750677 |
| 1755751 | 1746644 | 1738167 |
| 1755757 | 1753975 | 1753984 |
| 1755763 | 1753981 | 1753984 |
| 1757465 | 1746643 | 1757454 |
| 1757468 | 1746644 | 1753740 |
| 1757471 | 1753975 | 1757456 |
| 1757474 | 1753976 | 1757458 |
| 1757477 | 1753977 | 1757460 |
| 1757480 | 1753978 | 1757462 |
| 1779744 | 1753981 | 1757456 |
| 1758638 | 1753976 | 1753982 |
| 1809053 | 1801600 | 1757458 |
| 1809061 | 1801601 | 1757458 |
| 1809071 | 1805817 | 1753982 |
| 1809072 | 1801601 | 1753982 |
| 1809073 | 1801600 | 1753982 |

TABLE 16-continued

| Oligomeric duplexes targeted to human PLN | | |
|---|---|---|
| Compound Number | Antisense Compound No. | Sense Compound No. |
| 1809074 | 1801602 | 1753982 |
| 1758632 | 1746644 | 1738338 |
| 1779726 | 1753981 | 1750001 |

Example 2: Design of Modified Oligonucleotides Targeted to Human PLN

Modified oligonucleotides complementary to a human PLN RNA were designed as described in Tables 17-18. "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence. Each antisense oligonucleotide is 100% complementary to SEQ ID NO: 2 (GENBANK Accession No. (NC_000006.12 truncated from nucleosides 118545001 to 118565000).

The modified oligonucleotides in Tables 17-18 are 16 nucleosides in length, wherein the sugar motifs for the modified oligonucleotides are as designated in the column labeled "Sugar Motif (5' to 3')"; wherein each 'e' represents a 2'-MOE sugar moiety, each 'k' represents a cEt sugar moiety, and each 'd' represents a 2'-deoxy sugar moiety. The internucleoside linkage motifs for the modified oligonucleotides are presented in the column labeled "Internucleoside Linkage (5' to 3')", wherein each 's' represents a phosphorothioate internucleoside linkage, and each 'o' represents a phosphodiester internucleoside linkage. Each cytosine residue is a 5-methylcytosine.

Each modified oligonucleotide in Table 17 is conjugated to a 6-palmitamidohexyl phosphoryl conjugate group attached to the 5'-OH of the oligonucleotide. The structure for the conjugate group 5'-C16 is depicted in Example 1.

TABLE 17

| 5' 6-palmitamidohexyl conjugated modified oligonucleotides targeted to human PLN | | | | | | |
|---|---|---|---|---|---|---|
| Compound No. | SEQ ID No: 2 Start Site | SEQ ID No: 2 Stop Site | Sequence (5' to 3') | Sugar Motif (5' to 3') | Internucleoside Linkage (5' to 3') | SEQ ID NO |
| 1558169 | 5499 | 5514 | ACGAGTATATTAGG AA | kkddddddddddkekek | sossssssssssooos | 1017 |

Each modified oligonucleotide in Table 18 is conjugated at the 5'-end to a bicycle ligand, BCY17901, via click reaction to a 6-(BCN-carbamate)hexyl phosphoryl linker. BCY17901 contains the amino acid sequence CP[HyP] DAYLGC[tBuGly]SYCEPW[K(N₃)] (SEQ ID NO: 1253), wherein [HyP] represents trans-4-hydroxy-L-proline, [tBuGly] represents t-butyl-glycine, and [K(N₃)] represents 6-azido lysine. BCY17901 has an N-terminal acetyl modification and a C-terminal amide modification, and each cysteine forms a covalent bond with the molecular scaffold 1,1',1"-(1,3,5-triazinane-1,3,5-triyl)tris(2-bromoethanone) (TATB). The structure for the BCY17901 conjugate group, 5'-BCY17901, is depicted in Example 1.

TABLE 18

| | | | | | | |
|---|---|---|---|---|---|---|
| BCY17901 conjugated modified oligonucleotides targeted to human PLN | | | | | | |
| Compound No. | SEQ ID No: 2 Start Site | SEQ ID No: 2 Stop Site | Sequence (5' to 3') | Sugar Motif (5' to 3') | Internucleoside Linkage (5' to 3') | SEQ ID NO |
| 1696302 | 5499 | 5514 | ACGAGTATATTAGGAA | kkddddddddddkekek | sossssssssssooos | 1018 |

Example 3: Design of Modified Oligonucleotides Targeted to Mouse PLN RNA

Modified oligonucleotides complementary to a mouse PLN RNA were designed as described in Tables 19-21. "Start site" indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence. Each antisense oligonucleotide listed is 100% complementary to SEQ ID NO: 1052 (GENBANK Accession No. (NC_000076.6 truncated from nucleosides 53335001 to 53349000).

The modified oligonucleotides in Tables 19-21 are 16 nucleosides in length, wherein the sugar motifs for the modified oligonucleotide are as designated in the column labeled "Sugar Motif (5' to 3')"; wherein each 'e' represents a 2'-MOE sugar moiety, each 'k' represents a cEt sugar moiety, and each 'd' represents a 2'-deoxy sugar moiety. The internucleoside linkage motifs for the modified oligonucleotide are presented in the column labeled "Internucleoside Linkage (5' to 3')", wherein each 's' represents a phosphorothioate internucleoside linkage, and each 'o' represents a phosphodiester internucleoside linkage. Each cytosine residue is a 5-methylcytosine.

TABLE 19

| | | | | | | |
|---|---|---|---|---|---|---|
| Modified oligonucleotide targeted to mouse PLN | | | | | | |
| Compound No. | SEQ ID No: 1052 Start Site | SEQ ID No: 1052 Stop Site | Sequence (5' to 3') | Sugar Motif (5' to 3') | Internucleoside Linkage (5' to 3') | SEQ ID NO |
| 1639304 | 3812 | 3827 | TGAGAATTGTAGAGGT | kkkddddddddddkkke | ssssssssssssssss | 1019 |

Each modified oligonucleotide in Table 20 is conjugated to a 6-palmitamidohexyl phosphoryl conjugate group attached to the 5'-OH of the oligonucleotide. The structure for the conjugate group 5'-C16 is depicted in Example 1.

TABLE 20

| | | | | | | |
|---|---|---|---|---|---|---|
| 5' 6-palmitamidohexyl conjugated modified oligonucleotides targeted to mouse PLN | | | | | | |
| Compound No. | SEQ ID No: 1052 Start Site | SEQ ID No: 1052 Stop Site | Sequence (5' to 3') | Sugar Motif (5' to 3') | Internucleoside Linkage (5' to 3') | SEQ ID NO |
| 1604918 | 3812 | 3827 | TGAGAATTGTAGAGGT | kkkddddddddddkkke | ssssssssssssssss | 1020 |
| 1653557 | 3812 | 3827 | TGAGAATTGTAGAGGT | kkkddddddddddkkke | ooossssssssssooos | 1021 |

Each modified oligonucleotide in Table 21 is conjugated at the 5'-end to a bicycle ligand, BCY17901, via click reaction to a 6-(BCN-carbamate)hexyl phosphoryl linker. BCY17901 contains the amino acid sequence CP[HyP] DAYLGC[tBuGly]SYCEPW[K(N$_3$)] (SEQ ID NO: 1045), wherein [HyP] represents trans-4-hydroxy-L-proline, [tBuGly] represents t-butyl-glycine, and [K(N$_3$)] represents 6-azido lysine. BCY17901 has an N-terminal acetyl modification and a C-terminal amide modification, and each cysteine forms a covalent bond with the molecular scaffold 1,1',1"-(1,3,5-triazinane-1,3,5-triyl)tris(2-bromoethanone) (TATB). The structure for the BCY17901 conjugate group, 5'-BCY17901, is depicted in Example 1.

TABLE 21

BCY17901 conjugated modified oligonucleotides targeted to mouse PLN

| Compound No. | SEQ ID No: 1052 Start Site | SEQ ID No: 1052 Stop Site | Sequence (5' to 3') | Sugar Motif (5' to 3') | Internucleoside Linkage (5' to 3') | SEQ ID NO |
|---|---|---|---|---|---|---|
| 1683006 | 3812 | 3827 | TGAGAATTGTAGAGGT | kkkddddddddddkkke | sssssssssssssss | 1022 |
| 1683007 | 3812 | 3827 | TGAGAATTGTAGAGGT | kkkddddddddddkkke | ooossssssssssoos | 1023 |

Example 4: Potency of 5'-C16 or 5'-BCY17901 Conjugated Oligonucleotides Targeting Mouse PLN hTfR$^{+/-}$ knock-in mice were used to determine effects of modified oligonucleotides on mouse PLN, hTfR$^{+/-}$ knock-in mice were divided into groups of 3 mice each. Each mouse received intravenous injections of modified oligonucleotide once a week for three weeks for a total of 3 treatments (on Days 1, 6, and 13) at various doses. One group of 4 mice received intravenous injections of PBS once a week for three weeks (a total of 3 treatments). One group of 3 mice remained untreated (Naïve). PBS-injected group and non-treated naïve group served as control groups to which oligonucleotide-treated groups were compared.

Eight days post final treatment (Day 21), mice were sacrificed and RNA was extracted from mouse heart for real-time RTPCR analysis of PLN RNA expression. Mouse PLN primer probe set RTS37645 (forward sequence TCTGCTCTCTCTAGGGTTTGA, designated herein as SEQ ID NO: 1053; reverse sequence GGAGATACAT-GAGAGCGACAAG, designated herein as SEQ ID NO: 1054; probe sequence ACAGCCAACACAGCAA-GATGTTCC, designated herein as SEQ ID NO: 1055) was used to measure mouse PLN RNA levels. PLN RNA levels were normalized to total RNA content, as measured by RIBOGREENR. Results are presented as percent PLN RNA, relative to amount of PLN in a combination of the PBS treated animals and non-treated naïve animals (% control). Half maximal effective dose (ED50) of each modi-fied oligonucleotide was calculated using GraphPad Prism 7 software (GraphPad Software, San Diego, CA).

TABLE 22

Reduction of mouse PLN RNA

| Compound No. | Conjugate | Dose (mg/kg) | PLN RNA (% control) Heart | ED50 (mg/kg) |
|---|---|---|---|---|
| PBS + Naïve | — | — | 100 | — |
| 1604918 | 5'-C16 | 5.7 | 54 | 6.44 |
| | | 17.2 | 23 | |
| | | 51.7 | 7 | |
| 1639304 | None | 16.7 | 85 | 74.65 |
| | | 50.1 | 58 | |
| | | 150.3 | 34 | |
| 1653557 | 5'-C16 | 5.7 | 57 | 6.94 |
| | | 17.2 | 20 | |
| | | 51.7 | 4 | |
| 1683006 | 5'-BCY17901 | 5.8 | 60 | 33.05 |
| | | 17.5 | 64 | |
| | | 52.5 | 42 | |

TABLE 22-continued

Reduction of mouse PLN RNA

| Compound No. | Conjugate | Dose (mg/kg) | PLN RNA (% control) Heart | ED50 (mg/kg) |
|---|---|---|---|---|
| 1683007 | 5'-BCY17901 | 5.8 | 52 | 8.81 |
| | | 17.5 | 46 | |
| | | 52.5 | 36 | |

As shown in Table 22, modified oligonucleotide was more potent in decreasing the level of PLN RNA in hearts of transgenic mice when conjugated to a 6-palmitamidohexyl phosphoryl group (Compound Nos 1604918 and 1653557) or a human transferrin receptor 1-binding peptide, BCY17901 (Compound Nos 1683006 and 1683007) as compared to potency of unconjugated oligonucleotide (Compound No 1639304).

Example 5: Activity of Conjugated Oligomeric Duplexes Targeting Human PLN hPLN$^{tg/+}$ heterozygous mice were used to determine effects of 3'-C16-conjugated oligomeric duplexes on human PLN, hTfR$^{tg/+}$/hPLN$^{tg/tg}$ knock-in mice, generated by cross-ing hTfR$^{tg/+}$ and hPLN$^{tg/tg}$, were used to determine effects of 3'-BCY17901-conjugated oligomeric duplexes on human PLN. The antisense strand sugar motif (5' to 3') for all compounds in Table 23 is efyyyfyyyyyyyfyfyyyyyyy and the sense strand sugar motif (5' to 3') for all compounds in Table 23 is yyyyyyfyfffyyyyyyyyy. Transgenic mice (hPLN$^{tg/+}$ or hTfR$^{tg/+}$/hPLN$^{tg/tg}$ knock-in) were divided into groups of 3-4 mice each. Each mouse received a single subcutaneous injection of oligomeric duplex. C16-conju-gated oligomeric duplexes were administered at a dose of 50 mg/kg; and BCY17901-conjugated oligomeric duplexes were administered at a dose of 5 mg/kg. One group of 3-4 mice (for each strain) received a single subcutaneous injec-tion of PBS. PBS-injected group served as the control group to which duplex-treated groups were compared. Seven (7) days post final treatment, mice were sacrificed and RNA extracted from mouse heart for real-time RTPCR analysis of PLN RNA expression. Human PLN primer probe set ABI53044 (forward sequence CACCCGTAAGACTT-CATACAACACA, designated herein as SEQ ID NO: 1056; reverse sequence TGGCAGCCAAATATGAGATAACTGT, designated herein as SEQ ID NO: 1057: probe sequence TGCCAAGGCTACCTAA, designated herein as SEQ ID NO: 1058) was used to measure human PLN RNA levels. PLN RNA levels were normalized to total RNA content, as measured by RIBOGREEN®. Results are presented as per-cent human PLN RNA, relative to amount of human PLN RNA in corresponding PBS treated animals (% control), n/d refers to datapoints that were not determined.

TABLE 23

| Compound No. | Conjugate | Nucleobase Sequence of Antisense Strand (5' to 3') and Sense Strand (5' to 3') | SEQ ID NO: Antisense and Sense | Single Dose (mg/kg) | PLN RNA (% control) Heart |
|---|---|---|---|---|---|
| PBS | | | | | 100 |
| 1669057 | 3'-C16 | TUUAAGAUGAGACAGAAAUUGAU CAAUUUCUGUCUCAUCUUAAA | 939 978 | 50 | 38 |
| 1700644 | BCY17901 | TUUAAGAUGAGACAGAAAUUGAU CAAUUUCUGUCUCAUCUUAAA | 939 1001 | 5 | 64 |
| 1703266 | 3'-C16 | TUUCUUUGAAAAAAUUACUUAAA UAAGUAAUUUUUUCAAAGAAA | 941 979 | 50 | 91 |
| 1726639 | BCY17901 | TUUCUUUGAAAAAAUUACUUAAA UAAGUAAUUUUUUCAAAGAAA | 941 1003 | 5 | 89 |
| 1703330 | 3'-C16 | TUAAGUUUUAGUCUUAAUCUUGA AAGAUUAAGACUAAAACUUAA | 942 980 | 50 | 48 |
| 1726640 | BCY17901 | TUAAGUUUUAGUCUUAAUCUUGA AAGAUUAAGACUAAAACUUAA | 942 1004 | 5 | 37 |
| 1703395 | 3'-C16 | TAUGUUUACAAGAUCCAACAGAU CUGUUGGAUCUUGUAAACAUA | 943 981 | 50 | 48 |
| 1726641 | BCY17901 | TAUGUUUACAAGAUCCAACAGAU CUGUUGGAUCUUGUAAACAUA | 943 1005 | 5 | 47 |
| 1703527 | 3'-C16 | TCAUUUUAUACACUUAUUUUGAA CAAAAUAAGUGUAUAAAAUGA | 944 982 | 50 | 52 |
| 1726645 | BCY17901 | TCAUUUUAUACACUUAUUUUGAA CAAAAUAAGUGUAUAAAAUGA | 944 1006 | 5 | 46 |
| 1703530 | 3'-C16 | TAGUUUUAAAACUAAACUCUUCA AAGAGUUUAGUUUUAAAACUA | 945 983 | 50 | 89 |
| 1726646 | BCY17901 | TAGUUUUAAAACUAAACUCUUCA AAGAGUUUAGUUUUAAAACUA | 945 1007 | 5 | 85 |
| 1703608 | 3'-C16 | TCUAAACUCUUCAUCUUCAGAAA UCUGAAGAUGAAGAGUUUAGA | 946 984 | 50 | 70 |
| 1726647 | BCY17901 | TCUAAACUCUUCAUCUUCAGAAA UCUGAAGAUGAAGAGUUUAGA | 946 1008 | 5 | 78 |
| 1703668 | 3'-C16 | TUAGUAAAUAUAUUUUCUCUUUC AAGAGAAAAUAUAUUUACUAA | 947 985 | 50 | 49 |
| 1726648 | BCY17901 | TUAGUAAAUAUAUUUUCUCUUUC AAGAGAAAAUAUAUUUACUAA | 947 1009 | 5 | 55 |
| 1669056 | 3'-C16 | TAUAAAUAGAUUCUGUAGCUUUU AAGCUACAGAAUCUAUUUAUA | 940 977 | 50 | n/d |
| 1726638 | BCY17901 | TAUAAAUAGAUUCUGUAGCUUUU AAGCUACAGAAUCUAUUUAUA | 940 1002 | 5 | 34 |

As shown in Table 23, oligomeric duplexes conjugated to a bicycle ligand (BCY17901) were more potent in decreasing human PLN RNA levels in knock-in mouse heart than the same oligomeric duplexes conjugated to a 2-(hydroxymethyl)-6-palmitamidohexyl phosphoryl group, while rank trometry carried out on heart tissue extracted from treated animals. In cases where $ED_{50}/EC_{50}$ could not be reliably calculated, the values are presented as Not Defined (N.D).

Figure 1B:
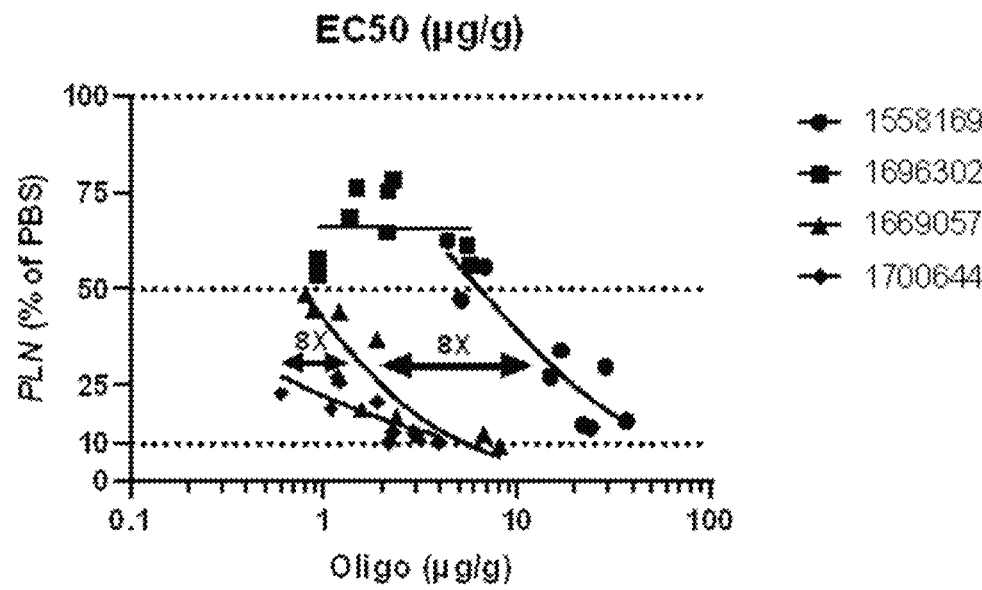

The data is also presented in graphical format in FIGS. 1A and 1B.

TABLE 24

| Potency of conjugated modified oligonucleotides and oligomeric duplex compounds | | | | | | |
|---|---|---|---|---|---|---|
| Compound | | Route of | Dose | | PLN RNA (% control) | |
| No. | Conjugate | Administration | (mg/kg) | Heart | ED50 (mg/kg) | EC50 (µg/kg) |
| PBS | — | IV | — | 100 | — | — |
| 1558169 | 5'-C16-ASO | IV | 3.3 | 55 | 4.13 | 6.43 |
| | | | 10 | 30 | | |
| | | | 30 | 15 | | |
| 1669057 | 3'-C16-duplex | IV | 3.3 | 46 | 2.69 | 0.75 |
| | | | 10 | 18‡ | | |
| | | | 30 | 11 | | |
| 1696302 | 5'-BCY17901-ASO | IV | 3.3 | 60 | N.D. | N.D. |
| | | | 10 | 72 | | |
| | | | 30 | 66 | | |
| 1700644 | 3'-BCY17901-duplex | IV | 3.3 | 25 | 0.25 | 0.10 |
| | | | 10 | 17 | | |
| | | | 30 | 12 | | |

‡Fewer than 3 samples were available order of potency of duplexes conjugated to BCY17901 was the same as the rank order of potency of duplexes conjugated to a 2-(hydroxymethyl)-6-palmitamidohexyl phosphoryl group.

Example 6: Potency of 5'-C16, 3'-C16, 5'-BCY17901, or 3'-BCY17901 Conjugated Modified Oligonucleotides and Oligomeric Duplex Compounds Targeting Human PLN $hTfR^{tg/+}/hPLN^{tg/+}$ mice, generated by crossing $hTfR^{tg/+}$ and $hPLN^{tg/+}$, were used to determine effects of modified oligonucleotides and oligomeric duplexes on human PLN, $hTfR^{tg/+}/hPLN^{tg/+}$ mice were divided into groups of 3 mice each. Each mouse received either intravenous (IV) injections of oligomeric duplex compounds or modified oligonucleotides on Days 1, 8, and 15 (a total of 3 treatments) at various doses as indicated. One group of 4 mice received IV injections of PBS as indicated. PBS-injected groups served as the control groups to which oligonucleotide-treated groups were compared. Seven days post final treatment (Day 22), mice were sacrificed and RNA extracted from mouse heart for real-time RTPCR analysis of PLN RNA expression. Human PLN primer probe set ABI53044 (described in Example 5) was used to measure human PLN RNA levels. PLN RNA levels were normalized to total RNA content, as measured by RIBOGREEN®. Results are presented as percent PLN RNA, relative to the amount of PLN in PBS treated animals (% control). Half maximal effective dose ($ED_{50}$) and the half maximal effective concentration ($EC_{50}$) of each modified oligonucleotide or oligomeric duplex was calculated using GraphPad Prism 7 software (GraphPad Software, San Diego, CA). $ED_{50}$ values are presented in mg/kg. $EC_{50}$ values are presented in µg/g and calculated based on concentration of the antisense oligonucleotide (either modified oligonucleotide or the antisense oligonucleotide of the oligomeric duplex) as measured by mass spec- $hTfR^{tg/+}/hPLN^{tg/+}$ mice, generated by crossing $hTfR^{tg/+}$ and $hPLN^{tg/+}$, were used to determine effects of oligomeric duplexes on human PLN, $hTfR^{tg/+}/hPLN^{tg/+}$ mice were divided into groups of 3 mice each. Each mouse received either intravenous (IV) or subcutaneous (SC) injections of conjugated duplex compound on Days 1, 8, 15 (a total of 3 treatments) at various doses as indicated. Groups of 2 mice received either IV or SC injections of PBS. PBS-injected groups served as the control groups to which compound-treated groups were compared. Seven days post final treatment (Day 22) mice were sacrificed and RNA extracted from mouse heart for real-time RTPCR analysis of PLN RNA expression. Human PLN primer probe set ABI53044 (described in Example 5) was used to measure human PLN RNA levels. PLN RNA levels were normalized to total RNA content, as measured by RIBOGREENR. Levels of PLN RNA in hearts of PBS-treated mice administered by IV and SC routes were averaged for comparison to compound treated group. Results are presented as percent PLN RNA, relative to the amount of PLN in PBS treated animals (% control). Half maximal effective dose (ED50) of each oligomeric duplex was calculated using GraphPad Prism 7 software (GraphPad Software, San Diego, CA).

TABLE 25

| Potency of BCY17901 conjugated oligomeric duplex compounds | | | | | |
|---|---|---|---|---|---|
| | | Route of | | PLN RNA (% control) | |
| Compound No. | Conjugate | Administration | Dose (mg/kg) | Heart | ED50 (mg/kg) |
| PBS | — | IV or SC | — | 100 | — |
| 1700644 | 3'-BCY17901 | IV | 0.1 | 84 | 1.04 |
| | | | 0.3 | 70 | |
| | | | 1.0 | 53 | |
| | | | 3.0 | 30 | |
| 1700644 | 3'-BCY17901 | SC | 0.1 | 84 | 0.94 |
| | | | 0.3 | 65 | |
| | | | 1.0 | 60 | |
| | | | 3.0 | 20 | |

$hTfR^{tg/+}/hPLN^{tg/tg}$ mice, generated by crossing $hTfR^{tg/+}$ and $hPLN^{tg/tg}$, were used to determine effects of a modified oligonucleotide and an oligomeric duplex on human PLN, hTfR$^{tg/+}$/hPLN$^{tg/tg}$ mice were divided into groups of 3 mice each. Each mouse received subcutaneous (SC) injections of conjugated oligomeric duplex compound or conjugated modified oligonucleotide on Days 1, 7, and 11 (a total of 3 treatments) at various doses as indicated. One group of 4 mice received SC injections of PBS as indicated. PBS-injected groups served as the control groups to which compound-treated groups were compared. Five days post final treatment (Day 16) mice were sacrificed and RNA extracted from mouse heart for real-time RTPCR analysis of PLN RNA expression. Human PLN primer probe set ABI53044 (described in Example 5) was used to measure human PLN RNA levels. PLN RNA levels were normalized to total RNA content, as measured by RIBOGREENR. Results are presented as percent PLN RNA, relative to the amount of PLN in PBS treated animals (% control). Half maximal effective dose (ED50) of each compound was calculated using GraphPad Prism 7 software (GraphPad Software, San Diego, CA).

TABLE 26

Potency of C16 conjugated modified oligonucleotides and oligomeric duplex compounds

| Compound No. | Conjugate | Route of Administration | Dose (mg/kg) | PLN RNA (% control) Heart | ED50 (mg/kg) |
|---|---|---|---|---|---|
| PBS | — | SC | — | 100 | — |
| 1558169 | 5'-C16 ASO | SC | 2.7 | 100 | 18.82 |
| | | | 8.0 | 71 | |
| | | | 24.0 | 44 | |
| 1669057 | 3'-C16 duplex | SC | 2.7 | 57 | 3.56 |
| | | | 8.0 | 29 | |
| | | | 24.0 | 11 | |

Results of intravenous and subcutaneous administration of oligonucleotide or oligomeric duplex compounds targeting human PLN RNA shown in Tables 24, 25 and 26 demonstrated both routes of administration yield similar potencies for BCY17901-conjugated oligomeric duplex (Compound No. 1700644) in decreasing hPLN RNA in knock-in mouse heart. Similarly, C16-conjugated oligomeric duplex (Compound No. 1669057) yielded similar potency in decreasing hPLN RNA in knock-in mouse heart when delivered intravenously or subcutaneously. C16-conjugated antisense oligonucleotide (Compound No. 1558169) was more potent in decreasing the amount of hPLN RNA in the mouse heart when administered intravenously as compared to subcutaneous administration.

As shown in Tables 24-26 and FIG. 1, ED50 for a BCY17901-conjugated oligomeric duplex (Compound No. 1700644) was about 2.7-fold lower than the ED50 for a corresponding C16-conjugated oligomeric duplex compound (Compound No. 1669057) and about 4-fold lower than that of a modified antisense oligonucleotide (ASO) conjugated to a C16 group (Compound No. 1558169): estimated EC50 for the antisense strand of the BCY17901-conjugated oligomeric duplex compound (Compound No. 1700644) was about 8-fold lower than the EC50 for the antisense strand of the corresponding C16-conjugated oligomeric duplex compound (Compound No. 1669057) and about 64-fold lower than the EC50 for a modified antisense oligonucleotide (ASO) conjugated to a C16 (Compound No. 1558169). Because of the potency of the BCY17901-conjugated oligomeric duplex (Compound No. 1700644), the four-point dose response shown in Table 25 yielding estimated ED50 1.04 mg/kg was used as a more accurate estimator, and data was also used to estimate EC50 in Table 24. Notably, BCY17901-conjugated antisense oligonucleotide (compound 1696302) failed to demonstrate dose dependent reduction in PLN activity.

Example 7: Activity of 5'-C16, 3'-C16, 5'-BCY17901, or 3'-BCY17901 Conjugated Oligomeric Duplex Compounds hPLN$^{tg/tg}$ the knock-in mice and hTfR$^{tg/+}$/hPLN$^{tg/tg}$ knock-in mice were used to determine effects of the conjugated oligomeric duplex compounds on human PLN, hPLN$^{tg/tg}$ and hTfR$^{tg/+}$/hPLN$^{tg/tg}$ knock-in mice were divided into groups of 3 mice each. Each mouse received a single subcutaneous injection of compound at a dose of either 30 mg/kg or 3 mg/kg. Two groups of 3 mice each received a single subcutaneous injection of PBS, serve as control groups. Seven days post treatment, mice were sacrificed and RNA extracted from mouse heart for real-time RTPCR analysis of PLN RNA expression. Human PLN primer probe set ABI53044 (described in Example 5) was used to measure human PLN RNA levels. PLN RNA levels were normalized to total RNA content, as measured by RIBOGREEN®. Results are presented as percent PLN RNA, relative to the amount of PLN in PBS treated animals (% control).

TABLE 27

Reduction of PLN RNA by conjugated oligomeric duplex compounds

| Mouse Strain | Compound No. | Conjugate | Dose (mg/kg) | PLN RNA (% control) Heart |
|---|---|---|---|---|
| hPLN$^{tg/tg}$ | PBS | — | — | 100 |
| hTfR$^{tg/+}$/hPLN$^{tg/tg}$ | PBS | — | — | 103 |
| hPLN$^{tg/tg}$ | 1669057 | 3'-C16 | 30 | 47 |
| hPLN$^{tg/tg}$ | 1722804 | 5'-C16 | 30 | 42 |
| hTfR$^{tg/+}$/hPLN$^{tg/tg}$ | 1700644 | 3'-BCY17901 | 3 | 67 |
| hTfR$^{tg/+}$/hPLN$^{tg/tg}$ | 1722807 | 5'-BCY17901 | 3 | 50 |
| hPLN$^{tg/tg}$ | 1722807 | 5'-BCY17901 | 3 | 104‡ |

‡fewer than 3 samples were available

As shown in Table 27, compounds having conjugate attached at the 5' end or 3' end of the sense strand of the duplex yielded similar activity in decreasing amount of hPLN RNA in hPLN knock-in mice. Oligomeric duplex compounds targeting human PLN RNA are significantly more potent when conjugated to the transferrin receptor 1-binding peptide BCY17901 as compared to a C16 conjugate group, and the activity of the BCY17901-conjugated duplex oligonucleotide compounds in heart in vivo requires human transferrin receptor 1.

Example 8: Potency of 3'-BCY17901 Conjugated Oligomeric Duplex Compounds Targeting Human PLN hTfR$^{tg/+}$/hPLN$^{tg/tg}$ knock-in mice were used to determine effects of the compounds on human PLN, hTfR$^{tg/+}$/hPLN$^{tg/tg}$ knock-in mice were divided into groups of 3 mice each. Each mouse received a single subcutaneous injection of compound at various doses. One group of 4 mice received a single subcutaneous injection of PBS and served as the control group to which compound-treated groups were compared. Two weeks post treatment, mice were sacrificed and RNA extracted from mouse heart for real-time RTPCR analysis of PLN RNA expression. Human PLN primer probe set ABI53044 (described in Example 5) was used to measure human PLN RNA levels as indicated in Table 28. PLN RNA levels were normalized to total RNA content, as measured by RIBOGREENR. Results are presented as percent PLN RNA, relative to the amount of PLN in PBS treated animals (% control). Half maximal effective dose (ED50) of each modified oligonucleotide was calculated using GraphPad Prism 7 software (GraphPad Software, San Diego, CA).

TABLE 28

Potency of 3'-BCY17901 conjugated oligomeric duplex compounds

| Compound No. | Dose (mg/kg) | PLN RNA (% control) Heart | ED50 (mg/kg) |
|---|---|---|---|
| PBS | — | 100 | — |
| 1700644 | 1 | 81 | 6.15 |
| | 3 | 61 | |
| | 9 | 44 | |
| 1726638 | 1 | 102 | 4.22 |
| | 3 | 59 | |
| | 9 | 25 | |
| 1726640 | 1 | 107 | 8.78 |
| | 3 | 76 | |
| | 9 | 51 | |
| 1726641 | 1 | 100 | 23.83 |
| | 3 | 88 | |
| | 9 | 75 | |
| 1726645 | 1 | 96 | 29.81 |
| | 3 | 90 | |
| | 9 | 75 | |
| 1726648 | 1 | 91 | 11.04 |
| | 3 | 67 | |
| | 9 | 56 | |

As shown in Table 28, 3' conjugated BCY17901 oligomeric duplex compounds demonstrated dose dependent activity decreasing the amount of hPLN RNA in hPLN knock-in mice.

Example 9: Activity of 5'-C16 Conjugated Oligomeric Duplex Compounds Targeting Human PLN hPLN$^{tg/tg}$ knock-in mice were used to determine effects of the oligomeric duplex compounds containing modified oligonucleotides on human PLN, hPLN$^{tg/tg}$ Knock-in mice were divided into groups of 3 mice each. Each mouse received a single subcutaneous injection of compound at a dose of 50 mg/kg. One group of 4 mice received a single subcutaneous injection of PBS and served as the control group to which compound-treated groups were compared. Two weeks post treatment, mice were sacrificed and RNA extracted from mouse heart for real-time RTPCR analysis of PLN RNA expression. Human PLN primer probe set ABI53044 (described in Example 5) was used to measure human PLN RNA levels. PLN RNA levels were normalized to total RNA content, as measured by RIBOGREENR. Results of evaluation of various chemical modifications of antisense and sense strands of oligonucleotide duplexes targeting human PLN RNA are presented in Table 29 (A-C) as percent human PLN RNA, relative to the amount of human PLN in PBS treated animals (% control). Several compounds were selected for dose-response studies to evaluate potency of the compounds in decreasing human PLN RNA in hPLN knock-in mouse heart cells in the following example.

TABLE 29

Reduction of human PLN RNA by 5'-C16 conjugated oligomeric duplex compounds

| A. | | B. | | C. | |
|---|---|---|---|---|---|
| Compound No. | PLN RNA (% control) Heart | Compound No. | PLN RNA (% control) Heart | Compound No. | PLN RNA (% control) Heart |
| PBS | 100 | PBS | 100 | PBS | 100 |
| 1722804 | 16 | 1722804 | 14 | 1722804 | 18 |
| 1735533 | 20 | 1739642 | 10 | 1750177 | 12 |
| 1735536 | 82 | 1739646 | 11 | 1750180 | 21 |
| 1735539 | 18 | 1739649 | 15 | 1750207 | 7 |
| 1735542 | 24 | 1739652 | 13 | 1750213 | 18 |
| 1735545 | 18 | 1739655 | 14 | 1750219 | 25 |
| 1735551 | 20 | 1739658 | 22 | 1750225 | 17 |
| 1735554 | 19 | 1739661 | 11‡ | 1750231 | 7 |
| 1735557 | 12 | 1739664 | 4 | 1750237 | 9 |
| 1735560 | 15 | 1739667 | 17 | 1750243 | 9 |
| 1735563 | 17 | 1739670 | 8 | 1750248 | 12 |
| 1735566 | 19 | 1739673 | 19 | 1750254 | 11 |
| 1735569 | 20 | 1739676 | 8 | 1750259 | 13 |
| 1735572 | 54 | 1739679 | 9 | 1750268 | 17 |
| 1735575 | 30 | 1739682 | 12 | 1750274 | 12 |
| 1735578 | 18 | 1739685 | 9 | 1750280 | 17 |
| 1735581 | 17 | 1739688 | 8 | 1750292 | 8 |
| 1735584 | 45 | 1739691 | 10 | 1750301 | 30 |
| 1735587 | 53 | 1739694 | 11 | 1750355 | 21 |
| 1735590 | 59 | 1739697 | 9 | 1750676 | 8 |
| | | 1739700 | 19 | 1750683 | 8 |

‡fewer than 3 samples

Example 10: Potency of 5'-C16 Conjugated Oligomeric Duplex Compounds Targeting Human PLN hPLN$^{tg/tg}$ mice were used to determine effects of compounds on human PLN, hPLN1 g/g mice were divided into groups of 3 mice each. Each mouse received a single subcutaneous injection of compound. One group of 4 mice received a single subcutaneous injection of PBS, served as the control group to which compound-treated groups were compared. Two weeks post treatment, mice were sacrificed and RNA extracted from mouse heart for real-time RTPCR analysis of PLN RNA expression. Human PLN primer probe set ABI53044 (described in Example 5) was used to measure human PLN RNA levels. PLN RNA levels were normalized to total RNA content, as measured by RIBOGREEN®. Results are presented in Table as percent PLN RNA, relative to the amount of PLN in PBS treated animals (% control). Half maximal effective dose (ED$_{50}$) of each modified oligonucleotide was calculated using GraphPad Prism 7 software (GraphPad Software, San Diego, CA). Compounds having reduced fluorine content and/or containing one or more deoxynucleosides were more potent in decreasing the amount of human PLN.

TABLE 30

Reduction of human PLN RNA by 5'-C16 conjugated oligomeric duplex compounds in hPLN$^{tg/tg}$ mice

| Compound No. | Dose (mg/kg) | PLN RNA (% control) Heart | ED50 (mg/kg) |
|---|---|---|---|
| PBS | — | 100 | — |
| 1722804 | 6 | 87 | 14.41 |
| | 18 | 37 | |
| | 54 | 13 | |
| 1750254 | 6 | 69 | 9.46 |
| | 18 | 23 | |
| | 54 | 8 | |
| 1750274 | 6 | 59 | 9.78 |
| | 18 | 40 | |
| | 54 | 12 | |
| 1750292 | 6 | 37 | 3.76 |
| | 18 | 13 | |
| | 54 | 5 | |
| 1750676 | 6 | 47 | 5.40 |
| | 18 | 16 | |
| | 54 | 7 | |
| 1750683 | 6 | 45 | 4.96 |
| | 18 | 19 | |
| | 54 | 7 | |

Example 11: Potency of BCY17901-Conjugated Oligomeric Duplex Compounds Targeting Human PLN Six compounds, directed to three different PLN sites and each containing one or two deoxynucleosides in the antisense strand and low compound fluorine content were analyzed in a 5-point dose response study, hTfR$^{tg/+}$/hPLN$^{tg/tg}$ knock-in mice were divided into groups of 3 mice each. Each mouse received subcutaneous injections of compound once a week for three weeks (a total of 3 treatments) at various doses indicated in Table 31. One group of 3 mice received subcutaneous injections of PBS once a week for three weeks (a total of 3 treatments) and served as a control group.

Figure 2A:
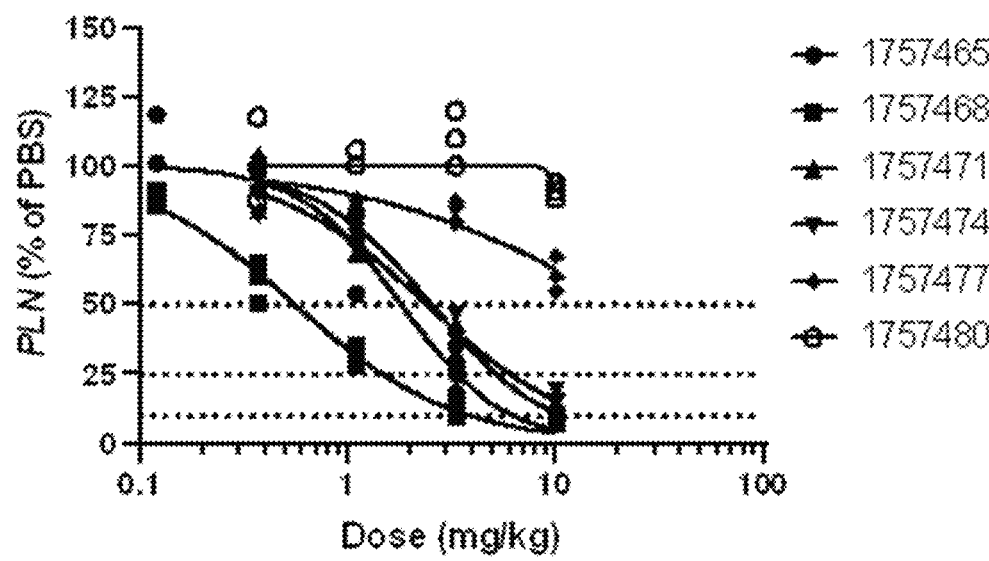
FIGS. 2A-2B depict experimental results from studies described in Example 11 showing potency of BCY17901-conjugated modified oligomeric duplexes targeting human PLN.
Figure 2B:
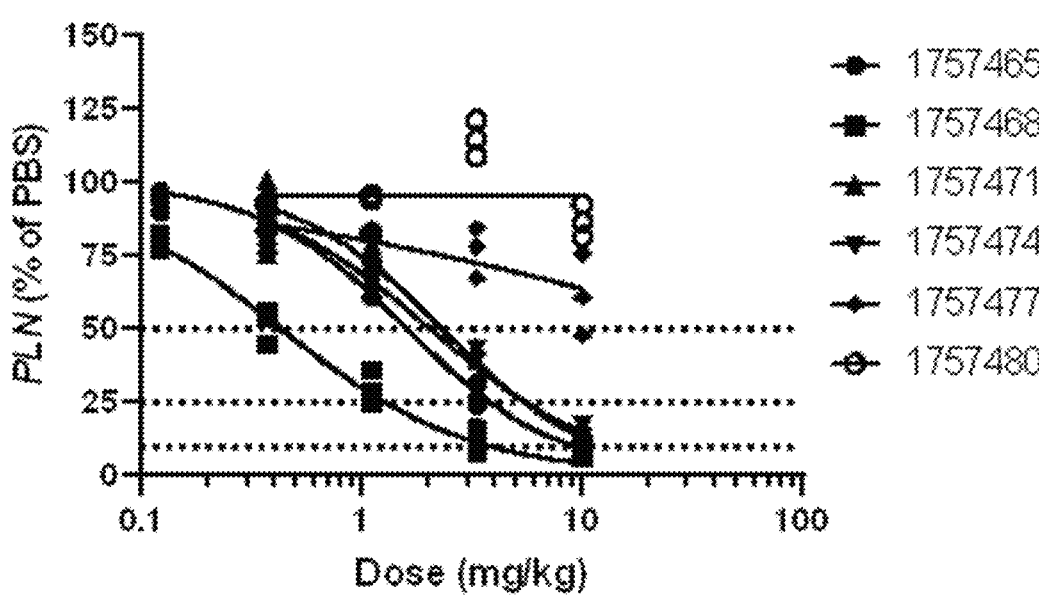

Seven days post final treatment, mice were sacrificed and RNA extracted from mouse heart for real-time RTPCR analysis of PLN RNA expression. Human PLN primer probe set ABI53044 (described in Example 5) was used to measure human PLN RNA levels. PLN RNA levels were normalized to total RNA content, as measured by RIBOGREENR and were normalized to mouse GAPDH RNA levels. Mouse GAPDH was amplified using mouse primer probe set mGapdh_LTS00102 (forward sequence GGCAAATT-CAACGGCACAGT, designated herein as SEQ ID NO: 1059; reverse sequence GGGTCTCGCTCCTGGAAGAT, designated herein as SEQ ID NO: 1060; probe sequence AAGGCCGAGAATGGGAAGCTTGTCATC, designated herein as SEQ ID NO: 1061). Results are presented as percent human PLN RNA, relative to the amount of human PLN RNA in tissue from PBS treated mice (% control). Half maximal effective dose (ED$_{50}$) of each compound was calculated using GraphPad Prism 7 software (GraphPad Software, San Diego, CA). "N.D." refers to ED$_{50}$ values that could not be reliably determined. The data is also presented in graphical format in FIGS. 2A and 2B.

TABLE 31

Reduction of human PLN by 5'-BCY17901-conjugated oligomeric duplex compounds

| | | PLN RNA (% control) | | | |
|---|---|---|---|---|---|
| | Dose | Ribogreen | | GAPDH | |
| Compound No. | (mg/kg) | Heart | ED50 (mg/kg) | Heart | ED50 (mg/kg) |
| PBS | — | 100 | — | 100 | — |
| 1757465 | 0.12 | 113 | 1.82 | 94 | 1.60 |
| | 0.37 | 96 | | 84 | |
| | 1.1 | 70 | | 66 | |
| | 3.3 | 24 | | 24 | |
| | 10 | 12 | | 11 | |
| 1757468 | 0.12 | 89 | 0.56 | 80 | 0.43 |
| | 0.37 | 59 | | 51 | |
| | 1.1 | 32 | | 30 | |
| | 3.3 | 11 | | 9 | |
| | 10 | 8 | | 6 | |
| 1757471 | 0.37 | 95 | 2.53 | 86 | 2.30 |
| | 1.1 | 79 | | 76 | |
| | 3.3 | 39 | | 38 | |
| | 10 | 12 | | 12 | |
| 1757474 | 0.37 | 88 | 2.40 | 85 | 2.03 |
| | 1.1 | 74 | | 68 | |
| | 3.3 | 39 | | 37 | |
| | 10 | 16 | | 14 | |
| 1757477 | 0.37 | 95 | 20.39 | 86 | 43.23 |
| | 1.1 | 84 | | 77 | |
| | 3.3 | 84 | | 77 | |
| | 10 | 61 | | 62 | |
| 1757480 | 0.37 | 102 | N.D. | 90 | N.D. |
| | 1.1 | 104 | | 91 | |
| | 3.3 | 110 | | 115 | |
| | 10 | 91 | | 87 | |

While single dose activity for each of the compounds compared to their respective parent counterparts appeared to yield similar improvements in initial studies (data not shown), dose response of compounds having the same modifications found certain sites demonstrate particularly significant and unexpected improvements in potency over parent compounds. See FIG. 2, and Table 31.

Example 12: Activity of Oligomeric Duplexes Targeting Human PLN hPLN$^{tg/tg}$ knock-in mice were used to determine effects of the oligomeric duplex compounds on human PLN. Mice were divided into groups of 3 mice; and each mouse received a single subcutaneous injection of oligomeric duplex compound at a dose of 45 mg/kg. One group of 4 mice served as a control group and each mouse received a single subcutaneous injection of PBS. Two weeks post treatment, mice were sacrificed and RNA extracted from mouse heart for real-time RTPCR analysis of PLN RNA expression. Human PLN primer probe set ABI53044 (described in Example 5) was used to measure human PLN RNA levels. PLN RNA levels were normalized to total RNA content, as measured by RIBOGREEN®. Results are presented in Table 32 as percent PLN RNA, relative to the amount of PLN in PBS treated animals (% control).

TABLE 32

| | PLN RNA (% control) |
| Reduction of human PLN RNA by oligomeric duplex compounds | |
| Compound No. | Heart |
| --- | --- |
| PBS | 100 |
| 1722804 | 13‡ |
| 1755748 | 16 |
| 1755751 | 7 |
| 1755757 | 27 |
| 1755763 | 15 |

‡indicates fewer than 3 samples available

Example 13: Potency of Oligomeric Duplexes Targeting Human PLN hTfR$^{g/+}$/hPLN$^{tg/tg}$ knock-in mice were used to determine effects of the oligomeric duplex compounds on human PLN, hTfR$^{tg/+}$/hPLN$^{tg/tg}$ knock-in mice were divided into groups of 3 mice each. Each mouse received subcutaneous injections of oligomeric duplex compound on Day 1, Day 5, and Day 8 (a total of 3 treatments) at various doses indicated in Table 33. One group of 4 mice received subcutaneous injections of PBS on Day 1, Day 5, and Day 8 (a total of 3 treatments) and served as the control group to which oligomeric duplex-treated groups were compared. 7 days post final treatment (Day 15), mice were sacrificed and RNA extracted from mouse heart for real-time RTPCR analysis of PLN RNA expression. Human PLN primer probe set ABI53044 (described in Example 5) was used to measure human PLN RNA levels, and PLN RNA levels were normalized to total RNA content, as measured by RIBOGREEN®. Results are presented in Table 33 as percent PLN RNA, relative to the amount of PLN RNA in PBS treated animals (% control). Half maximal effective dose (ED50) of each oligomeric duplex compound was calculated using GraphPad Prism 7 software (GraphPad Software, San Diego, CA).

TABLE 33

| | | PLN RNA (% control) | |
| Potency of oligomeric duplex compounds | | | |
| Compound No. | Dose (mg/kg) | Heart | ED$_{50}$ (mg/kg) |
| --- | --- | --- | --- |
| PBS | — | 100 | — |
| 1757471 | 1.1 | 68 | 1.82 |
| | 3.3 | 28 | |
| | 10 | 12 | |

TABLE 33-continued

| | | PLN RNA (% control) | |
| Potency of oligomeric duplex compounds | | | |
| Compound No. | Dose (mg/kg) | Heart | ED$_{50}$ (mg/kg) |
| --- | --- | --- | --- |
| 1779744 | 0.12 | 95 | 1.89 |
| | 0.37 | 102 | |
| | 1.1 | 68 | |
| | 3.3 | 28 | |
| | 10 | 11 | |

TABLE 34

| | | PLN RNA (% control) | |
| Potency of oligomeric duplex compounds | | | |
| Compound No. | Dose (mg/kg) | Heart | ED50 (mg/kg) |
| --- | --- | --- | --- |
| PBS | — | 100 | — |
| 1757468 | 0.37 | 59 | 0.50 |
| | 1.1 | 27 | |
| | 3.3 | 13 | |
| 1757474 | 0.37 | 102 | 1.57 |
| | 1.1 | 59 | |
| | 3.3 | 26 | |

The potency of oligomeric duplex compounds 1757468 and 1757474 was also evaluated in hTfR$^{tg/+}$/hPLN$^{tg/tg}$ knock-in mice. Each mouse received subcutaneous injections of oligomeric duplex compound on Day 1, Day 5, and Day 10 (a total of 3 treatments) at various doses indicated in Table 34. One group of 4 mice received subcutaneous injections of PBS on Day 1, Day 5, and Day 10 (a total of 3 treatments) and served as the control group to which oligomeric duplex-treated groups were compared. 6 days post final treatment (Day 16), mice were sacrificed and RNA extracted from mouse heart for real-time RTPCR analysis of PLN RNA expression. Human PLN primer probe set ABI53044 (described in Example 5) was used to measure human PLN RNA levels, and PLN RNA levels were normalized to total RNA content, as measured by RIBOGREENR. Results are presented in Table 34 as percent PLN RNA, relative to the amount of PLN in PBS treated animals (% control). Half maximal effective dose (ED$_{50}$) of each oligomeric duplex compound was calculated using GraphPad Prism 7 software (GraphPad Software, San Diego, CA).

Example 14: Duration of Action Study of Oligomeric Duplex Compounds Targeting Human PLN in hTfR$^{tg/+}$/hPLN$^{tg/tg}$ Knock-In Mice hTfR$^{tg/+}$/hPLN$^{tg/tg}$ knock-in mice (described herein above) were used to determine effects of the oligomeric duplex compounds on human PLN. Mice, divided into groups of 3 mice each, received subcutaneous injections of oligomeric duplex compound at a dose of either 6 mg/kg or 1.5 mg/kg, as specified in Table 35, on Day 1, 5, and 8 (a total of 3 treatments). One group of 3 mice received subcutaneous injections of PBS on Day 1, 5, and 8 (a total of 3 treatments) served as the control group to which oligomeric duplex-treated groups were compared. Following treatment, mice were sacrificed at various timepoints as indicated in Table 35, and RNA was extracted from mouse heart for real-time RTPCR analysis of PLN RNA expression. Human PLN primer probe set Hs00160179_ml (Integrated DNA Technologies) was used to measure human PLN RNA levels. PLN RNA levels of each sample were normalized to total RNA content of each sample, as measured by RIBOGREENR. Results are presented in Table 35 and FIG. 3 as percent PLN RNA, relative to the amount of PLN RNA averaged from all the PBS-treated animals at all timepoints (% control).

TABLE 35

Reduction of human PLN RNA in transgenic mouse heart by oligomeric duplex compounds

| Compound No. | Dose (mg/kg) | Timepoint (Days post final dose) | PLN RNA (% control) |
|---|---|---|---|
| PBS | — | 14 | 99 |
| | | 28 | 95 |
| | | 56 | 113 |
| | | 84 | 95‡ |
| | | 112 | 97 |
| 1757468 | 1.5 | 14 | 26 |
| | | 28 | 43 |
| | | 56 | 60 |
| | | 84 | 89 |
| | | 112 | 78 |
| 1757474 | 6 | 14 | 24 |
| | | 28 | 61 |
| | | 56 | 98 |
| | | 84 | 102 |
| | | 112 | 88 |
| 1779744 | 6 | 14 | 19 |
| | | 28 | 29 |
| | | 56 | 37 |
| | | 84 | 45 |
| | | 112 | 54 |

‡indicates fewer than 3 samples available

Figure 3:
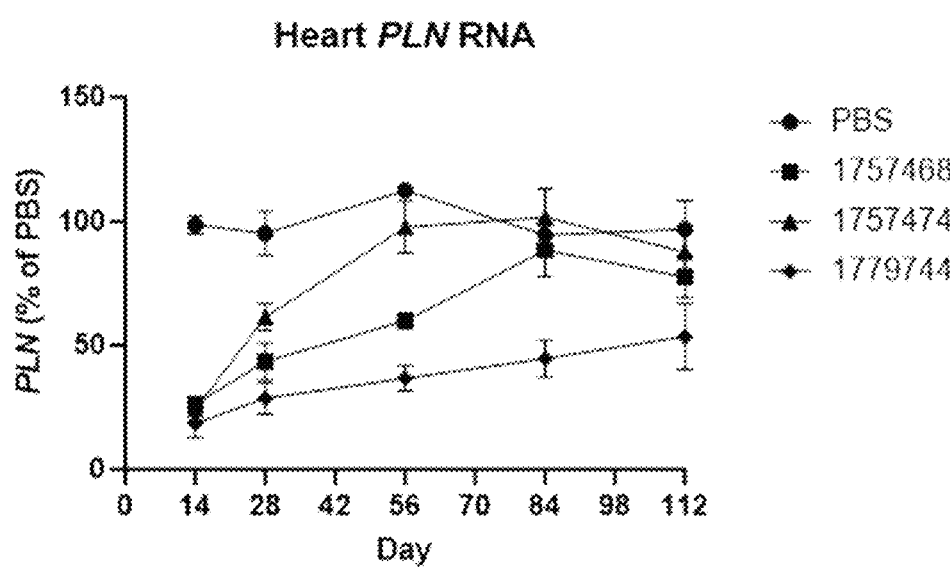
FIG. 3 depicts experimental results from duration study described in Example 14 showing potency and duration of BCY17901-conjugated modified oligomeric duplexes targeting human PLN.

Results presented in Table 35 and FIG. 3 confirm each of the three oligomeric compounds (U.S. Pat. Nos. 1,757,468, 1,757,474, 1,779,744) are potent compounds for reducing human PLN RNA in transgenic mouse heart, with durable effects following compound administration. Compound 1779744 provided the most sustained reduction of PLN RNA levels over time post treatment.

Example 15: Model of Improved Oligomeric Compounds

Figure 4:
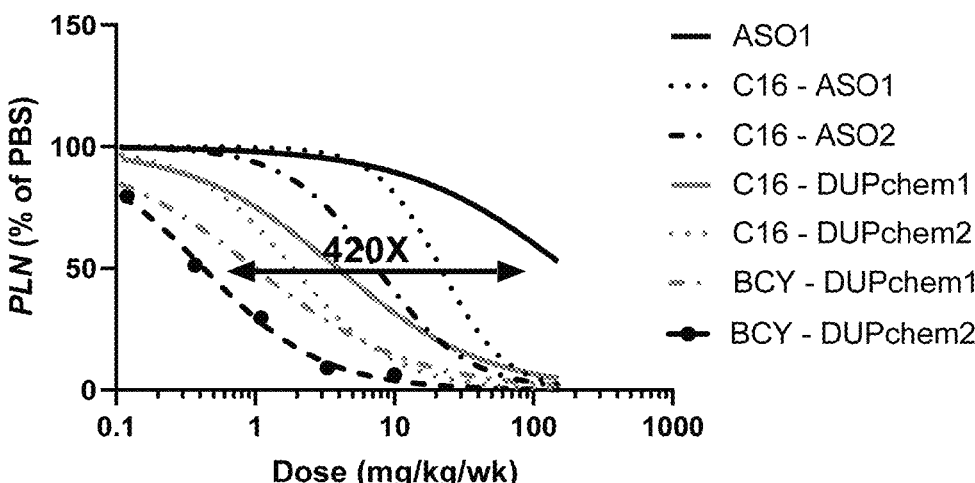
FIG. 4 depicts a model of PLN targeted compound activity improvements based on results described herein (see also Example 15).

FIG. 4 is a model depicting improvements in activity of compounds targeting human PLN that is based on results of experiments described herein as well as similar experiments not shown. Relative estimated monthly in vivo clinical doses (represented as estimated ED50 values) of different oligomeric compounds targeting PLN for RNA reduction were calculated using dose-response data from knock-in mice studies described herein and similar studies carried out. Compounds represented include a full phosphorothioate 3-10-3 cEt antisense oligonucleotide (ASO1), a C16-conjugated ASO (C16-ASO1), a C16-conjugated ASO having a mixed backbone with reduced phosphorothioate (C16-ASO2), a C16-conjugated first modified oligomeric duplex (C16-DUPchem1), a C16-conjugated second modified oligomeric duplex (C16-DUPchem2), a bicycle ligand-conjugated first modified oligomeric duplex (BCY-DUPchem1), and a bicycle ligand conjugated second modified oligomeric duplex (BCY-DUPchem2). Estimated ED50 for an oligomeric compound comprising a second modified duplex conjugated to a transferrin receptor 1-binding BCY peptide (BCY-DUPchem2) targeted to human PLN is about 420-fold lower than that for an unconjugated single-stranded antisense oligonucleotide (ASO1) targeted to human PLN, about 10-fold lower than an oligomeric compound comprising a modified duplex conjugated to C16 (C16-DUPchem2), and at least two-fold lower than a oligomeric compound having different modifications (BCY-DUPchem1). SEE FIG. 4.

The invention claimed is:

1. An oligomeric duplex comprising:

i) a modified oligonucleotide according to the following chemical notation:

(SEQ ID NO: 1255)

vPT$_{es}$A$_{fs}$U$_{yo}$A$_{yo}$A$_{yo}$A$_{yo}$U$_{yo}$A$_{yo}$G$_{yo}$A$_{yo}$U$_{yo}$U$_{yo}$C$_{yo}$U$_{fo}$G$_{yo}$U$_{fo}$

A$_{yo}$G$_{yo}$C$_{yo}$U$_{yo}$U$_{ys}$A$_{e}$sA$_{e}$;

wherein:

A=an adenine nucleobase,

C=a cytosine nucleobase,

G=a guanine nucleobase,

T=a thymine nucleobase,

U=a uracil nucleobase, e=a 2'-MOE sugar moiety, f=a 2'-fluoro sugar moiety, y=a 2'-OMe sugar moiety, o=a phosphodiester internucleoside linkage, s=a phosphorothioate internucleoside linkage, and vP=a 5' vinyl phosphonate group; and ii) a conjugated modified oligonucleotide according to the following chemical notation:

(SEQ ID NO: 1041)

[X]$_1$-

A$_{es}$A$_{es}$G$_{yo}$C$_{yo}$U$_{yo}$A$_{yo}$C$_{yo}$A$_{yo}$G$_{yo}$A$_{fo}$A$_{fo}$U$_{yo}$C$_{yo}$U$_{yo}$A$_{yo}$U$_{yo}$U$_{yo}$A$_{ys}$T$_{es}$A$_{e}$, wherein:

C=a cytosine nucleobase,

A=an adenine nucleobase,

G=a guanine nucleobase,

U=a uracil nucleobase,

T=a thymine nucleobase, e=a 2'-MOE sugar moiety, f=a 2'-fluoro sugar moiety, y=a 2'-OMe sugar moiety, o=a phosphodiester internucleoside linkage, s=a phosphorothioate internucleoside linkage,

[X]$_1$=a conjugate group having the following structure (SEQ ID NO: 1301):

or a pharmaceutically acceptable salt thereof.

2. The oligomeric duplex of claim 1, wherein the pharmaceutically acceptable salt is a sodium salt.

3. The oligomeric duplex of claim 1, wherein the pharmaceutically acceptable salt is a potassium salt.

4. A pharmaceutical composition comprising the oligomeric duplex of claim 1 and a pharmaceutically acceptable diluent or carrier.

5. An oligomeric duplex according to the following chemical structure:

(SEQ ID NO: 1255 and SEQ ID NO: 1041; peptide sequence disclosed as SEQ ID NO: 1295)

-continued

-continued or a pharmaceutically acceptable salt thereof.

6. The oligomeric duplex of claim 5, wherein the pharmaceutically acceptable salt is a sodium salt.

7. The oligomeric duplex of claim 5, wherein the pharmaceutically acceptable salt is a potassium salt.

8. A pharmaceutical composition comprising the oligomeric duplex of claim 5 and a pharmaceutically acceptable diluent or carrier.

9. An oligomeric duplex according to the following chemical structure:

(SEQ ID NO: 1255 and SEQ ID NO: 1041;peptide sequence disclosed as SEQ ID NO: 1295 )

1085                  1086

-continued

-continued

10. A pharmaceutical composition comprising the oligomeric duplex of claim 9 and a pharmaceutically acceptable diluent or carrier.

\* \* \* \* \*